(12) United States Patent
Oslob et al.

(10) Patent No.: US 10,053,450 B2
(45) Date of Patent: Aug. 21, 2018

(54) HETEROCYCLIC MODULATORS OF LIPID SYNTHESIS

(71) Applicant: 3-V Biosciences, Inc., Menlo Park, CA (US)

(72) Inventors: Johan D. Oslob, Sunnyvale, CA (US); Robert S. McDowell, San Francisco, CA (US); Russell Johnson, San Mateo, CA (US); Hanbiao Yang, Sunnyvale, CA (US); Marc Evanchik, San Jose, CA (US); Cristiana A. Zaharia, Redwood City, CA (US); Haiying Cai, Cupertino, CA (US); Lily W. Hu, Palo Alto, CA (US); Allan S. Wagman, Belmont, CA (US)

(73) Assignee: 3-V Biosciences, Inc., Menlo Park, CA (US)

( * ) Notice: Subject to any disclaimer, the term of this patent is extended or adjusted under 35 U.S.C. 154(b) by 1 day.

(21) Appl. No.: 15/201,824

(22) Filed: Jul. 5, 2016

(65) Prior Publication Data
US 2016/0311803 A1 Oct. 27, 2016

Related U.S. Application Data

(60) Division of application No. 14/587,908, filed on Dec. 31, 2014, now Pat. No. 9,428,502, which is a continuation of application No. PCT/US2013/048950, filed on Jul. 1, 2013.

(60) Provisional application No. 61/667,894, filed on Jul. 3, 2012, provisional application No. 61/698,511, filed on Sep. 7, 2012, provisional application No. 61/699,819, filed on Sep. 11, 2012, provisional application No. 61/785,933, filed on Mar. 14, 2013.

(51) Int. Cl.

| | | |
|---|---|---|
| C07D 487/04 | (2006.01) |
| C07D 403/14 | (2006.01) |
| C07D 401/14 | (2006.01) |
| C07D 403/10 | (2006.01) |
| C07D 205/04 | (2006.01) |
| C07D 405/04 | (2006.01) |
| C07D 211/16 | (2006.01) |
| C07D 413/14 | (2006.01) |
| C07D 405/14 | (2006.01) |
| C07D 401/10 | (2006.01) |
| C07D 471/04 | (2006.01) |
| C07D 401/04 | (2006.01) |

(52) U.S. Cl.
CPC ......... *C07D 403/14* (2013.01); *C07D 205/04* (2013.01); *C07D 211/16* (2013.01); *C07D 401/04* (2013.01); *C07D 401/10* (2013.01); *C07D 401/14* (2013.01); *C07D 403/10* (2013.01); *C07D 405/04* (2013.01); *C07D 405/14* (2013.01); *C07D 413/14* (2013.01); *C07D 471/04* (2013.01); *C07D 487/04* (2013.01)

(58) Field of Classification Search
CPC .. C07D 403/14; C07D 205/04; C07D 211/16; C07D 401/04; C07D 401/10; C07D 401/14; C07D 403/10; C07D 405/04; C07D 405/14; C07D 413/14; C07D 471/04; C07D 487/04
USPC .................................................... 514/210.18
See application file for complete search history.

(56) References Cited

U.S. PATENT DOCUMENTS

| | | | |
|---|---|---|---|
| 8,871,790 B2 | 10/2014 | Oslob et al. | |
| 2008/0103208 A1 | 5/2008 | Ossovskaya et al. | |
| 2009/0105305 A1 | 4/2009 | Butlin et al. | |
| 2009/0118332 A1 | 5/2009 | Butlin et al. | |
| 2012/0264737 A1 | 9/2012 | Oslob et al. | |
| 2014/0322355 A1 | 10/2014 | Oslob et al. | |
| 2015/0259292 A1* | 9/2015 | Oslob ................ | C07D 211/62 514/330 |
| 2016/0102091 A1* | 4/2016 | Oslob ................ | C07D 471/04 514/210.21 |
| 2016/0326141 A1* | 11/2016 | Wagman ............ | C07D 405/14 |
| 2016/0338998 A1* | 11/2016 | Heuer ................ | C07D 407/14 |
| 2017/0119786 A1* | 5/2017 | Buckley ............ | C07D 401/14 |

FOREIGN PATENT DOCUMENTS

| | | | |
|---|---|---|---|
| WO | WO 2007/063012 A1 | 6/2007 | |
| WO | WO 2008/059214 A1 | 5/2008 | |
| WO | WO 2008/075064 A1 | 6/2008 | |
| WO | WO 2008/075077 A1 | 6/2008 | |
| WO | WO 2012/122391 A1 | 9/2012 | |
| WO | WO 2016/025816 | * | 2/2016 |
| WO | WO 2016/149271 | * | 9/2016 |

OTHER PUBLICATIONS

Bentzien et al., "Pyrrolidinyl and piperidinyl compounds useful as NHE-1 inhibitors and their preparation and pharmaceutical compositions," CAPLUS 152:144485, 2010.
Cui, "Preparation of aminoheteroaryl compounds as protein kinase inhibitors," CAPLUS 141:260769, 2004.

(Continued)

*Primary Examiner* — Daniel R Carcanague
(74) *Attorney, Agent, or Firm* — Cooley LLP

(57) ABSTRACT

Heterocyclic modulators of lipid synthesis are provided as well as pharmaceutically acceptable salts thereof; pharmaceutical compositions comprising such compounds; and methods of treating conditions characterized by disregulation of a fatty acid synthase pathway by the administration of such compounds.

33 Claims, No Drawings

(56) References Cited

OTHER PUBLICATIONS

Knust et al., "Preparation of piperidine derivatives as NK-3 receptor antagonists," CAPLUS 153:456481, 2010.
Menet et al., "Novel triazolopyridine compounds as JAK kinase inhibitors useful for the treatement of degenerative and inflammatory diseases and their preparation," CAPLUS 152:192130, 2010.
Schneider et al., "Preparation of 5-alkynyl-pyrimidines as kinase inhibitors," CAPLUS 155:271283, 2011.

* cited by examiner

HETEROCYCLIC MODULATORS OF LIPID SYNTHESIS

CROSS-REFERENCE TO RELATED APPLICATIONS

This application is a division of U.S. patent application Ser. No. 14/587,908, which was filed on Dec. 31, 2014 (now allowed), which is a continuation of International PCT Patent Application No. PCT/US2013/048950, which was filed on Jul. 1, 2013, which claims the benefit under 35 U.S.C. § 119(e) of U.S. Provisional Patent Application No. 61/667,894, filed Jul. 3, 2012, U.S. Provisional Patent Application No. 61/698,511, filed Sep. 7, 2012, U.S. Provisional Patent Application No. 61/699,819, filed Sep. 11, 2012, and U.S. Provisional Patent Application No. 61/785,933, filed Mar. 14, 2103. The foregoing applications are incorporated herein by reference in their entireties.

FIELD

The present disclosure relates generally to heterocyclic modulators of lipid synthesis and methods of use thereof. The present heterocyclic modulators of lipid synthesis can be used for the treatment of disorders characterized by disregulation in the fatty acid synthase function in a subject by modulating the fatty acid synthase pathway and/or the fatty acid synthase function.

BACKGROUND

Viral disease is a significant health concern that threatens large segments of human populations. Some of the features related to viral infection which are of concern to health care professionals include its highly contagious nature (e.g., HIV, SARS, etc.) and high mutability. Some viruses are also oncogenic (such as HPV, EBV and HBV). While viruses are structurally amongst the simplest of organisms, they are regarded to be among the most difficult to control and present a formidable challenge for antiviral drug R&D.

Thus far, there have been a few antiviral drugs widely used in patients, such as Amantadine and Oseltamivir for influenza, Acyclovir for HSV-related infections, Ganciclovir for CMV infection, and multiple agents including co-formulated drugs (Efavirenz, emtricitabine, and tonfovir disoproxil fumarate) for AIDS treatments. These drugs possess a variety of undesirable neurological, metabolic and immunological side-effects. Therefore, development of new antiviral therapy has become a major focus of medical and pharmaceutical research and development.

Infection by hepatitis C virus (HCV) is a serious health issue. It is estimated that 170 million people worldwide are chronically infected with HCV. HCV infection can lead to chronic hepatitis, cirrhosis, liver failure and hepatocellular carcinoma. Chronic HCV infection is thus a major worldwide cause of liver-related premature mortality.

The present standard of care treatment regimen for HCV infection involves combination therapy with interferon-alpha and ribavirin, often with the addition of a direct-acting protease inhibitor (Telaprevir or Boceprevir). The treatment is cumbersome and sometimes has debilitating and severe side effects. For this reason, many patients are not treated in early stages of the disease. Additionally, some patient populations do not durably respond to treatment. New and effective methods of treating HCV infection are urgently needed.

The dominant therapeutic approaches that are currently employed to treat cancer include surgical removal of primary tumors, tumor irradiation, and parenteral application of anti-mitotic cytotoxic agents. Unfortunately, only a relatively small cross-section of cancer patients have tumors that are "addicted" to a specific pathway, and can therefore be treated with newer targeted agents. The continued dominance of these long established therapies is mirrored by the lack of improvement in survival rates for most cancers. In addition to limited clinical success, devastating side effects accompany classic therapies. Both radiation- and cytotoxic-based therapies result in the destruction of rapidly dividing hematopoietic and intestinal epithelial cells leading to compromised immune function, anemia, and impaired nutrient absorption. Surgical intervention often results in a release of tumor cells into the circulation or lymph systems from which metastatic tumors can subsequently be established. Improved methods for the treatment of cancer are needed.

SUMMARY

The present disclosure addresses the deficiencies for antiviral and anticancer treatments by providing novel heterocyclic modulators of lipid synthesis having improved antiviral and anticancer activities.

In various aspects, the present disclosure provides for compounds of Structure I:

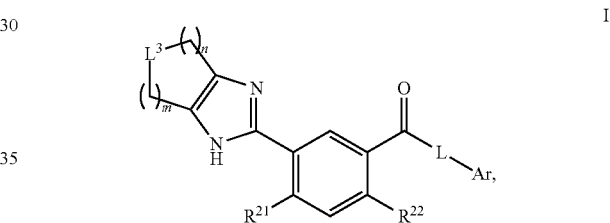

or pharmaceutically acceptable salts thereof, wherein:
$L^3$ is —$CH_2$—, —$CHR^{50}$—, —O—, —$NR^{50}$—, —NC(O)$R^{50}$— or —NC(O)O$R^{50}$—, wherein $R^{50}$ is $C_1$-$C_6$ alkyl, $C_3$-$C_5$ cycloalkyl, or 4- to 6-membered heterocycle;
n is 1, 2, or 3;
m is 1 or 2 with the proviso that n+m≥3;
L-Ar is

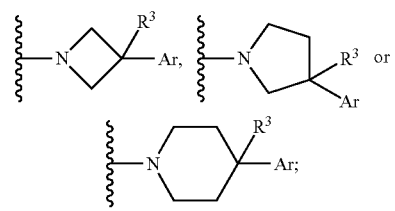

Ar is

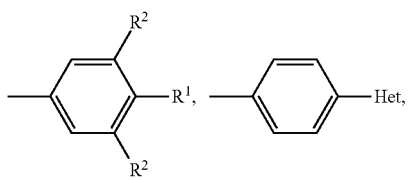

-continued

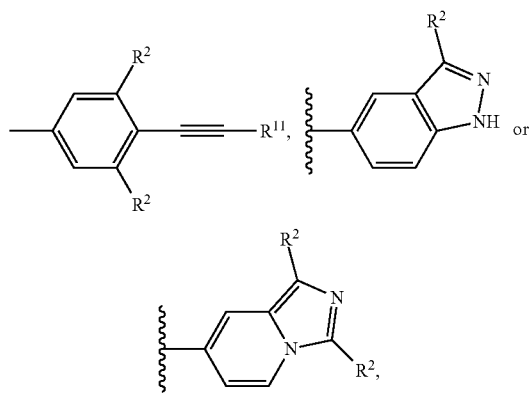

with the proviso that when L-Ar is

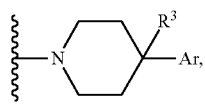

Ar is not

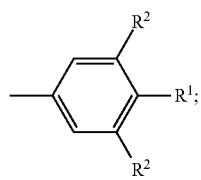

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or a 4- to 6-membered heterocycle; and $R^{22}$ is H, halogen, or $C_1$-$C_2$ alkyl.

In various aspects, the present disclosure provides for compounds of Structure II:

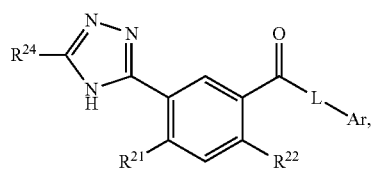

II or pharmaceutically acceptable salts thereof, wherein:

L-Ar is

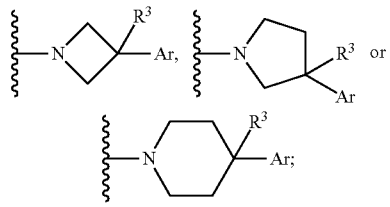

Ar is

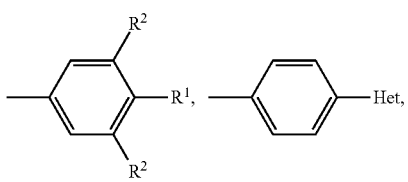

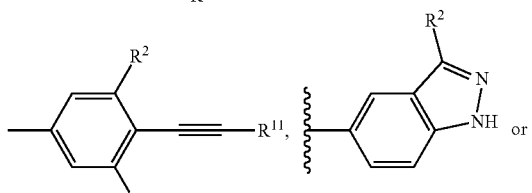

with the proviso that when L-Ar is

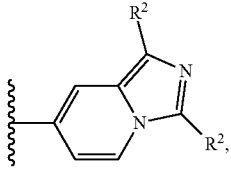

Ar is not

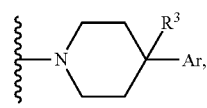

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

R²¹ is H, halogen, $C_1$-$C_4$ alkyl, $C_3$-$C_5$ cycloalkyl or 4- to 6-membered heterocycle;

R²² is H, halogen, or $C_1$-$C_2$ alkyl; and

R²⁴ is H, $C_1$-$C_4$ alkyl, —($C_1$-$C_4$ alkyl)-OH, —($C_1$-$C_4$ alkyl)$_t$-N(R²⁴¹)$_2$, —($C_1$-$C_4$ alkyl)$_t$-O$_t$-($C_3$-$C_5$ cycloalkyl), —($C_1$-$C_4$ alkyl)$_t$-O$_t$-(4- to 6-membered heterocycle) or —($C_1$-$C_4$ alkyl)$_t$-O—($C_1$-$C_4$ alkyl), wherein:
each t is independently 0 or 1; and
each R²⁴¹ is independently H or $C_1$-$C_2$ alkyl.

In various aspects, the present disclosure provides for compounds of Structure III:

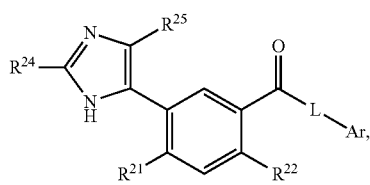

III or pharmaceutically acceptable salts thereof, wherein:
L-Ar is

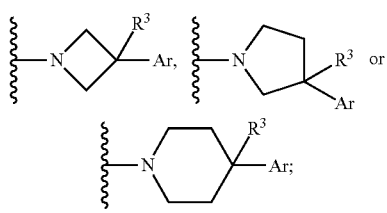

Ar is

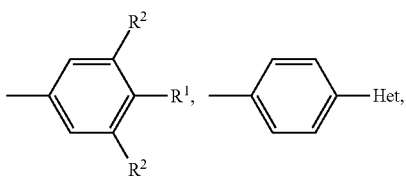

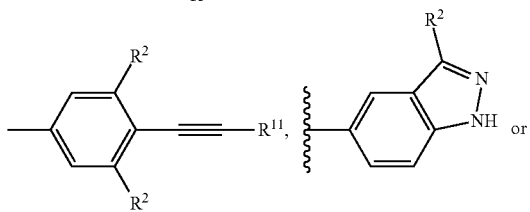

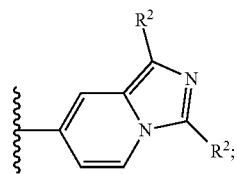

Het is a 5- to 6-membered heteroaryl;

R¹ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when R¹ is not H, —CN or halogen, R¹ is optionally substituted with one or more halogens;

each R² is independently hydrogen, halogen or $C_1$-$C_4$ alkyl;

R³ is H or F;

R¹¹ is H or —CH$_3$;

R²¹ is H, halogen, $C_1$-$C_4$ alkyl, $C_3$-$C_5$ cycloalkyl or 4- to 6-membered heterocycle;

R²² is H, halogen, or $C_1$-$C_2$ alkyl;

R²⁴ is H, —CN, —($C_1$-$C_4$ alkyl)-CN, $C_1$-$C_4$ alkyl, —($C_1$-$C_4$ alkyl)-OH, —($C_1$-$C_4$ alkyl)-N(R²⁴¹)$_2$, —($C_1$-$C_4$ alkyl)$_t$-O$_u$—($C_3$-$C_6$ cycloalkyl), —($C_1$-$C_4$ alkyl)$_t$-O$_u$-(4- to 6-membered heterocycle) or —($C_1$-$C_4$ alkyl)-O—($C_1$-$C_4$ alkyl), wherein:
t is 0 or 1;
u is 0 or 1;
with the proviso that when u is 1, t is 1; and
each R²⁴¹ is independently H or $C_1$-$C_2$ alkyl; and R²⁵ is halogen, —CN, —($C_1$-$C_4$ alkyl)-CN, $C_1$-$C_2$ alkyl or cyclopropyl.

In various aspects, the present disclosure provides for compounds of Structure IIIb:

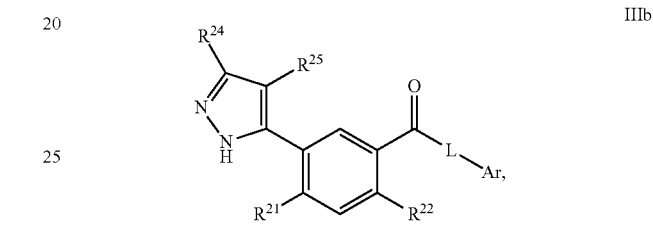

IIIb or pharmaceutically acceptable salts thereof, wherein:
L-Ar is

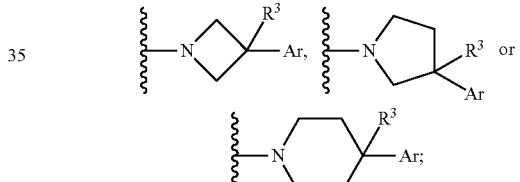

Ar is

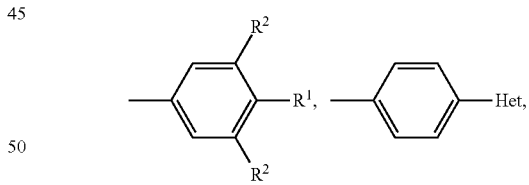

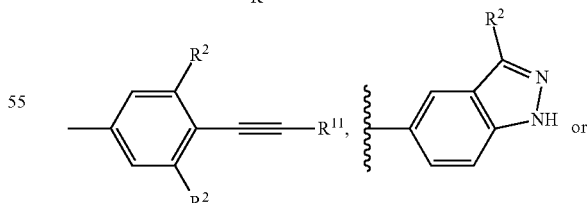

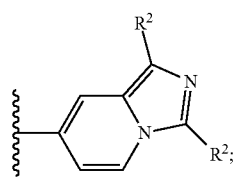

Het is a 5- to 6-membered heteroaryl;
$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;
each $R^2$ is independently hydrogen, halogen or $C_1$-$C_4$ alkyl;
$R^3$ is H or F;
$R^{11}$ is H or —$CH_3$;
$R^{21}$ is H, halogen, $C_1$-$C_4$ alkyl, $C_3$-$C_5$ cycloalkyl or 4- to 6-membered heterocycle;
$R^{22}$ is H, halogen or $C_1$-$C_2$ alkyl; and
each $R^{24}$ and $R^{25}$ is independently H, halogen, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$—C cycloalkyl), —($C_1$-$C_4$ alkyl)$_t$-$O_u$-(4- to 6-membered heterocycle) or —($C_1$-$C_4$ alkyl)$_t$-O—($C_1$-$C_4$ alkyl), wherein:
each t is independently 0 or 1;
each u is independently 0 or 1; and
each $R^{241}$ is independently H or $C_1$-$C_2$ alkyl,
wherein the compound is not:

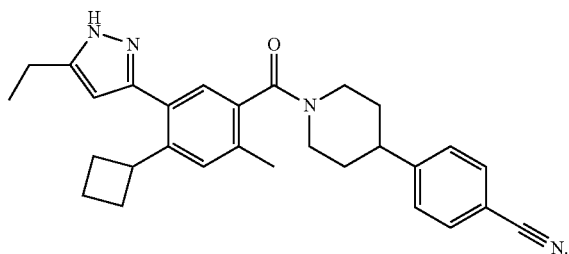 [SMILES: CCc1cc(-c2cc(C(=O)N3CCC(c4ccc(C#N)cc4)CC3)c(C)cc2C2CCC2)n[nH]1]

In various aspects, the present disclosure provides for compounds of Structure IIIc:

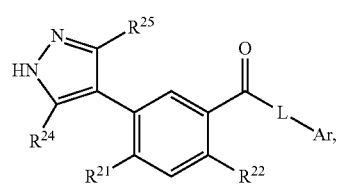

IIIc or pharmaceutically acceptable salts thereof, wherein:
L-Ar is

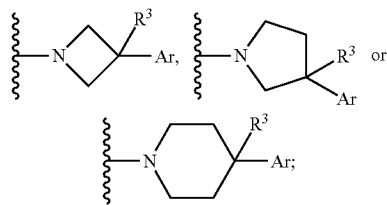

Ar is

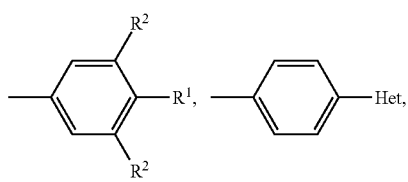

-continued

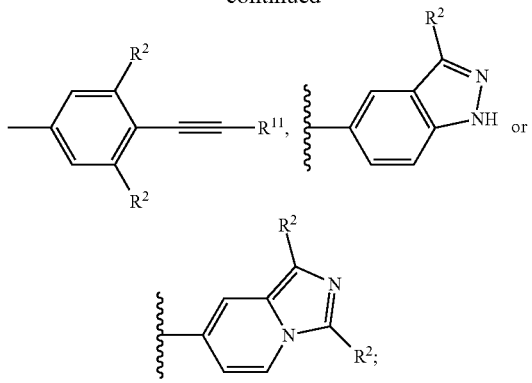

Het is a 5- to 6-membered heteroaryl;
$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;
each $R^2$ is independently hydrogen, halogen or $C_1$-$C_4$ alkyl;
$R^3$ is H or F;
$R^{11}$ is H or —$CH_3$;
$R^{21}$ is H, halogen, $C_1$-$C_4$ alkyl, $C_3$-$C_5$ cycloalkyl or 4- to 6-membered heterocycle;
$R^{22}$ is H, halogen or $C_1$-$C_2$ alkyl; and
each of $R^{24}$ and $R^{25}$ is independently H, —$C_1$-$C_4$ alkyl, or halogen.

In various aspects, the present disclosure provides for compounds of Structure IV:

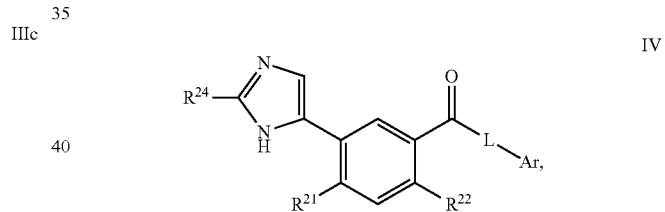

IV or pharmaceutically acceptable salts thereof, wherein:
L-Ar is

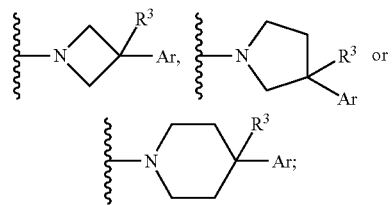

Ar is

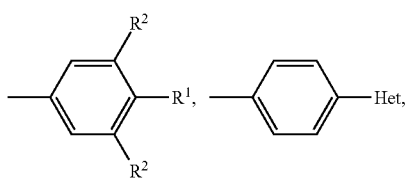

-continued with the proviso that when L-Ar is

Ar is not

Het is a 5- to 6-membered heteroaryl;
$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;
each $R^2$ is independently hydrogen, halogen or $C_1$-$C_4$ alkyl;
$R^3$ is H or F;
$R^{11}$ is H or —CH$_3$;
$R^{21}$ is H, halogen, $C_1$-$C_4$ alkyl, $C_3$-$C_5$ cycloalkyl or 4- to 6-membered heterocycle;
$R^{22}$ is H, halogen or $C_1$-$C_2$ alkyl; and
$R^{24}$ is H, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$-($C_3$-$C_5$ cycloalkyl), —($C_1$-$C_4$ alkyl)$_t$-O$_u$-(4- to 6-membered heterocycle) or —($C_1$-$C_4$ alkyl)-O—($C_1$-$C_4$ alkyl), wherein:
t is 0 or 1;
u is 0 or 1;
with the proviso that when u is 1, t is 1; and
$R^{241}$ is H or $C_1$-$C_2$ alkyl.

In various aspects, the present disclosure provides for compounds of Structure V:

or pharmaceutically acceptable salts thereof, wherein:
L-Ar is

Ar is with the proviso that when L-Ar is

Ar is not $L^2$ is —NHR$^{35}$ or —C(O)NHR$^{351}$, wherein R$^{351}$ is $C_1$-$C_6$ alkyl, $C_3$-$C_5$ cycloalkyl, 4- to 6-membered heterocycle, aryl or heteroaryl;
Het is a 5- to 6-membered heteroaryl;
$R^1$ is H, —CN, halogen, $C_1$-$C_4$ alkyl, —O—($C_3$-$C_5$ cycloalkyl), —O-(4- to 6-membered heterocycle), —O—($C_1$-$C_4$ alkyl) wherein when $R^1$ is not H, —CN or halogen, $R^1$ is optionally substituted with one or more halogens;

each $R^2$ is independently hydrogen, halogen or $C_1$-$C_4$ alkyl;
$R^3$ is H or F;
$R^{11}$ is H or —$CH_3$;
$R^{21}$ is H, halogen, $C_1$-$C_4$ alkyl, $C_3$-$C_5$ cycloalkyl or 4- to 6-membered heterocycle;
$R^{22}$ is H, halogen, or $C_1$-$C_2$ alkyl; and
$R^{35}$ is —C(O)$R^{351}$, —C(O)NH$R^{351}$, C(O)O$R^{351}$ or S(O)$_2$$R^{351}$ wherein $R^{351}$ is $C_1$-$C_6$ alkyl, $C_3$-$C_5$ cycloalkyl, 4- to 6-membered heterocycle, aryl or heteroaryl.

In various aspects the present disclosure provides for compounds of Structure VI:

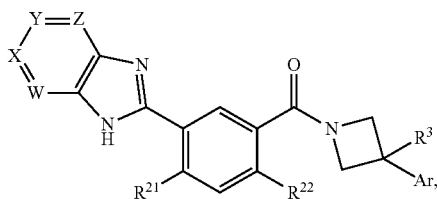

VI or pharmaceutically acceptable salts thereof, wherein:
each W, X, Y and Z is independently —N— or —$CR^{26}$— with the proviso that not more than 2 of W, X, Y and Z are —N—;
each $R^{26}$ is independently H, $C_1$-$C_4$ alkyl, —O—($C_1$-$C_4$ alkyl), —N($R^{27}$)$_2$, —S(O)$_2$—($C_1$-$C_4$ alkyl), or —C(O)—($C_1$-$C_4$ alkyl);
each $R^{27}$ is independently H or $C_1$-$C_4$ alkyl or both $R^{27}$ are $C_1$-$C_4$ alkyl and join to form a 3- to 6-membered ring together with the N to which they are attached and wherein the ring optionally includes one oxygen atom as one of the members of the ring;
Ar is

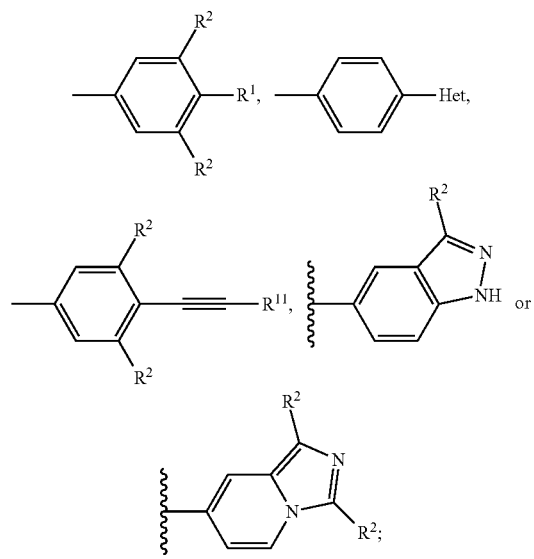

Het is a 5- to 6-membered heteroaryl;
$R^1$ is H, —CN, halogen, $C_1$-$C_4$ alkyl, —O—($C_3$-$C_5$ cycloalkyl), —O—(4- to 6-membered heterocycle), —O—($C_1$-$C_4$ alkyl) wherein when $R^1$ is not H, —CN or halogen, $R^1$ is optionally substituted with one or more halogens;

each $R^2$ is independently hydrogen, halogen or $C_1$-$C_4$ alkyl;
$R^3$ is H or F;
$R^{11}$ is H or —$CH_3$;
$R^{21}$ is H, halogen, $C_1$-$C_4$ alkyl, $C_3$-$C_5$ cycloalkyl or a 4- to 6-membered heterocycle; and
$R^{22}$ is H, halogen or $C_1$-$C_2$ alkyl.

In various aspects, the present disclosure provides pharmaceutical compositions comprising any one of the compounds of Structures I, II, III, IIIb, IIIc, IV, V and VI and a pharmaceutically acceptable carrier, excipient, or diluent.

In various aspects, the present disclosure provides methods of treating a condition characterized by disregulation of a fatty acid synthase pathway in subject, the method comprising administering to a subject in need of such treatment an effective amount of a compound of any one of the Structures I, II, III, IIIb, IIIc, IV, V and VI. In various aspects, the condition characterized by disregulation of a fatty acid synthase pathway is a viral infection or cancer. In various aspects, the viral infection is treated using a compound of any one of the Structures I, II, III, IIIb, IIIc, IV, V and VI in combination with one or more additional antiviral treatments. In various aspects, the cancer is treated using a compound of any one of the Structures I, II, III, IIIb, IIIc, IV, V and VI in combination with one or more additional cancer treatments. In various aspects, the viral infection is hepatitis C. In various aspects, the cancer is breast cancer. In various aspects, the cancer is pancreatic cancer. In various aspects, the cancer is colon cancer.

DETAILED DESCRIPTION

The present disclosure addresses the deficiencies in treating conditions characterized by disregulation of the FASN function in a subject, such as viral infection, cancer and metabolic disorders, by providing novel heterocyclic modulators of lipid synthesis.

In certain aspects, the present disclosure provides compositions and methods for treatment of viral infections. In general, the compositions and methods for treatment of viral infections are directed toward modulation of the fatty acid synthesis pathway. The fatty acid synthesis pathway is involved in the replication of viruses in the host cells. The present invention embodies methods for the treatment of viral infections that interact with the fatty acid synthesis pathway, such as hepatitis C.

In certain aspects, the present disclosure provides compositions and methods for the treatment of cancer. Fatty acid synthase is responsible for conversion of malonyl-CoA into long-chain fatty acids, which is an early reaction in fatty acid biosynthesis. Fatty acid synthase is overexpressed in many cancer cells. Without being bound by any particular theory, it is hypothesized that inhibition of fatty acid synthase expression or fatty acid synthase activity selectivity suppresses proliferation and induces cell death of cancer cells, with little toxicity towards normal cells.

Further, the present disclosure provides compounds and methods for modulating host cell targets that are targeted by viruses. Such modulation of host cell targets can include either activation or inhibition of the host cell targets. Accordingly, compounds that modulate components of the fatty acid synthesis pathway, such as the activity of a non-viral protein, e.g., a host cell protein, can be used as antiviral pharmaceutical agents.

Definitions

Chemical moieties referred to as univalent chemical moieties (e.g., alkyl, aryl, etc.) also encompass structurally permissible multivalent moieties, as understood by those skilled in the art. For example, while an "alkyl" moiety generally refers to a monovalent radical (e.g., CH₃CH₂—), in appropriate circumstances an "alkyl" moiety can also refer to a divalent radical (e.g., —CH₂CH₂—, which is equivalent to an "alkylene" group). Similarly, under circumstances where a divalent moiety is required, those skilled in the art will understand that the term "aryl" refers to the corresponding divalent arylene group.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as (A)$_a$B, wherein a is 0 or 1. In such instances, when a is 0 the moiety is B and when a is 1 the moiety is AB.

Where a substituent can vary in the number of atoms or groups of the same kind (e.g., alkyl groups can be $C_1$, $C_2$, $C_3$, etc.), the number of repeated atoms or groups can be represented by a range (e.g., $C_1$-$C_6$ alkyl) which includes each and every number in the range and any and all sub ranges. For example, $C_1$-$C_3$ alkyl includes $C_1$, $C_2$, $C_3$, $C_{1-2}$, $C_{1-3}$, and $C_{2-3}$ alkyl.

"Alkanoyl" refers to a carbonyl group with a lower alkyl group as a substituent.

"Alkylamino" refers to an amino group substituted by an alkyl group.

"Alkoxy" refers to an O-atom substituted by an alkyl group as defined herein, for example, methoxy [—OCH₃, a $C_1$alkoxy]. The term "$C_{1-6}$ alkoxy" encompasses $C_1$ alkoxy, $C_2$ alkoxy, $C_3$ alkoxy, $C_4$ alkoxy, $C_5$ alkoxy, $C_6$ alkoxy, and any sub-range thereof.

"Alkoxycarbonyl" refers to a carbonyl group with an alkoxy group as a substituent.

"Alkylcarbonyloxy" refers to the group —O—(C=O)-alkyl.

"Alkyl," "alkenyl," and "alkynyl," refer to optionally substituted, straight and branched chain aliphatic groups having from 1 to 30 carbon atoms, or preferably from 1 to 15 carbon atoms, or more preferably from 1 to 6 carbon atoms. Examples of alkyl groups include, without limitation, methyl, ethyl, propyl, isopropyl, butyl, tert-butyl, isobutyl, pentyl, hexyl, vinyl, allyl, isobutenyl, ethynyl, and propynyl. The term "heteroalkyl" as used herein contemplates an alkyl with one or more heteroatoms. The term "haloalkyl" as used herein contemplates an alkyl having one to three halogen substituents.

"Alkylene" refers to an optionally substituted divalent radical which is a branched or unbranched hydrocarbon fragment containing the specified number of carbon atoms, and having two points of attachment. An example is propylene [—CH₂CH₂CH₂—, a $C_3$alkylene].

"Amino" refers to the group —NH₂.

"Aryl" refers to optionally substituted aromatic groups which have at least one ring having a conjugated pi electron system and includes carbocyclic aryl, and biaryl groups, all of which can be optionally substituted. Phenyl and naphthyl groups are preferred carbocyclic aryl groups.

"Aralkyl" or "arylalkyl" refer to alkyl-substituted aryl groups. Examples of aralkyl groups include butylphenyl, propylphenyl, ethylphenyl, methylphenyl, 3,5-dimethylphenyl, tert-butylphenyl.

"Carbamoyl" as used herein contemplates a group of the structure

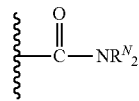

where in $R^N$ is selected from the group consisting of hydrogen, —OH, $C_1$ to $C_{12}$ alkyl, $C_1$ to $C_{12}$ heteroalkyl, alkenyl, alkynyl, cycloalkyl, heterocycle, aryl, heteroaryl, aralkyl, alkoxy, alkoxycarbonyl, alkanoyl, carbamoyl, sulfonyl, sulfonate and sulfonamide.

"Carbonyl" refers to a group of the structure

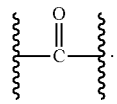

"Cycloalkyl" refers to an optionally substituted ring, which can be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Heterocycle" refers to an optionally substituted 5- to 7-membered cycloalkyl ring system containing 1, 2 or 3 heteroatoms, which can be the same or different, selected from N, O or S, and optionally containing one double bond. "Heterocycle" also refers to an optionally substituted 4- to 8-membered cycloalkyl ring system containing 1, 2 or 3 heteroatoms, which can be the same or different, selected from N, O or S, and optionally containing one double bond.

"Halogen" refers to a chloro, bromo, fluoro or iodo atom radical. The term "halogen" also contemplates terms "halo" or "halide."

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present disclosure.

"Heteroaryl" refers to optionally substituted aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include thienyl, pyrryl, furyl, pyridyl, pyrimidyl, pyrazinyl, pyrazolyl, oxazolyl, isoxazolyl, imidazolyl, thiazolyl, pyranyl, tetrazolyl, pyrrolyl, pyrrolinyl, pyridazinyl, triazolyl, indolyl, isoindolyl, indolizinyl, benzimidazolyl, quinolyl, isoquinolyl, indazolyl, benzotriazolyl, tetrazolopyridazinyl, oxadiazolyl, benzoxazolyl, benzoxadiazolyl, thiadiazolyl, benzothiazolyl, benzothiadiazolyl, and the like.

An "optionally substituted" moiety can be substituted with from one to four, or preferably from one to three, or more preferably one or two non-hydrogen substituents. Unless otherwise specified, when the substituent is on a carbon, it is selected from the group consisting of —OH, —CN, —NO₂, halogen, $C_1$-$C_{12}$ alkyl, $C_1$-$C_{12}$ heteroalkyl, cycloalkyl, heterocycle, aryl, heteroaryl, aralkyl, alkoxy, alkoxycarbonyl, alkanoyl, carbamoyl, sulfonyl, sulfonate, sulfonamide and amino, none of which are further substituted. Unless otherwise specified, when the substituent is on a carbon, it may also be selected from the group consisting of oxo. Unless otherwise specified, when the substituent is on a carbon, it may also be selected from the group consisting of alkylcarbonyloxy, which is not further substituted. Unless otherwise specified, when the substituent is on a carbon, it may also be selected from the group consisting of alkylamino, which is not further substituted. Unless otherwise specified, when the substituent is on a carbon, it may also be selected from the group consisting of $C_1$-$C_{12}$ alkenyl and $C_1$-$C_{12}$ alkynyl, neither of which are further substituted. Unless otherwise specified, when the substituent is on a nitrogen, it is selected from the group consisting of $C_1$-$C_{12}$ alkyl, $C_1$-$C_{12}$ heteroalkyl, cycloalkyl, heterocycle, aryl, heteroaryl, aralkyl, alkoxy, alkoxycarbonyl, alkanoyl, carbamoyl, sulfonyl, sulfonate and sulfonamide, none of which are further substituted. Unless otherwise specified, when the substituent is on a nitrogen, it may also be selected from the group consisting of $C_1$-$C_{12}$ alkenyl and $C_1$-$C_{12}$ alkynyl, neither of which are further substituted.

"Oxo" refers to the =O substituent.

The term "sulfonamide" as used herein contemplates a group having the structure

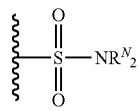

wherein $R^N$ is selected from the group consisting of hydrogen, —OH, $C_1$-$C_{12}$ alkyl, $C_1$-$C_{12}$ heteroalkyl, alkenyl, alkynyl, cycloalkyl, heterocycle, aryl, heteroaryl, aralkyl, alkoxy, alkoxycarbonyl, alkanoyl, carbamoyl, sulfonyl, sulfonate and sulfonamide.

The term "sulfonate" as used herein contemplates a group having the structure

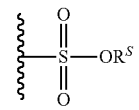

wherein $R^S$ is selected from the group consisting of hydrogen, $C_1$-$C_{10}$ alkyl, $C_2$-$C_{10}$ alkenyl, $C_2$-$C_{10}$ alkynyl, $C_1$-$C_{10}$ alkanoyl, or $C_1$-$C_{10}$ alkoxycarbonyl.

"Sulfonyl" as used herein alone or as part of another group, refers to an $SO_2$ group. The $SO_2$ moiety is optionally substituted. In particular, "sulfonyl" as used herein contemplates a group having the structure

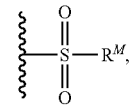

wherein $R^M$ is selected from the group consisting of hydrogen, $C_1$-$C_{12}$ alkyl, $C_1$-$C_{12}$ heteroalkyl, alkenyl, alkynyl, cycloalkyl, heterocycle, aryl, heteroaryl, aralkyl and alkoxy.

Compounds of the present disclosure can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present disclosure contemplates various stereoisomers and mixtures thereof and are specifically included within the scope of the present disclosure. Stereoisomers include enantiomers, diastereomers, and mixtures of enantiomers or diastereomers. Individual stereoisomers of compounds of the present disclosure can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Also, moieties disclosed herein which exist in multiple tautomeric forms include all such forms encompassed by a given tautomeric structure.

Individual atoms in the disclosed compounds may be any isotope of that element. For example hydrogen may be in the form of deuterium.

"Pharmaceutically acceptable" means approved or approvable by a regulatory agency of the Federal or state government or listed in the U.S. Pharmacopoeia or other generally recognized pharmacopoeia for use in animals, and more particularly in humans. It can be material which is not biologically or otherwise undesirable, i.e., the material can be administered to an individual without causing any undesirable biological effects or interacting in a deleterious manner with any of the components of the composition in which it is contained.

The term "pharmaceutically acceptable salt" of a compound means a salt that is pharmaceutically acceptable and that possesses the desired pharmacological activity of the parent compound. Such salts include, for example, acid addition salts and base addition salts.

"Acid addition salts" according to the present disclosure, are formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

"Base addition salts" according to the present disclosure are formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature can cause a single crystal form to dominate.

The term "treating" includes the administration of the compounds or agents of the present invention to a subject to prevent or delay, to alleviate, or to arrest or inhibit development of the symptoms or conditions associated with fatty acid synthase-associated disorders.

A "therapeutically effective amount" or "pharmaceutically effective amount" means the amount that, when administered to a subject, produces effects for which it is administered. For example, a "therapeutically effective amount," when administered to a subject to inhibit fatty acid synthase activity, is sufficient to inhibit fatty acid synthase activity. A "therapeutically effective amount," when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary aspect of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that are associated with the targeted or suspected disease or condition. These and other routine methods allow the clinician to select patients in need of therapy using the methods and formulations of the present invention.

Chemical names for the compounds of the present disclosure were generated using ChemDraw Ultra version 12.0 (CambridgeSoft Corp., Cambridge Mass.).

FASN Pathway Modulators

One aspect of the present disclosure includes a method of inhibiting viral infection or treating cancer by contacting a cell with an agent that modulates the fatty acid synthesis pathway. This method of inhibiting viral infection or treating cancer can be performed in vitro by contacting virally infected/cancerous cells with an agent that modulates the fatty acid synthesis pathway, or in vivo by administering an agent that modulates the fatty acid synthesis pathway to a subject infected with a virus/having cancer. In one aspect, an agent can be an inhibitor of the fatty acid synthesis pathway.

Examples of inhibitors of the fatty acid synthesis pathway that can be used in the methods and compositions of the present disclosure are described below.

In various aspects, the present disclosure provides for compounds of Structure I:

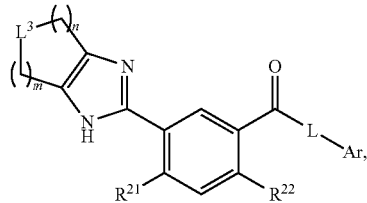

or pharmaceutically acceptable salts thereof, wherein:

$L^3$ is —$CH_2$—, —$CHR^{50}$—, —O—, —$NR^{50}$—, —$NC(O)R^{50}$— or —$NC(O)OR^{50}$—, wherein $R^{50}$ is $C_1$-$C_6$ alkyl, $C_3$-$C_5$ cycloalkyl, or 4- to 6-membered heterocycle;

n is 1, 2, or 3;

m is 1 or 2 with the proviso that n+m≥3:

L-Ar is

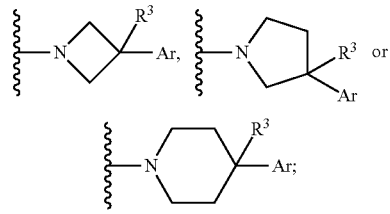

Ar is

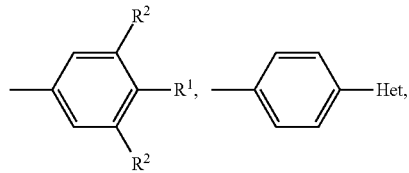

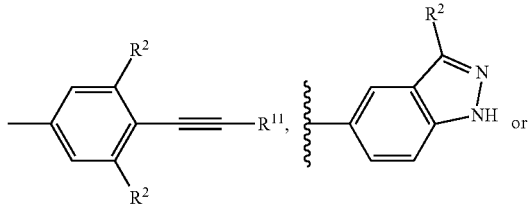

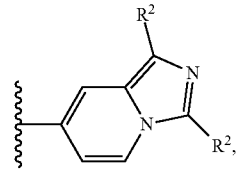

with the proviso that when L-Ar is

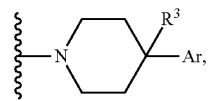

Ar is not

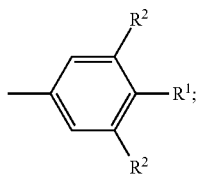

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —CH$_3$;

$R^{21}$ is H, halogen, $C_1$-$C_4$ alkyl, $C_3$-$C_5$ cycloalkyl or a 4- to 6-membered heterocycle; and $R^{22}$ is H, halogen, or $C_1$-$C_2$ alkyl.

As noted above, each of the $C_1$-$C_2$ alkyl, $C_1$-$C_4$ alkyl, $C_1$-$C_6$ alkyl, $C_3$-$C_5$ cycloalkyl, 4- to 6-membered heterocycle and 5- to 6-membered heteroaryl moieties may be optionally substituted. Accordingly, the present disclosure provides for compounds of Structure I wherein:

$L^3$ is —CH$_2$—, CHR$^{50}$, —O—, —NR$^{50}$—, —NC(O)R$^{50}$— or —NC(O)OR$^{50}$—, wherein R$^{50}$ is optionally substituted $C_1$-$C_6$ alkyl, optionally substituted $C_3$-$C_5$ cycloalkyl or optionally substituted 4- to 6-membered heterocycle;

n is 1, 2 or 3;

m is 1 or 2 with the proviso that n+m≥3;

L-Ar is

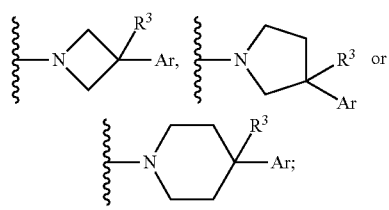

Ar is

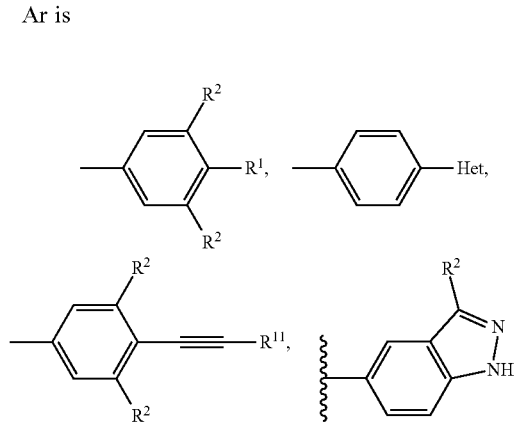

or

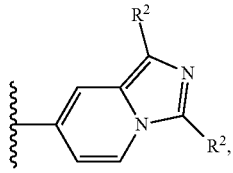

with the proviso that when L-Ar is

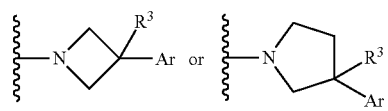

Ar is not

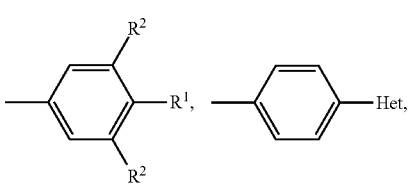

Het is a optionally substituted 5- to 6-membered heteroaryl;

$R^1$ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when $R^1$ is not H, —CN or halogen, $R^1$ is optionally substituted with one or more halogens;

each $R^2$ is independently hydrogen, halogen or optionally substituted $C_1$-$C_4$ alkyl;

$R^3$ is H or F;

$R^{11}$ is H or —CH$_3$;

$R^{21}$ is H, halogen, optionally substituted $C_1$-$C_4$ alkyl, optionally substituted $C_3$-$C_5$ cycloalkyl or an optionally substituted 4- to 6-membered heterocycle; and $R^{22}$ is H, halogen or optionally substituted $C_1$-$C_2$ alkyl.

In some embodiments, the present disclosure provides for compounds of Structure I wherein L-Ar is and Ar is

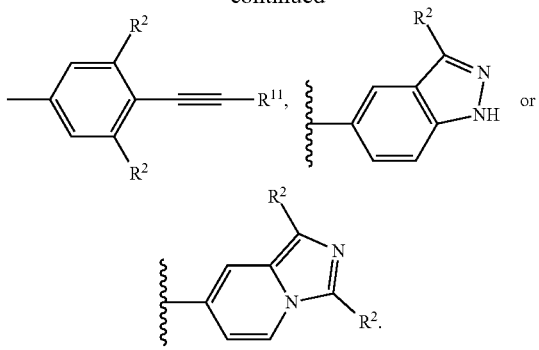

In some embodiments, the present disclosure provides for compounds of Structure I wherein L-Ar is

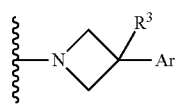

and Ar is

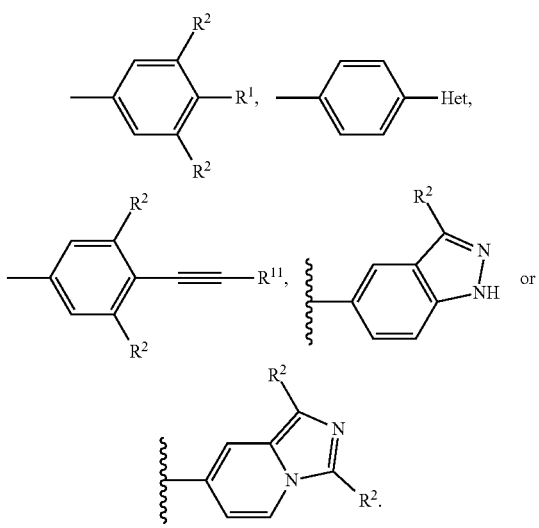

In some embodiments, the present disclosure provides for compounds of Structure I wherein $R^1$ is H, —CN, —$C_1$-$C_4$ alkyl, —O—($C_3$-$C_5$ cycloalkyl), —O-(4- to 6-membered heterocycle) or —O—($C_1$-$C_4$ alkyl) wherein when $R^1$ is not H or —CN, $R^1$ is optionally substituted with one or more halogens.

In some embodiments, the present disclosure provides for compounds of Structure I wherein $R^1$ is halogen, —CN or $C_1$-$C_2$ haloalkyl.

In some embodiments, the present disclosure provides for compounds of Structure I wherein $R^1$ is —CN or $C_1$-$C_2$ haloalkyl.

In some embodiments, the present disclosure provides for compounds of Structure I wherein $R^1$ is —CN.

In some embodiments, the present disclosure provides for compounds of Structure I wherein $R^1$ is —Cl.

In some embodiments, the present disclosure provides for compounds of Structure I wherein $R^2$ is H.

In some embodiments, the present disclosure provides for compounds of Structure I wherein $R^{21}$ is halogen, $C_1$-$C_4$ alkyl, $C_3$-$C_5$ cycloalkyl or 4- to 6-membered heterocycle.

In some embodiments, the present disclosure provides for compounds of Structure I wherein $R^{21}$ is $C_1$-$C_2$ alkyl or $C_3$-$C_5$ cycloalkyl.

In some embodiments, the present disclosure provides for compounds of Structure I wherein $R^{21}$ is $C_3$-$C_5$ cycloalkyl.

In some embodiments, the present disclosure provides for compounds of Structure I wherein $R^{22}$ is H or $C_1$-$C_2$ alkyl.

In some embodiments, the present disclosure provides for compounds of Structure I wherein $R^{22}$ is H.

In some embodiments, the present disclosure provides for compounds of Structure I wherein $R^{22}$ is $C_1$-$C_2$ alkyl.

In some embodiments, the present disclosure provides for compounds of Structure I wherein $R^{22}$ is —$CH_3$.

In some embodiments, the present disclosure provides for compounds of Structure I wherein $L^3$ is —N($CH_3$)—.

In some embodiments, the present disclosure provides for compounds of Structure I wherein n is 2 and m is 2.

In some embodiments, the present disclosure provides for compounds of Structure I wherein n is 1 or 2.

In some embodiments, the present disclosure provides for compounds of Structure I wherein n is 1 and m is 2.

In some embodiments, the present disclosure provides for compounds of Structure I wherein $R^{21}$ is $C_1$-$C_2$ alkyl or $C_3$-$C_5$ cycloalkyl and $R^{22}$ is $C_1$-$C_2$ alkyl.

In some embodiments, the present disclosure provides for compounds of Structure I wherein $R^{21}$ is $C_1$-$C_2$ alkyl or $C_3$-$C_5$ cycloalkyl and $R^{22}$ is H or $C_1$-$C_2$ alkyl.

In some embodiments, the present disclosure provides for compounds of Structure I wherein $R^{21}$ is $C_3$-$C_5$ cycloalkyl and $R^{22}$ is H or $C_1$-$C_2$ alkyl.

In some embodiments, the present disclosure provides for compounds of Structure I wherein $R^{21}$ is $C_3$-$C_5$ cycloalkyl and $R^{22}$ is H or —$CH_3$.

In various aspects, the present disclosure provides for compounds of Structure II:

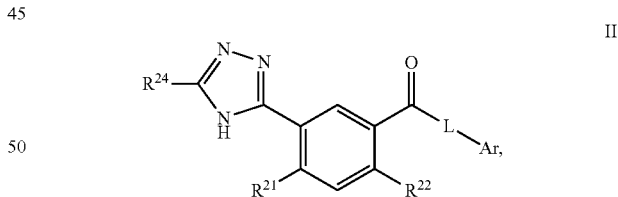

or pharmaceutically acceptable salts thereof, wherein:

L-Ar is

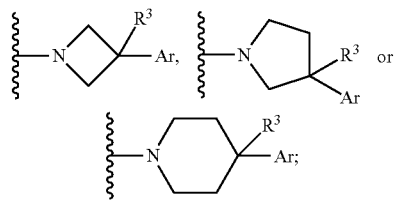

Ar is

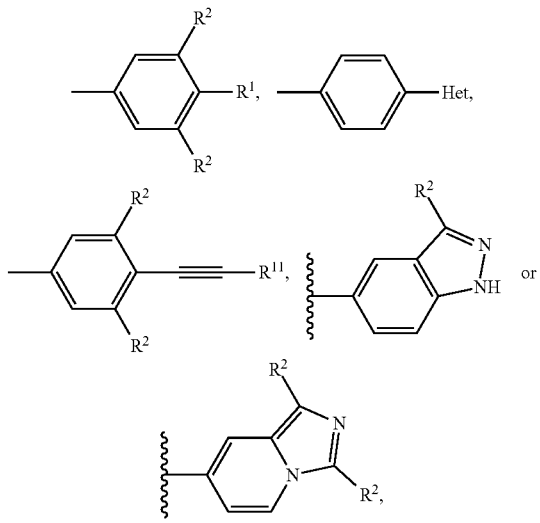

with the proviso that when L-Ar is

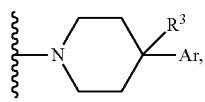

Ar is not

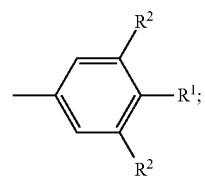

Het is a 5- to 6-membered heteroaryl;
$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;
each $R^2$ is independently hydrogen, halogen or $C_1$-$C_4$ alkyl;
$R^3$ is H or F;
$R^{11}$ is H or —CH$_3$;
$R^{21}$ is H, halogen, $C_1$-$C_4$ alkyl, $C_3$-$C_5$ cycloalkyl or 4- to 6-membered heterocycle;
$R^{22}$ is H, halogen, or $C_1$-$C_2$ alkyl; and
$R^{24}$ is H, $C_1$-$C_4$ alkyl, —($C_1$-$C_4$ alkyl)-OH, —($C_1$-$C_4$ alkyl)$_t$-N($R^{241}$)$_2$, —($C_1$-$C_4$ alkyl)$_t$-O$_t$—($C_3$-$C_5$ cycloalkyl), —($C_1$-$C_4$ alkyl)$_t$-O$_t$-(4- to 6-membered heterocycle) or —($C_1$-$C_4$ alkyl)$_t$-O—($C_1$-$C_4$ alkyl), wherein:
each t is independently 0 or 1; and
each $R^{241}$ is independently H or $C_1$-$C_2$ alkyl.

As noted above, each of the $C_1$-$C_2$ alkyl, $C_1$-$C_4$ alkyl, $C_3$-$C_5$ cycloalkyl, 4- to 6-membered heterocycle and 5- to 6-membered heteroaryl moieties may be optionally substituted. Accordingly, the present disclosure provides for compounds of Structure II wherein:

L-Ar is

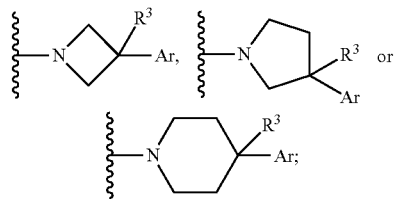

Ar is

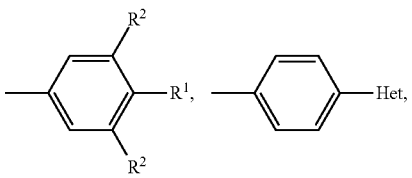

with the proviso that when L-Ar is

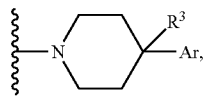

Ar is not

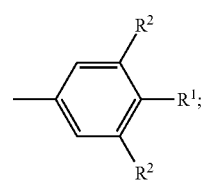

Het is an optionally substituted 5- to 6-membered heteroaryl;
$R^1$ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when $R^1$ is not H, —CN or halogen, $R^1$ is optionally substituted with one or more halogens;
each $R^2$ is independently hydrogen, halogen or optionally substituted $C_1$-$C_4$ alkyl;
$R^3$ is H or F;
$R^{11}$ is H or —CH$_3$;

$R^{21}$ is H, halogen, optionally substituted $C_1$-$C_4$ alkyl, optionally substituted $C_3$-$C_5$ cycloalkyl or optionally substituted 4- to 6-membered heterocycle;

$R^{22}$ is H, halogen or optionally substituted $C_1$-$C_2$ alkyl; and $R^{24}$ is H, optionally substituted $C_1$-$C_4$ alkyl, -(optionally substituted $C_1$-$C_4$ alkyl)-OH, -(optionally substituted $C_1$-$C_4$ alkyl)$_t$-N($R^{241}$)$_2$, -(optionally substituted $C_1$-$C_4$ alkyl)$_t$-O$_t$-(optionally substituted $C_3$-$C_5$ cycloalkyl), -(optionally substituted $C_1$-$C_4$ alkyl)$_t$-O$_t$-(optionally substituted 4- to 6-membered heterocycle) or -(optionally substituted $C_1$-$C_4$ alkyl)$_t$-O-(optionally substituted $C_1$-$C_4$ alkyl), wherein:

t is 0 or 1; and $R^{241}$ is H or optionally substituted $C_1$-$C_2$ alkyl.

In some embodiments, the present disclosure provides for compounds of Structure II wherein L-Ar is

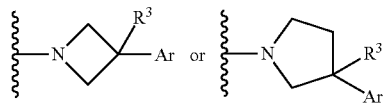

and Ar is

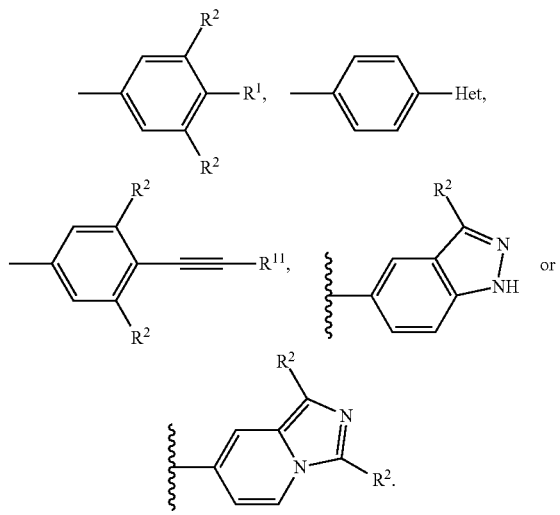

In some embodiments, the present disclosure provides for compounds of Structure II wherein L-Ar is

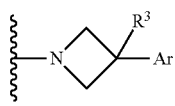

and Ar is

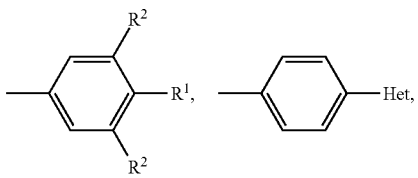

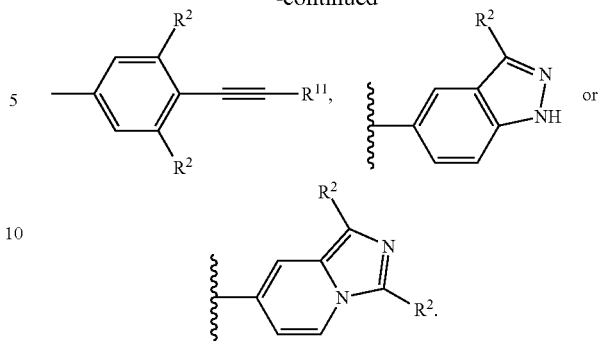

In some embodiments, the present disclosure provides for compounds of Structure II wherein Ar is

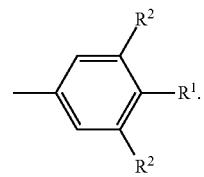

In some embodiments, the present disclosure provides for compounds of Structure II wherein $R^1$ is halogen, —CN or $C_1$-$C_2$ haloalkyl.

In some embodiments, the present disclosure provides for compounds of Structure II wherein $R^1$ is —CN.

In some embodiments, the present disclosure provides for compounds of Structure II wherein $R^2$ is H.

In some embodiments, the present disclosure provides for compounds of Structure II wherein $R^{21}$ is halogen, $C_1$-$C_4$ alkyl, $C_3$-$C_5$ cycloalkyl or 4- to 6-membered heterocycle.

In some embodiments, the present disclosure provides for compounds of Structure II wherein $R^{21}$ is H, $C_1$-$C_4$ alkyl, $C_3$-$C_5$ cycloalkyl or 4- to 6-membered heterocycle.

In some embodiments, the present disclosure provides for compounds of Structure II wherein $R^{21}$ is $C_1$-$C_2$ alkyl or $C_3$-$C_5$ cycloalkyl.

In some embodiments, the present disclosure provides for compounds of Structure II wherein $R^{21}$ is $C_1$-$C_2$ alkyl.

In some embodiments, the present disclosure provides for compounds of Structure II wherein $R^{21}$ is $C_3$-$C_5$ cycloalkyl.

In some embodiments, the present disclosure provides for compounds of Structure II wherein $R^{22}$ is H or $C_1$-$C_2$ alkyl.

In some embodiments, the present disclosure provides for compounds of Structure II wherein $R^{22}$ is H.

In some embodiments, the present disclosure provides for compounds of Structure II wherein $R^{22}$ is $C_1$-$C_2$ alkyl.

In some embodiments, the present disclosure provides for compounds of Structure II wherein $R^{22}$ is —CH$_3$.

In some embodiments, the present disclosure provides for compounds of Structure II wherein $R^{24}$ is $C_1$-$C_4$ alkyl or —($C_1$-$C_4$ alkyl)$_t$-O—($C_1$-$C_4$ alkyl).

In some embodiments, the present disclosure provides for compounds of Structure II wherein $R^{24}$ is —($C_1$-$C_2$ alkyl)$_t$-O—($C_1$-$C_2$ alkyl).

In some embodiments, the present disclosure provides for compounds of Structure II wherein $R^{24}$ is $C_1$-$C_4$ alkyl or —($C_1$-$C_4$ alkyl)$_t$-O—($C_1$-$C_4$ alkyl) wherein t is 0 or 1.

In some embodiments, the present disclosure provides for compounds of Structure II wherein $R^{21}$ is $C_1$-$C_2$ alkyl or $C_3$-$C_5$ cycloalkyl and $R^{22}$ is H or $C_1$-$C_2$ alkyl.

In some embodiments, the present disclosure provides for compounds of Structure II wherein $R^{21}$ is $C_1$-$C_2$ alkyl or $C_3$-$C_5$ cycloalkyl and $R^{22}$ is $C_1$-$C_2$ alkyl.

In some embodiments, the present disclosure provides for compounds of Structure II wherein $R^{21}$ is $C_1$-$C_2$ alkyl or $C_3$-$C_5$ cycloalkyl and $R^{22}$ is —$CH_3$.

In some embodiments, the present disclosure provides for compounds of Structure II wherein $R^{21}$ is $C_1$-$C_2$ alkyl or $C_3$-$C_5$ cycloalkyl and $R^{22}$ is H.

In some embodiments, the present disclosure provides for compounds of Structure II wherein $R^{21}$ is $C_3$-$C_5$ cycloalkyl and $R^{22}$ is H or $C_1$-$C_2$ alkyl.

In some embodiments, the present disclosure provides for compounds of Structure II wherein $R^{21}$ is $C_3$-$C_5$ cycloalkyl and $R^{22}$ is H or —$CH_3$.

In some embodiments, the present disclosure provides for compounds of Structure II wherein $R^{21}$ is $C_3$-$C_5$ cycloalkyl and $R^{22}$ is $C_1$-$C_2$ alkyl.

In some embodiments, the present disclosure provides for compounds of Structure II wherein $R^{21}$ is $C_3$-$C_5$ cycloalkyl and $R^{22}$ is —$CH_3$.

In some embodiments, the present disclosure provides for compounds of Structure II wherein $R^{21}$ is $C_3$-$C_5$ cycloalkyl and $R^{22}$ is H.

In some embodiments, the present disclosure provides for compounds of Structure II wherein $R^{24}$ is —($C_1$-$C_2$ alkyl)$_t$-O—($C_1$-$C_2$ alkyl) and wherein t is 0 or 1.

In some embodiments, the present disclosure provides for compounds of Structure II wherein $R^1$ is —CN and $R^2$ is H.

In various aspects, the present disclosure provides for compounds of Structure III:

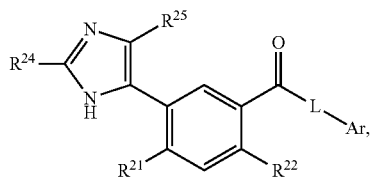

III or pharmaceutically acceptable salts thereof, wherein:

L-Ar is

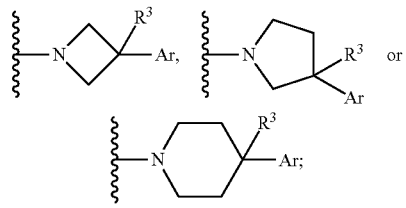

Ar is

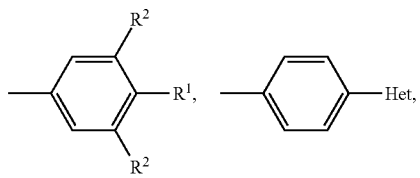

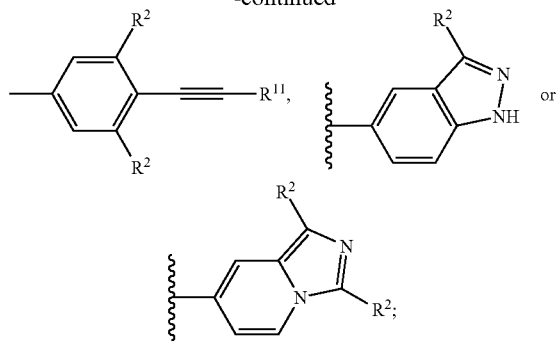

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl;

$R^{24}$ is H, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_6$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl), wherein:

t is 0 or 1;

u is 0 or 1;

with the proviso that when u is 1, t is 1; and each $R^{241}$ is independently H or $C_1$-$C_2$ alkyl; and $R^{25}$ is halogen, —CN, —($C_1$-$C_4$ alkyl)-CN, $C_1$-$C_2$ alkyl or cyclopropyl.

As noted above, each of the $C_1$-$C_2$ alkyl (i.e., methyl and ethyl), cyclopropyl, $C_1$-$C_2$ alkyl, $C_1$-$C_4$ alkyl, $C_3$-$C_5$ cycloalkyl, $C_3$-$C_6$ cycloalkyl, 4- to 6-membered heterocycle and 5- to 6-membered heteroaryl moieties may be optionally substituted. Accordingly, the present disclosure provides for compounds of Structure III wherein:

L-Ar is

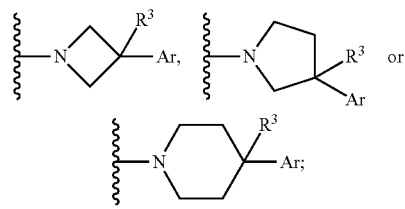

Ar is

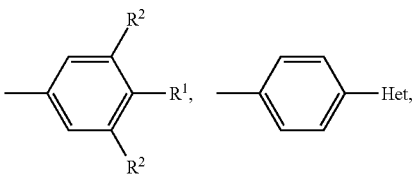

-continued

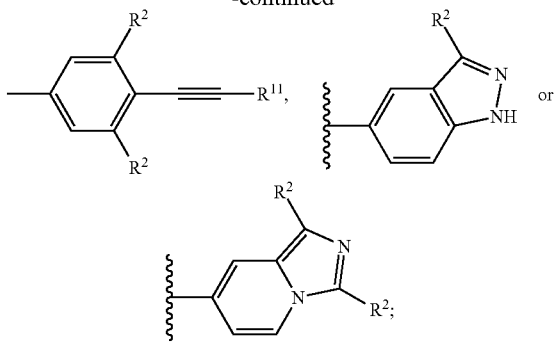

Het is an optionally substituted 5- to 6-membered heteroaryl;

$R^1$ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when $R^1$ is not H, —CN or halogen, $R^1$ is optionally substituted with one or more halogens;

each $R^2$ is independently hydrogen, halogen or optionally substituted $C_1$-$C_4$ alkyl;

$R^3$ is H or F;

$R^{11}$ is H or —CH$_3$;

$R^{21}$ is H, halogen, optionally substituted $C_1$-$C_4$ alkyl, optionally substituted $C_3$-$C_5$ cycloalkyl or optionally substituted 4- to 6-membered heterocycle;

$R^{22}$ is H, halogen or optionally substituted $C_1$-$C_2$ alkyl;

$R^{24}$ is H, —CN, -(optionally substituted $C_1$-$C_4$ alkyl)-CN, optionally substituted $C_1$-$C_4$ alkyl, -(optionally substituted $C_1$-$C_4$ alkyl)-OH, -(optionally substituted $C_1$-$C_4$ alkyl)-N($R^{241}$)$_2$, -(optionally substituted $C_1$-$C_4$ alkyl)$_t$-O$_u$-(optionally substituted $C_3$-$C_6$ cycloalkyl), -(optionally substituted $C_1$-$C_4$ alkyl)$_t$-O$_u$-(optionally substituted 4- to 6-membered heterocycle) or -(optionally substituted $C_1$-$C_4$ alkyl)-O-(optionally substituted $C_1$-$C_4$ alkyl), wherein:

t is 0 or 1;
u is 0 or 1;
with the proviso that when u is 1, t is 1; and
$R^{241}$ is H or optionally substituted $C_1$-$C_2$ alkyl; and $R^{25}$ is halogen, —CN, -(optionally substituted $C_1$-$C_4$ alkyl)-CN, optionally substituted methyl, optionally substituted ethyl or optionally substituted cyclopropyl.

In some embodiments, the present disclosure provides for compounds of Structure III wherein when L-Ar is

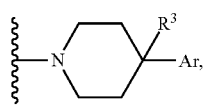

Ar is not

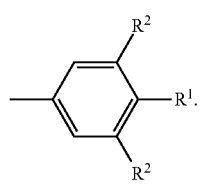

In some embodiments, the present disclosure provides for compounds of Structure III wherein L-Ar is

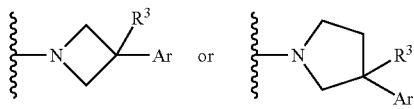

and Ar is

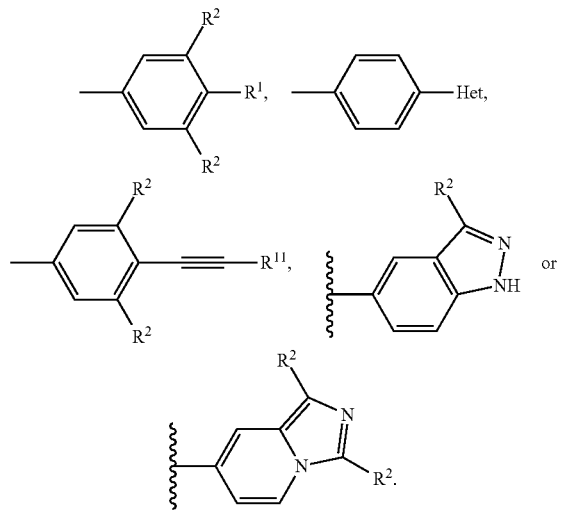

In some embodiments, the present disclosure provides for compounds of Structure III wherein L-Ar is

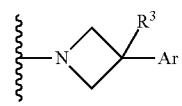

and Ar is

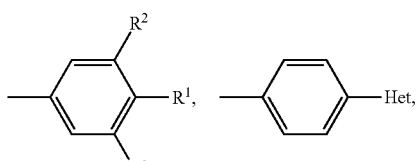

In some embodiments, the present disclosure provides for compounds of Structure III wherein Ar is

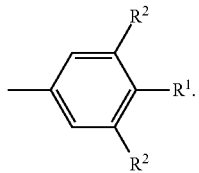

In some embodiments, the present disclosure provides for compounds of Structure III wherein $R^1$ is halogen, —CN or $C_1$-$C_2$ haloalkyl.

In some embodiments, the present disclosure provides for compounds of Structure III wherein $R^1$ is —CN.

In some embodiments, the present disclosure provides for compounds of Structure III wherein $R^2$ is H.

In some embodiments, the present disclosure provides for compounds of Structure III wherein $R^{21}$ is halogen, $C_1$-$C_4$ alkyl or $C_3$-$C_5$ cycloalkyl.

In some embodiments, the present disclosure provides for compounds of Structure III wherein $R^{21}$ is $C_1$-$C_4$ alkyl or $C_3$-$C_5$ cycloalkyl.

In some embodiments, the present disclosure provides for compounds of Structure III wherein $R^{21}$ is $C_1$-$C_2$ alkyl or $C_3$-$C_5$ cycloalkyl.

In some embodiments, the present disclosure provides for compounds of Structure III wherein $R^{21}$ is $C_1$-$C_2$ alkyl.

In some embodiments, the present disclosure provides for compounds of Structure III wherein $R^{21}$ is —$CH_3$.

In some embodiments, the present disclosure provides for compounds of Structure III wherein $R^{22}$ is H or $C_1$-$C_2$ alkyl.

In some embodiments, the present disclosure provides for compounds of Structure III wherein $R^{22}$ is H or —$CH_3$.

In some embodiments, the present disclosure provides for compounds of Structure III wherein $R^{22}$ is —$CH_3$.

In some embodiments, the present disclosure provides for compounds of Structure III wherein $R^{24}$ is H, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_6$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl).

In some embodiments, the present disclosure provides for compounds of Structure III wherein $R^{24}$ is H, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_6$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl).

In some embodiments, the present disclosure provides for compounds of Structure III wherein $R^{24}$ is $C_1$-$C_4$ alkyl or —($C_1$-$C_4$ alkyl)-O—($C_1$-$C_4$ alkyl).

In some embodiments, the present disclosure provides for compounds of Structure III wherein $R^{24}$ is —($C_1$-$C_2$ alkyl)-O—($C_1$-$C_2$ alkyl).

In some embodiments, the present disclosure provides for compounds of Structure III wherein $R^{24}$ is —$CH_2$—O—$CH_3$.

In some embodiments, the present disclosure provides for compounds of Structure III wherein $R^{24}$ is $C_1$-$C_2$ alkyl.

In some embodiments, the present disclosure provides for compounds of Structure III wherein $R^{24}$ is —$CH_3$.

In some embodiments, the present disclosure provides for compounds of Structure III wherein $R^{24}$ is $C_3$-$C_6$ cycloalkyl.

In some embodiments, the present disclosure provides for compounds of Structure III wherein $R^{24}$ is $C_3$-$C_5$ cycloalkyl.

In some embodiments, the present disclosure provides for compounds of Structure III wherein $R^{24}$ is —CN or —($C_1$-$C_2$ alkyl)-CN.

In some embodiments, the present disclosure provides for compounds of Structure III wherein $R^{24}$ is —CN.

In some embodiments, the present disclosure provides for compounds of Structure III wherein $R^{24}$ is —($C_1$-$C_2$ alkyl)-CN.

In some embodiments, the present disclosure provides for compounds of Structure III wherein $R^{24}$ is H, —$CH_3$, —$CH_2OH$, —$CH_2OCH_3$, —($CH_2$)$_2$OH, —($CH_2$)$_2$OCH$_3$ or —($CH_2$)$_2$N($CH_3$)$_2$.

In some embodiments, the present disclosure provides for compounds of Structure III wherein $R^{24}$ is methyl, isopropyl, cyclopropyl, —CN, or —($C_1$-$C_2$ alkyl)-CN.

In some embodiments, the present disclosure provides for compounds of Structure III wherein $R^{24}$ is substituted with one or more substituents selected from $C_1$-$C_2$ alkyl, oxo, —CN, halogen, alkanoyl, alkoxycarbonyl, —OH and $C_1$-$C_2$ alkoxy.

In some embodiments, the present disclosure provides for compounds of Structure III wherein $R^{24}$ is substituted with one or more substituents selected from methyl, —F, methoxy, —C(=O)CH$_3$ and —C(=O)—OCH$_3$.

In some embodiments, the present disclosure provides for compounds of Structure III wherein $R^{24}$ is substituted with two substituents that are the same or different.

In some embodiments, the present disclosure provides for compounds of Structure III wherein $R^{24}$ is substituted with three substituents that are the same or different.

In some embodiments, the present disclosure provides for compounds of Structure III wherein $R^{25}$ is halogen, —CN, $C_1$-$C_2$ alkyl or cyclopropyl.

In some embodiments, the present disclosure provides for compounds of Structure III wherein $R^{25}$ is halogen, $C_1$-$C_2$ alkyl or cyclopropyl.

In some embodiments, the present disclosure provides for compounds of Structure III wherein $R^{25}$ is —CN, —Cl or —$CH_3$.

In some embodiments, the present disclosure provides for compounds of Structure III wherein $R^{25}$ is —Cl.

In some embodiments, the present disclosure provides for compounds of Structure III wherein $R^{25}$ is —$CH_3$.

In some embodiments, the present disclosure provides for compounds of Structure III wherein $R^{25}$ is substituted with one or more substituents selected from —OH, halogen, $C_1$-$C_2$ alkyl and alkylcarbonyloxy.

In some embodiments, the present disclosure provides for compounds of Structure III wherein $R^{25}$ is substituted with one or more substituents selected from —F, methyl and —O—C(=O)—CH$_3$.

In some embodiments, the present disclosure provides for compounds of Structure III wherein $R^{25}$ is substituted with two substituents that are the same or different.

In some embodiments, the present disclosure provides for compounds of Structure III wherein $R^{25}$ is substituted with three substituents that are the same or different.

In some embodiments, the present disclosure provides for compounds of Structure III wherein $R^{24}$ is $C_1$-$C_4$ alkyl, —($C_1$-$C_4$ alkyl)-CN or —($C_3$-$C_6$ cycloalkyl).

In some embodiments, the present disclosure provides for compounds of Structure III wherein $R^{24}$ is —CN, —($C_1$-$C_2$ alkyl)-CN, —($C_3$-$C_6$ cycloalkyl) or methyl.

In some embodiments, the present disclosure provides for compounds of Structure III wherein $R^{25}$ is halogen, methyl, ethyl or cyclopropyl.

In some embodiments, the present disclosure provides for compounds of Structure III wherein $R^{25}$ is halogen, —CN, methyl, ethyl or cyclopropyl.

In some embodiments, the present disclosure provides for compounds of Structure III wherein $R^{21}$ is $C_1$-$C_2$ alkyl or $C_3$-$C_6$ cycloalkyl and $R^{22}$ is H or —$CH_3$.

In some embodiments, the present disclosure provides for compounds of Structure III wherein $R^{21}$ is $C_1$-$C_2$ alkyl or $C_3$-$C_6$ cycloalkyl, $R^{22}$ is H or —$CH_3$, $R^{24}$ is —$CH_2$—O—$CH_3$ and $R^{25}$ is —$CH_3$.

In some embodiments, the present disclosure provides for compounds of Structure III wherein $R^{21}$ is —$CH_3$ and $R^{22}$ is H.

In some embodiments, the present disclosure provides for compounds of Structure III wherein $R^1$ is —CN and $R^2$ is H In some embodiments, the present disclosure provides for compounds of Structure III wherein $R^{21}$ is $C_1$-$C_2$ alkyl or $C_3$-$C_6$ cycloalkyl and $R^{22}$ is H or $C_1$-$C_2$ alkyl.

In some embodiments, the present disclosure provides for compounds of Structure III wherein $R^{21}$ is $C_1$-$C_2$ alkyl or $C_3$-$C_6$ cycloalkyl, $R^{22}$ is H or $C_1$-$C_2$ alkyl, $R^{24}$ is —$CH_2$—O—$CH_3$ and $R^{25}$ is —$CH_3$.

In some embodiments, the present disclosure provides for compounds of Structure III wherein $R^{21}$ is $C_1$-$C_2$ alkyl and $R^{22}$ is H.

In various aspects, the present disclosure provides for compounds of Structure IIIb:

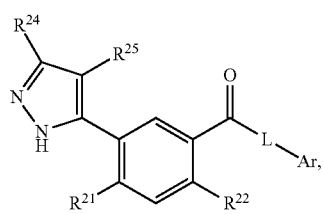

IIIb or pharmaceutically acceptable salts thereof, wherein:
L-Ar is

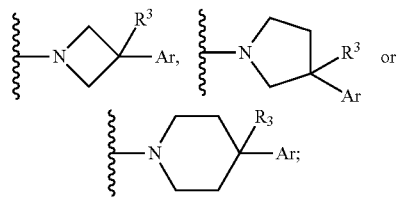

Ar is

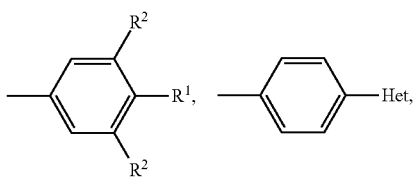

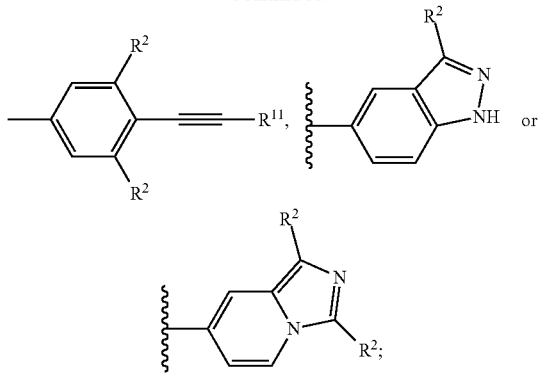

Het is an optionally substituted 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl; and each $R^{24}$ and $R^{25}$ is independently H, halogen, —CN, —($C_1$-$C_4$ alkyl)-CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$—C cycloalkyl), —($C_1$-$C_4$ alkyl)$_t$-O$_u$-(4- to 6-membered heterocycle) or —($C_1$-$C_4$ alkyl)$_t$-O—($C_1$-$C_4$ alkyl), wherein:

each t is independently 0 or 1;

each u is independently 0 or 1; and each $R^{241}$ is independently H or $C_1$-$C_2$ alkyl, wherein the compound is not:

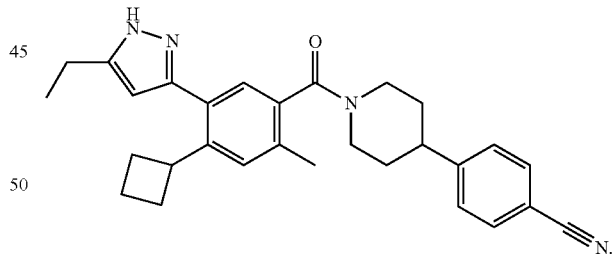

As noted above, each of the $C_1$-$C_2$ alkyl, $C_1$-$C_4$ alkyl, $C_3$-$C_5$ cycloalkyl, 4- to 6-membered heterocycle and 5- to 6-membered heteroaryl moieties may be optionally substituted. Accordingly, the present disclosure provides for compounds of Structure IIIb wherein:

L-Ar is

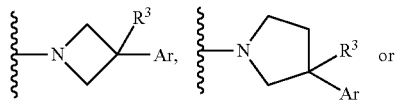

-continued

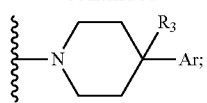

Ar is

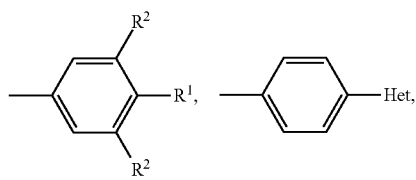

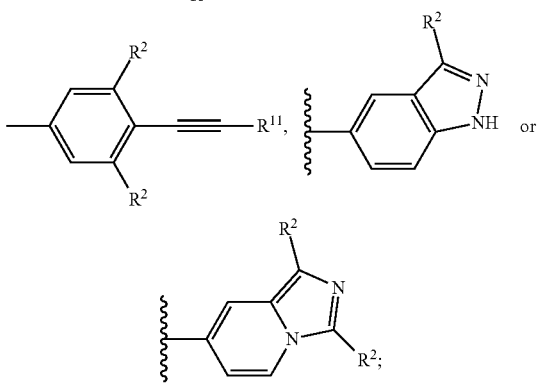

Het is an optionally substituted 5- to 6-membered heteroaryl;

$R^1$ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when $R^1$ is not H, —CN or halogen, $R^1$ is optionally substituted with one or more halogens;

each $R^2$ is independently hydrogen, halogen or optionally substituted $C_1$-$C_4$ alkyl;

$R^3$ is H or F;

$R^{11}$ is H or —$CH_3$;

$R^{21}$ is H, halogen, optionally substituted $C_1$-$C_4$ alkyl, optionally substituted $C_3$-$C_5$ cycloalkyl or optionally substituted 4- to 6-membered heterocycle;

$R^{22}$ is H, halogen or optionally substituted $C_1$-$C_2$ alkyl; and each $R^{24}$ and $R^{25}$ is independently H, halogen, —CN, -(optionally substituted $C_1$-$C_4$ alkyl)-CN, optionally substituted $C_1$-$C_4$ alkyl, -(optionally substituted $C_1$-$C_4$ alkyl)-OH, -(optionally substituted $C_1$-$C_4$ alkyl)-N($R^{241}$)$_2$, -(optionally substituted $C_1$-$C_4$ alkyl)$_t$-$O_u$-(optionally substituted $C_3$-$C_5$ cycloalkyl), -(optionally substituted $C_1$-$C_4$ alkyl)$_t$-$O_u$-(optionally substituted 4- to 6-membered heterocycle) or -(optionally substituted $C_1$-$C_4$ alkyl)$_t$-O-(optionally substituted $C_1$-$C_4$ alkyl), wherein:

t is 0 or 1;

u is 0 or 1; and $R^{241}$ is H or optionally substituted $C_1$-$C_2$ alkyl, wherein the compound is not:

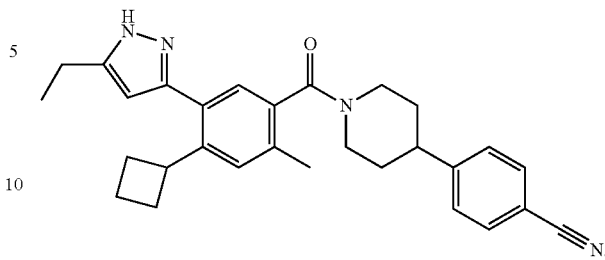

In some embodiments, the present disclosure provides for compounds of Structure IIIb wherein when L-Ar is

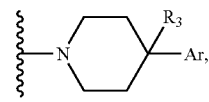

Ar is not

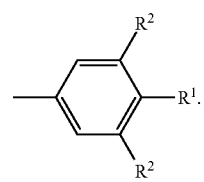

In some embodiments, the present disclosure provides for compounds of Structure IIIb wherein L-Ar is

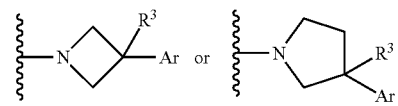

and Ar is

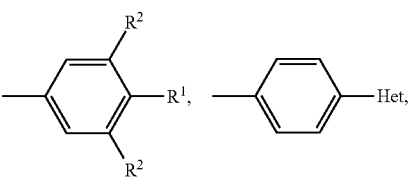

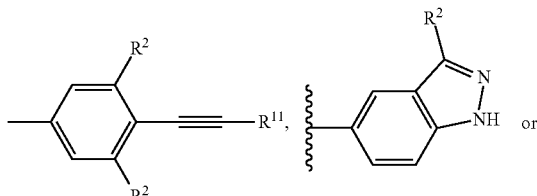

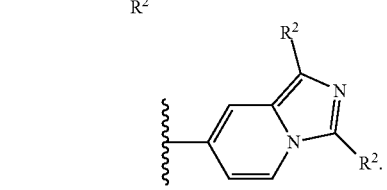

In some embodiments, the present disclosure provides for compounds of Structure IIIb wherein L-Ar is

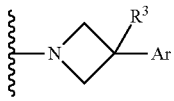

and Ar is

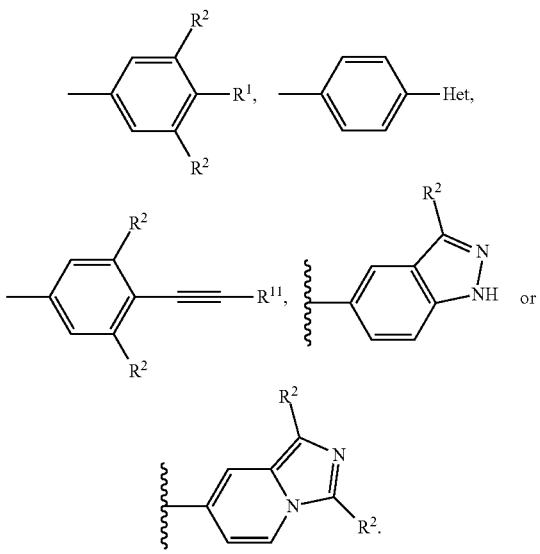

In some embodiments, the present disclosure provides for compounds of Structure IIIb wherein Ar is

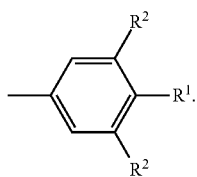

In some embodiments, the present disclosure provides for compounds of Structure IIIb wherein $R^1$ is halogen, —CN or $C_1$-$C_2$ haloalkyl.

In some embodiments, the present disclosure provides for compounds of Structure IIIb wherein $R^1$ is —CN.

In some embodiments, the present disclosure provides for compounds of Structure IIIb wherein $R^2$ is H.

In some embodiments, the present disclosure provides for compounds of Structure IIIb wherein $R^{21}$ is halogen, $C_1$-$C_4$ alkyl, $C_3$-$C_5$ cycloalkyl or 4- to 6-membered heterocycle.

In some embodiments, the present disclosure provides for compounds of Structure IIIb wherein $R^{21}$ is $C_1$-$C_4$ alkyl, $C_3$-$C_5$ cycloalkyl or 4- to 6-membered heterocycle.

In some embodiments, the present disclosure provides for compounds of Structure IIIb wherein $R^{21}$ is $C_1$-$C_2$ alkyl or $C_3$-$C_5$ cycloalkyl.

In some embodiments, the present disclosure provides for compounds of Structure IIIb wherein $R^{21}$ is $C_1$-$C_2$ alkyl.

In some embodiments, the present disclosure provides for compounds of Structure IIIb wherein $R^{21}$ is —CH$_3$.

In some embodiments, the present disclosure provides for compounds of Structure IIIb wherein $R^{22}$ is H or $C_1$-$C_2$ alkyl.

In some embodiments, the present disclosure provides for compounds of Structure IIIb wherein $R^{22}$ is H or —CH$_3$.

In some embodiments, the present disclosure provides for compounds of Structure IIIb wherein $R^{22}$ is —CH$_3$.

In some embodiments, the present disclosure provides for compounds of Structure IIIb wherein each $R^{24}$ and $R^{25}$ is independently H, —CN, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_5$ cycloalkyl), —($C_1$-$C_4$ alkyl)$_t$-O$_u$-(4- to 6-membered heterocycle) or —($C_1$-$C_4$ alkyl)-O—($C_1$-$C_4$ alkyl).

In some embodiments, the present disclosure provides for compounds of Structure IIIb wherein each $R^{24}$ and $R^{25}$ is independently H, $C_1$-$C_4$ alkyl, —($C_1$-$C_4$ alkyl)$_t$-O$_u$-(4- to 6-membered heterocycle) or —($C_1$-$C_4$ alkyl)-O—($C_1$-$C_4$ alkyl).

In some embodiments, the present disclosure provides for compounds of Structure IIIb wherein $R^{24}$ is H, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_5$ cycloalkyl), —($C_1$-$C_4$ alkyl)$_t$-O$_u$-(4- to 6-membered heterocycle) or —($C_1$-$C_4$ alkyl)-O—($C_1$-$C_4$ alkyl).

In some embodiments, the present disclosure provides for compounds of Structure IIIb wherein $R^{24}$ is —CN, —Cl, $C_1$-$C_4$ alkyl or —($C_1$-$C_4$ alkyl)-O—($C_1$-$C_4$ alkyl).

In some embodiments, the present disclosure provides for compounds of Structure IIIb wherein $R^{24}$ is $C_1$-$C_4$ alkyl or —($C_1$-$C_4$ alkyl)-O—($C_1$-$C_4$ alkyl).

In some embodiments, the present disclosure provides for compounds of Structure IIIb wherein $R^{24}$ is —($C_1$-$C_2$ alkyl)-O—($C_1$-$C_2$ alkyl).

In some embodiments, the present disclosure provides for compounds of Structure IIIb wherein $R^{24}$ is $C_1$-$C_4$ alkyl.

In some embodiments, the present disclosure provides for compounds of Structure IIIb wherein $R^{24}$ is —CH$_3$.

In some embodiments, the present disclosure provides for compounds of Structure IIIb wherein $R^{24}$ is hydrogen.

In some embodiments, the present disclosure provides for compounds of Structure IIIb wherein $R^{24}$ is substituted with one or more substituents selected from halogen, $C_3$-$C_5$ cycloalkyl and $C_1$-$C_2$ alkoxy.

In some embodiments, the present disclosure provides for compounds of Structure IIIb wherein $R^{24}$ is substituted with one or more substituents selected from —F, cyclopropyl and —OCH$_3$.

In some embodiments, the present disclosure provides for compounds of Structure IIIb wherein $R^{24}$ is substituted with two substituents that are the same or different.

In some embodiments, the present disclosure provides for compounds of Structure IIIb wherein $R^{24}$ is substituted with three substituents that are the same or different.

In some embodiments, the present disclosure provides for compounds of Structure IIIb wherein $R^{25}$ is halogen, methyl, ethyl or cyclopropyl.

In some embodiments, the present disclosure provides for compounds of Structure IIIb wherein $R^{25}$ is —CN, —Cl, $C_1$-$C_4$ alkyl, —($C_1$-$C_4$ alkyl)$_t$-O—($C_3$-$C_5$ cycloalkyl) or —($C_1$-$C_4$ alkyl)$_t$-O—($C_1$-$C_4$ alkyl).

In some embodiments, the present disclosure provides for compounds of Structure IIIb wherein $R^{25}$ is —CN, —Cl, —CH$_3$, —O—($C_3$-$C_5$ cycloalkyl) or —O—($C_1$-$C_2$ alkyl).

In some embodiments, the present disclosure provides for compounds of Structure IIIb wherein $R^{25}$ is —CN, —Cl or $C_1$-$C_4$ alkyl.

In some embodiments, the present disclosure provides for compounds of Structure IIIb wherein $R^{25}$ is —CH$_3$.

In some embodiments, the present disclosure provides for compounds of Structure IIIb wherein $R^{25}$ is —Cl.

In some embodiments, the present disclosure provides for compounds of Structure IIIb wherein $R^{25}$ is substituted with one or more halogen.

In some embodiments, the present disclosure provides for compounds of Structure IIIb wherein $R^{25}$ is substituted with one or more —F.

In some embodiments, the present disclosure provides for compounds of Structure IIIb wherein $R^{25}$ is substituted by two substituents.

In some embodiments, the present disclosure provides for compounds of Structure IIIb wherein $R^{25}$ is substituted by three substituents.

In some embodiments, the present disclosure provides for compounds of Structure IIIb wherein $R^{21}$ is —CH$_3$ and $R^{22}$ is H or methyl.

In some embodiments, the present disclosure provides for compounds of Structure IIIb wherein $R^{21}$ is C$_1$-C$_2$ alkyl or C$_3$-C$_5$ cycloalkyl and $R^{22}$ is H or —CH$_3$.

In some embodiments, the present disclosure provides for compounds of Structure IIIb wherein $R^{21}$ is —CH$_3$ and $R^{22}$ is H.

In some embodiments, the present disclosure provides for compounds of Structure IIIb wherein $R^{24}$ is H or —CH$_3$ and $R^{25}$ is —Cl.

In some embodiments, the present disclosure provides for compounds of Structure IIIb wherein $R^1$ is —CN and $R^2$ is H.

In some embodiments, the present disclosure provides for compounds of Structure IIIb wherein $R^{21}$ is C$_1$-C$_2$ alkyl or C$_3$-C$_5$ cycloalkyl and $R^{22}$ is C$_1$-C$_2$ alkyl.

In some embodiments, the present disclosure provides for compounds of Structure IIIb wherein $R^{21}$ is C$_1$-C$_2$ alkyl or C$_3$-C$_5$ cycloalkyl and $R^{22}$ is H or C$_1$-C$_2$ alkyl.

In some embodiments, the present disclosure provides for compounds of Structure IIIb wherein $R^{21}$ is C$_1$-C$_2$ alkyl and $R^{22}$ is H or —CH$_3$.

In some embodiments, the present disclosure provides for compounds of Structure IIIb wherein $R^{21}$ is C$_1$-C$_2$ alkyl and $R^{22}$ is H.

In various aspects, the present disclosure provides for compounds of Structure IIIc:

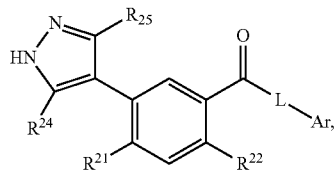

IIIc or pharmaceutically acceptable salts thereof, wherein:
L-Ar is

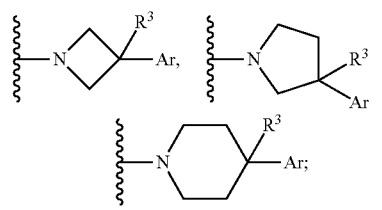

Ar is

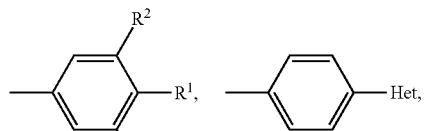

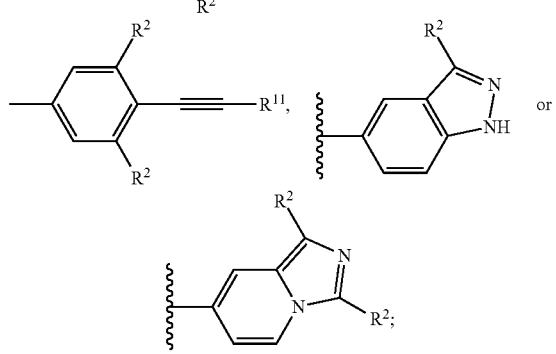

Het is a 5- to 6-membered heteroaryl;
$R^1$ is H, —CN, halogen, C$_1$-C$_4$ alkyl, —O—(C$_3$-C$_5$ cycloalkyl), —O-(4- to 6-membered heterocycle) or —O—(C$_1$-C$_4$ alkyl), wherein when $R^1$ is not H, —CN or halogen, $R^1$ is optionally substituted with one or more halogens;
each $R^2$ is independently hydrogen, halogen or C$_1$-C$_4$ alkyl;
$R^3$ is H or F;
$R^{11}$ is H or —CH$_3$;
$R^{21}$ is H, halogen, C$_1$-C$_4$ alkyl, C$_3$-C$_5$ cycloalkyl or 4- to 6-membered heterocycle;
$R^{22}$ is H, halogen or C$_1$-C$_2$ alkyl; and
each of $R^{24}$ and $R^{25}$ is independently H, —C$_1$-C$_4$ alkyl, or halogen.

As noted above, each of the C$_1$-C$_2$ alkyl, C$_1$-C$_4$ alkyl, C$_3$-C$_5$ cycloalkyl, 4- to 6-membered heterocycle and 5- to 6-membered heteroaryl moieties may be optionally substituted. Accordingly, the present disclosure provides for compounds of Structure IIIc wherein:

L-Ar is

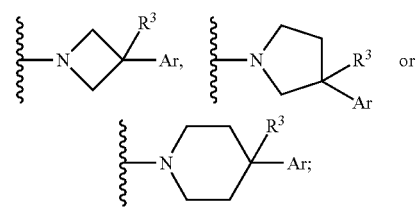

Ar is

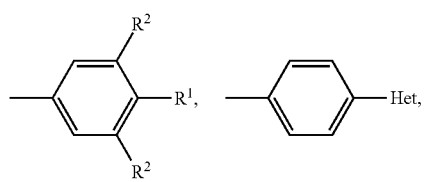

-continued

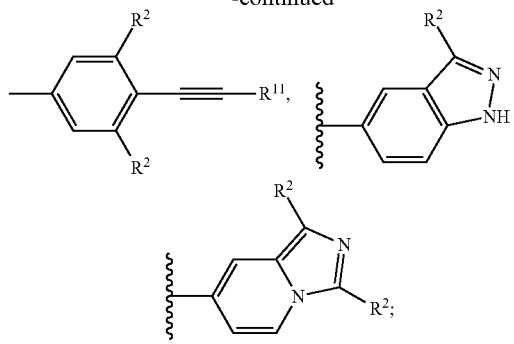

Het is an optionally substituted 5- to 6-membered heteroaryl;

$R^1$ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when $R^1$ is not H, —CN or halogen, $R^1$ is optionally substituted with one or more halogens;

each $R^2$ is independently hydrogen, halogen or optionally substituted $C_1$-$C_4$ alkyl;

$R^3$ is H or F;

$R^{11}$ is H or —CH$_3$;

$R^{21}$ is H, halogen, optionally substituted $C_1$-$C_4$ alkyl, optionally substituted $C_3$-$C_5$ cycloalkyl or optionally substituted 4- to 6-membered heterocycle;

$R^{22}$ is H, halogen or optionally substituted $C_1$-$C_2$ alkyl; and each of $R^{24}$ and $R^{25}$ is independently H, optionally substituted $C_1$-$C_4$ alkyl, or halogen.

In some embodiments, the present disclosure provides for compounds of Structure IIIc wherein L-Ar is

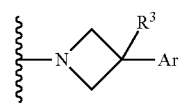

Ar is not

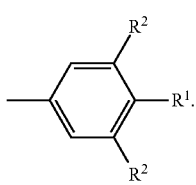

In some embodiments, the present disclosure provides for compounds of Structure IIIc wherein L-Ar is

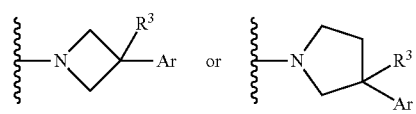

and Ar is

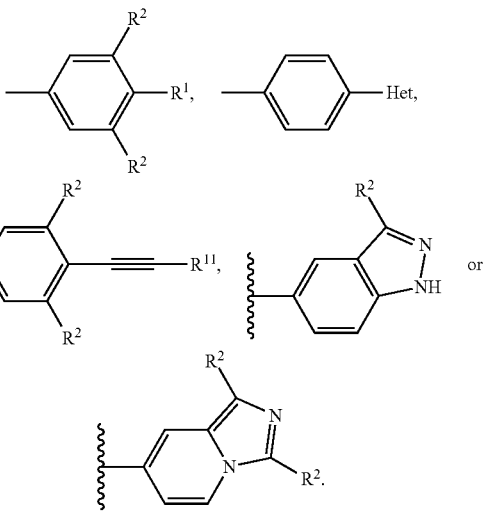

In some embodiments, the present disclosure provides for compounds of Structure IIIc wherein L-Ar is

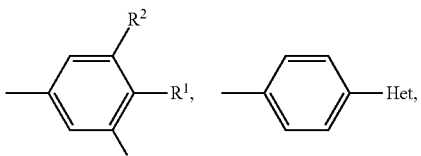

and Ar is

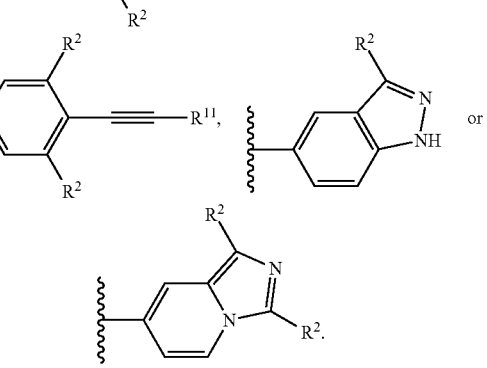

In some embodiments, the present disclosure provides for compounds of Structure IIIc wherein $R^1$ is halogen, —CN or $C_1$-$C_2$ haloalkyl.

In some embodiments, the present disclosure provides for compounds of Structure IIIc wherein $R^{21}$ is halogen, $C_1$-$C_4$ alkyl, $C_3$-$C_5$ cycloalkyl or 4- to 6-membered heterocycle.

In some embodiments, the present disclosure provides for compounds of Structure IIIc wherein $R^{21}$ is —CH$_3$.

In some embodiments, the present disclosure provides for compounds of Structure IIIc wherein $R^{22}$ is H.

In some embodiments, the present disclosure provides for compounds of Structure IIIc wherein $R^{21}$ is methyl, $R^{22}$ is H and L-Ar is

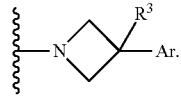

In various aspects, the present disclosure provides for compounds of Structure IV:

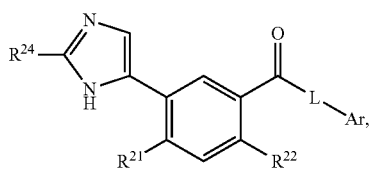

IV or pharmaceutically acceptable salts thereof, wherein:
L-Ar is

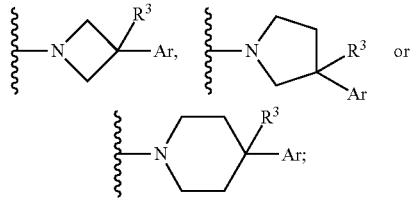

Ar is

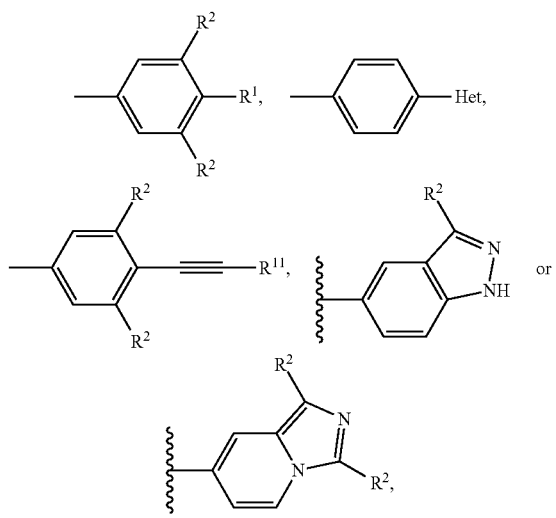

with the proviso that when L-Ar is

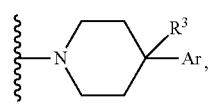

Ar is not

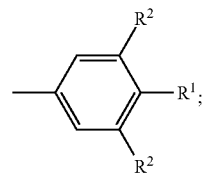

Het is a 5- to 6-membered heteroaryl;
$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;
each $R^2$ is independently hydrogen, halogen or $C_1$-$C_4$ alkyl;
$R^3$ is H or F;
$R^{11}$ is H or —CH$_3$;
$R^{21}$ is H, halogen, $C_1$-$C_4$ alkyl, $C_3$-$C_5$ cycloalkyl or 4- to 6-membered heterocycle;
$R^{22}$ is H, halogen or $C_1$-$C_2$ alkyl; and
$R^{24}$ is H, $C_1$-$C_4$ alkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_5$ cycloalkyl), —($C_1$-$C_4$ alkyl)$_t$-O$_u$-(4- to 6-membered heterocycle) or —($C_1$-$C_4$ alkyl)-O—($C_1$-$C_4$ alkyl), wherein:
t is 0 or 1;
u is 0 or 1;
with the proviso that when u is 1, t is 1; and
$R^{241}$ is H or $C_1$-$C_2$ alkyl.

As noted above, each of the $C_1$-$C_2$ alkyl, $C_1$-$C_4$ alkyl, $C_3$-$C_5$ cycloalkyl, 4- to 6-membered heterocycle and 5- to 6-membered heteroaryl moieties may be optionally substituted. Accordingly, the present disclosure provides for compounds of Structure IV wherein:
L-Ar is

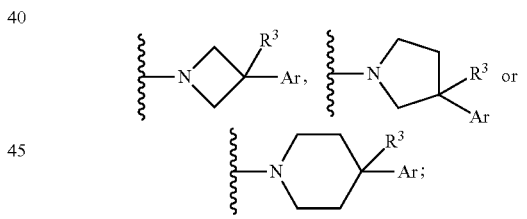

Ar is

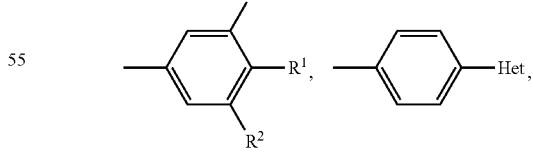

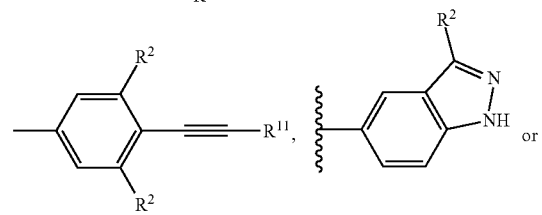

-continued

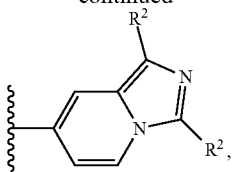

with the proviso that when L-Ar is

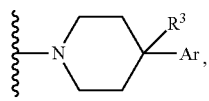

Ar is not

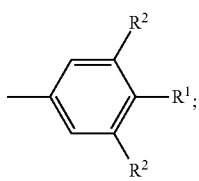

Het is an optionally substituted 5- to 6-membered heteroaryl;
$R^1$ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when $R^1$ is not H, —CN or halogen, $R^1$ is optionally substituted with one or more halogens;
each $R^2$ is independently hydrogen, halogen or optionally substituted $C_1$-$C_4$ alkyl;
$R^3$ is H or F;
$R^{11}$ is H or —$CH_3$;
$R^{21}$ is H, halogen, optionally substituted $C_1$-$C_4$ alkyl, optionally substituted $C_3$-$C_5$ cycloalkyl or optionally substituted 4- to 6-membered heterocycle;
$R^{22}$ is H, halogen or optionally substituted $C_1$-$C_2$ alkyl;
$R^{24}$ is H, optionally substituted $C_1$-$C_4$ alkyl, -(optionally substituted $C_1$-$C_4$ alkyl)-OH, -(optionally substituted $C_1$-$C_4$ alkyl)-N($R^{241}$)$_2$, -(optionally substituted $C_1$-$C_4$ alkyl)$_t$-O$_u$-(optionally substituted $C_3$-$C_5$ cycloalkyl), -(optionally substituted $C_1$-$C_4$ alkyl)$_t$-O$_u$-(optionally substituted 4- to 6-membered heterocycle) or -(optionally substituted $C_1$-$C_4$ alkyl)-O-(optionally substituted $C_1$-$C_4$ alkyl), wherein:
t is 0 or 1;
u is 0 or 1;
with the proviso that when u is 1, t is 1; and
$R^{241}$ is H or optionally substituted $C_1$-$C_2$ alkyl.

In some embodiments, the present disclosure provides for compounds of Structure IV wherein L-Ar is

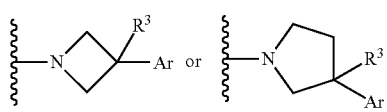

and Ar is

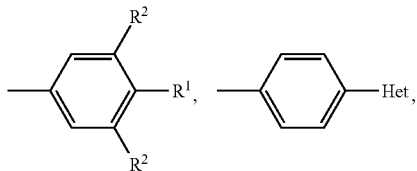

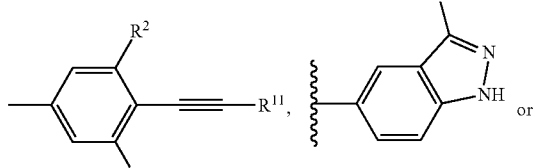

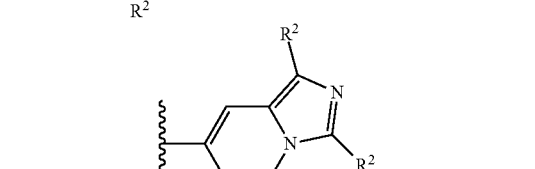

In some embodiments, the present disclosure provides for compounds of Structure IV wherein $R^1$ is halogen, —CN or $C_1$-$C_2$ haloalkyl.

In some embodiments, the present disclosure provides for compounds of Structure IV wherein $R^1$ is —CN.

In some embodiments, the present disclosure provides for compounds of Structure IV wherein $R^2$ is H.

In some embodiments, the present disclosure provides for compounds of Structure IV wherein $R^{21}$ is halogen, $C_1$-$C_4$ alkyl, $C_3$-$C_5$ cycloalkyl or 4- to 6-membered heterocycle.

In some embodiments, the present disclosure provides for compounds of Structure IV wherein $R^{21}$ is $C_1$-$C_2$ alkyl or $C_3$-$C_5$ cycloalkyl.

In some embodiments, the present disclosure provides for compounds of Structure IV wherein $R^{21}$ is $C_1$-$C_2$ alkyl.

In some embodiments, the present disclosure provides for compounds of Structure IV wherein $R^{21}$ is $C_3$-$C_5$ cycloalkyl.

In some embodiments, the present disclosure provides for compounds of Structure IV wherein $R^{22}$ is H or $C_1$-$C_2$ alkyl.

In some embodiments, the present disclosure provides for compounds of Structure IV wherein $R^{22}$ is H.

In some embodiments, the present disclosure provides for compounds of Structure IV wherein $R^{22}$ is $C_1$-$C_2$ alkyl.

In some embodiments, the present disclosure provides for compounds of Structure IV wherein $R^{22}$ is —$CH_3$.

In some embodiments, the present disclosure provides for compounds of Structure IV wherein $R^{24}$ is $C_1$-$C_4$ alkyl or —($C_1$-$C_4$ alkyl)-O—($C_1$-$C_4$ alkyl).

In some embodiments, the present disclosure provides for compounds of Structure IV wherein $R^{24}$ is —($C_1$-$C_2$ alkyl)-O—($C_1$-$C_2$ alkyl).

In some embodiments, the present disclosure provides for compounds of Structure IV wherein $R^{21}$ is $C_1$-$C_2$ alkyl or $C_3$-$C_5$ cycloalkyl and $R^{22}$ is $C_1$-$C_2$ alkyl.

In some embodiments, the present disclosure provides for compounds of Structure IV wherein $R^{21}$ is $C_3$-$C_5$ cycloalkyl and $R^{22}$ is H or $C_1$-$C_2$ alkyl.

In some embodiments, the present disclosure provides for compounds of Structure IV wherein $R^{21}$ is $C_3$-$C_5$ cycloalkyl and $R^{22}$ is H or —$CH_3$.

In some embodiments, the present disclosure provides for compounds of Structure IV wherein $R^{21}$ is $C_3$-$C_5$ cycloalkyl and $R^{22}$ is H or —$CH_3$.

In some embodiments, the present disclosure provides for compounds of Structure IV wherein R¹ is —CN and R² is H.

In various aspects, the present disclosure provides for compounds of Structure V:

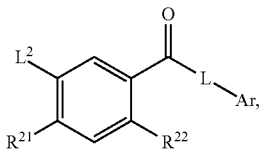

V or pharmaceutically acceptable salts thereof, wherein:
L-Ar is

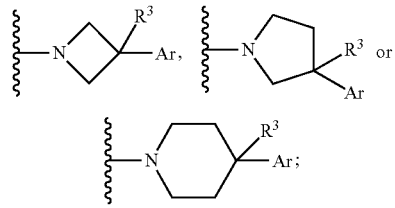

Ar is

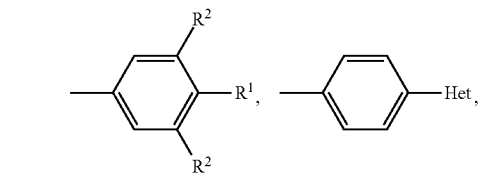

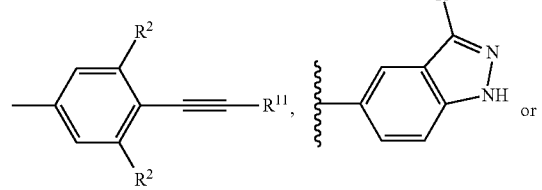

with the proviso that when L-Ar is

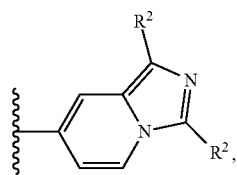

Ar is not

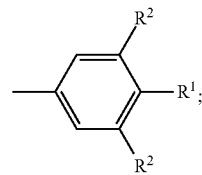

L² is —NHR³⁵ or —C(O)NHR³⁵¹, wherein R³⁵¹ is $C_1$-$C_6$ alkyl, $C_3$-$C_5$ cycloalkyl, 4- to 6-membered heterocycle, aryl or heteroaryl;

Het is a 5- to 6-membered heteroaryl;

R¹ is H, —CN, halogen, $C_1$-$C_4$ alkyl, —O—($C_3$-$C_5$ cycloalkyl), —O-(4- to 6-membered heterocycle), —O—($C_1$-$C_4$ alkyl) wherein when R¹ is not H, —CN or halogen, R¹ is optionally substituted with one or more halogens;

each R² is independently hydrogen, halogen or $C_1$-$C_4$ alkyl;

R³ is H or F;

R¹¹ is H or —CH₃;

R²¹ is H, halogen, $C_1$-$C_4$ alkyl, $C_3$-$C_5$ cycloalkyl or 4- to 6-membered heterocycle;

R²² is H, halogen, or $C_1$-$C_2$ alkyl; and

R³⁵ is —C(O)R³⁵¹, —C(O)NHR³⁵¹, C(O)OR³⁵¹ or S(O)₂R³⁵¹ wherein R³⁵¹ is $C_1$-$C_6$ alkyl, $C_3$-$C_5$ cycloalkyl, 4- to 6-membered heterocycle, aryl or heteroaryl.

As noted above, each of the $C_1$-$C_2$ alkyl, $C_1$-$C_4$ alkyl, $C_1$-$C_6$ alkyl, $C_3$-$C_5$ cycloalkyl, 4- to 6-membered heterocycle, 5- to 6-membered heteroaryl, aryl and heteroaryl moieties may be optionally substituted. Accordingly, the present disclosure provides for compounds of Structure V wherein:

L-Ar is

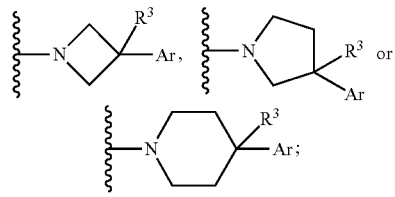

Ar is

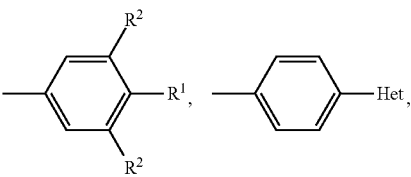

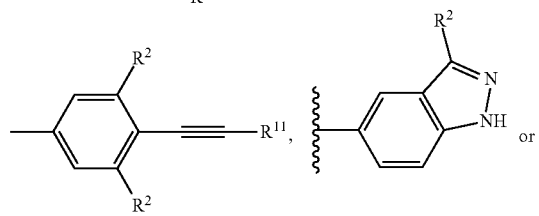

-continued

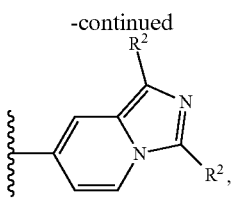

with the proviso that when L-Ar is

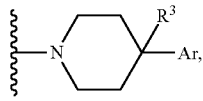

Ar is not

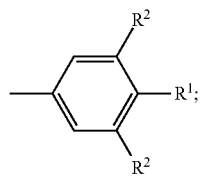

L² is —NHR³⁵ or —C(O)NHR³⁵¹, wherein R³⁵¹ is optionally substituted $C_1$-$C_6$ alkyl, optionally substituted $C_3$-$C_5$ cycloalkyl, optionally substituted 4- to 6-membered heterocycle, optionally substituted aryl or optionally substituted heteroaryl;

Het is an optionally substituted 5- to 6-membered heteroaryl;

R¹ is H, —CN, halogen, optionally substituted $C_1$-$C_4$ alkyl, —O-(optionally substituted $C_3$-$C_5$ cycloalkyl), —O-(optionally substituted 4- to 6-membered heterocycle) or —O-(optionally substituted $C_1$-$C_4$ alkyl), wherein when R¹ is not H, —CN or halogen, R¹ is optionally substituted with one or more halogens;

each R² is independently hydrogen, halogen or optionally substituted $C_1$-$C_4$ alkyl;

R³ is H or F;

R¹¹ is H or —CH₃;

R²¹ is H, halogen, optionally substituted $C_1$-$C_4$ alkyl, optionally substituted $C_3$-$C_5$ cycloalkyl or optionally substituted 4- to 6-membered heterocycle;

R²² is H, halogen, or optionally substituted $C_1$-$C_2$ alkyl; and

R³⁵ is —C(O)R³⁵¹, —C(O)NHR³⁵¹, —C(O)OR³⁵¹ or —S(O)₂R³⁵¹, wherein R³⁵¹ is optionally substituted $C_1$-$C_6$ alkyl, optionally substituted $C_3$-$C_5$ cycloalkyl, optionally substituted 4- to 6-membered heterocycle, optionally substituted aryl or optionally substituted heteroaryl.

In some embodiments, the present disclosure provides for compounds of Structure V wherein when L-Ar is

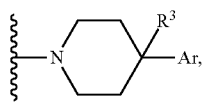

Ar is not

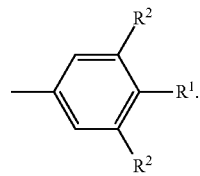

In some embodiments, the present disclosure provides for compounds of Structure V wherein L² is —NHR³⁵.

In some embodiments, the present disclosure provides for compounds of Structure V wherein L² is —C(O)NHR³⁵¹.

In various aspects, the present disclosure provides for compounds of Structure VI:

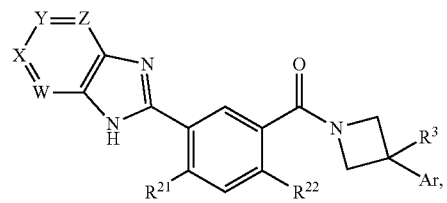

VI or pharmaceutically acceptable salts thereof, wherein:
each W, X, Y and Z is independently —N— or —CR²⁶— with the proviso that not more than 2 of W, X, Y and Z are —N—;
each R²⁶ is independently H, $C_1$-$C_4$ alkyl, —O—($C_1$-$C_4$ alkyl), —N(R²⁷)₂, —S(O)₂—($C_1$-$C_4$ alkyl), or —C(O)—($C_1$-$C_4$ alkyl);
each R²⁷ is independently H or $C_1$-$C_4$ alkyl or both R²⁷ are $C_1$-$C_4$ alkyl and join to form a 3- to 6-membered ring together with the N to which they are attached and wherein the ring optionally includes one oxygen atom as one of the members of the ring;
Ar is

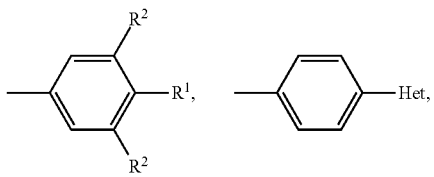

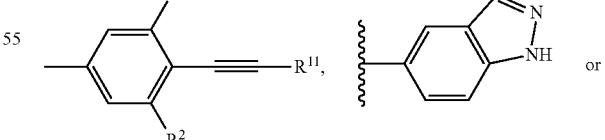

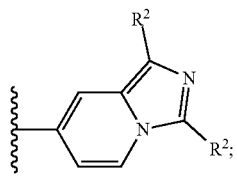

or

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle), —O—($C_1$-$C_4$ alkyl) wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —CH$_3$;

$R^{21}$ is H, halogen, $C_1$-$C_4$ alkyl, $C_3$-$C_5$ cycloalkyl or a 4- to 6-membered heterocycle; and $R^{22}$ is H, halogen or $C_1$-$C_2$ alkyl.

As noted above, each of the $C_1$-$C_2$ alkyl, $C_1$-$C_4$ alkyl, $C_3$-$C_5$ cycloalkyl, 4- to 6-membered heterocycle and 5- to 6-membered heteroaryl moieties may be optionally substituted. Accordingly, the present disclosure provides for compounds of Structure VI wherein:

each W, X, Y and Z is independently —N— or —CR$^{26}$— with the proviso that not more than 2 of W, X, Y and Z are —N—;

$R^{26}$ is H, optionally substituted $C_1$-$C_4$ alkyl, —O-(optionally substituted $C_1$-$C_4$ alkyl), —N(R$^{27}$)$_2$, —S(O)$_2$-(optionally substituted $C_1$-$C_4$ alkyl) or —C(O)-(optionally substituted $C_1$-$C_4$ alkyl);

each $R^{27}$ is independently H or optionally substituted $C_1$-$C_4$ alkyl or both $R^{27}$ are optionally substituted $C_1$-$C_4$ alkyl and join to form an optionally substituted 3- to 6-membered ring together with the N to which they are attached and wherein the ring optionally includes one oxygen atom as one of the members of the ring;

Ar is

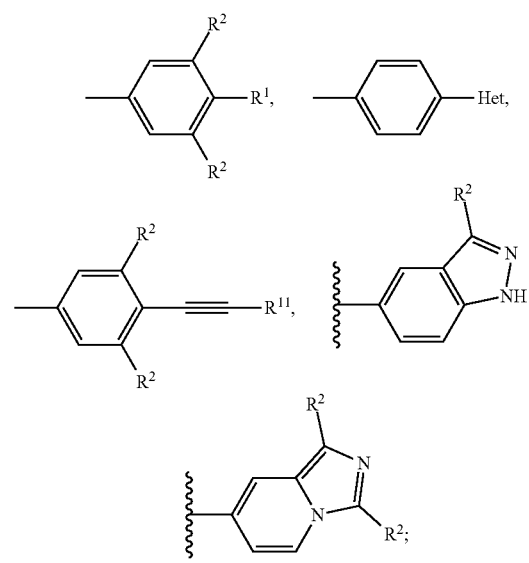

Het is an optionally substituted 5- to 6-membered heteroaryl;

$R^1$ is H, —CN, halogen, optionally substituted alkyl, —O-(optionally substituted $C_3$-$C_5$ cycloalkyl), —O-(optionally substituted 4- to 6-membered heterocycle) or —O-(optionally substituted alkyl), wherein when $R^1$ is not H, —CN or halogen, $R^1$ is optionally substituted with one or more halogens;

each $R^2$ is independently hydrogen, halogen or optionally substituted C alkyl;

$R^3$ is H or F;

$R^{11}$ is H or —CH$_3$;

$R^{21}$ is H, halogen, optionally substituted C alkyl, optionally substituted $C_3$-$C_5$ cycloalkyl or an optionally substituted 4- to 6-membered heterocycle; and $R^{22}$ is H, halogen or optionally substituted $C_1$-$C_2$ alkyl.

In some embodiments, the present disclosure provides for compounds of Structure VI wherein Ar is

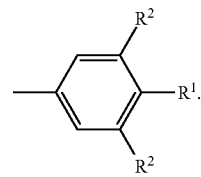

In some embodiments, the present disclosure provides for compounds of Structure VI wherein Y is —CR$^{26}$— wherein $R^{26}$ is —N(R$^{27}$)$_2$.

In some embodiments, the present disclosure provides for compounds of Structure VI wherein X is —N—.

Synthesis of Compounds

Also described herein are methods of synthesizing the compounds of the present disclosure. Compounds of the present disclosure can be synthesized according to the synthetic schemes provided below.

Scheme 1 provides methods useful for synthesizing the L moiety of Structures I-IV. In Scheme 1, each of m' and n' are independently 1 or 2. Ar is as defined in Structures I-V.

Scheme 1

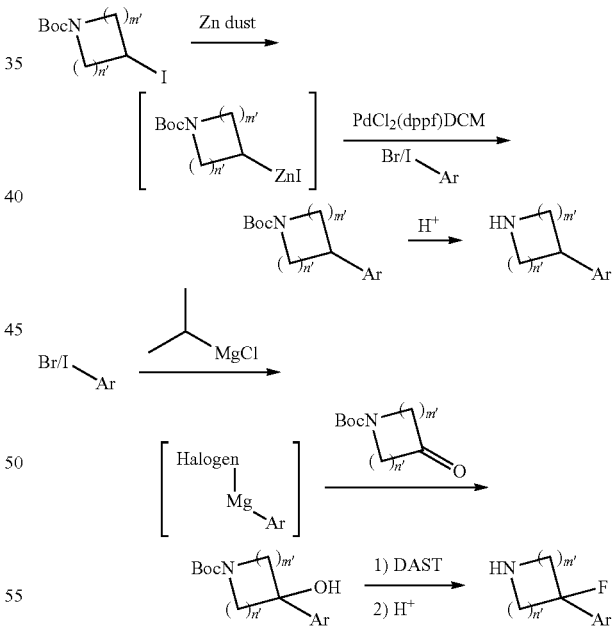

Scheme 2 provides methods useful for preparing the

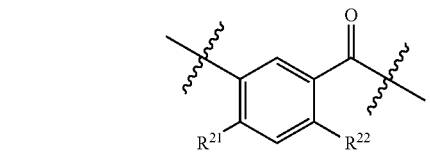

moiety in each of Structures I-IV.

Scheme 2
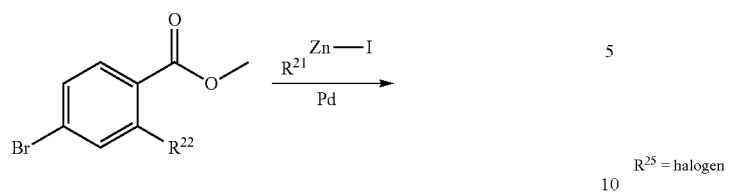
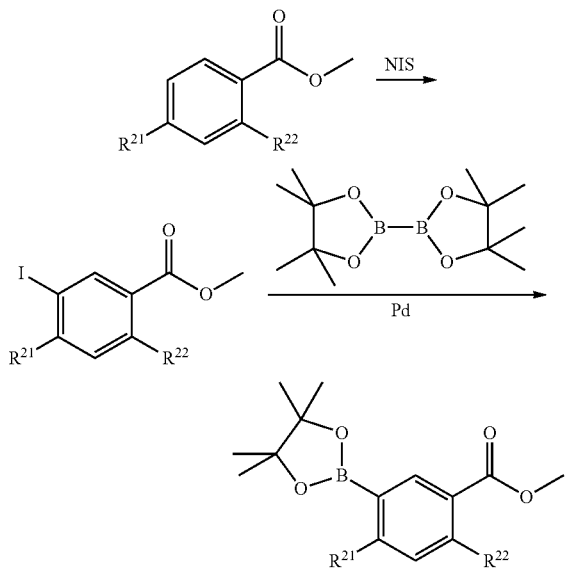
Schemes 3-5 provide methods useful in the synthesis of compounds of Structure III.
Scheme 3
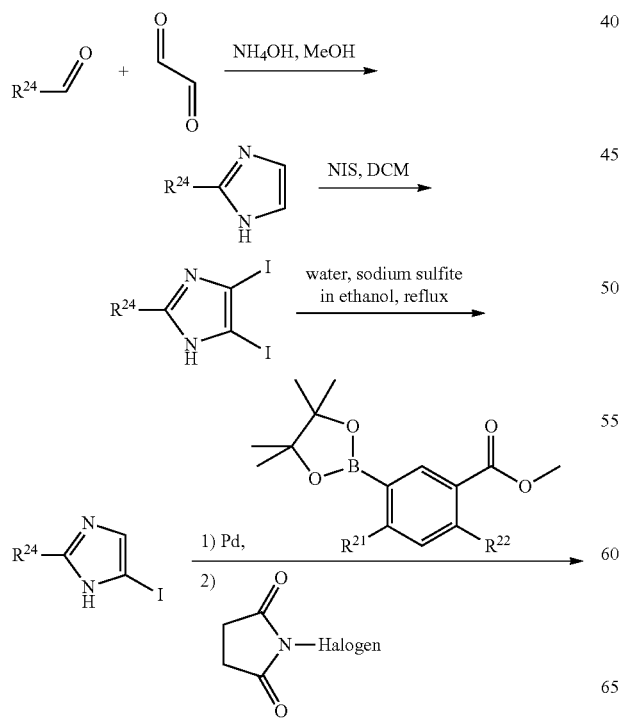
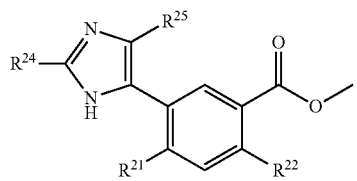
$R^{25}$ = halogen
Scheme 4
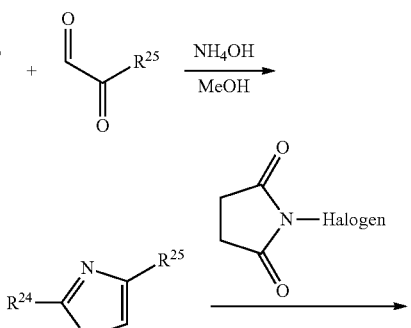
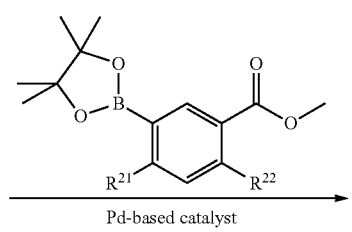
Scheme 5
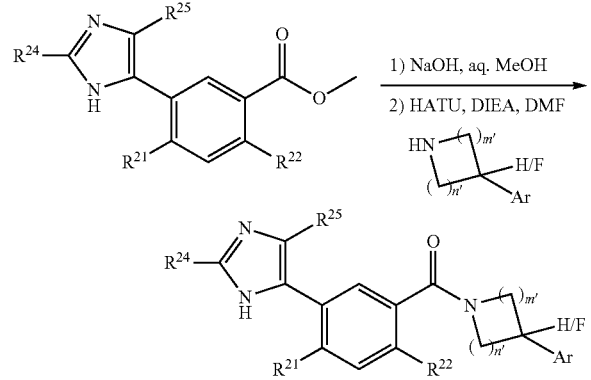
Schemes 6-7 provide methods useful in the synthesis of compounds of Structure II.

Scheme 6
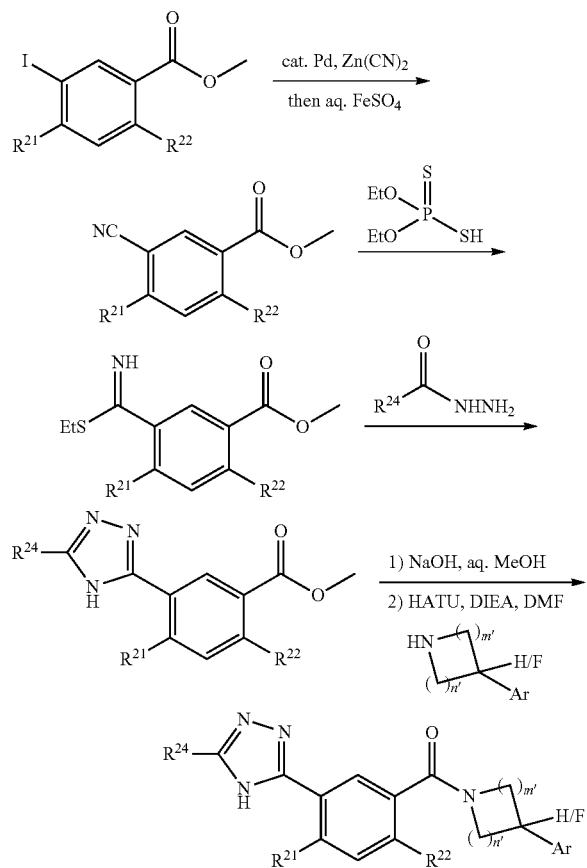
Scheme 7
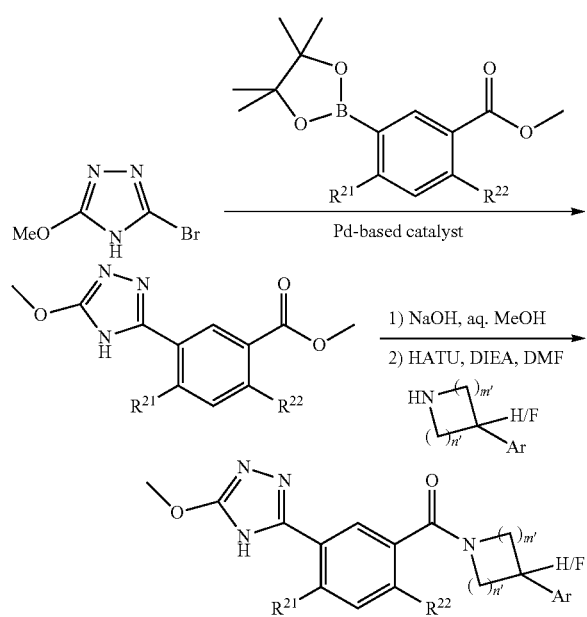
Scheme 8
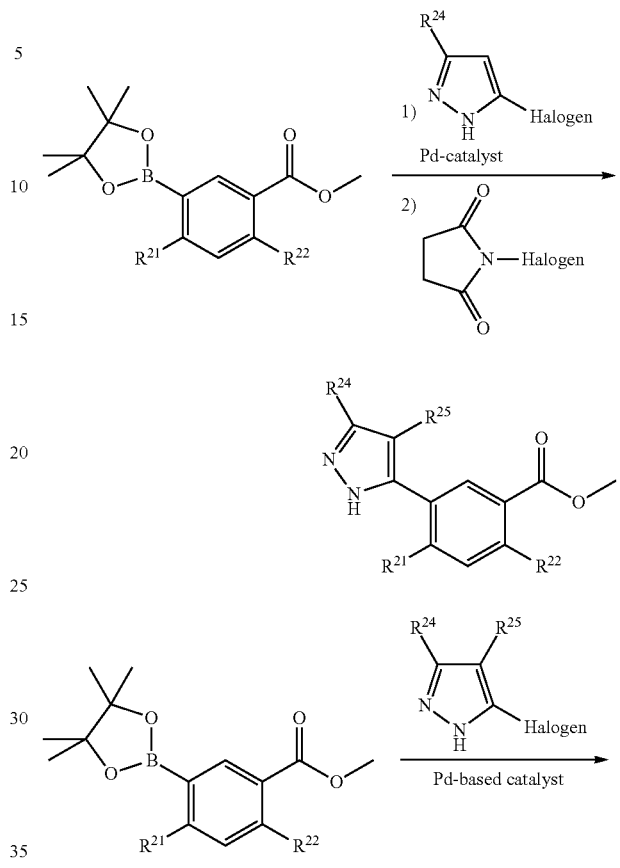
Scheme 8 provides methods useful in the synthesis of compounds of Structure IIIb.
Scheme 9 provides methods useful in the synthesis of compounds of Structure I.

Scheme 9

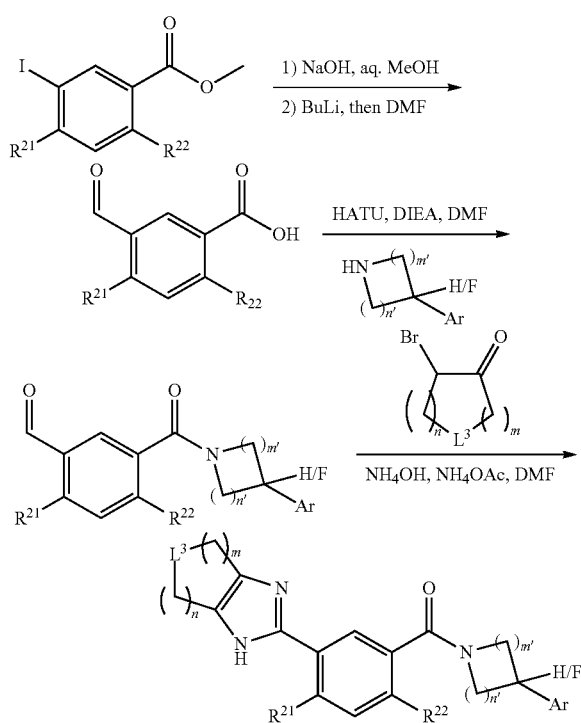

Additional methods for producing particular compounds according to the present disclosure are provided in the Examples. One skilled in the art will recognize that other compounds of structures can be made by modifications to the specifically disclosed schemes employing methods known to those of skill in the art. Additional examples can be found in TABLE 26.

Many such techniques are well known in the art. However, many of the known techniques are elaborated in *Compendium of Organic Synthetic Methods* (Vol. 1, 1971; Vol. 2, 1974; Vol. 3, 1977; Vol. 4, 1980; Vol. 5, 1984; and Vol. 6 as well as *March in Advanced Organic Chemistry* (1985); *Comprehensive Organic Synthesis. Selectivity, Strategy & Efficiency in Modern Organic Chemistry*. In 9 Volumes (1993); *Advanced Organic Chemistry Part B: Reactions and Synthesis*, Second Edition (1983); *Advanced Organic Chemistry, Reactions, Mechanisms, and Structure*, Second Edition (1977); *Protecting Groups in Organic Synthesis*, Second Edition; and *Comprehensive Organic Transformations* (1999).

Antiviral Methods of Treatment

In various aspects, the present disclosure provides methods for treating viral infection in a subject, the method comprising administering to a subject in need of such treatment an effective amount of a compound of Structures I, II, III, IIIb, IIIc, IV, V and VI or as provided in TABLE 26.

In various aspects, the disclosure provides methods for treating a viral infection, the method comprising administering the compounds of the present disclosure to a subject in need thereof the agent.

In various aspects, the present disclosure provides methods for treating hepatitis C infection by administering to the subject one or more compounds disclosed herein.

In certain aspects the compounds of the present disclosure may be used in combination with other antiviral treatments in the treating of viral infection.

In various aspects the compounds of the present disclosure can be used for the treatment of infection of an animal subject, such as a human.

Anticancer Activity

In various aspects, the present disclosure provides methods for treating cancer in subject, the method comprising administering to a subject in need of such treatment an effective amount of a compound of Structures I, II, III, IIIb, IIIc, IV, V and VI or as provided in TABLE 26. In further aspects, compounds having Structures I, II, III, IIIb, IIIc, IV, V and VI or as provided in TABLE 26 can be used for the manufacture of a medicament for treating cancer.

In certain aspects, the present disclosure provides a method for inhibiting tumor cell growth in a subject, the method comprising administering to a subject in need of such treatment an effective amount of a compound of Structure I, II, III, IIIb, IIIc, IV, V and VI or as provided in TABLE 26. In further aspects, the tumor can be derived from breast, lung, thyroid, lymph node, kidney, ureter, bladder, ovary, teste, prostate, bone, skeletal muscle, bone marrow, stomach, esophagus, small bowel, colon, rectum, pancreas, liver, smooth muscle, brain, spinal cord, nerves, ear, eye, nasopharynx, oropharynx, salivary gland, or heart tissue. In certain aspects, the present compounds can be administered concurrently with one or more additional anti-cancer treatments.

In certain aspects, the present disclosure provides a method for treating pancreatic cancer in a subject, the method comprising administering to a subject in need of such treatment an effective amount of a compound of Structure I, II, III, IIIb, IIIc, IV, V and VI or as provided in TABLE 26.

In certain aspects, the present disclosure provides for a method of treating colon cancer in a subject, the method comprising administering to a subject in need of such treatment an effective amount of a compound of Structure I, II, III, IIIb, IIIc, IV, V and VI or as provided in TABLE 26.

Rapidly proliferating cancer cells activate the fatty acid synthesis pathway to supply the high levels of lipids needed for membrane assembly and oxidative metabolism. (Flavin, R. et al. (2010) *Future Oncology*. 6(4):551-562) Inhibitors of fatty acid synthesis have demonstrated in vivo activity in preclinical cancer models. (Orita, H. et al. (2007) *Clinical Cancer Research*. 13(23):7139-7145 and Puig, T. et al. (2011) *Breast Cancer Research*, 13(6):R131) Additionally, fatty acid synthesis supports new blood vessel formation and inhibitors of this pathway have activity in in vitro models of angiogenesis. (Browne, C. D., et al. (2006) *The FASEB Journal*, 20(12):2027-2035).

Utility in Metabolic Disorders

In various aspects, the compounds of the present disclosure have utility in the treating of metabolic diseases. FASN has been demonstrated to be involved in regulation of glucose, lipids and cholesterol metabolism. Mice with a liver-specific inactivation of FASN have normal physiology unless fed a zero-fat diet, in which case they develop hypoglycemia and fatty liver, both of which are reversed with dietary fat. (Chakravarthy, M. V., et al. (2005) *Cell Metabolism* 1:309-322). Db/+ mice fed a high fructose diet exhibit reduced liver triglyceride levels and improved insulin sensitivity when treated for 28 days with platensimycin, a covealent inhibitor of FASN. (Wu, M. et al. (2011) *PNAS* 108(13):5378-5383). Ambient glucose levels are also reduced in db/db mice following treatment with platensimycin. These results provide evidence that inhibiting FASN can yield therapeutically relevant benefits in animal models of diabetes and related metabolic disorders. Thus the disclosed FASN inhibitors are useful in the treatment of disorders characterized by disregulation in these systems. Without limitation, examples include steatosis and diabetes.

Pharmaceutical Compositions, Formulations, Routes of Administration, and Effective Doses Also provided herein are pharmaceutical compositions comprising the compounds of the present disclosure.

In various aspects, the present disclosure provides pharmaceutical compositions comprising any one of the compounds of Structures I, II, III, IIIb, IIIc, IV, V and VI and a pharmaceutically acceptable carrier, excipient, or diluent.

In certain aspects, the present disclosure provides pharmaceutical compositions comprising any one of the compounds of TABLE 26 and a pharmaceutically acceptable carrier, excipient, or diluent.

Yet another aspect of the present invention relates to formulations, routes of administration and effective doses for pharmaceutical compositions comprising an agent or combination of agents of the instant invention. Such pharmaceutical compositions can be used to treat viral infections as described above.

Compounds of the invention can be administered as pharmaceutical formulations including those suitable for oral (including buccal and sub-lingual), rectal, nasal, topical, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., *Pharmaceutical Dosage Forms and Drug Delivery Systems* (Lippencott Williams & Wilkins, Baltimore Md. (1999).

In various aspects, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In another aspect, the pharmaceutical preparation is substantially free of preservatives. In another aspect, the pharmaceutical preparation can contain at least one preservative. General methodology on pharmaceutical dosage forms is found in Ansel et al., *Pharmaceutical Dosage Forms and Drug Delivery Systems* (Lippencott Williams & Wilkins, Baltimore Md. (1999)). It will be recognized that, while any suitable carrier known to those of ordinary skill in the art can be employed to administer the compositions of this invention, the type of carrier will vary depending on the mode of administration.

Compounds can also be encapsulated within liposomes using well-known technology. Biodegradable microspheres can also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The compound can be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," *Drug Carriers in Biology and Medicine*, pp. 2.sup.87-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The concentration of drug can be adjusted, the pH of the solution buffered and the isotonicity adjusted to be compatible with intravenous injection, as is well known in the art.

The compounds of the invention can be formulated as a sterile solution or suspension, in suitable vehicles, well known in the art. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration. Suitable formulations and additional carriers are described in Remington *The Science and Practice of Pharmacy* (20$^{th}$ Ed., Lippincott Williams & Wilkins, Baltimore Md.), the teachings of which are incorporated by reference in their entirety herein.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the agent(s) contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

The agent(s) (or pharmaceutically acceptable salts can be administered per se or in the form of a pharmaceutical composition wherein the active agent(s) is in an admixture or mixture with one or more pharmaceutically acceptable carriers.

EXAMPLES

Example 1

Synthesis of Compounds of the Present Disclosure

General:

All reactions and manipulations described were carried out in well ventilated fume-hoods. Operations and reactions carried out at elevated or reduced pressure were carried out behind blast shields. Abbreviations: ACN, acetonitrile; AcOH, acetic acid; AIBN, azobisisobutyronitrile; $BF_3$-$Et_2O$, boron trifluoride diethyl etherate; $(Boc)_2O$, di-tert-butyl dicarbonate; BuLi, butyl lithium; CDI, 1,1'-Carbonyldiimidazole; DBU, 1,8-Diazabicyclo[5.4.0]undec-7-ene; DCE, 1,2-dichloroethane; DCM, dichloromethane or methylene chloride; DIEA, N,N-Diisopropylethylamine; DMA, N,N-dimethylacetamide; DMAP, 4-dimethylaminopyridine; DME, 1,2-dimethoxyethane; DMEDA—N,N'-dimethylethylenediamine; DMF, N,N-dimethylformamide; DMSO, dimethylsulfoxide; DPPP, 1,3-bis(diphenylphosphino)propane; EDC, 1-ethyl-3-(3-dimethylaminopropyl)carbodiimide; EDCI, 1-ethyl-3-(3-dimethylaminopropyl)carbodiimide hydrochloride; EtOAc, ethyl acetate; EtOH, Ethanol; HATU, 2-(1H-7-Azabenzotriazol-1-yl)-1,1,3,3-tetramethyl uronium hexafluorophosphate; HBTU, O-Benzotriazole-N,N,N',N'-tetramethyl-uronium-hexafluoro-phosphate or 2-(1H-Benzotriazole-1-yl)-1,1,3,3-tetramethylaminium hexafluorophosphate; HMPA, hexamethylphosphoramide; HOAc, acetic acid; HOBT, 1-Hydroxybenzotriazole; LDA, lithium diisopropylamine; m-CPBA, 3-chloroperbenzoic acid; MeOH, methanol; MSCl, methanesulfonyl chloride; MsOH, methanesulfonic acid; NaHMDS, sodium hexamethyldisilazane, NBS, N-bromosuccinimide; NCS, N-chlorosuccinimide; NIS, N-iodosuccinimide; $Pd(dppf)Cl_2$, [1,1'-Bis(diphenylphosphino)ferrocene]dichloropalladium(II); PE, petroleum ether; PPA, polyphosporic acid; PTAT, phenyltrimethylammonium tribromide; PTSA, p-toluenesulfonic acid; Py, pyridine; Pyr, pyridine; TBAF, tetrabutylammonium fluoride; TEA, triethylamine; TFA, trifluoroacetic acid; TFAA, trifluoroacetic anhydride; THF, tetrahydrofuran; TMSCl, chlorotrimethylsilane; TMSCN, trimethylsilyl cyanide; TsOH, p-toluenesulfonic acid.

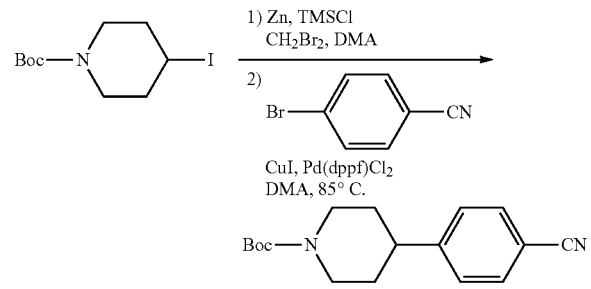

Compound 1.1. tert-Butyl 4-(4-cyanophenyl)piperidine-1-carboxylate

Into a 500-mL three neck round-bottom flask, which was purged and maintained with an inert atmosphere of nitrogen, was placed a suspension of Zn (21.6 g, 330 mmol) in DMA (53 mL). A 7:5 v/v mixture of TMSCl/1,2-dibromoethane (5.8 mL) was added to the mixture drop-wise at a rate to maintain the temperature below 65° C. The mixture was stirred for an additional 10 min, then a solution of tert-butyl 4-iodopiperidine-1-carboxylate (68.7 g, 220 mmol) in DMA (122 mL) was added drop-wise at 40-45° C. and the mixture was stirred at the same temperature for 30 min. The mixture was cooled to room temperature and stirring was ceased to allow for the zinc powder to settle. Into another 500-mL round-bottom flask, which was purged and maintained with an inert atmosphere of nitrogen, was placed a mixture of 4-bromobenzonitrile (20 g, 110 mmol), CuI (2.1 g, 11 mmol), $Pd(dppf)Cl_2$ (4.51 g, 5.5 mmol) and DMA (100 mL). The freshly prepared zinc reagent solution was decanted into an addition funnel and added drop-wise to the mixture at room temperature. The resulting mixture was stirred at 85° C. for 4 h, then cooled to 20° C. and diluted with methyl tert-butyl ether (500 mL) and carefully quenched with 1 M ammonium chloride (500 mL). The mixture was stirred at room temperature for 30 min and then filtered to remove solids. The organic layer was washed with saturated aqueous ammonium chloride (100 mL), followed by brine (3×100 mL), dried ($Na_2SO_4$), filtered, and concentrated under reduced pressure. The residue was purified by silica gel chromatography with ethyl acetate/petroleum ether (1:10) as the eluent to yield the title compound as a brown oil (20 g, crude) and used in the next step without additional purification.

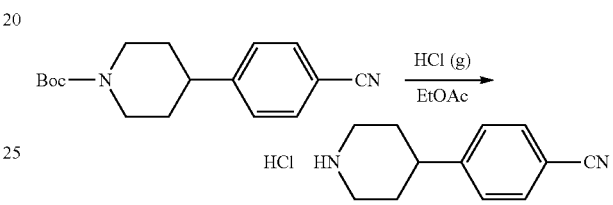

Compound 1.2. 4-(Piperidin-4-yl)benzonitrile hydrochloride

Into a 500-mL three neck round-bottom flask, was placed a solution of tert-butyl 4-(4-cyanophenyl)piperidine-1-carboxylate (compound 1.1, 20 g, crude) in ethyl acetate (200 mL). Hydrogen chloride (gas) was introduced to the solution and the resulting mixture was stirred for 30 min at room temperature. The solids were collected by filtration, then washed with ethyl acetate (100 mL) and ether (100 mL) to yield the title compound as a white solid (14 g, 57% over two steps).

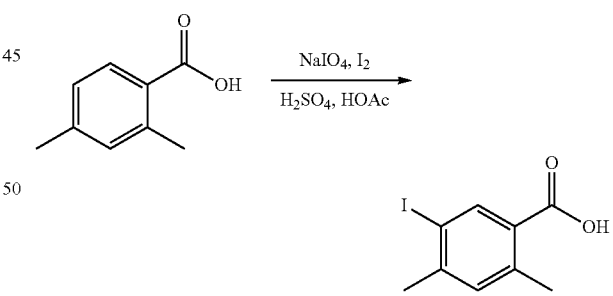

Compound 1.3. 5-Iodo-2,4-dimethylbenzoic acid

A solution of 2,4-dimethylbenzoic acid (20.0 g, 133 mmol), sodium periodate (14.27 g, 66.72 mmol), iodine (37.25 g, 146.8 mmol), and sulfuric acid (1.96 g, 20.0 mmol) in acetic acid (150 mL) was stirred at 110° C. for 6 h. The mixture was allowed to cool to ambient temperature then carefully diluted into water (1.2 L). To this mixture was carefully added saturated aqueous $Na_2S_2O_3$ (800 mL). The resulting solids were collected by filtration, then dissolved in ethyl acetate (1.2 L) and washed with saturated aqueous Na₂S₂O₃ (300 mL) followed by brine (400 mL). The organic layer was dried (Na₂SO₄), filtered, and concentrated under reduced pressure. The crude residue was re-crystallized from ethanol:H₂O (2:1) to yield the title compound as a white solid (30 g, 82%).

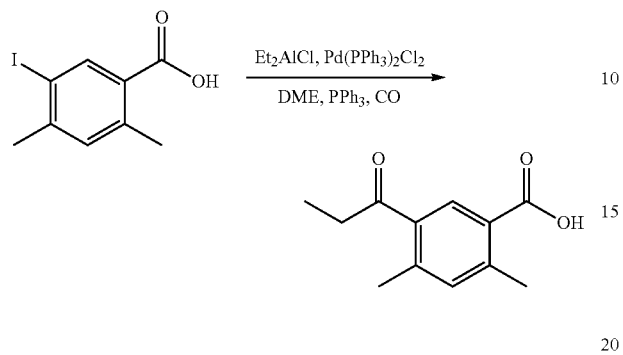

Compound 1.4. 2,4-Dimethyl-5-propionylbenzoic acid

Into a 100-mL autoclave (30 atm), was placed a solution of 5-iodo-2,4-dimethylbenzoic acid (compound 1.3, 2.00 g, 7.24 mmol) in ethylene glycol dimethyl ether (20 mL). Triphenylphosphine (190 mg, 0.73 mmol), Pd(PPh₃)₂Cl₂ (500 mg, 0.71 mmol) and diethylaluminum chloride (2M, 10.8 mL, 21.6 mmol) were added to the reaction mixture. The resulting mixture was stirred under pressure with carbon monoxide (gas, 30 atm) at 80° C. for 15 h. (CAUTION: Highly toxic gas at high pressure. All necessary safety precautions were performed). After cooling to room temperature, the mixture was carefully purged, then quenched with 20 mL of water. Aqueous HCl (2M) was added carefully to adjust the pH to 5-6 and the aqueous layer was extracted with ethyl acetate (100 mL). The combined organic layers were washed with brine (2×100 mL), dried (Na₂SO₄), filtered, and concentrated under reduced pressure. The residue was purified by silica gel column chromatography with ethyl acetate/petroleum ether (1:40-1:20) as the eluent to yield the title compound as a light yellow solid (1.2 g, 80%).

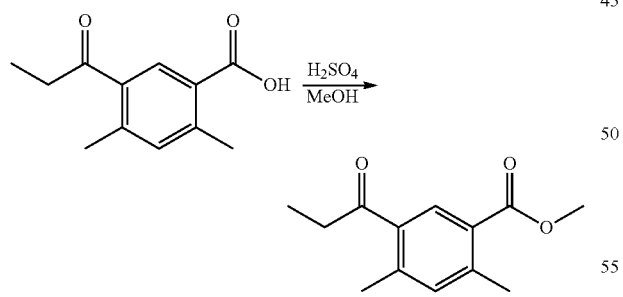

Compound 1.5. Methyl 2,4-dimethyl-5-propionylbenzoate

To a 100-mL round-bottom flask, was carefully added 2,4-dimethyl-5-propionylbenzoic acid (compound 1.4, 1.2 g, 5.8 mmol), sulfuric acid (1.0 mL, 19 mmol) and methanol (30 mL). The resulting solution was stirred at 70° C. for 5 h, then concentrated under reduced pressure. The residue was carefully diluted with H₂O (50 mL) and extracted ethyl acetate (100 mL). The organic layer was washed with H₂O (2×100 mL) and brine (100 mL), dried (Na₂SO₄), filtered, and concentrated under reduced pressure. The residue was purified by silica gel columnchromatography with ethyl acetate/petroleum ether (1:100) as the eluent to yield the title compound as a light yellow solid (0.90 g, 70%).

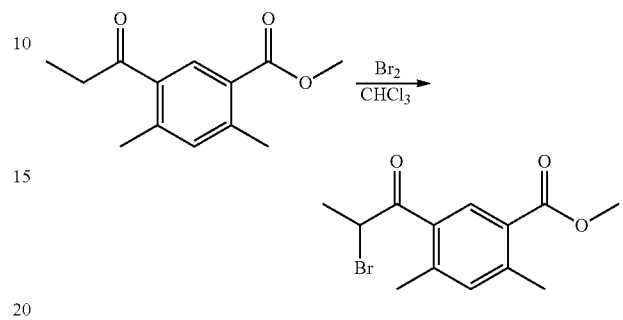

Compound 1.6. Methyl 5-(2-bromopropanoyl)-2,4-dimethylbenzoate

Into a 100-mL round-bottom flask, was placed a solution of methyl 2,4-dimethyl-5-propionylbenzoate (compound 1.5, 600 mg, 2.72 mmol) in chloroform (20 mL). Bromine (154 µL, 3.00 mmol) was added and the resulting solution was stirred at 20° C. for 2 h. The mixture was concentrated under reduced pressure to yield the title compound as a yellow oil (1.0 g, crude), which was used in the next step without further purification.

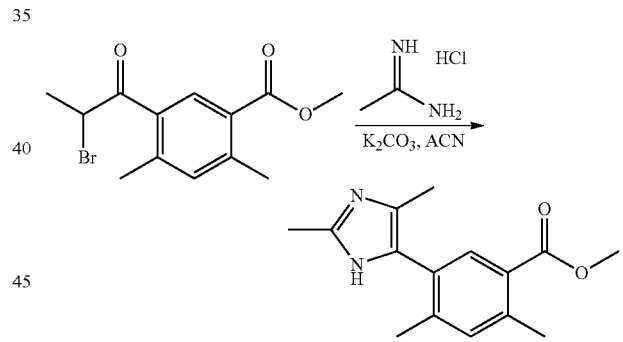

Compound 1.7. Methyl 5-(2,4-dimethyl-1H-imidazol-5-yl)-2,4-dimethylbenzoate

Into a round-bottom flask, was placed a solution of methyl 5-(2-bromopropanoyl)-2,4-dimethylbenzoate (compound 1.6, 400 mg, 1.34 mmol) in acetonitrile (30 mL). Acetimidamide hydrochloride (260 mg, 2.75 mmol) and potassium carbonate (550 mg, 3.99 mmol) were added and the resulting mixture was stirred at 80° C. for 15 h. After cooling to room temperature, the mixture was concentrated under reduced pressure and the residue was diluted with ethyl acetate (50 mL) and washed with brine (2×25 mL), dried (Na₂SO₄), filtered, and concentrated under reduced pressure. The residue was purified by silica gel column chromatography with ethyl acetate/petroleum ether (1:1) to ethyl acetate as the eluent to yield the title compound as a yellow oil (0.20 g, 58%).

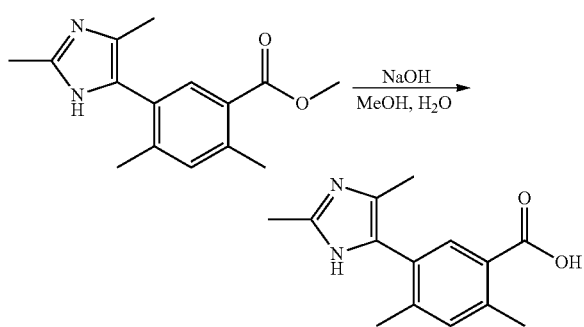

Compound 1.8. 5-(2,4-Dimethyl-1H-imidazol-5-yl)-2,4-dimethylbenzoic acid

Into a 50-mL round-bottom flask, were placed methyl 5-(2,4-dimethyl-1H-imidazol-5-yl)-2,4-dimethylbenzoate (compound 1.7, 300 mg, 1.16 mmol) and sodium hydroxide (465 mg, 11.6 mmol) in methanol (20 mL) and H$_2$O (5 mL). The resulting solution was stirred at 55° C. for 4 h, then after cooling to room temperature, aqueous HCl (2 M) was added to adjust the pH to 5. The resulting mixture was concentrated under reduced pressure and the residue was dissolved in methanol (5 mL). The solids were removed by filtration and the filtrate was concentrated under reduced pressure to yield the title compound as a light yellow solid (280 mg, crude), which was used in the next step without further purification.

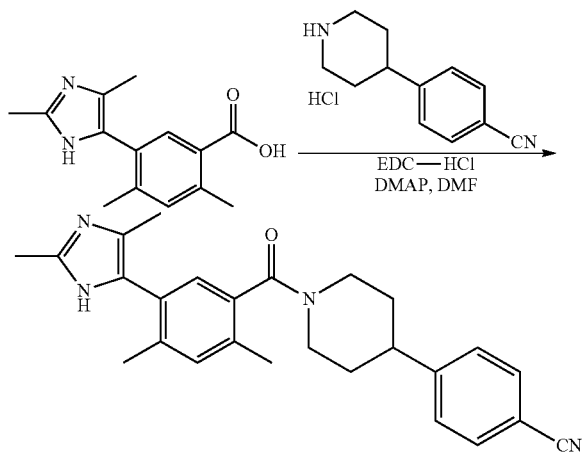

Compound 1. 4-(1-(5-(2,4-Dimethyl-1H-imidazol-5-yl)-2,4-dimethylbenzoyl)piperidin-4-yl)benzonitrile A mixture of 5-(2,4-dimethyl-1H-imidazol-5-yl)-2,4-dimethylbenzoic acid (compound 1.8, 280 mg, 1.15 mmol), EDC.HCl (330 mg, 1.72 mmol), 4-dimethylaminopyridine (420 mg, 3.44 mmol), and HOBT (180 mg, 1.33 mmol) in N,N-dimethylformamide (6 mL) was stirred at room temperature. After 5 min, 4-(piperidin-4-yl)benzonitrile hydrochloride (compound 1.2, 230 mg, 1.03 mmol) was added and the resulting solution was stirred at room temperature for 15 h, then quenched with ice water (20 mL). The aqueous was extracted with ethyl acetate (50 mL) and the combined organics was washed with brine (2×50 mL), dried (Na$_2$SO$_4$), filtered, and concentrated under reduced pressure. The residue was purified by Prep-HPLC with the following conditions (1#-Pre-HPLC-001(SHIMADZU)): Column, SunFire Prep C18 OBD Column, 5 um, 19*150 mm; mobile phase, water with 0.05% TFA and CH$_3$CN (22% CH$_3$CN up to 37% in 7 min, up to 100% in 2 min, down to 22% in 1 min); Detector, Waters 2489, 254 & 220 nm. The fractions containing pure compound were combined and lyophilized to yield the title compound as a white solid (214 mg, 50%). m/z (ES+) 413 (M+H)$^+$. $^1$H NMR (300 MHz, CD$_3$OD): δ 7.68 (d, J=7.8 Hz, 2H), 7.47 (d, J=8.4 Hz, 2H), 7.36 (br s, 1H), 7.27 & 7.16 (2 singlets, rotamers, Ar—H, 1H), 4.9-4.82 (m, 1H partially obscured by water peak), 3.72-3.55 (m, 1H), 3.35-3.20 (m, 1H partially overlapped with methanol solvent peak), 3.08-2.92 (m, 2H), 2.65 (s, 3H), 2.44 & 2.34 (2 singlets, rotamers, Ar—CH$_3$, 3H), 2.29 (s, 3H), 2.22 (s, 3H), 2.10-1.96 (m, 1H), 1.93-1.53 (m, 3H).

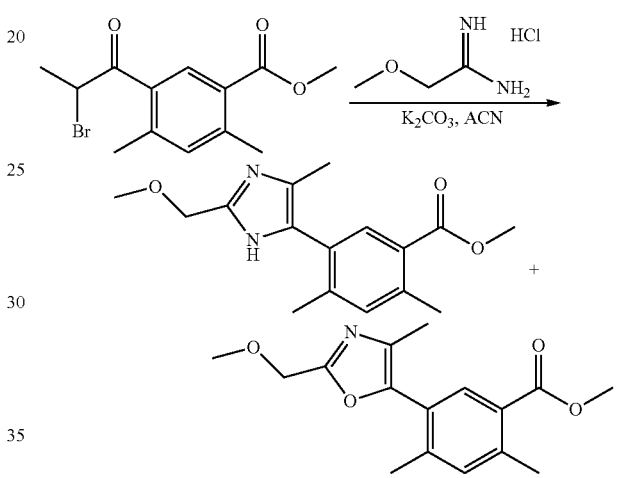

Compounds 2.1 and 2.2. Methyl 5-(2-(methoxymethyl)-4-methyl-1H-imidazol-5-yl)-2,4-dimethylbenzoate and methyl 5-(2-(methoxymethyl)-4-methyloxazol-5-yl)-2,4-dimethylbenzoate Into a 100-mL round-bottom flask, was placed a mixture of methyl 5-(2-bromopropanoyl)-2,4-dimethylbenzoate (compound 1.6, 600 mg, 2.01 mmol), 2-methoxyethanimidamide hydrochloride (510 mg, 4.09 mmol), potassium carbonate (840 mg, 6.08 mmol) and acetonitrile (30 mL). The resulting mixture was stirred at 80° C. overnight, then cooled to room temperature and concentrated under reduced pressure. The residue was diluted with H$_2$O (50 mL) and extracted with ethyl acetate (100 mL). The organics was washed brine (2×50 mL), dried (Na$_2$SO$_4$), filtered, and concentrated under reduced pressure. The residue was purified by silica gel chromatography with ethyl acetate/petroleum ether (1:2) as the eluent to yield methyl 5-(2-(methoxymethyl)-4-methyl-1H-imidazol-5-yl)-2,4-dimethylbenzoate (compound 2.1) (0.11 g, 19%) and methyl 5-(2-(methoxymethyl)-4-methyloxazol-5-yl)-2,4-dimethylbenzoate (compound 2.2) (0.30 g, 52%), both as a yellow oils.

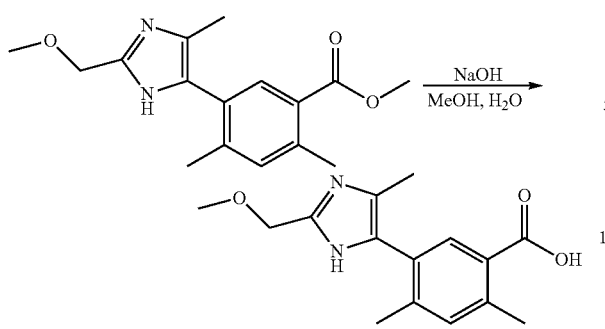

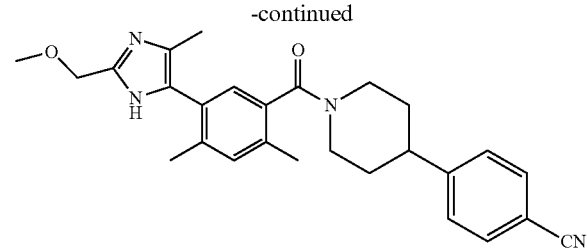

Compound 2. 4-(1-(5-(2-(Methoxymethyl)-4-methyl-1H-imidazol-5-yl)-2,4-dimethylbenzoyl)piperidin-4-yl)benzonitrile Compound 2.3. 5-(2-(Methoxymethyl)-4-methyl-1H-imidazol-5-yl)-2,4-dimethylbenzoic acid Into a 50-mL round-bottom flask, was placed a solution of methyl 5-(2-(methoxymethyl)-4-methyl-1H-imidazol-5-yl)-2,4-dimethylbenzoate (compound 2.1, 150 mg, 0.52 mmol) in methanol (15 mL) and H₂O (5 mL). Sodium hydroxide (280 mg, 7.00 mmol) was added and the resulting solution was stirred at 40° C. for 15 h. After cooled to room temperature, the solution was adjusted to pH 5 with aqueous HCl (2 M) and the resulting mixture was concentrated under reduced pressure. The residue was dissolved in methanol (5 mL) and the solids were filtered off. The filtrate was concentrated under reduced pressure to yield the title compound as a light yellow solid (140 mg, crude), which was used in the next step without further purification.

A mixture of 5-(2-(methoxymethyl)-4-methyl-1H-imidazol-5-yl)-2,4-dimethylbenzoic acid (compound 2.3, 140 mg, 0.51 mmol), EDC.HCl (150 mg, 0.78 mmol), 4-dimethylaminopyridine (190 mg, 1.56 mmol), and HOBT (80 mg, 0.59 mmol) in N,N-dimethylformamide (6 mL). The mixture was stirred at room temperature, then after 15 min, 4-(piperidin-4-yl)benzonitrile hydrochloride (compound 1.2, 100 mg, 0.45 mmol) was added. The resulting solution was stirred for 15 h at room temperature, then quenched with 20 mL of H₂O. The aqueous was extracted with ethyl acetate (40 mL) and the combined organics was washed with brine (2×30 mL), dried (Na₂SO₄), filtered, and concentrated under reduced pressure. The residue was purified by Prep-HPLC with the following conditions (1#-Pre-HPLC-001(SHI-MADZU)): Column, SunFire Prep C18 OBD Column, Sum, 19*150 mm; mobile phase, water with 0.05% TFA and CH₃CN (23% CH₃CN up to 38% in 7 min, up to 100% in 2 min, down to 23% in 1 min); Detector, Waters 2489, 254 &220 nm. The fractions containing pure compound were combined and lyophilized to yield the title compound as a white solid (70.4 mg, 35%).

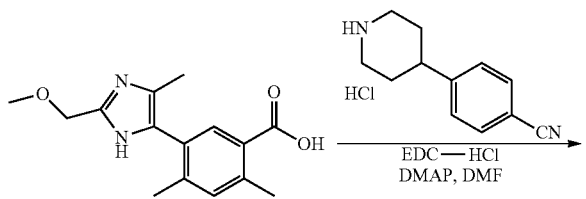

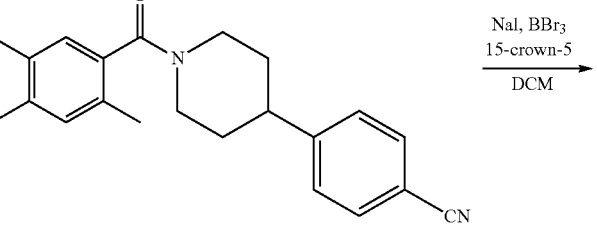

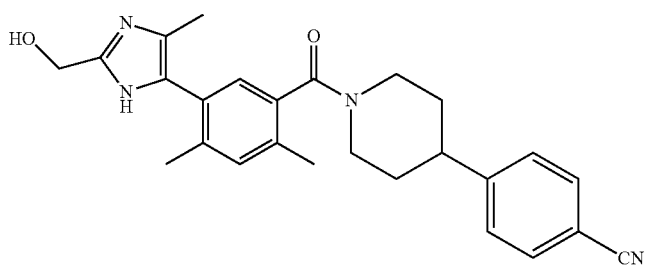

Compound 3. 4-(1-(5-(2-(Hydroxymethyl)-4-methyl-1H-imidazol-5-yl)-2,4-dimethylbenzoyl)piperidin-4-yl)benzonitrile Into a 50-mL 3-necked round-bottom flask, which was purged and maintained with an inert atmosphere of nitrogen, was placed a mixture of 4-(1-(5-(2-(methoxymethyl)-4-methyl-1H-imidazol-5-yl)-2,4-dimethylbenzoyl)piperidin-4-yl)benzonitrile (compound 2, 30 mg, 0.068 mmol), NaI (20 mg, 0.13 mmol), 15-crown-5 (30 mg, 0.14 mmol) and dichloromethane (10 mL). The mixture was cooled to −30° C. and boron tribromide (70 mg, 0.28 mmol) was added. The resulting mixture was allowed to warm to room temperature and stirred for 15 h. The reaction mixture was carefully quenched by the addition of saturated aqueous sodium bicarbonate (10 mL) and the resulting mixture was extracted dichloromethane (2×20 mL). The combined organics was washed with saturated aqueous $Na_2S_2O_3$ (2×20 mL), then dried ($Na_2SO_4$), filtered, and concentrated under reduced pressure. The crude product was purified by Prep-HPLC with the following conditions (1#-Pre-HPLC-001(SHIMADZU)): Column, SunFire Prep C18 OBD Column, Sum, 19*150 mm; mobile phase, water with 0.05% TFA and $CH_3CN$ (21% $CH_3CN$ up to 35% in 8 min, up to 100% in 2 min, down to 21% in 1 min); Detector, Waters 2489, 254&220 nm. The fractions containing pure compound were combined and lyophilized to yield the title compound as a white solid (5.0 mg, 17%). m/z (ES+) 429 (M+H)$^+$. $^1$H NMR (400 MHz, $CD_3OD$): δ 7.74-7.65 (m, 2), 7.48 (d, J=8.0 Hz, 2H), 7.38 (d, J=5.6 Hz, 1H), 7.29 & 7.16 (2 singlets, rotamers, Ar—H, 1H), 4.9 (1H obscured by water peak), 3.64 (app t, J=15.0 Hz, 1H), 3.35-3.21 (m, 1H partially overlapped with methanol solvent peak), 3.09-2.93 (m, 1H), 2.45 & 2.34 (2 singlets, rotamers, Ar—$CH_3$, 3H), 2.29 (s, 3H), 2.24 (s, 3H), 2.09-1.97 (m, 1H), 1.92-1.71 (m, 2H), 1.70-1.55 (m, 1H).

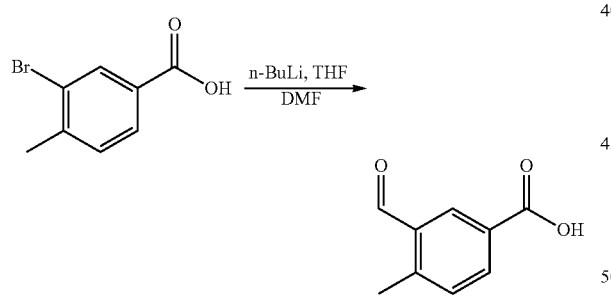

Compound 4.1. 3-Formyl-4-methylbenzoic acid

To a stirred solution of 3-bromo-4-methylbenzoic acid (2.14 g, 10.0 mmol) in tetrahydrofuran (30 mL) under nitrogen at −78° C. was added n-BuLi (10 mL, 2.5 M in THF, 25 mmol) drop-wise. The mixture was stirred for 1 h below −70° C., then DMF (5 mL) was slowly added. The resulting solution was slowly warmed to room temperature and stirred for 1 h, then carefully quenched by slow addition of water (50 mL). The pH was adjusted to 3-4 using aqueous HCl (6 M) and the resulting mixture was extracted with ethyl acetate (2×50 mL). The combined organics was dried ($Na_2SO_4$), filtered, and concentrated under reduced pressure to yield the title compound as a yellow solid (1.6 g, 98%).

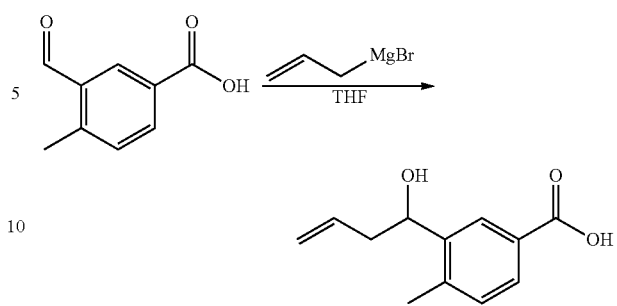

Compound 4.2. 3-(1-Hydroxybut-3-en-1-yl)-4-methylbenzoic acid

Into a 100-mL 3-necked round-bottom flask, which was purged and maintained with an inert atmosphere of nitrogen, was placed a solution of 3-formyl-4-methylbenzoic acid (compound 4.1, 2.00 g, 12.2 mmol) in tetrahydrofuran (50 mL). The mixture was cooled to −10 to 0° C. then allylmagnesium bromide (1M in $Et_2O$, 24.4 mL, 24.4 mmol) was added drop-wise. The resulting mixture was stirred for 1 hr at −10-0° C., then carefully quenched with saturated aqueous $NH_4Cl$ (50 mL) and diluted with ethyl acetate (200 mL). The organic layer was washed with saturated aqueous $NH_4Cl$ (80 mL) and brine (2×80 mL), dried ($Na_2SO_4$), filtered, and concentrated under reduced pressure to yield the title compound as a light red solid (2.4 g, crude), which was used in the next step without further purification.

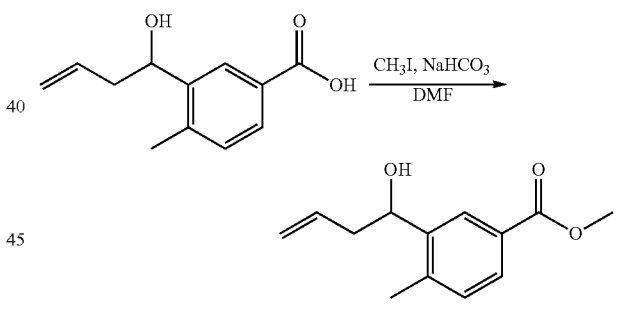

Compound 4.3. Methyl 3-(1-hydroxybut-3-en-1-yl)-4-methylbenzoate

Into a 100-mL round-bottom flask, was added a solution of 3-(1-hydroxybut-3-en-1-yl)-4-methylbenzoic acid (compound 4.2, 1.4 g, 6.79 mmol) in N,N-dimethylformamide (20 mL). Sodium bicarbonate (1.14 g, 13.6 mmol) and methyl iodide (0.847 mL, 13.6 mmol) were added and the resulting mixture was stirred overnight at 25° C. The reaction was quenched with saturated aqueous $Na_2S_2O_3$ (50 mL) and diluted with EtOAc (150 mL). The organic layer was washed with brine (3×50 mL), dried ($Na_2SO_4$), filtered, and concentrated under reduced pressure. The residue was purified by silica gel chromatography with ethyl acetate/petroleum ether (1:3) as the eluent to yield the title compound as a light yellow oil (800 mg, 53%).

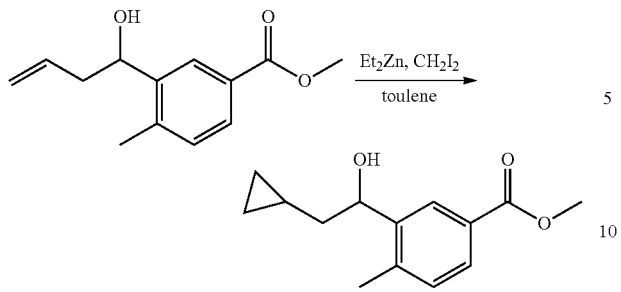

Compound 4.4. Methyl 3-(2-cyclopropyl-1-hydroxyethyl)-4-methylbenzoate

Into a 100-mL 3-necked round-bottom flask, which was purged and maintained with an inert atmosphere of nitrogen, was placed a solution of methyl 3-(1-hydroxybut-3-en-1-yl)-4-methylbenzoate (compound 4.3, 50 mg, 0.23 mmol). Diethylzinc (1 M in toluene) (3.45 mL, 3.45 mmol) in toluene (10 mL) was added and the mixture was cooled to 0-5° C., then diiodomethane (924 mg, 3.45 mmol) was added drop-wise. The resulting mixture was stirred for 2 h at room temperature, then carefully quenched with 1 M aqueous HCl (50 mL) and diluted with MTBE (50 mL). The aqueous phase was extracted with MTBE (3×20 mL) and the combined organics was washed with saturated sodium bicarbonate (2×20 mL), brine (2×20 mL), dried ($Na_2SO_4$), filtered, and concentrated under reduced pressure. The residue was purified by silica gel chromatography with ethyl acetate/petroleum ether (1:3) as the eluent to yield the title compound as a yellow oil (40 mg, 74%).

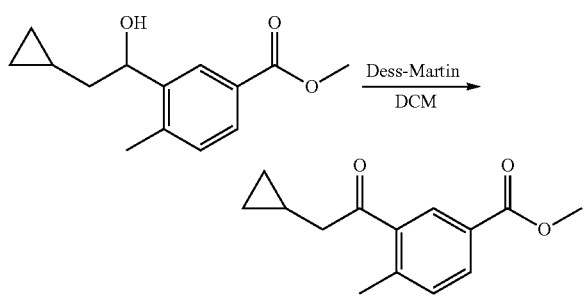

Compound 4.5. Methyl 3-(2-cyclopropylacetyl)-4-methylbenzoate

Into a 100-mL round-bottom flask, was placed a solution of methyl 3-(2-cyclopropyl-1-hydroxyethyl)-4-methylbenzoate (compound 4.4, 200 mg, 0.85 mmol) in dichloromethane (30 mL). This was followed by the addition of Dess-Martin periodinane (721 mg, 1.70 mmol) in portions at room temperature. The resulting solution was stirred for 1 h at room temperature, then quenched with saturated aqueous $Na_2S_2O_3$ (30 mL). The resulting mixture was extracted with DCM (3×20 mL) and the combined organics was washed with brine (2×20 mL), dried ($Na_2SO_4$), filtered, and concentrated under reduced pressure. The residue was purified by silica gel chromatography with ethyl acetate/petroleum ether (1:5) as the eluent to yield the title compound as a yellow oil (150 mg, 75%).

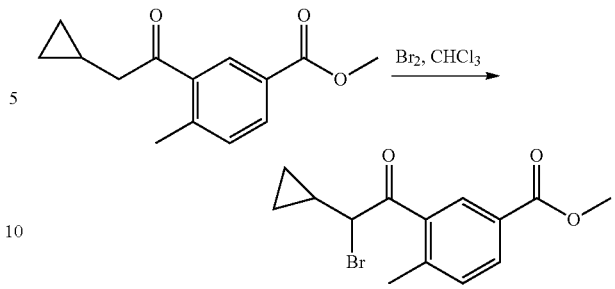

Compound 4.6. Methyl 3-(2-bromo-2-cyclopropylacetyl)-4-methylbenzoate

Into a 100-mL round-bottom flask, was placed a solution of methyl 3-(2-cyclopropylacetyl)-4-methylbenzoate (compound 4.5, 150 mg, 0.65 mmol) in chloroform (15 mL). Bromine (40 µL, 0.78 mmol) in chloroform (2 mL) was added drop-wise to the reaction mixture. The resulting solution was stirred for 2 h at room temperature, then concentrated under reduced pressure to yield the title compound as a yellow oil (200 mg, crude), which was used in the next step without further purification.

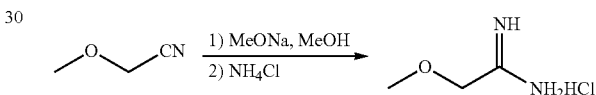

Compound 4.7. 2-Methoxyacetimidamide hydrochloride

Into a 250-mL round-bottom flask, was placed a solution of 2-methoxyacetonitrile (6.00 g, 84.4 mmol) in methanol (60 mL). Sodium methoxide (860 mg, 15.9 mmol) was added and the mixture was stirred at room temperature for 40 h. Ammonium chloride (4.52 g, 84.5 mmol) was then added and the mixture was stirred at 40° C. for 12 h then concentrated under reduced pressure. The residue was diluted with $H_2O$ (20 mL) and washed with ethyl acetate (2×20 mL). The aqueous was concentrated under reduced pressure to yield the title compound as a yellow solid (5 g, crude), which was used in the next step without further purification.

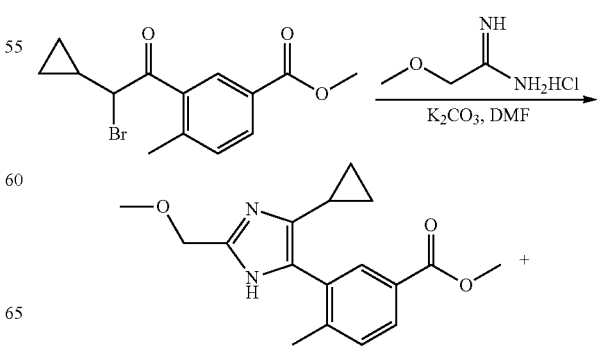

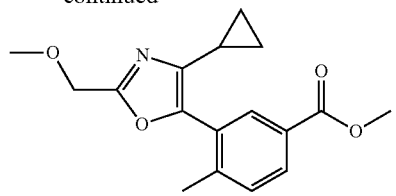

Compound 4.8 and compound 4.9. Methyl 3-(4-cyclopropyl-2-(methoxymethyl)-1H-imidazol-5-yl)-4-methylbenzoate and methyl 3-(4-cyclopropyl-2-(methoxymethyl)oxazol-5-yl)-4-methylbenzoate Into a 100-mL round-bottom flask, which was purged and maintained with an inert atmosphere of nitrogen, was placed methyl 3-(2-bromo-2-cyclopropylacetyl)-4-methylbenzoate (compound 4.6, 150 mg, 0.48 mmol), 2-methoxyacetimidamide hydrochloride (compound 4.7, 90 mg, 0.72 mmol), potassium carbonate (200 mg, 1.44 mmol), and N,N-dimethylformamide (15 mL). The resulting mixture was stirred at 80° C. for 3 h, then diluted with ethyl acetate (100 mL). The mixture was washed with brine (3×30 mL) and water (3×30 mL), dried (Na$_2$SO$_4$), filtered, and concentrated under reduced pressure. The residue was purified by silica gel chromatography with ethyl acetate/petroleum ether (1:2) as the eluent to yield methyl 3-(4-cyclopropyl-2-(methoxymethyl)-1H-imidazol-5-yl)-4-methylbenzoate (compound 4.8) (30 mg, 21%) and methyl 3-(4-cyclopropyl-2-(methoxymethyl)oxazol-5-yl)-4-methylbenzoate (compound 4.9) (60 mg, 41%), both as a yellow oils.

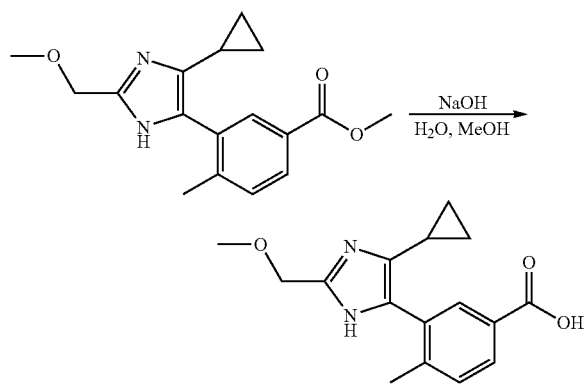

Compound 4.10. 3-(4-Cyclopropyl-2-(methoxymethyl)-1H-imidazol-5-yl)-4-methylbenzoic acid Into a round-bottom flask, was placed a solution of methyl 3-(4-cyclopropyl-2-(methoxymethyl)-1H-imidazol-5-yl)-4-methylbenzoate (compound 4.8, 35 mg, 0.12 mmol) in methanol (5 mL), a solution of sodium hydroxide (9.6 mg, 0.24 mmol) in water (0.3 mL) was added to the reaction mixture. The resulting solution was stirred for 2 h at room temperature, then diluted with water (5 mL). Aqueous HCl (6 M) was carefully added to adjust the pH to 1-2 and the mixture was extracted with dichloromethane (4×10 mL). The combined organics were dried (Na$_2$SO$_4$), filtered, and concentrated under reduced pressure to yield the title compound as a yellow oil (30 mg, crude), which was used in the next step without further purification.

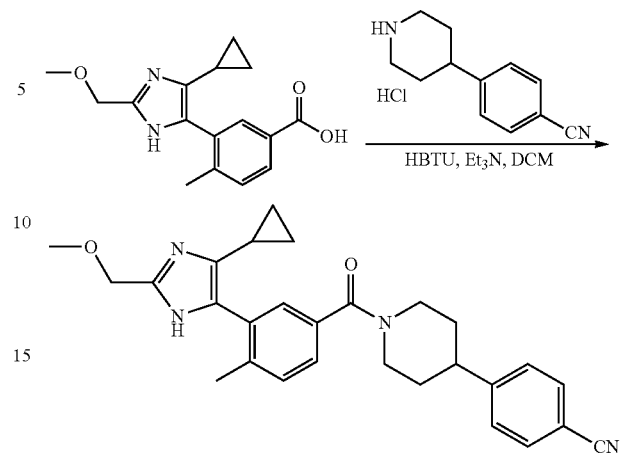

Compound 4. 4-(1-(3-(4-Cyclopropyl-2-(methoxymethyl)-1H-imidazol-5-yl)-4-methylbenzoyl)piperidin-4-yl)benzonitrile Into a round-bottom flask, was placed a solution of 3-(4-cyclopropyl-2-(methoxymethyl)-1H-imidazol-5-yl)-4-methylbenzoic acid (compound 4.10, 30 mg, 0.10 mmol) in dichloromethane (5 mL). HBTU (76 mg, 0.20 mmol), 4-(piperidin-4-yl)benzonitrile hydrochloride (compound 1.2, 35 mg, 0.15 mmol, 1.50 equiv) and triethylamine (28 µL, 0.20 mmol) were added and the mixture was stirred overnight at room temperature. The mixture was diluted with DCM (30 mL) and washed with water (3×15 mL), dried (Na$_2$SO$_4$), filtered, and concentrated under reduced pressure. The residue was purified by Prep-HPLC with the following conditions (1#-Pre-HPLC-001(SHIMADZU)): Column, SunFire Prep C18 OBD Column, 5 um, 19*150 mm; mobile phase, water with 0.05% TFA and CH$_3$CN (25.0% CH$_3$CN up to 38.0% in 7 min, up to 100.0% in 3 min, down to 25.0% in 1 min); Detector, Waters 2489, 254 & 220 nm. The fractions containing pure compound were combined and lyophilized to yield the title compound as a white solid (5.9 mg, 12%). m/z (ES+) 455 (M+H)$^+$. $^1$H NMR (400 MHz, CDCl$_3$): δ 7.69 (d, J=8.0 Hz, 2H), 7.59-7.53 (m, 2H), 7.53-7.47 (m, 3H), ~4.9-4.75 (m, 1H partially obscured by water peak), 4.72 (s, 2H), 3.99-3.85 (m, 1H), 3.52 (s, 3H), ~3.3 (m, 1H overlapped with methanol solvent peak), 3.08-2.93 (m, 2H), 2.37 (s, 3H), 2.08-1.93 (m, 1H), 1.93-1.65 (m, 4H), 1.02-0.94 (m, 2H), 0.74-0.68 (m, 2H).

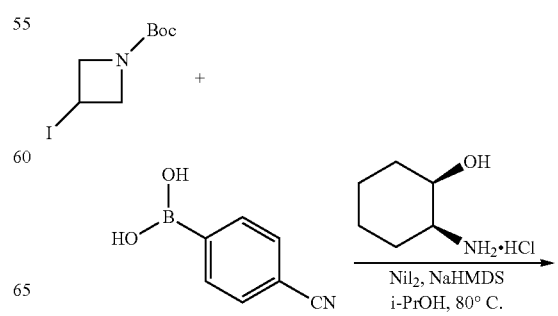

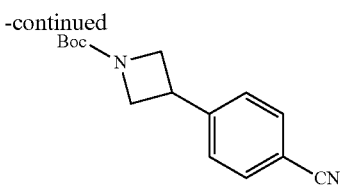

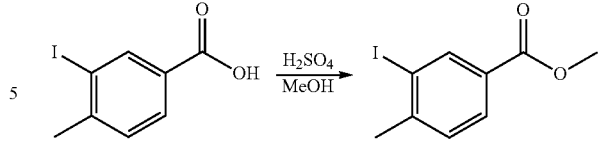

Compound 5.1. tert-Butyl 3-(4-cyanophenyl)azetidine-1-carboxylate

A modified procedure to that described in *Org. Lett.* 2008, 10, 3259 was performed as follows. To a 20-mL vial was added (4-cyanophenyl)boronic acid (1.01 g, 6.87 mmol), trans-2-aminocyclohexanol hydrochloride (32 mg, 0.21 mmol), nickel (II) iodide (66 mg, 0.21 mmol) and sodium hexamethyldisilazane (1.29 g, 7.06 mmol). The system was purged with nitrogen and charged with isopropyl alcohol (7 mL). The mixture was stirred at room temperature for 10 minutes then sonicated for 1 min. While stirring, tert-butyl 3-iodoazetidine-1-carboxylate (1.00 g, 3.53 mmol) was added and the syringe rinsed with isopropyl alcohol (2×500 µL). The suspension was stirred at 80° C. for 1 hour then concentrated under reduced pressure. The residue was purified by silica gel chromatography (hexanes to 25% ethyl acetate) to yield the title compound as a pale yellow oil which solidified upon standing (0.832 g, 46%). m/z (ES+) 203 (M-C$_4$H$_8$+H)$^+$. $^1$H NMR (400 MHz, CDCl$_3$): δ 7.65 (d with fine str., J=8.4 Hz, 2H), 7.43 (d with fine str., J=8.4 Hz, 2H), 4.37 (app t, J=8.8 Hz, 2H), 3.98-3.91 (m, 2H), 3.81-7.73 (m, 1H).

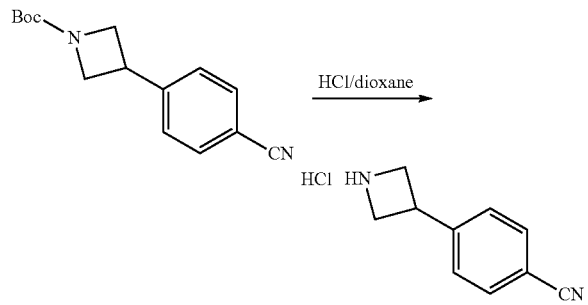

Compound 5.2. 4-(Azetidin-3-yl)benzonitrile hydrochloride tert-Butyl 3-(4-cyanophenyl)azetidine-1-carboxylate (compound 5.1, 100 mg, 0.387 mmol) was added to a 4-mL vial. HCl in dioxane (4 M, 500 µL, 2 mmol) was added and the unsealed mixture was stirred at room temperature for 1.5 hours. The mixture was concentrated under reduced pressure and the residue was dissolved in DCM and concentrated under reduced pressure. This was repeated with DCM twice to chase off any excess HCl to yield the title compound as a white powder (80 mg, over theory). m/z (ES+) 159 (M+H)$^+$.

Compound 5.3. Methyl 3-iodo-4-methylbenzoate

To a solution of 3-iodo-4-methylbenzoic acid (28.0 g, 0.107 mol) in MeOH (300 mL) at 0° C. was carefully added concentrated H$_2$SO$_4$ (30 mL). The mixture was heated at 60° C. overnight, then cooled and the solvent removed under reduced pressure. The residue was carefully poured onto ice-water (200 mL) and the mixture was extracted with EtOAc (500 mL). The organics was washed with water (100 mL), saturated NaHCO$_3$ (100 mL), brine (100 mL), dried (MgSO$_4$), filtered, and concentrated to yield the title compound as a brown oil (29.0 g, 98%). $^1$H NMR (400 MHz, CDCl$_3$) δ 8.47 (d, J=1.7 Hz, 1H), 7.90 (dd, J=7.9 Hz, 1.7 Hz, 1H), 7.29 (d, J=7.9 Hz, 1H), 3.90 (s, 2H), 2.48 (s, 3H).

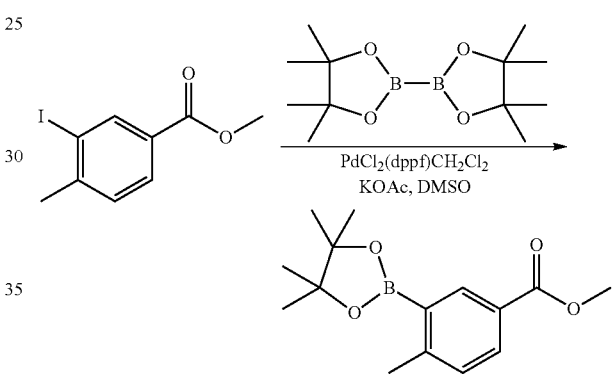

Compound 5.4. Methyl 4-methyl-3-(4,4,5,5-tetramethyl-1,3,2-dioxaborolan-2-yl)benzoate A mixture of methyl 3-iodo-4-methylbenzoate (compound 5.3, 5.00 g, 18.1 mmol), 4,4,4',4',5,5,5',5'-octamethyl-2,2'-bi(1,3,2-dioxaborolane) (5.20 g, 20.5 mmol), KOAc (5.33 g, 54.3 mmol) and PdCl$_2$(dppf).CH$_2$Cl$_2$ (0.74 g, 0.91 mmol) in DMSO (50 mL) was degassed with argon. The mixture was then heated at 80° C. under argon overnight. The mixture was allowed to cool then partitioned between EtOAc (400 mL) and water (80 mL). The organic phase was washed with water (80 mL), saturated aqueous NaHCO$_3$ (80 mL), brine (80 mL), dried (MgSO$_4$), filtered, and concentrated under reduced pressure. The residue was purified with silica gel chromatography (hexanes:EtOAc 20:1) to yield the title compound as a white crystalline solid (3.56 g, 71%). $^1$H NMR (400 MHz, CDCl$_3$) δ 8.41 (d, J=1.9 Hz, 1H), 7.97 (dd, J=8.0 Hz, 2.0 Hz, 1H), 7.23 (d, J=8.0 Hz, 1H), 3.90 (s, 3H), 2.58 (s, 3H), 1.35 (s, 12H).

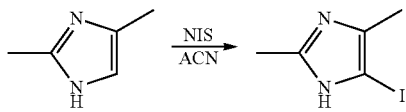

Compound 5.5. 5-Iodo-2,4-dimethyl-1H-imidazole

NIS (14.0 g, 62.4 mmol) was added portion-wise to a solution of 2,4-dimethyl-1H-imidazole (5.00 g, 52.0 mmol) in acetonitrile (100 mL). The mixture was heated at 80° C. for 16 hours, then cooled to room temperature. The solvent was removed under reduced pressure and the residue was partitioned between EtOAc (300 mL) and water (80 mL). The organic layer was washed with saturated sodium thiosulfate (50 mL), brine (50 mL), dried (MgSO$_4$) and concentrated under reduced pressure. The residue was purified with by silica gel column chromatography (hexanes:EtOAc 1:1 to 10% MeOH in EtOAc) to yield the title compound as a light yellow solid (8.56 g, 74%). m/z (ES+) 223 (M+H)$^+$. $^1$H NMR (400 MHz, CDCl$_3$) δ 9.69 (br s, 1H), 2.38 (s, 3H), 2.19 (s, 3H).)

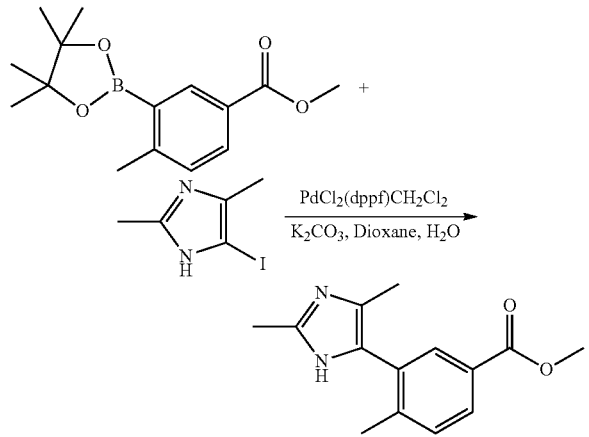

Compound 5.6. Methyl 3-(2,4-dimethyl-1H-imidazol-5-yl)-4-methylbenzoate

Methyl 4-methyl-3-(4,4,5,5-tetramethyl-1,3,2-dioxaborolan-2-yl)benzoate (compound 5.4, 3.56 g, 12.9 mmol), 5-iodo-2,4-dimethyl-1H-imidazole (compound 5.5, 3.43 g, 15.4 mmol), K$_2$CO$_3$ (5.33 g, 38.6 mmol) and PdCl$_2$(dppf).CH$_2$Cl$_2$ (1.05 g, 1.29 mmol) were added to a round bottom flask. The flask was purged with argon, then dioxane (70 mL) and water (20 mL) were added and the mixture was heated at 90° C. for 16 hours. The mixture was cooled then additional K$_2$CO$_3$ (1M, 25 mL, 25.0 mmol) and catalyst PdCl$_2$(dppf).CH$_2$Cl$_2$ (1.0 g, 1.2 mmol) were added. The mixture was heated at 90° C. for an additional 10 hours, then cooled to room temperature and filtered through Celite®. The solvent was removed under reduced pressure and the residue was cooled to 0° C. and acidified to pH 3-4 with aqueous HCl (2 M). The acidic mixture was washed with EtOAc (150 mL) and then the aqueous material was adjusted to pH 10-11 with aqueous sodium hydroxide (2 M) and extracted with EtOAc (5×200 mL). The combined organic phases were dried (MgSO$_4$), filtered, and concentrated under reduced pressure. The residue was purified by column chromatography (DCM to 5% MeOH in DCM) to yield the title compound as a thick brown oil (2.42 g, 77%). m/z (ES+) 245 (M+H)$^+$. $^1$H NMR (400 MHz, CDCl$_3$) δ 7.89-7.87 (m, 2H), 7.31 (d with fine str, J=8.6 Hz, 1H), 3.89 (s, 3H), 2.38 (s, 3H), 2.31 (s, 3H), 2.11 (s, 3H).

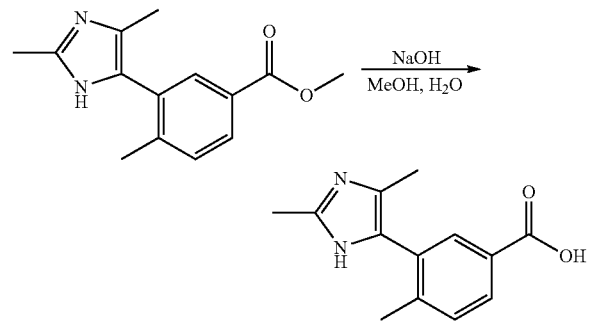

Compound 5.7. 3-(2,4-Dimethyl-1H-imidazol-5-yl)-4-methylbenzoic acid hydrochloride To a solution of methyl 3-(2,4-dimethyl-1H-imidazol-5-yl)-4-methylbenzoate (compound 5.6, 0.66 g, 2.7 mmol) in MeOH (5 mL) was added aqueous NaOH (2 M, 4.8 mL, 9.6 mmol). The mixture was stirred at room temperature for 3 hours then the organic solvent was removed under reduced pressure. The aqueous residue was cooled to 0° C. and acidified to pH 3-4 with aqueous HCl (1 M). The mixture was concentrated to dryness and 5% methanol in DCM (20 mL) was added to the residue. The mixture was stirred at room temperature for 5 minutes and the solids (inorganic salts) were filtered from solution. The filtrate was concentrated to yield the title compound as a brown foam (0.484 g, 67%). m/z (ES+) 231 (M+H)$^+$. $^1$H NMR (400 MHz, DMSO-d$_6$) δ 14.22 (br s, 1H), 14.16 (br s, 1H), 13.11 (br s, 1H), 7.97 (dd, J=8.0 Hz, 1.8 Hz, 1H), 7.85 (d, J=1.8 Hz, 1H), 7.54 (d, J=8.0 Hz, 1H), 2.58 (s, 3H), 2.31 (s, 3H), 2.15 (s, 3H).

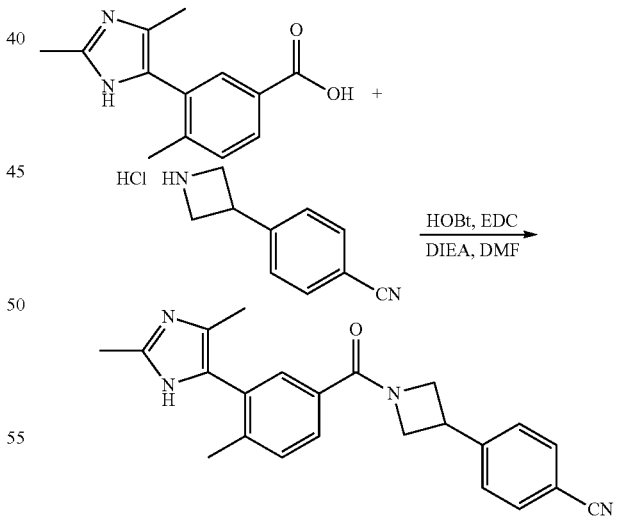

Compound 5. 4-(1-(3-(2,4-Dimethyl-1H-imidazol-5-yl)-4-methylbenzoyl)azetidin-3-yl)benzonitrile To a mixture of 3-(2,4-dimethyl-1H-imidazol-5-yl)-4-methylbenzoic acid (compound 5.7, 0.484 g, 2.10 mmol), 4-(azetidin-3-yl)benzonitrile hydrochloride (compound 5.2, 0.41 g, 2.10 mmol), HOBT (0.085 g, 7.40 mmol) and EDCI (0.603 g, 3.15 mmol) in DMF (8 mL) was added DIEA (1.09 mL, 6.3 mmol). The mixture was stirred at room temperature for 16 hours, then partitioned between EtOAc (300 mL) and water (30 mL). The organic layer was washed with brine (3×30 mL) and the combined aqueous phases were back extracted with EtOAc (2×50 mL). All organic extracts were combined, dried (MgSO$_4$), filtered, and concentrated under reduced pressure. The residue was purified by silica gel column chromatography (EtOAc to 5% MeOH in EtOAc) to yield the title compound as a white solid (0.35 g, 45%). m/z (ES+) 371 (M+H)$^+$. $^1$H NMR (400 MHz, CDCl$_3$) δ 7.66 (d with fine str., J=8.4 Hz, 2H), 7.54-7.48 (m, 2H), 7.44 (d with fine str., J=8.2 Hz, 2H), 7.30 (d, J=7.9 Hz, 1H), 4.77-4.56 (m, 2H), 4.35-4.18 (m, 2H), 3.97-3.87 (m, 1H), 2.38 (s, 3H), 2.30 (s, 3H), 2.10 (s, 3H).

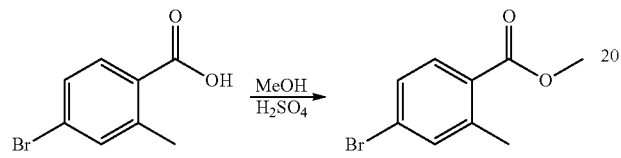

Compound 6.1. Methyl 4-bromo-2-methylbenzoate

To a solution of 4-bromo-2-methylbenzoic acid (5.11 g, 23.8 mmol, 1.0 equiv) in methanol (25 mL) was added dropwise ulfuric acid (2.0 mL) over about 3 minutes (mildly exothermic). The resulting mixture was refluxed for 4 hours. After cooling to room temperature, the reaction mixture was carefully quenched into saturated aqueous NaHCO$_3$ (100 mL) (note—significant gas evolution) and extracted with dichloromethane (200 mL×1 then 50 mL×1). The combined organic phases were washed with a mixture of brine/saturated NaHCO$_3$ (9:1)(50 mL), dried (Na$_2$SO$_4$), and concentrated under reduced pressure to yield the title compound as a colorless oil (5.28 g, 97%). $^1$H NMR (400 MHz, CDCl$_3$): δ 7.78 (d, J=8.0 Hz, 1H), 7.42 (d, J=1.6 Hz, 1H), 7.38 (dd, J=1.6 Hz, 1H), 3.89 (s, 3H), 2.58 (s, 3H).

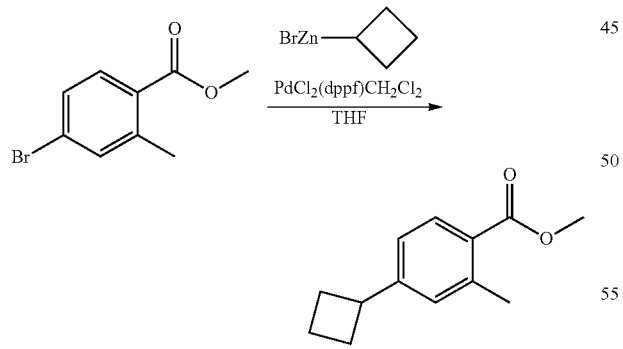

Compound 6.2. Methyl 4-cyclobutyl-2-methylbenzoate

Cyclobutylzinc(II) bromide (50 mL, 0.5 M in THF, 25.0 mmol) was added to a mixture of methyl 4-bromo-2-methylbenzoate (compound 6.1, 5.2 g, 22.7 mmol) and PdCl$_2$(dppf).CH$_2$Cl$_2$ (1.85 g, 2.27 mmol). The mixture was degassed and the flask was filled with argon through a balloon. The mixture was heated at 65° C. under argon for 24 hours, then cooled to 0° C. and carefully quenched with water (10 mL). The mixture was diluted with EtOAc (200 mL) and washed with water then brine, dried (Na$_2$SO$_4$), filtered, and concentrated under reduced pressure. The residue was purified using silica gel column chromatography (hexanes:EtOAc 30:1 to 20:1) to yield the title compound as a clear oil (4.1 g, 89%). $^1$H NMR (400 MHz, CDCl$_3$) δ 7.86 (d, 1H), 7.12-7.02 (m, 2H), 3.88 (s, 3H), 3.59-3.48 (m, 1H), 2.59 (s, 3H), 2.35 (m, 2H), 2.22-1.96 (m, 3H), 1.86-1.84 (m, 1H).

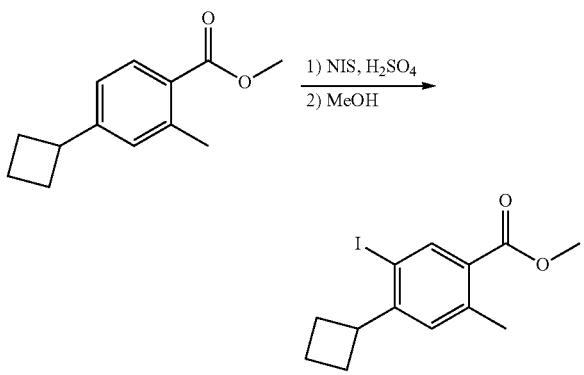

Compound 6.3. Methyl 4-cyclobutyl-5-iodo-2-methylbenzoate

N-Iodosuccinimide (3.52 g, 15.6 mmol) was added portion-wise to a solution of methyl 4-cyclobutyl-2-methylbenzoate (compound 6.2, 3.2 g, 15.6 mmol) in concentrated sulfuric acid (25 mL) at 0° C. The mixture was stirred at 0° C. for 30 min and at RT for 2 hours, upon where the mixture turned very thick. The mixture was again cooled to 0° C. and MeOH (30 mL) was slowly and carefully added. The mixture was heated at 60° C. for 2 hours. After cooling to room temperature, the solvent was removed under reduced pressure and the residue was poured onto ice water (100 mL). The mixture was extracted with EtOAc (2×). The combined organic layers were washed with brine, then aqueous 1M NaHCO$_3$ (note-significant gas evolution), dried (Na$_2$SO$_4$), filtered, and concentrated. The residue was purified by silica gel column chromatography (hexanes:EtOAc 30:1 to 20:1) to yield the title compound as a light yellow oil (4.17 g, 81%). $^1$H NMR (400 MHz, CDCl$_3$) δ 8.33 (s, 1H), 7.14 (s, 1H), 3.87 (s, 3H), 3.67-3.54 (m, 1H), 2.57 (s, 3H), 2.51-2.40 (m, 2H), 2.14-1.97 (m, 3H), 1.82-1.79 (m, 1H).

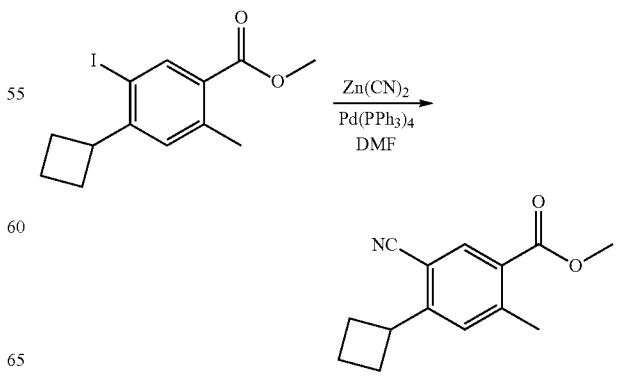

Compound 6.4. Methyl 5-cyano-4-cyclobutyl-2-methylbenzoate

A mixture of methyl 4-cyclobutyl-5-iodo-2-methylbenzoate (compound 6.3, 4.17 g, 12.6 mmol), Zn(CN)$_2$ (2.96 g, 25.2 mmol) and Pd(PPh$_3$)$_4$ (0.73 g, 0.63 mmol) in DMF (30 mL) was degassed and the flask was charged with argon. The mixture was heated at 100° C. under argon overnight. After cooling to ambient temperature, the mixture was quenched with saturated aq. FeSO$_4$ (20 mL) and diluted with EtOAc (200 mL). The greenish solid was removed by filtration through Celite® and the filtrate was partitioned between water and EtOAc. The organics was washed with brine, dried (Na$_2$SO$_4$), filtered, and concentrated under reduced pressure. The residue was purified using silica gel column chromatography (hexanes:EtOAc 30:1 to 20:1) to yield the title compound as a white solid (2.55 g, 88%). $^1$H NMR (400 MHz, CDCl$_3$) δ 8.16 (s, 1H), 7.28 (s, 1H), 3.90 (s, 3H), 3.86-3.82 (m, 1H), 2.68 (s, 3H), 2.55-2.45 (m, 2H), 2.27-2.04 (m, 3H), 1.89-1.87 (m, 1H).

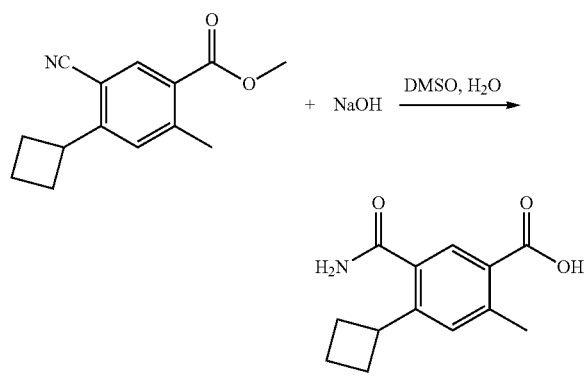

Compound 6.5. 5-Carbamoyl-4-cyclobutyl-2-methylbenzoic acid

To a 1-L round bottom flask was added methyl 5-cyano-4-cyclobutyl-2-methylbenzoate (compound 6.4, 12.00 g, 52.3 mmol) and dissolved in DMSO (100 mL). With stirring, aqueous sodium hydroxide (1 M, 260 mL, 260 mmol) was added carefully and the mixture was purged with nitrogen. The mixture was stirred at 95° C. for 13 hours and then cooled to room temperature. The solution was washed with diethyl ether (100 mL) and the basic aqueous was acidified to pH~2 by slow addition of aqueous HCl (1M) followed by aqueous H$_3$PO$_4$ (1M). The precipitated solids were filtered, and washed with water (2×100 mL), then dried to constant mass to yield the title compound as a white powder (11.68 g, 96%). m/z (ES−) 232 (M−H)$^−$. $^1$H NMR (400 MHz, DMSO-d$_6$): δ 12.75 (br s, 1H), 7.75 (s, 1H), 7.74 (br s, 1H), 7.34 (br s, 1H), 7.28 (s, 1H), 3.90 (app p, J=9.0 Hz, 1H), 2.56 (s, 3H), 2.32-2.20 (m, 2H), 2.16-2.02 (m, 2H), 2.00-1.87 (m, 1H), 1.82-1.71 (m, 1H).

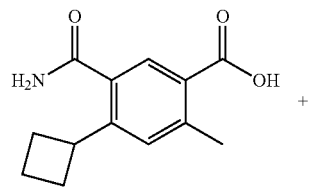

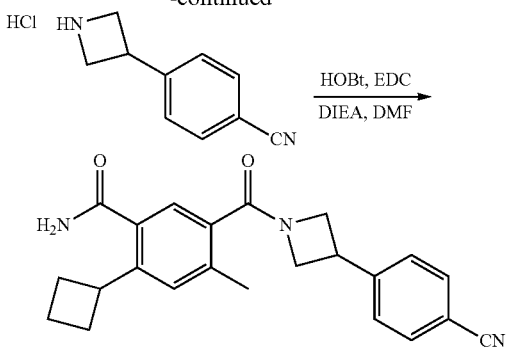

Compound 6. 5-(3-(4-Cyanophenyl)azetidine-1-carbonyl)-2-cyclobutyl-4-methylbenzamide To a 4-mL vial was added 4-(azetidin-3-yl)benzonitrile hydrochloride (compound 5.2, 27 mg, ~90% pure, 0.13 mmol), HOBt (20 wt % H$_2$O)(22 mg, 0.13 mmol), EDC (27 mg, 0.14 mmol). A solution of 5-carbamoyl-4-cyclobutyl-2-methylbenzoic acid (compound 6.5, 28 mg, 0.12 mmol) in DMF (500 µL) was added followed by DIEA (83 µL, 0.48 mmol). The mixture was sealed and stirred at room temperature for 18 hours. Additional amine (3 mg, ~0.015 mmol) and EDC (5 mg, ~0.026 mmol) were added and the mixture was stirred at room temperature for an additional 27 hours. The mixture was diluted with ethyl acetate (5 mL) and washed with brine (8 mL). The aqueous was extracted with ethyl acetate (2 mL) and the combined organics was washed with brine, 1 M NaH$_2$PO$_4$, saturated NaHCO$_3$ and brine (7 mL each). The product began precipitating out of solution after the final brine wash, so the organics was diluted with DCM (3 mL) and MeOH (~200 µL). The organics was dried (Na$_2$SO$_4$), filtered, and concentrated under reduced pressure. The crude product was triturated with Et$_2$O (1.5 mL), filtered, and washed with Et$_2$O (0.5 mL) to yield the title compound as an off white powder (41.4 mg, 92%). m/z (ES+) 374 (M+H)$^+$. $^1$H NMR (400 MHz, CDCl$_3$): δ 7.67 (d with fine str., J=8.4 Hz, 2H), 7.40 (d with fine str., J=8.4 Hz, 2H), 7.32 (s, 1H), 7.25 (s, 1H), 5.79 (br s, 1H), 5.70 (br s, 1H), 4.67-4.57 (m, 1H), 4.39-4.30 (m, 1H), 4.28-4.18 (m, 1H), 4.00-3.86 (m, 3H), 2.46 (s, 3H), 2.42-2.31 (m, 2H), 2.19-1.96 (m, 3H), 1.88-1.77 (m, 1H).

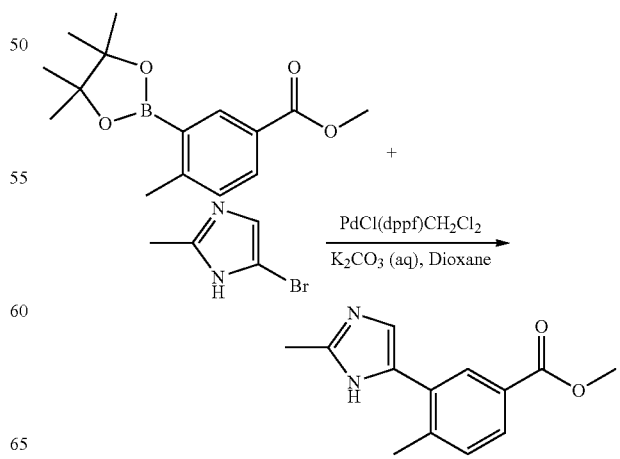

Compound 7.1. Methyl 4-methyl-3-(2-methyl-1H-imidazol-5-yl)benzoate

To a solution of methyl 4-methyl-3-(4,4,5,5-tetramethyl-1,3,2-dioxaborolan-2-yl)benzoate (compound 5.4, 600 mg, 2.17 mmol) in dioxane (20 mL) was added 2-methyl-4-bromo imidazole (419 mg, 2.6 mmol), Pd(dppf)Cl$_2$.CH$_2$Cl$_2$ (180 mg, 0.22 mmol). The mixture was degassed argon and stirred for 10 minutes then aqueous potassium carbonate (1M, 10 mL, 10 mmol) was added and the mixture was stirred at 90° C. for 18 h. After cooling to ambient temperature, the reaction mixture was diluted with EtOAc and filtered through Celite®. The organic phase was washed by brine, dried (MgSO$_4$), filtered, and concentrated under reduced pressure. The residue was purified by silica gel column chromatography (0-5% MeOH in EtOAc) to yield the title compound as a foam (324 mg, 65%). m/z (ES+) 231 (M+H)$^+$. $^1$H NMR (400 MHz, CDCl$_3$) δ 8.30 (br s, 1H), 7.86 (dd, J=7.9, 1.9 Hz, 1H), 7.32 (d, J=7.9 Hz, 1H), 7.08 (s, 1H), 3.92 (s, 3H), 2.53 (s, 3H), 2.51 (s, 3H).

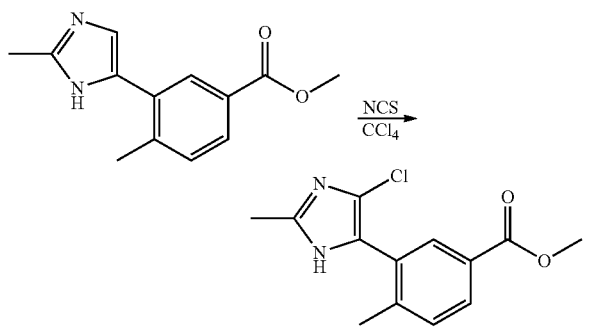

Compound 7.2. Methyl 3-(5-chloro-2-methyl-1H-imidazol-4-yl)-4-methylbenzoate To a solution of methyl 4-methyl-3-(2-methyl-1H-imidazol-5-yl) benzoate (compound 7.1, 317 mg, 1.38 mmol) in carbon tetrachloride (30 mL) was added NCS (184 mg, 1.38 mmol). The mixture was stirred at 50° C. for 16 hours, then cooled to room temperature and washed with brine, dried (MgSO$_4$), filtered, and concentrated under reduced pressure. The residue was purified by silica gel column chromatography (0-50% EtOAc in hexanes) to yield the title compound as a solid (300 mg, 82%). m/z (ES+) 265 (M+H)$^+$. $^1$H NMR (400 MHz, CDCl$_3$) δ 9.55 (br s, 1H), 8.01-7.87 (m, 2H), 7.37 (d, J=7.8 Hz, 1H), 3.91 (s, 3H), 2.42 (s, 3H), 2.40 (s, 3H).

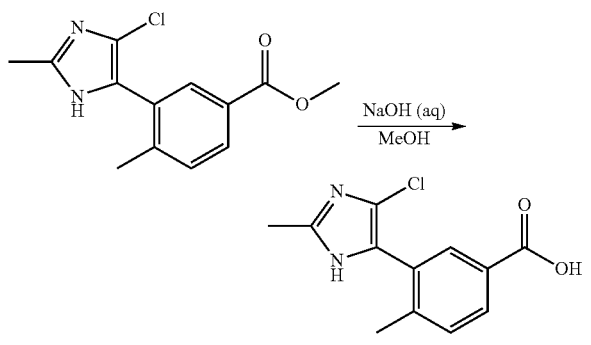

Compound 7.3. 3-(5-Chloro-2-methyl-1H-imidazol-4-yl)-4-methylbenzoic acid

A mixture of methyl 3-(5-chloro-2-methyl-1H-imidazol-4-yl)-4-methylbenzoate (compound 7.2, 10 mg, 0.038 mmol) in methanol (2 mL) and aqueous NaOH (2M, 0.2 mL, 0.4 mmol) was stirred at 50° C. for 16 hrs. The organic solvent was removed under reduced pressure and aqueous HCl (2 M) was added to the residue until a pH ~3-4 was attained. The solvents were removed under reduced pressure to produce a white solid which was a mixture of the title compound and salts and used in the next step without further purification. m/z (ES-) 249 (M-H)$^-$.

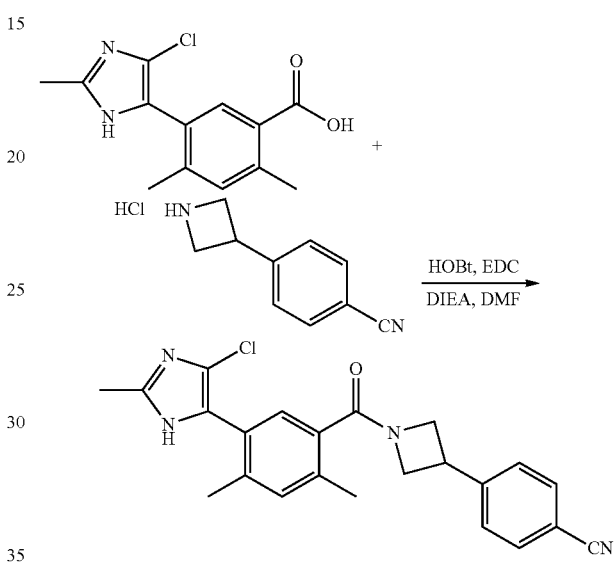

Compound 7. 4-(1-(3-(4-Chloro-2-methyl-1H-imidazol-5-yl)-4-methylbenzoyl)azetidin-3-yl)benzonitrile A mixture of 3-(5-chloro-2-methyl-1H-imidazol-4-yl)-4-methylbenzoic acid (compound 7.3, ~0.038 mmol), 4-(azetidin-3-yl)benzonitrile hydrochloride (compound 5.2, 8.6 mg, 0.044 mmol), EDCI (12 mg, 0.063 mmol), HOBt (8 mg, 0.044 mmol) and DIEA (28 µl, 0.16 mmol) in DMF (1 mL) was stirred at room temperature for 16 hours. The reaction was diluted with water and extracted with EtOAc. The organic phase was washed with brine (how much), dried (MgSO$_4$), filtered, and concentrated under reduced pressure. The residue was purified by silica gel preparative TLC (8% MeOH in DCM) to yield the title compound as a foam (2.8 mg, 19% over 2 steps). m/z (ES+) 391 (M+H)$^+$. $^1$H NMR (400 MHz, CDCl3) δ 10.62 (s, 1H), 7.69 (d, J=8.3 Hz, 2H), 7.54-7.40 (m, 3H), 7.37 (d, J=1.9 Hz, 1H), 7.23 (d, J=8.0 Hz, 1H), 4.80-4.58 (m, 2H), 4.41-4.19 (m, 2H), 4.03-3.92 (m, 1H), 2.49 (s, 3H), 2.32 (s, 3H).

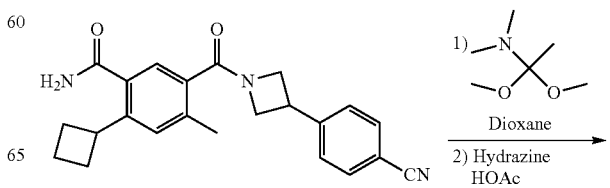

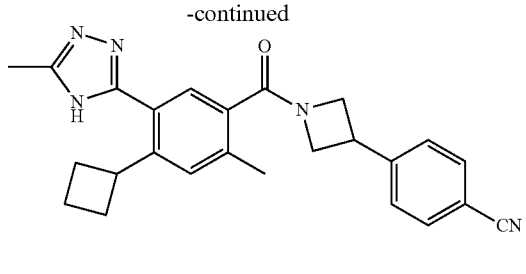

Compound 8. 4-(1-(4-Cyclobutyl-2-methyl-5-(5-methyl-4H-1,2,4-triazol-3-yl)benzoyl)azetidin-3-yl)benzonitrile To a 4-mL vial was added 5-(3-(4-cyanophenyl)azetidine-1-carbonyl)-2-cyclobutyl-4-methylbenzamide (compound 6, 39 mg, 0.104 mmol), dioxane (200 μL) and 1,1-dimethoxy-N,N-dimethylethanamine (76 μL, 0.52 mmol). The mixture was heated at 90° C. for 3 hours then cooled to room temperature. Acetic acid (42 μL, 0.73 mmol) and hydrazine hydrate (30 μL, 0.62 mmol) were added and the mixture was stirred at 90° C. for 1 hour. The mixture was diluted with DCM (5 mL) and washed with aqueous NaH$_2$PO$_4$ (1M, 5 mL) then saturated aqueous NaHCO$_3$ (5 mL). The organics was dried (Na$_2$SO$_4$), filtered, and concentrated under reduced pressure. The residue was purified by silica gel preparative thin layer chromatography (DCM/8% MeOH) to yield the title compound as a white powder (18.7 mg, 43%). m/z (ES+) 412 (M+H)$^+$. $^1$H NMR (400 MHz, CD$_3$OD): δ 7.65 (d with fine str., J=8.4 Hz, 2H), 7.57 (s, 1H), 7.39 (d with fine str., J=8.4 Hz, 2H), 7.29 (s, 1H), 4.61 (app t, J=9.6 Hz, 1H), 4.39 (app t, J=8.8 Hz, 1H), 4.27-4.18 (m, 1H), 4.17-4.07 (m, 1H), 4.02-3.94 (m, 1H), 3.94-3.84 (m, 1H), 2.50 (s, 3H), 2.48 (s, 3H), 2.25-2.11 (m, 2H), 2.11-1.88 (m, 3H), 1.82-1.71 (m, 1H).

concentrated under reduced pressure to yield the title compound as a light yellow oil (18.0 g, crude).

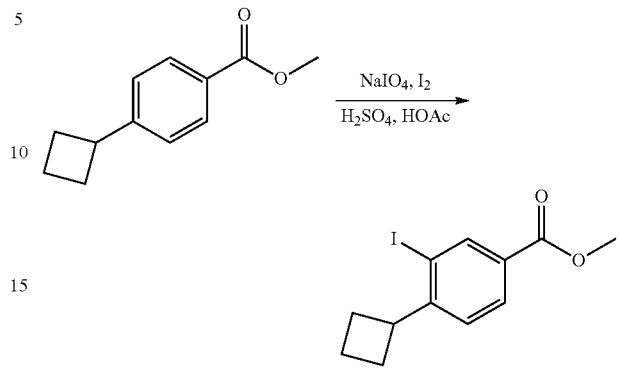

Compound 9.2. Methyl 4-cyclobutyl-3-iodobenzoate

To a solution of methyl 4-cyclobutylbenzoate (compound 9.1, 2.00 g, 10.5 mmol) in acetic acid (30 mL) was carefully added sodium periodate (1.00 g, 4.68 mmol), iodine (3.00 g, 11.8 mmol) and sulfuric acid (0.15 g). The resulting mixture was stirred overnight at 100° C. After cooling to room temperature, the reaction was then carefully quenched with saturated aqueous Na$_2$S$_2$O$_3$ (30 mL) and the resulting mixture was extracted with ethyl acetate (3×20 mL). The combined organic layers were washed with brine (3×20 mL), dried (Na$_2$SO$_4$), filtered, and concentrated under reduced pressure to yield of the title compound as a yellow oil (1.50 g, 45%).

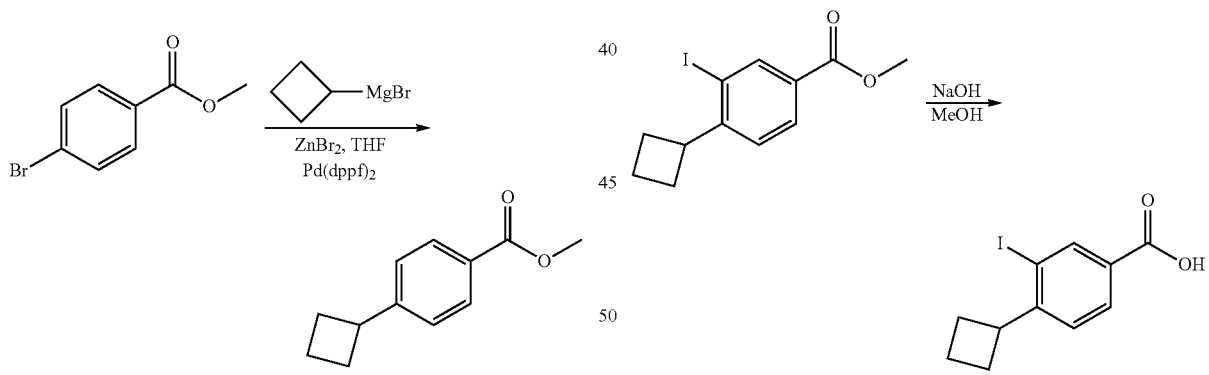

Compound 9.1. Methyl 4-cyclobutylbenzoate

To a stirred mixture of ZnBr$_2$ (83.0 g, 369 mmol) in THF (500 mL) under nitrogen at 0° C. was added a solution of bromo(cyclobutyl)magnesium (242 mL, 363 mmol, 1.5 M in THF) dropwise over 20 min. The resulting mixture was cooled to −40° C. and Pd(dppf)Cl$_2$ (2.00 g, 2.73 mmol) and methyl 4-bromobenzoate (20.0 g, 93.0 mmol) were added. The resulting mixture was stirred at −40° C. for 1 h under nitrogen, and then carefully quenched with saturated aqueous NH$_4$Cl (500 mL). The mixture was extracted with ethyl acetate (3×500 mL) and the combined organic layers were washed with brine (3×500 mL), dried (Na$_2$SO$_4$), filtered, and

Compound 9.3. 4-Cyclobutyl-3-iodobenzoic acid

A solution of methyl 4-cyclobutyl-3-iodobenzoate (compound 9.2, 11.0 g, 34.8 mmol) and sodium hydroxide (4.00 g, 100 mmol) in methanol (100 mL) and water (50 mL) was stirred at 50° C. overnight. After cooling to ambient temperature, the volatile solvent was removed under reduced pressure. The residual aqueous material was washed with ethyl acetate (20 mL). The pH of the aqueous was then adjusted to 3-4 with aqueous hydrogen chloride (6 M). The resulting precipitate was collected by filtration and dried to yield the title compound as a white solid (8.60 g, 82%).

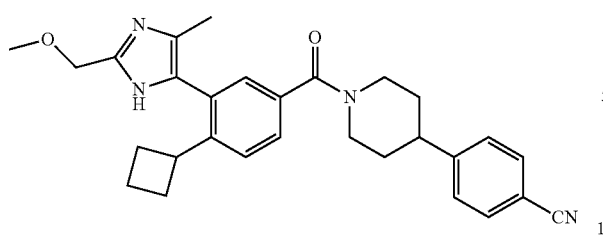

Compound 9. 4-(1-(4-Cyclobutyl-3-(2-(methoxymethyl)-4-methyl-1H-imidazol-5-yl)benzoyl)piperidin-4-yl)benzonitrile The title compound was prepared using standard chemical manipulations and procedures similar to those used for the preparation of compound 1, except 4-cyclobutyl-3-iodobenzoic acid (compound 9.3) was used in place of 5-iodo-2,4-dimethylbenzoic acid (compound 1.3) and 2-methoxyacetimidamide hydrochloride (compound 4.7) was used in place of acetimidamide hydrochloride. m/z (ES+) 469 (M+H)$^+$.

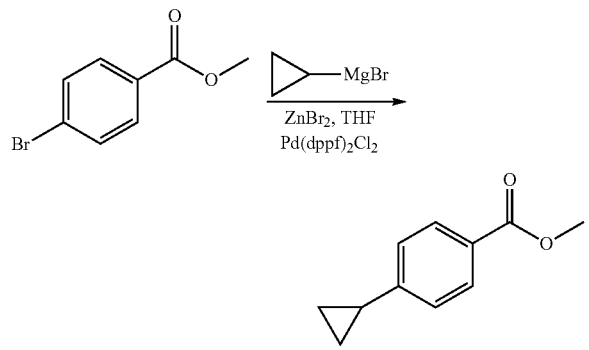

Compound 10.1. Methyl 4-cyclopropylbenzoate

Into a 1-L three neck round-bottom flask, which was purged and maintained with an inert atmosphere of nitrogen, was placed a solution mixture of ZnBr$_2$ (41.5 g, 184 mmol) and tetrahydrofuran (500 mL). The mixture was cooled to 0° C., then cyclopropylmagnesium bromide (2 M in THF)(92 mL, 184 mmol) was added drop-wise with stirring over 30 min. The mixture was then cooled to −40° C. and Pd(dppf)Cl$_2$ (3.00 g, 4.1 mmol) was added portion-wise over 1 min. Methyl 4-bromobenzoate (10.0 g, 46.50 mmol) in THF (50 mL) was added drop-wise over 30 min at −40° C. The resulting mixture was allowed to warm to room temperature and stirred overnight. The reaction was then carefully quenched by the addition of aqueous NH$_4$Cl (sat., 500 mL). The mixture was extracted with ethyl acetate (3×300 mL) and the combined organic layers were washed with brine (3×300 mL), dried (Na$_2$SO$_4$), filtered, and concentrated under reduced pressure. The residue was purified by silica gel column chromatography with petroleum ether as the eluent to yield 8.87 g (crude) of the title compound as a yellow oil.

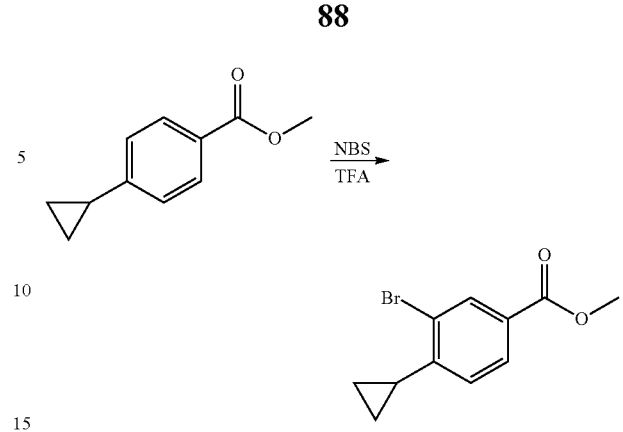

Compound 10.2. Methyl 3-bromo-4-cyclopropylbenzoate

Into a 50-mL round-bottom flask, was placed a mixture of methyl 4-cyclopropylbenzoate (compound 10.1, 500 mg, 2.84 mmol), N-bromosuccinimide (500 mg, 2.81 mmol) and trifluoroacetic acid (20 mL). The mixture was stirred overnight at 50° C., then cooled and carefully quenched with water (10 mL). The mixture was extracted with ethyl acetate (3×30 mL) and the combined organic layers were washed with brine (3×30 mL), dried (Na$_2$SO$_4$), filtered, and concentrated under reduced pressure. The residue was purified by silica gel column chromatography with petroleum ether as the eluent to yield 0.5 g (69%) of the title compound as a yellow oil.

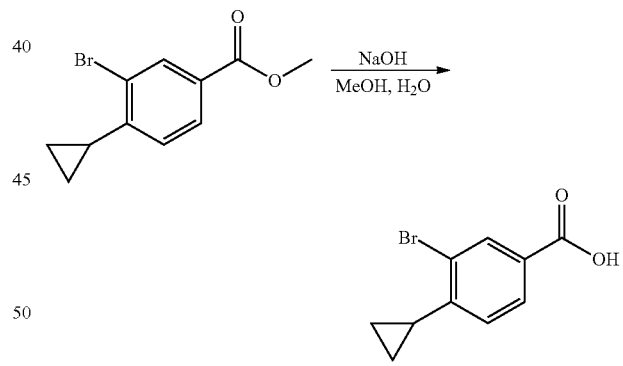

Compound 10.3. 3-Bromo-4-cyclopropylbenzoic acid

Into a 50-mL round-bottom flask, was placed a solution of methyl 3-bromo-4-cyclopropylbenzoate (compound 10.2, 500 mg, 1.96 mmol) in methanol (10 mL) and a solution of sodium hydroxide (500 mg, 12.5 mmol) in water (5 mL). The resulting solution was stirred overnight at 50° C., then the volatiles were removed under reduced pressure. The pH of the residual solution was adjusted to 6-7 with aqueous HCl (6 M). The resulting solids were collected by filtration to yield 0.3 g (63%) of the title compound as a white solid.

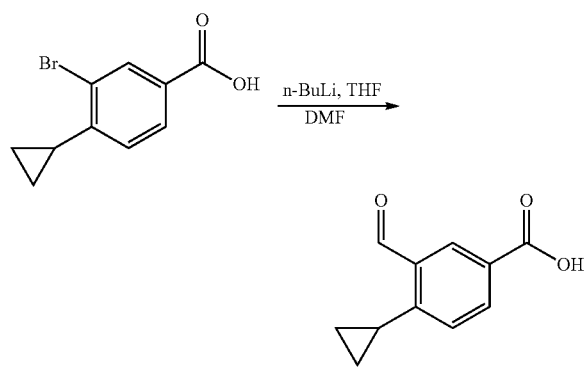

Compound 10.4. 4-Cyclopropyl-3-formylbenzoic acid

Into a 100-mL three neck round-bottom flask, which was purged and maintained with an inert atmosphere of nitrogen, was placed a solution of 3-bromo-4-cyclopropylbenzoic acid (compound 10.3, 500 mg, 2.07 mmol) in tetrahydrofuran/Et$_2$O (1:1, 20 mL). The solution was cooled to −78° C. then n-BuLi (2.5 M in THF) (1.8 mL, 4.5 mmol) was added drop-wise with stirring. The resulting solution was stirred for an additional 30 min at −78° C., then N,N-dimethylformamide (0.49 mL, 6.3 mmol) was added drop-wise over 10 min. The mixture was stirred for 2 h at −78° C., then quenched with water (100 mL). The pH of the solution was adjusted to 3-4 with aqueous HCl (6 M), then extracted with ethyl acetate (3×30 mL). The combined organic layers were washed with brine (3×30 mL), dried (Na$_2$SO$_4$), filtered, and concentrated under reduced pressure. The residue was purified by silica gel column chromatography with ethyl acetate/petroleum ether (1:5) as the eluent to yield 0.3 g (76%) of the title compound as a white solid.

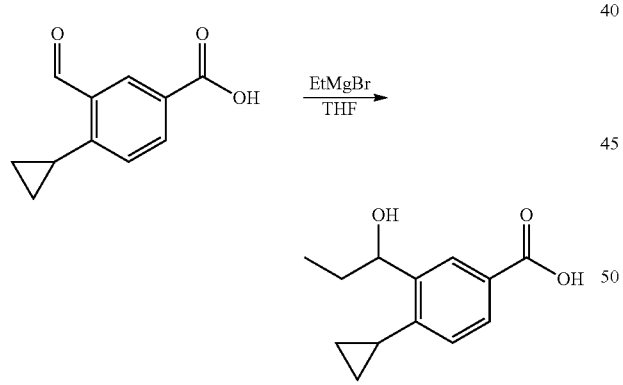

Compound 10.5. 4-Cyclopropyl-3-(1-hydroxypropyl)benzoic acid

Into a 250-mL 3-necked round-bottom flask, purged and maintained with an inert atmosphere of nitrogen and containing THF (60 mL), was placed a solution of ethylmagnesium bromide (3 M in diethyl ether) (24.6 mL, 73.8 mmol). A solution of 4-cyclopropyl-3-formylbenzoic acid (compound 10.4, 3.5 g, 18.4 mmol) in THF (40 mL) was added drop-wise at room temperature over 45 min. The resulting mixture was stirred for 1.5 h at room temperature, then carefully quenched with water/ice (50 mL). The mixture was diluted with EtOAc (100 mL) and the organic layer was washed with aqueous NH$_4$Cl (sat., 2×100 mL) and the aqueous layers combined. The pH of the aqueous phase was adjusted to 3-4 with aqueous hydrogen chloride (2 M) and extracted with ethyl acetate (2×150 mL). The combined organic extracts were washed with brine (30 mL), dried (Na$_2$SO$_4$), filtered, and concentrated under reduced pressure. The residue was purified by silica gel column chromatography with ethyl acetate:PE (1:10-2:1) as the eluent to yield 3.4 g (84%) of the title compound as a white solid.

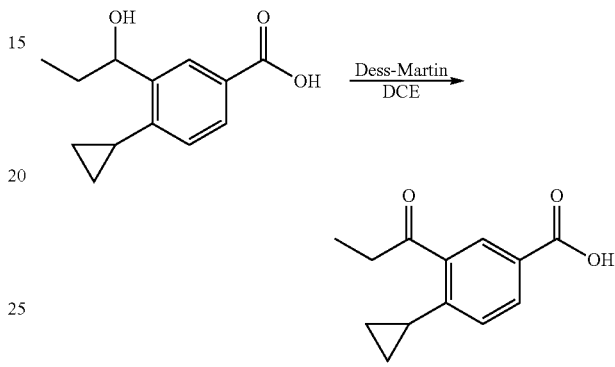

Compound 10.6. 4-Cyclopropyl-3-propionylbenzoic acid

Into a 500-mL round-bottom flask, was placed a mixture of 4-cyclopropyl-3-(1-hydroxypropyl)benzoic acid (compound 10.5, 3.4 g, 15.44 mmol) in 1,2-dichloroethane (300 mL) and Dess-Martin periodinane (7.2 g, 16.9 mmol). The mixture was stirred for 1.5 h at room temperature and then the solids were removed with filtration. The filtrate was concentrated under reduced pressure and the residue was purified by silica gel column chromatography with ethyl acetate:PE (1:9) to methanol/ethyl acetate (20:1) as the eluent to yield 2.3 g (68%) of the title compound as a light yellow solid.

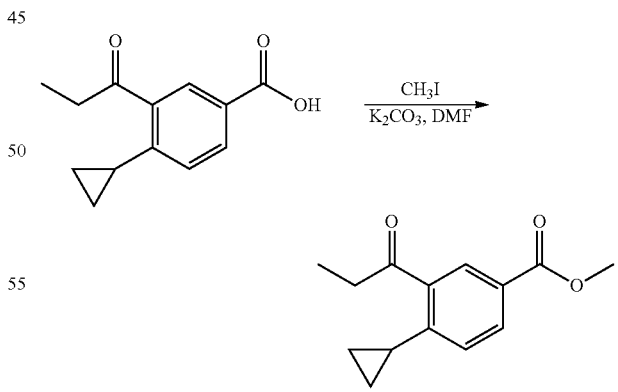

Compound 10.7. Methyl 4-cyclopropyl-3-propionylbenzoate

Into a 50-mL round-bottom flask, was placed a solution of 4-cyclopropyl-3-propanoylbenzoic acid (compound 10.6, 500 mg, 2.29 mmol) in N,N-dimethylformamide (20 mL)

and potassium carbonate (633 mg, 4.55 mmol). The mixture was cooled to 0-5° C. then iodomethane (157 µL, 2.52 mmol) was added drop-wise. The resulting mixture was stirred for 1 h at 5-10° C., then quenched with water/ice (80 mL). The aqueous phase was extracted with ethyl acetate (2×150 mL) and the combined organic layers were washed with brine (20 mL), sodium carbonate (sat., 20 mL), dried (Na$_2$SO$_4$), filtered, and concentrated under reduced pressure. Obtained 400 mg (75%) of the title compound as a light brown oil.

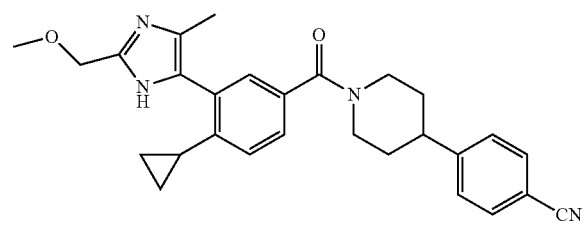 [SMILES: COCc1nc(C)c(-c2cc(C(=O)N3CCC(c4ccc(C#N)cc4)CC3)ccc2C2CC2)[nH]1]

Compound 10. 4-(1-(4-Cyclopropyl-3-(2-(methoxymethyl)-4-methyl-1H-imidazol-5-yl)benzoyl)piperidin-4-yl)benzonitrile The title compound was prepared using standard chemical manipulations and procedures similar to those used for the preparation of compound 1, except methyl 4-cyclopropyl-3-propionylbenzoate (compound 10.7) was used in place of methyl 2,4-dimethyl-5-propionylbenzoate (compound 1.5) and 2-methoxyacetimidamide hydrochloride (compound 4.7) was used in place of acetimidamide hydrochloride. m/z (ES+) 455 (M+H)$^+$.

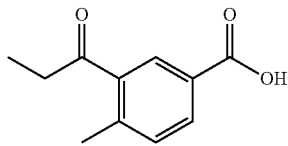

Compound 11.1. 4-Methyl-3-propionylbenzoic acid

The title compound was prepared using standard chemical manipulations and procedures similar to those used for the preparation of compound 10.6, except 3-bromo-4-methylbenzoic acid was used in place of 3-bromo-4-cyclopropylbenzoic acid (compound 10.3).

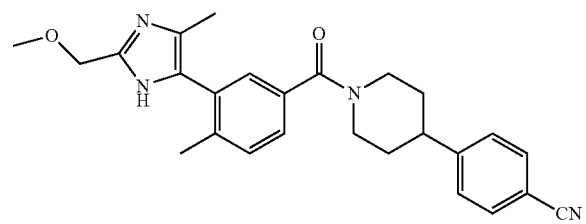 [SMILES: COCc1nc(C)c(-c2cc(C(=O)N3CCC(c4ccc(C#N)cc4)CC3)ccc2C)[nH]1]

Compound 11. 4-(1-(3-(2-(Methoxymethyl)-4-methyl-1H-imidazol-5-yl)-4-methylbenzoyl)piperidin-4-yl)benzonitrile The title compound was prepared using standard chemical manipulations and procedures similar to those used for the preparation of compound 1, except 4-methyl-3-propionylbenzoic acid (compound 11.1) was used in place of 2,4-dimethyl-5-propionylbenzoic acid (compound 1.4) and 2-methoxyacetimidamide hydrochloride (compound 4.7) was used in place of acetimidamide hydrochloride. m/z (ES+) 429 (M+H)$^+$.

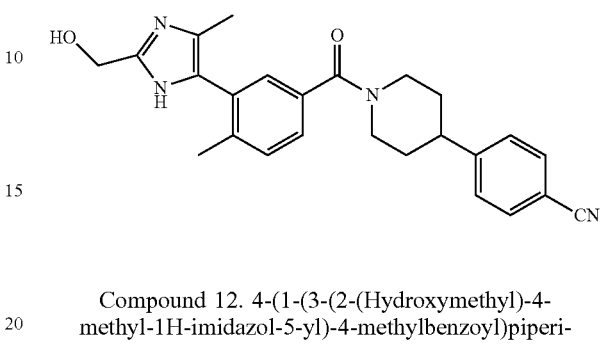

Compound 12. 4-(1-(3-(2-(Hydroxymethyl)-4-methyl-1H-imidazol-5-yl)-4-methylbenzoyl)piperidin-4-yl)benzonitrile The title compound was prepared using standard chemical manipulations and procedures similar to those used for the preparation of compound 3, except 4-(1-(3-(2-(methoxymethyl)-4-methyl-1H-imidazol-5-yl)-4-methylbenzoyl)piperidin-4-yl)benzonitrile (compound 11) was used in place of 4-(1-(5-(2-(methoxymethyl)-4-methyl-1H-imidazol-5-yl)-2,4-dimethylbenzoyl)piperidin-4-yl)benzonitrile (compound 2). m/z (ES+) 415 (M+H)$^+$.

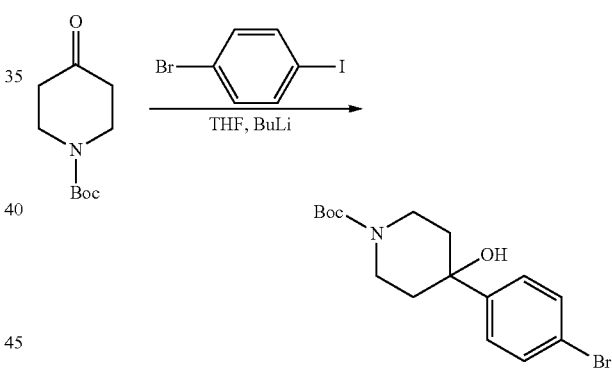

Compound 13.1. tert-Butyl 4-(4-bromophenyl)-4-hydroxypiperidine-1-carboxylate

To a stirred solution of 1-bromo-4-iodobenzene (93.7 g, 331 mmol) in tetrahydrofuran (800 mL) under nitrogen at −78° C. was added drop-wise a solution of butyllithium (150 mL, 2.43 M in THF) over 30 min. The resulting solution was stirred for 2 h at −78° C. A solution of tert-butyl 4-oxopiperidine-1-carboxylate (60 g, 301 mmol) in tetrahydrofuran (800 mL) was then added drop-wise with stirring at −78° C. over 30 min. The mixture was stirred for 1 h at −78° C., then the reaction was carefully quenched with water (350 mL). The resulting mixture was extracted with ethyl acetate (2×400 mL) and the combined organic layers were dried (Na$_2$SO$_4$), filtered, and concentrated under reduced pressure. The residue was purified using silica gel column chromatography with ethyl acetate/petroleum ether (1:200-1:10) as the eluent to yield 91 g (85%) of the title compound as a yellow oil.

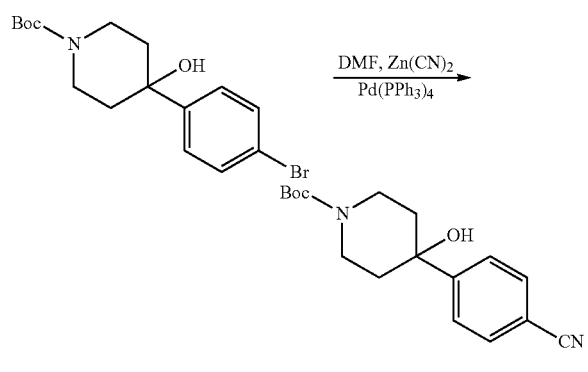

Compound 13.2. tert-Butyl 4-(4-cyanophenyl)-4-hydroxypiperidine-1-carboxylate A mixture of tert-butyl 4-(4-bromophenyl)-4-hydroxypiperidine-1-carboxylate (compound 13.1, 36 g, 101 mmol), Pd(PPh$_3$)$_4$ (11.7 g, 10.1 mmol), and Zn(CN)$_2$ (17.9 g, 152.4 mmol) in DMF (400 mL) under nitrogen was stirred overnight at 80° C. The mixture was cooled to ambient temperature, then the reaction was quenched by the addition of 600 mL of FeSO$_4$ (aq., sat.) and diluted with ethyl acetate. The resulting mixture was stirred vigorously then filtered through Celite® and washed with 1 M FeSO$_4$, water, and ethyl acetate. The layers were separated and the aqueous phase was extracted with ethyl acetate (2×300 mL). The combined organic layers were washed with potassium carbonate (aq., sat., 200 mL), followed by brine (200 mL), dried (Na$_2$SO$_4$), filtered, and concentrated under reduced pressure. The residue was purified using silica gel column chromatography with ethyl acetate/petroleum ether (1:200-1:5) as the eluent to yield 23 g (75%) of the title compound as a white solid.

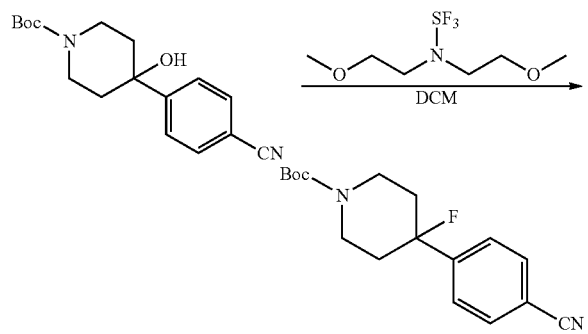

Compound 13.3. tert-Butyl 4-(4-cyanophenyl)-4-fluoropiperidine-1-carboxylate To a stirred solution of compound 13.2 (5.00 g, 16.5 mmol) in dichloromethane (250 mL) at −78° C. under nitrogen was added drop-wise Deoxo-Fluor® (4.4 g, 19.9 mmol). The resulting mixture was stirred for 1 h at −78° C. The reaction mixture was then carefully quenched by the addition of sodium bicarbonate (aq., sat., 50 mL) and extracted with dichloromethane (3×100 mL). The combined organic layers were washed with brine (150 mL), dried over anhydrous magnesium sulfate, filtered, and concentrated under reduced pressure. The residue was purified using silica gel column chromatography with ethyl acetate/petroleum ether (1:30) as the eluent to yield 2.5 g (35%) of the title compound as a white solid.

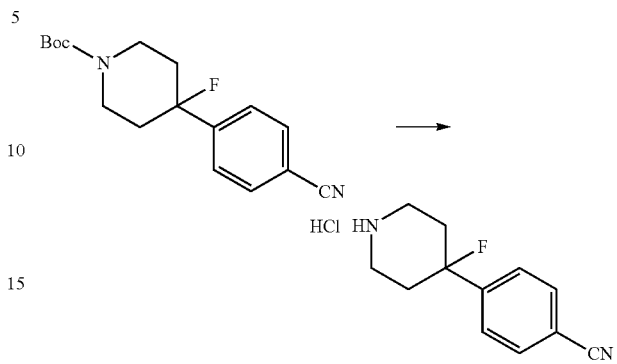

Compound 13.4. 4-(4-Fluoropiperidin-4-yl)benzonitrile hydrochloride

The title compound was prepared using standard chemical manipulations and a procedure similar to that used for the preparation of compound 1.2, except using compound 13.3 in place of compound 1.1. m/z (ES+) 205 (M+H)$^+$. $^1$H NMR (300 MHz, CD$_3$OD): δ 7.83 (d, J=6.3 Hz, 2H), 7.68 (d, J=6.3 Hz, 2H), 3.55-3.32 (m, 4H), 2.58-2.40 (m, 2H), 2.28-2.22 (m, 2H).

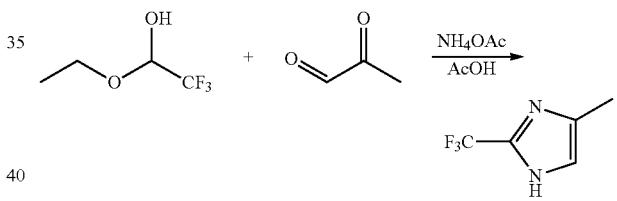

Compound 14.1. 4-Methyl-2-(trifluoromethyl)-1H-imidazole

Into a 250-mL round-bottom flask, purged and maintained with an inert atmosphere of nitrogen, was placed 2-oxopropanal (5 g, 27.8 mmol), acetic acid (150 mL), 1-ethoxy-2,2,2-trifluoroethanol (13.3 g, 83.2 mmol), and ammonium acetate (17.1 g, 222 mmol). The mixture was stirred for 18 h at 110° C., then cooled to room temperature and concentrated under reduced pressure. The residue was quenched with water/ice (30 mL) and the aqueous phase was extracted with ethyl acetate (2×100 mL). The combined organic layers were washed with brine (30 mL) and concentrated under reduced pressure. The residue was dissolved in aqueous hydrogen chloride (5 M, 20 mL) and washed with ethyl acetate (2×50 mL). The pH of the aqueous layer was adjusted to 8-9 with sodium carbonate, then extracted with ethyl acetate (2×100 mL). The combined organic layers were washed with brine (30 mL), dried (Na$_2$SO$_4$), filtered, and concentrated under reduced pressure. The crude product was purified by silica gel column chromatography with ethyl acetate:PE (1:5) as the eluent to yield 1.2 g (29%) of the title compound as a brown oil.

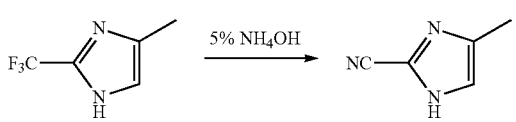

Compound 14.2.
4-Methyl-1H-imidazole-2-carbonitrile

Into a 250-mL round-bottom flask, which was purged and maintained with an inert atmosphere of nitrogen, was placed 4-methyl-2-(trifluoromethyl)-1H-imidazole (compound 14.1, 800 mg, 5.33 mmol) and 5% aqueous ammonium hydroxide (50 mL). The resulting solution was stirred for 40 h at 25-30° C., then the pH of the solution was adjusted to 5-6 with acetic acid. The aqueous phase was extracted with ethyl acetate (3×150 mL) and the combined organic extracts were washed with brine (2×50 mL) and aqueous $Na_2CO_3$ (sat., 2×20 mL), dried ($Na_2SO_4$), filtered, and concentrated under reduced pressure. The residue was purified by silica gel column chromatography with ethyl acetate:PE (1:20-1:10) as the eluent to yield 350 mg (61%) of the title compound as a white solid.

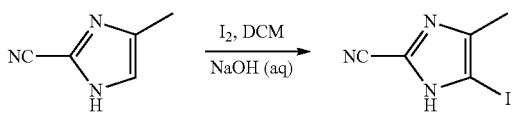

Compound 14.3.
5-Iodo-4-methyl-1H-imidazole-2-carbonitrile

Into a 25-mL round bottom flask, which was purged and maintained with an inert atmosphere of nitrogen, was placed a mixture of 4-methyl-1H-imidazole-2-carbonitrile (compound 14.2, 350 mg, 3.27 mmol) and aqueous sodium hydroxide (2 M, 5 mL) and stirred for 15 min at room temperature. This was followed by the drop-wise addition of a solution of iodine (1.25 g, 4.92 mmol) in dichloromethane (5 mL). The resulting mixture was stirred for 24 h at room temperature, then diluted with water/ice (10 mL). The aqueous layer was washed with DCM (10 mL), and then the aqueous layer was acidified to pH 5-6 with acetic acid. The aqueous phase was extracted with EtOAc (5×50 mL) and the combined organic layers were dried ($Na_2SO_4$), filtered, and concentrated under reduced pressure to yield 500 mg (66%) of the title compound as a brown solid.

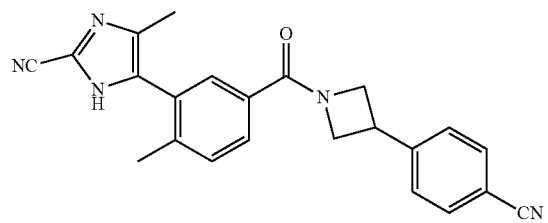 [SMILES: Cc1ccc(C(=O)N2CC(c3ccc(C#N)cc3)C2)cc1-c1[nH]c(C#N)nc1C]

Compound 14. 5-(5-(3-(4-Cyanophenyl)azetidine-1-carbonyl)-2-methylphenyl)-4-methyl-1H-imidazole-2-carbonitrile The title compound was prepared using standard chemical manipulations and procedures similar to those used for the preparation of compound 5, except 5-Iodo-4-methyl-1H-imidazole-2-carbonitrile (compound 14.3) was used in place of 5-iodo-2,4-dimethyl-1H-imidazole (compound 5.5). m/z (ES+) 382 (M+H)$^+$.

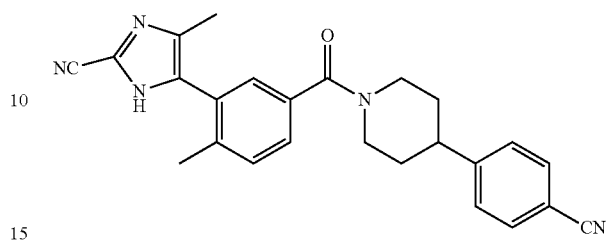

Compound 15. 5-(5-(4-(4-Cyanophenyl)piperidine-1-carbonyl)-2-methylphenyl)-4-methyl-1H-imidazole-2-carbonitrile The title compound was prepared using standard chemical manipulations and procedures similar to those used for the preparation of compound 5, except 5-Iodo-4-methyl-1H-imidazole-2-carbonitrile (compound 14.3) was used in place of 5-iodo-2,4-dimethyl-1H-imidazole (compound 5.5) and 4-(piperidin-4-yl)benzonitrile hydrochloride (compound 1.2) was used in place of 4-(azetidin-3-yl)benzonitrile hydrochloride (compound 5.2). m/z (ES+) 410 (M+H)$^+$.

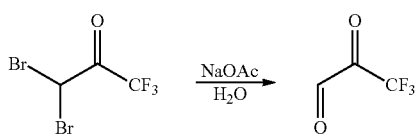 [SMILES: O=C(C(Br)Br)C(F)(F)F ; O ; O=CC(=O)C(F)(F)F ; "NaOAc"]

Compound 16.1. 3,3,3-Trifluoro-2-oxopropanal

Into a 100-mL round-bottom flask, was placed a mixture of 3,3-dibromo-1,1,1-trifluoropropan-2-one (10.37 g, 38.43 mmol) and sodium acetate (12.61 g, 153.7 mmol) in water (50 mL). The resulting solution was stirred overnight at 100° C., then cooled to room temperature and extracted with ethyl acetate (3×20 mL). The combined organic extracts were dried ($Na_2SO_4$), filtered, and concentrated under reduced pressure to yield 1.52 g (31%) of the title compound as light yellow oil.

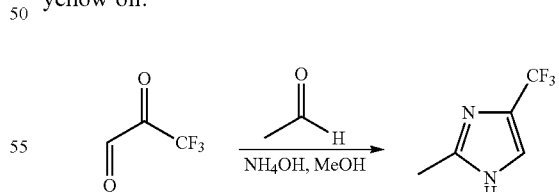

Compound 16.2.
2-Methyl-4-(trifluoromethyl)-1H-imidazole

Into a 10-mL sealed tube, was placed a solution of acetaldehyde (296 µL, 5.29 mmol), 3,3,3-trifluoro-2-oxopropanal (compound 16.1, 1.0 g, 7.9 mmol), and 25% ammonium hydroxide (0.8 mL) in methanol (5 mL). The solution was stirred for 3 h at 0° C., then stirred at room temperature overnight. The resulting mixture was concentrated under reduced pressure and then the residue was diluted with water (50 mL) The aqueous phase was extracted with ethyl acetate (3×20 mL) and the combined organic extracts were dried (Na₂SO₄), filtered, and concentrated under reduced pressure. The crude product was purified by chromatography to yield 430 mg (54%) of the title compound as a light yellow solid.

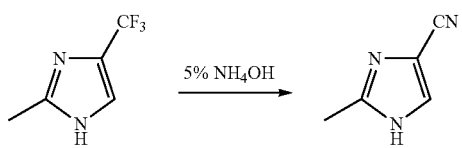

Compound 16.3.
2-Methyl-1H-imidazole-4-carbonitrile

Into a 100-mL round-bottom flask, was placed a solution of 2-methyl-4-(trifluoromethyl)-1H-imidazole (compound 16.2, 300 mg, 2.00 mmol) in 5% ammonium hydroxide (35 mL). The resulting solution was stirred for 4 days at room temperature, then the pH of the solution was adjusted to 7 with acetic acid. The aqueous phase was extracted with of ethyl acetate (3×10 mL) and the combined organic layers were dried (Na₂SO₄), filtered, and concentrated under reduced pressure to yield 170 mg (79%) of the title compound as a light yellow solid.

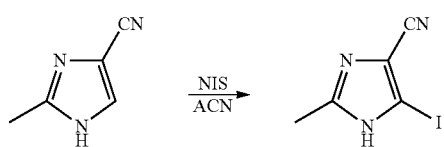

Compound 16.4.
5-Iodo-2-methyl-1H-imidazole-4-carbonitrile

Into a 25-mL round-bottom flask, was placed a mixture of 2-methyl-1H-imidazole-4-carbonitrile (compound 16.3, 50 mg, 0.47 mmol), N-iodosuccinimide (116 mg, 0.52 mmol) in ACN (5 mL). The resulting solution was heated at reflux overnight, then cooled to room temperature and concentrated under reduced pressure. The residue was purified by silica gel column chromatography with ethyl acetate/petroleum ether (1/2) to yield 60 mg (55%) of the title compound as a light yellow solid.

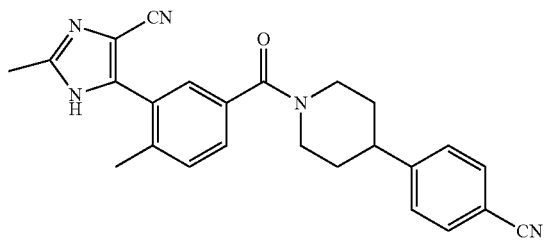 [SMILES: Cc1nc(C#N)c(-c2cc(C(=O)N3CCC(c4ccc(C#N)cc4)CC3)ccc2C)[nH]1]

Compound 16. 5-(5-(4-(4-Cyanophenyl)piperidine-1-carbonyl)-2-methylphenyl)-2-methyl-1H-imidazole-4-carbonitrile The title compound was prepared using standard chemical manipulations and procedures similar to those used for the preparation of compound 5, except 5-iodo-2-methyl-1H-imidazole-4-carbonitrile (compound 16.4) was used in place of 5-iodo-2,4-dimethyl-1H-imidazole (compound 5.5) and 4-(piperidin-4-yl)benzonitrile hydrochloride (compound 1.2) was used in place of 4-(azetidin-3-yl)benzonitrile hydrochloride (compound 5.2). m/z (ES+) 410 (M+H)⁺.

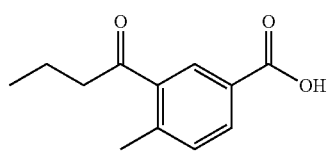

Compound 17.1. 3-Butyryl-4-methylbenzoic acid

The title compound was prepared using standard chemical manipulations and procedures similar to those used for the preparation of compound 10.6, except 3-bromo-4-methylbenzoic acid was used in place of 3-bromo-4-cyclopropylbenzoic acid (compound 10.3) and propylmagnesium bromide was used in place of ethylmagnesium bromide.

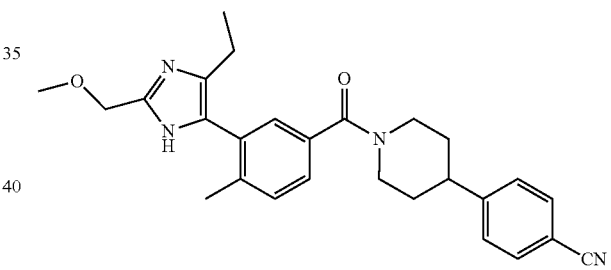

Compound 17. 4-(1-(3-(4-ethyl-2-(methoxymethyl)-1H-imidazol-5-yl)-4-methylbenzoyl)piperidin-4-yl)benzonitrile The title compound was prepared using standard chemical manipulations and procedures similar to those used for the preparation of compound 1, except 3-butyryl-4-methylbenzoic acid (compound 17.1) was used in place of 2,4-dimethyl-5-propionylbenzoic acid (compound 1.4) and 2-methoxyacetimidamide hydrochloride (compound 4.7) was used in place of acetimidamide hydrochloride. m/z (ES+) 443 (M+H)⁺.

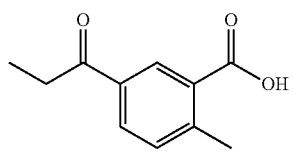

Compound 18.1. 2-Methyl-5-propionylbenzoic acid

The title compound was prepared using standard chemical manipulations and procedures similar to those used for the preparation of compound 10.6, except 5-bromo-2-methyl-benzoic acid was used in place of 3-bromo-4-cyclopropyl-benzoic acid (compound 10.3).

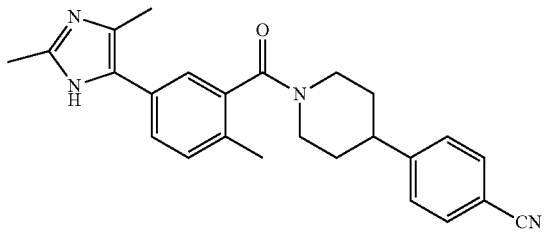 [SMILES: Cc1nc(C)c(-c2ccc(C)c(C(=O)N3CCC(c4ccc(C#N)cc4)CC3)c2)[nH]1]

Compound 18. 4-(1-(5-(2,4-Dimethyl-1H-imidazol-5-yl)-2-methylbenzoyl)piperidin-4-yl)benzonitrile The title compound was prepared using standard chemical manipulations and procedures similar to those used for the preparation of compound 1, except 2-methyl-5-propionyl-benzoic acid (compound 18.1) was used in place of 2,4-dimethyl-5-propionylbenzoic acid (compound 1.4). m/z (ES+) 399 (M+H)$^+$.

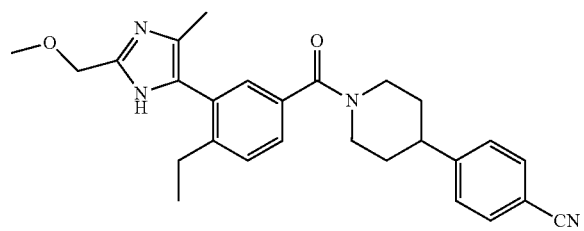 [SMILES: CCc1ccc(C(=O)N2CCC(c3ccc(C#N)cc3)CC2)cc1-c1[nH]c(COC)nc1C]

Compound 19. 4-(1-(4-Ethyl-3-(2-(methoxymethyl)-4-methyl-1H-imidazol-5-yl)benzoyl)piperidin-4-yl)benzonitrile The title compound was prepared using standard chemical manipulations and procedures similar to those used for the preparation of compound 1, except 4-ethylbenzoic acid was used in place of 2,4-dimethylbenzoic acid and 2-methoxy-acetimidamide hydrochloride (compound 4.7) was used in place of acetimidamide hydrochloride. m/z (ES+) 443 (M+H)$^+$.

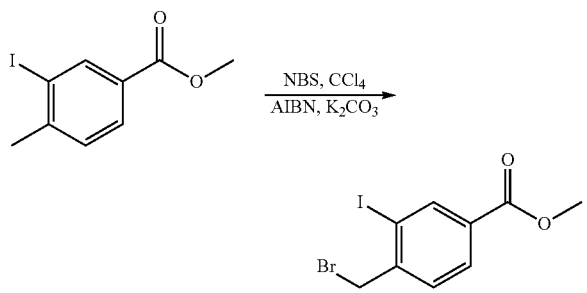

Compound 20.1. Methyl 4-(bromomethyl)-3-iodobenzoate

Into a 100-mL round-bottom flask, was placed a mixture of methyl 3-iodo-4-methylbenzoate (compound 5.3, 3.00 g, 10.9 mmol) in CCl$_4$ (50 mL), NBS (2.9 g, 16.3 mmol), azobisisobutyronitrile (360 mg, 2.19 mmol) and potassium carbonate (1.65 g, 11.9 mmol). The resulting mixture was stirred overnight at 70° C., then cooled to room temperature and concentrated under reduced pressure. The residue was diluted with EtOAc (100 mL) and the mixture was washed with brine (2×50 mL), dried (Na$_2$SO$_4$), filtered, and concentrated under reduced pressure. The residue was purified by silica gel column chromatography with ethyl acetate/petroleum ether (1:20) as the eluent to yield 3.0 g (78%) of the title compound as a yellow solid.

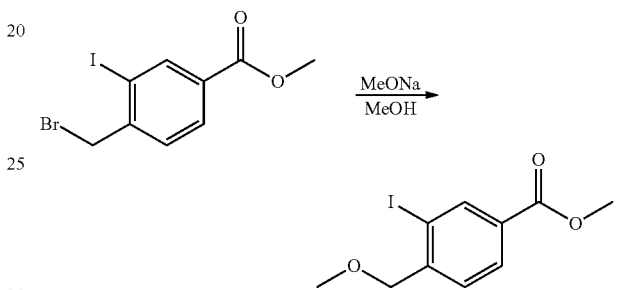

Compound 20.2. Methyl 3-iodo-4-(methoxymethyl)benzoate

Into a 250-mL round-bottom flask, was placed a mixture of methyl 4-(bromomethyl)-3-iodobenzoate (compound 20.1, 3.0 g, 8.5 mmol) and sodium methoxide (1.8 g, 33 mmol) in methanol (100 mL). The resulting solution was stirred for 2 h at 50° C., then cooled to room temperature and concentrated under reduced pressure. The residue was diluted with ethyl acetate (50 mL) and the solids were filtered off. The filtrate was concentrated under reduced pressure to yield 2.0 g (77%) of the title compound as a yellow solid.

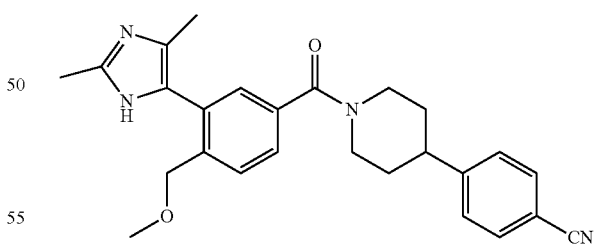

Compound 20. 4-(1-(3-(2,4-dimethyl-1H-imidazol-5-yl)-4-(methoxymethyl)benzoyl)piperidin-4-yl)benzonitrile The title compound was prepared using standard chemical manipulations and procedures similar to those used for the preparation of compound 5, except methyl 3-iodo-4-(methoxymethyl)benzoate (compound 20.2) was used in place of methyl-3-iodo-4-methylbenzoate (compound 5.3)

and 4-(piperidin-4-yl)benzonitrile hydrochloride (compound 1.2) was used in place of 4-(azetidin-3-yl)benzonitrile hydrochloride (compound 5.2). m/z (ES+) 429 (M+H)+.

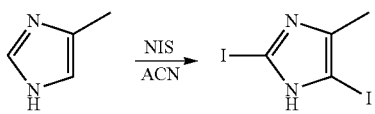

Compound 21.1. 2,5-Diiodo-4-methyl-1H-imidazole

The title compound was prepared using standard chemical manipulations and procedures similar to those used for the preparation of compound 5.5, except 4-methyl-1H-imidazole (2.0 g, 24.4 mmol) was used in place of 2,4-dimethyl-1H-imidazole and 2 equivalents of NIS was used to yield 4.0 g (49%) of the title compound as a white solid.

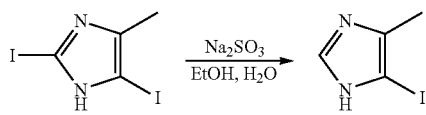

Compound 21.2. 5-Iodo-4-methyl-1H-imidazole

Into a 250-mL round-bottom flask, was placed 2,5-diiodo-4-methyl-1H-imidazole (compound 21.1, 1.0 g, 3.0 mmol), $Na_2SO_3$ (3.0 g, 25.4 mmol) and ethanol/water (20/40 mL). The resulting mixture was stirred overnight at reflux, then cooled and concentrated under reduced pressure. The residue was dissolved in water (100 mL) and extracted with ethyl acetate (2×100 mL). The combined organic layers were dried ($Na_2SO_4$), filtered, and concentrated under reduced pressure to yield 0.60 g (96%) of the title compound as a white solid.

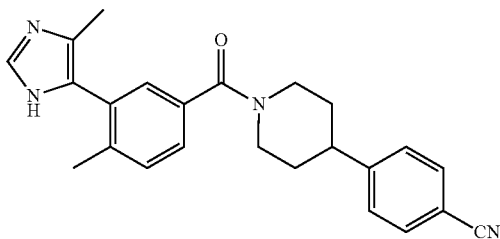 [SMILES: Cc1ccc(C(=O)N2CCC(c3ccc(C#N)cc3)CC2)cc1-c1[nH]cnc1C]

Compound 21. 4-(1-(4-methyl-3-(4-methyl-1H-imidazol-5-yl)benzoyl)piperidin-4-yl)benzonitrile The title compound was prepared using standard chemical manipulations and procedures similar to those used for the preparation of compound 5, except 5-iodo-4-methyl-1H-imidazole (compound 21.2) was used in place of 5-iodo-2,4-dimethyl-1H-imidazole (compound 5.5) and 4-(piperidin-4-yl)benzonitrile hydrochloride (compound 1.2) was used in place of 4-(azetidin-3-yl)benzonitrile hydrochloride (compound 5.2). m/z (ES+) 385 (M+H)+.

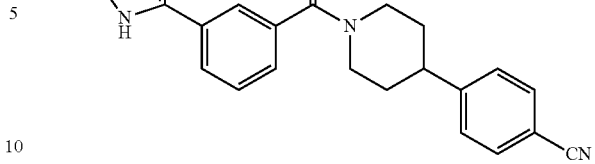

Compound 22. 4-(1-(3-(2,4-Dimethyl-1H-imidazol-5-yl)benzoyl)piperidin-4-yl)benzonitrile The title compound was prepared using standard chemical manipulations and procedures similar to those used for the preparation of compound 1, except 3-iodobenzoic acid was used in place of 5-iodo-2,4-dimethylbenzoic acid (compound 1.3). m/z (ES+) 385 (M+H)+.

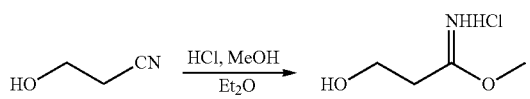

Compound 23.1. Methyl 3-hydroxypropanimidate hydrochloride

Into a 50-mL 3-necked round-bottom flask, was placed a solution of 3-hydroxypropanenitrile (2.00 g, 28.1 mmol) in ether (10 mL) and methanol (5 mL). HCl gas was introduced by bubbling through the solution. The resulting solution was stirred for 2 h at room temperature, then the resulting mixture was carefully concentrated under reduced pressure. The residue was washed with ether (2×20 mL) and the solids were collected by filtration to yield 1.3 g (33%) of the title compound as a white solid.

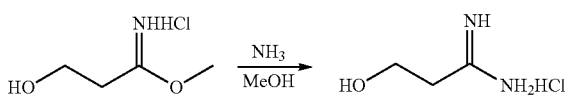

Compound 23.2. 3-Hydroxypropanimidamide hydrochloride

Into a 50-mL 3-necked round-bottom flask, was placed a solution of methyl 3-hydroxypropanecarboximidate hydrochloride (compound 23.1, 2.00 g, 14.3 mmol) in methanol (5 mL). The solution was cooled to 0° C. and ammonia (gas) was introduced over 20 min. The resulting solution was stirred for 2 h at room temperature, then concentrated under reduced pressure. The residue was washed with petroleum ether (2×20 mL) and EtOAc (2×20 mL) and the solids were collected by filtration to yield 1.6 g (crude) of the title compound as a white solid.

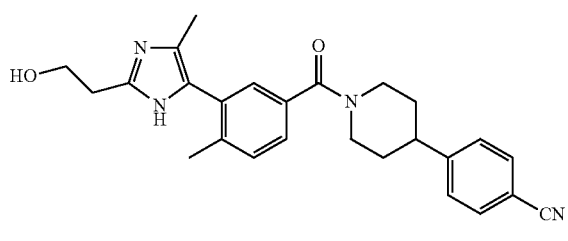 [SMILES: Cc1ccc(C(=O)N2CCC(c3ccc(C#N)cc3)CC2)cc1-c1[nH]c(CCO)nc1C]

Compound 23. 4-(1-(3-(2-(2-Hydroxyethyl)-4-methyl-1H-imidazol-5-yl)-4-methylbenzoyl)piperidin-4-yl)benzonitrile The title compound was prepared using standard chemical manipulations and procedures similar to those used for the preparation of compound 1, except 4-methyl-3-propionylbenzoic acid (compound 11.1) was used in place of 2,4-dimethyl-5-propionylbenzoic acid (compound 1.4) and 3-hydroxypropanimidamide hydrochloride (compound 23.2) was used in place of acetimidamide hydrochloride. m/z (ES+) 429 (M+H)$^+$.

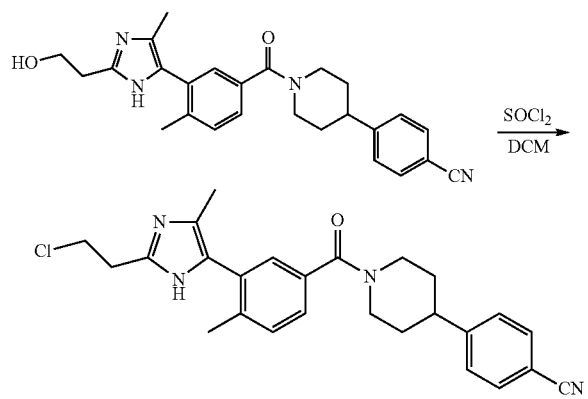

Compound 24.1. 4-(1-(3-(2-(2-Chloroethyl)-4-methyl-1H-imidazol-5-yl)-4-methylbenzoyl)piperidin-4-yl)benzonitrile Into a 50-mL round-bottom flask, was placed a solution of 4-(1-(3-(2-(2-hydroxyethyl)-4-methyl-1H-imidazol-5-yl)-4-methylbenzoyl)piperidin-4-yl)benzonitrile (compound 23, 75 mg, 0.18 mmol) in dichloromethane (5 mL). Thionyl chloride (25 μL, 0.35 mmol) was added and the resulting solution was stirred for 3 h at room temperature. The solvents were carefully removed under reduced pressure to yield 50 mg (crude) of the title compound as a yellow solid.

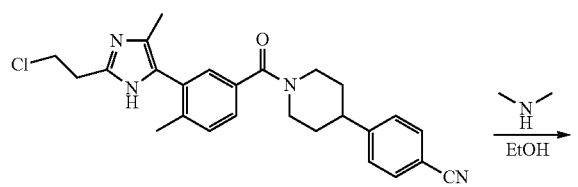

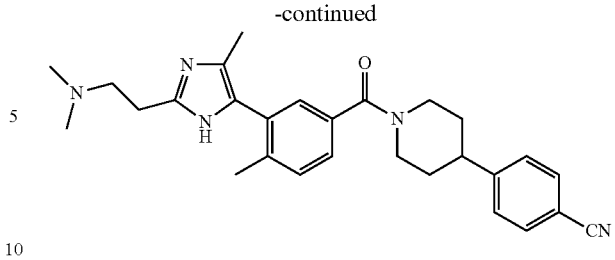

Compound 24. 4-(1-(3-(2-(2-(Dimethylamino)ethyl)-4-methyl-1H-imidazol-5-yl)-4-methylbenzoyl)piperidin-4-yl)benzonitrile Into a vessel with condensor, was placed a solution of 4-(1-(3-(2-(2-chloroethyl)-4-methyl-1H-imidazol-5-yl)-4-methylbenzoyl)piperidin-4-yl)benzonitrile (compound 24.1, 26 mg, 0.06 mmol, 1.00 equiv) in EtOH (10 mL). Dimethylamine (1 M in THF, 0.3 mL, 0.3 mmol) was added and the mixture was sealed under a nitrogen balloon. The resulting solution was stirred overnight with a 100° C. oil bath. After cooling to room temperature, the resulting mixture was concentrated under reduced pressure and the crude product was purified by Prep-HPLC with the following conditions (1#-Pre-HPLC-001(SHIMADZU)): Column, XBridge Shield RP18 OBD Column, 5 um, 19*150 mm; mobile phase, WATER WITH 0.03% $NH_3H_2O$ and $CH_3CN$ (31% $CH_3CN$ up to 43% in 7 min, up to 100% in 0.5 min, down to 31% in 3.5 min); Detector, Waters 2489, 254 & 220 nm. The fractions containing pure compound were combined and lyophilized to yield 6.3 mg (24%) of the title compound as a white solid. m/z (ES+) 456 (M+H)$^+$.

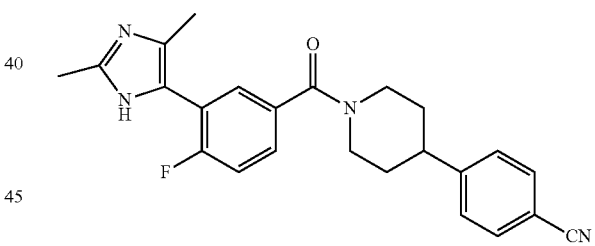

Compound 25.1. 4-(1-(3-(2,4-Dimethyl-1H-imidazol-5-yl)-4-fluorobenzoyl)piperidin-4-yl)benzonitrile The title compound was prepared using standard chemical manipulations and procedures similar to those used for the preparation of compound 1, except 4-fluorobenzoic acid was used in place of 2,4-dimethylbenzoic acid.

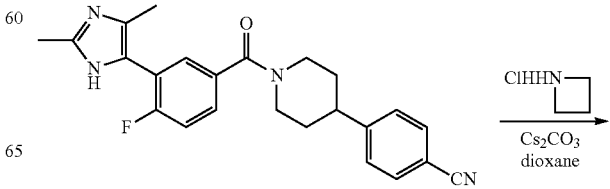

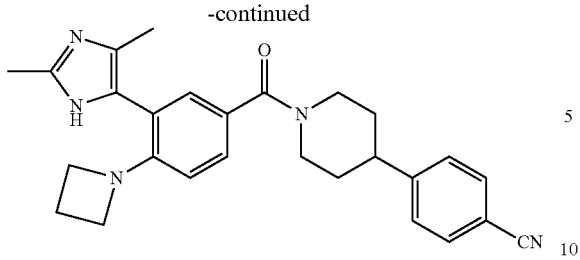

Compound 25. 4-(1-(4-(Azetidin-1-yl)-3-(2,4-dimethyl-1H-imidazol-5-yl)benzoyl)piperidin-4-yl)benzonitrile Into a 10-mL sealed tube, was placed a solution of 4-(1-(3-(2,4-dimethyl-1H-imidazol-5-yl)-4-fluorobenzoyl)piperidin-4-yl)benzonitrile (compound 25.1, 200 mg, 0.50 mmol) in 1,4-dioxane (4 mL). Azetidine hydrochloride (50 mg, 0.53 mmol) and cesium carbonate (500 mg, 1.53 mmol) were added and the mixture was stirred for 48 h at 120° C. behind a blast shield. The mixture was cooled and the solids were removed by filtration. The filtrate was concentrated under reduced pressure and the crude product was purified by Prep-HPLC with the following conditions (1#-Pre-HPLC-001(SHIMADZU)): Column, SunFire Prep C18 OBD Column, 5 um, 19*150 mm; mobile phase, Water with 50 mmol $NH_4HCO_3$ and $CH_3CN$ (33.0% $CH_3CN$ up to 46.0% in 10 min, up to 100.0% in 3 min, down to 33.0% in 1 min); Detector, Waters 2489, 254 & 220 nm. The fractions containing pure compound were combined and lyophilized to yield 59.6 mg (27%) of the title compound as a white solid. m/z (ES+) 440 (M+H)$^+$.

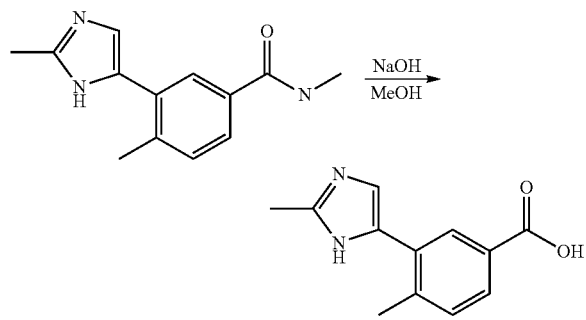

Compound 26.1. 4-Methyl-3-(2-methyl-1H-imidazol-4-yl)benzoic acid

Methyl 4-methyl-3-(2-methyl-1H-imidazol-5-yl) benzoate (compound 7.1, 219 mg, 0.95 mmol) was dissolved in a mixture of methanol (20 mL) and aqueous sodium hydroxide (5 mL, 2M). The resulting solution was heated at 50° C. for 16 hrs, then the reaction was cooled to room temperature and the organic solvent was removed under reduced pressure. The resulting aqueous residue was acidified to pH 3-4 with aqueous HCl (2 M). The resulting solids were collected and dried to yield 128 mg (62%) of the title compound as a white solid. m/z (ES−) 215 (M−H)$^−$.

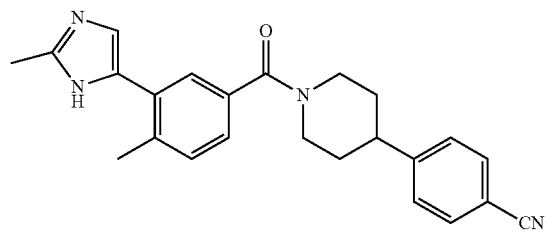 [SMILES: Cc1ncc(-c2cc(C(=O)N3CCC(c4ccc(C#N)cc4)CC3)ccc2C)[nH]1]

Compound 26. 4-(1-(4-Methyl-3-(2-methyl-1H-imidazol-5-yl)benzoyl)piperidin-4-yl)benzonitrile The title compound was prepared using standard chemical manipulations and procedures similar to those used for the preparation of compound 5, except 4-methyl-3-(2-methyl-1H-imidazol-4-yl)benzoic acid (compound 26.1, 65 mg, 0.30 mmol) was used in place of 3-(2,4-dimethyl-1H-imidazol-5-yl)-4-methylbenzoic acid (compound 5.7) and 4-(piperidin-4-yl)benzonitrile hydrochloride (compound 1.2, 74 mg, 0.33 mmol) was used in place of 4-(azetidin-3-yl)benzonitrile hydrochloride (compound 5.2). 79 mg (68%) of the title compound was obtained as a white solid. m/z (ES+) 385 (M+H)$^+$.

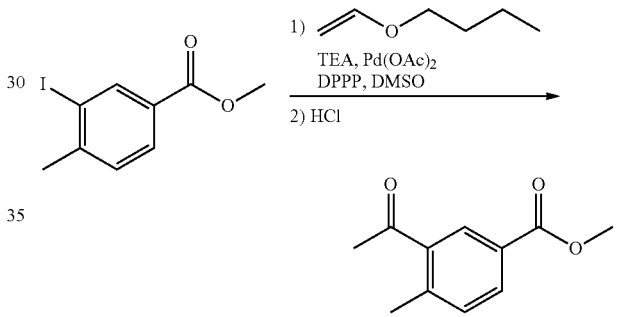

Compound 27.1. Methyl 3-acetyl-4-methylbenzoate

Into a 250-mL round-bottom flask, which was purged and maintained with an inert atmosphere of nitrogen, was placed a mixture of methyl 3-iodo-4-methylbenzoate (compound 5.3, 4.50 g, 16.3 mmol), 1-(vinyloxy)butane (4.21 mL, 32.6 mmol), TEA (4.53 mL, 32.5 mmol), 1,3-bis(diphenylphosphino)propane (672 mg, 1.63 mmol) and Pd(OAc)$_2$ (349 mg, 1.55 mmol) in DMSO (50 mL). The mixture was stirred for 12 hours at 120° C., then cooled to room temperature. The pH was adjusted to 1-2 with aqueous hydrogen chloride (2 M) and stirred for 1 hour. The aqueous phase was extracted with ethyl acetate (3×200 mL) and the combined organic layers were washed with water (100 mL), then brine (3×100 mL), dried (Na$_2$SO$_4$), filtered, and concentrated under reduced pressure. The residue was purified by silica gel column chromatography with ethyl acetate/petroleum ether (1:50) as the eluent to yield 1.45 g (46%) of the title compound as a yellow solid.

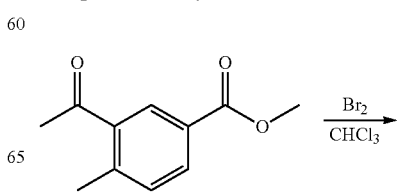

107

-continued

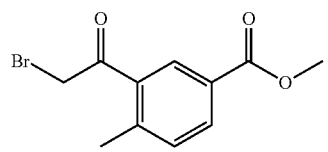

Compound 27.2. Methyl 3-(2-bromoacetyl)-4-methylbenzoate

Into a 50-mL round-bottom flask, which was purged and maintained with an inert atmosphere of nitrogen, was placed a solution of methyl 3-acetyl-4-methylbenzoate (compound 27.1, 200 mg, 1.04 mmol) in chloroform (4 mL). Bromine (53 µL, 1.04 mmol) was added drop-wise and the solution was stirred for 2 h at room temperature, then concentrated under reduced pressure. Obtained 300 mg (crude) of the title compound as a brown solid.

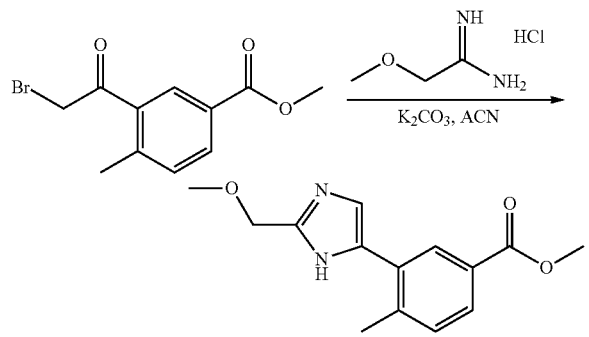

Compound 27.3. Methyl 3-(2-(methoxymethyl)-1H-imidazol-5-yl)-4-methylbenzoate Into a 50-mL round-bottom flask, which was purged and maintained with an inert atmosphere of nitrogen, was placed a solution of methyl 3-(2-bromoacetyl)-4-methylbenzoate (compound 27.2, 281 mg, 1.04 mmol) in ACN (5 mL). 2-Methoxyacetimidamide (compound 4.7, 194 mg, 1.56 mmol) and potassium carbonate (434 mg, 3.14 mmol) were added and the resulting mixture was stirred for 12 hours at 80° C., then concentrated under reduced pressure. The residue was diluted with water (50 mL) and extracted with ethyl acetate (3×30 mL). The combined organic layers were washed with brine (3×50 mL), dried (Na$_2$SO$_4$), filtered, and concentrated under reduced pressure. The residue was purified by silica gel column chromatography with ethyl acetate/petroleum ether (1:1) as the eluent to yield 50 mg (19%) of the title compound as a brown solid.

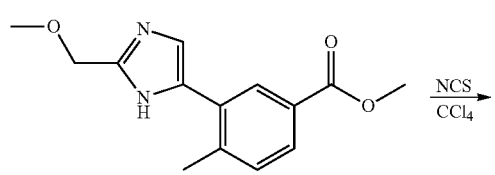

108

-continued

Compound 27.4. Methyl 3-(4-chloro-2-(methoxymethyl)-1H-imidazol-5-yl)-4-methylbenzoate Into a 50-mL round-bottom flask, which was purged and maintained with an inert atmosphere of nitrogen, was placed a solution of methyl 3-(2-(methoxymethyl)-1H-imidazol-5-yl)-4-methylbenzoate (compound 27.3, 40 mg, 0.15 mmol) and NCS (24.6 mg, 0.18 mmol) in CCl$_4$ (20 mL). The resulting mixture was stirred for 2 h at 50° C., then cooled to room temperature and quenched with water (100 mL). The aqueous phase was extracted with ethyl acetate (100 mL) and the combined organic layers were washed with brine (3×30 mL), dried (Na$_2$SO$_4$), filtered, and concentrated under reduced pressure to yield 30 mg (crude) of the title compound as a yellow solid.

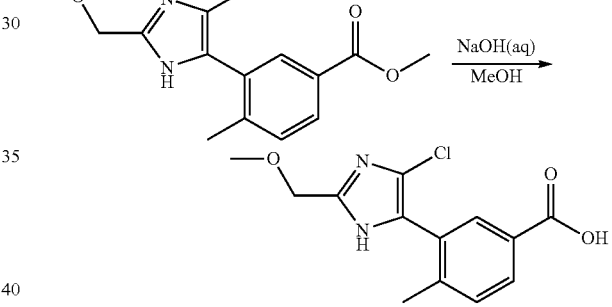

Compound 27.5. 3-(4-Chloro-2-(methoxymethyl)-1H-imidazol-5-yl)-4-methylbenzoic acid Into a 50-mL round-bottom flask, which was purged and maintained with an inert atmosphere of nitrogen, was added methyl 3-(4-chloro-2-(methoxymethyl)-1H-imidazol-5-yl)-4-methylbenzoate (compound 27.4, 50 mg, 0.19 mmol) and sodium hydroxide (31 mg, 0.76 mmol) in methanol/water (3 mL/3 mL). The resulting solution was stirred for 12 hours at room temperature. The pH of the solution was adjusted to 1-2 with hydrogen chloride (6 M), then concentrated under reduced pressure to yield 150 mg (crude) of the title compound as the HCl salt as white solid.

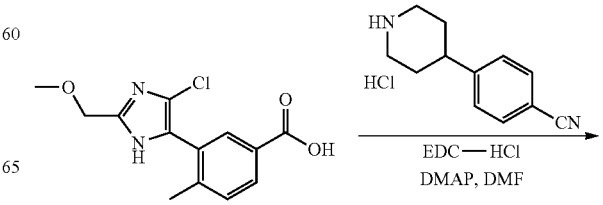

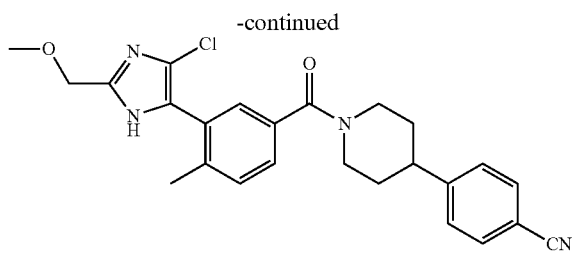

Compound 27. 4-(1-(3-(4-Chloro-2-(methoxymethyl)-1H-imidazol-5-yl)-4-methylbenzoyl)piperidin-4-yl)benzonitrile Into a 50-mL round-bottom flask, which was purged and maintained with an inert atmosphere of nitrogen, was placed a solution of 3-(4-chloro-2-(methoxymethyl)-1H-imidazol-5-yl)-4-methylbenzoic acid (compound 27.5, 20 mg, 0.07 mmol) in N,N-dimethylformamide (3 mL). 4-Dimethylaminopyridine (17.4 mg, 0.14 mmol), EDC.HCl (27 mg, 0.14 mmol), 4-(piperidin-4-yl)benzonitrile hydrochloride (compound 1.2, 15.5 mg, 0.07 mmol, 1.00 equiv) were added and the resulting solution was stirred for 12 h at room temperature. The reaction was quenched with water (10 mL) and extracted with ethyl acetate (3×10 mL). The combined organic layers were washed with brine (10 mL), dried (Na$_2$SO$_4$), filtered, and concentrated under reduced pressure. The residue was purified by Prep-HPLC with the following conditions (1#-Pre-HPLC-001(SHIMADZU)): Column, SunFire Prep C18 OBD Column, 5 um, 19*150 mm; mobile phase, water with 0.05% TFA and CH$_3$CN (35% CH$_3$CN up to 50% in 7 min, up to 100% in 3 min, down to 35% in 1 min); Detector, Waters 2489, 254 & 220 nm. The fractions containing pure compound were combined and lyophilized to yield 15 mg (47%) of the title compound as a white solid. m/z (ES+) 449 (M+H)$^+$.

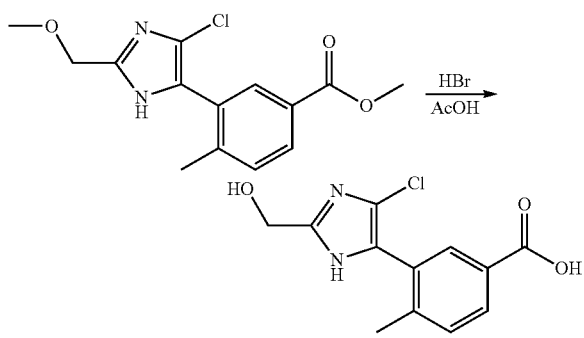

Compound 28.1. 3-(4-Chloro-2-(hydroxymethyl)-1H-imidazol-5-yl)-4-methylbenzoic acid Into a 50-mL round-bottom flask, was placed a solution of methyl 3-(4-chloro-2-(methoxymethyl)-1H-imidazol-5-yl)-4-methylbenzoate (compound 27.4, 380 mg, 1.29 mmol, 1.00 equiv) in HBr (40% in AcOH)(10 mL). The solution was stirred overnight at 80° C., then cooled and concentrated under reduced pressure. The crude residue was purified by prep-HPLC (WATER WITH 0.05% TFA and CH$_3$CN (0% CH$_3$CN in 3 min, then up to 100% for 5 min, down to 0% in 1 min); Detector, 254 & 220 nm. The fractions containing clean product were combined and lyophilized to yield 171 mg (50%) of the title compound as yellow crude oil.

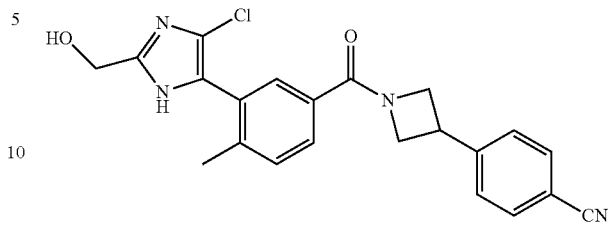

Compound 28. 4-(1-(3-(4-Chloro-2-(hydroxymethyl)-1H-imidazol-5-yl)-4-methylbenzoyl)azetidin-3-yl)benzonitrile The title compound was prepared using standard chemical manipulations and procedures similar to those used for the preparation of compound 27, except 3-(4-chloro-2-(hydroxymethyl)-1H-imidazol-5-yl)-4-methylbenzoic acid (compound 28.1) was used in place of 3-(4-chloro-2-(methoxymethyl)-1H-imidazol-5-yl)-4-methylbenzoic acid (compound 27.5) and 4-(azetidin-3-yl)benzonitrile hydrochloride (compound 5.2) was used in place of 4-(piperidin-4-yl)benzonitrile hydrochloride (compound 1.2). m/z (ES+) 407 (M+H)$^+$.

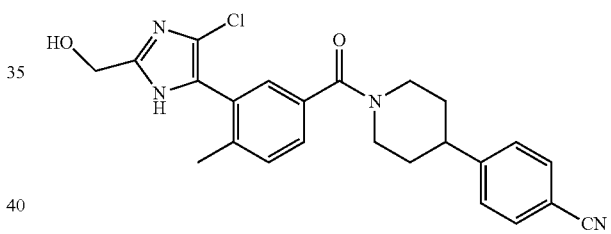

Compound 29. 4-(1-(3-(4-Chloro-2-(hydroxymethyl)-1H-imidazol-5-yl)-4-methylbenzoyl)piperidin-4-yl)benzonitrile The title compound was prepared using standard chemical manipulations and procedures similar to those used for the preparation of compound 27, except 3-(4-chloro-2-(hydroxymethyl)-1H-imidazol-5-yl)-4-methylbenzoic acid (compound 28.1) was used in place of 3-(4-chloro-2-(methoxymethyl)-1H-imidazol-5-yl)-4-methylbenzoic acid (compound 27.5). m/z (ES+) 435 (M+H)$^+$.

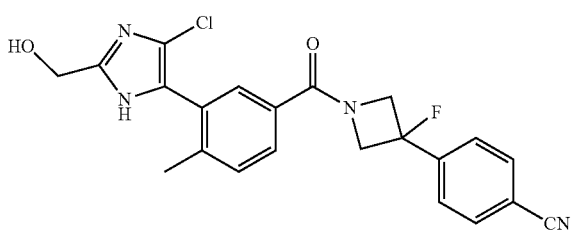

Compound 30. 4-(1-(3-(4-Chloro-2-(hydroxymethyl)-1H-imidazol-5-yl)-4-methylbenzoyl)-3-fluoroazetidin-3-yl)benzonitrile The title compound was prepared using standard chemical manipulations and procedures similar to those used for the preparation of compound 27, except 3-(4-chloro-2-(hydroxymethyl)-1H-imidazol-5-yl)-4-methylbenzoic acid (compound 28.1) was used in place of 3-(4-chloro-2-(methoxymethyl)-1H-imidazol-5-yl)-4-methylbenzoic acid (compound 27.5) and 4-(3-Fluoroazetidin-3-yl)benzonitrile hydrochloride (compound 43.4) was used in place of 4-(piperidin-4-yl)benzonitrile hydrochloride (compound 1.2). m/z (ES+) 425 (M+H)+.

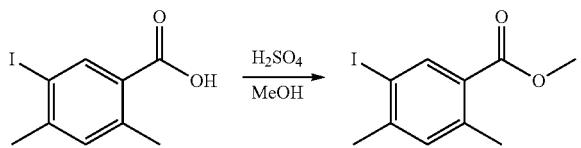

Compound 31.1. Methyl 5-iodo-2,4-dimethylbenzoate

A solution of 5-iodo-2,4-dimethylbenzoic acid (compound 1.3, 10.0 g, 32.6 mmol, 90%) and sulfuric acid (10 mL) in methanol (100 mL) was stirred overnight at 80° C. After cooling to room temperature, the mixture was concentrated under reduced pressure and the residue was diluted with of ethyl acetate (200 mL). The resulting mixture was washed with water (3×50 mL), sodium bicarbonate (aq. sat., 2×50 mL, caution: gas evolution), followed by brine (2×50 mL). The organic phase was dried over anhydrous sodium sulfate, filtered, and concentrated under reduced pressure to yield 9.2 g (88%) of the title compound as a yellow oil.

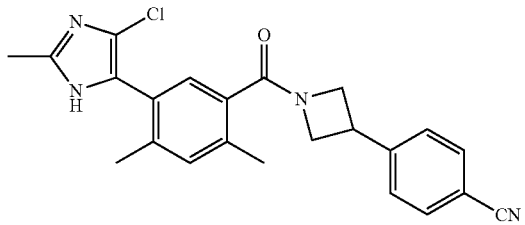 [SMILES: Cc1nc(Cl)c(-c2cc(C(=O)N3CC(c4ccc(C#N)cc4)C3)c(C)cc2C)[nH]1]

Compound 31. 4-(1-(5-(4-Chloro-2-methyl-1H-imidazol-5-yl)-2,4-dimethylbenzoyl)azetidin-3-yl)benzonitrile The title compound was prepared using standard chemical manipulations and procedures similar to those used for preparation of compound 27, except methyl 5-iodo-2,4-dimethylbenzoate (compound 31.1) was used in place of methyl 3-iodo-4-methylbenzoate (compound 5.3), acetimidamide hydrochloride was used in place of 2-methoxyacetimidamide (compound 4.7) and 4-(azetidin-3-yl)benzonitrile hydrochloride (compound 5.2) was used in place of 4-(piperidin-4-yl)benzonitrile hydrochloride (compound 1.2). m/z (ES+) 405 (M+H)+.

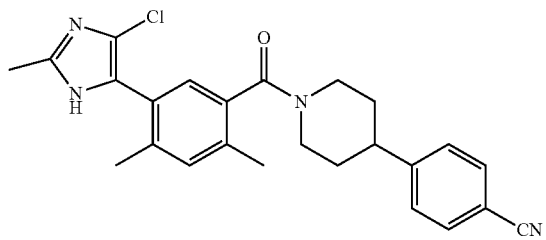 [SMILES: Cc1nc(Cl)c(-c2cc(C(=O)N3CCC(c4ccc(C#N)cc4)CC3)c(C)cc2C)[nH]1]

Compound 32. 4-(1-(5-(4-Chloro-2-methyl-1H-imidazol-5-yl)-2,4-dimethylbenzoyl)piperidin-4-yl)benzonitrile The title compound was prepared using standard chemical manipulations and procedures similar to those used for preparation of compound 27, except methyl 5-iodo-2,4-dimethylbenzoate (compound 31.1) was used in place of methyl 3-iodo-4-methylbenzoate (compound 5.3) and acetimidamide hydrochloride was used in place of 2-methoxyacetimidamide (compound 4.7). m/z (ES+) 433 (M+H)+.

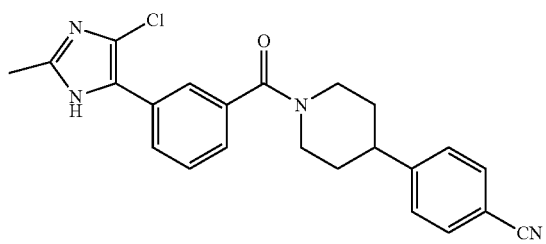 [SMILES: Cc1nc(Cl)c(-c2cccc(C(=O)N3CCC(c4ccc(C#N)cc4)CC3)c2)[nH]1]

Compound 33. 4-(1-(3-(4-Chloro-2-methyl-1H-imidazol-5-yl)benzoyl)piperidin-4-yl)benzonitrile The title compound was prepared using standard chemical manipulations and procedures similar to those used for preparation of compound 27, except methyl 3-iodobenzoate was used in place of methyl 3-iodo-4-methylbenzoate (compound 5.3) and acetimidamide hydrochloride was used in place of 2-methoxyacetimidamide (compound 4.7). m/z (ES+) 405 (M+H)+.

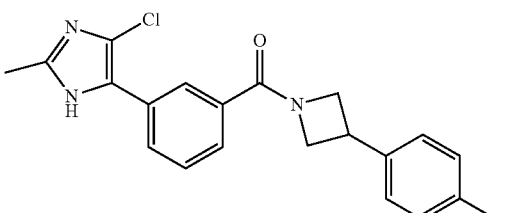

Compound 34. 4-(1-(3-(4-Chloro-2-methyl-1H-imidazol-5-yl)benzoyl)azetidin-3-yl)benzonitrile The title compound was prepared using standard chemical manipulations and procedures similar to those used for preparation of compound 27, except methyl 3-iodobenzoate was used in place of methyl 3-iodo-4-methylbenzoate (compound 5.3), acetimidamide hydrochloride was used in place of 2-methoxyacetimidamide (compound 4.7) and 4-(azetidin-3-yl)benzonitrile hydrochloride (compound 5.2) was used in place of 4-(piperidin-4-yl)benzonitrile hydrochloride (compound 1.2). m/z (ES+) 377 (M+H)+.

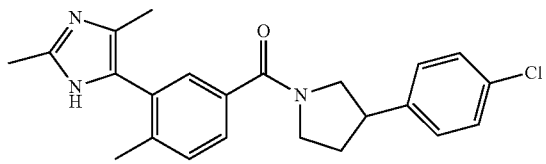 [SMILES: Cc1nc(C)c(-c2cc(C(=O)N3CCC(c4ccc(Cl)cc4)C3)ccc2C)[nH]1]

Compound 35. (3-(4-chlorophenyl)pyrrolidin-1-yl) (3-(2,4-dimethyl-1H-imidazol-5-yl)-4-methylphenyl) methanone The title compound was prepared using standard chemical manipulations and procedures similar to those used for the preparation of compound 5, except 3-(4-chlorophenyl)pyrrolidine was used in place 4-(azetidin-3-yl)benzonitrile hydrochloride (compound 5.2). m/z (ES+) 394 (M+H)+.

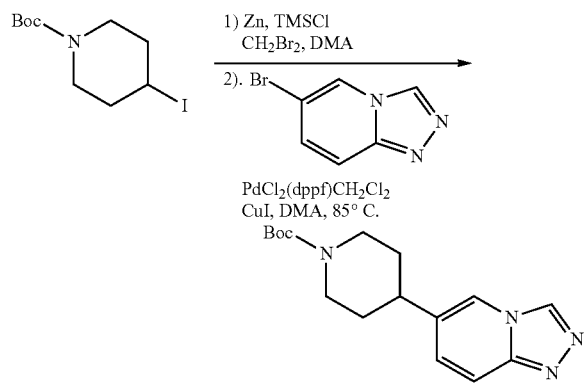

Compound 36.1. tert-Butyl 4-([1,2,4]triazolo[4,3-a] pyridin-6-yl)piperidine-1-carboxylate The title compound was prepared using standard chemical manipulations and procedures similar to those used for the preparation of compound 1.1, except 6-bromo-[1,2,4]triazolo[4,3-a]pyridine was used in place of 4-bromobenzonitrile. m/z (ES+) 303 (M+H)+.

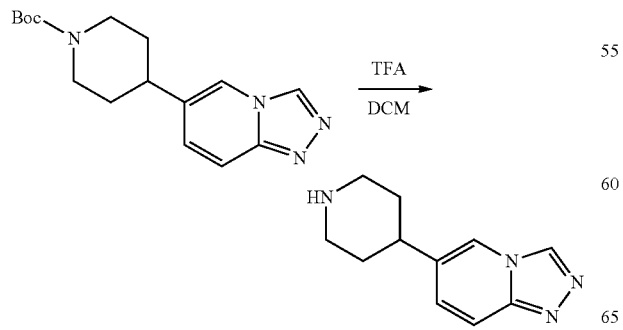

Compound 36.2. 6-(Piperidin-4-yl)-[1,2,4]triazolo [4,3-a]pyridine

To a solution of tert-Butyl 4-([1,2,4]triazolo[4,3-a]pyridin-6-yl)piperidine-1-carboxylate (compound 36.1, 0.05 g, 0.165 mmol) in dichloromethane (2 mL) was added TFA (0.2 mL). The mixture was stirred at room temperature for 3 hours. The solvents were removed under reduced pressure. The residue was purified by prep-TLC (10% MeOH in dichloromethane+~0.5% NH4OH) to give 0.25 g (76%) of the title compound as a light brown oil. m/z (ES+) 203 (M+H)+.

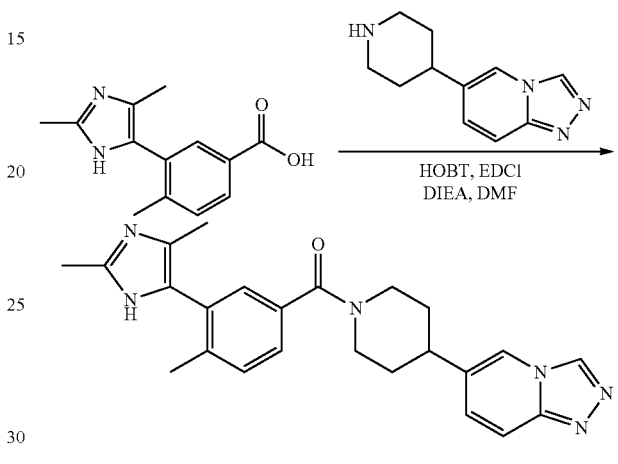

Compound 36. (4-([1,2,4]Triazolo[4,3-a]pyridin-6-yl)piperidin-1-yl)(3-(2,4-dimethyl-1H-imidazol-5-yl)-4-methylphenyl)methanone The title compound was prepared using standard chemical manipulations and procedures similar to those used for the preparation of compound 5, except 6-(piperidin-4-yl)-[1,2,4]triazolo[4,3-a]pyridine (compound 36.2) was used in place of 4-(azetidin-3-yl)benzonitrile hydrochloride (compound 5.2). m/z (ES+) 415 (M+H)+. $^1$H NMR (400 MHz, Methanol-d4) δ 9.12 (d, J=0.8 Hz, 1H), 8.41 (d, J=1.4 Hz, 1H), 7.73 (dt, J=9.6, 1.0, 1.0 Hz, 1H), 7.53 (dd, J=9.5, 1.6 Hz, 1H), 7.47-7.37 (m, 2H), 7.33 (d, J=1.7 Hz, 1H), 4.84 (m, 1H), 4.00 (m, 1H), 3.00 (m, 2H), 2.42 (s, 3H), 2.32 (s, 3H), 2.14 (s, 3H), 2.10 (m, 1H), 1.96 (m, 1H), 1.77 (m, 3H).

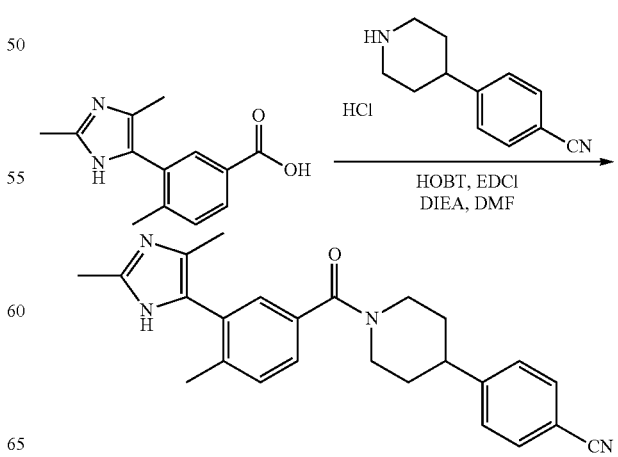

Compound 37. 4-(1-(3-(2,4-Dimethyl-1H-imidazol-5-yl)-4-methylbenzoyl)piperidin-4-yl)benzonitrile The title compound was prepared using standard chemical manipulations and procedures similar to those used for the preparation of compound 5, except 4-(piperidin-4-yl)benzonitrile hydrochloride (compound 1.2) was used in place of 4-(azetidin-3-yl)benzonitrile hydrochloride (compound 5.2). m/z (ES+) 399 (M+H)+. $^1$H NMR (400 MHz, Methanol-d4) δ 7.65 (d, J=8.4 Hz, 2H), 7.48 (d, J=8.0 Hz, 2H), 7.38 (d, J=8.0 Hz, 1H), 7.34 (dd, J=7.20, 2.0 Hz, 1H), 7.28 (d, J=2.0 Hz, 1H) 4.84-4.71 (m, 1H), 4.02-3.89 (m, 1H), 3.03-2.91 (m, 2H), 2.36 (s, 3H), 2.29 (s, 3H), 2.09 (s, 3H), 2.00-1.64 (m, 5H).

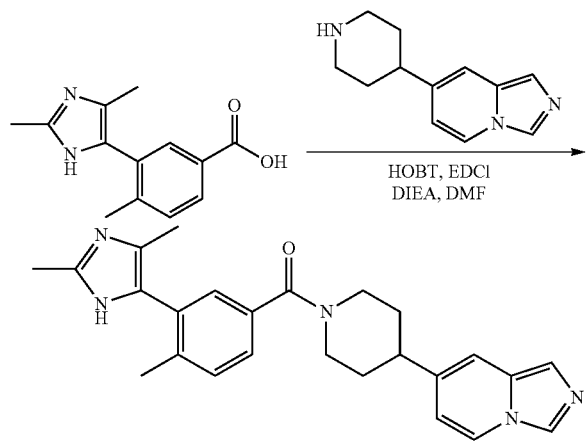

Compound 38. (3-(2,4-Dimethyl-1H-imidazol-5-yl)-4-methylphenyl)(4-(imidazo[1,5-a]pyridin-7-yl)piperidin-1-yl)methanone The title compound was prepared using standard chemical manipulations and procedures similar to those used for the preparation of compound 5, except 7-(piperidin-4-yl)imidazo[1,5-a]pyridine hydrochloride (compound 39.5) was used in place of 4-(azetidin-3-yl)benzonitrile hydrochloride (compound 5.2). m/z (ES+) 399 (M+H)+. $^1$H NMR (400 MHz, Methanol-d4) δ 8.25 (s, 1H), 8.18 (d, J=7.6 Hz, 1H), 7.43-7.34 (m, 3H), 7.31-7.27 (m, 2H), 6.68 (dd, J=7.6, 1.6 Hz, 1H), 4.85-4.76 (m, 1H), 4.04-3.93 (m, 1H), 3.05-2.80 (m, 2H), 2.37 (s, 3H), 2.31 (s, 3H), 2.11 (s, 3H), 1.95-1.58 (m, 5H).

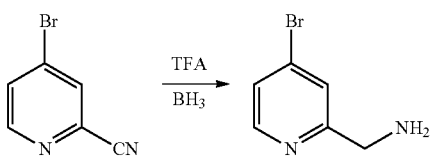

Compound 39.1. (4-Bromopyridin-2-yl)methanamine

To a 1-L round-bottom flask, was placed a solution of 4-bromopyridine-2-carbonitrile (10 g, 95%, 51.9 mmol; patent US 2009/0239876 A1, example 2) in tetrahydrofuran (220 mL), then BH$_3$-THF complex (1 M) (330 mL) was added drop-wise with stirring at room temperature. The resulting solution was stirred overnight at room temperature, then carefully quenched with formic acid (100 mL). The mixture was concentrated under reduced pressure to yield the title compound as the formate salt which was a light yellow solid and was used in the next step without further purification (8 g, crude).

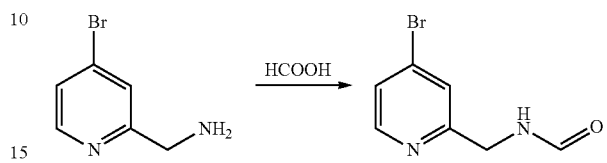

Compound 39.2. N-((4-Bromopyridin-2-yl)methyl)formamide

To a 500-mL round-bottom flask, was placed (4-bromopyridin-2-yl)methanamine (compound 39.1, 8.0 g, crude) and formic acid (200 mL). The solution was stirred for 2 h at 100° C., then cooled and the pH was adjusted to 7 by careful and slow addition of aqueous sodium carbonate (sat.). The aqueous phase was extracted with ethyl acetate (3×200 mL) and the combined organic layers were washed with brine (3×30 mL), dried (Na$_2$SO$_4$), filtered, and concentrated under reduced pressure. The residue was purified by silica gel column chromatography with ethyl acetate as the eluent to yield the title compound as a yellow oil (8.0 g, 90% pure, 65% yield over 2 steps).

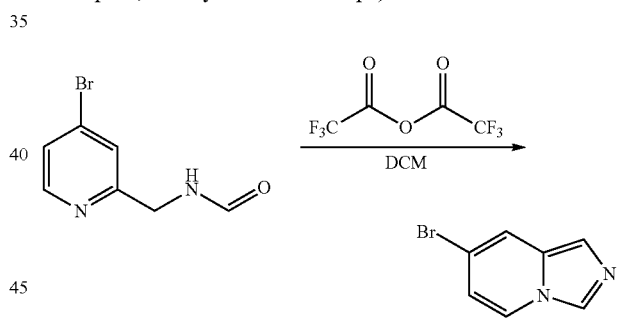

Compound 39.3. 7-bromoimidazo[1,5-a]pyridine

To a 100-mL round-bottom flask, was placed a solution of N-((4-bromopyridin-2-yl)methyl)formamide (compound 39.2, 3.0 g, 90%, 12.6 mmol) in dichloromethane (20 mL). The solution was cooled to 0-5° C. then trifluoroacetic anhydride (1.93 mL, 13.9 mmol) was added drop-wise. The resulting solution was stirred for 1 h at room temperature, then the pH was adjusted to 7 by careful and slow addition of aqueous sodium carbonate (sat.). The aqueous phase was extracted with dichloromethane (3×20 mL) and the combined organic layers were washed with brine (3×20 mL), dried (Na$_2$SO$_4$), filtered, and concentrated under reduced pressure. The residue was purified by silica gel column chromatography with ethyl acetate/petroleum ether (1/1) as the eluent to yield the title compound as a brown solid (1.0 g, 40%).

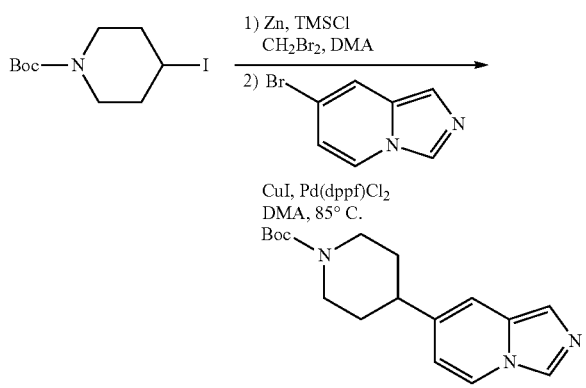

Compound 39.4. tert-Butyl 4-(imidazo[1,5-a]pyridin-7-yl)piperidine-1-carboxylate The title compound was prepared using standard chemical manipulations and procedures similar to those used for the preparation of compound 1.1, except 7-bromoimidazo[1,5-a]pyridine (compound 39.3) was used in place of 4-bromobenzonitrile.

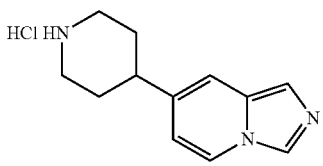

Compound 39.5. 7-(Piperidin-4-yl)imidazo[1,5-a]pyridine hydrochloride

The title compound was prepared using standard chemical manipulations and procedures similar to those used for the preparation of compound 1.2, except tert-butyl 4-(imidazo[1,5-a]pyridin-7-yl)piperidine-1-carboxylate (compound 39.4) was used in place of tert-butyl 4-(4-cyanophenyl)piperidine-1-carboxylate (compound 1.1).

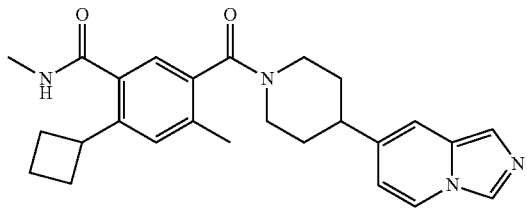 [SMILES: CNC(=O)c1cc(C(=O)N2CCC(c3ccn4cncc4c3)CC2)c(C)cc1C1CCC1]

Compound 39. 2-Cyclobutyl-5-(4-(imidazo[1,5-a]pyridin-7-yl)piperidine-1-carbonyl)-N,4-dimethylbenzamide The title compound was prepared using standard chemical manipulations and procedures similar to those used for the preparation of compound 62, except 7-(piperidin-4-yl)imidazo[1,5-a]pyridine hydrochloride (compound 39.5) was used in place of 5-(piperidin-4-yl)-1H-indazole (compound 62.5) to yield the title compound as a white solid. m/z (ES+) 431 (M+H)⁺.

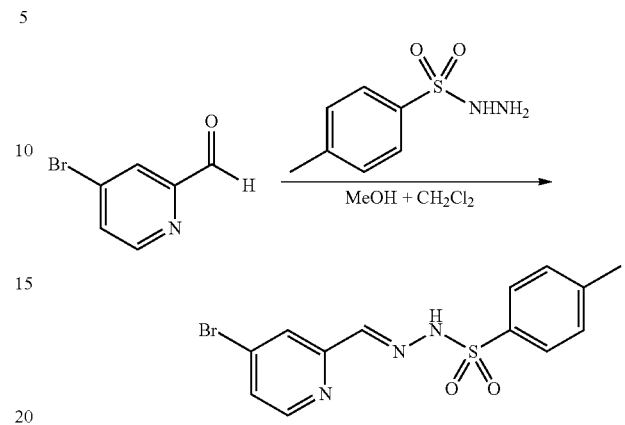

Compound 40.1. (E)-N'-((4-Bromopyridin-2-yl)methylene)-4-methylbenzenesulfonohydrazide 4-Bromopicolinaldehyde (2.0 g, 10.8 mmol) and 4-methylbenzenesulfonohydrazide (2.0 g, 10.8 mmol) were mixed in MeOH (20 mL) and dichloromethane (20 mL). The mixture was stirred at room temperature for 1 hour. The solvents were removed under reduced pressure to give 3.80 g (theoretical) of the title compound as a yellow solid. m/z ES+354, 356 (M+H)⁺.

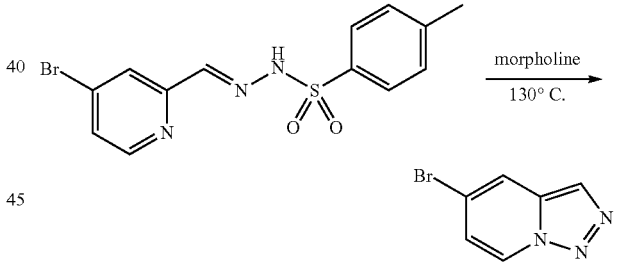

Compound 40.2. 5-Bromo-[1,2,3]triazolo[1,5-a]pyridine

A solution of (E)-N-((4-bromopyridin-2-yl)methylene)-4-methylbenzenesulfonohydrazide (compound 40.1, 3.8 g, 10.7 mmol) in morpholine (12 mL) was heated at 130° C. for 3 hours. The reaction mixture was cooled to room temperature, then diluted with EtOAc (150 mL) and washed with water (2×30 mL). The organic layer was dried (MgSO₄), filtered, and concentrated under reduced pressure. The residue was purified by silica gel column chromatography (hexanes:EtOAc 4:1) to yield 2.10 g (99%) of the title compound as a light yellow solid. m/z (ES+) 198, 200 (M+H)⁺.

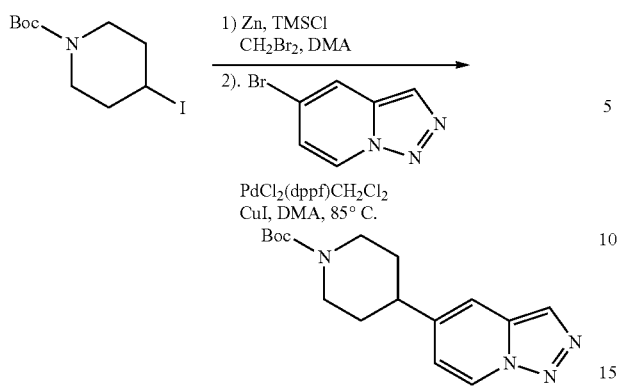

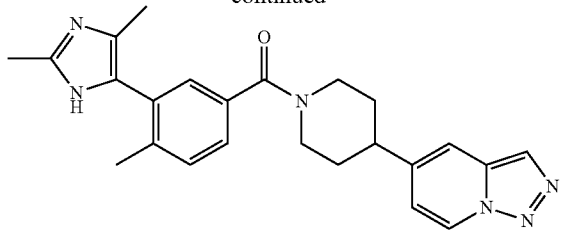

Compound 40. (4-([1,2,3]Triazolo[1,5-a]pyridin-5-yl)piperidin-1-yl)(3-(2,4-dimethyl-1H-imidazol-5-yl)-4-methylphenyl)methanone The title compound was prepared using standard chemical manipulations and procedures similar to those used for the preparation of compound 5, except 5-(piperidin-4-yl)-[1,2,3]triazolo[1,5-a]pyridine (compound 40.4) was used in place of 4-(azetidin-3-yl)benzonitrile hydrochloride (compound 5.2). m/z (ES+) 415 (M+H)$^+$. $^1$H NMR (400 MHz, Methanol-d4) δ 8.84 (d, J=7.2 Hz, 1H), 8.07 (d, J=0.8 Hz, 1H), 7.77 (t, J=0.8, 0.8 Hz, 1H), 7.44-7.34 (m, 2H), 7.32 (d, J=1.6 Hz, 1H), 7.18 (dd, J=7.6, 2.0 Hz, 1H), 4.87-4.76 (m, 1H), 4.08-3.92 (m, 1H), 3.11-2.95 (m, 2H), 2.37 (s, 3H), 2.31 (s, 3H), 2.11 (s, 3H), 2.00-1.67 (m, 5H).

Compound 40.3. tert-Butyl 4-([1,2,3]triazolo[1,5-a]pyridin-5-yl)piperidine-1-carboxylate The title compound was prepared using standard chemical manipulations and procedures similar to those used for the preparation of compound 1.1, except tert-butyl 4-([1,2,3]triazolo[1,5-a]pyridin-5-yl)piperidine-1-carboxylate (compound 40.2) was used in place of 4-bromobenzonitrile. m/z (ES+) 303 (M+H)$^+$.

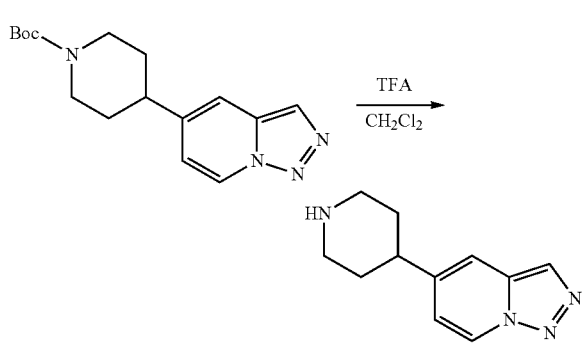

Compound 40.4. 5-(Piperidin-4-yl)-[1,2,3]triazolo[1,5-a]pyridine

The title compound was prepared using standard chemical manipulations and procedures similar to those used for the preparation of compound 36.2, except tert-butyl 4-([1,2,3]triazolo[1,5-a]pyridin-5-yl)piperidine-1-carboxylate (compound 40.3) was used in place of tert-butyl 4-([1,2,4]triazolo[4,3-a]pyridin-6-yl)piperidine-1-carboxylate (compound 36.1). m/z (ES+) 203 (M+H)$^+$.

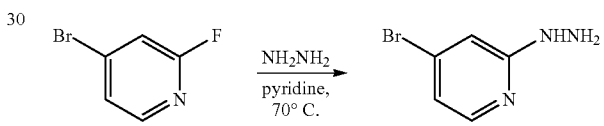

Compound 41.1. 4-Bromo-2-hydrazinylpyridine

To a solution of 4-bromo-2-fluoropyridine (2.0 g, 11.4 mmol) in pyridine (10 mL) was added hydrazine (5 mL, 159 mmol). The mixture was heated at 70° C. for 2 hours, then cooled to room temperature. The volatile organics were removed under reduced pressure, then water (60 mL) was added to the residue and an off-white solid precipitated. The solid was filtered, washed with water, and dried under reduced pressure at 50° C. to give 1.77 g (84%) of the title compound as an off-white solid. m/z (ES+) 188, 190 (M+H)$^+$.

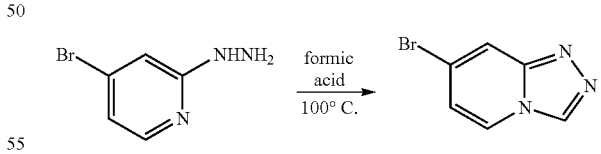

Compound 41.2. 7-Bromo-[1,2,4]triazolo[4,3-a]pyridine

4-Bromo-2-hydrazinylpyridine (compound 41.1) was suspended in formic acid (3 mL). The mixture was heated at 100° C. for one hour, then upon complete reaction, the mixture cooled to room temperature. The volatile organics were removed under reduced pressure, then water (50 mL) was added to the residue. The solids that formed were filtered, washed with water and dried under reduced pressure

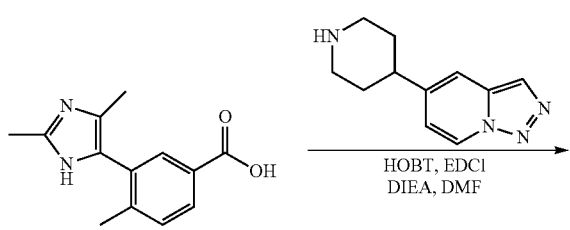

at 50° C. to give 1.68 g (90%) of the title compound as an off-white solid. m/z (ES+) 198, 200 (M+H)+.

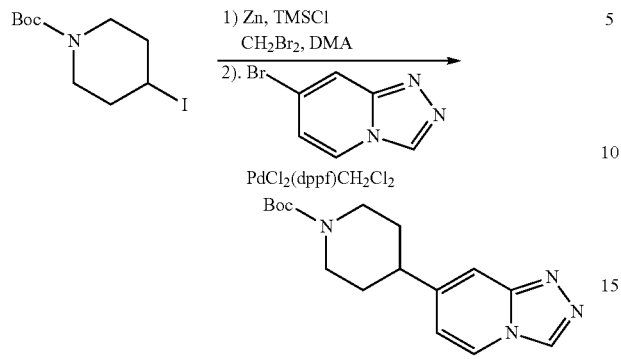

Compound 41.3. tert-Butyl 4-([1,2,4]triazolo[4,3-a]pyridin-7-yl)piperidine-1-carboxylate The title compound was prepared using standard chemical manipulations and procedures similar to those used for the preparation of compound 1.1, except 7-bromo-[1,2,4]triazolo[4,3-a]pyridine (compound 41.2) was used in place of 4-bromobenzonitrile. m/z (ES+) 303 (M+H)+.

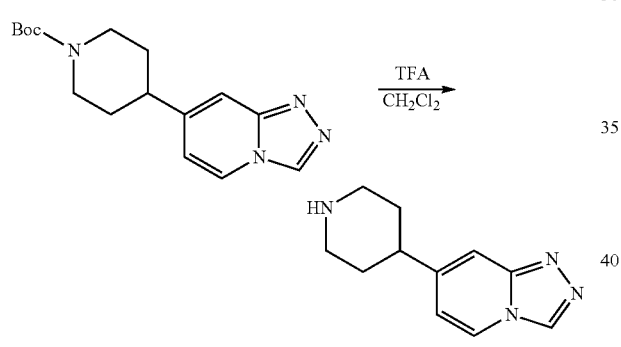

Compound 41.4. 7-(Piperidin-4-yl)-[1,2,4]triazolo[4,3-a]pyridine

The title compound was prepared using standard chemical manipulations and procedures similar to those used for the preparation of compound 36.2, except tert-butyl 4-([1,2,4]triazolo[4,3-a]pyridin-7-yl)piperidine-1-carboxylate (compound 41.3) was used in place of tert-butyl 4-([1,2,4]triazolo[4,3-a]pyridin-6-yl)piperidine-1-carboxylate (compound 36.1) m/z (ES+) 203 (M+H)+.

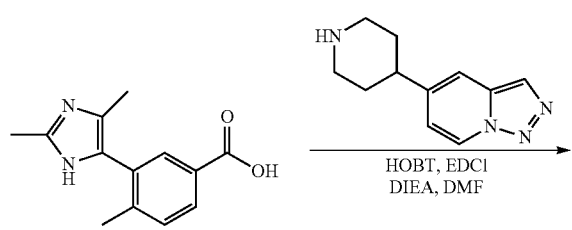

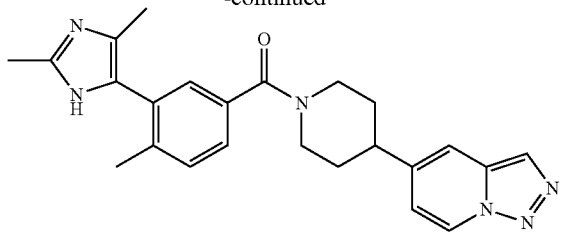

Compound 41. (4-([1,2,4]Triazolo[4,3-a]pyridin-7-yl)piperidin-1-yl)(3-(2,4-dimethyl-1H-imidazol-5-yl)-4-methylphenyl)methanone The title compound was prepared using standard chemical manipulations and procedures similar to those used for the preparation of compound 5, except 7-(piperidin-4-yl)-[1,2,4]triazolo[4,3-a]pyridine (compound 41.4) was used in place of 4-(azetidin-3-yl)benzonitrile hydrochloride (compound 5.2). m/z (ES+) 415 (M+H)+. $^1$H NMR (400 MHz, Methanol-d4) δ 9.13 (s, 1H), 8.45 (d, J=8.0 Hz, 1H), 7.59 (s, 1H), 7.44-7.36 (m, 2H), 7.33 (d, J=1.6 Hz, 1H), 7.07 (dd, J=7.2, 1.6 Hz, 1H), 4.87-4.78 (m, 1H), 4.08-3.96 (m, 1H), 3.11-2.95 (m, 2H), 2.40 (s, 3H), 2.32 (s, 3H), 2.13 (s, 3H), 2.10-1.73 (m, 5H).

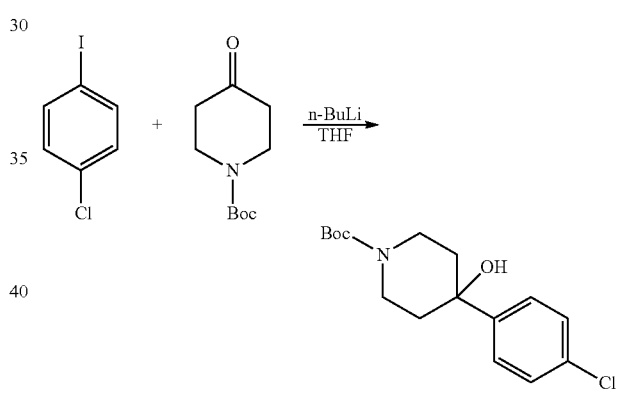

Compound 42.1. tert-Butyl 4-(4-chlorophenyl)-4-hydroxypiperidine-1-carboxylate Into a 1-L 3-necked round-bottom flask, which was purged and maintained with an inert atmosphere of nitrogen, was placed a solution of 1-chloro-4-iodobenzene (10.0 g, 41.9 mmol) in tetrahydrofuran (150 mL). The solution was cooled to −78° C., then n-BuLi (2.4 M) (16.6 mL, 39.8 mmol) was added dropwise and the resulting mixture was stirred for 0.5 h at −78° C. A solution of tert-butyl 4-oxopiperidine-1-carboxylate (7.60 g, 38.1 mmol) in tetrahydrofuran (50 mL) was added dropwise and the resulting mixture was stirred for 1 h at −78° C. The reaction was then warmed to 0° C., and carefully quenched by the slow addition of water (150 mL). The layers were separated and the aqueous phase was extracted with ethyl acetate (150 mL). The combined organic layers were dried (Na$_2$SO$_4$), filtered, and concentrated under reduced pressure. The residue was purified by silica gel column chromatography with ethyl acetate/petroleum ether (1:50 to 1:3) to yield the title compound as a light yellow solid (9.3 g, 78%).

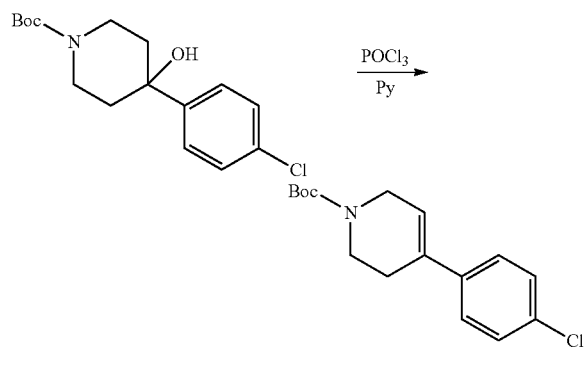

Compound 42.2. tert-Butyl 4-(4-chlorophenyl)-5,6-dihydropyridine-1(2H)-carboxylate Into a 250-mL round-bottom flask, was placed a solution of tert-butyl 4-(4-chlorophenyl)-4-hydroxypiperidine-1-carboxylate (compound 42.1, 9.00 g, 28.9 mmol) in pyridine (50 mL). With stirring, phosphoroyl trichloride (7.93 mL, 84.8 mmol) was added drop-wise. The resulting mixture was stirred overnight at room temperature and then concentrated under reduced pressure. The residue was diluted with ethyl acetate (20 mL) and carefully quenched by slow addition of aqueous sodium bicarbonate. The layers were separated and the organic layer was washed with aqueous sodium bicarbonate (2×30 mL), dried (Na$_2$SO$_4$), filtered, and concentrated under reduced pressure. The residue was purified by silica gel column chromatography with ethyl acetate/petroleum ether (1:100 to 1:10) to yield the title compound as a colorless oil (6.1 g, 72%).

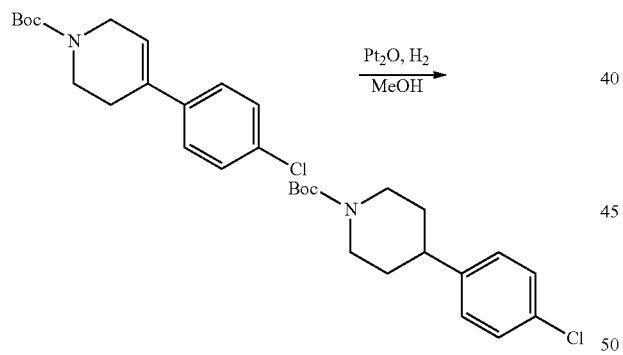

Compound 42.3. tert-Butyl 4-(4-chlorophenyl)piperidine-1-carboxylate

Into a 250-mL round-bottom flask, was placed a mixture of Pt$_2$O (200 mg) and methanol (50 mL). The mixture was purged with nitrogen, then hydrogen was introduced and the mixture was stirred for 15 min. A solution of tert-butyl 4-(4-chlorophenyl)-5,6-dihydropyridine-1(2H)-carboxylate (compound 42.2, 6.00 g, 20.4 mmol) in methanol (50 mL) was added and the resulting mixture was stirred under hydrogen overnight at room temperature. After purging with nitrogen, the solids were filtered off and the resulting solution was concentrated under vacuum to yield the title compound as a light green oil (5.30 g, 88%).

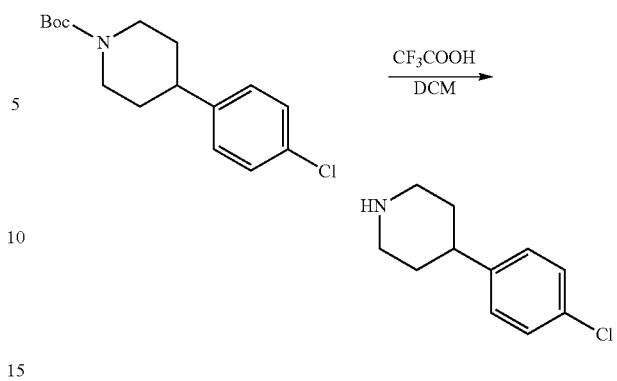

Compound 42.4. 4-(4-Chlorophenyl)piperidine

Into a 250-mL round-bottom flask, was placed a solution of tert-butyl 4-(4-chlorophenyl)piperidine-1-carboxylate (compound 42.3, 5.00 g, 16.9 mmol) in dichloromethane (100 mL), trifluoroacetic acid (9.6 g, 84 mmol). The resulting solution was stirred overnight at room temperature and then concentrated under reduced pressure. The residue was carefully diluted with ethyl acetate (100 mL) and aqueous sodium bicarbonate was added until a pH of 8 was attained. The resulting mixture was washed with brine (100 mL) and the organic layer was dried (Na$_2$SO$_4$), filtered, and concentrated under reduced pressure to yield the title compound as a light yellow solid (2.30 g, 70%).

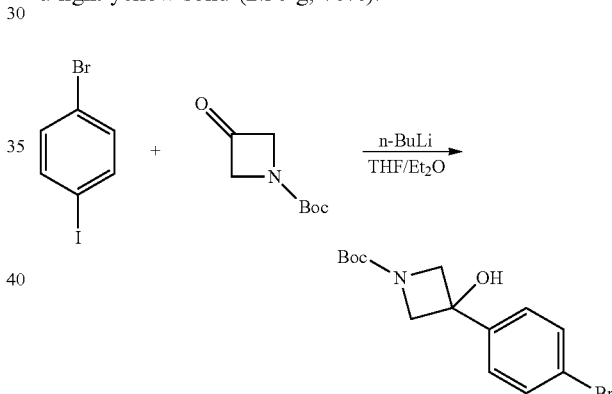

Compound 43.1. tert-Butyl 3-(4-bromophenyl)-3-hydroxyazetidine-1-carboxylate Into a 1-L 3-necked round-bottom flask, purged and maintained with an inert atmosphere of nitrogen, was placed a solution of 1-bromo-4-iodobenzene (25.0 g, 88.4 mmol) in tetrahydrofuran/diethyl ether (400/200 mL). The solution was cooled to −78° C. then n-BuLi (2.5 M, 37.1 mL, 92.8 mmol) was added drop-wise over 10 min. To the resulting mixture was added tert-butyl 3-oxoazetidine-1-carboxylate (16.6 g, 97.0 mmol) in THF (100 mL) drop-wise at −78° C. The resulting mixture was stirred for 1.5 h at −78° C., then carefully quenched with water (300 mL). The aqueous phase was extracted with ethyl acetate (200 mL) and the combined organic layers were washed with brine (2×100 mL), dried (Na$_2$SO$_4$), filtered, and concentrated under reduced pressure. The residue was purified by silica gel column chromatography with ethyl acetate/petroleum ether (1:20-1:5) as the eluent followed by re-crystallized from ethyl acetate:PE in the ratio of 1:100 to yield 8.0 g (28%) of the title compound as a white solid.

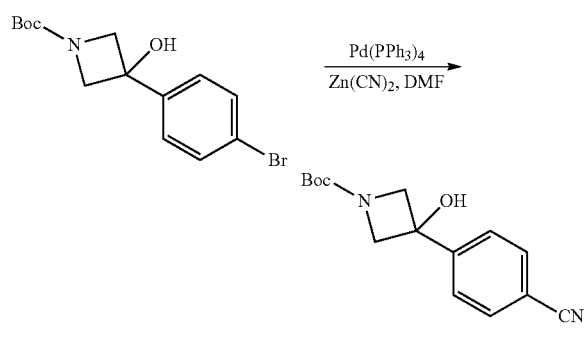

Compound 43.2. tert-Butyl 3-(4-cyanophenyl)-3-hydroxyazetidine-1-carboxylate

Into a 500-mL round-bottom flask, purged and maintained with an inert atmosphere of nitrogen, was placed a mixture of tert-butyl 3-(4-bromophenyl)-3-hydroxyazetidine-1-carboxylate (compound 43.1, 16.3 g, 49.7 mmol) in N,N-dimethylformamide (250 mL), zinc cyanide (8.7 g, 75 mmol) and Pd(PPh$_3$)$_4$ (5.77 g, 5.00 mmol). The resulting mixture was stirred for 15 h at 100° C., then cooled to room temperature. The reaction was quenched with saturated aqueous FeSO$_4$ (500 mL) and stirred vigorously. The mixture was filtered through Celite® and the layers from the filtrate were separated. The aqueous phase was extracted with ethyl acetate (300 mL) and the combined organic layers were washed with brine (2×100 mL), dried (Na$_2$SO$_4$), filtered, and concentrated under reduced pressure. The residue was purified by silica gel column chromatography with ethyl acetate/petroleum ether (1/100-1/3) as the eluent to yield 14 g (crude) of the title compound as a white solid.

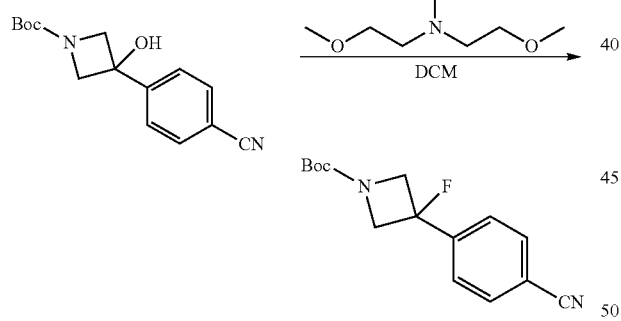

Compound 43.3. tert-Butyl 3-(4-cyanophenyl)-3-fluoroazetidine-1-carboxylate

Into a 250-mL 3-necked round-bottom flask, purged and maintained with an inert atmosphere of nitrogen, was placed a solution of tert-butyl 3-(4-cyanophenyl)-3-hydroxyazetidine-1-carboxylate (compound 43.2, 5.00 g, 18.2 mmol) in dichloromethane (120 mL). The solution was cooled to −78° C. and Deoxo-Fluor® (bis(2-methoxyethyl)aminosulfur trifluoride) (5.99 g, 27.1 mmol) was added drop-wise. The resulting mixture was stirred for 1.5 h at −78° C., then carefully quenched with sodium bicarbonate (50 mL, 1 M). The organic layer was additionally washed with brine (2×50 mL), dried (Na$_2$SO$_4$), filtered, and concentrated under reduced pressure. The residue was purified by silica gel column chromatography with ethyl acetate/petroleum ether (1/50-1/30) as the eluent to yield 3.2 g (64%) of the title compound as colorless oil.

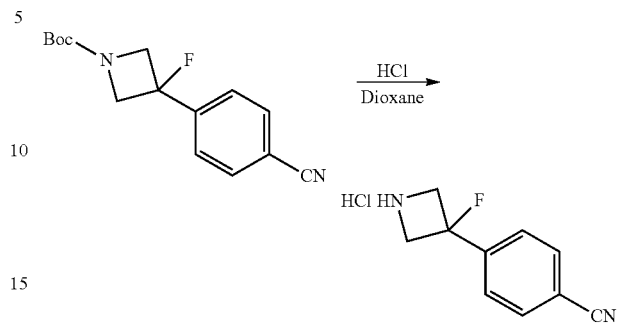

Compound 43.4. 4-(3-Fluoroazetidin-3-yl)benzonitrile hydrochloride

Into a 100-mL round-bottom flask, was placed a solution of tert-butyl 3-(4-cyanophenyl)-3-fluoroazetidine-1-carboxylate (compound 43.3, 1.00 g, 3.62 mmol) in dioxane (10 mL) and HCl in dioxane (4 M in dioxane, 10 mL, 40 mmol). The resulting mixture was stirred for 1 h at 60° C., then cooled and concentrated under reduced pressure. The residue was washed with EtOAc (20 mL) and the product solids were collected by filtration to yield 522 mg (68%) of the title compound as a white solid. m/z (ES+) 177 (M+H)$^+$. $^1$H NMR (300 MHz, CD3OD): δ 7.91 (d, J=7.8 Hz, 2H), 7.82 (d, J=8.1 Hz, 2H), 4.85-4.52 (m, 4H).

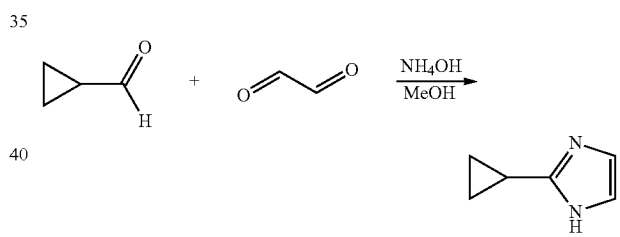

Compound 44.1. 2-Cyclopropyl-1H-imidazole

Into a 25-mL round-bottom flask, was placed a solution of cyclopropanecarbaldehyde (500 mg, 7.13 mmol), oxaldehyde (455 mg, 7.84 mmol) in methanol (5 mL). The solution was cooled to 0° C., then 25% ammonium hydroxide (1 mL) was added drop-wise. The resulting solution was stirred for 3 h at 0° C., then stirred at room temperature overnight. The resulting mixture was concentrated under reduced pressure and the residue was dissolved in brine (50 mL). The aqueous phase was extracted with ethyl acetate (3×10 mL) and the combined organic layers were dried (Na$_2$SO$_4$), filtered, and concentrated under reduced pressure to yield 600 mg (78%) of the title compound as a light brown solid.

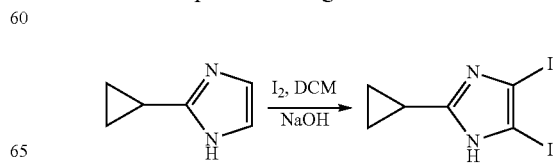

Compound 44.2.
2-Cyclopropyl-4,5-diiodo-1H-imidazole

Into a 100-mL round-bottom flask, was placed a solution of 2-cyclopropyl-1H-imidazole (compound 44.1, 1.8 g, 16.6 mmol) in sodium hydroxide (2 M, 40 mL). A solution of iodine (8.5 g, 33.5 mmol) in dichloromethane (40 mL) was added drop-wise and the resulting mixture was stirred overnight at room temperature. The aqueous layer was separated and neutralized with acetic acid and quenched by the addition of $Na_2S_2O_3$ (sat. aq.). The solids were collected by filtration to yield 3.8 g (63%) of the title compound as a brown solid.

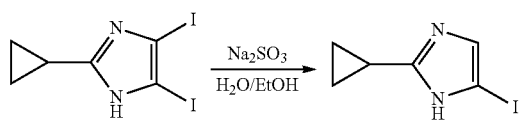

Compound 44.3.
2-Cyclopropyl-4-iodo-1H-imidazole

Into a 100-mL round-bottom flask, was placed a solution of sodium sulfite (11.3 g, 89.7 mmol) in $H_2O$/EtOH (30/15 mL). 2-Cyclopropyl-4,5-diiodo-1H-imidazole (compound 44.2, 3.8 g, 10.6 mmol) was added and the resulting solution was heated at reflux overnight. The reaction was cooled and the volatiles were removed under reduced pressure. The solids were collected by filtration to yield 1.8 g (73%) of the title compound as a light brown solid.

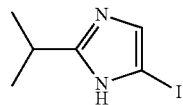

Compound 45.1. 5-Iodo-2-isopropyl-1H-imidazole

The title compound was prepared using standard chemical manipulations and a procedure similar to that used for the preparation of compound 44.3, except 2-isopropyl-1H-imidazole was used in place of 2-cyclopropyl-1H-imidazole (compound 44.1).

The compounds in TABLE 1 were prepared using standard chemical manipulations and procedures with readily available starting materials or building blocks described in this manuscript. The utilized procedures were similar to that used for the preparation of compound 7 using the respective imidazoles (2-methyl-4-bromo imidazole, compound 44.3, or compound 45.1) and the respective amines (compound 1.2, compound 13.4, compound 42.4, compound 5.2, or compound 43.4).

TABLE 1

| Cpd | Name | Structure | m/z (ES+) (M + H)+ |
|---|---|---|---|
| 46 | 4-(1-(3-(4-chloro-2-methyl-1H-imidazol-5-yl)-4-methylbenzoyl)piperidin-4-yl)benzonitrile | 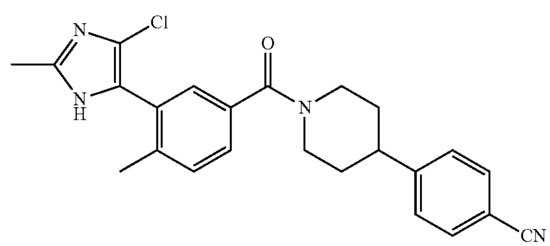 [SMILES: Cc1nc(Cl)c(-c2cc(C(=O)N3CCC(c4ccc(C#N)cc4)CC3)ccc2C)[nH]1] | 419 |
| 13 | 4-(1-(3-(4-chloro-2-methyl-1H-imidazol-5-yl)-4-methylbenzoyl)-4-fluoropiperidin-4-yl)benzonitrile | 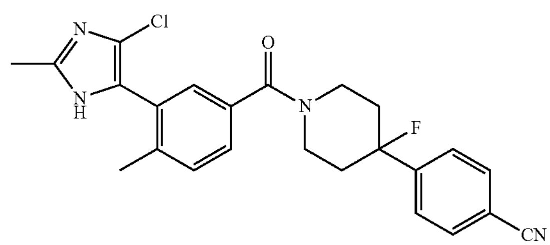 [SMILES: Cc1nc(Cl)c(-c2cc(C(=O)N3CCC(F)(c4ccc(C#N)cc4)CC3)ccc2C)[nH]1] | 437 |
| 42 | (3-(4-chloro-2-methyl-1H-imidazol-5-yl)-4-methylphenyl)(4-(4-chlorophenyl)piperidin-1-yl)methanone | 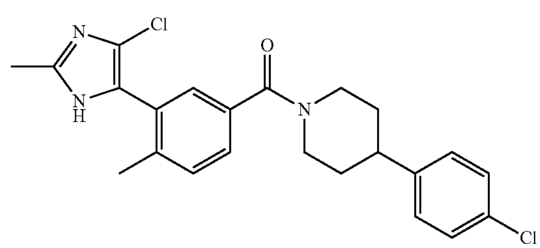 [SMILES: Cc1nc(Cl)c(-c2cc(C(=O)N3CCC(c4ccc(Cl)cc4)CC3)ccc2C)[nH]1] | 408 |

TABLE 1-continued

| Cpd | Name | Structure | m/z (ES+) (M + H)+ |
|---|---|---|---|
| 44 | 4-(1-(3-(4-chloro-2-cyclopropyl-1H-imidazol-5-yl)-4-methylbenzoyl)azetidin-3-yl)benzonitrile | 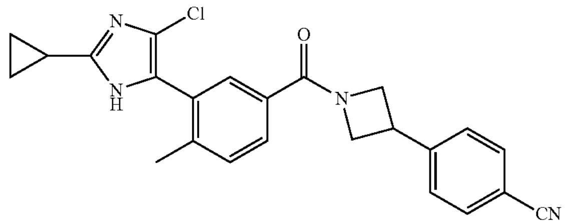 [SMILES: Cc1ccc(C(=O)N2CC(c3ccc(C#N)cc3)C2)cc1-c1[nH]c(C2CC2)nc1Cl] | 417 |
| 47 | 4-(1-(3-(4-chloro-2-cyclopropyl-1H-imidazol-5-yl)-4-methylbenzoyl)piperidin-4-yl)benzonitrile | 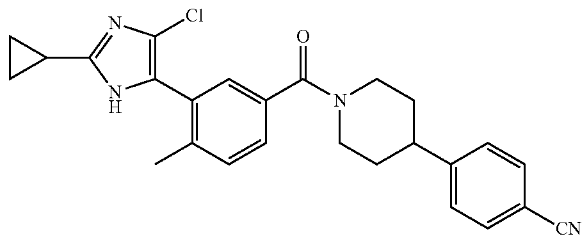 [SMILES: Cc1ccc(C(=O)N2CCC(c3ccc(C#N)cc3)CC2)cc1-c1[nH]c(C2CC2)nc1Cl] | 445 |
| 43 | 4-(1-(3-(4-chloro-2-cyclopropyl-1H-imidazol-5-yl)-4-methylbenzoyl)-3-fluoroazetidin-3-yl)benzonitrile | 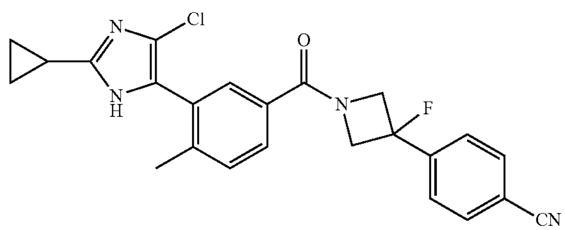 [SMILES: Cc1ccc(C(=O)N2CC(F)(c3ccc(C#N)cc3)C2)cc1-c1[nH]c(C2CC2)nc1Cl] | 435 |
| 48 | 4-(1-(3-(4-chloro-2-cyclopropyl-1H-imidazol-5-yl)-4-methylbenzoyl)-4-fluoropiperidin-4-yl)benzonitrile | 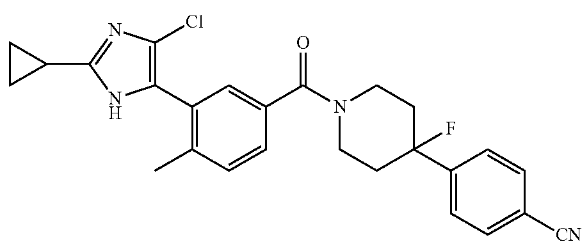 [SMILES: Cc1ccc(C(=O)N2CCC(F)(c3ccc(C#N)cc3)CC2)cc1-c1[nH]c(C2CC2)nc1Cl] | 463 |
| 45 | 4-(1-(3-(4-chloro-2-isopropyl-1H-imidazol-5-yl)-4-methylbenzoyl)azetidin-3-yl)benzonitrile | 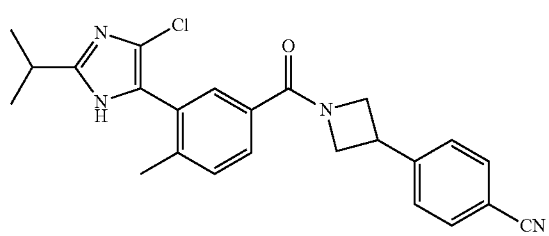 [SMILES: Cc1ccc(C(=O)N2CC(c3ccc(C#N)cc3)C2)cc1-c1[nH]c(C(C)C)nc1Cl] | 419 |
| 49 | 4-(1-(3-(4-chloro-2-isopropyl-1H-imidazol-5-yl)-4-methylbenzoyl)piperidin-4-yl)benzonitrile | 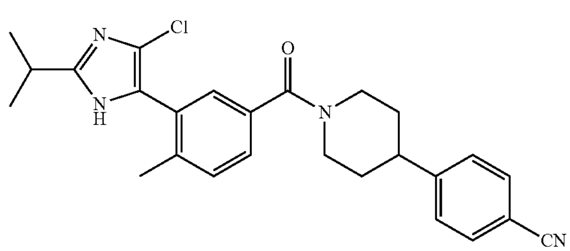 [SMILES: Cc1ccc(C(=O)N2CCC(c3ccc(C#N)cc3)CC2)cc1-c1[nH]c(C(C)C)nc1Cl] | 447 |

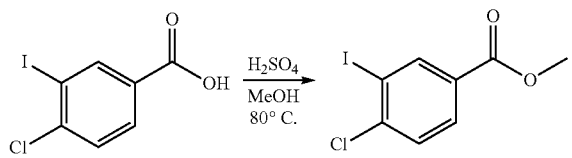

Compound 50.1. Methyl 4-chloro-3-iodo-benzoate

4-Chloro-3-iodo-benzoic acid (5.31 g, 18.8 mmol) was dissolved in methanol (50 mL) and concentrated sulfuric acid (3 mL) was carefully added. The solution was stirred at 80° C. for 4 hours, then cooled to room temperature and the volatile organics were removed under reduced pressure. The residue was partitioned between EtOAc (50 mL) and water (50 mL) and the organic layer was washed with brine, dried ($Na_2SO_4$), filtered, and concentrated under reduced pressure. The residue was purified by flash chromatography ($SiO_2$; 0-10% EtOAc in hexanes) to yield 5.32 g (95%) of the title compound as an oil. $^1$H NMR (400 MHz, Chloroform-d) δ 8.54 (d, J=2.0 Hz, 1H), 7.96 (dd, J=8.4, 2.0 Hz, 1H), 7.53 (d, J=8.4 Hz, 1H), 3.94 (s, 3H).

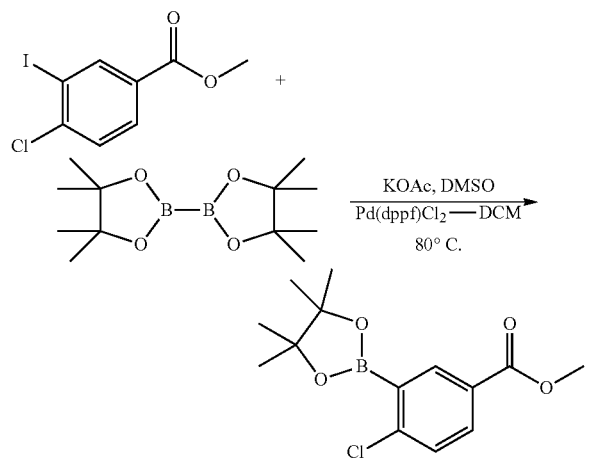

Compound 50.2. Methyl 4-chloro-3-(4,4,5,5-tetramethyl-1,3,2-dioxaborolan-2-yl)benzoate A mixture of methyl 4-chloro-3-iodo-benzoate (compound 50.1, 3.85 g, 13.0 mmol), bis(pinacolato)diboron (3.96 g, 15.6 mmol), Pd(dppf)$Cl_2$.DCM (531 mg, 0.65 mmol) and potassium acetate (3.83 g, 39.0 mmol) in DMSO (40 mL) was degassed with argon and then heated to 80° C. for 18 hours. The reaction mixture was cooled then diluted with ethyl acetate (200 mL) and sequentially washed with water, aqueous HCl (1 M), saturated aqueous $NaHCO_3$, and brine, then dried ($MgSO_4$), filtered, and concentrated under reduced pressure. The residue was purified by flash chromatography ($SiO_2$; 0-10% EtOAc in hexanes) to yield 1.92 g (49%) of the title compound as a white solid. $^1$H NMR (400 MHz, Chloroform-d) δ 8.36 (d, J=2.3 Hz, 1H), 8.01 (dd, J=8.4, 2.3 Hz, 1H), 7.44 (d, J=8.4 Hz, 1H), 3.94 (s, 3H), 1.40 (s, 12H).

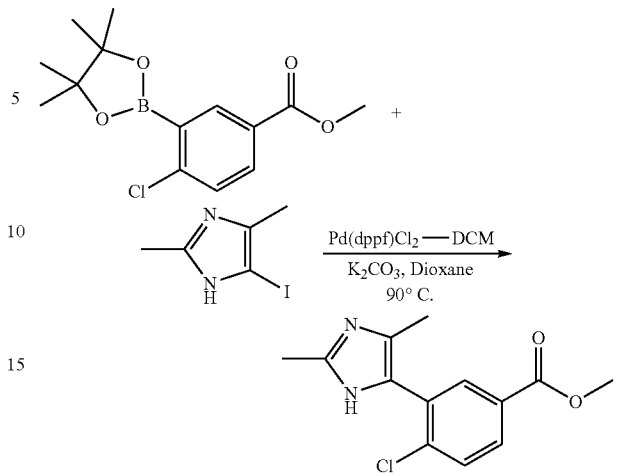

Compound 50.3. Methyl 4-chloro-3-(2,4-dimethyl-1H-imidazol-5-yl)benzoate

To methyl 4-chloro-3-(4,4,5,5-tetramethyl-1,3,2-dioxaborolan-2-yl)benzoate (compound 50.2, 600 mg, 2.02 mmol) in dioxane (20 mL) was added 5-iodo-2,4-dimethyl-1H-imidazole (compound 5.5, 538 mg, 2.42 mmol) and Pd(dppf)$Cl_2$.DCM (165 mg, 0.20 mmol). The mixture was degassed with argon and stirred for 10 minutes at room temperature, then an aqueous solution of potassium carbonate solution (1M, 10 mL) was added and the mixture was stirred at 90° C. for 18 h. The mixture was cooled and diluted with EtOAc, then filtered through Celite®. The filtrate was washed with brine, dried ($MgSO_4$), filtered, and concentrated under reduced pressure. The residue was purified by flash chromatography ($SiO_2$; 0-100% EtOAc in hexanes) to yield 270 mg (50%) of the title compound as a foam. m/z (ES+) 265 (M+H)$^+$. $^1$H NMR (400 MHz, Chloroform-d) δ 8.07 (d, J=2.2 Hz, 1H), 7.90 (dd, J=8.4, 2.2 Hz, 1H), 7.50 (d, J=8.4 Hz, 1H), 3.91 (s, 3H), 2.40 (s, 3H), 2.19 (s, 3H).

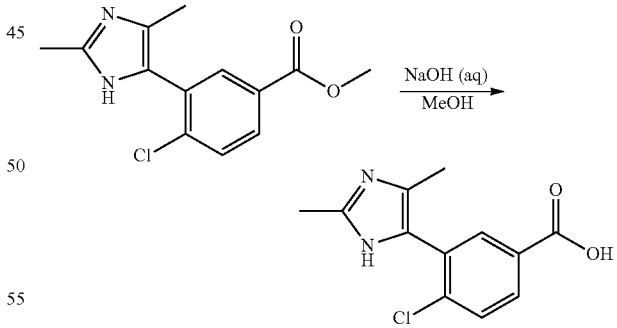

Compound 50.4. 4-Chloro-3-(2,4-dimethyl-1H-imidazol-5-yl)benzoic acid

Methyl 4-chloro-3-(2,4-dimethyl-1H-imidazol-5-yl)benzoate (compound 50.3, 270 mg, 1.02 mmol) was dissolved in methanol (20 mL) and aqueous NaOH (2 M, 6 mL) then heated to 50° C. for 16 hrs. The volatile solvents were removed under reduced pressure and the resulting aqueous phase was acidified to pH 5-6 with aqueous HCl (2M). The precipitated solids were filtered, and dried to yield 230 mg (94%) of the title compound as a white solid. m/z (ES−) 249 (M−H)−.

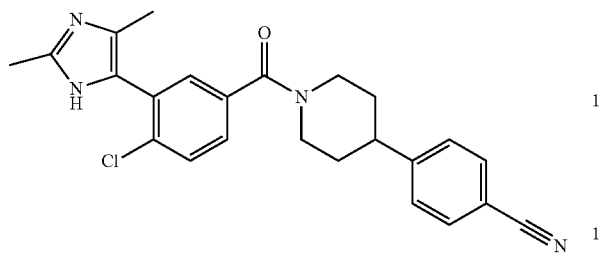

Compound 50. 4-(1-(4-Chloro-3-(2,4-dimethyl-1H-imidazol-5-yl)benzoyl)piperidin-4-yl)benzonitrile The title compound was obtained as a white solid (77 mg, 54%) using standard chemical manipulations and procedures similar to those used for the preparation of compound 5, except 4-chloro-3-(2,4-dimethyl-1H-imidazol-5-yl)benzoic acid (compound 50.4, 85 mg, 0.34 mmol) was used in place of 3-(2,4-dimethyl-1H-imidazol-5-yl)-4-methylbenzoic acid (compound 5.7) and 4-(piperidin-4-yl)benzonitrile hydrochloride (compound 1.2) was used in place of 4-(azetidin-3-yl)benzonitrile hydrochloride (compound 5.2). m/z (ES+) 419 (M+H)+.

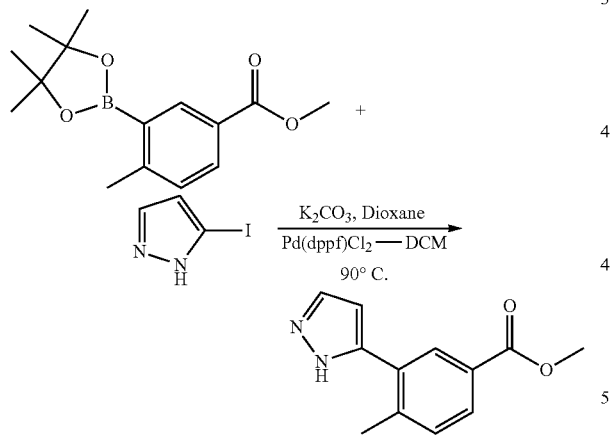

Compound 51.1. Methyl 4-methyl-3-(1H-pyrazol-5-yl)benzoate

To methyl 4-methyl-3-(4,4,5,5-tetramethyl-1,3,2-dioxaborolan-2-yl)benzoate (compound 5.4, 800 mg, 2.9 mmol) in dioxane (30 mL) was added 5-iodo-1H-pyrazole (674 mg, 3.5 mmol), and Pd(dppf)Cl2.DCM (237 mg, 0.29 mmol). The mixture was degassed with argon and stirred for 10 minutes then an aqueous potassium carbonate solution (2 M, 8 mL) was added. The mixture was heated at 90° C. for 18 h, then cooled and diluted with EtOAc and filtered through Celite®. The filtrate was washed with brine, dried (MgSO4), filtered, and concentrated under reduced pressure. The residue was purified by flash chromatography (SiO2; 0-30% EtOAc in hexanes) to yield 258 mg (41%) of the title compound as a solid. m/z (ES+) 217 (M+H)+.

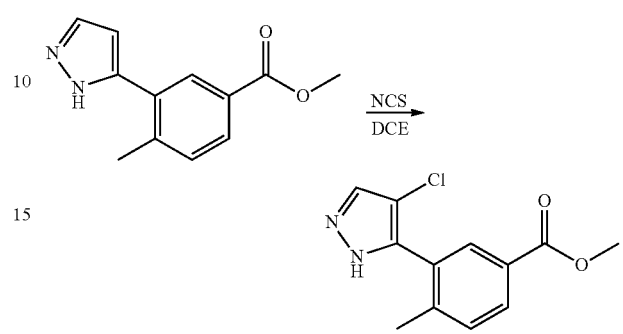

Compound 51.2. Methyl 3-(4-chloro-1H-pyrazol-5-yl)-4-methylbenzoate

Methyl 4-methyl-3-(1H-pyrazol-5-yl)benzoate (compound 51.1, 385 mg, 1.78 mmol) was dissolved in 1,2-dichloroethane (60 mL), then N-chlorosuccinimide (250 mg, 1.87 mmol) was added. The mixture was stirred at room temperature for 16 hours then washed with brine, dried (MgSO4), filtered, and concentrated under reduced pressure. The residue was purified by flash chromatography (SiO2; 0-20% EtOAc in hexanes) to yield 152 mg (34%) of the title compound as an oil. m/z (ES+) 251 (M+H)+. 1H NMR (400 MHz, Chloroform-d) δ 8.07-7.94 (m, 2H), 7.63 (d, J=0.7 Hz, 1H), 7.47-7.34 (m, 1H), 3.93 (s, 3H), 2.36 (s, 3H).

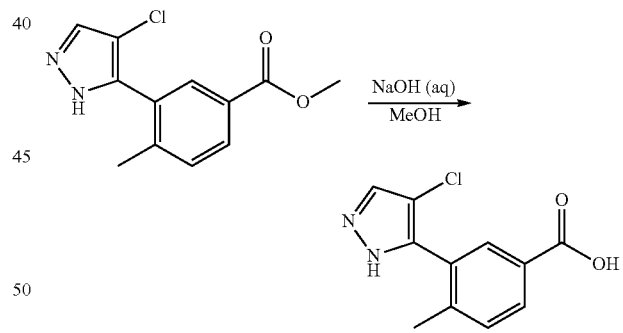

Compound 51.3. 3-(4-Chloro-1H-pyrazol-5-yl)-4-methylbenzoic acid

Methyl 3-(4-chloro-1H-pyrazol-5-yl)-4-methylbenzoate (compound 51.2, 133 mg, 0.53 mmol) was dissolved in a mixture of aqueous NaOH (2 M, 3 mL) and methanol (10 mL). The solution was heated at 50° C. for 16 hrs then the volatiles were removed under reduced pressure. Aqueous HCl (2 M) was added to adjust the pH to 4-5 then concentrated to yield 150 mg of a white solid which was used in the next step without further purification. m/z (ES−) 235 (M−H)−.

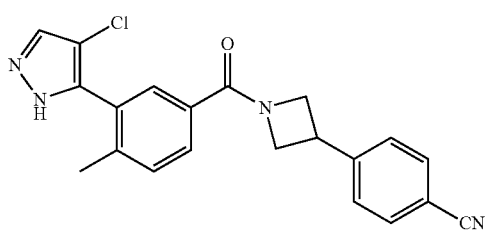 [SMILES: Cc1ccc(C(=O)N2CC(c3ccc(C#N)cc3)C2)cc1-c1[nH]ncc1Cl]

Compound 51. 4-(1-(3-(4-Chloro-1H-pyrazol-5-yl)-4-methylbenzoyl)azetidin-3-yl)benzonitrile The title compound was obtained as a white solid (69 mg, 34% over 2 steps) using standard chemical manipulations and procedures similar to those used for the preparation of compound 5, except 3-(4-chloro-1H-pyrazol-5-yl)-4-methylbenzoic acid (compound 51.3, ~0.53 mmol) was used in place of 3-(2,4-dimethyl-1H-imidazol-5-yl)-4-methylbenzoic acid (compound 5.7). m/z (ES+) 377 (M+H)+.

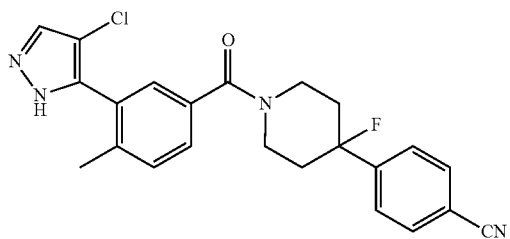 [SMILES: Cc1ccc(C(=O)N2CCC(F)(c3ccc(C#N)cc3)CC2)cc1-c1[nH]ncc1Cl]

Compound 52. 4-(1-(3-(4-Chloro-1H-pyrazol-5-yl)-4-methylbenzoyl)-4-fluoropiperidin-4-yl)benzonitrile The title compound was prepared using standard chemical manipulations and procedures similar to those used for preparation of compound 5, except 3-(4-chloro-1H-pyrazol-5-yl)-4-methylbenzoic acid (compound 51.3) was used in place of 3-(2,4-dimethyl-1H-imidazol-5-yl)-4-methylbenzoic acid (compound 5.7) and 4-(4-fluoropiperidin-4-yl)benzonitrile hydrochloride (compound 13.4) was used in place of 4-(azetidin-3-yl)benzonitrile hydrochloride (compound 5.2). m/z (ES+) 423 (M+H)+.

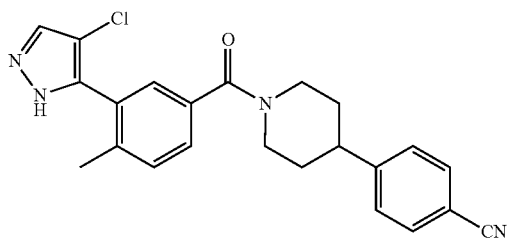 [SMILES: Cc1ccc(C(=O)N2CCC(c3ccc(C#N)cc3)CC2)cc1-c1[nH]ncc1Cl]

Compound 53. 4-(1-(3-(4-Chloro-1H-pyrazol-5-yl)-4-methylbenzoyl)piperidin-4-yl)benzonitrile The title compound was prepared using standard chemical manipulations and procedures similar to those used for preparation of compound 5, except 3-(4-chloro-1H-pyrazol-5-yl)-4-methylbenzoic acid (compound 51.3) was used in place of 3-(2,4-dimethyl-1H-imidazol-5-yl)-4-methylbenzoic acid (compound 5.7) and 4-(piperidin-4-yl)benzonitrile hydrochloride (compound 1.2) was used in place of 4-(azetidin-3-yl)benzonitrile hydrochloride (compound 5.2). m/z (ES+) 405 (M+H)+.

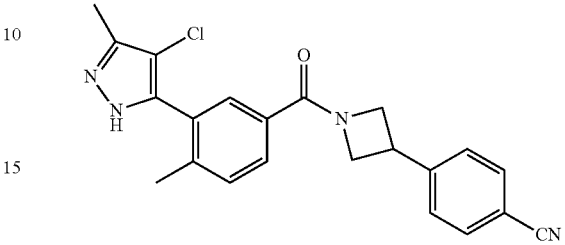

Compound 54. 4-(1-(3-(4-Chloro-3-methyl-1H-pyrazol-5-yl)-4-methylbenzoyl)azetidin-3-yl)benzonitrile The title compound was prepared using standard chemical manipulations and procedures similar to those used for preparation of compound 51 and compound 5, except 3-bromo-5-methyl-1H-pyrazole was used in place of 5-iodo-1H-pyrazole. m/z (ES+) 391 (M+H)+. $^1$H NMR (300 MHz, Methanol-d4): δ 7.77-7.69 (n, 3H), 7.64-7.59 (m, 3H), 7.46 (d, J=8.1 Hz, 1H), 4.84 (m, 1H), 4.64 (m, 1H), 4.48 (m, 1H), 4.23 (m, 1H), 4.09 (m, 1H), 2.34 (s, 3H), 2.33 (s, 3H).

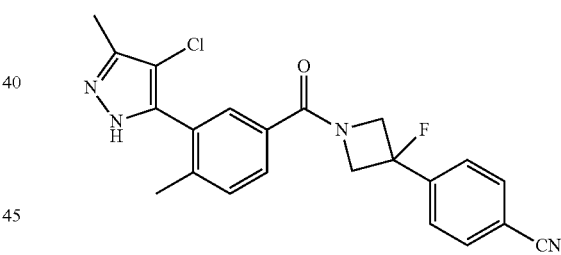

Compound 55. 4-(1-(3-(4-Chloro-3-methyl-1H-pyrazol-5-yl)-4-methylbenzoyl)-3-fluoroazetidin-3-yl)benzonitrile The title compound was prepared using standard chemical manipulations and procedures similar to those used for preparation of compound 51 and compound 5, except 3-bromo-5-methyl-1H-pyrazole was used in place of 5-iodo-1H-pyrazole and 4-(3-fluoroazetidin-3-yl)benzonitrile hydrochloride (compound 43.4) was used in place of 4-(azetidin-3-yl)benzonitrile hydrochloride (compound 5.2). m/z (ES+) 409 (M+H)+.

The compounds in TABLE 2 were prepared using standard chemical manipulations and procedures similar to those used for the preparation of compounds 51, 52, 53, 54 and 55.

TABLE 2

| Cpd | Name | Structure | m/z (ES+) (M + H)+ |
|---|---|---|---|
| 94 | 4-(1-(5-(4-chloro-1H-pyrazol-5-yl)-2,4-dimethylbenzoyl)-3-fluoroazetidin-3-yl)benzonitrile | 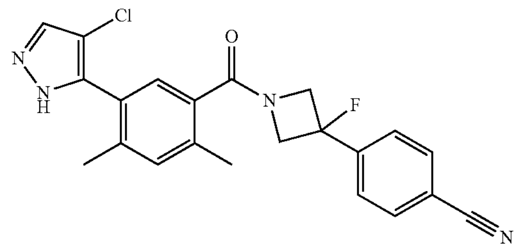 [SMILES: Cc1cc(C)c(-c2[nH]ncc2Cl)cc1C(=O)N1CC(F)(c2ccc(C#N)cc2)C1] | 409 |
| 136 | 4-(1-(5-(4-chloro-3-methyl-1H-pyrazol-5-yl)-2,4-dimethylbenzoyl)azetidin-3-yl)benzonitrile | 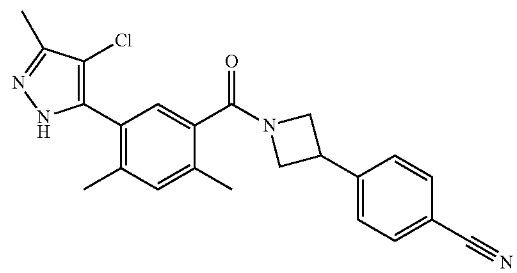 [SMILES: Cc1cc(C)c(-c2[nH]nc(C)c2Cl)cc1C(=O)N1CC(c2ccc(C#N)cc2)C1] | 405 |
| 140 | 4-(1-(3-(4-chloro-3-methyl-1H-pyrazol-5-yl)-4-methylbenzoyl)piperidin-4-yl)benzonitrile | 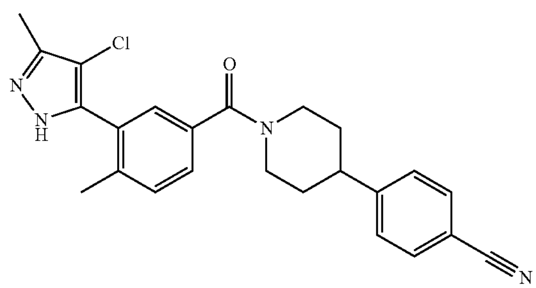 [SMILES: Cc1ccc(C(=O)N2CCC(c3ccc(C#N)cc3)CC2)cc1-c1[nH]nc(C)c1Cl] | 419 |
| 141 | 4-(1-(3-(4-chloro-3-methyl-1H-pyrazol-5-yl)-4-methylbenzoyl)-4-fluoropiperidin-4-yl)benzonitrile | 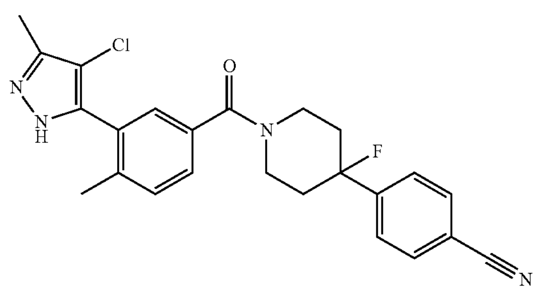 [SMILES: Cc1ccc(C(=O)N2CCC(F)(c3ccc(C#N)cc3)CC2)cc1-c1[nH]nc(C)c1Cl] | 437 |
| 142 | 4-(1-(5-(4-chloro-1H-pyrazol-5-yl)-2,4-dimethylbenzoyl)azetidin-3-yl)benzonitrile | 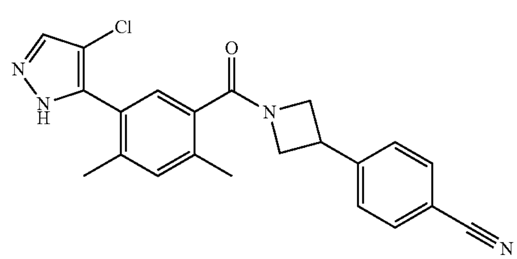 [SMILES: Cc1cc(C)c(-c2[nH]ncc2Cl)cc1C(=O)N1CC(c2ccc(C#N)cc2)C1] | 391 |

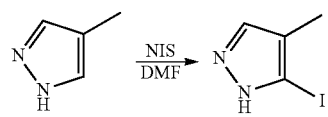

Compound 56.1. 5-Iodo-4-methyl-1H-pyrazole

To a solution of 4-methyl-1H-pyrazole (2.15 g, 26.1 mmol) dissolved in DMF (20 mL) was added N-iodosuccinimide (6.19 g, 26.1 mmol). The mixture was stirred at RT for 16 hours and then diluted with water and filtered. The filtrate was extracted with EtOAc (2×50 mL), then the combined organic extracts were washed with brine, dried (Na₂SO₄), filtered, and concentrated under reduced pressure. The residue was purified by flash chromatography (SiO₂; 0-50% EtOAc in hexanes) to yield 2.19 g (41%) of the title compound as a white solid. m/z (ES+) 209 (M+H)⁺.

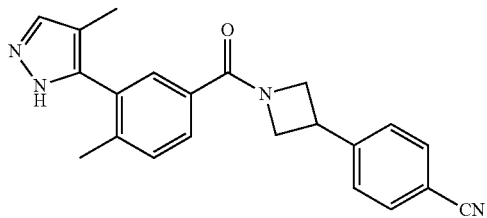 [SMILES: Cc1ccc(C(=O)N2CC(c3ccc(C#N)cc3)C2)cc1-c1[nH]ncc1C]

Compound 56. 4-(1-(4-Methyl-3-(4-methyl-1H-pyrazol-5-yl)benzoyl)azetidin-3-yl)benzonitrile The title compound was prepared using standard chemical manipulations and procedures similar to those used for preparation of compound 5, except 5-iodo-4-methyl-1H-pyrazole (compound 56.1) was used in place of 5-iodo-2,4-dimethyl-1H-imidazole (compound 5.5) to yield the title compound as white solid. m/z (ES+) 357 (M+H)⁺.

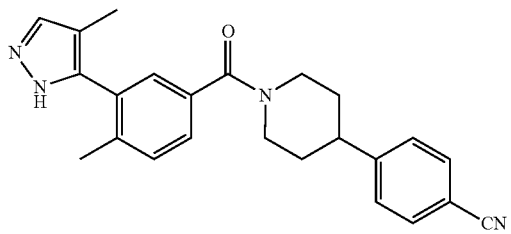 [SMILES: Cc1ccc(C(=O)N2CCC(c3ccc(C#N)cc3)CC2)cc1-c1[nH]ncc1C]

Compound 57. 4-(1-(4-Methyl-3-(4-methyl-1H-pyrazol-5-yl)benzoyl)piperidin-4-yl)benzonitrile The title compound was prepared using standard chemical manipulations and procedures similar to those used for preparation of compound 5, except 5-iodo-4-methyl-1H-pyrazole (compound 56.1) was used in place of 5-iodo-2,4-dimethyl-1H-imidazole (compound 5.5) and 4-(piperidin-4-yl)benzonitrile hydrochloride (compound 1.2) was used in place of 4-(azetidin-3-yl)benzonitrile hydrochloride (compound 5.2). m/z (ES+) 385 (M+H)⁺.

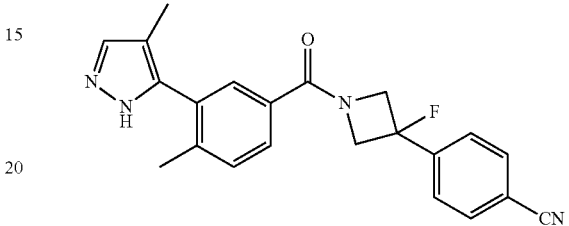

Compound 58. 4-(3-Fluoro-1-(4-methyl-3-(4-methyl-1H-pyrazol-5-yl)benzoyl)azetidin-3-yl)benzonitrile The title compound was prepared using standard chemical manipulations and procedures similar to those used for preparation of compound 5, except 5-iodo-4-methyl-1H-pyrazole (compound 56.1) was used in place of 5-iodo-2,4-dimethyl-1H-imidazole (compound 5.5) and 4-(3-fluoroazetidin-3-yl)benzonitrile hydrochloride (compound 43.4) was used in place of 4-(azetidin-3-yl)benzonitrile hydrochloride (compound 5.2). m/z (ES+) 375 (M+H)⁺.

The compounds in TABLE 3 were prepared using standard chemical manipulations and procedures similar to those used for the preparation of compounds 51, 56, 57 and 58.

TABLE 3

| Cpd | Name | Structure | m/z (ES+) (M + H)⁺ |
|---|---|---|---|
| 145 | 4-(1-(4-methyl-3-(1H-pyrazol-5-yl)benzoyl)piperidin-4-yl)benzonitrile | 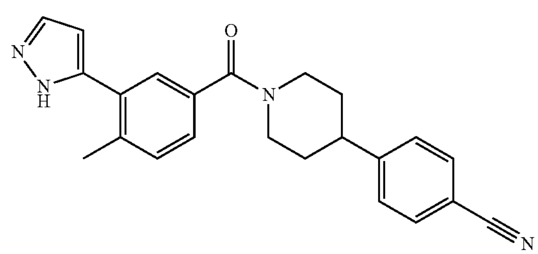 [SMILES: Cc1ccc(C(=O)N2CCC(c3ccc(C#N)cc3)CC2)cc1-c1ccn[nH]1] | 371 |
| 146 | 4-(1-(2,4-dimethyl-5-(4-methyl-1H-pyrazol-5-yl)benzoyl)azetidin-3-yl)benzonitrile | 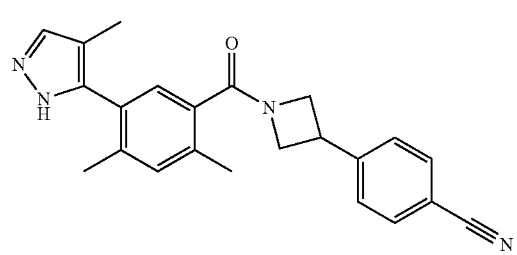 [SMILES: Cc1cc(C)c(-c2[nH]ncc2C)cc1C(=O)N1CC(c2ccc(C#N)cc2)C1] | 371 |

TABLE 3-continued

| Cpd | Name | Structure | m/z (ES+) (M + H)+ |
|---|---|---|---|
| 147 | 4-(1-(2,4-dimethyl-5-(4-methyl-1H-pyrazol-5-yl)benzoyl)-3-fluoroazetidin-3-yl)benzonitrile | 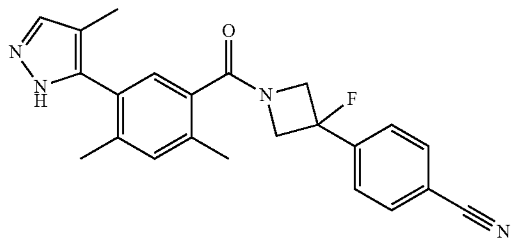 | 389 |
| 148 | 4-(1-(2,4-dimethyl-5-(4-methyl-1H-pyrazol-5-yl)benzoyl)piperidin-4-yl)benzonitrile | 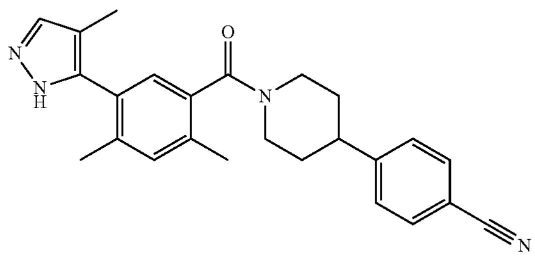 [SMILES: Cc1cc(C)c(-c2[nH]ncc2C)cc1C(=O)N1CCC(c2ccc(C#N)cc2)CC1] | 399 |

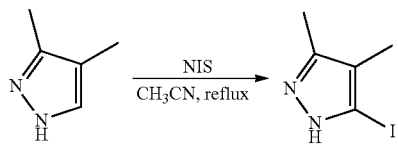

Compound 59.1. 5-Iodo-3,4-dimethyl-1H-pyrazole

NIS (5.62 g, 24.9 mmol) was added portion-wise to a solution of 3,4-dimethyl-1H-pyrazole (2.0 g, 20.8 mmol) in CH₃CN (50 mL). The mixture was heated at 80° C. for 16 hours, upon where thick off-white solids formed. The mixture was cooled to room temperature and the solid were filtered, washed with cold CH₃CN and dried under reduced pressure to yield 4.32 g (94%) of the title compound as an off-white solid. m/z (ES+) 223 (M+H)⁺.

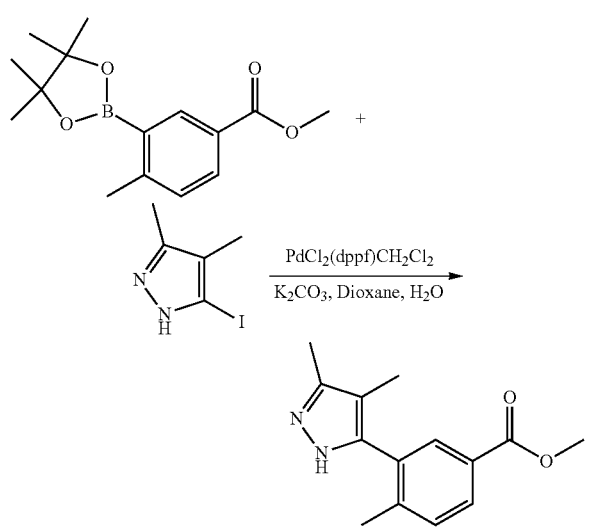

Compound 59.2. Methyl 3-(3,4-dimethyl-1H-pyrazol-5-yl)-4-methylbenzoate

The title compound was prepared using standard chemical manipulations and procedures similar to those used for the preparation of compound 5.6, except 5-iodo-3,4-dimethyl-1H-pyrazole (compound 59.1) was used in place of 5-iodo-2,4-dimethyl-1H-imidazole (compound 5.5). m/z (ES+) 245 (M+H)⁺.

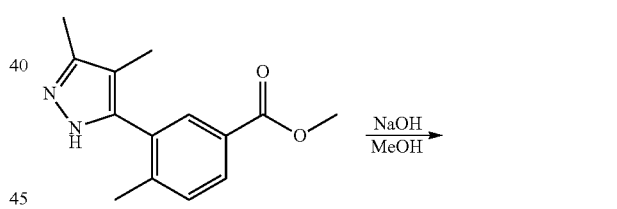

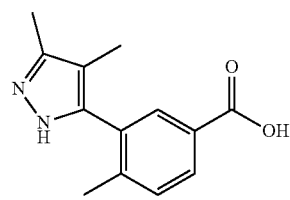

Compound 59.3. 3-(3,4-Dimethyl-1H-pyrazol-5-yl)-4-methylbenzoic acid

The title compound was prepared using standard chemical manipulations and procedures similar to those used for the preparation of compound 5.7, except methyl 3-(3,4-dimethyl-1H-pyrazol-5-yl)-4-methylbenzoate (compound 59.2) was used in place of methyl 3-(2,4-dimethyl-1H-imidazol-5-yl)-4-methylbenzoate (compound 5.6). m/z (ES+) 231 (M+H)⁺.

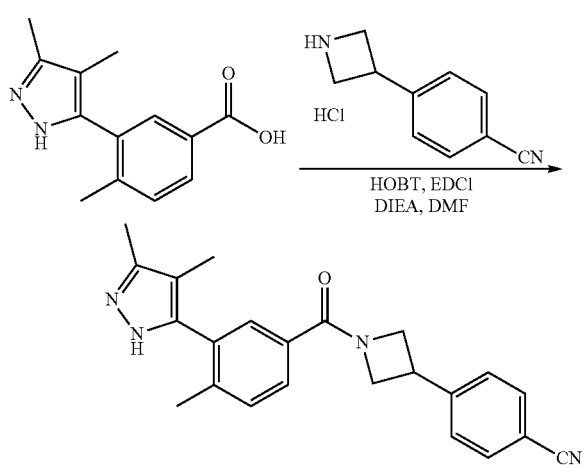

Compound 59. 4-(1-(3-(3,4-Dimethyl-1H-pyrazol-5-yl)-4-methylbenzoyl)azetidin-3-yl)benzonitrile The title compound was prepared using standard chemical manipulations and procedures similar to those used for the preparation of compound 5, except 3-(3,4-dimethyl-1H-pyrazol-5-yl)-4-methylbenzoic acid (compound 59.3) was used in place of 3-(2,4-dimethyl-1H-imidazol-5-yl)-4-methylbenzoic acid (compound 5.7). m/z (ES+) 371 (M+H)+. $^1$H NMR (400 MHz, DMSO-d6) δ 12.43-12.17 (br, 1H), 7.83 (d, J=8.4 Hz, 2H), 7.63 (d, J=8.4 Hz, 2H), 7.60 (dd, J=8.4 Hz, 2.0 Hz, 1H), 7.47 (d, J=1.6 Hz, 1H), 7.38 (d, J=8.0 Hz, 1H), 4.71 (m, 1H), 4.54-4.35 (m, 2H), 4.09-4.00 (m, 2H), 2.24 (s, 3H), 2.17 (s, 3H), 1.83 (s, 3H).

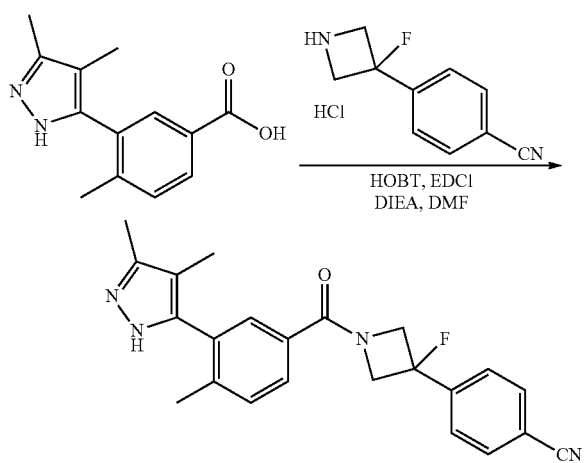

Compound 60. 4-(1-(3-(3,4-Dimethyl-1H-pyrazol-5-yl)-4-methylbenzoyl)-3-fluoroazetidin-3-yl)benzonitrile The title compound was prepared using standard chemical manipulations and procedures similar to those used for the preparation of compound 5, except 3-(3,4-dimethyl-1H-pyrazol-5-yl)-4-methylbenzoic acid (compound 59.3) and 4-(3-fluoroazetidin-3-yl)benzonitrile (compound 43.4) were used in place of 3-(2,4-dimethyl-1H-imidazol-5-yl)-4-methylbenzoic acid (compound 5.7) and 4-(azetidin-3-yl)benzonitrile hydrochloride (compound 5.2), respectively. m/z (ES+) 389 (M+H)+. $^1$H NMR (400 MHz, DMSO-d6) δ 12.45-12.26 (br, 1H), 7.95 (d, J=8.0 Hz, 2H), 7.79 (d, J=8.0 Hz, 2H), 7.65 (d, J=7.2 Hz, 1H), 7.52 (d, J=2.0 Hz, 1H), 7.40 (d, J=8.0 Hz, 1H), 4.98-4.42 (m, 4H), 2.25 (s, 3H), 2.17 (s, 3H), 1.83 (s, 3H).

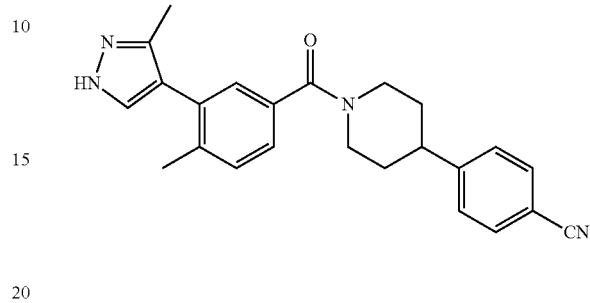

Compound 61. 4-(1-(4-Methyl-3-(5-methyl-1H-pyrazol-4-yl)benzoyl)piperidin-4-yl)benzonitrile The title compound was prepared using standard chemical manipulations and procedures similar to those used for preparation of compound 5, except 4-bromo-5-methyl-1H-pyrazole was used in place of 5-iodo-2,4-dimethyl-1H-imidazole (compound 5.5) and 4-(piperidin-4-yl)benzonitrile hydrochloride (compound 1.2) was used in place of 4-(azetidin-3-yl)benzonitrile hydrochloride (compound 5.2). m/z (ES+) 385 (M+H)+.

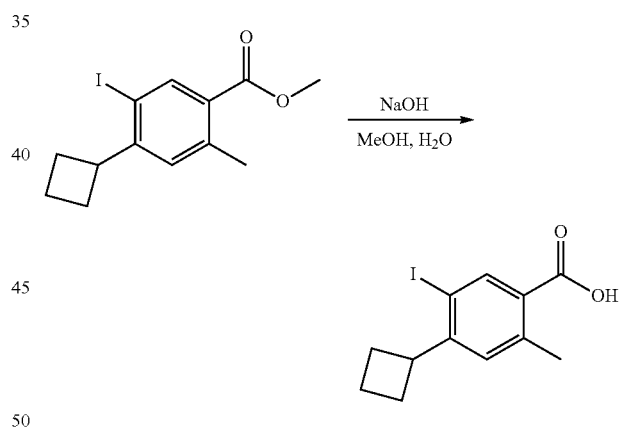

Compound 62.1.
4-Cyclobutyl-5-iodo-2-methylbenzoic acid

To a solution of methyl 4-cyclobutyl-5-iodo-2-methylbenzoate (compound 6.3, 35.0 g, 106 mmol) in methanol (200 mL) at 0-5° C. was added aqueous sodium hydroxide (12.7 g, 318 mmol in 100 mL water) drop-wise. The resulting mixture was stirred for 3 h at 60° C., then cooled to ambient temperature and the volatile organics were removed under reduced pressure. The pH of the remaining aqueous material was adjusted to ~4 with hydrogen chloride (aqueous, 2 M). The resulting solids were collected by filtration and dried in an oven under reduced pressure to yield the title compound as a white solid (31.0 g, 93%).

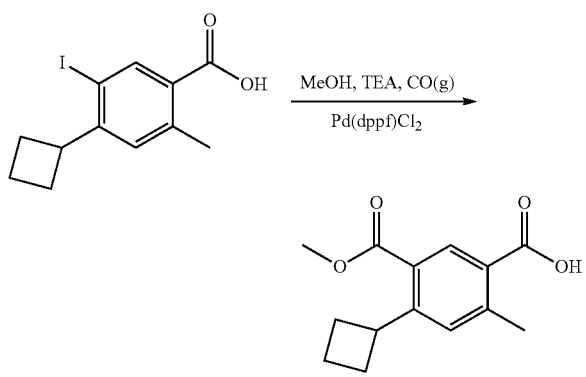

Compound 62.2.
4-Cyclobutyl-5-(methoxycarbonyl)-2-methylbenzoic acid

Into a 50-mL high pressure autoclave reactor, was placed a solution of 4-cyclobutyl-5-iodo-2-methylbenzoic acid (compound 62.1, 1.50 g, 4.74 mmol) in methanol (20 mL). Pd(dppf)Cl$_2$ (320 mg, 0.44 mmol) and triethylamine (1.27 mL, 9.09 mmol) were added and carbon monoxide (gas, 40 atm) was introduced. (CAUTION: Highly toxic gas at high pressure. All necessary safety precautions were performed). The resulting mixture was stirred overnight at 90° C., then cooled to room temperature. The reaction was vented carefully using the necessary precautions, then the resulting mixture was concentrated under reduced pressure. The residue was dissolved in water (20 mL) and the pH of the solution was adjusted to 3-4 with aqueous HCl (1 M) and the resulting mixture was extracted with ethyl acetate (3×20 mL). The combined organic extracts were dried (Na$_2$SO$_4$), filtered, and concentrated under reduced pressure. The residue was purified by silica gel column chromatography with ethyl acetate/petroleum ether (1/2-1/1) as the eluent to yield the title compound as a white solid (1.0 g, 85%).

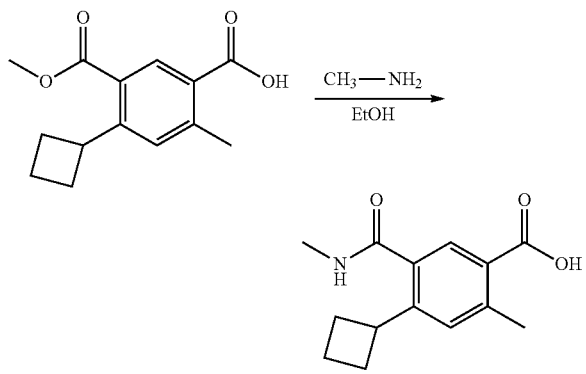

Compound 62.3.
4-Cyclobutyl-2-methyl-5-(methylcarbamoyl)benzoic acid

Into a 20-mL sealed tube, was placed 4-cyclobutyl-5-(methoxycarbonyl)-2-methylbenzoic acid (compound 62.2, 1.0 g, 4.0 mmol) and methylamine (30% in ethanol) (8 mL). The resulting solution was stirred overnight at 120° C. behind a blast shield, then cooled and diluted with H$_2$O (20 mL). The pH of the solution was adjusted to 4-5 with hydrogen chloride (1 M) and the solids were collected by filtration. The crude product was re-crystallized from ethyl acetate/petroleum ether in the ratio of 1:10 to yield the title compound as an off-white solid (500 mg, 50%).

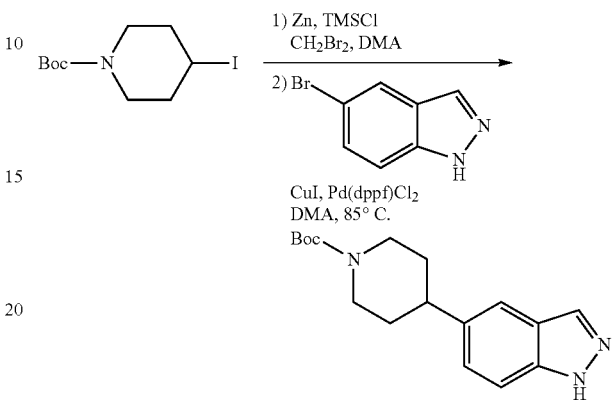

Compound 62.4. tert-Butyl 4-(1H-indazol-5-yl)piperidine-1-carboxylate

Into a 50-mL three neck round-bottom flask, which was purged and maintained with an inert atmosphere of nitrogen, was placed a suspension of Zn (990 mg, 15.1 mmol) in DMA (1 mL). A 7:5 v/v mixture of TMSCl/1,2-dibromoethane (0.12 mL) was added drop-wise at a rate to maintain the temperature below 65° C., then the mixture was stirred for an additional 10 min. A solution of tert-butyl 4-iodopiperidine-1-carboxylate (3.17 g, 10.2 mmol) in DMA (2 mL) was added drop-wise and stirred at 40-45° C. for 30 min. The resulting mixture was added to a mixture of 5-bromo-1H-indazole (1.00 g, 5.08 mmol), CuI (80 mg, 0.42 mmol) and Pd(dppf)Cl$_2$ (260 mg, 0.36 mmol) in DMA (1 mL) in a 50-mL round-bottom flask under a nitrogen atmosphere. The resulting mixture was stirred overnight at 85° C., then cooled and diluted with ethyl acetate (50 mL) and washed with brine (3×20 mL), dried (Na$_2$SO$_4$), filtered, and concentrated under reduced pressure. The residue was purified by silica gel column chromatography with ethyl acetate/petroleum ether (1/5) as the eluent to yield the title compound as a yellow solid (200 mg, 12%).

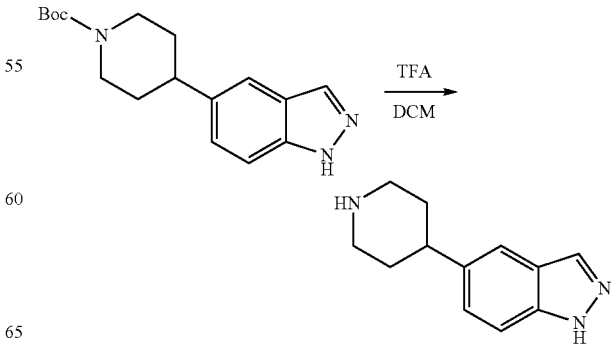

Compound 62.5. 5-(Piperidin-4-yl)-1H-indazole

Into a 50-mL round-bottom flask, was placed a solution of tert-butyl 4-(1H-indazol-5-yl)piperidine-1-carboxylate (compound 62.4, 200 mg, 0.60 mmol) in dichloromethane (3 mL) and trifluoroacetic acid (1 mL). The resulting solution was stirred for 1 h at room temperature, then the pH of the solution was carefully adjusted to 8-9 with aqueous sodium bicarbonate (aq. sat.). The mixture was extracted with dichloromethane (3×30 mL) and the combined organic layers were dried (Na$_2$SO$_4$), filtered, and concentrated under reduced pressure to yield the title compounds as a yellow oil (100 mg, 75%).

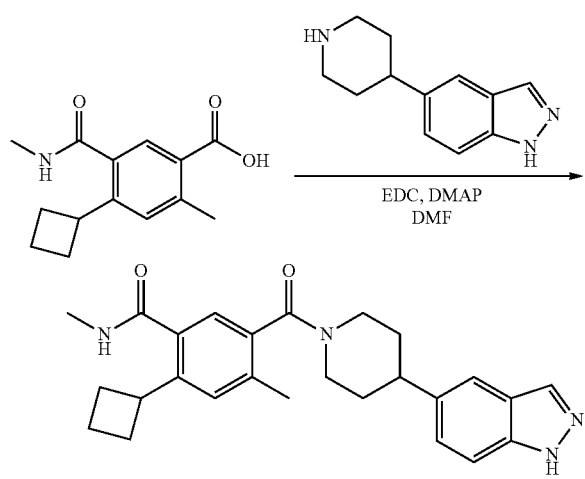

Compound 62. 5-(4-(1H-Indazol-5-yl)piperidine-1-carbonyl)-2-cyclobutyl-N,4-dimethylbenzamide Into a 50-mL round-bottom flask, was placed a solution of 5-(piperidin-4-yl)-1H-indazole (compound 62.5, 100 mg, 0.50 mmol) in N,N-dimethylformamide (3 mL). EDC.HCl (192 mg, 1.00 mmol), 4-dimethylaminopyridine (122 mg, 1.00 mmol) and 4-cyclobutyl-2-methyl-5-(methylcarbamoyl)benzoic acid (compound 62.3, 122 mg, 0.49 mmol) were added and the resulting solution was stirred for 4 h at room temperature. The reaction was diluted with water (20 mL) and extracted with of ethyl acetate (2×25 mL). The combined organic layers were washed with brine (2×15 mL), dried (Na$_2$SO$_4$), filtered, and concentrated under reduced pressure. The residue was purified by silica gel column chromatography with ethyl acetate as the eluent, followed by additional purification by Prep-HPLC with the following conditions (1#-Pre-HPLC-001(SHIMADZU)): Column, SunFire Prep C18 OBD Column, 5 um, 19*150 mm; mobile phase, water with 0.05% TFA and CH$_3$CN (30% CH$_3$CN up to 47% in 7 min, up to 100% in 3 min, down to 30% in 1 min); Detector, Waters 2489, 254 & 220 nm. The fractions containing pure compound were combined and lyophilized to yield the title compound as a white solid (71.2 mg, 33%). m/z (ES+) 431 (M+H)$^+$.

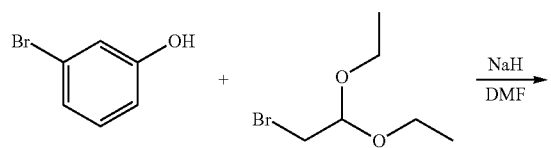

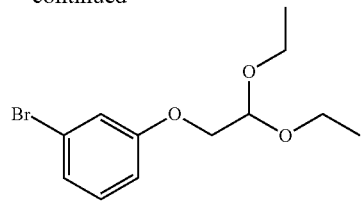

Compound 63.1. 1-Bromo-3-(2,2-diethoxyethoxy)benzene

Into a 3-L three neck round-bottom flask, was placed a solution of 3-bromophenol (50.00 g, 289.0 mmol) in N,N-dimethylformamide (1 L). The system was purged with nitrogen and the solution was cooled to 0° C., then sodium hydride (60%, 12.8 g, 320 mmol) was added portion-wise. To the resulting mixture was added 2-bromo-1,1-diethoxyethane (53.1 mL, 345 mmol) drop-wise at 0° C. The resulting mixture was stirred overnight at 120° C., behind a blast shield (CAUTION: NaH and DMF can become a runaway reaction. All necessary safety precautions were performed). The mixture was cooled to room temperature, then diluted with ethyl acetate (3 L). The mixture was washed with brine (4×500 mL), dried (Na$_2$SO$_4$), filtered, and concentrated under reduced pressure. The residue was purified by silica gel column chromatography with ethyl acetate/petroleum ether (1/50-1/30) as the eluent to yield the title compound as a light yellow oil (78.9 g, 94%).

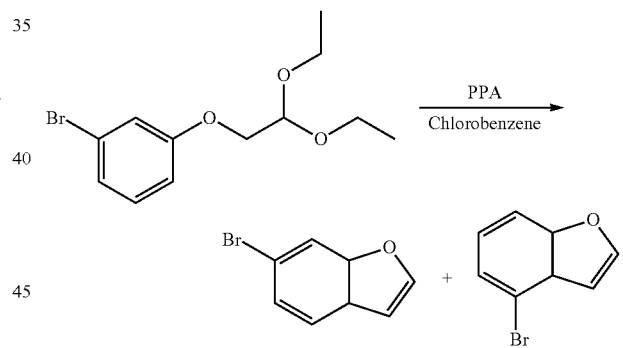

Compound 63.2 and compound 63.3. 6-Bromo-3a,7a-dihydrobenzofuran and 4-bromo-3a,7a-dihydrobenzofuran Into a 1-L round-bottom flask, was carefully placed a mixture of 1-bromo-3-(2,2-diethoxyethoxy)benzene (compound 63.1, 62.9 g, 218 mmol) and polyphosphoric acid (157 g) in chlorobenzene (320 mL). The mixture was stirred overnight at 90° C., then the mixture was cooled to room temperature and concentrated under reduced pressure. The residue was carefully and slowly diluted with water (200 mL) and extracted with EtOAc (3×200 mL). The organic extracts were dried (Na$_2$SO$_4$), filtered and concentrated under reduced pressure. The residue was purified by silica gel column chromatography with ethyl acetate/petroleum ether (1:50-1:30) as the eluent to yield a mixture of the title compounds as a brown oil (20 g, crude).

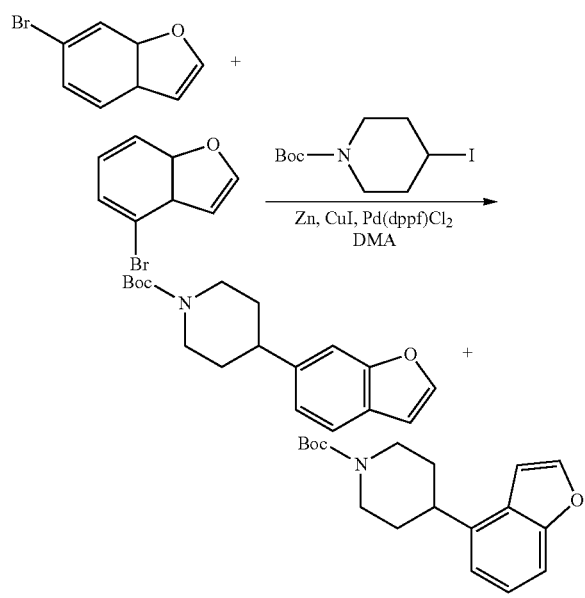

Compound 63.4 and compound 63.5. tert-Butyl 4-(benzofuran-6-yl)piperidine-1-carboxylate and tert-butyl 4-(benzofuran-4-yl)piperidine-1-carboxylate Into a 50-mL three neck round-bottom flask, which was purged and maintained with an inert atmosphere of nitrogen, was placed a suspension of Zn (1.13 g, 17.3 mmol) in DMA (5 mL). A 7:5 v/v mixture of TMSCl/1,2-dibromoethane (0.5 mL) was added to the reaction flask drop-wise to maintain the temperature below 65° C., then the mixture was stirred for an additional 10 min. To this mixture was added a solution of tert-butyl 4-iodopiperidine-1-carboxylate (5.40 g, 17.4 mmol) in DMA (40 mL) drop-wise with stirring and the resulting mixture was stirred at room temperature for 1 hour. The above mixture was filtered, and added to a mixture of 6-bromo-3a,7a-dihydrobenzofuran (compound 63.2) and 4-bromo-3a,7a-dihydrobenzofuran (compound 63.3) (2.83 g, 14.2 mmol), and CuI (274 mg, 1.44 mmol), Pd(dppf)Cl₂ (1.18 g, 1.6 mmol) in DMA (30 mL). The resulting mixture was stirred overnight at 85° C., then cooled to room temperature. The solids were removed by filtration and the filtrate was diluted with ethyl acetate (200 mL) and washed with brine (3×80 mL), dried (Na₂SO₄), filtered, and concentrated under reduced pressure. The residue was purified by silica gel column chromatography with ethyl acetate/petroleum ether (1/30-1/20) as the eluent to yield tert-butyl 4-(1-benzofuran-6-yl)piperidine-1-carboxylate (compound 63.4) as a colorless oil (267 mg, 6%) and tert-butyl 4-(1-benzofuran-4-yl)piperidine-1-carboxylate (compound 63.5) as an off-white solid (320 mg, 7%).

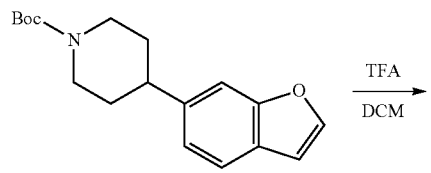

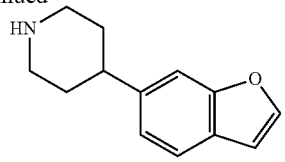

Compound 63.6. 4-(Benzofuran-6-yl)piperidine

Into a 50-mL round-bottom flask, was placed a solution of tert-butyl 4-(1-benzofuran-6-yl)piperidine-1-carboxylate (compound 63.4, 200 mg, 0.66 mmol) in dichloromethane (3 mL) and trifluoroacetic acid (1 mL). The resulting solution was stirred at 15° C. for 1 hour, then the pH was carefully adjusted to ~9 with aqueous sodium hydroxide (2 M). The mixture was diluted with H₂O (20 mL) and the layers were separated. The aqueous phase was extracted with dichloromethane (4×20 mL) and the combined organic layers were washed with brine (30 mL), dried (Na₂SO₄), filtered, and concentrated under reduced pressure to yield the title compound as a brown oil (150 mg, crude).

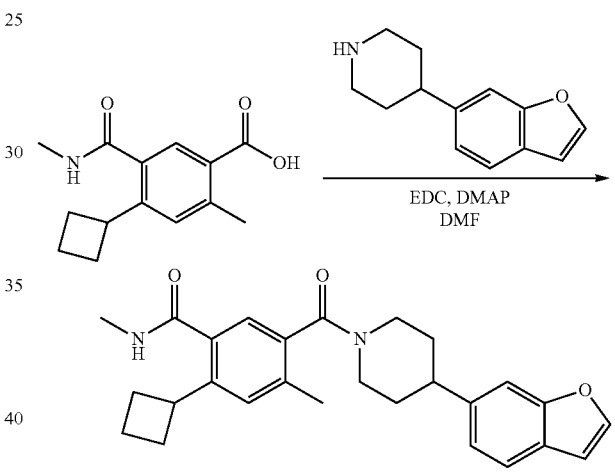

Compound 63. 5-(4-(Benzofuran-6-yl)piperidine-1-carbonyl)-2-cyclobutyl-N,4-dimethylbenzamide Into a 25-mL round-bottom flask, was placed a solution of 4-(benzofuran-6-yl)piperidine (compound 63.6) (110 mg, 0.55 mmol), 4-cyclobutyl-2-methyl-5-(methylcarbamoyl) benzoic acid (compound 62.3, 135 mg, 0.55 mmol), EDC.HCl (210 mg, 1.10 mmol) and 4-dimethylaminopyridine (133.5 mg, 1.09 mmol) in N,N-dimethylformamide (3 mL). The resulting solution was stirred for 2 h at 15° C. then diluted EtOAc (60 mL). The resulting mixture was washed with aqueous saturated NH₄Cl (2×20 mL) and brine (20 mL), dried (Na₂SO₄), filtered, and concentrated under reduced pressure. The crude product (110 mg) was purified by Prep-HPLC with the following conditions (1#-Pre-HPLC-001(SHIMADZU)): Column, SunFire Prep C18 OBD Column, 5 um, 19*150 mm; mobile phase, water with 0.05% TFA and CH₃CN (51.0% CH₃CN up to 60.0% in 9 min, up to 100.0% in 5 min, down to 51.0% in 1 min); Detector, Waters 2489, 254 & 220 nm. The fractions containing pure compound were combined and lyophilized to yield the title compound as a white solid (46.0 mg, 20%). m/z (ES+) 431 (M+H)⁺.

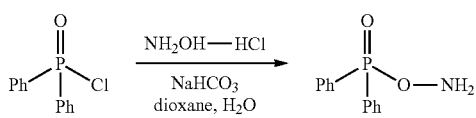

Compound 64.1. (Aminooxy)diphenylphosphine oxide

Into a 500-mL three neck round-bottom flask, was placed a solution of hydroxylamine hydrochloride (30.0 g, 432 mmol) in H₂O/dioxane (90/45 mL). The solution was cooled to 0-5° C., then sodium bicarbonate (36.5 g, 434 mmol) was added portion-wise over 10 min and the mixture was stirred at 0-5° C. for 30 min. A solution of diphenylphosphinoyl chloride (41.0 g, 173 mmol) in dioxane (45 mL) was added drop-wise at 0-5° C. over 30 min, then the resulting mixture was stirred for an additional 2 h at ambient temperature. The resulting solids were collected by filtration and washed with water (200 mL), NaOH (0.25 M, 200 mL) and PE (200 mL). The product was dried to yield the title compound as a white solid (20 g, crude).

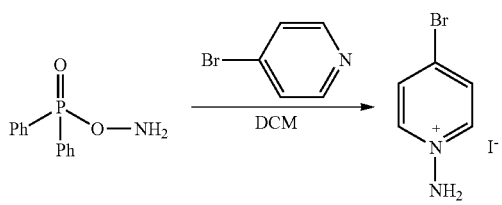

Compound 64.2. 1-Amino-4-bromopyridin-1-ium iodide

Into a 250-mL round-bottom flask, was placed a solution of 4-bromopyridine hydrochloride (13.8 g, 71.0 mmol) in water (50 mL). The solution was cooled to 0-5° C. then sodium bicarbonate (12.0 g, 141 mmol) was added portion-wise over 10 min and the mixture was stirred at 0-5° C. for 30 min. The mixture was extracted with DCM (4×50 mL) and the combined organic layers were washed with brine (50 mL), dried (Na₂SO₄), and filtered. The filtrate was placed into a 500-mL round-bottom flask, then purged and maintained with an inert atmosphere of nitrogen. (Aminooxy)diphenylphosphine oxide (compound 64.1, 20 g, ~70% purity, 60 mmol) was added and the mixture was stirred overnight at room temperature. The reaction was carefully quenched with aqueous HI (8 mL, 45%) and stirred for 30 min. The solids were collected by filtration, and washed with DCM (200 mL) and hexanes (200 mL) to yield the title compound as a brown solid (15 g, crude).

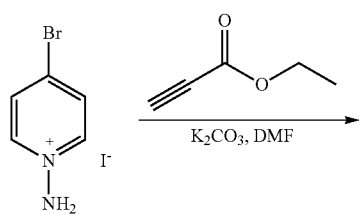

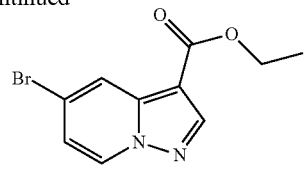

Compound 64.3. Ethyl 5-bromopyrazolo[1,5-a]pyridine-3-carboxylate

Into a 250-mL three neck round-bottom flask, was placed a solution of 1-amino-4-bromopyridin-1-ium iodide (compound 64.2, 15 g, ~50% purity, 24.9 mmol) in N,N-dimethylformamide (80 mL). Potassium carbonate (10.6 g, 76.7 mmol) was added portion-wise followed by the addition of ethyl propiolate (11.7 mL, 115 mmol) drop-wise over 10 min. The resulting mixture was stirred overnight at room temperature, then diluted with EtOAc (300 mL) and water (100 mL). The solids were removed by filtration and the organic layer was washed with brine (3×50 mL), dried (Na₂SO₄), filtered, and concentrated under reduced pressure. The residue was purified by silica gel column chromatography with ethyl acetate/petroleum ether (1:10) as the eluent to yield the title compound as a brown solid (300 mg, 6%).

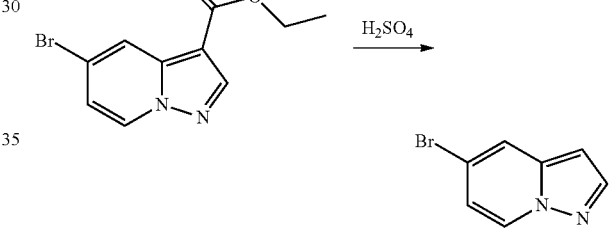

Compound 64.4. 5-Bromopyrazolo[1,5-a]pyridine

Into a 50-mL round-bottom flask, was placed ethyl 5-bromopyrazolo[1,5-a]pyridine-3-carboxylate (compound 64.3, 100 mg, 0.37 mmol). Sulfuric acid (50%, 4 mL) was added carefully in portions at room temperature, then the resulting solution was stirred overnight at 80° C. After cooling to room temperature, the pH of the solution was carefully adjusted to 8-9 with aqueous sodium hydroxide (5 M) and then extracted with ethyl acetate (2×20 mL). The combined organic extracts were washed with brine (20 mL), dried (Na₂SO₄), filtered, and concentrated under reduced pressure. The residue was purified by silica gel column chromatography with ethyl acetate/petroleum ether (1:10) as the eluent to yield the title compound as a brown solid (40 mg, 55%).

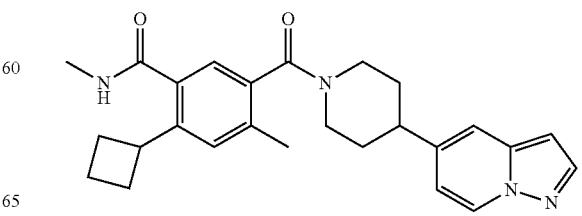

Compound 64. 2-Cyclobutyl-N,4-dimethyl-5-(4-(pyrazolo[1,5-a]pyridin-5-yl)piperidine-1-carbonyl)benzamide The title compound was prepared using standard chemical manipulations and procedures similar to those used for the preparation of compound 62, except 5-bromopyrazolo[1,5-a]pyridine (compound 64.4) was used in place of 5-bromo-1H-indazole to yield the title compound as a white solid. m/z (ES+) 431 (M+H)+.

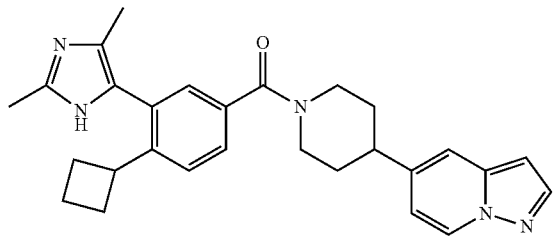 [SMILES: Cc1nc(C)c(-c2cc(C(=O)N3CCC(c4ccn5nccc5c4)CC3)ccc2C2CCC2)[nH]1]

Compound 65. (4-Cyclobutyl-3-(2,4-dimethyl-1H-imidazol-5-yl)phenyl)(4-(imidazo[1,5-a]pyridin-7-yl)piperidin-1-yl)methanone The title compound was prepared using standard chemical manipulations and procedures similar to those used for the preparation of compound 1, except 4-cyclobutyl-3-iodobenzoic acid (compound 9.3) was used in place of 5-iodo-2,4-dimethylbenzoic acid (compound 1.3) and 7-(piperidin-4-yl)imidazo[1,5-a]pyridine hydrochloride (compound 39.5) was used in place of 4-(piperidin-4-yl)benzonitrile hydrochloride (compound 1.2) to yield the title compound. m/z (ES+) 454 (M+H)+.

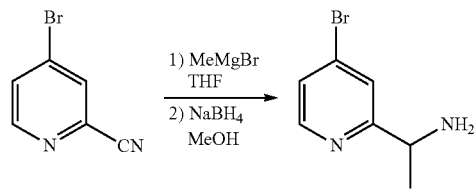

Compound 66.1. 1-(4-Bromopyridin-2-yl)ethanamine

Into a 500-mL 3-necked round-bottom flask, purged and maintained with an inert atmosphere of nitrogen, was placed a solution of methylmagnesium bromide (3 M in THF) (63.4 mL, 190 mmol) in THF (100 mL). A solution of 4-bromopyridine-2-carbonitrile (11.6 g, 63.4 mmol; patent US 2009/0239876 A1, example 2) in THF (40 mL) was added drop-wise at room temperature over 40 min. Methanol (40 mL) was then added drop-wise followed by portion-wise addition of sodium borohydride (11.8 g, 312 mmol) in several batches. The resulting mixture was stirred at room temperature for 2 h, then diluted with ethyl acetate (200 mL). The pH of the mixture was adjusted to 9 with aqueous sodium hydroxide (1 M) and the solids were removed by filtration. The filtrate was extracted with ethyl acetate (2×100 mL) and the combined organic layers were dried over anhydrous sodium sulfate, filtered, and concentrated under reduced pressure to yield 10.3 g (crude) of the title compound as a yellow oil.

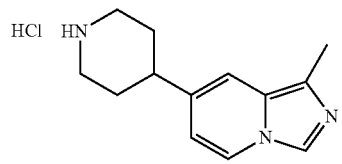 [SMILES: Cl ; Cc1ncn2ccc(C3CCNCC3)cc12]

Compound 66.2. 1-Methyl-7-(piperidin-4-yl)imidazo[1,5-a]pyridine hydrochloride The title compound was prepared using standard chemical manipulations and procedures similar to those used for the preparation of compound 39.5, except 1-(4-bromopyridin-2-yl)ethanamine (compound 66.1) was used in place of (4-bromopyridin-2-yl)methanamine (compound 39.1).

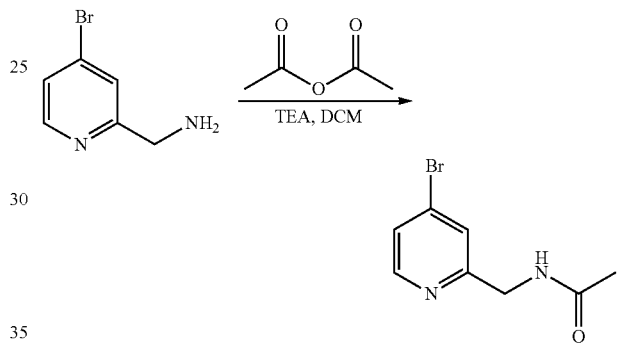

Compound 67.1. N-((4-Bromopyridin-2-yl)methyl)acetamide

Into a 500-mL round-bottom flask, purged and maintained with an inert atmosphere of nitrogen, was placed a solution of (4-bromopyridin-2-yl)methanamine (compound 39.1, 4.5 g, 24.1 mmol) in dichloromethane (160 mL). Triethylamine (6.72 mL, 48.2 mmol) and acetic anhydride (2.29 mL, 24.2 mmol) were carefully added and the resulting solution was stirred at room temperature for 12 h. The volatiles were removed under reduced pressure and the residue was slowly quenched with water (200 mL). The pH of the solution was slowly adjusted to 9-12 with aqueous sodium carbonate (3 M) and the aqueous phase was extracted with ethyl acetate (3×60 mL). The combined organic layers were dried over anhydrous sodium sulfate, filtered, and concentrated under reduced pressure. The residue was purified by silica gel column chromatography with dichloromethane/methanol (100:1-10:1) as the eluent to yield 4.0 g (73%) of the title compound as yellow oil.

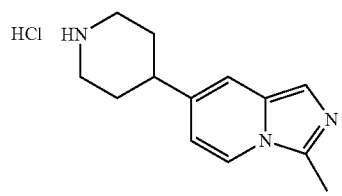 [SMILES: Cl ; Cc1ncc2cc(C3CCNCC3)ccn12]

Compound 67.2. 3-Methyl-7-(piperidin-4-yl)imidazo[1,5-a]pyridine hydrochloride The title compound was prepared using standard chemical manipulations and procedures similar to those used for the preparation of compound 39.5, except N-((4-bromopyridin-2-yl)methyl)acetamide (compound 67.1) was used in place of N-((4-bromopyridin-2-yl)methyl)formamide (compound 39.2).

Compound 68.1 and compound 68.2. tert-Butyl 4-(1-chloroimidazo[1,5-a]pyridin-7-yl)piperidine-1-carboxylate and tert-butyl 4-(3-chloroimidazo[1,5-a]pyridin-7-yl)piperidine-1-carboxylate Into a 25-mL round-bottom flask, was placed a solution of tert-butyl 4-(imidazo[1,5-a]pyridin-7-yl)piperidine-1-carboxylate (compound 39.4, 170 mg, 0.56 mmol) in $CCl_4$ (3 mL). N-Chlorosuccinimide (75 mg, 0.56 mmol) was added and the resulting mixture was stirred for 5 h at room temperature. The mixture was diluted with EtOAc (30 mL) and washed with brine (3×20 mL), dried ($Na_2SO_4$), filtered, and concentrated under reduced pressure. The residue was purified by preparative TLC with ethyl acetate/petroleum ether (1/1) to yield 45 mg (24%) of tert-butyl 4-(1-chloroimidazo[1,5-a]pyridin-7-yl)piperidine-1-carboxylate (compound 68.1) as a yellow solid and 64 mg (34%) of tert-butyl 4-(3-chloroimidazo[1,5-a]pyridin-7-yl)piperidine-1-carboxylate (compound 68.2) as a yellow solid.

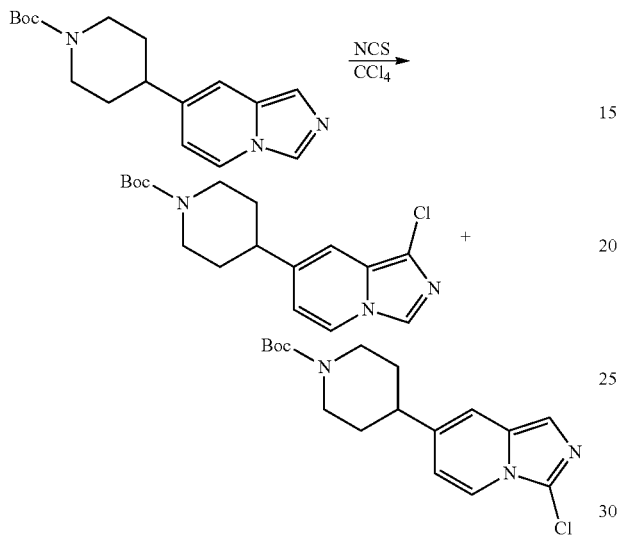

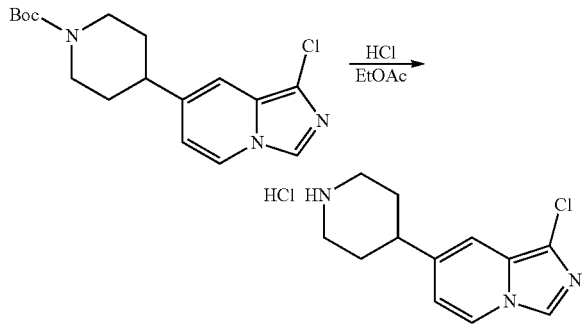

Compound 68.3. 1-Chloro-7-(piperidin-4-yl)imidazo[1,5-a]pyridine hydrochloride The title compound was prepared using standard chemical manipulations and procedures similar to those used for the preparation of compound 1.2, except tert-butyl 4-(1-chloroimidazo[1,5-a]pyridin-7-yl)piperidine-1-carboxylate (compound 68.1) was used in place of tert-butyl 4-(4-cyanophenyl)piperidine-1-carboxylate (compound 1.1) to yield the title compound as a yellow solid.

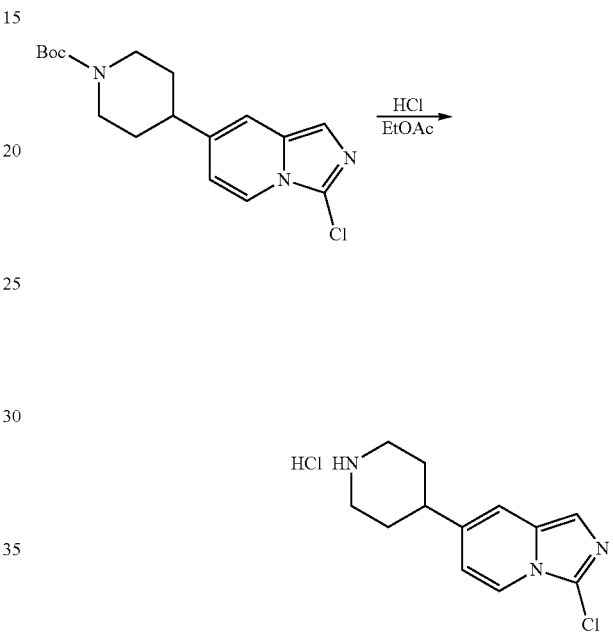

Compound 71.1. 3-Chloro-7-(piperidin-4-yl)imidazo[1,5-a]pyridine hydrochloride The title compound was prepared using standard chemical manipulations and procedures similar to those used for the preparation of compound 1.2, except tert-butyl 4-(3-chloroimidazo[1,5-a]pyridin-7-yl)piperidine-1-carboxylate (compound 68.2) was used in place of tert-butyl 4-(4-cyanophenyl)piperidine-1-carboxylate (compound 1.1) to yield the title compound as a yellow solid.

The compounds in TABLE 4 were prepared using standard chemical manipulations and procedures with readily available starting materials or building blocks described in this manuscript. The utilized procedures were similar to that used for the preparation of compound 1, using 5-(2,4-dimethyl-1H-imidazol-5-yl)-2,4-dimethylbenzoic acid (compound 1.8) and the respective amines (compound 5.2, compound 39.5, compound 66.2, compound 67.2, compound 68.3, or compound 71.1).

TABLE 4

| Cpd | Name | Structure | m/z (ES+) (M + H)+ |
|---|---|---|---|
| 69 | 4-(1-(5-(2,4-dimethyl-1H-imidazol-5-yl)-2,4-dimethylbenzoyl)azetidin-3-yl)benzonitrile | 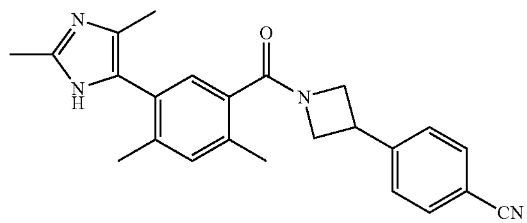 [SMILES: Cc1nc(C)c(-c2cc(C(=O)N3CC(c4ccc(C#N)cc4)C3)c(C)cc2C)[nH]1] | 385 |
| 70 | (5-(2,4-dimethyl-1H-imidazol-5-yl)-2,4-dimethylphenyl)(4-(imidazo[1,5-a]pyridin-7-yl)piperidin-1-yl)methanone | 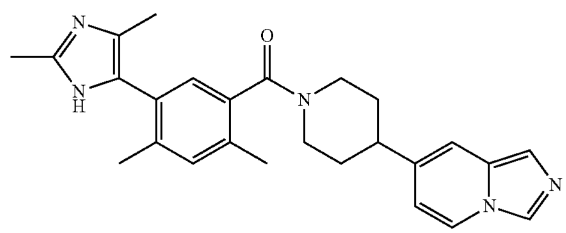 [SMILES: Cc1nc(C)c(-c2cc(C(=O)N3CCC(c4ccn5cncc5c4)CC3)c(C)cc2C)[nH]1] | 428 |
| 66 | (5-(2,4-dimethyl-1H-imidazol-5-yl)-2,4-dimethylphenyl)(4-(1-methylimidazo[1,5-a]pyridin-7-yl)piperidin-1-yl)methanone | 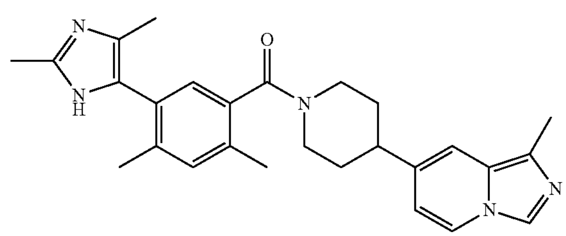 [SMILES: Cc1nc(C)c(-c2cc(C(=O)N3CCC(c4ccn5cnc(C)c5c4)CC3)c(C)cc2C)[nH]1] | 442 |
| 67 | (5-(2,4-dimethyl-1H-imidazol-5-yl)-2,4-dimethylphenyl)(4-(3-methylimidazo[1,5-a]pyridin-7-yl)piperidin-1-yl)methanone | 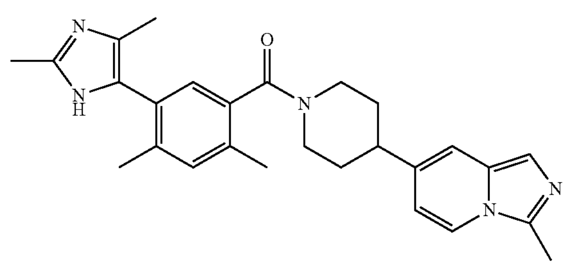 [SMILES: Cc1nc(C)c(-c2cc(C(=O)N3CCC(c4ccn5c(C)ncc5c4)CC3)c(C)cc2C)[nH]1] | 442 |
| 68 | (4-(1-chloroimidazo[1,5-a]pyridin-7-yl)piperidin-1-yl)(5-(2,4-dimethyl-1H-imidazol-5-yl)-2,4-dimethylphenyl)methanone | 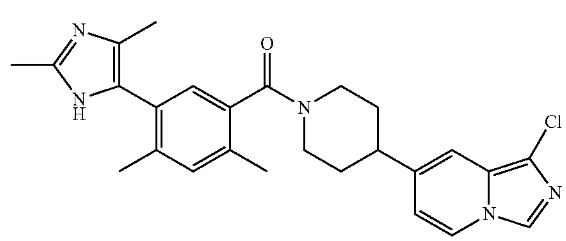 | 462 |
| 71 | (4-(3-chloroimidazo[1,5-a]pyridin-7-yl)piperidin-1-yl)(5-(2,4-dimethyl-1H-imidazol-5-yl)-2,4-dimethylphenyl)methanone | 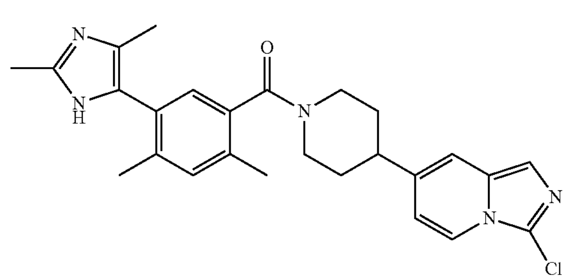 [SMILES: Cc1nc(C)c(-c2cc(C(=O)N3CCC(c4ccn5c(Cl)ncc5c4)CC3)c(C)cc2C)[nH]1] | 462 |

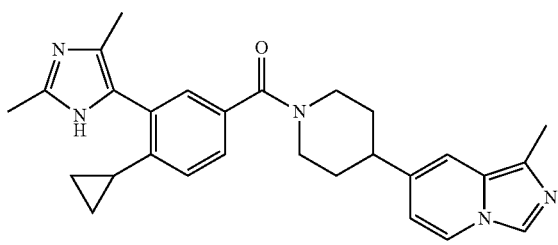 [SMILES: Cc1nc(C)c(-c2cc(C(=O)N3CCC(c4ccn5cnc(C)c5c4)CC3)ccc2C2CC2)[nH]1]

Compound 72. (4-Cyclopropyl-3-(2,4-dimethyl-1H-imidazol-5-yl)phenyl)(4-(1-methylimidazo[1,5-a]pyridin-7-yl)piperidin-1-yl)methanone The title compound was prepared using standard chemical manipulations and procedures similar to those used for the preparation of compound 1, except methyl 4-cyclopropyl-3-propionylbenzoate (compound 10.7) was used in place of methyl 2,4-dimethyl-5-propionylbenzoate (compound 1.5) and 1-methyl-7-(piperidin-4-yl)imidazo[1,5-a]pyridine hydrochloride (compound 66.2) was used in place of 4-(piperidin-4-yl)benzonitrile hydrochloride (compound 1.2). m/z (ES+) 454 (M+H)+.

Compound 73. (4-Cyclopropyl-3-(2,4-dimethyl-1H-imidazol-5-yl)phenyl)(4-(3-methylimidazo[1,5-a]pyridin-7-yl)piperidin-1-yl)methanone The title compound was prepared using standard chemical manipulations and procedures similar to those used for the preparation of compound 1, except methyl 4-cyclopropyl-3-propionylbenzoate (compound 10.7) was used in place of methyl 2,4-dimethyl-5-propionylbenzoate (compound 1.5) and 3-methyl-7-(piperidin-4-yl)imidazo[1,5-a]pyridine hydrochloride (compound 67.2) was used in place of 4-(piperidin-4-yl)benzonitrile hydrochloride (compound 1.2). m/z (ES+) 454 (M+H)+.

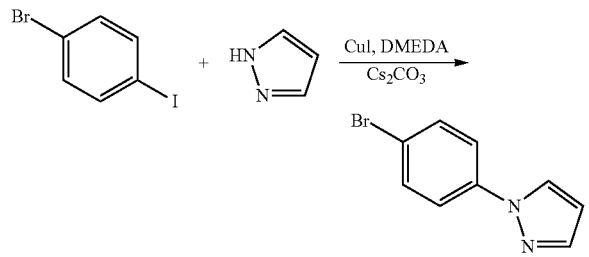

Compound 74.1. 1-(4-Bromophenyl)-1H-pyrazole

Into a 100-mL round-bottom flask, which was purged and maintained with an inert atmosphere of nitrogen, was placed a mixture of 1-bromo-4-iodobenzene (2.82 g, 9.97 mmol), 1H-pyrazole (680 mg, 9.99 mmol), CuI (380 mg, 2.00 mmol), DMEDA (430 µL, 4.00 mmol, 0.40 equiv), Cs$_2$CO$_3$ (6.52 g, 20.00 mmol) an CH$_3$CN (40 mL). The resulting mixture was stirred overnight at 82° C. After cooling to ambient temperature, the solids were removed by filtration and the filtrate was concentrated under reduced pressure. The residue was purified by silica gel column chromatography with ethyl acetate/petroleum ether (1:12) as the eluent to yield the title compound as a white solid (2.1 g, 94%).

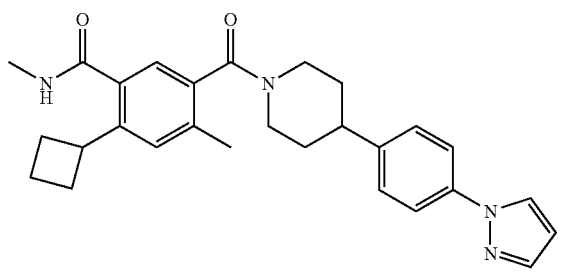 [SMILES: CNC(=O)c1cc(C(=O)N2CCC(c3ccc(-n4cccn4)cc3)CC2)c(C)cc1C1CCC1]

Compound 74. 5-(4-(4-(1H-Pyrazol-1-yl)phenyl)piperidine-1-carbonyl)-2-cyclobutyl-N,4-dimethylbenzamide The title compound was prepared using standard chemical manipulations and procedures similar to those used for the preparation of compound 62, except 1-(4-bromophenyl)-1H-pyrazole (compound 74.1) was used in place of 5-bromo-1H-indazole to yield the title compound as a white solid. m/z (ES+) 457 (M+H)+.

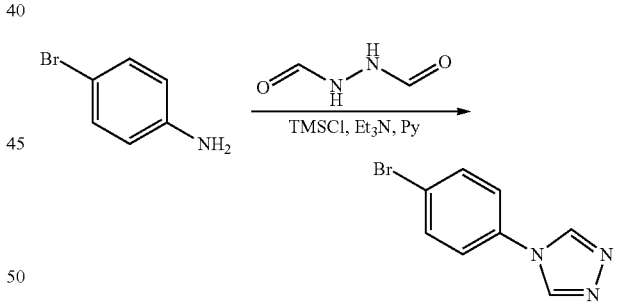

Compound 75.1. 4-(4-Bromophenyl)-4H-1,2,4-triazole

Into a 100-mL round-bottom flask, was placed a solution of 4-bromoaniline (1.71 g, 9.94 mmol), N'-formylformohydrazide (2.64 g, 30.0 mmol), and triethylamine (9.74 mL, 69.9 mmol, 7.00 equiv) in pyridine (40 mL). Chlorotrimethylsilane (19.2 mL, 151 mmol) was added drop-wise and the resulting solution was stirred for 18 h at 100° C., then cooled to room temperature. The resulting mixture was concentrated under reduced pressure and the residue was diluted with brine (50 mL) and extracted with ethyl acetate (6×50 mL). The combined organic layers were dried (Na$_2$SO$_4$), filtered, and concentrated under reduced pressure.

The residue was washed with ether (30 mL) and the solids were collected by filtration to yield the title compound as a pink solid (1.6 g, 72%).

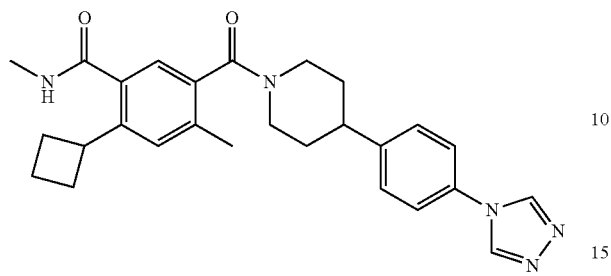

Compound 75. 5-(4-(4-(4H-1,2,4-Triazol-4-yl)phenyl)piperidine-1-carbonyl)-2-cyclobutyl-N,4-dimethylbenzamide The title compound was prepared using standard chemical manipulations and procedures similar to those used for the preparation of compound 62, except 4-(4-bromophenyl)-4H-1,2,4-triazole (compound 75.1) was used in place of 5-bromo-1H-indazole to yield the title compound as a yellow solid. m/z (ES+) 458 (M+H)+.

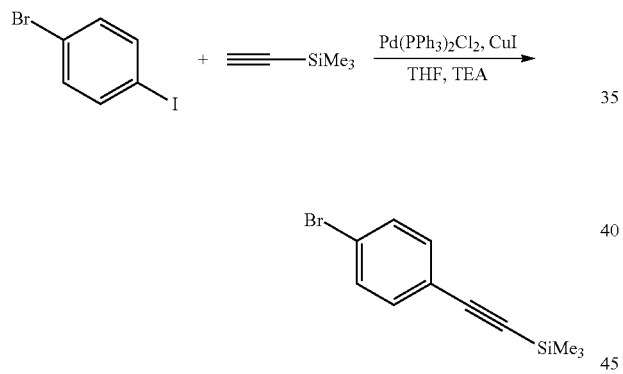

Compound 76.1. ((4-Bromophenyl)ethynyl)trimethylsilane

Into a 100-mL three neck round-bottom flask, which was maintained with an inert atmosphere of nitrogen, was placed a solution of 1-bromo-4-iodobenzene (1.00 g, 3.53 mmol) in tetrahydrofuran/TEA (9:1) (30 mL). PdCl$_2$(PPh$_3$)$_2$ (50 mg, 0.07 mmol), CuI (13.4 mg, 0.07 mmol), and ethynyltrimethylsilane (748 μL, 5.29 mmol) were added and the mixture was stirred for 18 h at room temperature, then concentrated under reduced pressure. The residue was diluted with water (50 mL) and extracted with ethyl acetate (3×20 mL), dried (Na$_2$SO$_4$), filtered, and concentrated under reduced pressure. The residue was purified by silica gel column chromatography with petroleum ether as the eluent to yield the title compound as a light yellow solid (0.83 g, 93%).

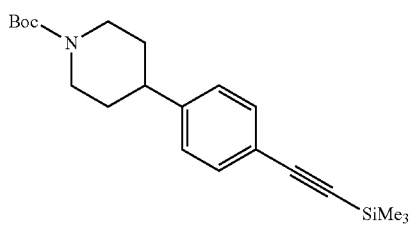 [SMILES: CC(C)(C)OC(=O)N1CCC(c2ccc(C#C[Si](C)(C)C)cc2)CC1]

Compound 76.2. tert-Butyl 4-(4-((trimethylsilyl)ethynyl)phenyl)piperidine-1-carboxylate The title compound was prepared using standard chemical manipulations and procedures similar to those used for the preparation of compound 62.4, except ((4-bromophenyl)ethynyl)trimethylsilane (compound 76.1, 850 mg, 3.36 mmol) was used in place of 5-bromo-1H-indazole to yield the title compound as a yellow oil (0.80 g, 67%).

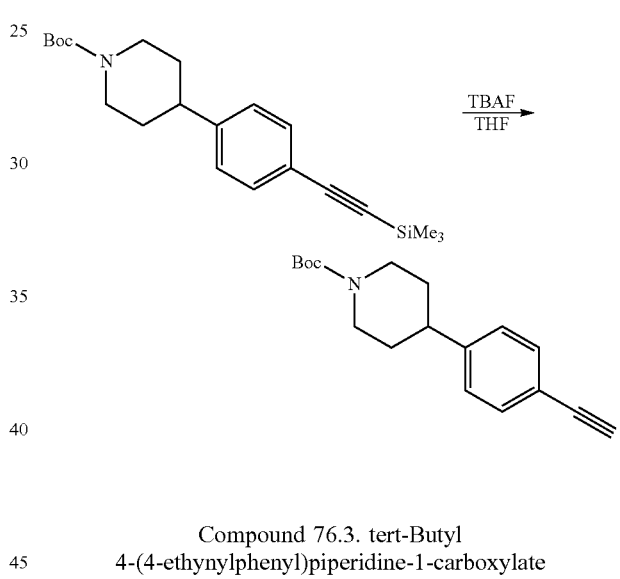

Compound 76.3. tert-Butyl 4-(4-ethynylphenyl)piperidine-1-carboxylate

Into a 50-mL round-bottom flask, was placed a solution of tert-butyl 4-(4-((trimethylsilyl)ethynyl)phenyl)piperidine-1-carboxylate (compound 76.2, 1.34 g, 3.75 mmol) in tetrahydrofuran (20 mL). Tetrabutylammonium fluoride (1.95 g, 7.47 mmol) was added and the resulting solution was stirred for 10 min at room temperature. The mixture was diluted with water (30 mL) and extracted with EtOAc (3×20 mL). The organic layers were combined, dried (Na$_2$SO$_4$), filtered and concentrated under reduced pressure to yield the title compound as a brown oil (1.0 g, crude).

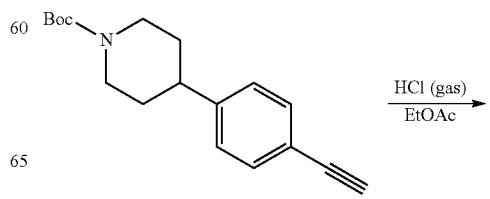

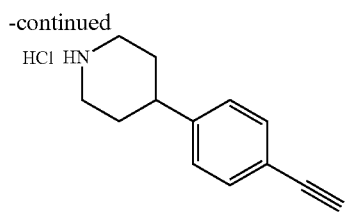

Compound 76.4. 4-(4-Ethynylphenyl)piperidine hydrochloride

Into a 100-mL round-bottom flask, was placed a solution of tert-butyl 4-(4-ethynylphenyl)piperidine-1-carboxylate (compound 76.3, 1.0 g, 3.5 mmol) in ethyl acetate (20 mL). Hydrogen chloride (g) was introduced by bubbling through the solution and the resulting solution was stirred for 1 hour at room temperature. The solids that formed were collected by filtration and washed with hexanes (3×10 mL) to yield the title compound as a brown solid (630 mg, 81%).

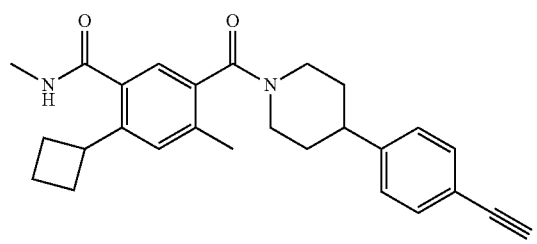 [SMILES: C#Cc1ccc(C2CCN(C(=O)c3cc(C(=O)NC)c(C4CCC4)cc3C)CC2)cc1]

Compound 76. 2-Cyclobutyl-5-(4-(4-ethynylphenyl) piperidine-1-carbonyl)-N,4-dimethylbenzamide The title compound was prepared using standard chemical manipulations and procedures similar to those used for the preparation of compound 62, except 4-(4-ethynylphenyl) piperidine hydrochloride (compound 76.4, 178 mg, 0.81 mmol) was used in place of 5-(piperidin-4-yl)-1H-indazole (compound 62.5) to yield the title compound as a white solid (20.1 mg, 12%). m/z (ES+) 415 (M+H)+.

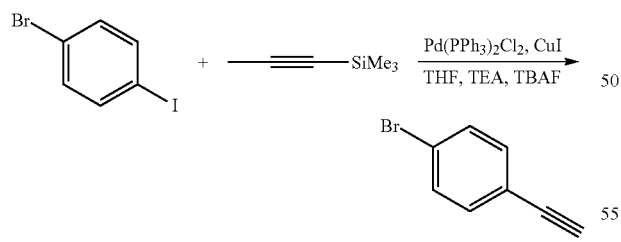

Compound 77.1. 1-Bromo-4-(prop-1-yn-1-yl)benzene

Into a 250-mL three neck round-bottom flask, which was maintained with an inert atmosphere of nitrogen, was placed 1-bromo-4-iodobenzene (2.00 g, 7.07 mmol), PdCl$_2$(PPh$_3$)$_2$ (99.2 mg, 0.14 mmol), CuI (26.8 mg, 0.14 mmol), trimethyl (prop-1-yn-1-yl)silane (2.08 mL, 14.1 mmol) and tetrahydrofuran/TEA (9:1) (100 mL). Stirring was initiated and tetrabutylammonium fluoride (3.69 g, 14.1 mmol) was added rapidly to the mixture. The resulting mixture was stirred for 18 h at room temperature, then concentrated under reduced pressure. The residue diluted with water (100 mL) and extracted with ethyl acetate (3×50 mL). The organic extracts were dried (Na$_2$SO$_4$), filtered, and concentrated under reduced pressure. The residue was purified by silica gel column chromatography with petroleum ether as the eluent to yield the title compound as a light yellow oil (1.0 g, 73%).

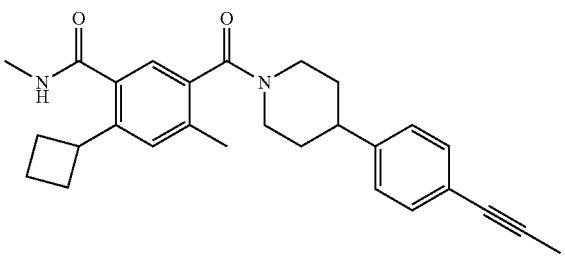 [SMILES: CC#Cc1ccc(C2CCN(C(=O)c3cc(C(=O)NC)c(C4CCC4)cc3C)CC2)cc1]

Compound 77. 2-Cyclobutyl-N,4-dimethyl-5-(4-(4-(prop-1-yn-1-yl)phenyl)piperidine-1-carbonyl)benzamide The title compound was prepared using standard chemical manipulations and procedures similar to those used for the preparation of compound 62, except 1-bromo-4-(prop-1-yn-1-yl)benzene (compound 77.1) was used in place of 5-bromo-1H-indazole to yield the title compound as a white solid. m/z (ES+) 429 (M+H)+.

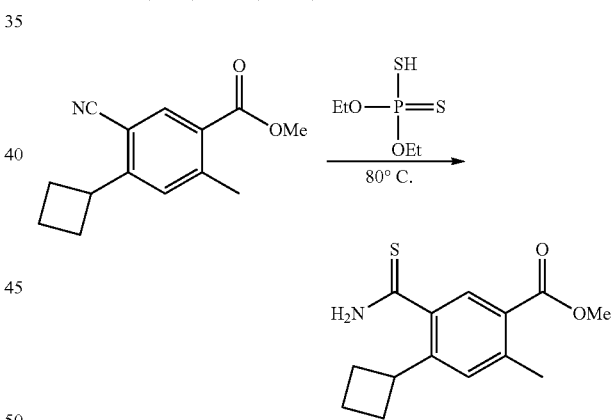

Compound 78.1. Methyl 5-carbamothioyl-4-cyclobutyl-2-methylbenzoate

To a round-bottom flask was added methyl 5-cyano-4-cyclobutyl-2-methylbenzoate (compound 6.4, 3.63 g, 0.015 mol), O,O'-diethyl dithiophosphate (10 mL) and water (1 mL). The reaction mixture was heated to 80° C. for 3 hours (CAUTION: significant gas evolution occurs—this and all other reactions described herein should be carried out in well ventilated fume hoods). After cooling to room temperature, the reaction mixture was partitioned between ethyl acetate (50 mL) and water (50 mL). The organic layer was washed successively with saturated aqueous NaHCO$_3$ (50 mL) and brine (50 mL), dried (Na$_2$SO$_4$), filtered, and concentrated under reduced pressure. The crude product was purified by silica gel flash chromatography (hexanes/ethyl acetate=80/20 to 50/50) to yield the title compound as a yellow solid (3.06 g, 78% yield). m/z (ES+) 264 (M+H)+. $^1$H NMR (400 MHz, CDCl$_3$): δ 7.93 (s, 1H), 7.82 (s, 1H), 7.26 (s, 1H), 6.92 (s, 1H), 4.19 (m, 1H), 3.89 (s, 3H), 2.64 (s, 3H), 2.40 (m, 2H), 2.29-2.15 (m, 2H), 2.12-2.00 (m, 1H), 1.95-1.84 (m, 1H).

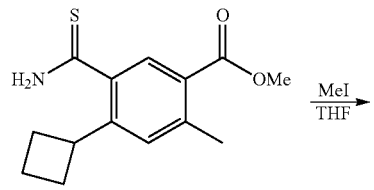

Compound 78.2. Methyl 4-cyclobutyl-5-(imino(methylthio)methyl)-2-methylbenzoate

To a round-bottom flask was added methyl 5-carbamothioyl-4-cyclobutyl-2-methylbenzoate (compound 78.1, 861 mg, 3.27 mmol) in THF (10 mL). Iodomethane (400 μL, 6.42 mmol) was added drop-wise and the reaction mixture was stirred at room temperature for 7 hours. The reaction mixture was concentrated under reduced pressure and the residue was purified by silica gel flash chromatography (ethyl acetate to ethyl acetate/methanol=95/5) to yield the title compound as a yellowish oil (807 mg, 89% yield). m/z (ES+) 278 (M+H)+. $^1$H NMR (400 MHz, DMSO-d$_6$): δ 7.67 (s, 1H), 7.40 (s, 1H), 3.88-3.71 (m, 4H), 2.57 (s, 3H), 2.44 (s, 3H), 2.22-2.19 (m, 2H), 2.12 (m, 2H), 1.98-1.86 (m, 1H), 1.82-1.70 (m, 1H).

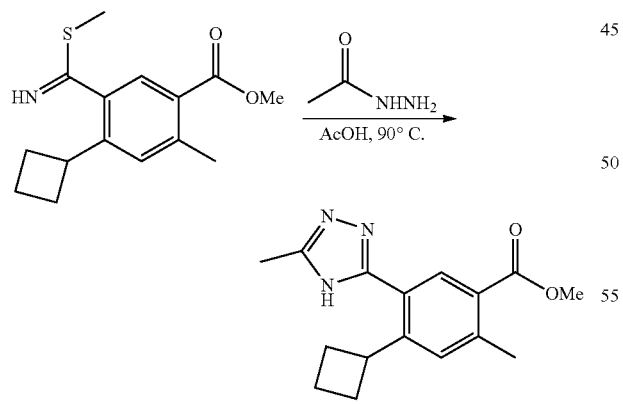

Compound 78.3. Methyl 4-cyclobutyl-2-methyl-5-(5-methyl-4H-1,2,4-triazol-3-yl)benzoate To a round-bottom flask was added methyl 4-cyclobutyl-5-(imino(methylthio)methyl)-2-methylbenzoate (compound 78.2, 556 mg, 2.00 mmol) and acetohydrazide (223 mg, 3.00 mol) in acetic acid (6 mL). The mixture was heated at 90° C. for 3 hours then cooled to room temperature. The reaction mixture was partitioned between water (50 mL) and ethyl acetate (50 mL) and the organic layer was washed with brine (2×50 mL), dried (Na$_2$SO$_4$), filtered, and concentrated under reduced pressure. The residue was purified by silica gel flash chromatography (hexanes/ethyl acetate=50/50 to 30/70) to yield the compound as a white solid (243 mg, 43% yield). m/z (ES+) 286 (M+H)+. $^1$H NMR (400 MHz, CDCl$_3$): δ 8.23 (s, 1H), 7.32 (s, 1H), 4.24-4.05 (m, 1H), 3.89 (s, 3H), 2.69 (s, 3H), 2.54 (s, 3H), 2.23-2.20 (m, 2H), 2.16-2.05 (m, 2H), 2.05-1.88 (m, 1H), 1.88-1.71 (m, 1H).

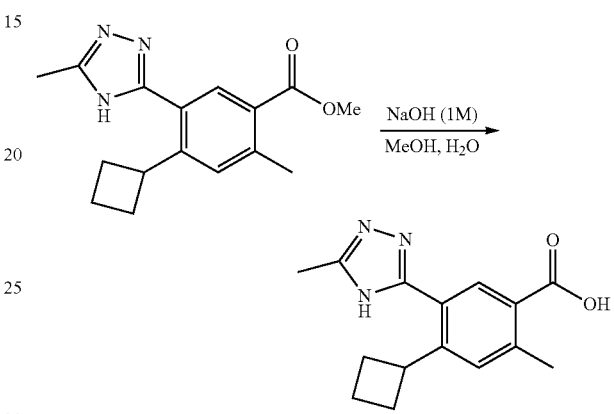

Compound 78.4. 4-Cyclobutyl-2-methyl-5-(5-methyl-4H-1,2,4-triazol-3-yl)benzoic acid To a solution of methyl 4-cyclobutyl-2-methyl-5-(5-methyl-4H-1,2,4-triazol-3-yl)benzoate (compound 78.3, 240 mg, 0.842 mmol) in methanol (5 mL) was added aqueous NaOH (6 mL, 1 M). The resulting mixture was heated to 50° C. for 6 hours then cooled to ambient temperature and acidified to pH 2 with aqueous 1 M HCl and extracted with ethyl acetate (3×50 mL). The combined organic extracts were washed with brine (50 mL), dried (Na$_2$SO$_4$), filtered, and concentrated under reduced pressure to yield the title compound as a white solid (260 mg, quantitative). m/z (ES+) 272 (M+H)+.

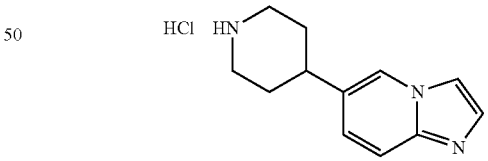

Compound 78.5. 6-(Piperidin-4-yl)imidazo[1,2-a]pyridine hydrochloride

The title compound was prepared using standard chemical manipulations and procedures similar to those used for the preparation of compound 1.2 except 6-bromoimidazo[1,2-a]pyridine (500 mg) was used in place of 4-bromobenzonitrile to yield the title compound as a brown solid (400 mg, 66% over 2 steps).

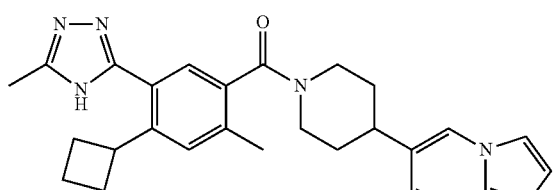

Compound 78. (4-Cyclobutyl-2-methyl-5-(5-methyl-4H-1,2,4-triazol-3-yl)phenyl)(4-(imidazo[1,2-a]pyridin-6-yl)piperidin-1-yl)methanone The title compound was prepared using standard chemical manipulations and procedures similar to those used for the preparation of compound 62, except 4-cyclobutyl-2-methyl-5-(5-methyl-4H-1,2,4-triazol-3-yl)benzoic acid (compound 78.4, 100 mg) was used in place of 4-cyclobutyl-2-methyl-5-(methylcarbamoyl)benzoic acid (compound 62.3) and 6-(piperidin-4-yl)imidazo[1,2-a]pyridine hydrochloride (compound 78.5, 88 mg) was used in place of 5-(piperidin-4-yl)-1H-indazole (compound 62.5). The title compound was obtained as a white solid (35.6 mg, 21%). m/z (ES+) 455 (M+H)+.

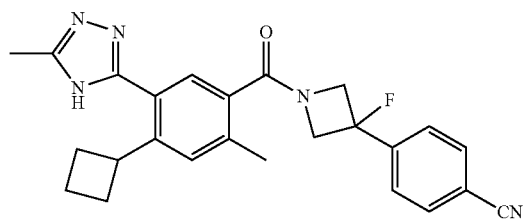 [SMILES: Cc1nnc(-c2cc(C(=O)N3CC(F)(c4ccc(C#N)cc4)C3)c(C)cc2C2CCC2)[nH]1]

Compound 79. 4-(1-(4-Cyclobutyl-2-methyl-5-(5-methyl-4H-1,2,4-triazol-3-yl)benzoyl)-3-fluoroazetidin-3-yl)benzonitrile The title compound was prepared using standard chemical manipulations and procedures similar to those used for the preparation of compound 62, except 4-cyclobutyl-2-methyl-5-(5-methyl-4H-1,2,4-triazol-3-yl)benzoic acid (compound 78.4) was used in place of 4-cyclobutyl-2-methyl-5-(methylcarbamoyl)benzoic acid (compound 62.3) and 4-(3-fluoroazetidin-3-yl)benzonitrile hydrochloride (compound 43.4) was used in place of 5-(piperidin-4-yl)-1H-indazole (compound 62.5). m/z (ES+) 430 (M+H)+.

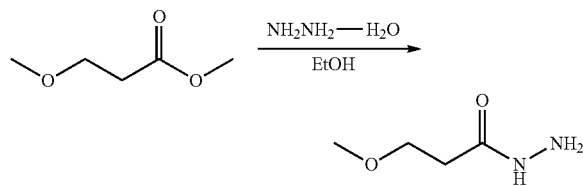

Compound 80.1. 3-Methoxypropanehydrazide

Into a 500-mL round-bottom flask, was placed a solution of methyl 3-methoxypropanoate (30.0 g, 254 mmol) in ethanol (100 mL) and hydrazine hydrate (24.7 mL, 507 mmol). The resulting solution was stirred overnight at 80° C., then cooled and concentrated under reduced pressure to yield 26.3 g (88%, crude) of the title compound as colorless oil.

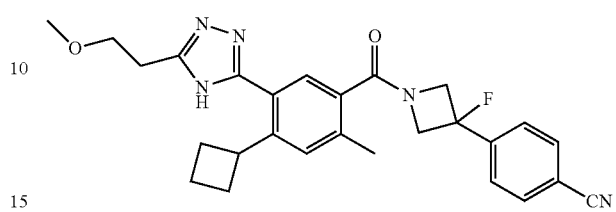

Compound 80. 4-(1-(4-Cyclobutyl-5-(5-(2-methoxyethyl)-4H-1,2,4-triazol-3-yl)-2-methylbenzoyl)-3-fluoroazetidin-3-yl)benzonitrile The title compound was prepared using standard chemical manipulations and procedures similar to those used for the preparation of compound 78, except 3-methoxypropanehydrazide (compound 80.1) was used in place of acetohydrazide and 4-(3-fluoroazetidin-3-yl)benzonitrile hydrochloride (compound 43.4) was used in place of 6-(piperidin-4-yl)imidazo[1,2-a]pyridine hydrochloride (compound 78.5). m/z (ES+) 474 (M+H)+.

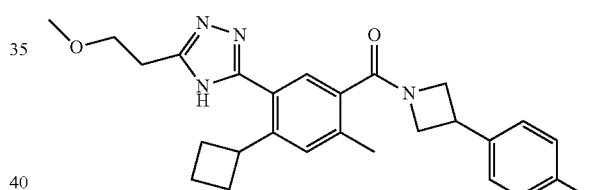

Compound 81. 4-(1-(4-Cyclobutyl-5-(5-(2-methoxyethyl)-4H-1,2,4-triazol-3-yl)-2-methylbenzoyl)azetidin-3-yl)benzonitrile The title compound was prepared using standard chemical manipulations and procedures similar to those used for the preparation of compound 78, except 3-methoxypropanehydrazide (compound 80.1) was used in place of acetohydrazide and 4-(azetidin-3-yl)benzonitrile hydrochloride (compound 5.2) was used in place of 6-(piperidin-4-yl)imidazo[1,2-a]pyridine hydrochloride (compound 78.5). m/z (ES+) 456 (M+H)+.

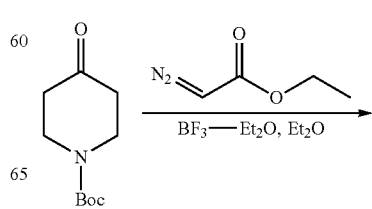

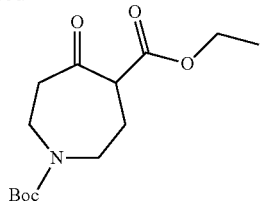 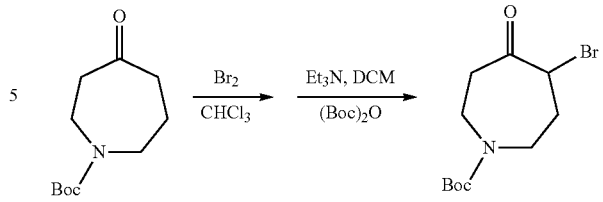

Compound 82.1. 1-tert-Butyl 4-ethyl 5-oxoazepane-1,4-dicarboxylate

Compound 82.3. tert-Butyl 4-bromo-5-oxoazepane-1-carboxylate

To a solution of tert-butyl 4-oxopiperidine-1-carboxylate (20.0 g, 100 mmol) in diethylether (60 mL) under nitrogen at −30° C., was added drop-wise a solution of $BF_3.Et_2O$ (16.0 mL, 130 mmol) in ether (20 mL). After stirring for 30 min at −30° C., a solution of ethyl 2-diazoacetate (16.0 g, 140 mmol) in ether (20 mL) was added drop-wise to the reaction at −30° C. The resulting solution was stirred for 1 h at −30° C., then at room temperature for 2 h. The reaction was carefully quenched with 30% aqueous potassium carbonate (100 mL) and the resulting mixture was extracted with ethyl acetate (2×250 mL). The combined organic extracts were washed with brine (2×50 mL), dried over anhydrous sodium sulfate, filtered, and concentrated under reduced pressure. The residue was purified by silica gel column chromatography with ethyl acetate/petroleum ether (1/10) as the eluent to furnish 19 g (66%) of the title compound as a light yellow oil.

To a solution tert-butyl 4-oxoazepane-1-carboxylate (compound 82.2, 11.0 g, 51.6 mmol) in chloroform (220 mL) at 0° C. was added drop-wise a solution of bromine (3.98 mL, 77.6 mmol) in chloroform (110 mL). The resulting mixture was stirred at room temperature overnight, then the solids that formed were collected by filtration and dissolved in dichloromethane (200 mL). Triethylamine (16.8 mL, 121 mmol) and $(Boc)_2O$ (8.70 g, 40.3 mmol) were added to the mixture at 0° C. and the resulting solution was stirred for 3 h at room temperature, and then concentrated under reduced pressure. The crude residue was purified by silica gel chromatography using ethyl acetate/petroleum ether (1:10) as the eluent to give 4.0 g (27%) of the title compound as a yellow oil.

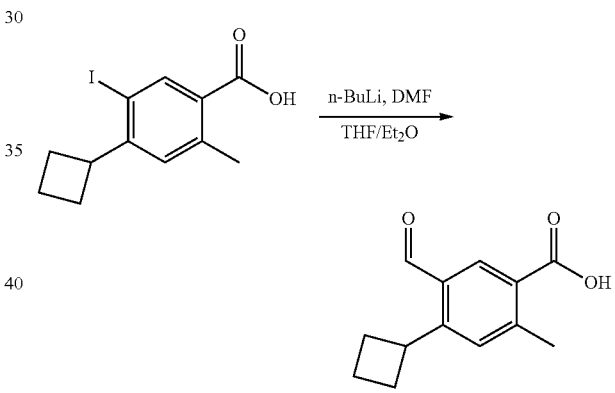

Compound 82.4. 4-Cyclobutyl-5-formyl-2-methylbenzoic acid

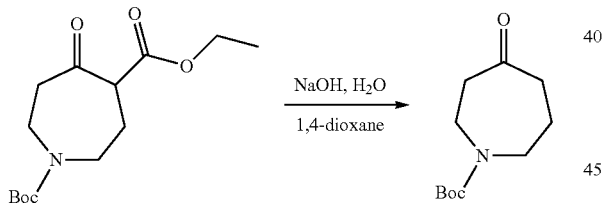

Compound 82.2. tert-Butyl 4-oxoazepane-1-carboxylate

To a solution 1-tert-butyl 4-ethyl 5-oxoazepane-1,4-dicarboxylate (compound 82.1, 19.0 g, 66.6 mmol) in 1,4-dioxane (190 mL) was added drop-wise a solution of sodium hydroxide (4.00 g, 100 mmol) in water (100 mL). The resulting mixture was stirred at room temperature overnight. The pH was then adjusted to 4-5 with hydrogen chloride (aq. 3 M) and the resulting solution was extracted with ethyl acetate (2×50 mL). The combined organic extracts were washed with brine (2×10 mL), dried over anhydrous sodium sulfate, filtered, and concentrated under reduced pressure. The crude residue was purified by silica gel column chromatography using ethyl acetate/petroleum ether (1:3) as the eluent to furnish 11 g (77%) of the title compound as a yellow oil.

Into a three neck round-bottom flask, which was purged and maintained with an inert atmosphere of nitrogen, was placed a solution of 4-cyclobutyl-5-iodo-2-methylbenzoic acid (compound 62.1, 5.00 g, 80%, 12.7 mmol) in a solvent mixture of tetrahydrofuran and $Et_2O$ (50 mL/50 mL). The solution was cooled to −78° C. then n-butyllithium (15 mL, 2.5 M in hexanes) was added drop-wise with stirring. N,N-Dimethylformamide (2.64 mL, 34.2 mmol) was added and the resulting mixture was stirred for 1 h at −78° C., then carefully quenched by slow addition of aqueous $NH_4Cl$ (sat., 50 mL). The pH was adjusted to 1-2 with aqueous hydrogen chloride (6 M), then diluted with ethyl acetate (100 mL) and washed with brine (4×50 mL). The organic layer was dried over anhydrous sodium sulfate, filtered and concentrated under reduced pressure. The residue was purified using silica gel column chromatography with ethyl acetate/petroleum ether (1:1) as the eluent to furnish 1.62 g (41%) of the title compound as a white solid.

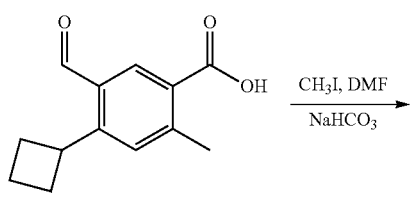

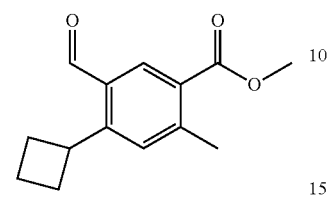

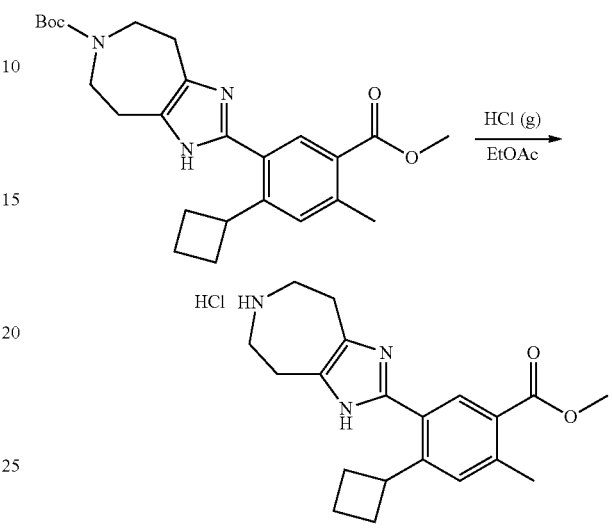

with brine (3×10 mL), dried (Na₂SO₄), filtered, and concentrated under reduced pressure. The residue was purified by silica gel column chromatography with ethyl acetate/petroleum ether (1/1) as the eluent to yield 0.10 g (18%) of the title compound as a white solid.

Compound 82.5. Methyl 4-cyclobutyl-5-formyl-2-methylbenzoate

Into a 100-mL round-bottom flask, was placed a mixture of 4-cyclobutyl-5-formyl-2-methylbenzoic acid (compound 82.4, 500 mg, 2.29 mmol) in N,N-dimethylformamide (10 mL) and sodium bicarbonate (390 mg, 4.64 mmol). With stirring, methyl iodide (430 μL, 6.90 mmol) was added drop-wise and the resulting mixture was stirred for 5 h at room temperature. The reaction was then diluted with EtOAc (50 mL) and the mixture was washed with brine (4×10 mL). The organic layer was dried (Na₂SO₄), filtered, and concentrated under reduced pressure to yield 0.40 g (crude) of the title compound as a brown oil

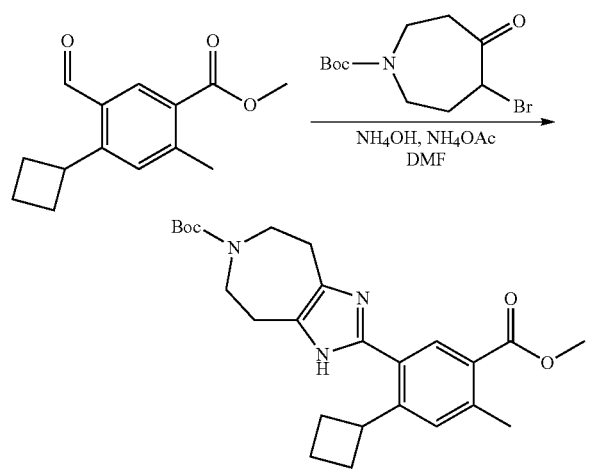

Compound 82.6. tert-Butyl 2-(2-cyclobutyl-5-(methoxycarbonyl)-4-methylphenyl)-4,5,7,8-tetrahydroimidazo[4,5-d]azepine-6(1H)-carboxylate Into a 100-mL round-bottom flask, was placed a mixture of methyl 4-cyclobutyl-5-formyl-2-methylbenzoate (compound 82.5, 300 mg, 1.29 mmol), ammonium acetate (449 mg, 5.83 mmol), tert-butyl 4-bromo-5-oxoazepane-1-carboxylate (compound 82.3, 564 mg, 1.93 mmol) and ammonium hydroxide (25%)(597 μL, 3.87 mmol) in N,N-dimethylformamide (8 mL). The resulting mixture was stirred for 4 h at 130° C., then cooled and quenched with water/ice (10 mL). The aqueous phase was extracted with ethyl acetate (2×30 mL) and the combined organic layers were washed Compound 82.7. Methyl 4-cyclobutyl-5-(1,4,5,6,7,8-hexahydroimidazo[4,5-d]azepin-2-yl)-2-methylbenzoate hydrochloride Into a 50-mL 3-necked round-bottom flask, was placed a solution of tert-butyl 2-(2-cyclobutyl-5-(methoxycarbonyl)-4-methylphenyl)-4,5,7,8-tetrahydroimidazo[4,5-d]azepine-6(1H)-carboxylate (compound 82.6, 200 mg, 0.46 mmol) in EtOAc (10 mL). Hydrogen chloride (gas) was introduced into the solution by bubbling and the solution was stirred for 30 min at room temperature. The resulting mixture was concentrated under reduced pressure to yield 136 mg (crude) of the title compound as a yellow solid.

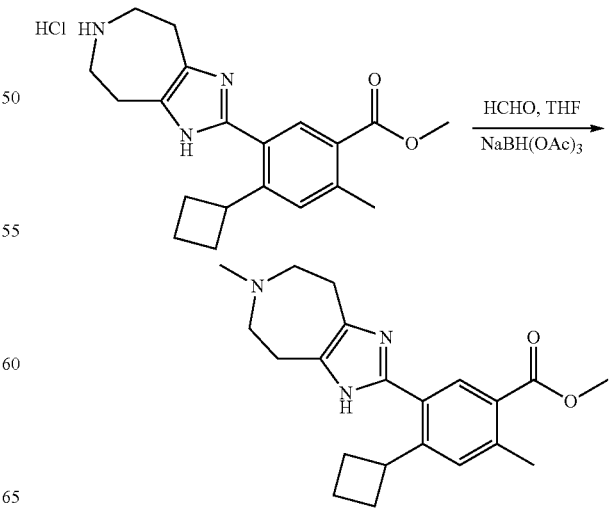

Compound 82.8. Methyl 4-cyclobutyl-2-methyl-5-(6-methyl-1,4,5,6,7,8-hexahydroimidazo[4,5-d]azepin-2-yl)benzoate Into a 100-mL round-bottom flask, was placed a mixture of methyl 4-cyclobutyl-5-(1,4,5,6,7,8-hexahydroimidazo[4,5-d]azepin-2-yl)-2-methylbenzoate hydrochloride (compound 82.7, 40 mg, 0.11 mmol), NaBH(OAc)₃ (75 mg, 0.35 mmol), and formaldehyde (37 wt %) (26 µL, 0.33 mmol) in tetrahydrofuran (4 mL). The resulting mixture was stirred for 2 h at 40° C., then cooled and the pH of the solution was adjusted to 8-9 with sodium bicarbonate (sat.). The aqueous phase was extracted with ethyl acetate (2×20 mL) and the combined organic layers were dried (Na₂SO₄), filtered, and concentrated under reduced pressure to yield 20 mg (crude) of the title compound as a yellow solid.

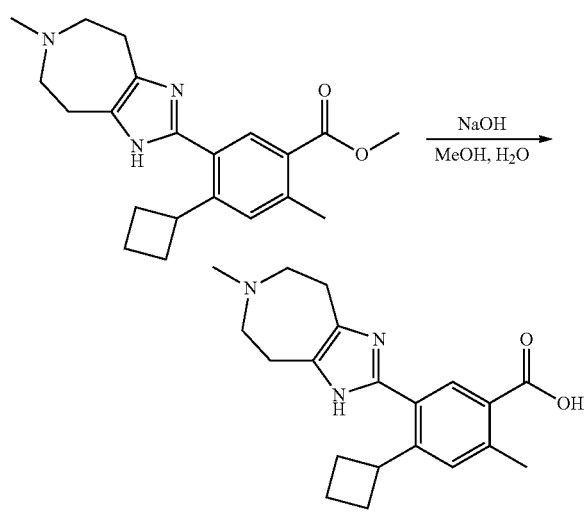

Compound 82.9. 4-Cyclobutyl-2-methyl-5-(6-methyl-1,4,5,6,7,8-hexahydroimidazo[4,5-d]azepin-2-yl)benzoic acid Into a 50-mL round-bottom flask, was placed a mixture of methyl 4-cyclobutyl-2-methyl-5-(6-methyl-1,4,5,6,7,8-hexahydroimidazo[4,5-d]azepin-2-yl)benzoate (compound 82.8, 40 mg, 0.11 mmol) and NaOH (18 mg, 0.44 mmol) in methanol (4 mL), water (2 mL). The resulting solution was stirred for 2 h at 60° C. After cooling to room temperature, the volatiles were removed under reduced pressure. The pH of the residual solution was adjusted to about 1 with hydrogen chloride (3 M) and concentrated under reduced pressure to yield 0.10 g (crude) of the title product as the HCl salt as a yellow solid.

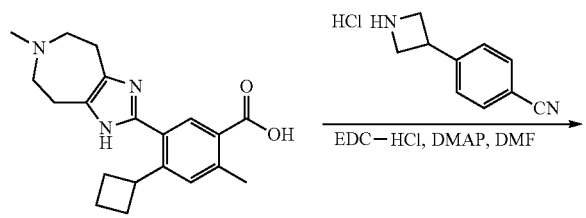

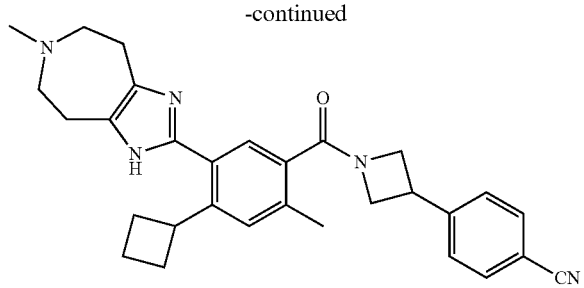

Compound 82. 4-(1-(4-Cyclobutyl-2-methyl-5-(6-methyl-1,4,5,6,7,8-hexahydroimidazo[4,5-d]azepin-2-yl)benzoyl)azetidin-3-yl)benzonitrile Into a 100-mL round-bottom flask, was placed a mixture of 4-cyclobutyl-2-methyl-5-(6-methyl-1,4,5,6,7,8-hexahydroimidazo[4,5-d]azepin-2-yl)benzoic acid (compound 82.9, 40 mg, 0.12 mmol), EDC.HCl (45.4 mg, 0.24 mmol, 2.00 equiv), 4-dimethylaminopyridine (29 mg, 0.24 mmol) and 4-(azetidin-3-yl)benzonitrile hydrochloride (compound 5.2, 23 mg, 0.12 mmol) in N,N-dimethylformamide (5 mL). The resulting solution was stirred for 4 h at room temperature then quenched by the addition of water/ice (10 mL). The resulting mixture was extracted with ethyl acetate (2×20 mL) and the combined organic layers were washed with brine (2×10 mL). The organic layer was dried (Na₂SO₄), filtered, and concentrated under reduced pressure to yield the crude product which was purified by Prep-HPLC using the following conditions (1#-Pre-HPLC-001(SHIMADZU)): Column, XBridge Shield RP18 OBD Column, 5 um, 19*150 mm; mobile phase, WATER WITH 0.03% NH4OH and CH3CN (30% CH3CN up to 43% in 8 min, up to 100% in 4 min, down to 30% in 2 min); Detector, Waters 2489, 254 & 220 nm. The fractions containing clean product were combined to yield 2.2 mg (4%) of the title compound as a white solid. m/z (ES+) 480 (M+H)⁺.

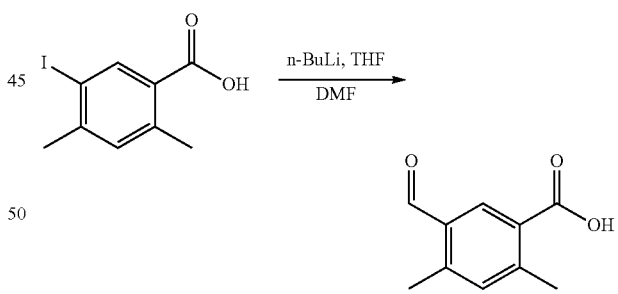

Compound 83.1. 5-Formyl-2,4-dimethylbenzoic acid

To a stirred solution of 5-iodo-2,4-dimethylbenzoic acid (compound 1.3, 5.00 g, 18.1 mmol) in tetrahydrofuran (150 mL) under nitrogen at −78° C. was added n-BuLi (2.5 M in THF, 18 mL, 45 mmol) drop-wise. The mixture was stirred at −78° C. for 1 h and then DMF (5.3 mL, 68 mmol) was added drop-wise. The resulting mixture was stirred at −78° C. for 0.5 h and then carefully quenched by slow addition of water (50 mL). The pH of the mixture was adjusted to ~3-4 with aqueous HCl (6 M) and then extracted with ethyl acetate (3×200 mL). The combined organic layers were dried (Na₂SO₄), filtered, and concentrated under reduced pressure. The residue was purified using silica gel column chromatography with ethyl acetate/petroleum ether (1:10-1:5) as the eluent to yield the title compound as a white solid (2.4 g, 74%).

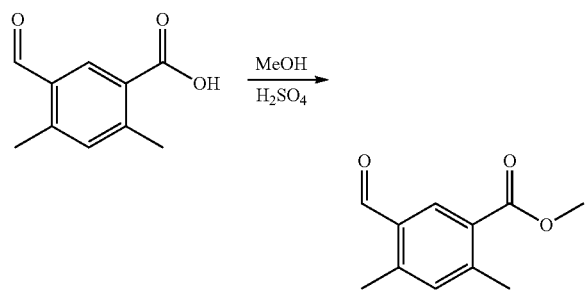

Compound 83.2. Methyl 5-formyl-2,4-dimethylbenzoate

Into a 250-mL round-bottom flask, was placed 5-formyl-2,4-dimethylbenzoic acid (compound 83.1, 2.00 g, 11.2 mmol) and methanol (50 mL). Concentrated sulfuric acid (2 mL) was carefully added drop-wise and the resulting solution was stirred for 2 h at 80° C., then cooled and the volatiles were removed under reduced pressure. The pH of the residue was adjusted to 9 with sodium bicarbonate (sat.), then the aqueous phase was extracted with ethyl acetate (3×50 mL). The combined organic layers were washed with brine (2×20 mL), dried (Na₂SO₄), filtered, and concentrated under reduced pressure to yield 2.0 g (crude) of the title compound as yellow oil. The crude product was used in next step without further purification.

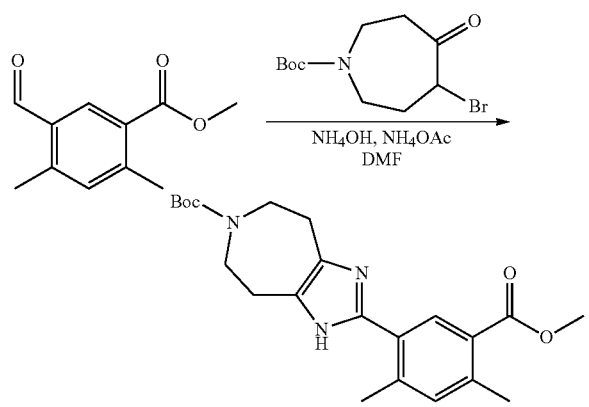

Compound 83.3. tert-Butyl 2-(5-(methoxycarbonyl)-2,4-dimethylphenyl)-4,5,7,8-tetrahydroimidazo[4,5-d]azepine-6(1H)-carboxylate Into a 10-mL sealed tube, was placed methyl 5-formyl-2,4-dimethylbenzoate (compound 83.2, 500 mg, 2.60 mmol), tert-butyl 4-bromo-5-oxoazepane-1-carboxylate (compound 82.3, 1.1 g, 3.8 mmol), ammonium hydroxide (25%) (1.2 mL, 7.8 mmol), ammonium acetate (900 mg, 11.7 mmol) in N,N-dimethylformamide (6 mL). The resulting mixture was stirred for 3 h at 130° C. behind a blast shield, then cooled to room temperature and diluted with ethyl acetate (150 mL). The mixture was washed with brine (5×20 mL), dried (Na₂SO₄), filtered, and concentrated under reduced pressure. The residue was purified by silica gel column chromatography with dichloromethane/methanol (10:1) as the eluent to yield 0.80 g (46%) of the title compound as yellow oil.

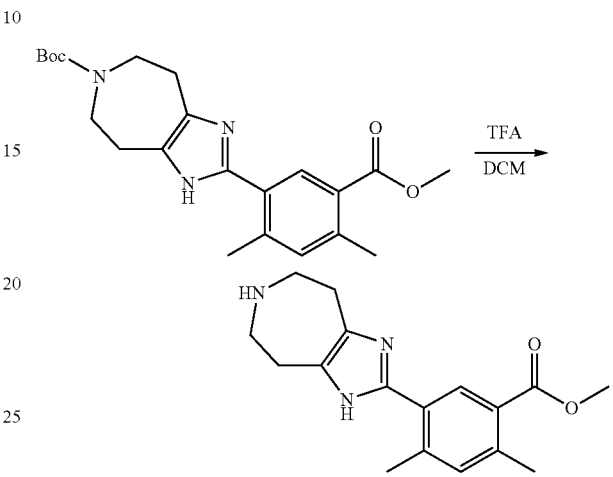

Compound 83.4. Methyl 5-(1,4,5,6,7,8-hexahydroimidazo[4,5-d]azepin-2-yl)-2,4-dimethylbenzoate Into a 100-mL round-bottom flask, was placed a solution of tert-butyl 2-(5-(methoxycarbonyl)-2,4-dimethylphenyl)-4,5,7,8-tetrahydroimidazo[4,5-d]azepine-6(1H)-carboxylate (compound 83.3, 800 mg, 2.00 mmol) in dichloromethane (16 mL). Trifluoroacetic acid (4 mL) was added drop-wise and the resulting solution was stirred for 5 h at room temperature. The pH of the solution was carefully adjusted to 8-9 with NaHCO₃ (sat.) and the aqueous phase was extracted with DCM (3×30 mL), and the combined organics were dried (Na₂SO₄), filtered, and concentrated under reduced pressure to yield 0.60 mg (crude) of the title compound as brown oil.

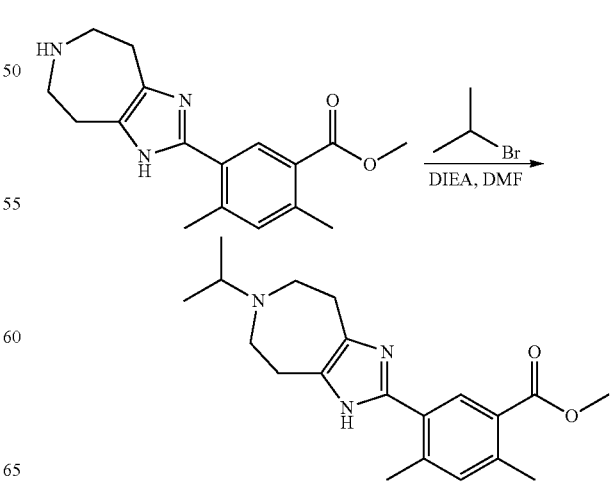

Compound 83.5. Methyl 5-(6-isopropyl-1,4,5,6,7,8-hexahydroimidazo[4,5-d]azepin-2-yl)-2,4-dimethylbenzoate Into a 100-mL round-bottom flask, was placed methyl 5-(1,4,5,6,7,8-hexahydroimidazo[4,5-d]azepin-2-yl)-2,4-dimethylbenzoate (compound 83.4, 347 mg, 0.84 mmol), 2-bromopropane (790 µL, 8.40 mmol), N,N-diisopropylethylamine (1.46 mL, 8.4 mmol) in N,N-dimethylformamide (5 mL). The solution was stirred for 4 h at 80° C., then cooled to room temperature. The resulting solution was diluted with ethyl acetate (50 mL) and washed with brine (4×20 mL), dried (Na$_2$SO$_4$), filtered, and concentrated under reduced pressure to yield 0.22 g (crude) of the title compound as brown oil.

Compound 84. 4-(1-(2,4-Dimethyl-5-(6-methyl-1,4,5,6,7,8-hexahydroimidazo[4,5-d]azepin-2-yl)benzoyl)azetidin-3-yl)benzonitrile The title compound was prepared using standard chemical manipulations and procedures similar to those used for the preparation of compound 82, except methyl 5-(1,4,5,6,7,8-hexahydroimidazo[4,5-d]azepin-2-yl)-2,4-dimethylbenzoate (compound 83.4) was used in place of methyl 4-cyclobutyl-5-(1,4,5,6,7,8-hexahydroimidazo[4,5-d]azepin-2-yl)-2-methylbenzoate hydrochloride (compound 82.7). m/z (ES+) 440 (M+H)$^+$.

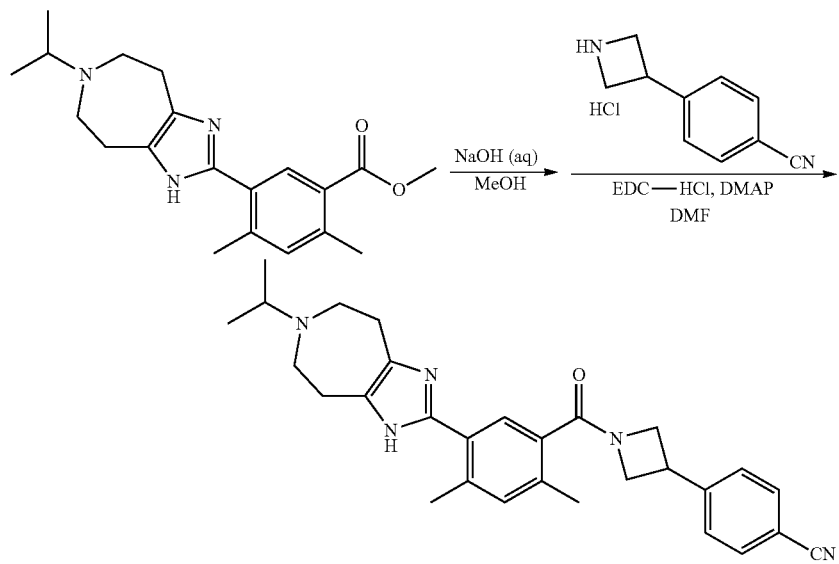

Compound 83. 4-(1-(5-(6-Isopropyl-1,4,5,6,7,8-hexahydroimidazo[4,5-d]azepin-2-yl)-2,4-dimethylbenzoyl)azetidin-3-yl)benzonitrile The title compound was prepared using standard chemical manipulations and procedures similar to those used for the preparation of compound 82, except methyl 5-(6-isopropyl-1,4,5,6,7,8-hexahydroimidazo[4,5-d]azepin-2-yl)-2,4-dimethylbenzoate (compound 83.5) was used in place of 4-cyclobutyl-2-methyl-5-(6-methyl-1,4,5,6,7,8-hexahydroimidazo[4,5-d]azepin-2-yl)benzoate (compound 82.8). m/z (ES+) 468 (M+H)$^+$.

Compound 85.1. 3-(4-Chlorophenyl)azetidine hydrochloride

The title compound was prepared using standard chemical manipulations and procedures similar to those used for the preparation of compound 5.2, except (4-chlorophenyl)boronic acid was used in place of (4-cyanophenyl)boronic acid. The title compound was obtained in 20% yield over two steps.

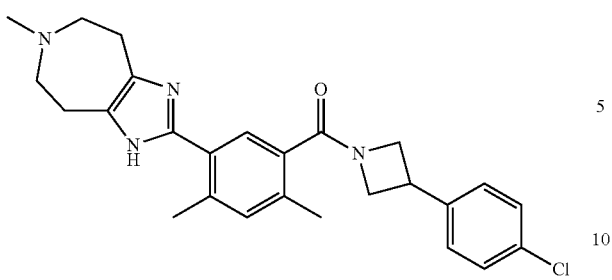

Compound 85. (3-(4-Chlorophenyl)azetidin-1-yl)(2,4-dimethyl-5-(6-methyl-1,4,5,6,7,8-hexahydroimidazo[4,5-d]azepin-2-yl)phenyl)methanone The title compound was prepared using standard chemical manipulations and procedures similar to those used for the preparation of compound 82, except methyl 5-(1,4,5,6,7,8-hexahydroimidazo[4,5-d]azepin-2-yl)-2,4-dimethylbenzoate (compound 83.4) was used in place of methyl 4-cyclobutyl-5-(1,4,5,6,7,8-hexahydroimidazo[4,5-d]azepin-2-yl)-2-methylbenzoate hydrochloride (compound 82.7) and 3-(4-chlorophenyl)azetidine hydrochloride (compound 85.1) was used in place of 4-(azetidin-3-yl)benzonitrile hydrochloride (compound 5.2). m/z (ES+) 449 (M+H)+.

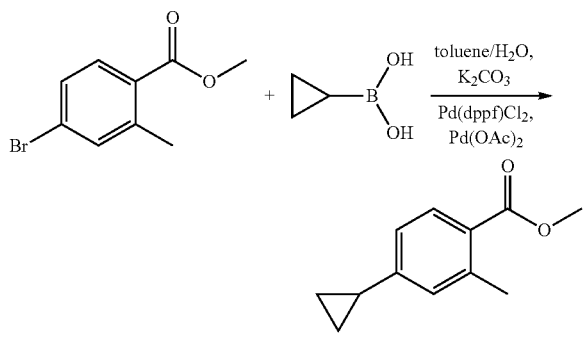

Compound 86.1. Methyl 4-cyclopropyl-2-methylbenzoate

To a solution of methyl 4-bromo-2-methylbenzoate (compound 6.1, 5.00 g, 20.7 mmol, 95%) in a mixture of toluene and H$_2$O (20 mL/1 mL) were added potassium carbonate (6.10 g, 44.1 mmol), cyclopropylboronic acid (2.30 g, 26.8 mmol), Pd(dppf)Cl$_2$ (900 mg, 1.23 mmol), and Pd(OAc)$_2$ (250 mg, 1.12 mmol). The reaction mixture was purged with nitrogen and stirred at 80° C. overnight. After cooling to room temperature, the mixture was then concentrated under reduced pressure. The resulting residue was purified by silica gel column chromatography with ethyl acetate/petroleum ether (1:50) as the eluent to yield 2.68 g (61%) of the title compound as a colorless oil.

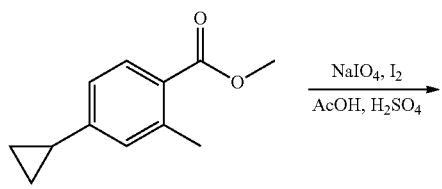

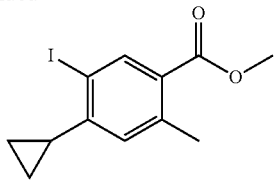

Compound 86.2. Methyl 4-cyclopropyl-5-iodo-2-methylbenzoate

To a solution of methyl 4-cyclopropyl-2-methylbenzoate (compound 86.1, 2.68 g, 13.4 mmol, 95%) in AcOH (50 mL) were added NaIO$_4$ (1.51 g, 7.08 mmol), iodine (3.58 g, 14.1 mmol), and sulfuric acid (106 µL, 2.0 mmol, 0.15 equiv). The reaction mixture was stirred overnight at 110° C. After cooling to ambient temperature, water (100 mL) was slowly added and the mixture was extracted with ethyl acetate (100 mL). The organic layer was washed with Na$_2$S$_2$O$_3$ (aq., sat., 3×30 mL) and brine (30 mL), dried (Na$_2$SO$_4$), filtered, and concentrated under reduced pressure. The residue was purified by silica gel column chromatography with ethyl acetate/petroleum ether (1/50) as the eluent to yield 2.0 g (45%) of the title compound as a colorless oil.

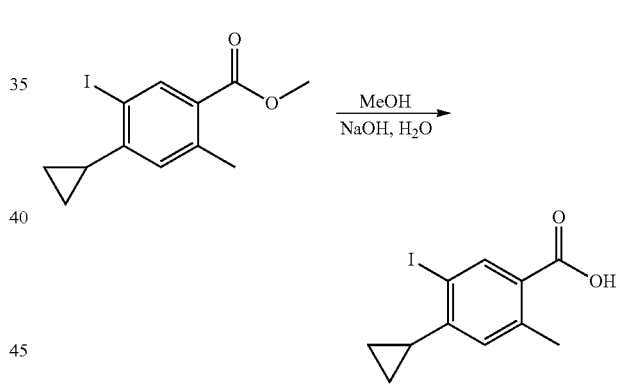

Compound 86.3. 4-Cyclopropyl-5-iodo-2-methylbenzoic acid

Into a 500-mL round-bottom flask, was placed a solution of methyl 4-cyclopropyl-5-iodo-2-methylbenzoate (compound 86.2, 15.0 g, 47.5 mmol) in methanol (150 mL). A solution of sodium hydroxide (5.70 g, 143 mmol) in water (75 mL) was added and the resulting solution was stirred for 4 h at 60° C., then cooled to room temperature. The volatiles were removed under reduced pressure and the remaining solution was adjusted to pH 3 with aqueous hydrogen chloride (12 M). The mixture was extracted with ethyl acetate (2×200 mL) and the combined organic extracts were washed with NH$_4$Cl (aq.) (2×400 mL) and brine (400 mL). The organic layer was dried (Na$_2$SO$_4$), filtered, and concentrated under reduced pressure to yield 13.0 g (91%) of the title compound as a light yellow solid.

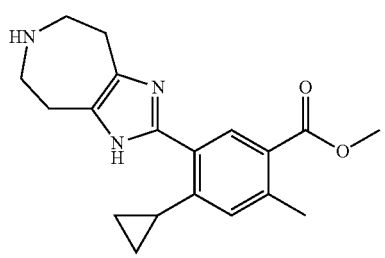 [SMILES: COC(=O)c1cc(-c2nc3c([nH]2)CCNCC3)c(C2CC2)cc1C]

Compound 86.4. Methyl 4-cyclopropyl-5-(1,4,5,6,7,8-hexahydroimidazo[4,5-d]azepin-2-yl)-2-methylbenzoate The title compound was prepared using standard chemical manipulations and procedures similar to those used for the preparation of compound 83.4, except 4-cyclopropyl-5-iodo-2-methylbenzoic acid (compound 86.3) was used in place of 5-iodo-2,4-dimethylbenzoic acid (compound 1.3).

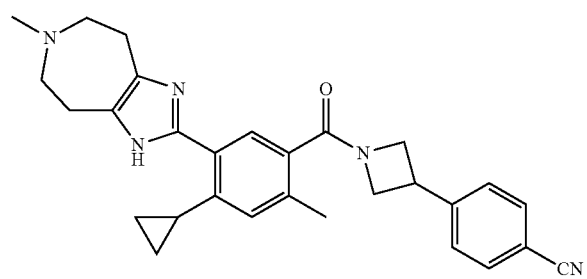 [SMILES: Cc1cc(C2CC2)c(-c2nc3c([nH]2)CCN(C)CC3)cc1C(=O)N1CC(c2ccc(C#N)cc2)C1]

Compound 86. 4-(1-(4-Cyclopropyl-2-methyl-5-(6-methyl-1,4,5,6,7,8-hexahydroimidazo[4,5-d]azepin-2-yl)benzoyl)azetidin-3-yl)benzonitrile The title compound was prepared using standard chemical manipulations and procedures similar to those used for the preparation of compound 82, except methyl 4-cyclopropyl-5-(1,4,5,6,7,8-hexahydroimidazo[4,5-d]azepin-2-yl)-2-methylbenzoate (compound 86.4) was used in place of methyl 4-cyclobutyl-5-(1,4,5,6,7,8-hexahydroimidazo[4,5-d]azepin-2-yl)-2-methylbenzoate hydrochloride (compound 82.7). m/z (ES+) 466 (M+H)$^+$.

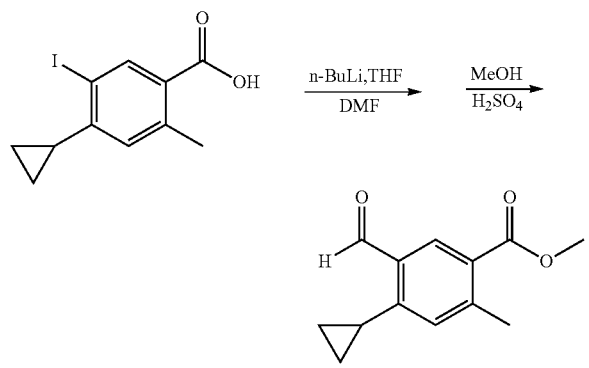

Compound 87.1. Methyl 4-cyclopropyl-5-formyl-2-methylbenzoate

The title compound was prepared using standard chemical manipulations and procedures similar to those used for the preparation of compound 83.2, except 4-cyclopropyl-5-iodo-2-methylbenzoic acid (compound 86.3) was used in place of 5-iodo-2,4-dimethylbenzoic acid (compound 1.3).

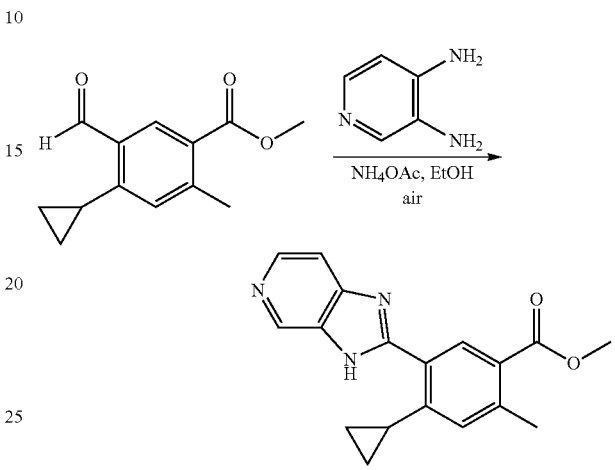

Compound 87.2. Methyl 4-cyclopropyl-5-(3H-imidazo[4,5-c]pyridin-2-yl)-2-methylbenzoate Into a 100-mL round-bottom flask was placed a mixture of methyl 4-cyclopropyl-5-formyl-2-methylbenzoate (compound 87.1, 500 mg, 2.29 mmol), pyridine-3,4-diamine (500 mg, 4.58 mmol), NH$_4$OAc (1.42 g, 18.4 mmol) and ethanol (50 mL). The resulting mixture was stirred open to the air for 3 days at 70° C., then cooled to room temperature and diluted with aqueous sodium bicarbonate (sat., 50 mL). The aqueous phase was extracted with ethyl acetate (2×50 mL) and the combined organic layers were dried (Na$_2$SO$_4$), filtered, and concentrated under reduced pressure. The residue was purified by silica gel column chromatography with ethyl acetate as the eluent to yield 268 mg (38%) of the title compound as a yellow semi-solid.

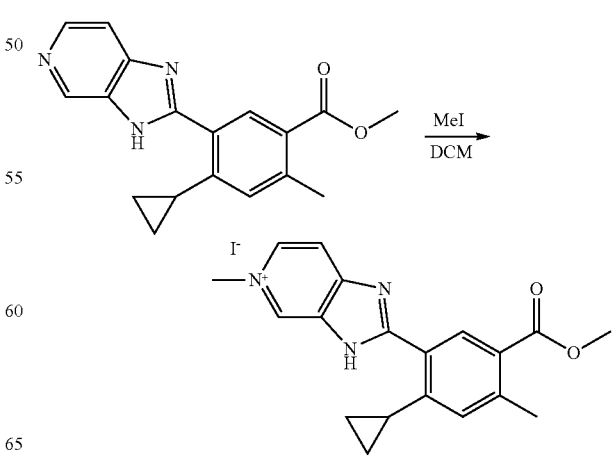

Compound 87.3. 2-(2-Cyclopropyl-5-(methoxycarbonyl)-4-methylphenyl)-5-methyl-3H-imidazo[4,5-c]pyridin-5-ium iodide Into a 50-mL round-bottom flask, was placed a solution of methyl 4-cyclopropyl-5-(3H-imidazo[4,5-c]pyridin-2-yl)-2-methylbenzoate (compound 87.2, 500 mg, 1.63 mmol) in dichloromethane (15 mL). Iodomethane (203 μL, 3.26 mmol) was added drop-wise and the resulting solution was stirred overnight at room temperature. The mixture was concentrated under reduced pressure to yield 0.30 g (41%) of the title compound as a yellow solid.

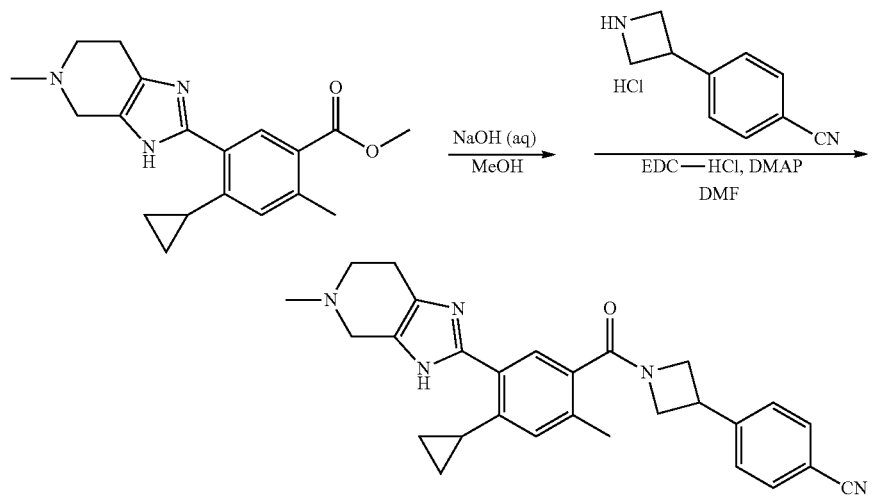

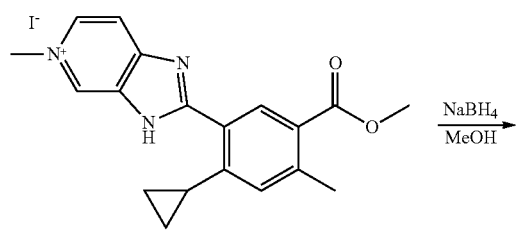

Compound 87.4. Methyl 4-cyclopropyl-2-methyl-5-(5-methyl-4,5,6,7-tetrahydro-3H-imidazo[4,5-c]pyridin-2-yl)benzoate Into a 100-mL round-bottom flask, was placed a mixture of 2-(2-cyclopropyl-5-(methoxycarbonyl)-4-methylphenyl)-5-methyl-3H-imidazo[4,5-c]pyridin-5-ium iodide (compound 87.3, 300 mg, 0.67 mmol) and NaBH₄ (1.42 g, 37.5 mmol) in methanol (30 mL). The resulting mixture was stirred for 4 h at room temperature, then concentrated under reduced pressure. The residue was diluted with EtOAc (120 mL) and the mixture was washed with brine (2×40 mL), dried (Na₂SO₄), filtered, and concentrated under reduced pressure. The residue was purified by silica gel column chromatography with EtOAc/MeOH (20/1) as the eluent to yield 170 mg (78%) the title compound as a light yellow oil.

Compound 87. 4-(1-(4-Cyclopropyl-2-methyl-5-(5-methyl-4,5,6,7-tetrahydro-3H-imidazo[4,5-c]pyridin-2-yl)benzoyl)azetidin-3-yl)benzonitrile The title compound was prepared using standard chemical manipulations and procedures similar to those used for the preparation of compound 82, except methyl 4-cyclopropyl-2-methyl-5-(5-methyl-4,5,6,7-tetrahydro-3H-imidazo[4,5-c]pyridin-2-yl)benzoate (compound 87.4) was used in place of 4-cyclobutyl-2-methyl-5-(6-methyl-1,4,5,6,7,8-hexahydroimidazo[4,5-d]azepin-2-yl)benzoate (compound 82.8). m/z (ES+) 452 (M+H)⁺.

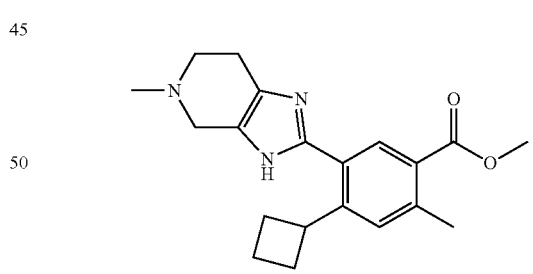

Compound 88.1. Methyl 4-cyclobutyl-2-methyl-5-(5-methyl-4,5,6,7-tetrahydro-3H-imidazo[4,5-c]pyridin-2-yl)benzoate The title compound was prepared using standard chemical manipulations and procedures similar to those used for the preparation of compound 87.4, except methyl 4-cyclobutyl-5-formyl-2-methylbenzoate (compound 82.5) was used in place of methyl 4-cyclopropyl-5-formyl-2-methylbenzoate (compound 87.1).

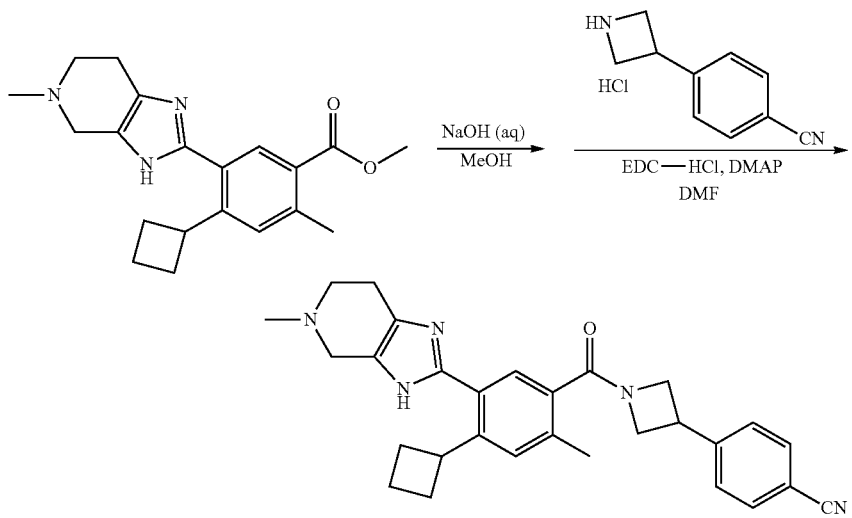

Compound 88. 4-(1-(4-cyclobutyl-2-methyl-5-(5-methyl-4,5,6,7-tetrahydro-3H-imidazo[4,5-c]pyridin-2-yl)benzoyl)azetidin-3-yl)benzonitrile The title compound was prepared using standard chemical manipulations and procedures similar to those used for the preparation of compound 82, except methyl 4-cyclobutyl-2-methyl-5-(5-methyl-4,5,6,7-tetrahydro-3H-imidazo[4,5-c]pyridin-2-yl)benzoate (compound 88.1) was used in place of 4-cyclobutyl-2-methyl-5-(6-methyl-1,4,5,6,7,8-hexahydroimidazo[4,5-d]azepin-2-yl)benzoate (compound 82.8). m/z (ES+) 466 (M+H)$^+$.

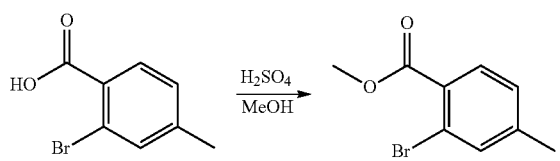

Compound 89.1. Methyl 2-bromo-4-methylbenzoate

A solution of 2-bromo-4-methylbenzoic acid (10.0 g, 46.5 mmol) in MeOH (50 mL) was cooled to 0° C., then concentrated sulfuric acid (10 mL) was carefully added. The mixture was heated at 70° C. for 2 hours. After cooling to room temperature, the volatile organics were removed under reduced pressure, and the residue was poured onto ice-water (100 mL). The mixture was extracted with EtOAc (×2) and the combined organic extracts were washed with aq. NaHCO$_3$, brine, dried (MgSO$_4$), filtered, and concentrated to yield 10.5 g (99%) of the title compound as a clear oil. $^1$H NMR (400 MHz, Chloroform-d) δ 7.73 (d, 1H), 7.50 (d, 1H), 7.19-7.11 (m, 1H), 3.92 (s, 3H), 2.36 (s, 3H).

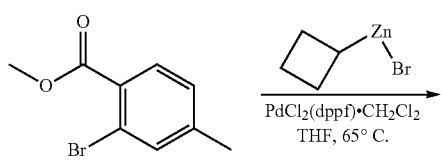

-continued

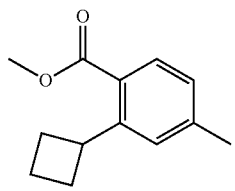

Compound 89.2. Methyl 2-cyclobutyl-4-methylbenzoate

Cyclobutylzinc(II) bromide (50 mL, 0.5 M in THF, 25.0 mmol) was added to a mixture of methyl 2-bromo-4-methylbenzoate (compound 89.1, 5.0 g, 21.8 mmol) and PdCl$_2$(dppf)CH$_2$Cl$_2$ (1.78 g, 2.20 mmol). The mixture was degassed with argon, then heated at 65° C. under argon for 24 hours. The mixture was cooled to 0° C., then carefully quenched with water (10 mL). The mixture was diluted with EtOAc (200 mL) and washed with water then brine. The organic layer was dried (Na$_2$SO$_4$), filtered, and concentrated under reduced pressure. The residue was purified by silica gel column chromatography (hexanes:EtOAc 30:1 to 20:1) to yield 3.6 g (81%) of the title compound. $^1$H NMR (400 MHz, Chloroform-d) δ 7.68 (d, 1H), 7.23-7.17 (s, 1H), 7.03 (d, 1H), 4.16 (m, 1H), 3.86 (s, 3H), 2.39 (s, 3H), 2.34 (m, 2H), 2.16-1.96 (m, 3H), 1.80 (m, 1H).

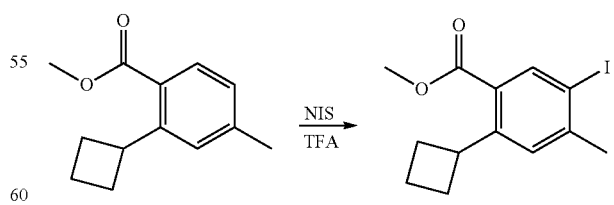

Compound 89.3. Methyl 2-cyclobutyl-5-iodo-4-methylbenzoate

To a solution methyl 2-cyclobutyl-4-methylbenzoate (compound 89.2, 4.77 g, 23.3 mmol) in concentrated sulfuric acid (100 mL) at 0° C., was added N-iodosuccinimide (5.25 g, 23.3 mmol) portion-wise. The mixture was stirred at 0° C. for 30 min and then at RT for 2 hours. The thick, dark mixture was cooled back to 0° C., then MeOH (100 mL) was added slowly and carefully. The mixture was heated at 60° C. for 2 hours. After cooling to room temperature, the volatile solvents were removed under reduced pressure and the residue was carefully poured onto ice water (200 mL). The mixture was extracted with EtOAc (2×) and the combined organic extracts were washed with brine, aqueous NaHCO$_3$ (1 M), dried (Na$_2$SO$_4$), filtered and concentrated under reduced pressure. The residue was purified by silica gel column chromatography (hexanes:EtOAc 30:1 to 20:1) to yield 5.0 g (65%) of the title compound as a clear oil. $^1$H NMR (400 MHz, Chloroform-d) δ 8.19 (s, 1H), 7.24 (s, 1H), 4.17-4.04 (m, 1H), 3.86 (s, 3H), 2.48-2.44 (s, 3H), 2.40-2.28 (m, 2H), 2.13-1.92 (m, 3H), 1.85-1.75 (m, 1H).

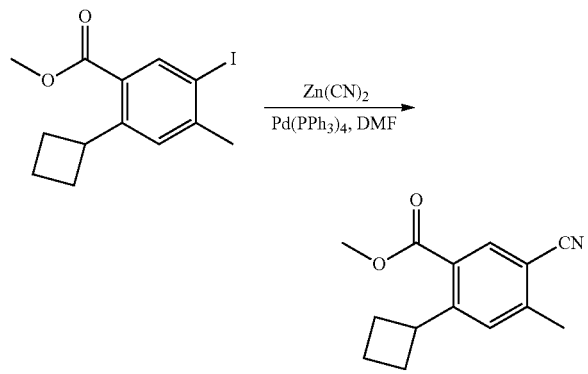

Compound 89.4. Methyl 5-cyano-2-cyclobutyl-4-methylbenzoate

A mixture of methyl 2-cyclobutyl-5-iodo-4-methylbenzoate (compound 89.3, 3.0 g, 9.1 mmol), Zn(CN)$_2$ (2.3 g, 19.6 mmol) and Pd(PPh$_3$)$_4$ (0.55 g, 0.47 mmol) in DMF (50 mL) was degassed and the system was charged with argon. The mixture was heated at 100° C. overnight, then cooled to room temperature. The mixture was quenched with saturated aqueous FeSO$_4$ (20 mL), then diluted with EtOAc (200 mL). The solids were removed by filtration through Celite® and the filtrate was partitioned between water and EtOAc. The organic layer was washed with brine, dried (Na$_2$SO$_4$), filtered, and concentrated under reduced pressure. The residue was purified by silica gel column chromatography (hexanes: EtOAc 30:1 to 20:1) to yield 2.0 g (96%) of the title compound. $^1$H NMR (400 MHz, Chloroform-d) δ 8.03 (s, 1H), 7.34 (s, 1H), 4.26-4.13 (m, 1H), 3.89 (s, 3H), 2.59 (s, 3H), 2.46-2.32 (m, 2H), 2.16-1.98 (m, 3H), 1.90-1.78 (m, 1H).

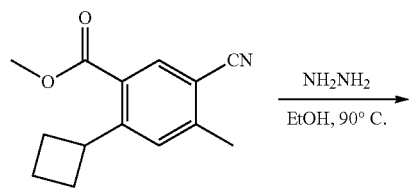

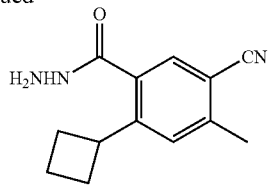

Compound 89.5. 5-Cyano-2-cyclobutyl-4-methylbenzohydrazide

To a solution of methyl 5-cyano-2-cyclobutyl-4-methylbenzoate (compound 89.4, 2.0 g, 8.73 mmol) in EtOH (10 mL) was added anhydrous hydrazine (2 mL, excess) at room temperature. The mixture was heated at 90° C. overnight, then the mixture was cooled to room temperature and partitioned between water (60 mL) and EtOAc (200 mL). The organic layer was washed with water (×2), brine, dried (Na$_2$SO$_4$), filtered, and concentrated to yield 1.9 g (95%) of the title compound as a white solid. m/z (ES+) 230 (M+H)$^+$. $^1$H NMR (400 MHz, Chloroform-d) δ 7.52 (s, 1H), 7.32 (s, 1H), 6.91 (br, 1H), 4.08 (br, 2H), 3.89 (m, 1H), 2.61-2.52 (m, 3H), 2.42-2.28 (m, 2H), 2.18-1.98 (m, 3H), 1.91-1.78 (m, 1H).

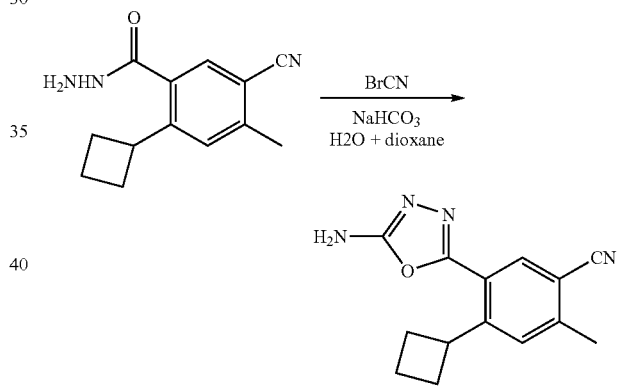

Compound 89.6. 5-(5-Amino-1,3,4-oxadiazol-2-yl)-4-cyclobutyl-2-methylbenzonitrile To a solution of 5-cyano-2-cyclobutyl-4-methylbenzohydrazide (compound 89.5, 0.5 g, 2.18 mmol) in H$_2$O (10 mL) and dioxane (15 mL) was added NaHCO$_3$ (0.55 g, 6.55 mmol). After the mixture was stirred at room temperature for 5 minutes, BrCN (1.3 mL, 5 M in CH$_3$CN, 6.55 mmol) was added drop-wise. The mixture was stirred at room temperature for 30 minutes, where upon white solids formed. The mixture was diluted with EtOAc and washed with water, then brine. The organic layer was dried (Na$_2$SO$_4$), filtered, and concentrated under reduced pressure. The residue was purified by silica gel column chromatography (hexanes: EtOAc 1:1 to EtOAc) to yield 0.55 g (theoretical) of the title compound as a white solid. m/z (ES+) 255 (M+H)$^+$. $^1$H NMR (400 MHz, Chloroform-d) δ 7.93 (s, 1H), 7.45 (s, 1H), 5.10 (br, 2H), 4.38 (m, 1H), 2.61 (s, 3H), 2.48-2.34 (m, 2H), 2.17-1.98 (m, 3H), 1.91-1.79 (m, 1H).

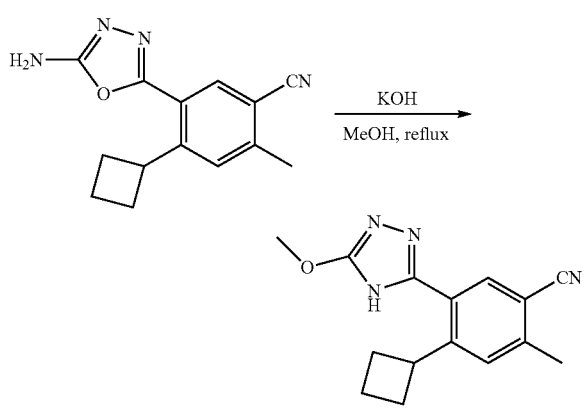

Compound 89.7. 4-Cyclobutyl-5-(5-methoxy-4H-1,2,4-triazol-3-yl)-2-methylbenzonitrile To a solution of 5-(5-amino-1,3,4-oxadiazol-2-yl)-4-cyclobutyl-2-methylbenzonitrile (compound 89.6, 0.5 g, 2.0 mmol) in MeOH (40 mL) was added KOH (1.11 g, 20.0 mmol). The mixture was heated at 85° C. overnight, then cooled to 0° C. and neutralized to pH 7 with aqueous 1 M HCl. The mixture was extracted with EtOAc (×2), and the combined organic extracts were dried ($Na_2SO_4$), filtered, and concentrated under reduced pressure. The residue was purified by silica gel column chromatography (hexanes: EtOAc 1:1 to EtOAc) to yield 0.2 g (34%) of the title compound as a white solid. m/z (ES+) 269 (M+H)+. $^1$H NMR (400 MHz, Chloroform-d) δ 10.96 (br, 1H), 7.82 (s, 1H), 7.35 (s, 1H), 4.11 (s, 3H), 4.15-4.05 (m, 1H), 2.59 (s, 3H), 2.31-2.16 (m, 2H), 2.14-1.89 (m, 3H), 1.87-1.71 (m, 1H).

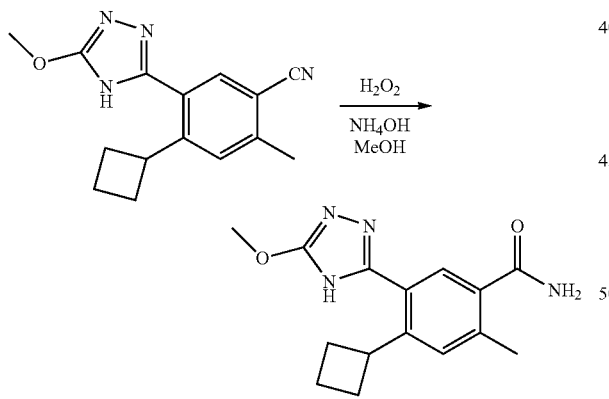

Compound 89.8. 4-Cyclobutyl-5-(5-methoxy-4H-1,2,4-triazol-3-yl)-2-methylbenzamide To a solution of 4-cyclobutyl-5-(5-methoxy-4H-1,2,4-triazol-3-yl)-2-methylbenzonitrile (compound 89.7, 0.15 g, 0.53 mmol) in EtOH (10 mL) was added $NH_4OH$ (0.18 mL, 2.66 mmol, 14.8 M in $H_2O$), followed by $H_2O_2$ (1.8 mL, 26.6 mmol, 50% in $H_2O$). The mixture was stirred at room temperature overnight, then cooled to 0° C. and carefully quenched with 1 M $Na_2S_2O_3$ solution (26 mL). The mixture was extracted with EtOAc (×2) and the combined organic extracts were dried ($Na_2SO_4$), filtered, and concentrated under reduced pressure. The residue was purified by prep-TLC (5% MeOH in $CH_2Cl_2$) to yield 0.1 g (63%) of the title compound as a white solid. m/z (ES+) 287 (M+H)+. $^1$H NMR (400 MHz, Methanol-d4) δ 7.50 (s, 1H), 7.33 (s, 1H), 4.03 (s, 3H), 3.95-4.05 (m, 1H), 2.51 (s, 3H), 2.23-2.11 (m, 2H), 2.11-1.88 (m, 3H), 1.83-1.71 (m, 1H).

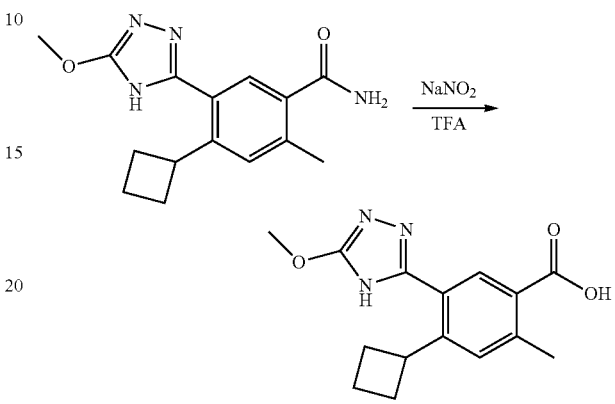

Compound 89.9 4-Cyclobutyl-5-(5-methoxy-4H-1,2,4-triazol-3-yl)-2-methylbenzoic acid To a solution of 4-cyclobutyl-5-(5-methoxy-4H-1,2,4-triazol-3-yl)-2-methylbenzamide (compound 89.8, 0.1 g, 0.33 mmol) in TFA (5 mL) at 0° C., was added $NaNO_2$ (46 mg, 0.66 mmol). The mixture was stirred at 0° C. for 1 hour, then at room temperature for 2 hours. The mixture was concentrated under reduced pressure and the residue was partitioned between EtOAc and brine. The aqueous layer was extracted with EtOAc and the combined organic layers were dried ($Na_2SO_4$), filtered and concentrated under reduced pressure to yield 0.1 g (theoretical) of the title compound as a clear oil. m/z (ES+) 288 (M+H)+.

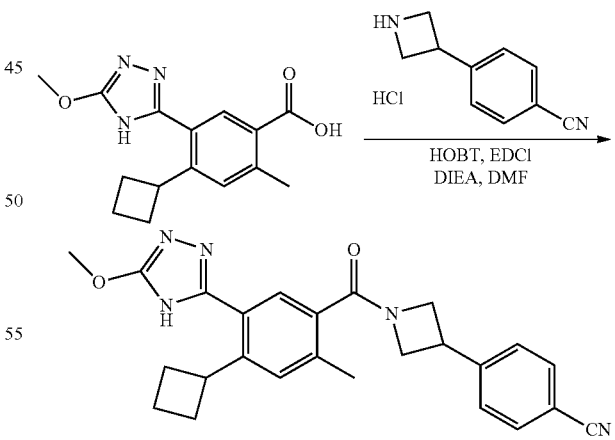

Compound 89. 4-(1-(4-Cyclobutyl-5-(5-methoxy-4H-1,2,4-triazol-3-yl)-2-methylbenzoyl)azetidin-3-yl)benzonitrile The title compound was prepared using standard chemical manipulations and procedures similar to those used for the preparation of compound 5, except 4-cyclobutyl-5-(5-methoxy-4H-1,2,4-triazol-3-yl)-2-methylbenzoic acid (compound 89.9) was used in place of 3-(2,4-dimethyl-1H-imidazol-5-yl)-4-methylbenzoic acid (compound 5.7). m/z (ES+) 428 (M+H)+. 1H NMR (400 MHz, DMSO-d6) δ 13.63-13.17 (br, 1H), 7.83 (d, J=8.4 Hz, 2H), 7.58 (d, J=8.4 Hz, 2H), 7.49 (s, 1H), 7.39 (s, 1H), 4.48 (m, 1H), 4.32 (m, 1H), 4.15 (m, 1H), 4.07-3.95 (m, 3H), 3.93 (s, 3H), 2.41 (s, 3H), 2.21-2.11 (m, 2H), 2.06-1.97 (m, 2H), 1.94-1.84 (m, 1H), 1.78-1.68 (m, 1H).

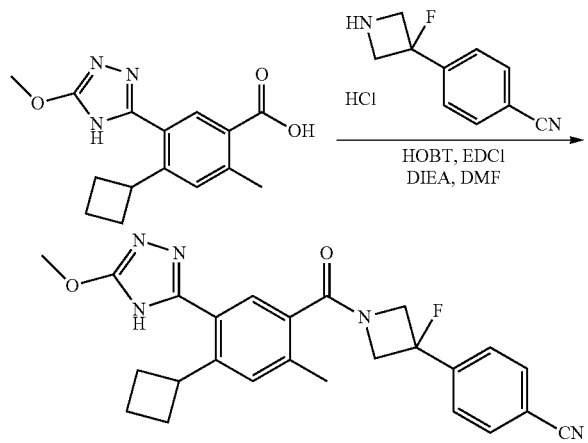

Compound 90. 4-(1-(4-Cyclobutyl-5-(5-methoxy-4H-1,2,4-triazol-3-yl)-2-methylbenzoyl)-3-fluoro-azetidin-3-yl)benzonitrile The title compound was prepared using standard chemical manipulations and procedures similar to those used for the preparation of compound 5, except 4-cyclobutyl-5-(5-methoxy-4H-1,2,4-triazol-3-yl)-2-methylbenzoic acid (compound 89.9) and 4-(3-fluoroazetidin-3-yl)benzonitrile hydrochloride (compound 43.4) were used in place of 3-(2,4-dimethyl-1H-imidazol-5-yl)-4-methylbenzoic acid (compound 5.7) and 4-(azetidin-3-yl)benzonitrile hydrochloride (compound 5.2), respectively. m/z (ES+) 446 (M+H)+. 1H NMR (400 MHz, DMSO-d6) δ 13.64-13.05 (br, 1H), 7.96 (d, J=8.0 Hz, 2H), 7.76 (d, J=8.0 Hz, 2H), 7.56 (s, 1H), 7.41 (s, 1H), 4.61-4.38 (m, 4H), 4.19 (m, 1H), 3.92 (s, 3H), 2.42 (s, 3H), 2.16 (m, 1H), 2.02 (m, 1H), 1.89 (m, 1H), 1.75 (m, 1H).

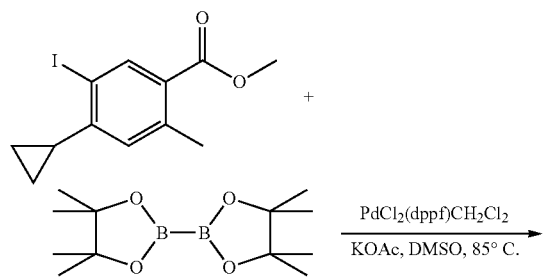

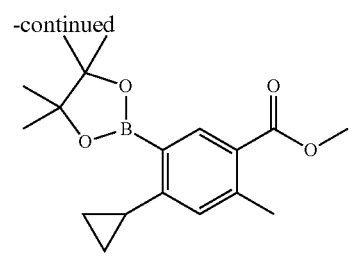

Compound 91.1. Methyl 4-cyclopropyl-2-methyl-5-(4,4,5,5-tetramethyl-1,3,2-dioxaborolan-2-yl)benzoate A mixture of methyl 4-cyclopropyl-5-iodo-2-methylbenzoate (compound 86.2, 4.0 g, 12.7 mmol), 4,4,4',4',5,5,5',5'-octamethyl-2,2'-bi(1,3,2-dioxaborolane) (3.86 g, 15.2 mmol), PdCl2(dppf)CH2Cl2 (0.52 g, 0.64 mmol) and potassium acetate (3.73 g, 38.10 mmol) in DMSO (50 mL) was degassed with argon. The mixture was heated at 80° C. for 18 hours under argon, then cooled to room temperature and diluted with ethyl acetate (300 mL). The mixture was washed with water, aqueous HCl (1 M), saturated aqueous NaHCO3, and brine, then dried (MgSO4), filtered, and concentrated under reduced pressure. The residue was purified by silica gel column chromatography (hexanes:EtOAc 50:1 to 30:1) to yield 2.63 g (65.6%) of the title compound as a white solid. m/z (ES+) 317 (M+H)+.

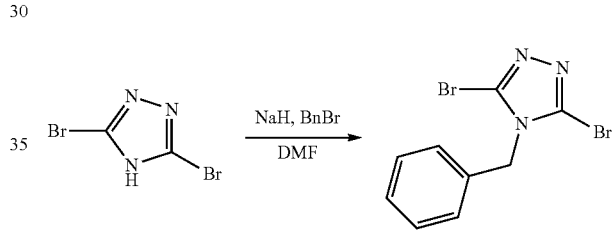

Compound 91.2. 4-Benzyl-3,5-dibromo-4H-1,2,4-triazole

To a solution of 3,5-dibromo-4H-1,2,4-triazole (3.0 g, 13.3 mmol) in DMF (10 mL) at 0° C. was added NaH (60% in mineral oil, 0.58 g, 14.5 mmol)(CAUTION: NaH and DMF can become a runaway reaction. All necessary safety precautions were performed). After the mixture was stirred at 0° C. for 30 minutes, benzyl bromide (1.57 mL, 13.2 mmol) was added. The mixture was stirred at 0° C. for 2 hours, then the mixture was partitioned between EtOAc (150 mL) and water (30 mL). The organic layer was washed with brine (2×30 mL), dried (MgSO4), filtered and concentrated under reduced pressure. The residue was purified by silica gel column chromatography (hexanes:EtOAc 50:1 to 10:1) to yield 3.71 g (89%) of the title compound as a white solid. m/z (ES+) 316, 318, 320 (M+H)+.

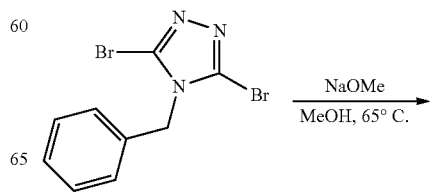

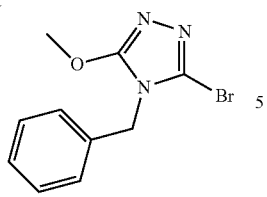

Compound 91.3. 4-Benzyl-3-bromo-5-methoxy-4H-1,2,4-triazole

To a solution of 4-benzyl-3,5-dibromo-4H-1,2,4-triazole (compound 91.2, 3.71 g, 11.7 mmol) in MeOH (15 mL) was added NaOMe (1.26 g, 23.4 mmol) and the mixture was refluxed for 18 hours. The mixture was cooled somewhat and additional NaOMe was added (1.26 g, 23.4 mmol). The mixture was refluxed for an additional 5 hours, then cooled to room temperature, and the solvent was removed under reduced pressure. The residue was dissolved in EtOAc (200 mL) and washed with water (30 mL). The organic layer was dried (MgSO$_4$), filtered and concentrated under reduced pressure to yield 3.13 g (theoretical) of the title compound as a clear oil. m/z (ES+) 269 (M+H)$^+$.

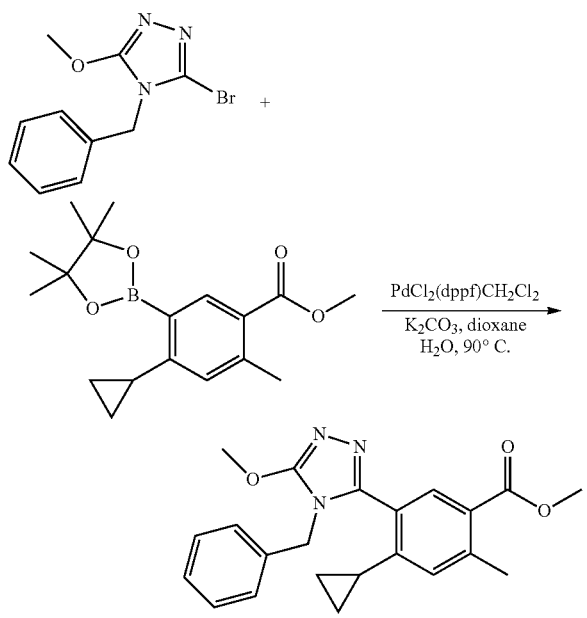

Compound 91.4. Methyl 5-(4-benzyl-5-methoxy-4H-1,2,4-triazol-3-yl)-4-cyclopropyl-2-methylbenzoate A mixture of 4-benzyl-3-bromo-5-methoxy-4H-1,2,4-triazole (compound 91.3, 1.2 g, 4.48 mmol), methyl 4-cyclopropyl-2-methyl-5-(4,4,5,5-tetramethyl-1,3,2-dioxaborolan-2-yl)benzoate (compound 91.1, 1.56 g, 4.93 mmol), PdCl$_2$(dppf)CH$_2$Cl$_2$ (0.37 g, 0.45 mmol) and potassium carbonate (3.10 g, 22.5 mmol) in dioxane (50 mL) and water (20 mL) was degassed with argon. The mixture was heated at 90° C. for 18 hours under argon, then cooled to room temperature. The mixture was diluted with ethyl acetate (300 mL) and washed with water then brine, dried (MgSO$_4$), filtered, and concentrated under reduced pressure. The residue was purified by silica gel column chromatography (hexanes:EtOAc 10:1 to 4:1) to yield 1.51 g (89%) of the title compound as thick oil. m/z (ES+) 378 (M+H)$^+$.

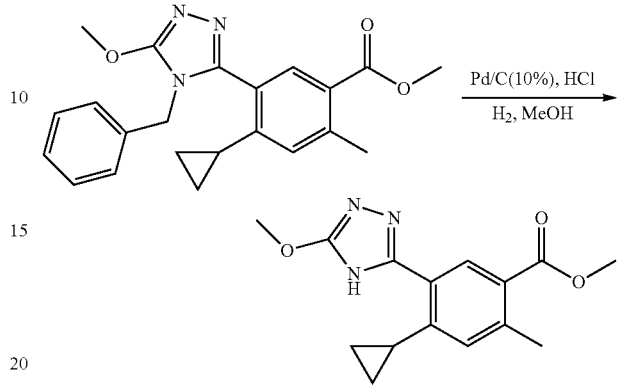

Compound 91.5. Methyl 4-cyclopropyl-5-(5-methoxy-4H-1,2,4-triazol-3-yl)-2-methylbenzoate A flask containing methyl 5-(4-benzyl-5-methoxy-4H-1,2,4-triazol-3-yl)-4-cyclopropyl-2-methylbenzoate (compound 91.4, 0.55 g, 1.46 mmol) and Pd/C (10%, 0.25 g) was purged with nitrogen, then MeOH (10 mL) and HCl (4 M in dioxane, 37 μL, 0.15 mmol) were carefully added. The system was then charged with hydrogen and the mixture was stirred at room temperature for 3 hours. Upon completion, the system was purged with nitrogen, then the mixture was neutralized with a few drops of NH$_4$OH and filtered through Celite®. The filtrate was concentrated under reduced pressure and the residue was purified using prep-TLC (hexanes: EtOAc 1:1) to yield 0.3 g (71%) of the title compound as a clear oil. m/z (ES+) 288 (M+H)$^+$.

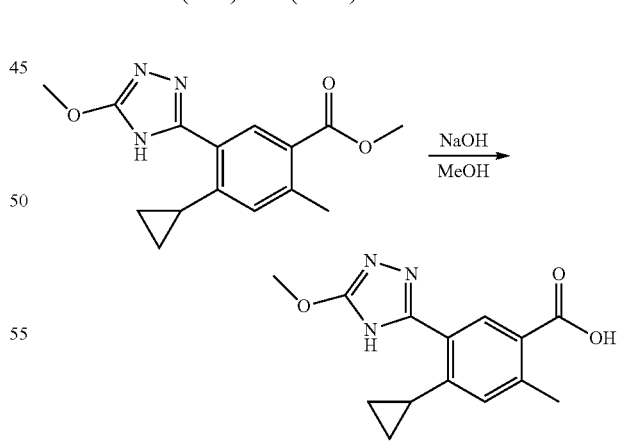

Compound 91.6. 4-Cyclopropyl-5-(5-methoxy-4H-1,2,4-triazol-3-yl)-2-methylbenzoic acid The title compound was prepared using standard chemical manipulations and procedures similar to those used for the preparation of compound 5.7, except methyl 4-cyclopropyl-5-(5-methoxy-4H-1,2,4-triazol-3-yl)-2-methylbenzoate (compound 91.5) was used in place of methyl 3-(2,4-dimethyl-1H-imidazol-5-yl)-4-methylbenzoate (compound 5.6). m/z (ES+) 274 (M+H)⁺.

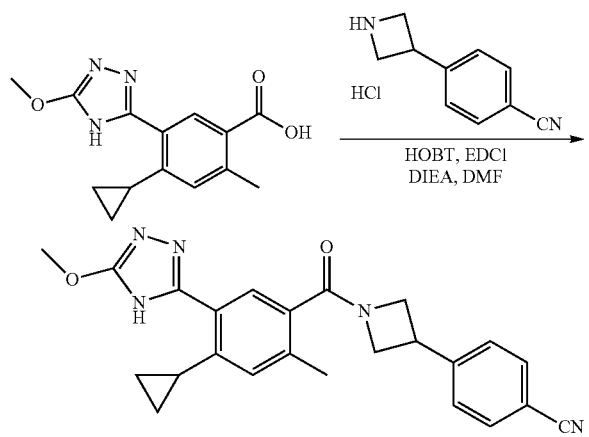

Compound 91. 4-(1-(4-Cyclopropyl-5-(5-methoxy-4H-1,2,4-triazol-3-yl)-2-methylbenzoyl)azetidin-3-yl)benzonitrile The title compound was prepared using standard chemical manipulations and procedures similar to those used for the preparation of compound 5, except 4-cyclopropyl-5-(5-methoxy-4H-1,2,4-triazol-3-yl)-2-methylbenzoic acid (compound 91.6) was used in place of 3-(2,4-dimethyl-1H-imidazol-5-yl)-4-methylbenzoic acid (compound 5.7). m/z (ES+) 414 (M+H)⁺. ¹H NMR (400 MHz, DMSO-d6) δ 13.84-12.92 (br, 1H), 7.86-7.80 (m, 2H), 7.61-7.53 (m, 3H), 6.85 (s, 1H), 4.47 (m, 1H), 4.32 (m, 1H), 4.08-3.94 (m, 3H), 2.79 (m, 1H), 0.94 (m, 2H), 0.70 (n, 2H).

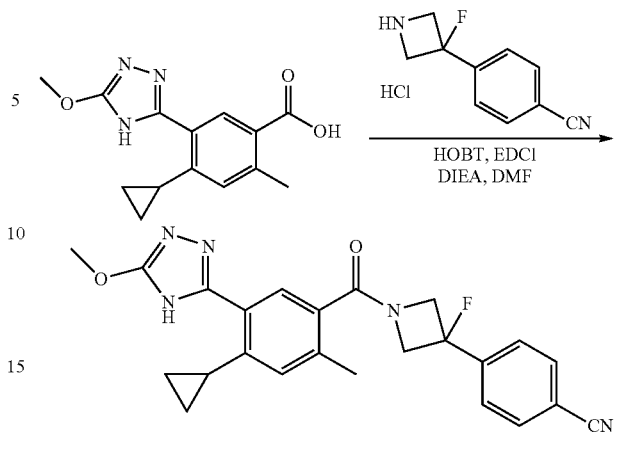

Compound 92. 4-(1-(4-Cyclopropyl-5-(5-methoxy-4H-1,2,4-triazol-3-yl)-2-methylbenzoyl)-3-fluoro-azetidin-3-yl)benzonitrile The title compound was prepared using standard chemical manipulations and procedures similar to those used for the preparation of compound 5, except 4-cyclopropyl-5-(5-methoxy-4H-1,2,4-triazol-3-yl)-2-methylbenzoic acid (compound 91.6) and 4-(3-fluoroazetidin-3-yl)benzonitrile (compound 43.4) were used in place of 3-(2,4-dimethyl-1H-imidazol-5-yl)-4-methylbenzoic acid (compound 5.7) and 4-(azetidin-3-yl)benzonitrile hydrochloride (compound 5.2), respectively. m/z (ES+) 432 (M+H)⁺. ¹H NMR (400 MHz, DMSO-d6) δ 13.66-13.01 (br, 1H), 7.96 (d, J=8.0 Hz, 2H), 7.76 (d, J=8.0 Hz, 2H), 7.61 (s, 1H), 6.86 (s, 1H), 4.60-4.38 (m, 4H), 3.91 (s, 3H), 2.82 (m, 1H), 2.34 (s, 3H), 0.94 (m, 2H), 0.71 (m, 2H).

The compounds in TABLE 5 were prepared using standard chemical manipulations and procedures similar to those used for the preparation of compounds 78 and 79.

TABLE 5

| Cpd | Name | Structure | m/z (ES+) (M + H)⁺ |
|---|---|---|---|
| 96 | 4-(1-(4-((1S,3S)-3-methoxycyclobutyl)-2-methyl-5-(5-methyl-4H-1,2,4-triazol-3-yl)benzoyl)piperidin-4-yl)benzonitrile | 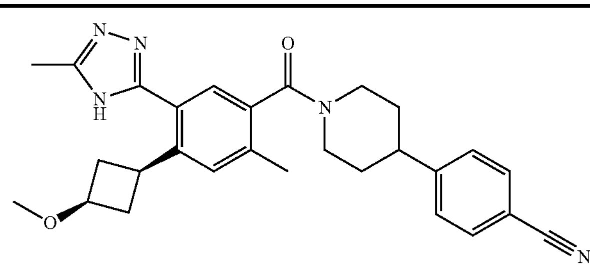 | 470 |
| 97 | 4-(1-(4-((1R,3R)-3-methoxycyclobutyl)-2-methyl-5-(5-methyl-4H-1,2,4-triazol-3-yl)benzoyl)piperidin-4-yl)benzonitrile | 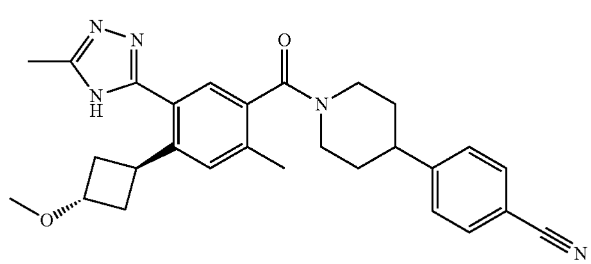 [SMILES: CO[C@H]1C[C@H](c2cc(C)c(C(=O)N3CCC(c4ccc(C#N)cc4)CC3)cc2-c2nnc(C)[nH]2)C1] | 470 |

TABLE 5-continued

| Cpd | Name | Structure | m/z (ES+) (M + H)+ |
|---|---|---|---|
| 98 | 4-(1-(4-((1S,3S)-3-hydroxycyclobutyl)-2-methyl-5-(5-methyl-4H-1,2,4-triazol-3-yl)benzoyl)piperidin-4-yl)benzonitrile | 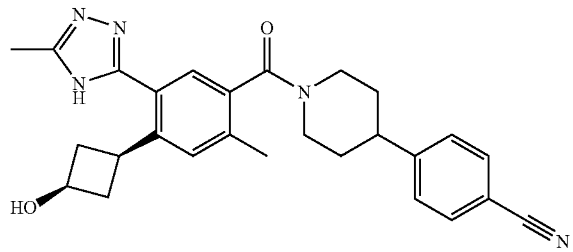 [SMILES: Cc1nnc(-c2cc(C(=O)N3CCC(c4ccc(C#N)cc4)CC3)c(C)cc2[C@H]2C[C@@H](O)C2)[nH]1] | 456 |
| 104 | 4-(1-(4-((1R,3R)-3-hydroxycyclobutyl)-2-methyl-5-(5-methyl-4H-1,2,4-triazol-3-yl)benzoyl)piperidin-4-yl)benzonitrile | 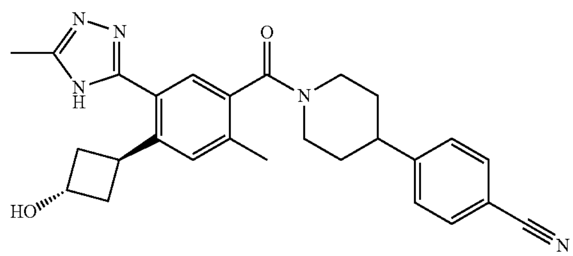 [SMILES: Cc1nnc(-c2cc(C(=O)N3CCC(c4ccc(C#N)cc4)CC3)c(C)cc2[C@H]2C[C@H](O)C2)[nH]1] | 456 |
| 107 | 4-(1-(4-((1S,3S)-3-fluorocyclobutyl)-2-methyl-5-(5-methyl-4H-1,2,4-triazol-3-yl)benzoyl)piperidin-4-yl)benzonitrile | 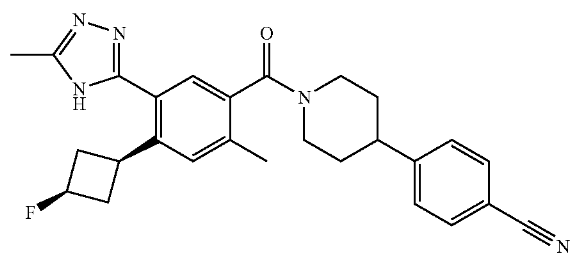 [SMILES: Cc1nnc(-c2cc(C(=O)N3CCC(c4ccc(C#N)cc4)CC3)c(C)cc2[C@H]2C[C@@H](F)C2)[nH]1] | 458 |
| 108 | 4-(1-(4-((1R,3R)-3-fluorocyclobutyl)-2-methyl-5-(5-methyl-4H-1,2,4-triazol-3-yl)benzoyl)piperidin-4-yl)benzonitrile | 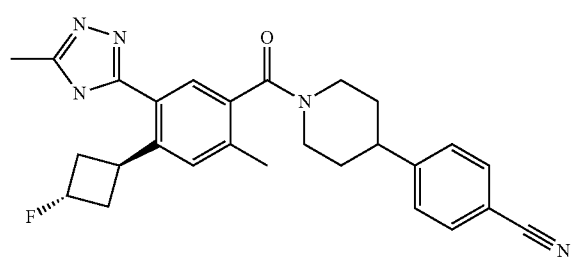 [SMILES: Cc1nnc(-c2cc(C(=O)N3CCC(c4ccc(C#N)cc4)CC3)c(C)cc2[C@H]2C[C@H](F)C2)[nH]1] | 458 |
| 112 | 4-(1-(2-methyl-5-(5-methyl-4H-1,2,4-triazol-3-yl)-4-(tetrahydrofuran-2-yl)benzoyl)piperidin-4-yl)benzonitrile | 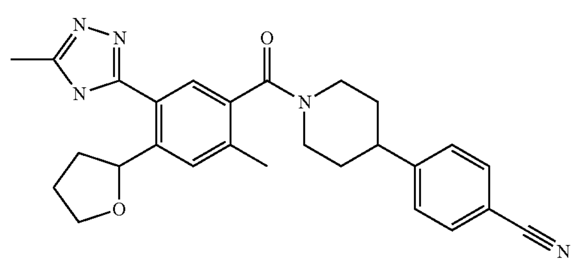 [SMILES: Cc1nnc(-c2cc(C(=O)N3CCC(c4ccc(C#N)cc4)CC3)c(C)cc2C2CCCO2)[nH]1] | 456 |

The compounds in TABLE 6 were prepared using standard chemical manipulations and procedures similar to those used for the preparation of compounds 89, 90, 91, and 92.

TABLE 6

| Cpd | Name | Structure | m/z (ES+) (M + H)+ |
|---|---|---|---|
| 99 | 4-(1-(4-cyclobutyl-5-(5-(2-methoxyethoxy)-4H-1,2,4-triazol-3-yl)-2-methylbenzoyl)piperidin-4-yl)benzonitrile | 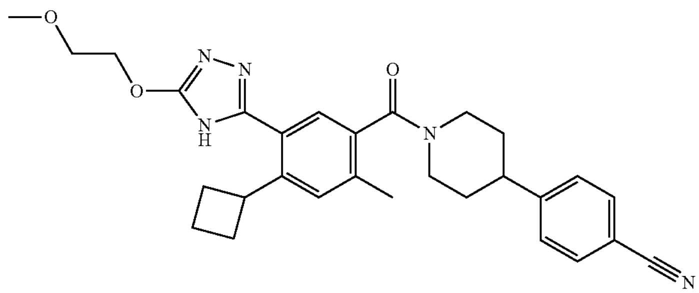 [SMILES: COCCOc1nnc(-c2cc(C(=O)N3CCC(c4ccc(C#N)cc4)CC3)c(C)cc2C2CCC2)[nH]1] | 500 |
| 100 | 4-(1-(4-cyclobutyl-5-(5-(2-hydroxyethoxy)-4H-1,2,4-triazol-3-yl)-2-methylbenzoyl)piperidin-4-yl)benzonitrile | 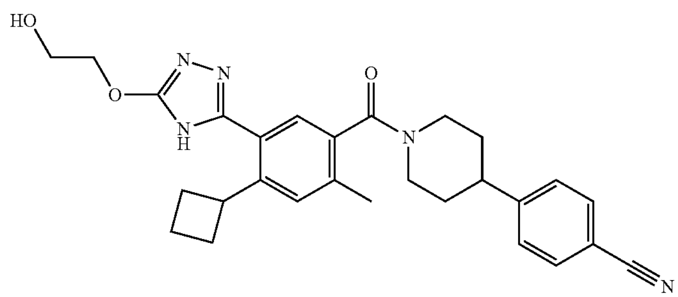 [SMILES: Cc1cc(C2CCC2)c(-c2nnc(OCCO)[nH]2)cc1C(=O)N1CCC(c2ccc(C#N)cc2)CC1] | 486 |
| 133 | 4-(1-(4-cyclopropyl-5-(5-methoxy-4H-1,2,4-triazol-3-yl)-2-methylbenzoyl)-4-fluoropiperidin-4-yl)benzonitrile | 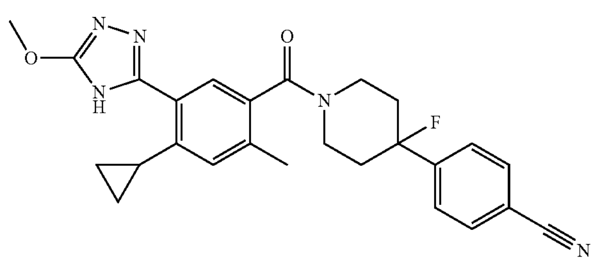 [SMILES: COc1nnc(-c2cc(C(=O)N3CCC(F)(c4ccc(C#N)cc4)CC3)c(C)cc2C2CC2)[nH]1] | 460 |
| 134 | 4-(1-(4-cyclopropyl-5-(5-methoxy-4H-1,2,4-triazol-3-yl)-2-methylbenzoyl)piperidin-4-yl)benzonitrile | 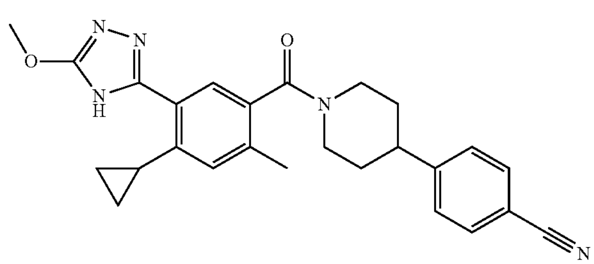 [SMILES: COc1nnc(-c2cc(C(=O)N3CCC(c4ccc(C#N)cc4)CC3)c(C)cc2C2CC2)[nH]1] | 442 |
| 137 | 4-(1-(4-cyclopropyl-2-ethyl-5-(5-methoxy-4H-1,2,4-triazol-3-yl)benzoyl)azetidin-3-yl)benzonitrile | 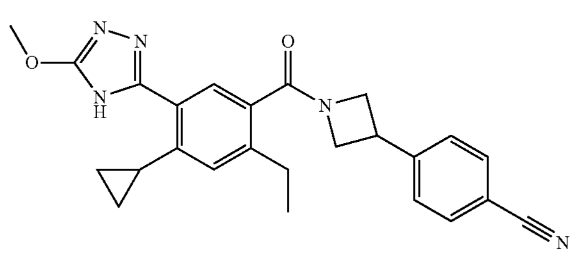 [SMILES: CCc1cc(C2CC2)c(-c2nnc(OC)[nH]2)cc1C(=O)N1CC(c2ccc(C#N)cc2)C1] | 428 |

TABLE 6-continued

| Cpd | Name | Structure | m/z (ES+) (M + H)+ |
|---|---|---|---|
| 138 | 4-(1-(4-cyclopropyl-2-ethyl-5-(5-methoxy-4H-1,2,4-triazol-3-yl)benzoyl)-3-fluoroazetidin-3-yl)benzonitrile | 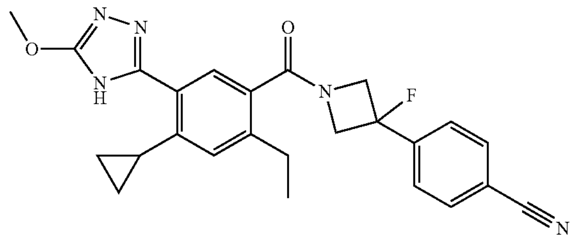 [SMILES: CCc1cc(C2CC2)c(-c2nnc(OC)[nH]2)cc1C(=O)N1CC(F)(c2ccc(C#N)cc2)C1] | 446 |

The compounds in TABLE 7 were prepared using standard chemical manipulations and procedures similar to those used for the preparation of compounds 62, 63 and 64.

TABLE 7

| Cpd | Name | Structure | m/z (ES+) (M + H)+ |
|---|---|---|---|
| 103 | 5-(4-(4-cyanophenyl)piperidine-1-carbonyl)-2-cyclobutyl-4-methylbenzamide | 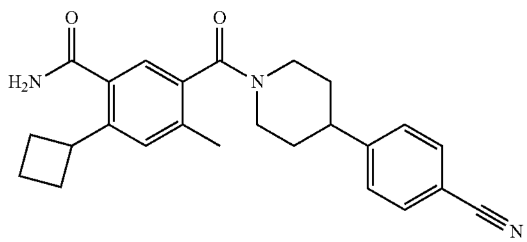 [SMILES: Cc1cc(C2CCC2)c(C(N)=O)cc1C(=O)N1CCC(c2ccc(C#N)cc2)CC1] | 402 |
| 106 | 2-cyclobutyl-5-(4-(imidazo[1,2-a]pyridin-7-yl)piperidine-1-carbonyl)-N,4-dimethylbenzamide | 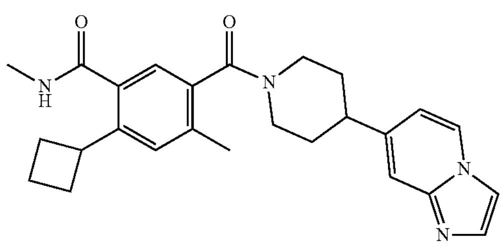 [SMILES: CNC(=O)c1cc(C(=O)N2CCC(c3ccn4ccnc4c3)CC2)c(C)cc1C1CCC1] | 431 |
| 110 | 2-cyclobutyl-5-(4-(imidazo[1,2-a]pyridin-6-yl)piperidine-1-carbonyl)-N,4-dimethylbenzamide | 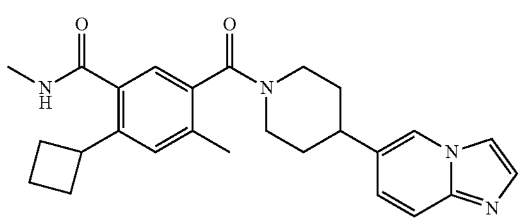 [SMILES: CNC(=O)c1cc(C(=O)N2CCC(c3ccc4nccn4c3)CC2)c(C)cc1C1CCC1] | 431 |
| 116 | 5-(4-(benzofuran-7-yl)piperidine-1-carbonyl)-2-cyclobutyl-N,4-dimethylbenzamide | 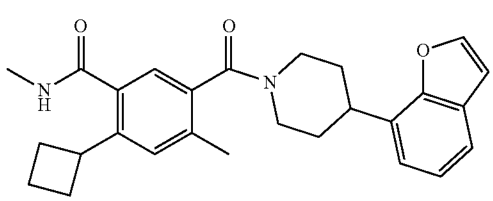 [SMILES: CNC(=O)c1cc(C(=O)N2CCC(c3cccc4ccoc34)CC2)c(C)cc1C1CCC1] | 431 |

The compounds in TABLE 8 were prepared using standard chemical manipulations and procedures similar to those used for the preparation of compounds 78, 79, 80 and 81.

TABLE 8

| Cpd | Name | Structure | m/z (ES+) (M + H)+ |
|---|---|---|---|
| 111 | 4-(1-(4-cyclobutyl-2-methyl-5-(5-methyl-4H-1,2,4-triazol-3-yl)benzoyl)piperidin-4-yl)-2-methylbenzonitrile | 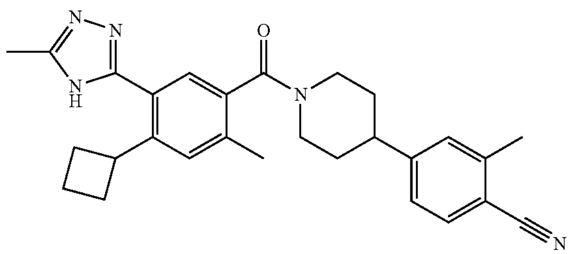 [SMILES: Cc1nnc(-c2cc(C(=O)N3CCC(c4ccc(C#N)c(C)c4)CC3)c(C)cc2C2CCC2)[nH]1] | 454 |
| 113 | 4-(1-(4-cyclobutyl-2-methyl-5-(5-methyl-4H-1,2,4-triazol-3-yl)benzoyl)piperidin-4-yl)-2-fluorobenzonitrile | 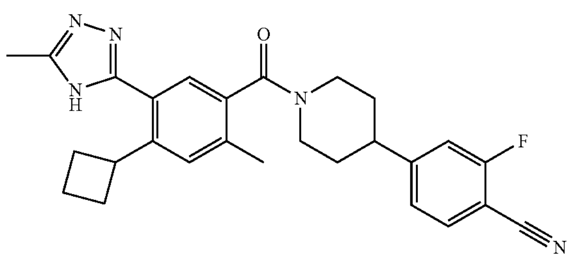 | 458 |
| 114 | 4-(1-(4-cyclobutyl-2-methyl-5-(5-methyl-4H-1,2,4-triazol-3-yl)benzoyl)piperidin-4-yl)-3-fluorobenzonitrile | 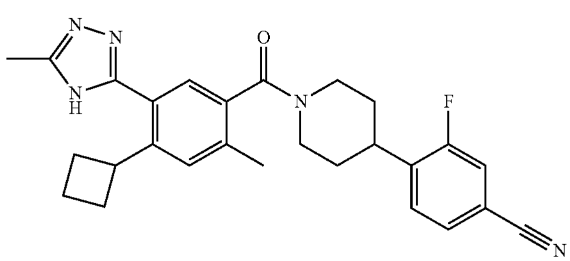 [SMILES: Cc1nnc(-c2cc(C(=O)N3CCC(c4ccc(C#N)cc4F)CC3)c(C)cc2C2CCC2)[nH]1] | 458 |
| 115 | 2-chloro-4-(1-(4-cyclobutyl-2-methyl-5-(5-methyl-4H-1,2,4-triazol-3-yl)benzoyl)piperidin-4-yl)benzonitrile | 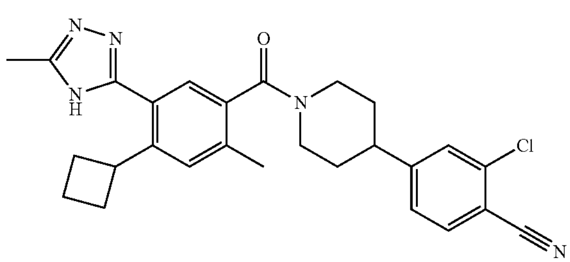 | 474 |
| 117 | 4-(1-(4-cyclobutyl-2-methyl-5-(5-methyl-4H-1,2,4-triazol-3-yl)benzoyl)piperidin-4-yl)-3-methylbenzonitrile | 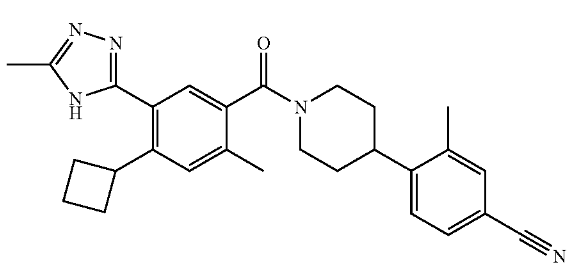 [SMILES: Cc1nnc(-c2cc(C(=O)N3CCC(c4ccc(C#N)cc4C)CC3)c(C)cc2C2CCC2)[nH]1] | 454 |

TABLE 8-continued

| Cpd | Name | Structure | m/z (ES+) (M + H)+ |
|---|---|---|---|
| 118 | 3-chloro-4-(1-(4-cyclobutyl-2-methyl-5-(5-methyl-4H-1,2,4-triazol-3-yl)benzoyl)piperidin-4-yl)benzonitrile | 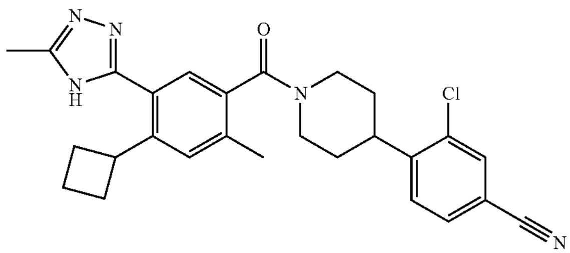 [SMILES: Cc1nnc(-c2cc(C(=O)N3CCC(c4ccc(C#N)cc4Cl)CC3)c(C)cc2C2CCC2)[nH]1] | 474 |
| 119 | 4-(1-(4-cyclobutyl-2-methyl-5-(5-methyl-4H-1,2,4-triazol-3-yl)benzoyl)piperidin-4-yl)-3-methoxybenzonitrile | 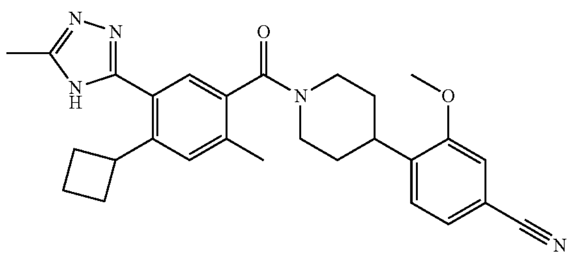 [SMILES: COc1cc(C#N)ccc1C1CCN(C(=O)c2cc(-c3nnc(C)[nH]3)c(C3CCC3)cc2C)CC1] | 470 |
| 120 | 4-(1-(4-cyclobutyl-2-methyl-5-(5-methyl-4H-1,2,4-triazol-3-yl)benzoyl)piperidin-4-yl)-2-methoxybenzonitrile | 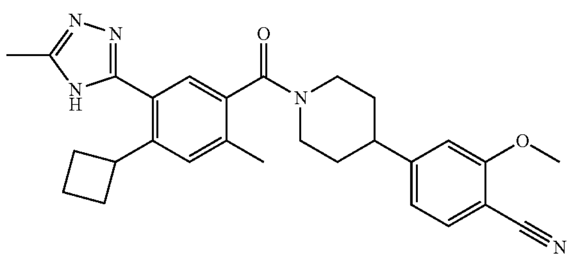 | 470 |
| 135 | (4-(4-bromophenyl)piperidin-1-yl)(4-cyclobutyl-2-methyl-5-(5-methyl-4H-1,2,4-triazol-3-yl)phenyl)methanone | 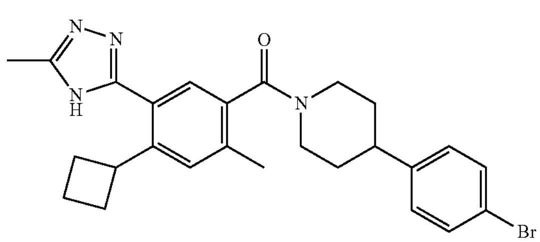 [SMILES: Cc1nnc(-c2cc(C(=O)N3CCC(c4ccc(Br)cc4)CC3)c(C)cc2C2CCC2)[nH]1] | 493 |
| 150 | 4-(1-(4-cyclobutyl-3-(5-methyl-4H-1,2,4-triazol-3-yl)benzoyl)azetidin-3-yl)benzonitrile | 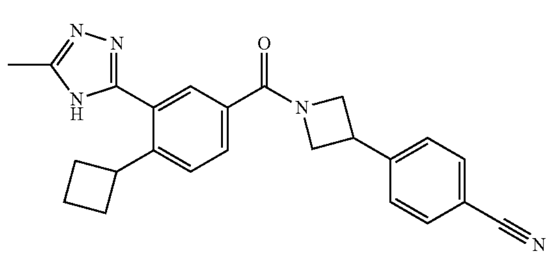 [SMILES: Cc1nnc(-c2cc(C(=O)N3CC(c4ccc(C#N)cc4)C3)ccc2C2CCC2)[nH]1] | 398 |

The compounds in TABLE 9 were prepared using standard chemical manipulations and procedures similar to those used for the preparation of compounds 78, 79, 80 and 81.

TABLE 9

| Cpd | Name | Structure | m/z (ES+) (M + H)+ |
|---|---|---|---|
| 121 | 4-(1-(4-cyclobutyl-5-(5-(hydroxymethyl)-4H-1,2,4-triazol-3-yl)-2-methylbenzoyl)-4-fluoropiperidin-4-yl)benzonitrile | 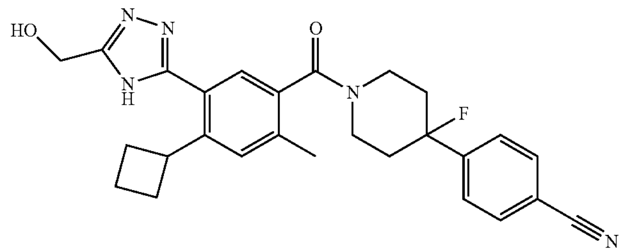 [SMILES: Cc1cc(C2CCC2)c(-c2nnc(CO)[nH]2)cc1C(=O)N1CCC(F)(c2ccc(C#N)cc2)CC1] | 474 |
| 123 | 5-(5-(4-(4-cyanophenyl)piperidine-1-carbonyl)-2-cyclobutyl-4-methylphenyl)-4H-1,2,4-triazole-3-carbonitrile | 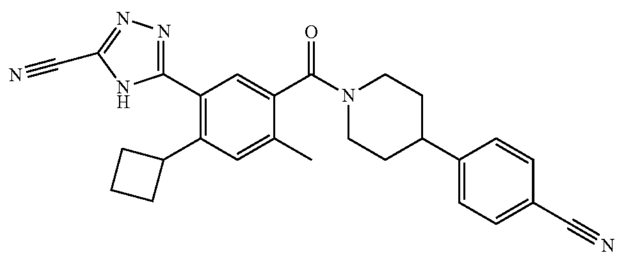 [SMILES: Cc1cc(C2CCC2)c(-c2nnc(C#N)[nH]2)cc1C(=O)N1CCC(c2ccc(C#N)cc2)CC1] | 451 |
| 130 | methyl 2-(5-(5-(4-(4-cyanophenyl)piperidine-1-carbonyl)-2-cyclobutyl-4-methylphenyl)-4H-1,2,4-triazol-3-yl)acetate | 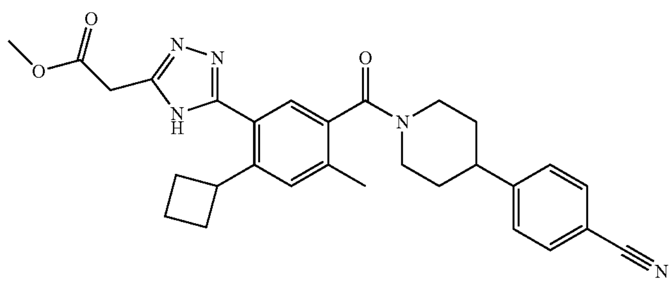 [SMILES: COC(=O)Cc1nnc(-c2cc(C(=O)N3CCC(c4ccc(C#N)cc4)CC3)c(C)cc2C2CCC2)[nH]1] | 498 |
| 131 | 2-(5-(5-(4-(4-cyanophenyl)piperidine-1-carbonyl)-2-cyclobutyl-4-methylphenyl)-4H-1,2,4-triazol-3-yl)acetic acid | 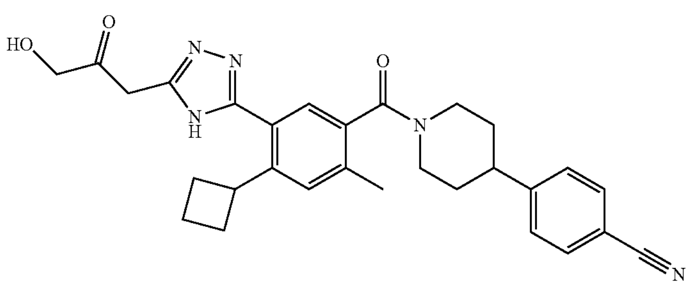 [SMILES: Cc1cc(C2CCC2)c(-c2nnc(CC(=O)CO)[nH]2)cc1C(=O)N1CCC(c2ccc(C#N)cc2)CC1] | 484 |

Compound 95. 4-(1-(3-(3-Chloro-4-methyl-1H-pyrazol-5-yl)-4-methylbenzoyl)azetidin-3-yl)benzonitrile The title compound was prepared using standard chemical manipulations and procedures similar to those used for the preparation of compound 250, except methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1). m/z (ES+) 391 (M+H)+.

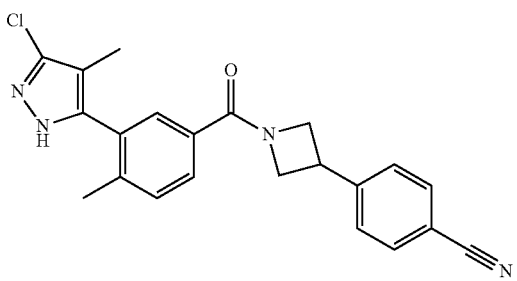

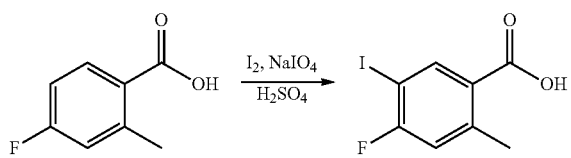

Compound 101.1. 4-Fluoro-5-iodo-2-methylbenzoic acid

The title compound was prepared using standard chemical manipulations and procedures similar to those used for the preparation of compound 1.3, except 4-fluoro-2-methylbenzoic acid was used in place of 2,4-dimethylbenzoic acid.

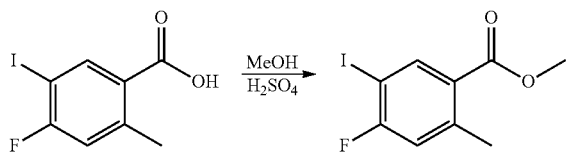

Compound 101.2. Methyl 4-fluoro-5-iodo-2-methylbenzoate

The title compound was prepared using standard chemical manipulations and procedures similar to those used for the preparation of compound 6.1, except 4-fluoro-5-iodo-2-methylbenzoic acid (compound 101.1) was used in place of 4-bromo-2-methylbenzoic acid.

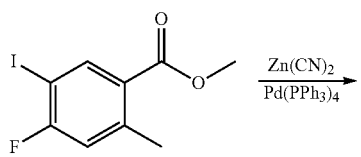

Compound 101.3. Methyl 5-cyano-4-fluoro-2-methylbenzoate

The title compound was prepared using standard chemical manipulations and procedures similar to those used for the preparation of compound 6.4, except methyl 4-fluoro-5-iodo-2-methylbenzoate (compound 101.2) was used in place of methyl 4-cyclobutyl-5-iodo-2-methylbenzoate (compound 6.3).

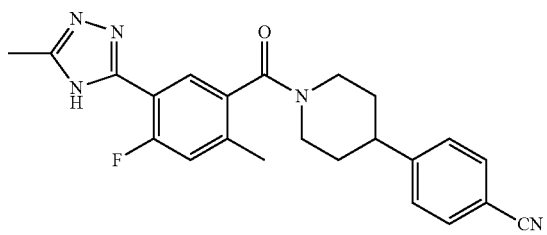 [SMILES: Cc1nnc(-c2cc(C(=O)N3CCC(c4ccc(C#N)cc4)CC3)c(C)cc2F)[nH]1]

Compound 101.4. 4-(1-(4-Fluoro-2-methyl-5-(5-methyl-4H-1,2,4-triazol-3-yl)benzoyl)piperidin-4-yl)benzonitrile The title compound was prepared using standard chemical manipulations and procedures similar to those used for the preparation of compound 78, except methyl 5-cyano-4-fluoro-2-methylbenzoate (compound 101.3) was used in place of methyl 5-cyano-4-cyclobutyl-2-methylbenzoate (compound 6.4) and 4-(piperidin-4-yl)benzonitrile hydrochloride (compound 1.2) was used in place of 6-(piperidin-4-yl)imidazo[1,2-a]pyridine hydrochloride (compound 78.5).

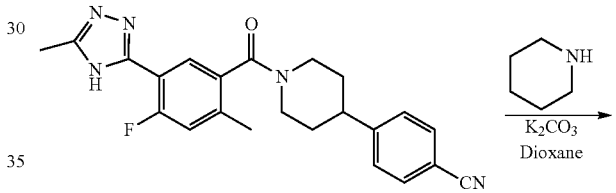

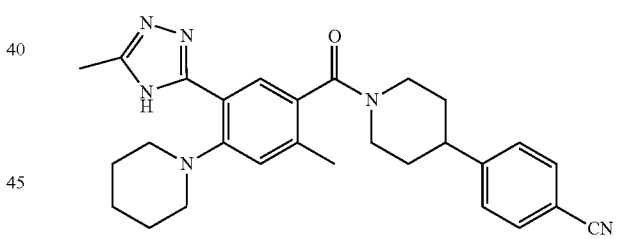

Compound 101. 4-(1-(2-Methyl-5-(5-methyl-4H-1,2,4-triazol-3-yl)-4-(piperidin-1-yl)benzoyl)piperidin-4-yl)benzonitrile The title compound was prepared using standard chemical manipulations and procedures similar to those used for the preparation of compound 25, except 4-(1-(4-fluoro-2-methyl-5-(5-methyl-4H-1,2,4-triazol-3-yl)benzoyl)piperidin-4-yl)benzonitrile (compound 101.4) was used in place of 4-(1-(3-(2,4-dimethyl-1H-imidazol-5-yl)-4-fluorobenzoyl)piperidin-4-yl)benzonitrile (compound 25.1) and piperidine was used in place of azetidine hydrochloride. m/z (ES+) 469 (M+H)$^+$.

The compounds in TABLE 10 were prepared using standard chemical manipulations and procedures similar to those used for the preparation of compound 101.

TABLE 10

| Cpd | Name | Structure | m/z (ES+) (M + H)+ |
|---|---|---|---|
| 102 | 4-(1-(2-methyl-5-(5-methyl-4H-1,2,4-triazol-3-yl)-4-morpholinobenzoyl)piperidin-4-yl)benzonitrile | 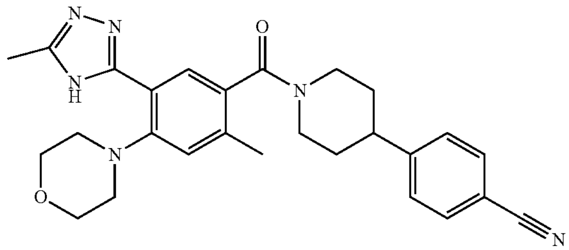 [SMILES: Cc1nnc(-c2cc(C(=O)N3CCC(c4ccc(C#N)cc4)CC3)c(C)cc2N2CCOCC2)[nH]1] | 471 |
| 105 | 4-(1-(2-methyl-5-(5-methyl-4H-1,2,4-triazol-3-yl)-4-(3-methylpyrrolidin-1-yl)benzoyl)piperidin-4-yl)benzonitrile | 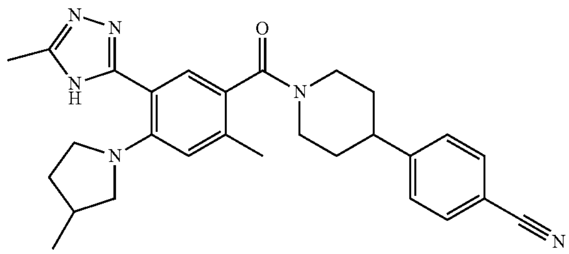 [SMILES: Cc1nnc(-c2cc(C(=O)N3CCC(c4ccc(C#N)cc4)CC3)c(C)cc2N2CCC(C)C2)[nH]1] | 469 |
| 109 | 4-(1-(4-(dimethylamino)-2-methyl-5-(5-methyl-4H-1,2,4-triazol-3-yl)benzoyl)piperidin-4-yl)benzonitrile | 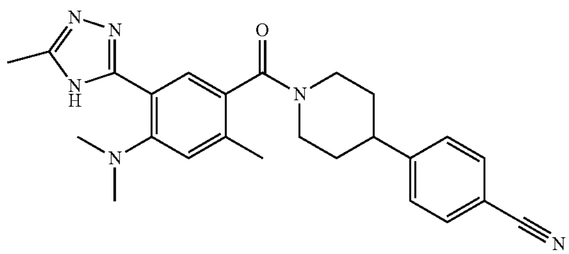 [SMILES: Cc1nnc(-c2cc(C(=O)N3CCC(c4ccc(C#N)cc4)CC3)c(C)cc2N(C)C)[nH]1] | 429 |
| 122 | 4-(1-(2-methyl-5-(5-methyl-4H-1,2,4-triazol-3-yl)-4-(4-methylpiperazin-1-yl)benzoyl)piperidin-4-yl)benzonitrile | 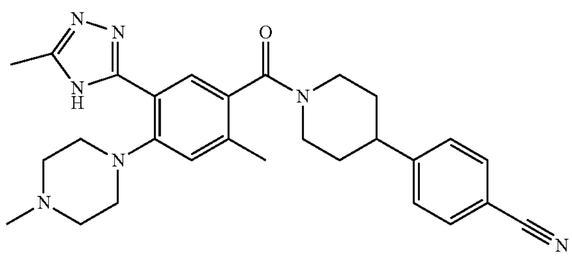 [SMILES: Cc1nnc(-c2cc(C(=O)N3CCC(c4ccc(C#N)cc4)CC3)c(C)cc2N2CCN(C)CC2)[nH]1] | 484 |
| 124 | (S)-4-(1-(2-methyl-5-(5-methyl-4H-1,2,4-triazol-3-yl)-4-(2-methylpyrrolidin-1-yl)benzoyl)piperidin-4-yl)benzonitrile | 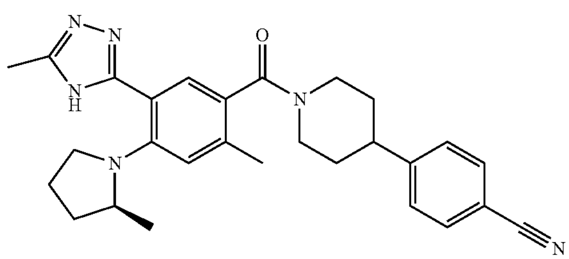 [SMILES: Cc1nnc(-c2cc(C(=O)N3CCC(c4ccc(C#N)cc4)CC3)c(C)cc2N2CCC[C@@H]2C)[nH]1] | 469 |
| 125 | (S)-4-(1-(4-(3-methoxypyrrolidin-1-yl)-2-methyl-5-(5-methyl-4H-1,2,4-triazol-3-yl)benzoyl)piperidin-4-yl)benzonitrile | 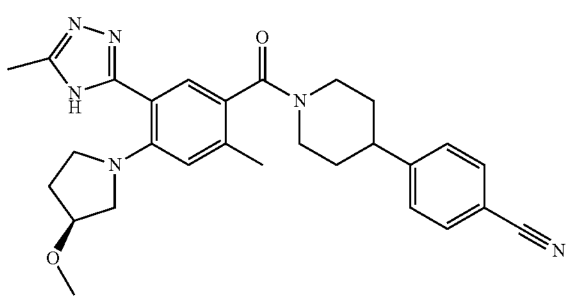 [SMILES: CO[C@H]1CCN(c2cc(C)c(C(=O)N3CCC(c4ccc(C#N)cc4)CC3)cc2-c2nnc(C)[nH]2)C1] | 485 |

TABLE 10-continued

| Cpd | Name | Structure | m/z (ES+) (M + H)+ |
|---|---|---|---|
| 126 | (R)-4-(1-(4-(3-methoxypyrrolidin-1-yl)-2-methyl-5-(5-methyl-4H-1,2,4-triazol-3-yl)benzoyl)piperidin-4-yl)benzonitrile | 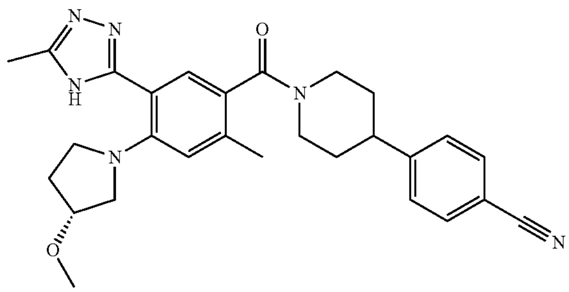 [SMILES: CO[C@@H]1CCN(c2cc(C)c(C(=O)N3CCC(c4ccc(C#N)cc4)CC3)cc2-c2nnc(C)[nH]2)C1] | 485 |
| 127 | (R)-4-(1-(2-methyl-5-(5-methyl-4H-1,2,4-triazol-3-yl)-4-(2-methylpyrrolidin-1-yl)benzoyl)piperidin-4-yl)benzonitrile | 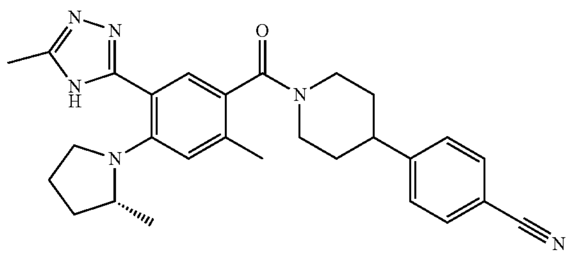 [SMILES: Cc1nnc(-c2cc(C(=O)N3CCC(c4ccc(C#N)cc4)CC3)c(C)cc2N2CCC[C@H]2C)[nH]1] | 469 |
| 128 | 4-(1-(2-methyl-5-(5-methyl-4H-1,2,4-triazol-3-yl)-4-(3-methylazetidin-1-yl)benzoyl)piperidin-4-yl)benzonitrile | 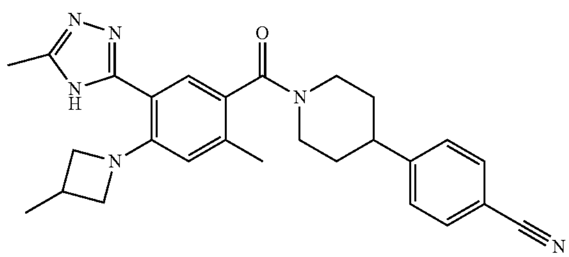 [SMILES: Cc1nnc(-c2cc(C(=O)N3CCC(c4ccc(C#N)cc4)CC3)c(C)cc2N2CC(C)C2)[nH]1] | 455 |
| 129 | 4-(1-(4-(diethylamino)-2-methyl-5-(5-methyl-4H-1,2,4-triazol-3-yl)benzoyl)piperidin-4-yl)benzonitrile | 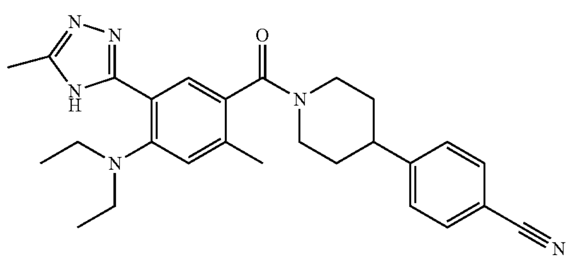 [SMILES: CCN(CC)c1cc(C)c(C(=O)N2CCC(c3ccc(C#N)cc3)CC2)cc1-c1nnc(C)[nH]1] | 457 |

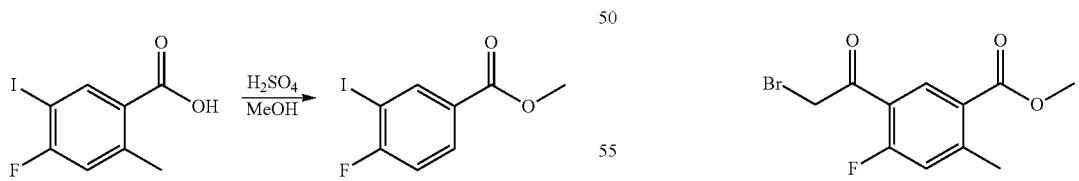

Compound 132.1. Methyl 4-fluoro-3-iodobenzoate

Compound 132.2. Methyl 3-(2-bromoacetyl)-4-fluorobenzoate

The title compound was prepared using standard chemical manipulations and procedures similar to those used for the preparation of compound 6.1, except 4-fluoro-3-iodobenzoic acid was used in place of 4-bromo-2-methylbenzoic acid.

The title compound was prepared using standard chemical manipulations and procedures similar to those used for the preparation of compound 27.3, except methyl 4-fluoro-3-iodobenzoate (compound 132.1) was used in place of methyl 3-(2-bromoacetyl)-4-methylbenzoate (compound 27.2).

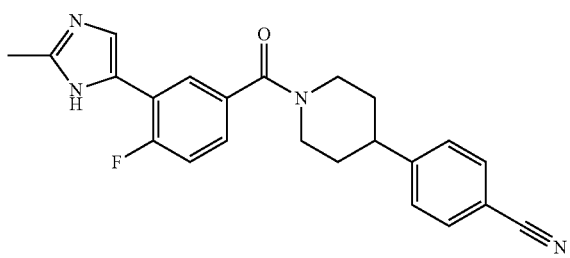 [SMILES: Cc1ncc(-c2cc(C(=O)N3CCC(c4ccc(C#N)cc4)CC3)ccc2F)[nH]1]

Compound 132.3. 4-(1-(4-Fluoro-3-(2-methyl-1H-imidazol-5-yl)benzoyl)piperidin-4-yl)benzonitrile The title compound was prepared using standard chemical manipulations and procedures similar to those used for the preparation of compound 1, except methyl 3-(2-bromoacetyl)-4-fluorobenzoate (compound 132.1) was used in place of methyl 5-(2-bromopropanoyl)-2,4-dimethylbenzoate (compound 1.6).

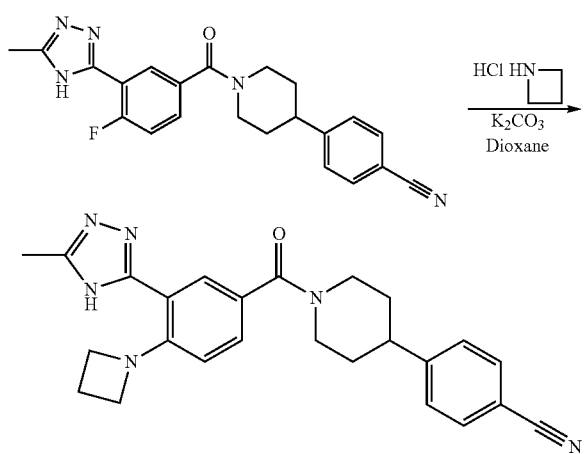

Compound 132. 4-(1-(4-(Azetidin-1-yl)-3-(2-methyl-1H-imidazol-5-yl)benzoyl)piperidin-4-yl)benzonitrile The title compound was prepared using standard chemical manipulations and procedures similar to those used for the preparation of compound 25, except 4-(1-(4-fluoro-3-(2-methyl-1H-imidazol-5-yl)benzoyl)piperidin-4-yl)benzonitrile (compound 132.3) was used in place of 4-(1-(3-(2,4-dimethyl-1H-imidazol-5-yl)-4-fluorobenzoyl)piperidin-4-yl)benzonitrile (compound 25.1). m/z (ES+) 426 (M+H)$^+$.

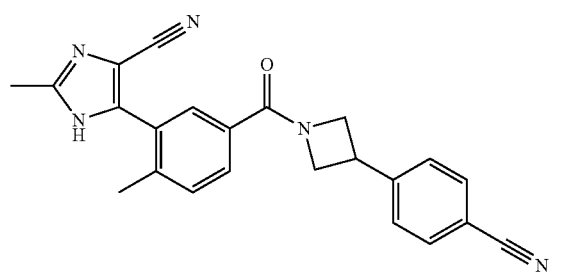 [SMILES: Cc1nc(C#N)c(-c2cc(C(=O)N3CC(c4ccc(C#N)cc4)C3)ccc2C)[nH]1]

Compound 139. 5-(5-(3-(4-Cyanophenyl)azetidine-1-carbonyl)-2-methylphenyl)-2-methyl-1H-imidazole-4-carbonitrile The title compound was prepared using standard chemical manipulations and procedures similar to those used for the preparation of compound 16, except 4-(azetidin-3-yl)benzonitrile hydrochloride (compound 5.2) was used instead of 4-(piperidin-4-yl)benzonitrile hydrochloride (compound 1.2). m/z (ES+) 382 (M+H)$^+$.

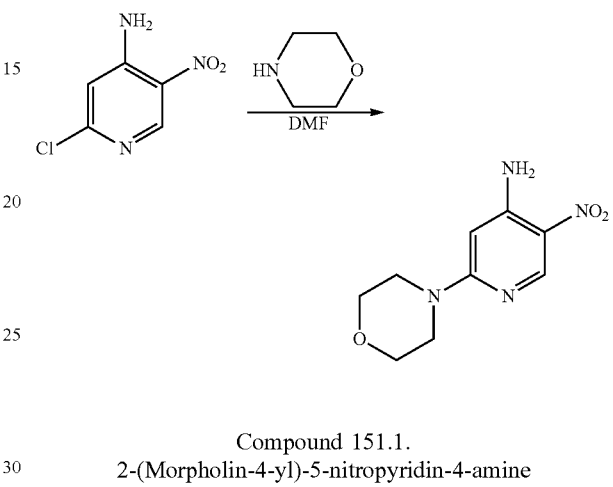

Compound 151.1.
2-(Morpholin-4-yl)-5-nitropyridin-4-amine

Into a 50-mL sealed tube, were placed a solution of 2-chloro-5-nitropyridin-4-amine (500 mg, 2.88 mmol) in N,N-dimethylformamide (20 mL) and morpholine (503 μL, 5.77 mmol). The reaction mixture was stirred overnight at 55° C. The reaction was then quenched by the addition of 100 mL of water. The reaction mixture was extracted with 3×150 mL of ethyl acetate. The organic layers were combined, dried over anhydrous magnesium sulfate, and concentrated under reduced pressure. This resulted in 733 mg (crude) of the title compound as a yellow solid.

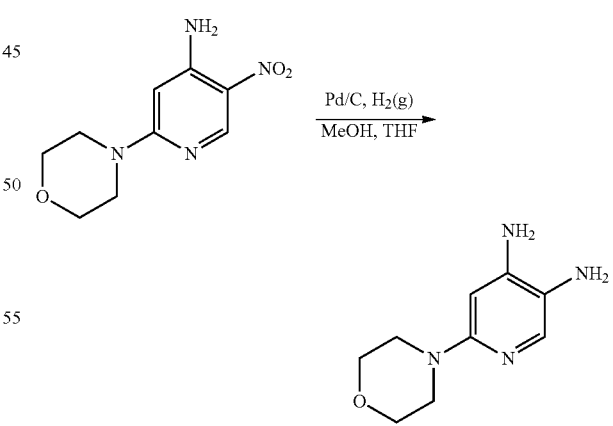

Compound 151.2.
6-Morpholinopyridine-3,4-diamine

Into a 50-mL round-bottom flask were placed 2-(morpholin-4-yl)-5-nitropyridin-4-amine (compound 151.1, 350 mg, 1.56 mmol), methanol (20 mL), THF (10 mL), and Pd/C (35 mg). The above solution was purged with N₂ and then H₂. The reaction mixture was stirred for 4 h at room temperature. The solids were filtered out. The resulting mixture was concentrated under reduced pressure. This resulted in 280 mg (92%) of the title compound as a pink solid.

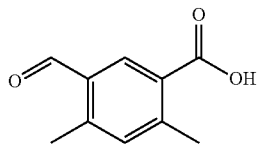

Compound 151.3. 5-Formyl-2,4-dimethylbenzoic acid

The title compound was prepared using standard chemical manipulations and procedures similar to those used for the preparation of compound 4.1, except 5-iodo-2,4-dimethylbenzoic acid (compound 1.3) was used in place of 3-bromo-4-methylbenzoic acid.

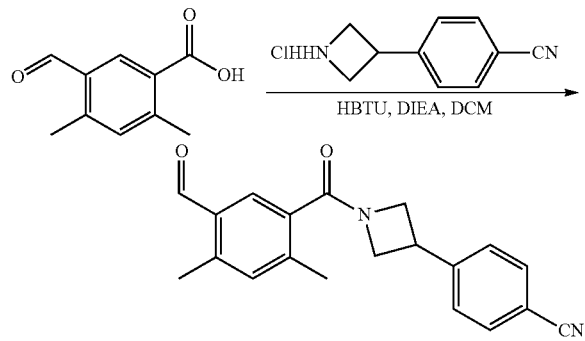

Compound 151.4. 4-(1-(5-Formyl-2,4-dimethylbenzoyl)azetidin-3-yl)benzonitrile

Into a 50-mL round-bottom flask, was placed a solution of 5-formyl-2,4-dimethylbenzoic acid (compound 151.3, 500 mg, 2.81 mmol) in DCM (10 mL). 4-(azetidin-3-yl)benzonitrile hydrochloride (compound 5.2, 545 mg, 2.80 mmol), DIEA (1.4 mL, 8.41 mmol) and HBTU (1.60 g, 4.22 mmol) were added. The reaction mixture was stirred for 3 h at room temperature. The reaction mixture was diluted with 150 mL of EtOAc, then washed with 2×50 mL of NH₄Cl (sat.) and 1×50 mL of brine, dried over anhydrous sodium sulfate and concentrated under reduced pressure. The residue was purified by silica gel chromatography with ethyl acetate/petroleum ether (1/1) as eluent to furnish 480 mg (54%) of the title compound as a white solid.

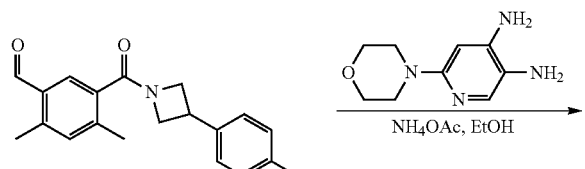

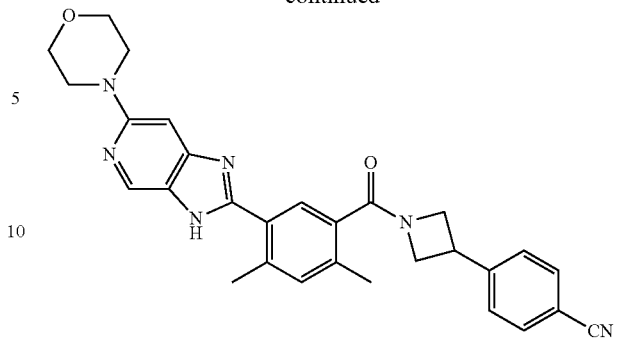

Compound 151. 4-(1-(2,4-Dimethyl-5-(6-morpholino-3H-imidazo[4,5-c]pyridin-2-yl)benzoyl)azetidin-3-yl)benzonitrile Into a 50-mL round-bottom flask, was placed a solution of 4-(1-(5-formyl-2,4-dimethylbenzoyl)azetidin-3-yl)benzonitrile (compound 151.4, 159 mg, 0.50 mmol) in ethanol (16 mL). 6-Morpholinopyridine-3,4-diamine (compound 151.2, 194 mg, 1.00 mmol) and NH₄OAc (308 mg, 4.00 mmol) were added to the reaction. The reaction mixture was stirred for 3 days at 70° C. under air. The pH of the solution was adjusted to 8-9 with sodium bicarbonate (sat.). The reaction mixture was extracted with 1×100 mL of ethyl acetate. The organic layer was washed with 3×50 mL of brine, dried over anhydrous sodium sulfate and concentrated under reduced pressure. The crude product (200 mg) was purified by Prep-HPLC with the following conditions (1#-Pre-HPLC-010(Waters)): Column, SunFire Prep C18 OBD Column, 5 m, 19*150 mm; mobile phase, WATER WITH 0.05% TFA and CH₃CN (20.0% CH₃CN up to 36.0% in 10 min, up to 100.0% in 1 min, down to 20.0% in 2 min); Detector, UV 254 and 220 nm. This resulted in 94.1 mg (38%) of the title compound as a brown solid. m/z (ES+) 493 (M+H)⁺.

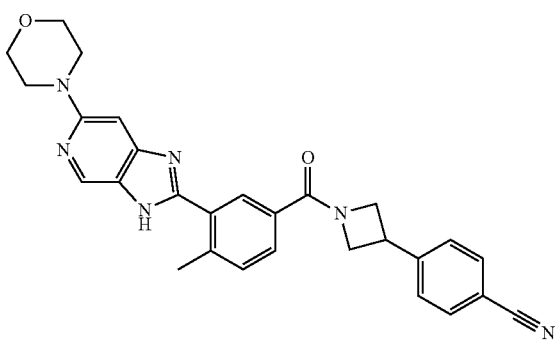 [SMILES: Cc1ccc(C(=O)N2CC(c3ccc(C#N)cc3)C2)cc1-c1nc2cc(N3CCOCC3)ncc2[nH]1]

Compound 152. 4-(1-(4-Methyl-3-(6-morpholino-3H-imidazo[4,5-c]pyridin-2-yl)benzoyl)azetidin-3-yl)benzonitrile The title compound was prepared using standard chemical manipulations and procedures similar to those used for the preparation of compound 151, except 3-formyl-4-methylbenzoic acid (compound 4.1) was used in place of 5-formyl-2,4-dimethylbenzoic acid (compound 151.3). m/z (ES+) 479 (M+H)⁺.

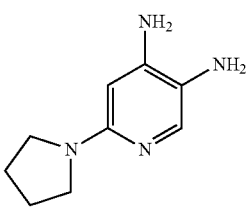 [SMILES: Nc1cnc(N2CCCC2)cc1N]

Compound 153.1.
6-(Pyrrolidin-1-yl)pyridine-3,4-diamine

The title compound was prepared using standard chemical manipulations and procedures similar to those used for the preparation of compound 151.1 and 151.2, except pyrrolidine was used in place of morpholine.

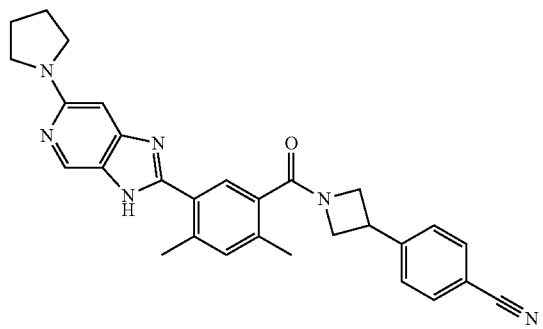 [SMILES: Cc1cc(C)c(-c2nc3cc(N4CCCC4)ncc3[nH]2)cc1C(=O)N1CC(c2ccc(C#N)cc2)C1]

Compound 153. 4-(1-(2,4-Dimethyl-5-(6-(pyrrolidin-1-yl)-3H-imidazo[4,5-c]pyridin-2-yl)benzoyl)azetidin-3-yl)benzonitrile The title compound was prepared using standard chemical manipulations and procedures similar to those used for the preparation of compound 151, except 6-(pyrrolidin-1-yl)pyridine-3,4-diamine (compound 153.1) was used in place of 6-morpholinopyridine-3,4-diamine (compound 151.2). m/z (ES+) 477 (M+H)$^+$.

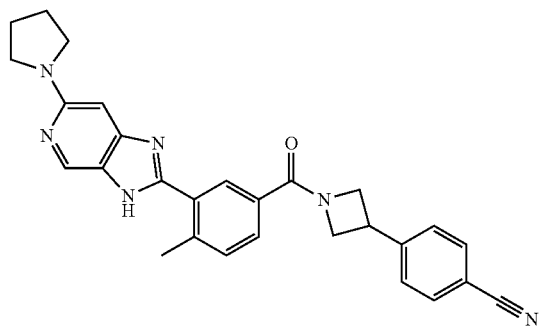 [SMILES: Cc1ccc(C(=O)N2CC(c3ccc(C#N)cc3)C2)cc1-c1nc2cc(N3CCCC3)ncc2[nH]1]

Compound 154. 4-(1-(4-Methyl-3-(6-(pyrrolidin-1-yl)-3H-imidazo[4,5-c]pyridin-2-yl)benzoyl)azetidin-3-yl)benzonitrile The title compound was prepared using standard chemical manipulations and procedures similar to those used for the preparation of compound 151, except 3-formyl-4-methylbenzoic acid (compound 4.1) was used in place of 5-formyl-2,4-dimethylbenzoic acid (compound 151.3) and 6-(pyrrolidin-1-yl)pyridine-3,4-diamine (compound 153.1) was used in place of 6-morpholinopyridine-3,4-diamine (compound 151.2). m/z (ES+) 463 (M+H)$^+$.

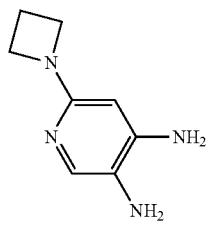 [SMILES: Nc1cnc(N2CCC2)cc1N]

Compound 155.1.
6-(Azetidin-1-yl)pyridine-3,4-diamine

The title compound was prepared using standard chemical manipulations and procedures similar to those used for the preparation of compound 151.1 and 151.2, except azetidine was used in place of morpholine.

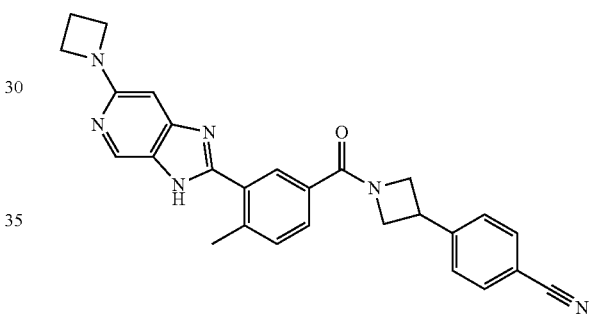

Compound 155. 4-(1-(3-(6-(Azetidin-1-yl)-3H-imidazo[4,5-c]pyridin-2-yl)-4-methylbenzoyl)azetidin-3-yl)benzonitrile The title compound was prepared using standard chemical manipulations and procedures similar to those used for the preparation of compound 151, except 3-formyl-4-methylbenzoic acid (compound 4.1) was used in place of 5-formyl-2,4-dimethylbenzoic acid (compound 151.3) and 6-(azetidin-1-yl)pyridine-3,4-diamine (compound 155.1) was used in place of 6-morpholinopyridine-3,4-diamine (compound 151.2). m/z (ES+) 449 (M+H)$^+$.

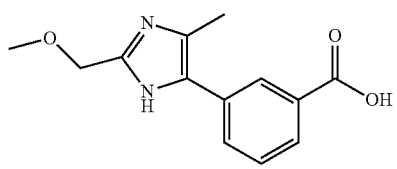 [SMILES: COCc1nc(C)c(-c2cccc(C(=O)O)c2)[nH]1]

Compound 156.1. 3-(2-(Methoxymethyl)-4-methyl-1H-imidazol-5-yl)benzoic acid

The title compound was prepared using standard chemical manipulations and procedures similar to those used for the preparation of compound 2.3, except 3-iodobenzoic acid was used in place of 5-iodo-2,4-dimethylbenzoic acid (compound 1.3).

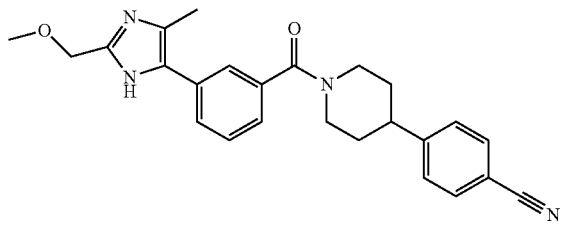 [SMILES: COCc1nc(C)c(-c2cccc(C(=O)N3CCC(c4ccc(C#N)cc4)CC3)c2)[nH]1]

Compound 156. 4-(1-(3-(2-(Methoxymethyl)-4-methyl-1H-imidazol-5-yl)benzoyl)piperidin-4-yl)benzonitrile The title compound was prepared using standard chemical manipulations and procedures similar to those used for the preparation of compound 2, except 3-(2-(methoxymethyl)-4-methyl-1H-imidazol-5-yl)benzoic acid (compound 156.1) was used in place of 5-(2-(methoxymethyl)-4-methyl-1H-imidazol-5-yl)-2,4-dimethylbenzoic acid (compound 2.3). m/z (ES+) 415 (M+H)$^+$.

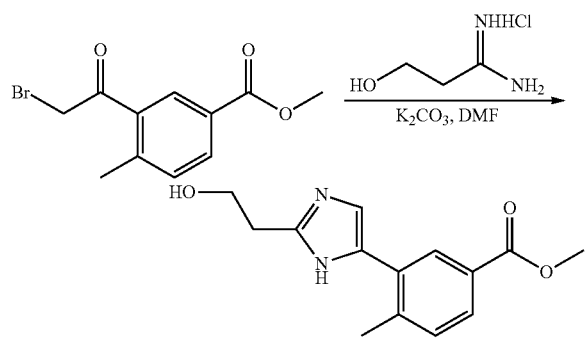

Compound 157.1. Methyl 3-(2-(2-hydroxyethyl)-1H-imidazol-5-yl)-4-methylbenzoate

Into a 250-mL round-bottom flask, which was purged and maintained with an inert atmosphere of nitrogen, was placed a solution of methyl 3-(2-bromoacetyl)-4-methylbenzoate (compound 27.2, 10 g, 36.89 mmol) in N,N-dimethylformamide (150 mL). K$_2$CO$_3$ (30 g, 215.5 mmol) and 3-hydroxypropanimidamide hydrochloride (compound 23.1, 15 g, 120.4 mmol) were added to the reaction. The reaction mixture was stirred for 12 h at 80° C., then concentrated under reduced pressure. The residue was purified by silica gel chromatography with ethyl acetate/petroleum ether (2:1) as eluent to furnish 2 g (21%) of the title compound as a light yellow oil.

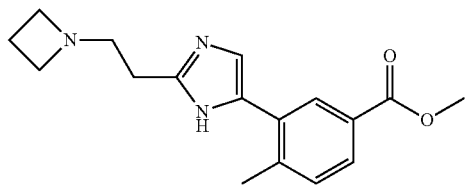 [SMILES: COC(=O)c1ccc(C)c(-c2cnc(CCN3CCC3)[nH]2)c1]

Compound 157.2. Methyl 3-(2-(2-(azetidin-1-yl)ethyl)-1H-imidazol-5-yl)-4-methylbenzoate The title compound was prepared using standard chemical manipulations and procedures similar to those used for the preparation of compounds 24.1 and 24, except methyl 3-(2-(2-hydroxyethyl)-1H-imidazol-5-yl)-4-methylbenzoate (compound 157.1) was used in place of 4-(1-(3-(2-(2-hydroxyethyl)-4-methyl-1H-imidazol-5-yl)-4-methylbenzoyl)piperidin-4-yl)benzonitrile (compound 23) and azetidine was used in place of dimethylamine.

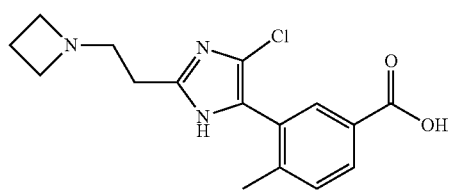 [SMILES: Cc1ccc(C(=O)O)cc1-c1[nH]c(CCN2CCC2)nc1Cl]

Compound 157.3. 3-(2-(2-(Azetidin-1-yl)ethyl)-4-chloro-1H-imidazol-5-yl)-4-methylbenzoic acid The title compound was prepared using standard chemical manipulations and procedures similar to those used for the preparation of compounds 27.4 and 27.5, except methyl 3-(2-(2-(azetidin-1-yl)ethyl)-1H-imidazol-5-yl)-4-methylbenzoate (compound 157.2) was used in place of methyl 3-(2-(methoxymethyl)-1H-imidazol-5-yl)-4-methylbenzoate (compound 27.3).

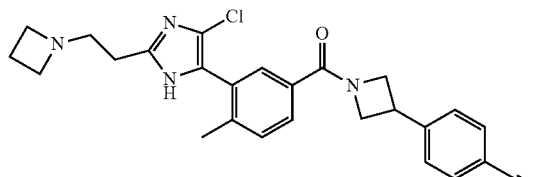

Compound 157. 4-(1-(3-(2-(2-(Azetidin-1-yl)ethyl)-4-chloro-1H-imidazol-5-yl)-4-methylbenzoyl)azetidin-3-yl)benzonitrile The title compound was prepared using standard chemical manipulations and procedures similar to those used for the preparation of compound 27, except 3-(2-(2-(azetidin-1-yl)ethyl)-4-chloro-1H-imidazol-5-yl)-4-methylbenzoic acid (compound 157.3) was used in place of 3-(4-chloro-2-(methoxymethyl)-1H-imidazol-5-yl)-4-methylbenzoic acid (compound 27.5) and 4-(azetidin-3-yl)benzonitrile hydrochloride (compound 5.2) was used in place of 4-(piperidin-4-yl)benzonitrile hydrochloride (compound 1.2). m/z (ES+) 460 (M+H)$^+$.

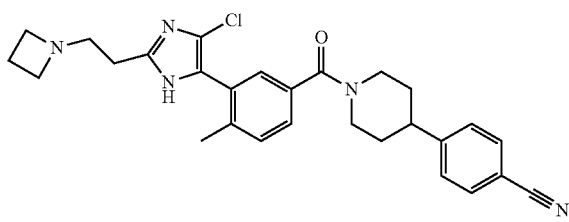 [SMILES: Cc1ccc(C(=O)N2CCC(c3ccc(C#N)cc3)CC2)cc1-c1[nH]c(CCN2CCC2)nc1Cl]

Compound 158. 4-(1-(3-(2-(2-(Azetidin-1-yl)ethyl)-4-chloro-1H-imidazol-5-yl)-4-methylbenzoyl)piperidin-4-yl)benzonitrile The title compound was prepared using standard chemical manipulations and procedures similar to those used for the preparation of compound 27, except 3-(2-(2-(azetidin-1-yl)ethyl)-4-chloro-1H-imidazol-5-yl)-4-methylbenzoic acid (compound 157.3) was used in place of 4-(piperidin-4-yl)benzonitrile hydrochloride (compound 1.2). m/z (ES+) 488 (M+H)+.

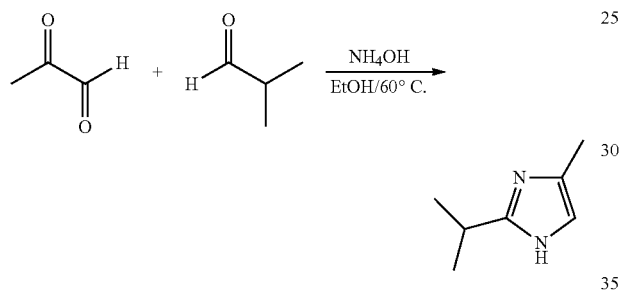

Compound 159.1.
2-Isopropyl-4-methyl-1H-imidazole

A solution of isobutyraldehyde (4.5 mL, 50 mmol) in ethanol (25 mL) was treated with ammonium hydroxide (28% w/w, 25 mL) at 55° C. Methylglyoxal (40% in H$_2$O, 28 mL, 63 mmol) was added dropwise. The resulting mixture was stirred at 60° C. for 16 hours and the solvent was removed under reduced pressure. The residue was partitioned between EtOAc (50 mL) and water (30 mL). The organic phase was washed by brine, dried over MgSO$_4$ and concentrated under reduced pressure. The residue was purified by flash chromatography (SiO$_2$; 0-4% MeOH in dichloromethane) to give 3.96 g (64%) of the title compound as a yellow solid. m/z (ES+) 125 (M+H)+.

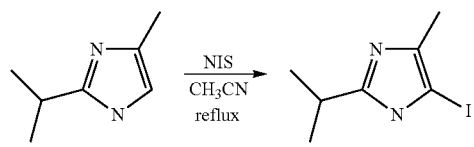

Compound 159.2.
5-Iodo-2-isopropyl-4-methyl-1H-imidazole

2-Isopropyl-4-methyl-1H-imidazole (3.96 g, 32 mmol) and N-iodosuccinimide (8.33 g, 35 mmol) were dissolved in acetonitrile (100 mL) and heated to reflux for 16 hours. The reaction was concentrated under reduced pressure and the residue was partitioned between EtOAc (50 mL) and water (50 mL). The organic phase was washed with brine, dried over MgSO$_4$ and concentrated under reduced pressure. The residue was purified by flash chromatography (SiO$_2$; 0-40% EtOAc in hexane) to give 4.87 g (61%) of the title compound as a yellow solid. m/z (ES+) 251 (M+H)+.

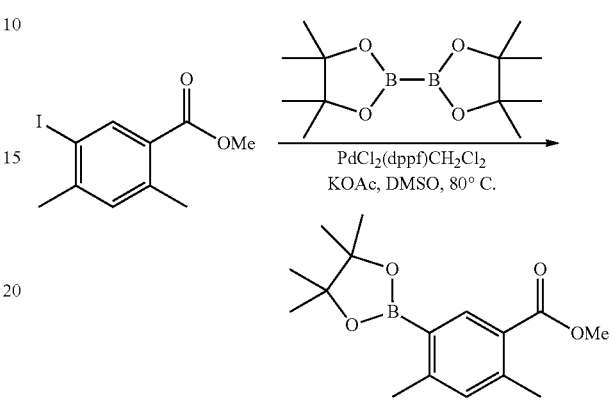

Compound 160.1. Methyl 2,4-dimethyl-5-(4,4,5,5-tetramethyl-1,3,2-dioxaborolan-2-yl)benzoate The title compound was prepared using standard chemical manipulations and procedures similar to those used for the preparation of compound 5.4, except methyl 5-iodo-2,4-dimethylbenzoate (compound 31.1) was used in place of methyl 3-iodo-4-methylbenzoate (compound 5.3). m/z (ES+) 291 (M+H)+.

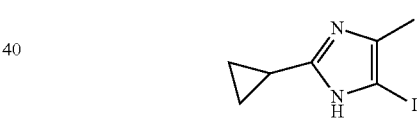

Compound 160.2.
2-Cyclopropyl-5-iodo-4-methyl-1H-imidazole

The title compound was prepared using standard chemical manipulations and procedures similar to those used for the preparation of compound 159.2, except cyclopropanecarbaldehyde was used in place of isobutyraldehyde.

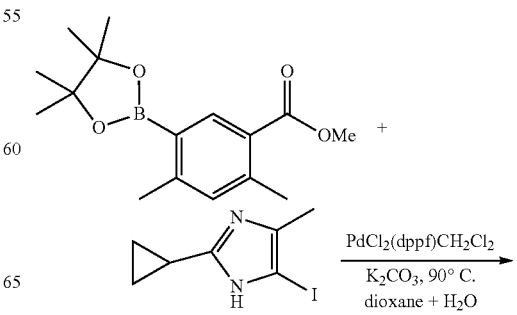

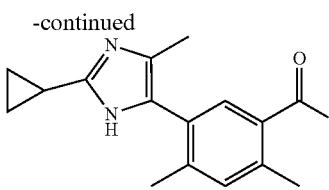

Compound 160.3. Methyl 5-(2-cyclopropyl-4-methyl-1H-imidazol-5-yl)-2,4-dimethylbenzoate The title compound was prepared using standard chemical manipulations and procedures similar to those used for the preparation of compound 5.6, except methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4) and 2-cyclopropyl-5-iodo-4-methyl-1H-imidazole (compound 160.2) was used in place of 5-iodo-2,4-dimethyl-1H-imidazole (compound 5.5). m/z (ES+) 285 (M+H)$^+$.

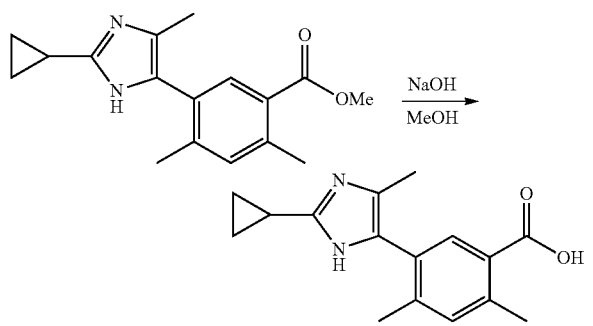

Compound 160.4. 5-(2-Cyclopropyl-4-methyl-1H-imidazol-5-yl)-2,4-dimethylbenzoic acid The title compound was prepared using standard chemical manipulations and procedures similar to those used for the preparation of compound 5.7, except methyl 5-(2-cyclopropyl-4-methyl-1H-imidazol-5-yl)-2,4-dimethylbenzoate (compound 160.3) was used in place of methyl 3-(2,4-dimethyl-1H-imidazol-5-yl)-4-methylbenzoate (compound 5.6). m/z (ES+) 271 (M+H)$^+$.

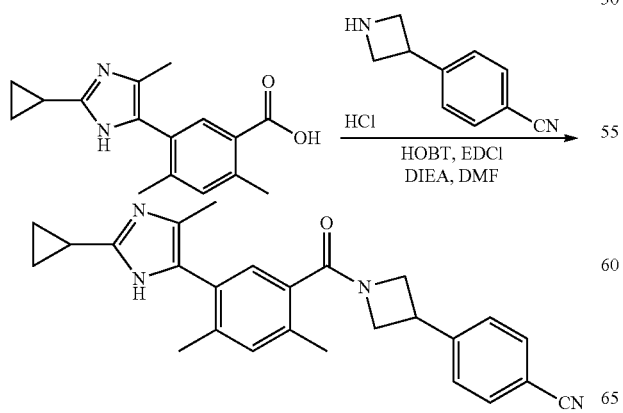

Compound 160. 4-(1-(5-(2-Cyclopropyl-4-methyl-1H-imidazol-5-yl)-2,4-dimethylbenzoyl)azetidin-3-yl)benzonitrile The title compound was prepared using standard chemical manipulations and procedures similar to those used for the preparation of compound 5, except 5-(2-cyclopropyl-4-methyl-1H-imidazol-5-yl)-2,4-dimethylbenzoic acid (compound 160.4) was used in place of 3-(2,4-dimethyl-1H-imidazol-5-yl)-4-methylbenzoic acid (compound 5.7). m/z (ES+) 411 (M+H)$^+$. $^1$H NMR (400 MHz, DMSO-d$_6$): δ 11.51 (br, 1H), 7.85-7.80 (m, 2H), 7.62-7.56 (m, 2H), 7.20 and 7.13 (2 singlets, Ar—H, 1H), 7.10 and 7.07 (2 singlets, Ar—H, 1H), 4.49-4.40 (m, 1H), 4.36-4.28 (m, 1H), 4.06-3.88 (m, 3H), 2.33 and 2.30 (2 singlets, CH$_3$, 3H), 2.23 and 2.18 (2 singlets, CH$_3$, 3H), 2.07 and 1.93 (2 singlets, amide rotamers, CH$_3$, 3H), 1.89-1.82 (m, 1H), 0.88-0.074 (m, 4H).

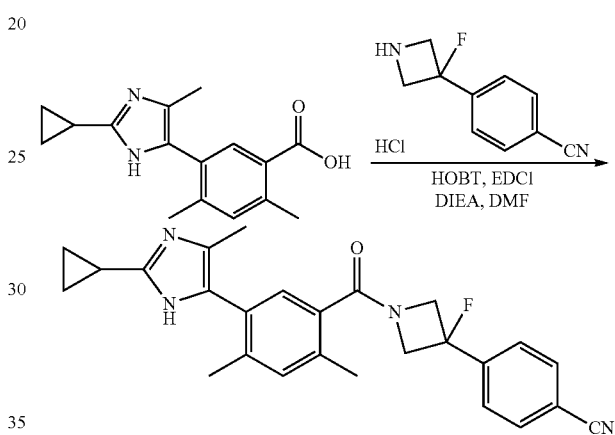

Compound 161. 4-(1-(5-(2-Cyclopropyl-4-methyl-1H-imidazol-5-yl)-2,4-dimethylbenzoyl)-3-fluoro-azetidin-3-yl)benzonitrile The title compound was prepared using standard chemical manipulations and procedures similar to those used for the preparation of compound 5, except 5-(2-cyclopropyl-4-methyl-1H-imidazol-5-yl)-2,4-dimethylbenzoic acid (compound 160.4) was used in place of 3-(2,4-dimethyl-1H-imidazol-5-yl)-4-methylbenzoic acid (compound 5.7) and 4-(3-fluoroazetidin-3-yl)benzonitrile hydrochloride (compound 43.4) was used in place of 4-(azetidin-3-yl)benzonitrile hydrochloride (compound 5.2). m/z (ES+) 429 (M+H)$^+$. $^1$H NMR (400 MHz, DMSO-d$_6$): δ 11.52 (br, 1H), 7.95 (d, J=8.4 Hz, 2H), 7.76 (dd, J=8.4 Hz, 3.2 Hz, 2H), 7.21 (d, J=6.8 Hz, 1H), 7.13 (s, 1H), 4.56-4.34 (m, 4H), 2.35 and 2.32 (2 singlets, CH$_3$, 3H), 2.43 and 2.18 (2 singlets, CH$_3$, 3H), 2.07 and 1.93 (2 singlets, CH$_3$, 3H), 1.90-1.80 (m, 1H), 0.88-0.74 (m, 4H).

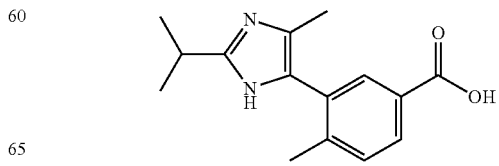

Compound 159.3. 5-(2-Isopropyl-4-methyl-1H-imidazol-5-yl)-2,4-dimethylbenzoic acid The title compound was prepared using standard chemical manipulations and procedures similar to those used for the preparation of compound 5.7, except 5-iodo-2-isopropyl-4-methyl-1H-imidazole (compound 159.2) was used in place of 5-iodo-2,4-dimethyl-1H-imidazole (compound 5.5) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4).

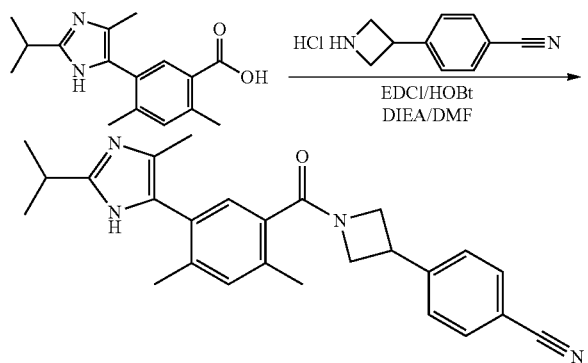

Compound 159. 4-(1-(5-(2-Isopropyl-5-methyl-1H-imidazol-4-yl)-2,4-dimethylbenzoyl)azetidin-3-yl)benzonitrile The mixture of 5-(2-isopropyl-5-methyl-1H-imidazol-4-yl)-2, 4-dimethylbenzoic acid (compound 159.3, 250 mg, 0.92 mmol), 4-(azetidin-3-yl)benzonitrile hydrochloride (compound 5.2, 195 mg, 1.0 mmol), EDCI (264 mg, 1.4 mmol), HOBt (170 mg, 1.0 mmol) and DIEA (640 μL, 3.7 mmol) in DMF (10 mL) was stirred at room temperature for 16 hours. The reaction was diluted with saturated NaHCO₃ and extracted with EtOAc (60 mL). The organic phase was washed with brine (3×20 mL), dried over MgSO₄ and concentrated under reduced pressure. The residue was purified by preparative TLC with 8% methanol in dichloromethane and lyophilized to give 85 mg (22%) of the title compound as a white solid. m/z (ES+) 413 (M+H)⁺.

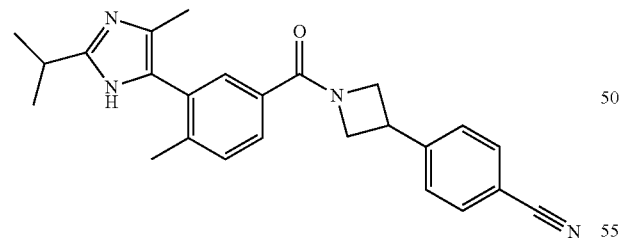

Compound 162. 4-(1-(3-(2-Isopropyl-4-methyl-1H-imidazol-5-yl)-4-methylbenzoyl)azetidin-3-yl)benzonitrile The title compound was prepared using standard chemical manipulations and procedures similar to those used for the preparation of compound 159, except methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1). m/z (ES+) 399 (M+H)⁺.

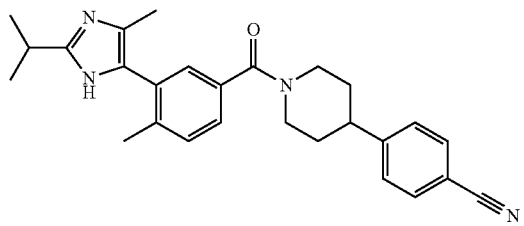 [SMILES: Cc1ccc(C(=O)N2CCC(c3ccc(C#N)cc3)CC2)cc1-c1[nH]c(C(C)C)nc1C]

Compound 163. 4-(1-(3-(2-Isopropyl-4-methyl-1H-imidazol-5-yl)-4-methylbenzoyl)piperidin-4-yl)benzonitrile The title compound was prepared using standard chemical manipulations and procedures similar to those used for the preparation of compound 159, except 4-(piperidin-4-yl)benzonitrile hydrochloride (compound 1.2) was used in place of 4-(azetidin-3-yl)benzonitrile hydrochloride (compound 5.2) and methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1). m/z (ES+) 427 (M+H)⁺.

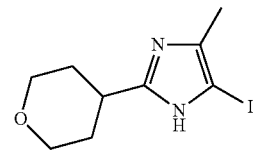

Compound 164.1. 5-Iodo-4-methyl-2-(tetrahydro-2H-pyran-4-yl)-1H-imidazole

The title compound was prepared using standard chemical manipulations and procedures similar to those used for the preparation of compound 159.2, except tetrahydro-2H-pyran-4-carbaldehyde was used in place of isobutyraldehyde.

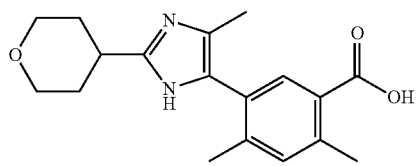 [SMILES: Cc1cc(C)c(-c2[nH]c(C3CCOCC3)nc2C)cc1C(=O)O]

Compound 164.2. 2,4-Dimethyl-5-(4-methyl-2-(tetrahydro-2H-pyran-4-yl)-1H-imidazol-5-yl)benzoic acid The title compound was prepared using standard chemical manipulations and procedures similar to those used for the preparation of compound 5.7, except 5-iodo-4-methyl-2-(tetrahydro-2H-pyran-4-yl)-1H-imidazole (compound 164.1) was used in place of 5-iodo-2,4-dimethyl-1H-imidazole (compound 5.5) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4).

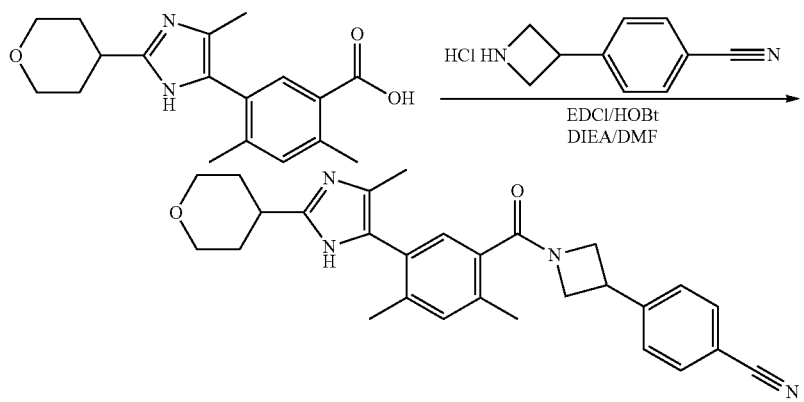

Compound 164. 4-(1-(2,4-Dimethyl-5-(4-methyl-2-(tetrahydro-2H-pyran-4-yl)-1H-imidazol-5-yl)benzoyl)azetidin-3-yl)benzonitrile The mixture of 2,4-dimethyl-5-(5-methyl-2-(tetrahydro-2H-pyran-4-yl)-1H-imidazol-4-yl)benzoic acid (compound 164.2, 157 mg, 0.5 mmol), 4-(azetidin-3-yl)benzonitrile hydrochloride (compound 5.2, 126 mg, 0.65 mmol), EDCI (143 mg, 0.75 mmol), HOBt (93 mg, 0.55 mmol) and DIEA (345 µL, 2.00 mmol) in DMF (4 mL) was stirred at room temperature for 16 hours. The reaction was diluted with water and extracted with EtOAc (30 mL). The organic phase was washed with saturated NaHCO$_3$ (10 mL), brine (3×20 mL), dried over MgSO$_4$ and concentrated under reduced pressure. The residue was purified by preparative TLC with 5% methanol in dichloromethane and lyophilized to give 95 mg (42%) of the title compound as a white solid. m/z (ES+) 455 (M+H)$^+$.

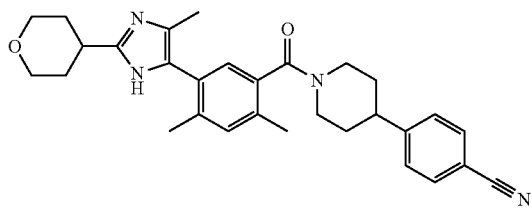

Compound 165. 4-(1-(2,4-Dimethyl-5-(4-methyl-2-(tetrahydro-2H-pyran-4-yl)-1H-imidazol-5-yl)benzoyl)piperidin-4-yl)benzonitrile The title compound was prepared using standard chemical manipulations and procedures similar to those used for the preparation of compound 164, except 4-(piperidin-4-yl)benzonitrile hydrochloride (compound 1.2) was used in place of 4-(azetidin-3-yl)benzonitrile hydrochloride (compound 5.2). m/z (ES+) 483 (M+H)$^+$.

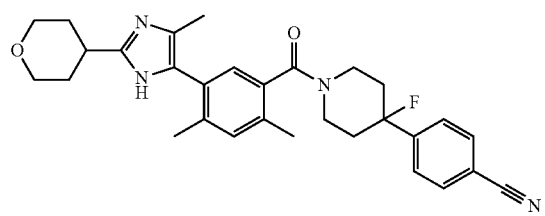 [SMILES: Cc1cc(C)c(-c2[nH]c(C3CCOCC3)nc2C)cc1C(=O)N1CCC(c2ccc(C#N)cc2)CC1]

Compound 166. 4-(4-Fluoro-1-(4-methyl-3-(4-methyl-2-(tetrahydro-2H-pyran-4-yl)-1H-imidazol-5-yl)benzoyl)piperidin-4-yl)benzonitrile The title compound was prepared using standard chemical manipulations and procedures similar to those used for the preparation of compound 164, except 4-(4-fluoropiperidin-4-yl)benzonitrile hydrochloride (compound 13.4) was used in place of 4-(azetidin-3-yl)benzonitrile hydrochloride (compound 5.2). m/z (ES+) 501 (M+H)$^+$.

Compound 167. 4-(1-(2,4-Dimethyl-5-(4-methyl-2-(tetrahydro-2H-pyran-4-yl)-1H-imidazol-5-yl) benzoyl)-3-fluoroazetidin-3-yl)benzonitrile The title compound was prepared using standard chemical manipulations and procedures similar to those used for the preparation of compound 164, except 4-(3-fluoroazetidin-3-yl)benzonitrile hydrochloride (compound 43.4) was used in place of 4-(azetidin-3-yl)benzonitrile hydrochloride (compound 5.2). m/z (ES+) 459 (M+H)$^+$.

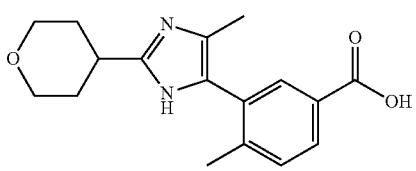 [SMILES: Cc1ccc(C(=O)O)cc1-c1[nH]c(C2CCOCC2)nc1C]

Compound 168.1. 4-Methyl-3-(4-methyl-2-(tetra-hydro-2H-pyran-4-yl)-1H-imidazol-5-yl)benzoic acid The title compound was prepared using standard chemical manipulations and procedures similar to those used for the preparation of compound 5.7, except 5-iodo-4-methyl-2-(tetrahydro-2H-pyran-4-yl)-1H-imidazole (compound 164.1) was used in place of 5-iodo-2,4-dimethyl-1H-imidazole (compound 5.5).

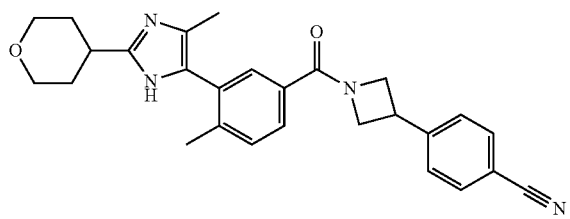 [SMILES: Cc1ccc(C(=O)N2CC(c3ccc(C#N)cc3)C2)cc1-c1[nH]c(C2CCOCC2)nc1C]

Compound 168. 4-(1-(4-Methyl-3-(5-methyl-2-(tetrahydro-2H-pyran-4-yl)-1H-imidazol-4-yl)benzoyl) azetidin-3-yl)benzonitrile The title compound was prepared using standard chemical manipulations and procedures similar to those used for the preparation of compound 164, except 4-methyl-3-(4-methyl-2-(tetrahydro-2H-pyran-4-yl)-1H-imidazol-5-yl) benzoic acid (compound 168.1) was used in place of 2,4-dimethyl-5-(4-methyl-2-(tetrahydro-2H-pyran-4-yl)-1H-imidazol-5-yl)benzoic acid (compound 164.2). m/z (ES+) 441 (M+H)+.

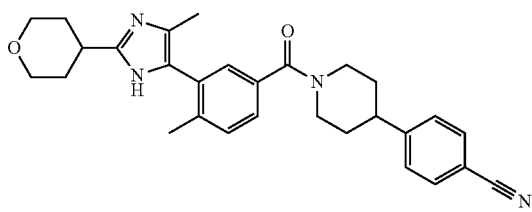 [SMILES: Cc1ccc(C(=O)N2CCC(c3ccc(C#N)cc3)CC2)cc1-c1[nH]c(C2CCOCC2)nc1C]

Compound 169. 4-(1-(4-Methyl-3-(4-methyl-2-(tetrahydro-2H-pyran-4-yl)-1H-imidazol-5-yl)benzoyl) piperidin-4-yl)benzonitrile The title compound was prepared using standard chemical manipulations and procedures similar to those used for the preparation of compound 164, except 4-methyl-3-(4-methyl-2-(tetrahydro-2H-pyran-4-yl)-1H-imidazol-5-yl) benzoic acid (compound 168.1) was used in place of 2,4-dimethyl-5-(4-methyl-2-(tetrahydro-2H-pyran-4-yl)-1H-imidazol-5-yl)benzoic acid (compound 164.2) and 4-(piperidin-4-yl)benzonitrile hydrochloride (compound 1.2) was used in place of 4-(azetidin-3-yl)benzonitrile hydrochloride (compound 5.2) m/z (ES+) 469 (M+H)+.

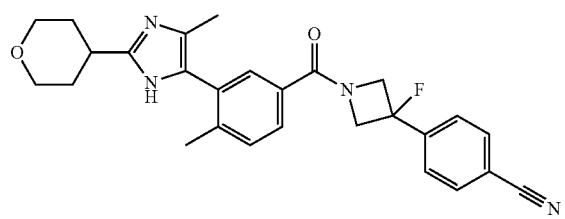 [SMILES: Cc1ccc(C(=O)N2CC(F)(c3ccc(C#N)cc3)C2)cc1-c1[nH]c(C2CCOCC2)nc1C]

Compound 170. 4-(3-Fluoro-1-(4-methyl-3-(4-methyl-2-(tetrahydro-2H-pyran-4-yl)-1H-imidazol-5-yl) benzoyl) azetidin-3-yl)benzonitrile The title compound was prepared using standard chemical manipulations and procedures similar to those used for the preparation of compound 164, except 4-methyl-3-(4-methyl-2-(tetrahydro-2H-pyran-4-yl)-1H-imidazol-5-yl) benzoic acid (compound 168.1) was used in place of 2,4-dimethyl-5-(4-methyl-2-(tetrahydro-2H-pyran-4-yl)-1H-imidazol-5-yl)benzoic acid (compound 164.2) and 4-(3-fluoroazetidin-3-yl)benzonitrile hydrochloride (compound 43.4) was used in place of 4-(azetidin-3-yl)benzonitrile hydrochloride (compound 5.2). m/z (ES+) 459 (M+H)+.

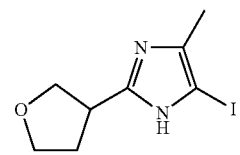

Compound 171.1. 5-Iodo-4-methyl-2-(tetrahydrofuran-3-yl)-1H-imidazole

The title compound was prepared using standard chemical manipulations and procedures similar to those used for the preparation of compound 159.2, except tetrahydrofuran-3-carbaldehyde was used in place of isobutyraldehyde.

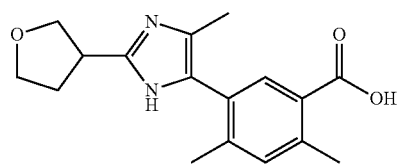 [SMILES: Cc1cc(C)c(-c2[nH]c(C3CCOC3)nc2C)cc1C(=O)O]

Compound 171.2. 2,4-Dimethyl-5-(4-methyl-2-(tetrahydrofuran-3-yl)-1H-imidazol-5-yl)benzoic acid The title compound was prepared using standard chemical manipulations and procedures similar to those used for the preparation of compound 5.7, except 5-iodo-4-methyl-2-(tetrahydrofuran-3-yl)-1H-imidazole (compound 171.1) was used in place of 5-iodo-2,4-dimethyl-1H-imidazole (compound 5.5) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4).

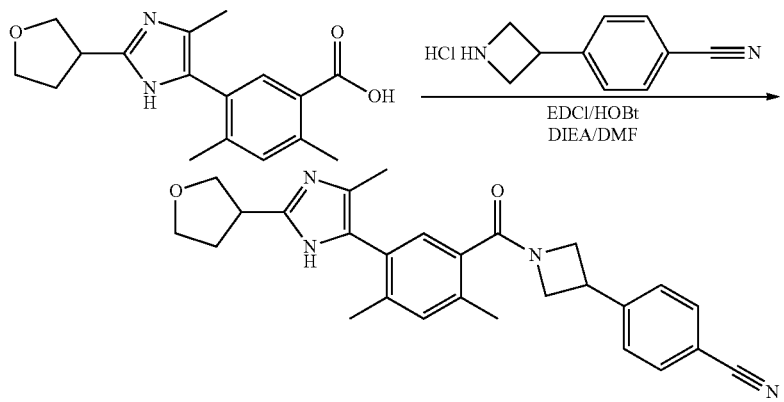

Compound 171. 4-(1-(2,4-Dimethyl-5-(5-methyl-2-(tetrahydrofuran-3-yl)-1H-imidazol-4-yl)benzoyl)azetidin-3-yl)benzonitrile The mixture of 2,4-dimethyl-5-(5-methyl-2-(tetrahydrofuran-3-yl)-1H-imidazol-4-yl)benzoic acid (compound 171.2, 100 mg, 0.30 mmol), 4-(azetidin-3-yl)benzonitrile hydrochloride (compound 5.2, 71 mg, 0.37 mmol), EDCI (95 mg, 0.50 mmol), HOBt (20 mg, 0.10 mmol) and DIEA (207 µL, 1.20 mmol) in DMF (5 mL) was stirred at room temperature for 16 hours. The reaction was concentrated under reduced pressure, diluted with saturated NaHCO$_3$ (10 mL) and extracted with EtOAc (30 mL). The organic phase was washed with brine (3×10 mL), dried over MgSO$_4$ and concentrated under reduce pressure. The residue was purified by preparative TLC with 6% methanol in dichloromethane and lyophilized to give 16 mg (12%) of the title compound as a white solid. m/z (ES+) 441 (M+H)$^+$.

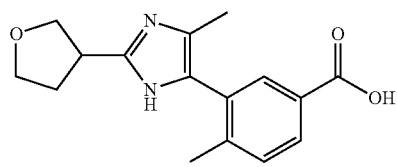 [SMILES: Cc1ccc(C(=O)O)cc1-c1[nH]c(C2CCOC2)nc1C]

Compound 172.1. 4-Methyl-3-(4-methyl-2-(tetrahydrofuran-3-yl)-1H-imidazol-5-yl)benzoic acid The title compound was prepared using standard chemical manipulations and procedures similar to those used for the preparation of compound 5.7, except 5-iodo-4-methyl-2-(tetrahydrofuran-3-yl)-1H-imidazole (compound 171.1) was used in place of 5-iodo-2,4-dimethyl-1H-imidazole (compound 5.5).

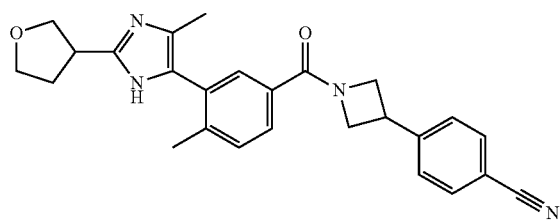 [SMILES: Cc1ccc(C(=O)N2CC(c3ccc(C#N)cc3)C2)cc1-c1[nH]c(C2CCOC2)nc1C]

Compound 172. 4-(1-(4-Methyl-3-(4-methyl-2-(tetrahydrofuran-3-yl)-1H-imidazol-5-yl)benzoyl)azetidin-3-yl)benzonitrile The title compound was prepared using standard chemical manipulations and procedures similar to those used for the preparation of compound 171, except 4-methyl-3-(4-methyl-2-(tetrahydrofuran-3-yl)-1H-imidazol-5-yl)benzoic acid (compound 172.1) was used in place of 2,4-dimethyl-5-(4-methyl-2-(tetrahydrofuran-3-yl)-1H-imidazol-5-yl)benzoic acid (compound 171.2). m/z (ES+) 427 (M+H)$^+$.

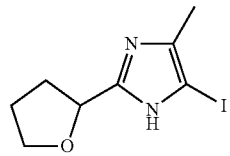

Compound 173.1. 5-Iodo-4-methyl-2-(tetrahydrofuran-2-yl)-1H-imidazole

The title compound was prepared using standard chemical manipulations and procedures similar to those used for the preparation of compound 159.2, except tetrahydrofuran-2-carbaldehyde was used in place of isobutyraldehyde. m/z (ES+) 279 (M+H)$^+$.

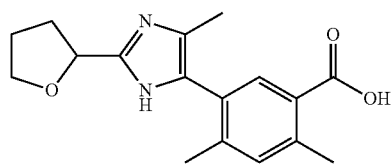 [SMILES: Cc1cc(C)c(-c2[nH]c(C3CCCO3)nc2C)cc1C(=O)O]

Compound 173.2. 2,4-Dimethyl-5-(4-methyl-2-(tetrahydrofuran-2-yl)-1H-imidazol-5-yl)benzoic acid The title compound was prepared using standard chemical manipulations and procedures similar to those used for the preparation of compound 5.7, except 5-iodo-4-methyl-2-(tetrahydrofuran-2-yl)-1H-imidazole (compound 173.1) was used in place of 5-iodo-2,4-dimethyl-1H-imidazole (compound 5.5) and methyl 2,4-dimethyl-5-(4,4,5,5-tetramethyl- 1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4).

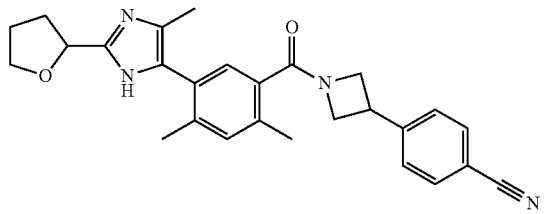 [SMILES: Cc1cc(C)c(-c2[nH]c(C3CCCO3)nc2C)cc1C(=O)N1CC(c2ccc(C#N)cc2)C1]

Compound 173. 4-(1-(2,4-Dimethyl-5-(5-methyl-2-(tetrahydrofuran-2-yl)-1H-imidazol-4-yl)benzoyl)azetidin-3-yl)benzonitrile The title compound was prepared using standard chemical manipulations and procedures similar to those used for the preparation of compound 171, except 2,4-dimethyl-5-(4-methyl-2-(tetrahydrofuran-2-yl)-1H-imidazol-5-yl)benzoic acid (compound 173.2) was used in place of 2,4-dimethyl-5-(4-methyl-2-(tetrahydrofuran-3-yl)-1H-imidazol-5-yl)benzoic acid (compound 171.2). m/z (ES+) 441 (M+H)+.

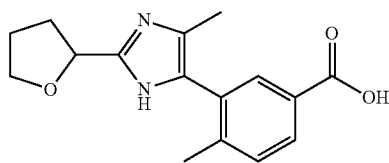 [SMILES: Cc1ccc(C(=O)O)cc1-c1[nH]c(C2CCCO2)nc1C]

Compound 174.1. 4-Methyl-3-(4-methyl-2-(tetrahydrofuran-2-yl)-1H-imidazol-5-yl)benzoic acid The title compound was prepared using standard chemical manipulations and procedures similar to those used for the preparation of compound 5.7, except 5-iodo-4-methyl-2-(tetrahydrofuran-2-yl)-1H-imidazole (compound 173.1) was used in place of 5-iodo-2,4-dimethyl-1H-imidazole (compound 5.5).

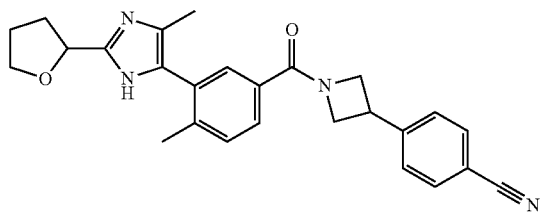 [SMILES: Cc1ccc(C(=O)N2CC(c3ccc(C#N)cc3)C2)cc1-c1[nH]c(C2CCCO2)nc1C]

Compound 174. 4-(1-(4-Methyl-3-(4-methyl-2-(tetrahydrofuran-2-yl)-1H-imidazol-5-yl)benzoyl)azetidin-3-yl)benzonitrile The title compound was prepared using standard chemical manipulations and procedures similar to those used for the preparation of compound 171, except 4-methyl-3-(4-methyl-2-(tetrahydrofuran-2-yl)-1H-imidazol-5-yl)benzoic acid (compound 174.1) was used in place of 2,4-dimethyl-5-(4-methyl-2(tetrahydrofuran-3-yl)-1H-imidazol-5-yl)benzoic acid (compound 171.2). m/z (ES+) 427 (M+H)+.

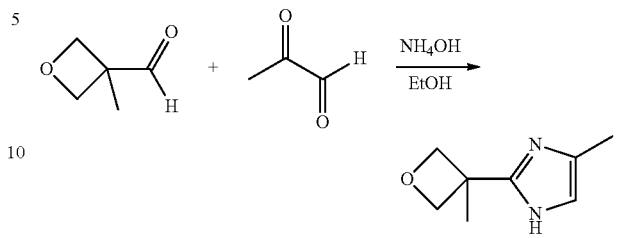

Compound 175.1. 4-Methyl-2-(3-methyloxetan-3-yl)-1H-imidazole

The title compound was prepared using standard chemical manipulations and procedures similar to those used for the preparation of compound 16.2, except 3-methyloxetane-3-carbaldehyde was used in place of acetaldehyde and 2-oxopropanal was used in place of 3,3,3-trifluoro-2-oxopropanal (compound 16.1). m/z (ES+) 153 (M+H)+.

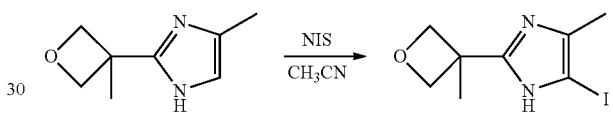

Compound 175.2. 5-Iodo-4-methyl-2-(3-methyloxetan-3-yl)-1H-imidazole

NIS (2.61 g, 11.58 mmol) was added portion-wise to a solution of 4-methyl-2-(3-methyloxetan-3-yl)-1H-imidazole (compound 175.1, 1.76 g, 11.58 mmol) in acetonitrile (60 mL). The mixture was stirred at room temperature for 1 hour, then was partitioned between EtOAc (300 mL) and water (80 mL). The organic layer was washed with saturated sodium thiosulfate (50 mL), brine (50 mL), dried (MgSO4) and concentrated under reduced pressure to give the title compound as a light yellow solid (3.0 g, 93%). m/z (ES+) 279 (M+H)+.

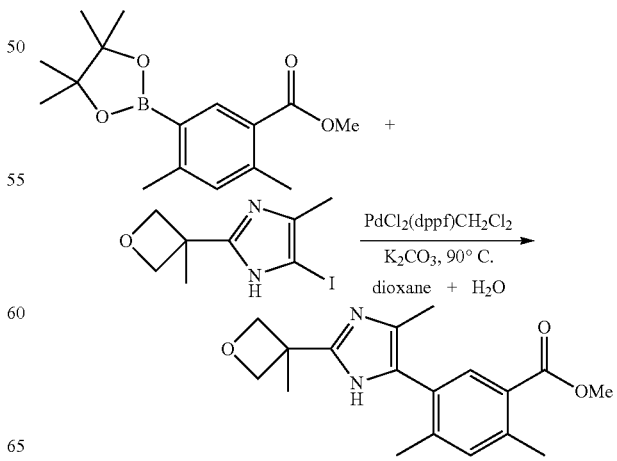

Compound 175.3. Methyl 2,4-dimethyl-5-(4-methyl-2-(3-methyloxetan-3-yl)-1H-imidazol-5-yl)benzoate The title compound was prepared using standard chemical manipulations and procedures similar to those used for the preparation of compound 5.6, except methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4) and 5-iodo-4-methyl-2-(3-methyloxetan-3-yl)-1H-imidazole (compound 175.2) was used in place of 5-iodo-2,4-dimethyl-1H-imidazole (compound 5.5). m/z (ES+) 315 (M+H)$^+$.

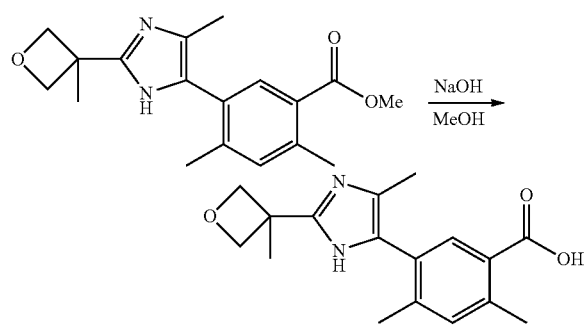

Compound 175.4. 2,4-Dimethyl-5-(4-methyl-2-(3-methyloxetan-3-yl)-1H-imidazol-5-yl)benzoic acid The title compound was prepared using standard chemical manipulations and procedures similar to those used for the preparation of compound 5.7, except methyl 2,4-dimethyl-5-(4-methyl-2-(3-methyloxetan-3-yl)-1H-imidazol-5-yl)benzoate (compound 175.3) was used in place of methyl 3-(2,4-dimethyl-1H-imidazol-5-yl)-4-methylbenzoate (compound 5.6). m/z (ES+) 301 (M+H)$^+$.

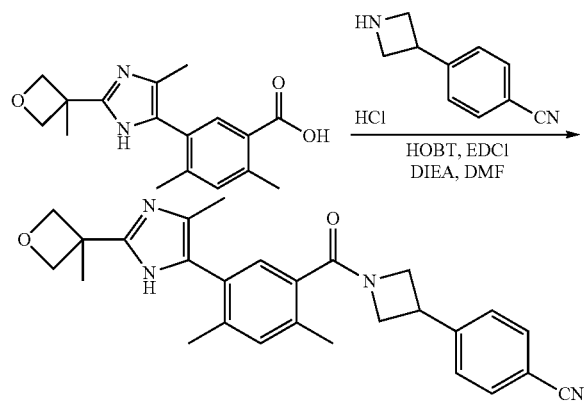

Compound 175. 4-(1-(2,4-Dimethyl-5-(4-methyl-2-(3-methyloxetan-3-yl)-1H-imidazol-5-yl)benzoyl)azetidin-3-yl)benzonitrile The title compound was prepared using standard chemical manipulations and procedures similar to those used for the preparation of compound 5, except 2,4-dimethyl-5-(4-methyl-2-(3-methyloxetan-3-yl)-1H-imidazol-5-yl)benzoic acid (compound 175.4) was used in place of 3-(2,4-dimethyl-1H-imidazol-5-yl)-4-methylbenzoic acid (compound 5.7). m/z (ES+) 441 (M+H)$^+$. $^1$H NMR (400 MHz, DMSO-d$_6$): δ 11.72 (br, 1H), 7.83 (d, J=8.4 Hz, 2H), 7.59 (d, J=8.0 Hz, 2H), 7.21 and 7.18 (2 singlets, Ar—H, 1H), 7.13 (s, 1H), 4.90 (d, J=4.8 Hz, 2H), 4.5-4.43 (m, 1H), 4.12 (d, J=5.6 Hz, 2H), 4.36-4.28 (m, 1H), 4.07-3.90 (m, 3H), 2.32 (s, 3H), 2.28 and 2.18 (2 singlets, CH$_3$, 3H), 2.13 and 2.00 (2 singlets, CH$_3$, 3H), 1.67 (s, 3H).

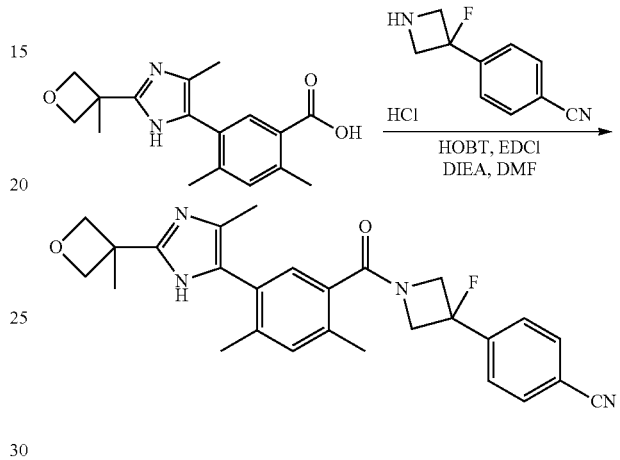

Compound 176. 4-(1-(2,4-Dimethyl-5-(4-methyl-2-(3-methyloxetan-3-yl)-1H-imidazol-5-yl)benzoyl)-3-fluoroazetidin-3-yl)benzonitrile The title compound was prepared using standard chemical manipulations and procedures similar to those used for the preparation of compound 5, except 2,4-dimethyl-5-(4-methyl-2-(3-methyloxetan-3-yl)-1H-imidazol-5-yl)benzoic acid (compound 175.4) was used in place of 3-(2,4-dimethyl-1H-imidazol-5-yl)-4-methylbenzoic acid (compound 5.7) and 4-(3-fluoroazetidin-3-yl)benzonitrile hydrochloride (compound 43.4) was used in place of 4-(azetidin-3-yl)benzonitrile hydrochloride (compound 5.2). m/z (ES+) 459 (M+H)$^+$. $^1$H NMR (400 MHz, DMSO-d$_6$): δ 11.73 (br, 1H), 7.95 (d, J=8.0 Hz, 2H), 7.76 (d, J=8.4 Hz, 2H), 7.25 and 7.24 (2 singlets, Ar—H, 1H), 7.19 and 7.16 (2 singlets, Ar—H, 1H), 4.94-4.86 (m, 2H), 4.57-4.35 (m, 6H), 2.36 and 2.34 (2 singlets, CH$_3$, 3H), 2.29 and 2.19 (2 singlets, CH$_3$, 3H), 2.14 and 2.00 (2 singlets, CH$_3$, 3H), 1.67 (s, 3H).

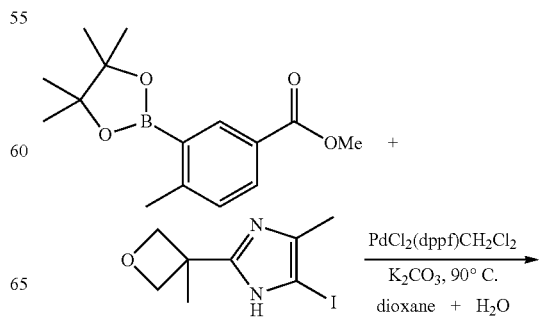

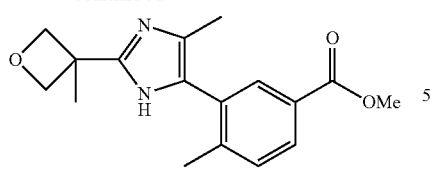

Compound 177.1. Methyl 4-methyl-3-(4-methyl-2-(3-methyloxetan-3-yl)-1H-imidazol-5-yl)benzoate The title compound was prepared using standard chemical manipulations and procedures similar to those used for the preparation of compound 5.6, except 5-iodo-4-methyl-2-(3-methyloxetan-3-yl)-1H-imidazole (compound 175.2) was used in place of 5-iodo-2,4-dimethyl-1H-imidazole (compound 5.5). m/z (ES+) 301 (M+H)+.

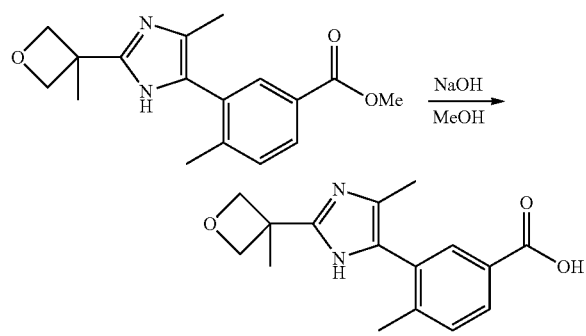

Compound 177.2. 4-Methyl-3-(4-methyl-2-(3-methyloxetan-3-yl)-1H-imidazol-5-yl)benzoic acid The title compound was prepared using standard chemical manipulations and procedures similar to those used for the preparation of compound 5.7, except methyl 4-methyl-3-(4-methyl-2-(3-methyloxetan-3-yl)-1H-imidazol-5-yl)benzoate (compound 177.1) was used in place of methyl 3-(2,4-dimethyl-1H-imidazol-5-yl)-4-methylbenzoate (compound 5.6). m/z (ES+) 287 (M+H)+.

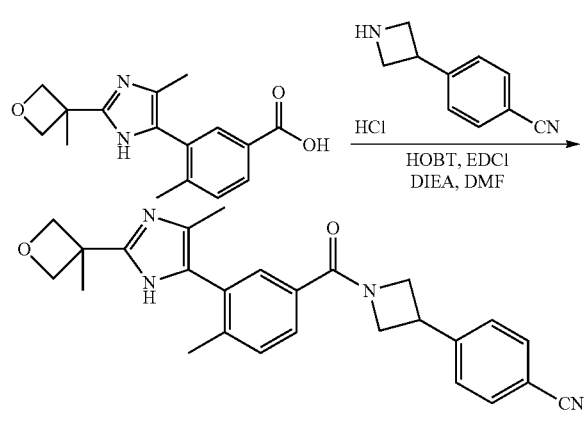

Compound 177. 4-(1-(4-Methyl-3-(4-methyl-2-(3-methyloxetan-3-yl)-1H-imidazol-5-yl)benzoyl)azetidin-3-yl)benzonitrile The title compound was prepared using standard chemical manipulations and procedures similar to those used for the preparation of compound 5, except 4-methyl-3-(4-methyl-2-(3-methyloxetan-3-yl)-1H-imidazol-5-yl)benzoic acid (compound 177.2) was used in place of 3-(2,4-dimethyl-1H-imidazol-5-yl)-4-methylbenzoic acid (compound 5.7). m/z (ES+) 427 (M+H)+. $^1$H NMR (400 MHz, DMSO-$d_6$): δ 11.79 (br, 1H), 7.84 (d, J=8.4 Hz, 2H), 7.63 (d, J=8.4 Hz, 2H), 7.60-7.46 (m, 2H), 7.42-7.28 (m, 1H), 4.91 (d, J=5.2 Hz, 2H), 4.76-4.67 (m, 1H), 4.52-4.36 (m, 4H), 4.09-3.97 (m, 2H), 2.34 and 2.24 (2 singlets, CH$_3$, 3H), 2.16 and 2.02 (2 singlets, CH$_3$, 3H), 1.68 (s, 3H).

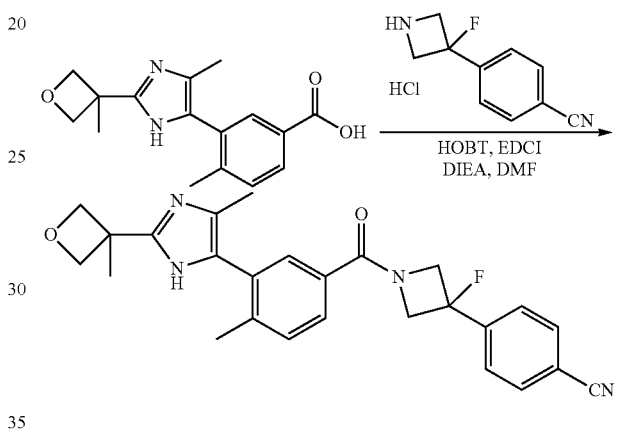

Compound 178. 4-(3-Fluoro-1-(4-methyl-3-(4-methyl-2-(3-methyloxetan-3-yl)-1H-imidazol-5-yl)benzoyl)azetidin-3-yl)benzonitrile The title compound was prepared using standard chemical manipulations and procedures similar to those used for the preparation of compound 5, except 4-methyl-3-(4-methyl-2-(3-methyloxetan-3-yl)-1H-imidazol-5-yl)benzoic acid (compound 177.2) was used in place of 3-(2,4-dimethyl-1H-imidazol-5-yl)-4-methylbenzoic acid (compound 5.7) and 4-(3-fluoroazetidin-3-yl)benzonitrile hydrochloride (compound 43.4) was used in place of 4-(azetidin-3-yl)benzonitrile hydrochloride (compound 5.2). m/z (ES+) 445 (M+H)+. $^1$H NMR (400 MHz, DMSO-$d_6$): δ 11.80 (br, 1H), 7.96 (dd, J=8.0 Hz, 2.4 Hz, 2H), 7.80 (d, J=8.4 Hz, 2H), 7.67-7.52 (m, 2H), 7.44-7.33 (m, 1H), 4.95-4.89 (m, 2H), 4.89-4.46 (m, 4H), 4.46-4.40 (m, 2H), 3.36 and 2.26 (2 singlets, CH$_3$, 3H), 2.17 and 2.03 (2 singlets, CH$_3$, 3H), 1.69 and 1.68 (2 singlets, CH$_3$, 3H).

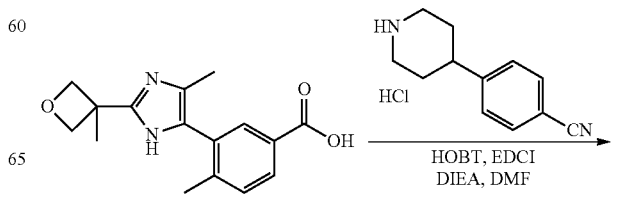

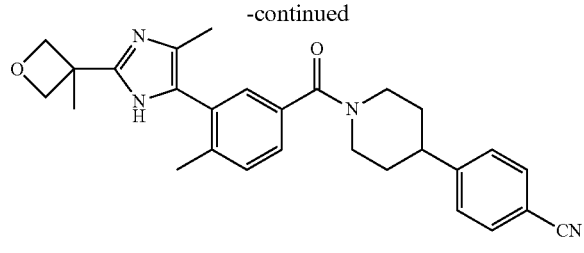

Compound 179. 4-(1-(4-Methyl-3-(4-methyl-2-(3-methyloxetan-3-yl)-1H-imidazol-5-yl)benzoyl)piperidin-4-yl)benzonitrile The title compound was prepared using standard chemical manipulations and procedures similar to those used for the preparation of compound 5, except 4-methyl-3-(4-methyl-2-(3-methyloxetan-3-yl)-1H-imidazol-5-yl)benzoic acid (compound 177.2) was used in place of 3-(2,4-dimethyl-1H-imidazol-5-yl)-4-methylbenzoic acid (compound 5.7) and 4-(piperidin-4-yl)benzonitrile hydrochloride (compound 1.2) was used in place of 4-(azetidin-3-yl)benzonitrile hydrochloride (compound 5.2). m/z (ES+) 455 (M+H)+. 1H NMR (400 MHz, DMSO-d6): δ 11.78 (br, 1H), 7.78 (d, J=8.0 Hz, 2H), 7.53 (d, J=8.0 Hz, 2H), 7.40-7.23 (m, 3H), 4.92 (t, J=6.0 Hz, 5.2 Hz, 2H), 4.78-4.52 (m, 1H), 4.43 (t, J=5.2 Hz, 4.8 Hz, 2H), 3.91-3.71 (m, 1H), 3.24-3.08 (m, 1H), 2.98-2.88 (m, 2H), 2.34 and 2.25 (2 singlets, CH3, 3H), 2.16 and 2.03 (2 singlets, amide rotamers, CH3, 3H), 1.91-1.59 (m, 4H), 1.69 and 1.68 (2 singlets, CH3, 3H).

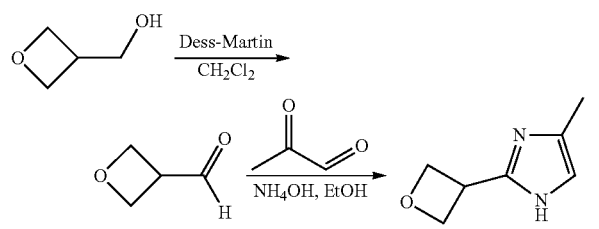

Compound 180.1. 4-Methyl-2-(oxetan-3-yl)-1H-imidazole

Dess-Martin reagent (4.33 g, 10.21 mmol) was added to a solution of oxetan-3-ylmethanol (0.9 g, 10.21 mmol) in CH2Cl2 (10 mL) at 0° C. The mixture was stirred at 0° C. for 30 minutes and at room temperature for 2 hours. CH2Cl2 was then removed under reduced pressure. The residue was dissolved in EtOH (10 mL). NH4OH (5 mL) was added, followed by 2-oxopropanal (40% in water, 2.76 mL, 15.32 mmol). The mixture was stirred at room temperature for 4 hours. Water (10 mL) was added to the mixture and the mixture was lyophilized. The dried residue was purified with column chromatography (2.5% MeOH to 5% MeOH in CH2Cl2) to give the title product as a brown oil (0.61 g, 43.3% for two steps). m/z (ES+) 139 (M+H)+.

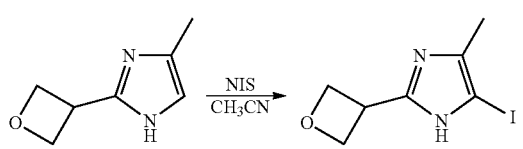

Compound 180.2. 5-Iodo-4-methyl-2-(oxetan-3-yl)-1H-imidazole

The title compound was prepared using standard chemical manipulations and procedures similar to those used for the preparation of compound 175.2, except 4-methyl-2-(oxetan-3-yl)-1H-imidazole (compound 180.1) was used in place of 4-methyl-2-(3-methyloxetan-3-yl)-1H-imidazole (compound 175.1). m/z (ES+) 265 (M+H)+.

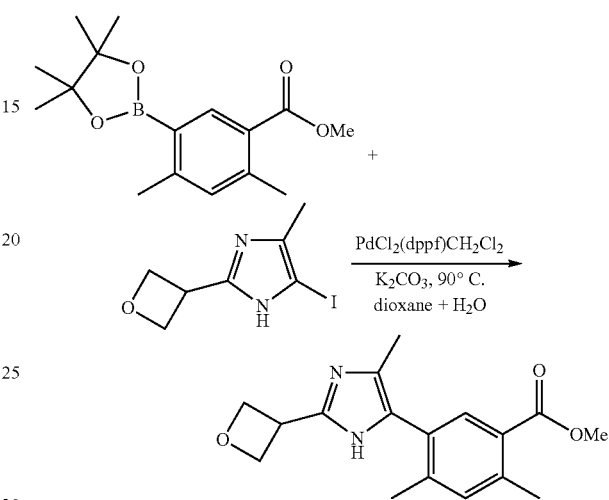

Compound 180.3. Methyl 2,4-dimethyl-5-(4-methyl-2-(oxetan-3-yl)-1H-imidazol-5-yl)benzoate The title compound was prepared using standard chemical manipulations and procedures similar to those used for the preparation of compound 5.6, except methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4) and 5-iodo-4-methyl-2-(oxetan-3-yl)-1H-imidazole (compound 180.2) was used in place of 5-iodo-2,4-dimethyl-1H-imidazole (compound 5.5). m/z (ES+) 301 (M+H)+.

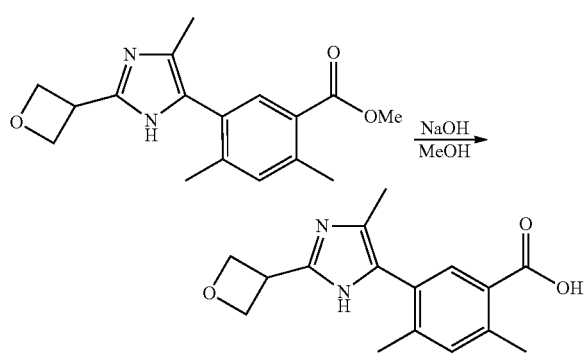

Compound 180.4. 2,4-Dimethyl-5-(4-methyl-2-(oxetan-3-yl)-1H-imidazol-5-yl)benzoic acid The title compound was prepared using standard chemical manipulations and procedures similar to those used for the preparation of compound 5.7, except methyl 2,4-dimethyl-5-(4-methyl-2-(oxetan-3-yl)-1H-imidazol-5-yl)benzoate (compound 180.3) was used in place of methyl 3-(2,4-dimethyl-1H-imidazol-5-yl)-4-methylbenzoate (compound 5.6). m/z (ES+) 287 (M+H)+.

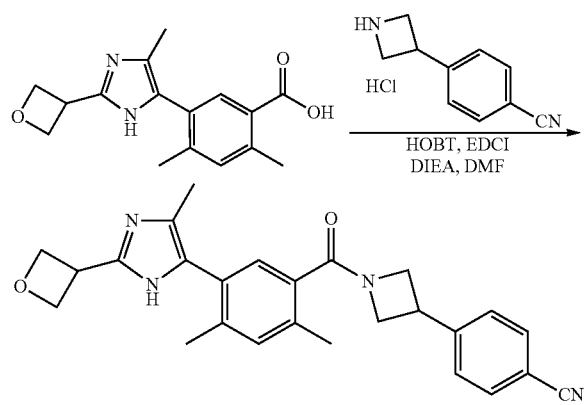

Compound 180. 4-(1-(2,4-Dimethyl-5-(4-methyl-2-(oxetan-3-yl)-1H-imidazol-5-yl)benzoyl)azetidin-3-yl)benzonitrile The title compound was prepared using standard chemical manipulations and procedures similar to those used for the preparation of compound 5, except 2,4-dimethyl-5-(4-methyl-2-(oxetan-3-yl)-1H-imidazol-5-yl)benzoic acid (compound 180.4) was used in place of 3-(2,4-dimethyl-1H-imidazol-5-yl)-4-methylbenzoic acid (compound 5.7). m/z (ES+) 427 (M+H)+. $^1$H NMR (400 MHz, DMSO-d$_6$): δ 11.81 (br, 1H), 7.84 (d, J=8.4 Hz, 2H), 7.60 (d, J=8.4 Hz, 2H), 7.26-7.10 (m, 2H), 4.87-4.75 (m, 4H), 4.51-4.42 (m, 1H), 4.37-4.21 (m, 2H), 4.07-3.91 (m, 3H), 2.33 (s, 3H), 2.27 and 2.19 (2 singlets, CH$_3$, 3H), 2.12 and 2.02 (2 singlets, CH$_3$, 3H).

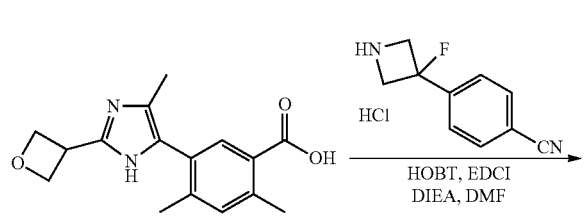

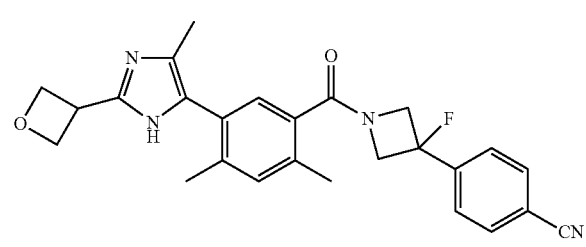

Compound 181. 4-(1-(2,4-Dimethyl-5-(4-methyl-2-(oxetan-3-yl)-1H-imidazol-5-yl)benzoyl)-3-fluoro-azetidin-3-yl)benzonitrile The title compound was prepared using standard chemical manipulations and procedures similar to those used for the preparation of compound 5, except 2,4-dimethyl-5-(4-methyl-2-(oxetan-3-yl)-1H-imidazol-5-yl)benzoic acid (compound 180.4) was used in place of 3-(2,4-dimethyl-1H-imidazol-5-yl)-4-methylbenzoic acid (compound 5.7) and 4-(3-fluoroazetidin-3-yl)benzonitrile hydrochloride (compound 43.4) was used in place of 4-(azetidin-3-yl)benzonitrile hydrochloride (compound 5.2). m/z (ES+) 445 (M+H)+. $^1$H NMR (400 MHz, DMSO-d$_6$): δ 11.80 (br, 1H), 7.96 (d, J=8.4 Hz, 2H), 7.77 (d, J=8.0 Hz, 2H), 7.24 (s, 1H), 7.18 (d, J=7.2 Hz, 2H), 4.87-4.75 (m, 4H), 4.60-4.36 (m, 4H), 4.31-4.21 (m, 1H), 2.35 (s, CH3, 3H), 2.90 and 2.20 (2 singlets, CH$_3$, 3H), 2.13 and 2.02 (2 singlets, CH$_3$, 3H).

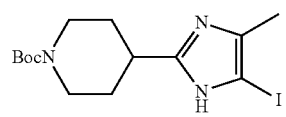 [SMILES: Cc1nc(C2CCN(C(=O)OC(C)(C)C)CC2)[nH]c1I]

Compound 182.1. tert-Butyl 4-(5-iodo-4-methyl-1H-imidazol-2-yl)piperidine-1-carboxylate The title compound was prepared using standard chemical manipulations and procedures similar to those used for the preparation of compound 159.2, except tert-butyl 4-formylpiperidine-1-carboxylate was used in place of isobutyraldehyde. m/z (ES+) 392 (M+H)+.

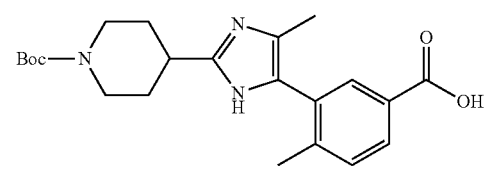 [SMILES: Cc1ccc(C(=O)O)cc1-c1[nH]c(C2CCN(C(=O)OC(C)(C)C)CC2)nc1C]

Compound 182.2. 3-(2-(1-(tert-Butoxycarbonyl)piperidin-4-yl)-4-methyl-1H-imidazol-5-yl)-4-methylbenzoic acid The title compound was prepared using standard chemical manipulations and procedures similar to those used for the preparation of compound 5.7, except tert-butyl 4-(5-iodo-4-methyl-1H-imidazol-2-yl)piperidine-1-carboxylate (compound 182.1) was used in place of 5-iodo-2,4-dimethyl-1H-imidazole (compound 5.5).

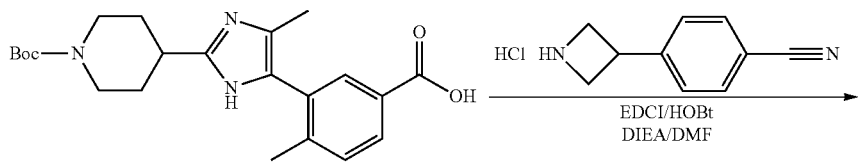

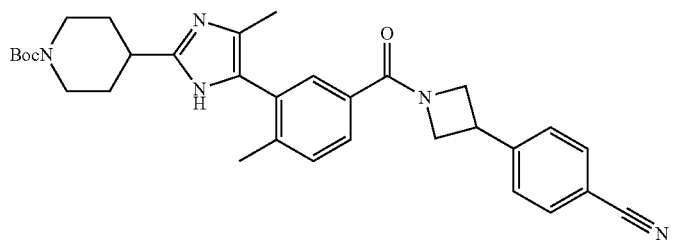

Compound 182.3. tert-Butyl 4-(4-(5-(3-(4-cyano-phenyl)azetidine-1-carbonyl)-2-methylphenyl)-5-methyl-1H-imidazol-2-yl)piperidine-1-carboxylate A mixture of 3-(2-(1-(tert-butoxycarbonyl)piperidin-4-yl)-4-methyl-1H-imidazol-5-yl)-4-methylbenzoic acid (compound 182.2, 506 mg), 4-(azetidin-3-yl)benzonitrile hydrochloride (compound 5.2, 296 mg, 1.52 mmol), EDCI (315 mg, 1.65 mmol), HOBt (107 mg, 0.64 mmol) and DIEA (877 µL, 5.08 mmol) in DMF (25 mL) was stirred at room temperature for 16 hours. The reaction was concentrated under reduced pressure, diluted with saturated NaHCO₃ (20 mL) and extracted with EtOAc (50 mL). The organic phase was washed with brine (3×10 mL), dried over MgSO₄ and concentrated under reduced pressure. The residue was purified by preparative TLC with 8% methanol in dichloromethane to give 476 mg (69%) of the title compound as a foam. m/z (ES+) 540 (M+H)⁺.

Compound 182. 4-(1-(4-Methyl-3-(4-methyl-2-(1-methylpiperidin-4-yl)-1H-imidazol-5-yl) benzoyl) azetidin-3-yl)benzonitrile To a solution of tert-butyl 4-(4-(5-(3-(4-cyanophenyl) azetidine-1-carbonyl)-2-methylphenyl)-5-methyl-1H-imidazol-2-yl)piperidine-1-carboxylate (compound 182.3, 475 mg, 0.88 mmol) in 20 mL CH₂Cl₂, was added trifluoroacetic acid (4 mL). The reaction stirred for 1.5 hours and concentrated under reduced pressure, neutralized with 10 mL Na₂CO₃ (1M) and lyophilized to afford 4-(1-(4-methyl-3-(4-methyl-2-(piperidin-4-yl)-1H-imidazol-5-yl)benzoyl) azetidin-3-yl)benzonitrile. The mixture of 4-(1-(4-methyl-3-(4-methyl-2-(piperidin-4-yl)-1H-imidazol-5-yl) benzoyl) azetidin-3-yl)benzonitrile (135 mg, 0.31 mmol), formic acid (300 µL, 6.76 mmol), formaldehyde (37% in water, 300 µL, 3.41 mmol) and water (1.5 mL) was heated to reflux for 10 hours. The reaction was diluted with saturated NaHCO₃ until pH 9 and extracted with CH₂Cl₂ (3×20 mL). The residue was purified by preparative TLC with 10% methanol and 1% ammonium hydroxide in dichloromethane and lyophilized to give 43 mg (30% two steps) of the title compound as a white solid. m/z (ES+) 540 (M+H)⁺.

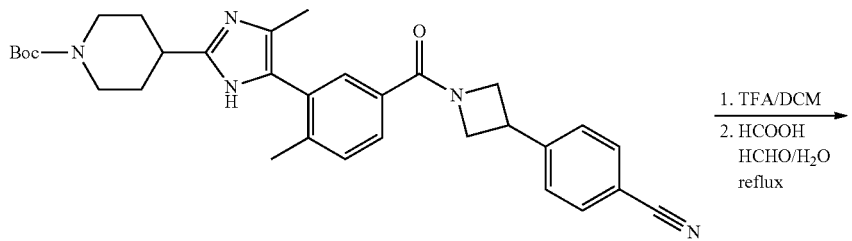

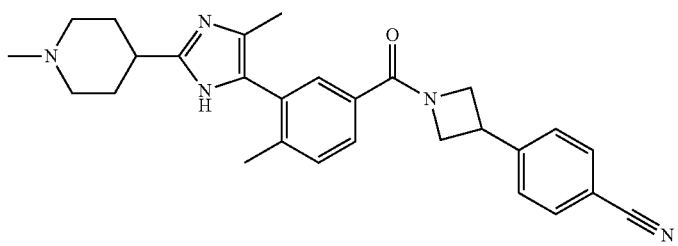

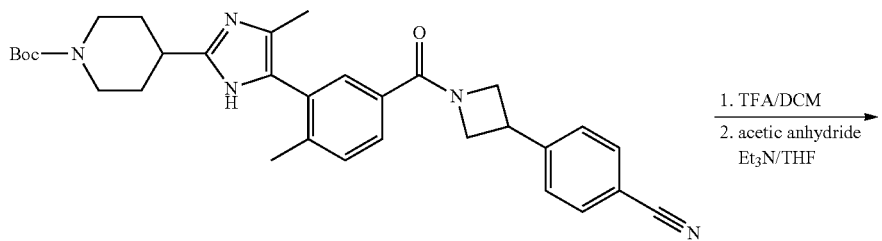

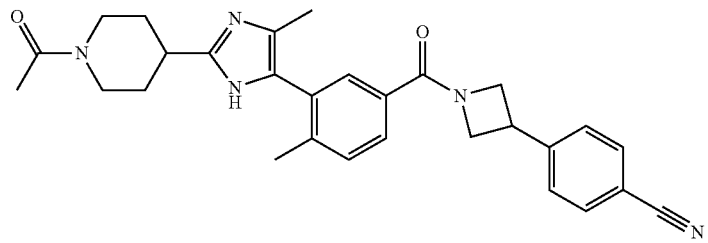

Compound 183. 4-(1-(3-(2-(1-Acetylpiperidin-4-yl)-4-methyl-1H-imidazol-5-yl)-4-methylbenzoyl) azetidin-3-yl)benzonitrile To a solution of tert-butyl 4-(4-(5-(3-(4-cyanophenyl)azetidine-1-carbonyl)-2-methylphenyl)-5-methyl-1H-imidazol-2-yl)piperidine-1-carboxylate (compound 182.3, 475 mg, 0.88 mmol) in 20 mL DCM, was added trifluoroacetic acid (4 mL). The reaction was stirred for 1.5 hours, concentrated under reduced pressure and neutralized with 10 mL Na$_2$CO$_3$ (1M) to obtain a crude product after lyophilization. A mixture of 4-(1-(4-methyl-3-(4-methyl-2-(piperidin-4-yl)-1H-imidazol-5-yl)benzoyl)azetidin-3-yl)benzonitrile (252 mg, 0.57 mmol), acetic anhydride (71 µL, 0.75 mmol) and triethylamine (120 µL, 0.86 mmol) was stirred at room temperature for 16 hours. The reaction was concentrated under reduced pressure, then diluted with saturated NaH$_2$PO$_4$ (20 mL) and extracted with EtOAc (3×20 mL). The organic phase was dried over MgSO$_4$ and concentrated under reduced pressure. The residue was purified by preparative TLC with 10% methanol in dichloromethane and lyophilized to give 235 mg (80%-2 steps) of the title compound as a white solid. m/z (ES+) 482 (M+H)$^+$.

Compound 184. Methyl 4-(5-(5-(3-(4-cyanophenyl) azetidine-1-carbonyl)-2-methylphenyl)-4-methyl-1H-imidazol-2-yl) piperidine-1-carboxylate To a solution of tert-butyl 4-(4-(5-(3-(4-cyanophenyl) azetidine-1-carbonyl)-2-methylphenyl)-5-methyl-1H-imidazol-2-yl) piperidine-1-carboxylate (compound 182.3, 227 mg, 0.42 mmol) in CH$_2$Cl$_2$ (10 mL), was added trifluoroacetic acid (2 ml). The reaction was stirred for 1.5 hours and concentrated under reduced pressure. The reaction mixture was neutralized with 2 mL Na$_2$CO$_3$ (1M) to afford the crude intermediate after lyophilization. A mixture of 4-(1-(4-methyl-3-(4-methyl-2-(piperidin-4-yl)-1H-imidazol-5-yl) benzoyl)azetidin-3-yl)benzonitrile (185 mg, 0.42 mmol) and diisopropyl ethylamine (363 µL, 2.1 mmol) were dissolved in DMF (6 mL). Methyl chloroformate (36 µL, 0.46 mmol) was added and the mixture was stirred at room temperature for 1 hour. The reaction was concentrated, diluted with saturated NaH$_2$PO$_4$ (20 mL) and extracted with EtOAc (3×20 ml). The organic phase was washed by brine, dried over MgSO$_4$ and concentrated under reduced pressure. The residue was purified by preparative TLC with 10% methanol

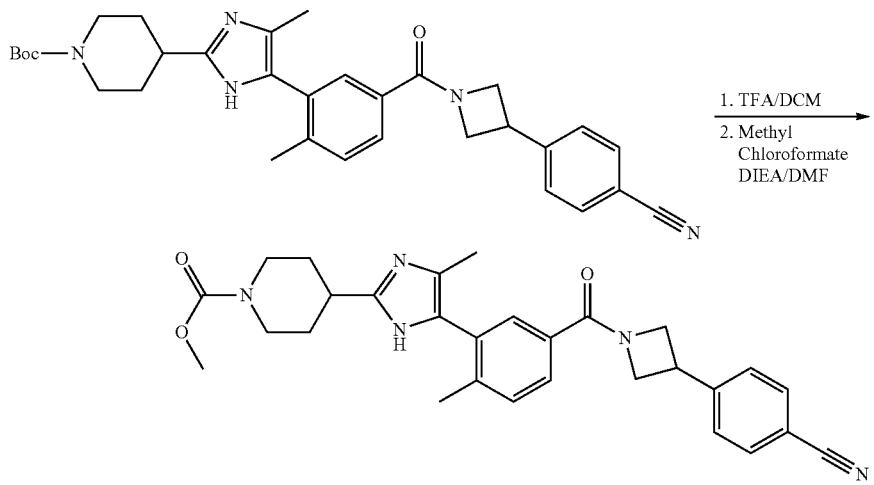

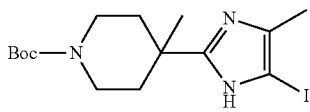

Compound 185.1. tert-Butyl 4-(5-iodo-4-methyl-1H-imidazol-2-yl)-4-methylpiperidine-1-carboxylate The title compound was prepared using standard chemical manipulations and procedures similar to those used for the preparation of compound 159.2, except tert-butyl 4-formyl-4-methylpiperidine-1-carboxylate was used in place of isobutyraldehyde. m/z (ES+) 406 (M+H)+.

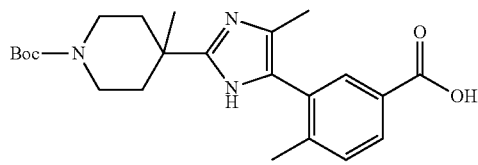 [SMILES: Cc1ccc(C(=O)O)cc1-c1[nH]c(C2(C)CCN(C(=O)OC(C)(C)C)CC2)nc1C]

Compound 185.2. 3-(2-(1-(tert-Butoxycarbonyl)-4-methylpiperidin-4-yl)-4-methyl-1H-imidazol-5-yl)-4-methylbenzoic acid The title compound was prepared using standard chemical manipulations and procedures similar to those used for the preparation of compound 5.7, except tert-butyl 4-(5-iodo-4-methyl-1H-imidazol-2-yl)-4-methylpiperidine-1-carboxylate (compound 185.1) was used in place of 5-iodo-2,4-dimethyl-1H-imidazole (compound 5.5).

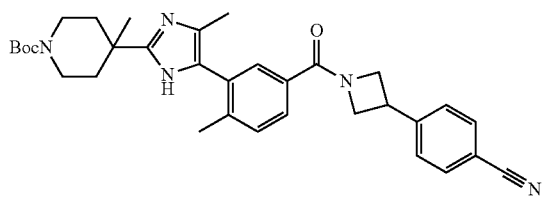 [SMILES: Cc1ccc(C(=O)N2CC(c3ccc(C#N)cc3)C2)cc1-c1[nH]c(C2(C)CCN(C(=O)OC(C)(C)C)CC2)nc1C]

Compound 185.3. tert-Butyl 4-(5-(5-(3-(4-cyanophenyl)azetidine-1-carbonyl)-2-methylphenyl)-4-methyl-1H-imidazol-2-yl)-4-methylpiperidine-1-carboxylate The title compound was prepared using standard chemical manipulations and procedures similar to those used for the preparation of compound 182.3, except 3-(2-(1-(tert-butoxycarbonyl)-4-methylpiperidin-4-yl)-4-methyl-1H-imidazol-5-yl)-4-methylbenzoic acid (compound 185.2) was used in place of 3-(2-(1-(tert-butoxycarbonyl)piperidin-4-yl)-4-methyl-1H-imidazol-5-yl)-4-methylbenzoic acid (compound 182.2).

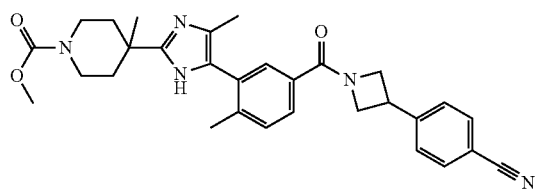 [SMILES: COC(=O)N1CCC(C)(c2nc(C)c(-c3cc(C(=O)N4CC(F)(c5ccc(C#N)cc5)C4)ccc3C)[nH]2)CC1]

Compound 185. Methyl 4-(5-(5-(3-(4-cyanophenyl)azetidine-1-carbonyl)-2-methylphenyl)-4-methyl-1H-imidazol-2-yl)-4-methylpiperidine-1-carboxylate The title compound was prepared using standard chemical manipulations and procedures similar to those used for the preparation of compound 184, except tert-butyl 4-(5-(5-(3-(4-cyanophenyl)azetidine-1-carbonyl)-2-methylphenyl)-4-methyl-1H-imidazol-2-yl)-4-methylpiperidine-1-carboxylate (compound 185.3) was used in place of tert-butyl 4-(4-(5-(3-(4-cyanophenyl)azetidine-1-carbonyl)-2-methylphenyl)-5-methyl-1H-imidazol-2-yl) piperidine-1-carboxylate (compound 182.3). m/z (ES+) 512 M+H+.

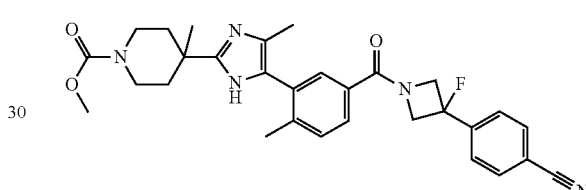

Compound 186. Methyl 4-(5-(5-(3-(4-cyanophenyl)-3-fluoroazetidine-1-carbonyl)-2-methylphenyl)-4-methyl-1H-imidazol-2-yl)-4-methylpiperidine-1-carboxylate The title compound was prepared using standard chemical manipulations and procedures similar to those used for the preparation of compound 184, except tert-butyl 4-(5-(5-(3-(4-cyanophenyl)azetidine-1-carbonyl)-2-methylphenyl)-4-methyl-1H-imidazol-2-yl)-4-methylpiperidine-1-carboxylate (compound 185.3) was used in place of tert-butyl 4-(4-(5-(3-(4-cyanophenyl)azetidine-1-carbonyl)-2-methylphenyl)-5-methyl-1H-imidazol-2-yl)piperidine-1-carboxylate (compound 182.3) and 4-(3-fluoroazetidin-3-yl)benzonitrile hydrochloride (compound 43.4) was used in place of 4-(azetidin-3-yl)benzonitrile hydrochloride (compound 5.2). m/z (ES+) 530 (M+H)+.

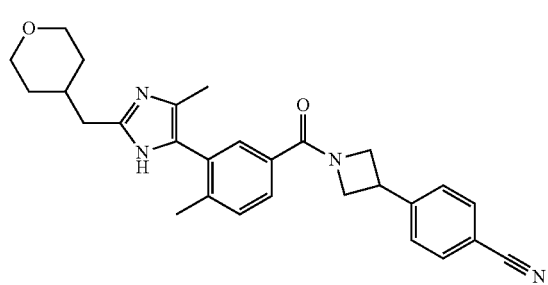 [SMILES: Cc1ccc(C(=O)N2CC(c3ccc(C#N)cc3)C2)cc1-c1[nH]c(CC2CCOCC2)nc1C]

in dichloromethane and lyophilized to give 141 mg (67%, over 2 steps) of the title compound as a white solid. m/z (ES+) 498 (M+H)+.

Compound 187. 4-(1-(4-Methyl-3-(4-methyl-2-((tetrahydro-2H-pyran-4-yl)methyl)-1H-imidazol-5-yl)benzoyl)azetidin-3-yl)benzonitrile The title compound was prepared using standard chemical manipulations and procedures similar to those used for the preparation of compound 159, except 2-(tetrahydro-2H-pyran-4-yl)acetaldehyde was used in place of isobutyraldehyde and methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1). m/z (ES+) 455 (M+H)$^+$.

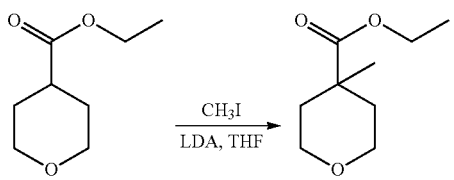

Compound 188.1. Ethyl 4-methyltetrahydro-2H-pyran-4-carboxylate

Into a 500-mL three neck round-bottom flask, which was purged and maintained with an inert atmosphere of nitrogen, was placed a solution of ethyl tetrahydro-2H-pyran-4-carboxylate (8 g, 50.6 mmol) in tetrahydrofuran (100 mL). This was followed by the addition of LDA (50 mL, 101.1 mmol, 2M in THF) dropwise at −78° C. and stirred for 3 h. To this was added a solution of CH$_3$I (9.5 mL, 151.9 mmol) in tetrahydrofuran (50 mL) dropwise at −78° C. The reaction mixture was stirred for 3 h at −78° C., then carefully quenched with 400 mL of NH$_4$Cl (sat.). The aqueous phase was extracted with 300 mL of ethyl acetate and the combined organic layers were dried over anhydrous sodium sulfate and concentrated under reduced pressure. This resulted in 8 g (92%) of the title compound as a yellow oil.

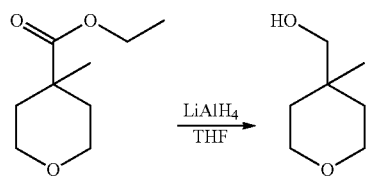

Compound 188.2. (4-Methyltetrahydro-2H-pyran-4-yl)methanol

Into a 100-mL three neck round-bottom flask, which was purged and maintained with an inert atmosphere of nitrogen, was placed a solution of ethyl 4-methyltetrahydro-2H-pyran-4-carboxylate (compound 188.1, 500 mg, 2.90 mmol) in tetrahydrofuran (12 mL). This was followed by the addition of lithium aluminum hydride (221 mg, 5.82 mmol) in portions at 0° C. The reaction mixture was stirred for 1 h at room temperature, then carefully quenched with 1.2 mL of H$_2$O, 1.2 mL of NaOH (15%), 3.5 mL of H$_2$O. The solids were removed by filtration and the filtrate was concentrated under reduced pressure. This resulted in 300 mg (crude) of the title compound as a yellow oil.

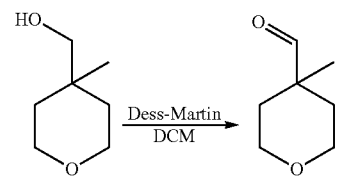

Compound 188.3. 4-Methyltetrahydro-2H-pyran-4-carbaldehyde

Into a 100-mL 3-neck round-bottom flask, was placed a solution of (4-methyltetrahydro-2H-pyran-4-yl)methanol (compound 188.2, 300 mg, 2.30 mmol) in dichloromethane (15 mL). Dess-Martin reagent (1.17 g, 2.76 mmol) was added to the reaction. The reaction mixture was stirred for 2 h at room temperature, then quenched with 15 mL of water. The aqueous phase was extracted with 20 mL of dichloromethane. The combined organic layers were dried over anhydrous sodium sulfate and concentrated under reduced pressure. This resulted in 200 mg (68%) of the title compound as a yellow oil.

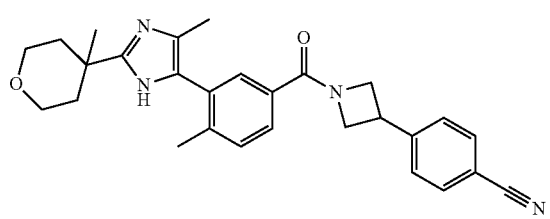 [SMILES: Cc1ccc(C(=O)N2CC(c3ccc(C#N)cc3)C2)cc1-c1[nH]c(C2(C)CCOCC2)nc1C]

Compound 188. 4-(1-(4-Methyl-3-(4-methyl-2-(4-methyltetrahydro-2H-pyran-4-yl)-1H-imidazol-5-yl)benzoyl)azetidin-3-yl)benzonitrile The title compound was prepared using standard chemical manipulations and procedures similar to those used for the preparation of compound 159, except 4-methyltetrahydro-2H-pyran-4-carbaldehyde (compound 188.3) was used in place of isobutyraldehyde and methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1). m/z (ES+) 455 (M+H)$^+$.

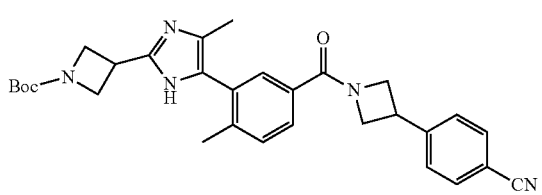 [SMILES: Cc1ccc(C(=O)N2CC(c3ccc(C#N)cc3)C2)cc1-c1[nH]c(C2CN(C(=O)OC(C)(C)C)C2)nc1C]

Compound 189.1. tert-Butyl 3-(5-(5-(3-(4-cyanophenyl)azetidine-1-carbonyl)-2-methylphenyl)-4-methyl-1H-imidazol-2-yl)azetidine-1-carboxylate The title compound was prepared using standard chemical manipulations and procedures similar to those used for the preparation of compound 182.3, except tert-butyl 3-formylazetidine-1-carboxylate was used in place of tert-butyl 4-formylpiperidine-1-carboxylate.

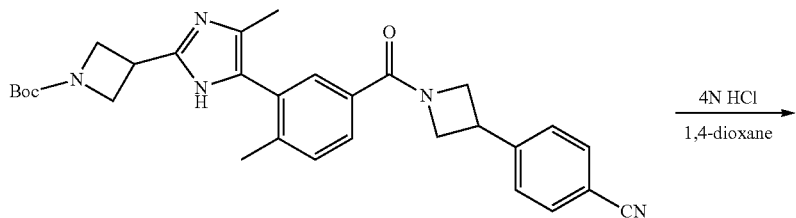

Compound 189.2. 4-(1-(3-(2-(Azetidin-3-yl)-4-methyl-1H-imidazol-5-yl)-4-methylbenzoyl)azetidin-3-yl)benzonitrile

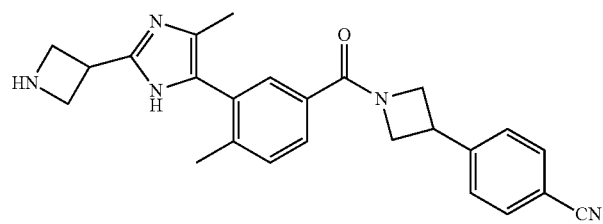

Into a 250-mL round-bottom flask, was placed a solution of tert-butyl 3-(5-(5-(3-(4-cyanophenyl)azetidine-1-carbonyl)-2-methylphenyl)-4-methyl-1H-imidazol-2-yl)azetidine-1-carboxylate (compound 189.1, 2 g, 3.91 mmol) in 1,4-dioxane (20 mL). Hydrogen chloride (4 M) (10 mL) was added to the reaction. The reaction mixture was stirred for 2 h at 30° C., then concentrated under reduced pressure. The pH of the solution was adjusted to 7-8 with sodium bicarbonate (sat.). The resulting mixture was concentrated under reduced pressure to give 800 mg (crude) of the title compound as a white solid.

Compound 189. 4-(1-(3-(2-(1-Acetylazetidin-3-yl)-4-methyl-1H-imidazol-5-yl)-4-methylbenzoyl)azetidin-3-yl)benzonitrile Into a 25-mL round-bottom flask, was placed a solution of 4-(1-(3-(2-(azetidin-3-yl)-4-methyl-1H-imidazol-5-yl)-4-methylbenzoyl)azetidin-3-yl)benzonitrile (compound 189.2, 80 mg, 0.19 mmol) in N,N-dimethylformamide (1 mL). Triethylamine (27 µL, 0.20 mmol) and acetic anhydride (19 µL, 0.20 mmol) were added to the reaction. The reaction mixture was stirred for 2 h at room temperature, then quenched with 10 mL of water. The aqueous phase was extracted with 3×3 mL of ethyl acetate and the combined organic extracts were concentrated under reduced pressure. The crude product (100 mg) was purified by Prep-HPLC with the following conditions (Prep-HPLC-020): Column, SunFire Prep C18 OBD Column, 5 m, 19*150 mm; mobile phase, Water with 50 mmol NH$_4$HCO$_3$ and MeCN (28% MeCN up to 40% in 7 min, up to 100% in 2 min, down to 28% in 1 min); Detector, Waters 2489 255 and 220 nm. This resulted in 32.8 mg (37%) of the title compound as a white solid. m/z (ES+) 454 (M+H)$^+$.

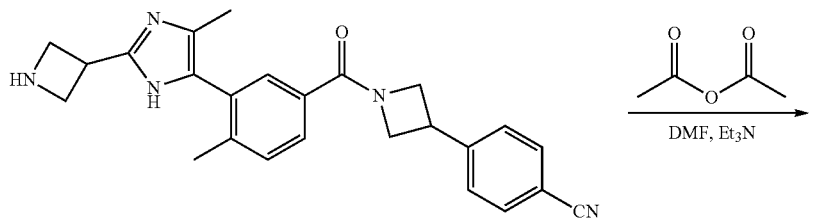

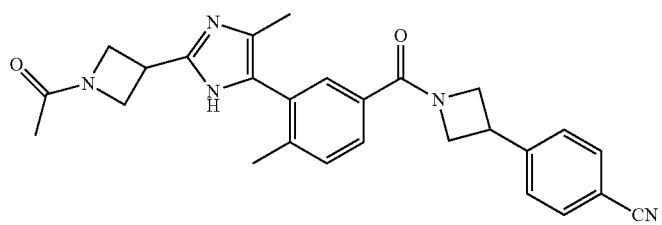

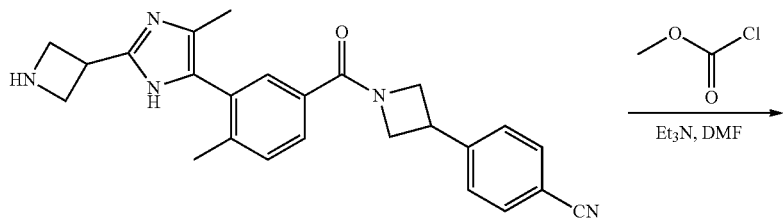

Compound 190. Methyl 3-(5-(5-(3-(4-cyanophenyl)azetidine-1-carbonyl)-2-methylphenyl)-4-methyl-1H-imidazol-2-yl)azetidine-1-carboxylate Compound 191. 4-(1-(4-Methyl-3-(4-methyl-2-(1-methylazetidin-3-yl)-1H-imidazol-5-yl)benzoyl)azetidin-3-yl)benzonitrile Into a 25-mL round-bottom flask, was placed a solution of 4-(1-(3-(2-(azetidin-3-yl)-4-methyl-1H-imidazol-5-yl)-4-methylbenzoyl)azetidin-3-yl)benzonitrile (compound 189.2, 100 mg, 0.24 mmol) in N,N-dimethylformamide (2 mL). Methyl chloroformate (33 μL, 0.42 mmol) and triethylamine (34 μL, 0.25 mmol) were added to the reaction. The reaction mixture was stirred for 2 h at room temperature, then was quenched with 10 mL of water. The aqueous phase was extracted with 3×5 mL of ethyl acetate. The combined organic layers were washed with 3×3 mL of brine and concentrated under reduced pressure. The residue was purified by silica gel chromatography with dichloromethane/methanol (10:1). The crude product (100 mg) was purified by Prep-HPLC with the following conditions (Prep-HPLC-020): Column, SunFire Prep C18 OBD Column, 5 m, 19*150 mm; mobile phase, Water with 50 mmol NH$_4$HCO$_3$ and MeCN (33.0% MeCN up to 45.0% in 7 min, up to 100.0% in 2 min, down to 33.0% in 1 min); Detector, Waters 2489, 254 and 220 nm. This resulted in 21.5 mg (19%) of the title compound as a white solid. m/z (ES+) 470 (M+H)$^+$.

Into a 50-mL round-bottom flask, was placed a solution of 4-(1-(3-(2-(azetidin-3-yl)-4-methyl-1H-imidazol-5-yl)-4-methylbenzoyl)azetidin-3-yl)benzonitrile (compound 189.2, 50 mg, 0.12 mmol) in tetrahydrofuran (1 mL). Formaldehyde (65 μL, 37% wt, 0.57 mmol) and NaBH$_3$CN (30 mg, 0.48 mmol) were added to the reaction. The reaction mixture was stirred for 1 h at room temperature. The reaction mixture was extracted with 3×3 mL of ethyl acetate and the combined organic extracts were washed with 3×1 mL of brine and concentrated under reduced pressure. The crude product (20 mg) was purified by Prep-HPLC with the following conditions (Prep-HPLC-020): Column, XBridge Prep C18 OBD Column, 5 μm, 19*150 mm; mobile phase, WATER WITH 0.03% NH$_3$H$_2$O and MeCN (26.0% MeCN up to 40.0% in 7 min, up to 100.0% in 2 min, down to 26.0% in 1 min); Detector, Waters 2489, 254 and 220 nm. This resulted in 1.8 mg (3%) of the title compound as a white solid. m/z (ES+) 426 (M+H)$^+$.

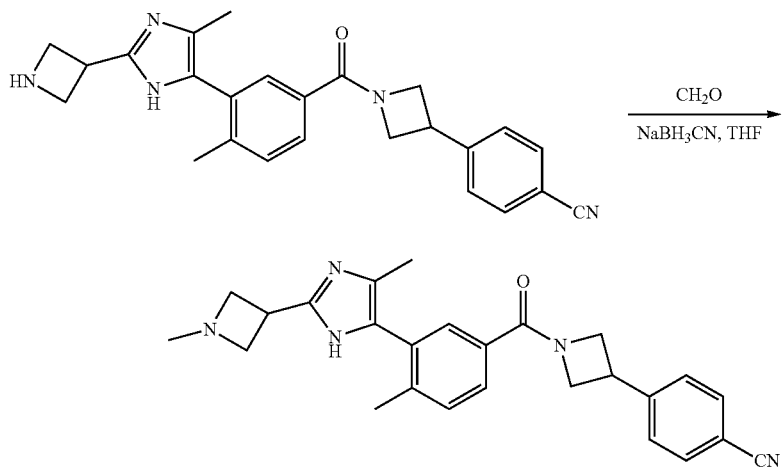

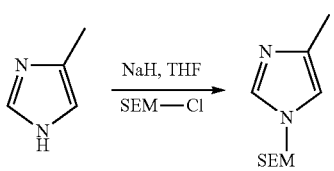

Compound 192.1. 4-Methyl-1-((2-(trimethylsilyl)ethoxy)methyl)-1H-imidazole

Into a 1-L three neck round-bottom flask, which was purged and maintained with an inert atmosphere of nitrogen, was placed a solution of 4-methyl-1H-imidazole (10 g, 121.8 mmol) in tetrahydrofuran (200 mL). This was followed by the addition of sodium hydride (7.32 g, 182.7 mmol, 60%) in several batches at 0° C. and stirred for 1 h at room temperature. To this was added SEM-Cl (30.5 g, 199.7 mmol) at 0° C. The mixture was stirred for 1 h at room temperature, then carefully quenched with 50 mL of brine. The aqueous phase was extracted with 1×800 mL of ethyl acetate. The organic layer was washed with 1×300 mL of brine, 2×300 mL of sodium bicarbonate (sat.), dried over anhydrous sodium sulfate and concentrated under reduced pressure. The residue was purified by silica gel chromatography with ethyl acetate/petroleum ether (1:1) ethyl acetate as eluent to furnish 9 g (35%) of the title compound as a yellow oil.

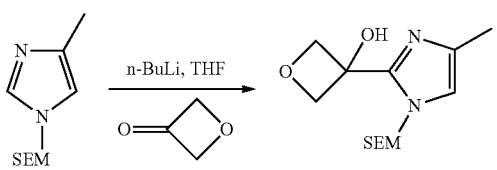 [SMILES: Cc1cn(COCC[Si](C)(C)C)cn1 ; O=C1COC1 ; Cc1cn(COCC[Si](C)(C)C)c(C2(O)COC2)n1]

Compound 192.2. 3-(4-Methyl-1-((2-(trimethylsilyl)ethoxy)methyl)-1H-imidazol-2-yl)oxetan-3-ol Into a 1000-mL three-neck round-bottom flask, which was purged and maintained with an inert atmosphere of nitrogen, was placed a solution of 4-methyl-1-((2-(trimethylsilyl)ethoxy)methyl)-1H-imidazole (compound 192.1, 9 g, 42.38 mmol) in tetrahydrofuran (200 mL). This was followed by the addition of n-BuLi (34 mL, 2.5 M in THF) dropwise at −78° C. and stirred for 1 h. To this was added a solution of oxetan-3-one (6.11 g, 84.79 mmol) in tetrahydrofuran (30 mL) dropwise at −78° C. The reaction mixture was stirred for 1 h at −78° C., then quenched with 50 mL of NH$_4$Cl (sat.). The aqueous phase was extracted with 1×600 mL of ethyl acetate. The organic layer was washed with 3×300 mL of brine, dried over anhydrous sodium sulfate and concentrated under reduced pressure. This resulted in 13 g (crude) of the title compound as a light yellow solid.

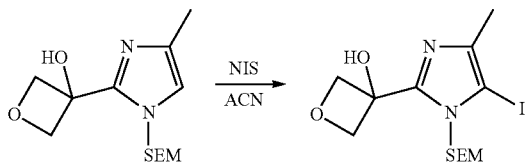

Compound 192.3. 3-(5-Iodo-4-methyl-1-((2-(trimethylsilyl)ethoxy)methyl)-1H-imidazol-2-yl)oxetan-3-ol Into a 100-mL round-bottom flask, was placed a solution of 3-(4-methyl-1-((2-(trimethylsilyl)ethoxy)methyl)-1H-imidazol-2-yl)oxetan-3-ol (compound 192.2, 200 mg, 0.70 mmol) in ACN (10 mL). NIS (237.7 mg, 1.06 mmol) was added to the reaction. The reaction mixture was stirred overnight at room temperature, then concentrated under reduced pressure. The reaction mixture was diluted with 40 mL of EtOAc. The organic layer was washed with 3×20 mL of brine, dried over anhydrous sodium sulfate and concentrated under reduced pressure. The residue was purified by silica gel chromatography with ethyl acetate/petroleum ether (2:3) as eluent to furnish 100 mg (35%) of the title compound as an orange oil.

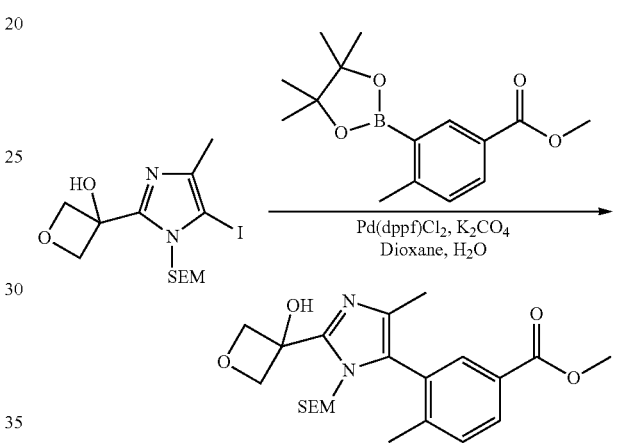

Compound 192.4. Methyl 3-(2-(3-hydroxyoxetan-3-yl)-4-methyl-1-((2-(trimethylsilyl)ethoxy)methyl)-1H-imidazol-5-yl)-4-methylbenzoate Into a 100-mL three neck round-bottom flask, which was purged and maintained with an inert atmosphere of nitrogen, was placed a solution of methyl 4-methyl-3-(tetramethyl-1,3,2-dioxaborolan-2-yl)benzoate (compound 5.4, 282.7 mg, 1.02 mmol) in dioxane (12 mL). A solution of K$_3$PO$_4$ (904.9 mg, 4.26 mmol) in water (1.2 mL), 3-(5-iodo-4-methyl-1-((2-(trimethylsilyl)ethoxy)methyl)-1H-imidazol-2-yl)oxetan-3-ol (compound 192.3, 350 mg, 0.85 mmol) and Pd(dppf)$_2$Cl$_2$ (62.4 mg, 0.09 mmol) were added to the reaction. The mixture was stirred for 7 h. The reaction mixture was cooled, then diluted with 60 mL of EtOAc. The solids were removed by filtration, the filtrate was dried over anhydrous sodium sulfate and concentrated under reduced pressure. The residue was purified by silica gel chromatography with ethyl acetate/petroleum ether (2:3) eluent to furnish 220 mg (60%) of the title compound as an orange oil.

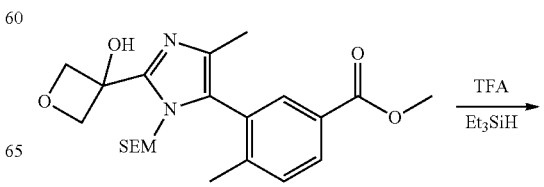

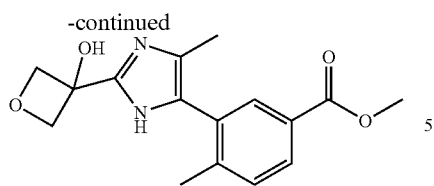

Compound 192.5. Methyl 3-(2-(3-hydroxyoxetan-3-yl)-4-methyl-1H-imidazol-5-yl)-4-methylbenzoate Into a 100-mL round-bottom flask, was placed methyl 3-(2-(3-hydroxyoxetan-3-yl)-4-methyl-1-((2-(trimethylsilyl)ethoxy)methyl)-1H-imidazol-5-yl)-4-methylbenzoate (compound 192.4, 180 mg, 0.42 mmol), Et₃SiH (1 mL) and trifluoroacetic acid (2 mL). The reaction mixture was stirred for 4 h at room temperature. The pH of the solution was adjusted to 8 with sodium hydroxide (1 M). The reaction mixture was diluted with 100 mL of brine. The aqueous phase was extracted with 2×30 mL of ethyl acetate, the combined organic layers were dried over anhydrous sodium sulfate and concentrated under reduced pressure. This resulted in 150 mg (crude) of the title compound as an orange oil.

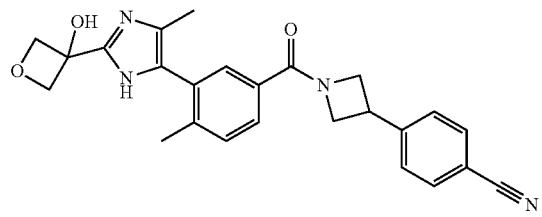 [SMILES: Cc1ccc(C(=O)N2CC(c3ccc(C#N)cc3)C2)cc1-c1[nH]c(C2(O)COC2)nc1C]

Compound 192. 4-(1-(3-(2-(3-Hydroxyoxetan-3-yl)-4-methyl-1H-imidazol-5-yl)-4-methylbenzoyl)azetidin-3-yl)benzonitrile The title compound was prepared using standard chemical manipulations and procedures similar to those used for the preparation of compound 5, except methyl 3-(2-(3-hydroxyoxetan-3-yl)-4-methyl-1H-imidazol-5-yl)-4-methylbenzoate (compound 192.5) was used in place of methyl 3-(2,4-dimethyl-1H-imidazol-5-yl)-4-methylbenzoate (compound 5.6). m/z (ES+) 429 (M+H)⁺.

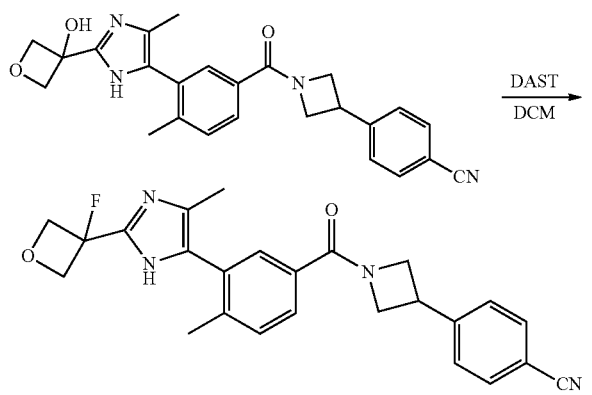

Compound 193. 4-(1-(3-(2-(3-Fluorooxetan-3-yl)-4-methyl-1H-imidazol-5-yl)-4-methylbenzoyl)azetidin-3-yl)benzonitrile Into a 50-mL three neck round-bottom flask, which was purged and maintained with an inert atmosphere of nitrogen, was placed a solution of 4-(1-(3-(2-(3-hydroxyoxetan-3-yl)-4-methyl-1H-imidazol-5-yl)-4-methylbenzoyl)azetidin-3-yl)benzonitrile (compound 192, 200 mg, 0.47 mmol) in dichloromethane (5 mL). This was followed by the addition of a solution of DAST (76.2 µL, 0.58 mmol) in dichloromethane (1 mL) dropwise at −78° C. The resulting solution was stirred for 1 h at room temperature, then quenched by the addition of 2 mL of sodium bicarbonate (sat.). The resulting solution was diluted with 60 mL of EtOAc and additional water. The organic layer was dried over anhydrous sodium sulfate and concentrated under reduced pressure. The residue was purified by silica gel chromatography with ethyl acetate as eluent. The crude product (50 mg) was purified by Prep-HPLC with the following conditions (Prep-HPLC-020): Column, SunFire Prep C18 OBD Column, 5 m, 19*150 mm; mobile phase, WATER WITH 0.05% TFA and MeCN (18.0% MeCN up to 28.0% in 9 min, up to 100.0% in 2 min, down to 18.0% in 1 min); Detector, Waters 2489, 254 and 220 nm. This resulted in 15.1 mg (8%) of the title compound as a white solid. m/z (ES+) 431 (M+H)⁺.

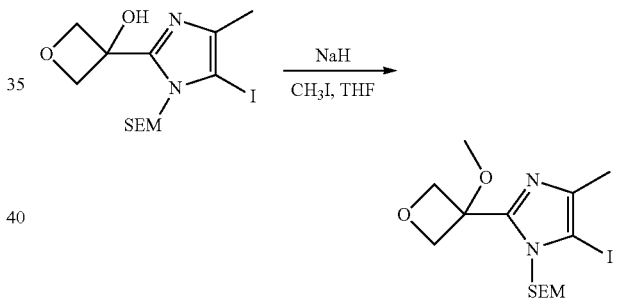

Compound 194.1. 5-Iodo-2-(3-methoxyoxetan-3-yl)-4-methyl-1-((2-(trimethylsilyl)ethoxy)methyl)-1H-imidazole Into a 100-mL round-bottom flask, was placed a solution of 3-(5-iodo-4-methyl-1-((2-(trimethylsilyl)ethoxy)methyl)-1H-imidazol-2-yl)oxetan-3-ol (compound 192.3, 800 mg, 1.95 mmol) in tetrahydrofuran (30 mL). This was followed by the addition of sodium hydride (156.2 mg, 3.9 mmol, 60%) at 0° C. and stirred for 20 min at room temperature. To this was added CH₃I (554.1 mg, 3.90 mmol) at 0° C. The resulting solution was stirred for 5 h at room temperature, then quenched with 30 mL of Na₂S₂O₃ (sat.). The aqueous phase was extracted with 3×40 mL of ethyl acetate, the combined organic layers were washed with 3×40 mL of brine, dried over anhydrous sodium sulfate, and concentrated under reduced pressure. The residue was purified by silica gel chromatography with ethyl acetate/petroleum ether (1:2) eluent to furnish 700 mg (85%) of the title compound as colorless oil.

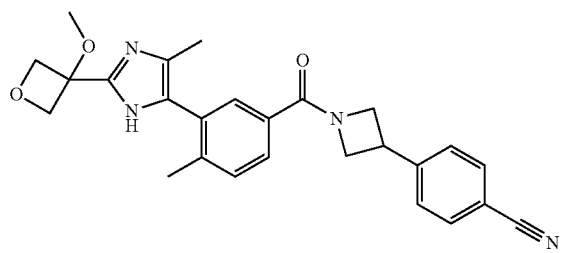 [SMILES: COC1(c2nc(C)c(-c3cc(C(=O)N4CC(c5ccc(C#N)cc5)C4)ccc3C)[nH]2)COC1]

Compound 194. 4-(1-(3-(2-(3-Methoxyoxetan-3-yl)-4-methyl-1H-imidazol-5-yl)-4-methylbenzoyl)azetidin-3-yl)benzonitrile The title compound was prepared using standard chemical manipulations and procedures similar to those used for the preparation of compound 192, except 5-iodo-2-(3-methoxyoxetan-3-yl)-4-methyl-1-((2-(trimethylsilyl)ethoxy)methyl)-1H-imidazole (compound 194.1) was used in place of 3-(5-iodo-4-methyl-1-((2-(trimethylsilyl)ethoxy)methyl)-1H-imidazol-2-yl)oxetan-3-ol (compound 192.3). m/z (ES+) 443 (M+H)+.

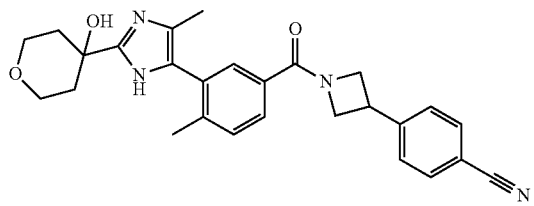 [SMILES: Cc1ccc(C(=O)N2CC(c3ccc(C#N)cc3)C2)cc1-c1[nH]c(C2(O)CCOCC2)nc1C]

Compound 195. 4-(1-(3-(2-(4-Hydroxytetrahydro-2H-pyran-4-yl)-4-methyl-1H-imidazol-5-yl)-4-methylbenzoyl)azetidin-3-yl)benzonitrile The title compound was prepared using standard chemical manipulations and procedures similar to those used for the preparation of compound 192, except dihydro-2H-pyran-4(3H)-one was used in place of oxetan-3-one. m/z (ES+) 457 (M+H)+.

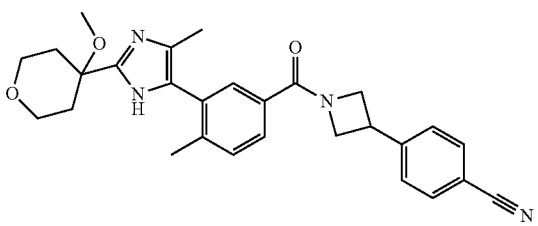 [SMILES: COC1(c2nc(C)c(-c3cc(C(=O)N4CC(c5ccc(C#N)cc5)C4)ccc3C)[nH]2)CCOCC1]

Compound 196. 4-(1-(3-(2-(4-Methoxytetrahydro-2H-pyran-4-yl)-4-methyl-1H-imidazol-5-yl)-4-methylbenzoyl)azetidin-3-yl)benzonitrile The title compound was prepared using standard chemical manipulations and procedures similar to those used for the preparation of compound 194, except dihydro-2H-pyran-4(3H)-one was used in place of oxetan-3-one. m/z (ES+) 471 (M+H).

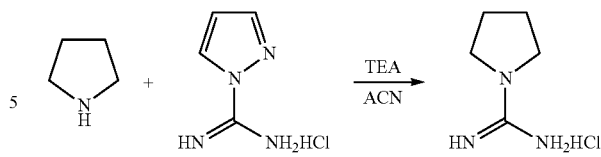

Compound 197.1. Pyrrolidine-1-carboximidamide hydrochloride

Into a 100-mL round-bottom flask, was placed a solution of pyrrolidine (5.8 mL, 70.30 mmol) in CH₃CN (30 mL). Triethylamine (9.8 mL, 70.17 mmol) and 1H-pyrazole-1-carboximidamide hydrochloride (10.2 g, 69.59 mmol) was added to the reaction. The reaction mixture was stirred overnight at 60° C. The product was collected by filtration to yield 7.5 g (71%) of the title compound as a white solid.

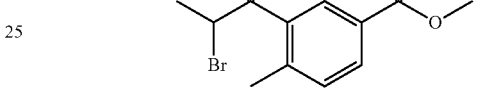

Compound 197.2. Methyl 3-(2-bromopropanoyl)-4-methylbenzoate

The title compound was prepared using standard chemical manipulations and procedures similar to those used for the preparation of compound 1.6, except 4-methylbenzoic acid was used in place of 2,4-dimethylbenzoic acid.

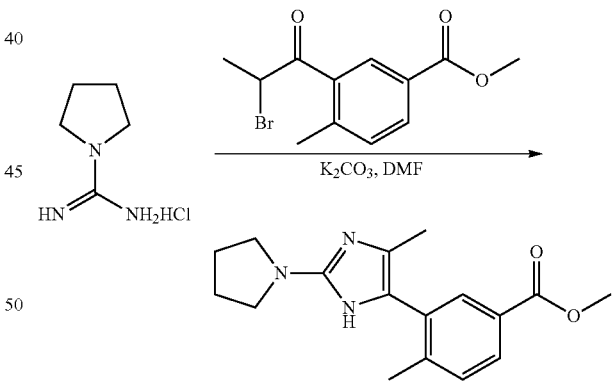

Compound 197.3. Methyl 4-methyl-3-(4-methyl-2-(pyrrolidin-1-yl)-1H-imidazol-5-yl)benzoate Into a 50-mL round-bottom flask, which was purged and maintained with an inert atmosphere of nitrogen, was placed a solution of methyl 3-(2-bromopropanoyl)-4-methylbenzoate (compound 197.2, 500.0 mg, 1.75 mmol) in N,N-dimethylformamide (15 mL). Pyrrolidine-1-carboximidamide hydrochloride (compound 197.1, 260.8 mg, 1.75 mmol) was treated with K₂CO₃, then added to the reaction. The reaction mixture was stirred for 1 h at 50° C. The reaction mixture was diluted with 30 mL of H₂O. The aqueous phase was extracted with 3×30 mL of ethyl acetate. The combined organic layers were dried over anhydrous sodium sulfate and concentrated under reduced pressure. The residue was purified by silica gel chromatography with PE/EtOAc (1:1)~EtOAc/methanol (15:1) as eluent to furnish 230.0 mg (44%) of the title compound as a dark blue solid.

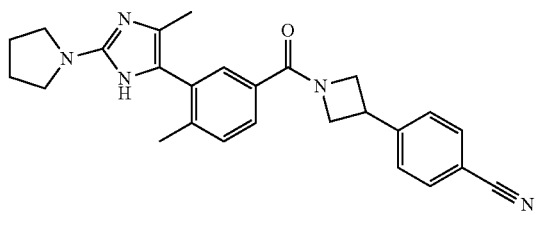 [SMILES: Cc1ccc(C(=O)N2CC(c3ccc(C#N)cc3)C2)cc1-c1[nH]c(N2CCCC2)nc1C]

Compound 197. 4-(1-(4-Methyl-3-(4-methyl-2-(pyrrolidin-1-yl)-1H-imidazol-5-yl)benzoyl)azetidin-3-yl)benzonitrile The title compound was prepared using standard chemical manipulations and procedures similar to those used for the preparation of compound 1, except methyl 4-methyl-3-(4-methyl-2-(pyrrolidin-1-yl)-1H-imidazol-5-yl)benzoate (compound 197.3) was used in place of methyl 5-(2,4-dimethyl-1H-imidazol-5-yl)-2,4-dimethylbenzoate (compound 1.7) and 4-(azetidin-3-yl)benzonitrile hydrochloride (compound 5.2) was used in place of 4-(piperidin-4-yl)benzonitrile hydrochloride (compound 1.2). m/z (ES+) 426 (M+H)+.

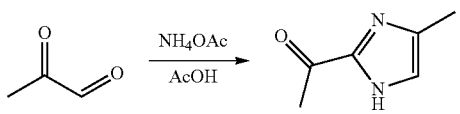

Compound 198.1. 1-(4-Methyl-1H-imidazol-2-yl)ethanone

Into a 500-mL round-bottom flask, was placed an aqueous solution of 2-oxopropanal (25.2 mL, 222.0 mmol, 50%). Ammonium acetate (85 g, 1.10 mol) and acetic acid (200 mL) were added to the reaction. The reaction mixture was stirred overnight at 100° C., then concentrated under reduced pressure. The residue was diluted with 300 mL of EtOAc. The organic layer was washed with 4×30 mL of brine, dried over anhydrous sodium sulfate and concentrated under reduced pressure. The residue was purified by a silica gel chromatography with ethyl acetate/hexane (1:1) as eluent to furnish 1.5 g (11%) of the title compound as a yellow solid.

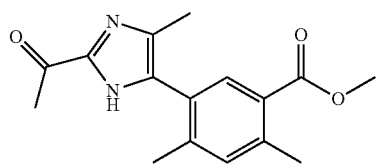 [SMILES: COC(=O)c1cc(-c2[nH]c(C(C)=O)nc2C)c(C)cc1C]

Compound 198.2. Methyl 5-(2-acetyl-4-methyl-1H-imidazol-5-yl)-2,4-dimethylbenzoate The title compound was prepared using standard chemical manipulations and procedures similar to those used for the preparation of compound 5.6, except methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4) and 1-(4-,ethyl-1H-imidazol-2-yl)ethanone (compound 198.1) was used in place of 2,4-dimethyl-1H-imidazole.

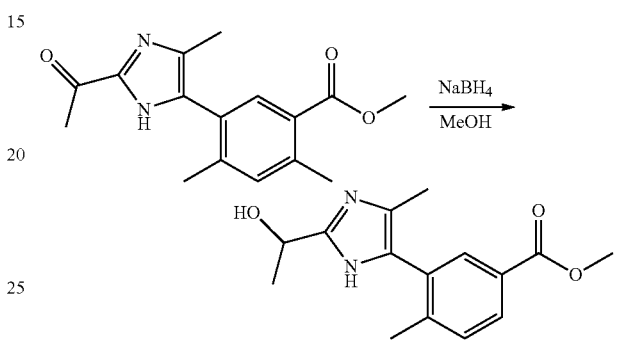

Compound 198.3. Methyl 5-(2-(1-hydroxyethyl)-4-methyl-1H-imidazol-5-yl)-2,4-dimethylbenzoate Into a 100-mL round-bottom flask, was placed a solution of methyl 5-(2-acetyl-4-methyl-1H-imidazol-5-yl)-2,4-dimethylbenzoate (compound 198.2, 300 mg, 1.10 mmol) in methanol (30 mL). This was followed by the addition of NaBH₄ (84 mg, 2.22 mmol) in portions at 0° C. The resulting solution was stirred for 1 h at room temperature, then carefully quenched with 1 mL of aqueous hydrogen chloride (2 M). The resulting mixture was concentrated under reduced pressure. This resulted in 330 mg (crude) of the title compound as a white solid.

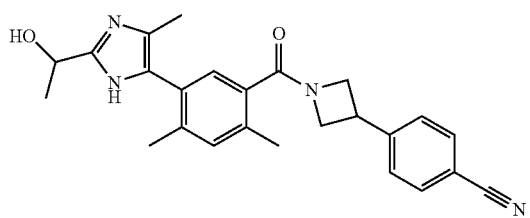

Compound 198. 4-(1-(5-(2-(1-Hydroxyethyl)-4-methyl-1H-imidazol-5-yl)-2,4-dimethylbenzoyl)azetidin-3-yl)benzonitrile The title compound was prepared using standard chemical manipulations and procedures similar to those used for the preparation of compound 5, except methyl 5-(2-(1-hydroxyethyl)-4-methyl-1H-imidazol-5-yl)-2,4-dimethylbenzoate (compound 198.3) was used in place of methyl 3-(2,4-dimethyl-1H-imidazol-5-yl)-4-methylbenzoate (compound 5.6). m/z (ES+) 415 (M+H)+.

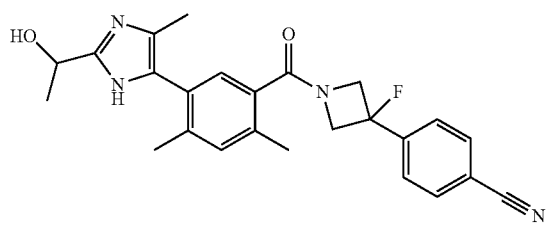

Compound 199. 4-(3-Fluoro-1-(5-(2-(1-hydroxyethyl)-4-methyl-1H-imidazol-5-yl)-2,4-dimethylbenzoyl)azetidin-3-yl)benzonitrile The title compound was prepared using standard chemical manipulations and procedures similar to those used for the preparation of compound 198, except 4-(3-fluoroazetidin-3-yl)benzonitrile hydrochloride (compound 43.4) was used in place of 4-(azetidin-3-yl)benzonitrile hydrochloride (compound 5.2). m/z (ES+) 433 (M+H)+.

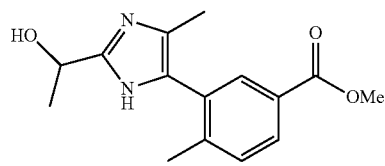 [SMILES: COC(=O)c1ccc(C)c(-c2[nH]c(C(C)O)nc2C)c1]

Compound 200.1. Methyl 3-(2-(1-hydroxyethyl)-4-methyl-1H-imidazol-5-yl)-4-methylbenzoate The title compound was prepared using standard chemical manipulations and procedures similar to those used for the preparation of compound 198.3, except methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1).

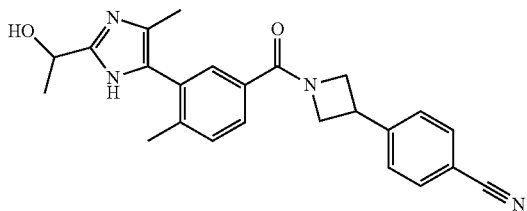 [SMILES: Cc1ccc(C(=O)N2CC(c3ccc(C#N)cc3)C2)cc1-c1[nH]c(C(C)O)nc1C]

Compound 200. 4-(1-(3-(2-(1-Hydroxyethyl)-4-methyl-1H-imidazol-5-yl)-4-methylbenzoyl)azetidin-3-yl)benzonitrile The title compound was prepared using standard chemical manipulations and procedures similar to those used for the preparation of compound 198, except methyl 3-(2-(1-hydroxyethyl)-4-methyl-1H-imidazol-5-yl)-4-methylbenzoate (compound 200.1) was used in place of methyl 5-(2-(1-hydroxyethyl)-4-methyl-1H-imidazol-5-yl)-2,4-dimethylbenzoate (compound 198.3). m/z (ES+) 401 (M+H)+.

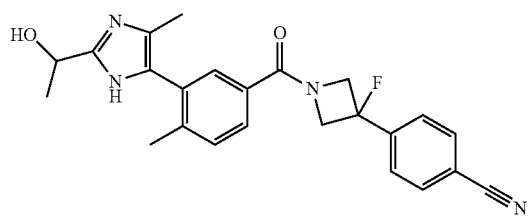 [SMILES: Cc1ccc(C(=O)N2CC(F)(c3ccc(C#N)cc3)C2)cc1-c1[nH]c(C(C)O)nc1C]

Compound 201. 4-(3-Fluoro-1-(3-(2-(1-hydroxyethyl)-4-methyl-1H-imidazol-5-yl)-4-methylbenzoyl)azetidin-3-yl)benzonitrile The title compound was prepared using standard chemical manipulations and procedures similar to those used for the preparation of compound 200, except 4-(3-fluoroazetidin-3-yl)benzonitrile hydrochloride (compound 43.4) was used in place of 4-(azetidin-3-yl)benzonitrile hydrochloride (compound 5.2). m/z (ES+) 419 (M+H)+.

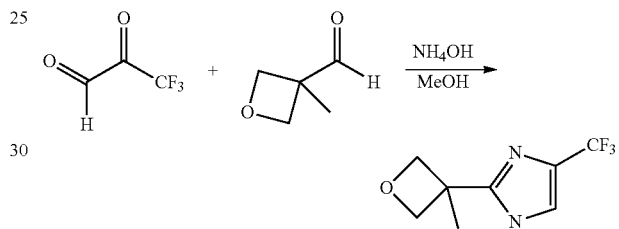

Compound 202.1. 2-(3-Methyloxetan-3-yl)-4-(trifluoromethyl)-1H-imidazole

The title compound was prepared using standard chemical manipulations and procedures similar to those used for the preparation of compound 16.2, except 3-methyloxetane-3-carbaldehyde was used in place of acetaldehyde. m/z (ES+) 207 (M+H)+.

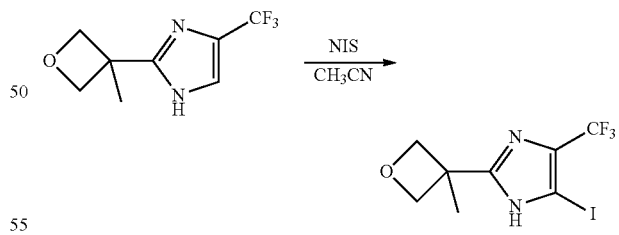

Compound 202.2. 5-Iodo-2-(3-methyloxetan-3-yl)-4-(trifluoromethyl)-1H-imidazole

The title compound was prepared using standard chemical manipulations and procedures similar to those used for the preparation of compound 175.2, except 2-(3-methyloxetan-3-yl)-4-(trifluoromethyl)-1H-imidazole (compound 202.1) was used in place of 4-methyl-2-(3-methyloxetan-3-yl)-1H-imidazole (compound 175.1). m/z (ES+) 333 (M+H)+.

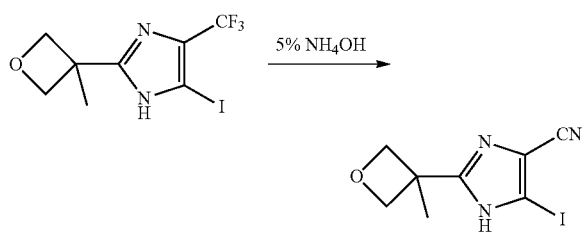

Compound 202.3. 5-Iodo-2-(3-methyloxetan-3-yl)-1H-imidazole-4-carbonitrile

The title compound was prepared using standard chemical manipulations and procedures similar to those used for the preparation of compound 16.3, except 5-iodo-2-(3-methyloxetan-3-yl)-4-(trifluoromethyl)-1H-imidazole (compound 202.2) was used in place of 2-methyl-4-(trifluoromethyl)-1H-imidazole (compound 16.2). m/z (ES+) 290 (M+H)$^+$.

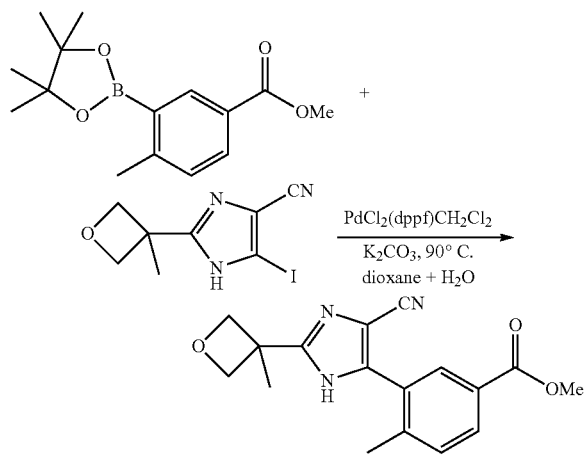

Compound 202.4. Methyl 3-(4-cyano-2-(3-methyloxetan-3-yl)-1H-imidazol-5-yl)-4-methylbenzoate The title compound was prepared using standard chemical manipulations and procedures similar to those used for the preparation of compound 5.6, except 5-iodo-2-(3-methyloxetan-3-yl)-1H-imidazole-4-carbonitrile (compound 202.3) was used in place of 5-iodo-2,4-dimethyl-1H-imidazole (compound 5.5). m/z (ES+) 312 (M+H)$^+$.

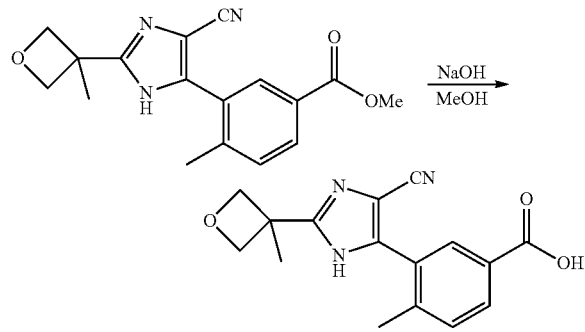

Compound 202.5. 3-(4-Cyano-2-(3-methyloxetan-3-yl)-1H-imidazol-5-yl)-4-methylbenzoic acid The title compound was prepared using standard chemical manipulations and procedures similar to those used for the preparation of compound 5.7, except methyl 3-(4-cyano-2-(3-methyloxetan-3-yl)-1H-imidazol-5-yl)-4-methylbenzoate (compound 202.4) was used in place of methyl 3-(2,4-dimethyl-1H-imidazol-5-yl)-4-methylbenzoate (compound 5.6). m/z (ES+) 298 (M+H)$^+$.

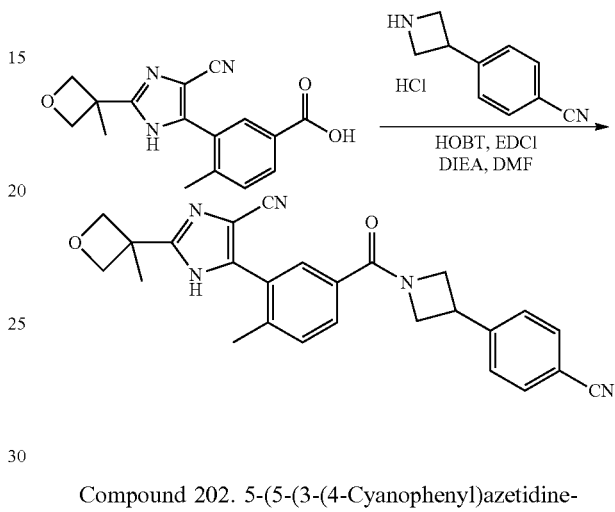

Compound 202. 5-(5-(3-(4-Cyanophenyl)azetidine-1-carbonyl)-2-methylphenyl)-2-(3-methyloxetan-3-yl)-1H-imidazole-4-carbonitrile The title compound was prepared using standard chemical manipulations and procedures similar to those used for the preparation of compound 5, except 3-(4-cyano-2-(3-methyloxetan-3-yl)-1H-imidazol-5-yl)-4-methylbenzoic acid (compound 202.5) was used in place of 3-(2,4-dimethyl-1H-imidazol-5-yl)-4-methylbenzoic acid (compound 5.7). m/z (ES+) 438 (M+H)$^+$. $^1$H NMR (400 MHz, DMSO-d$_6$): δ 13.13 (br, 1H), 7.85 (d, J=8.4 Hz, 2H), 7.73-7.66 (m, 2H), 7.63 (d, J=8.4 Hz, 2H), 7.47 (d, J=8.0 Hz, 1H), 4.95 (d, J=5.6 Hz, 2H), 4.78-4.70 (m, 1H), 4.57-4.45 (m, 2H), 4.46 (d, J=5.6 Hz, 2H), 4.11-4.01 (m, 2H), 2.39 (s, 3H), 1.71 (s, 3H).

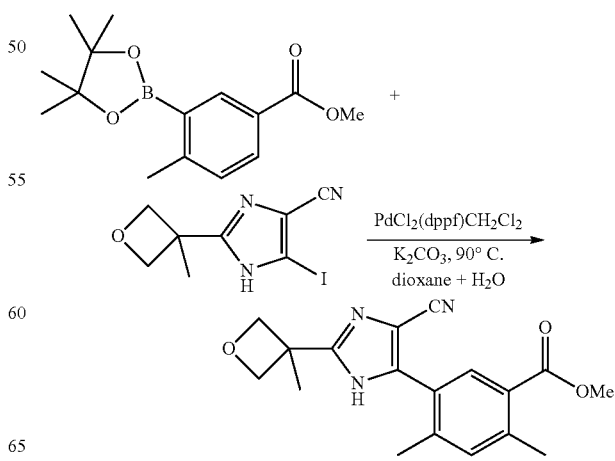

Compound 203.1. Methyl 5-(4-cyano-2-(3-methyl-oxetan-3-yl)-1H-imidazol-5-yl)-2,4-dimethylbenzoate The title compound was prepared using standard chemical manipulations and procedures similar to those used for the preparation of compound 5.6, except methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4) and 5-iodo-2-(3-methyloxetan-3-yl)-1H-imidazole-4-carbonitrile (compound 202.3) was used in place of 5-iodo-2,4-dimethyl-1H-imidazole (compound 5.5). m/z (ES+) 326 (M+H)$^+$.

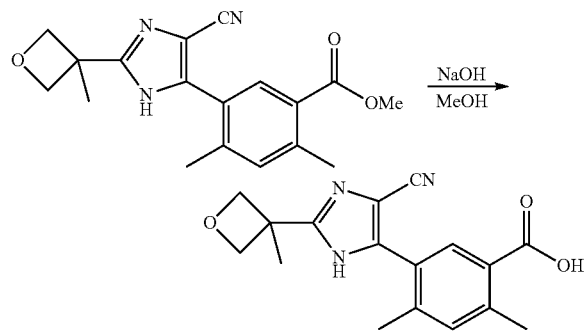

Compound 203.2. 5-(4-Cyano-2-(3-methyloxetan-3-yl)-1H-imidazol-5-yl)-2,4-dimethylbenzoic acid The title compound was prepared using standard chemical manipulations and procedures similar to those used for the preparation of compound 5.7, except methyl 5-(4-cyano-2-(3-methyloxetan-3-yl)-1H-imidazol-5-yl)-2,4-dimethylbenzoate (compound 203.1) was used in place of methyl 3-(2,4-dimethyl-1H-imidazol-5-yl)-4-methylbenzoate (compound 5.6). m/z (ES+) 312 (M+H)$^+$.

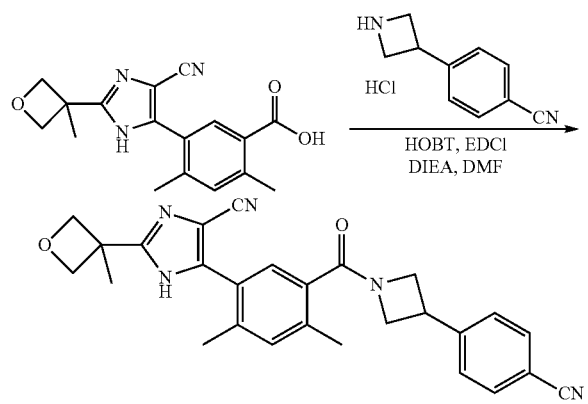

Compound 203. 5-(5-(3-(4-Cyanophenyl)azetidine-1-carbonyl)-2,4-dimethylphenyl)-2-(3-methyloxetan-3-yl)-1H-imidazole-4-carbonitrile The title compound was prepared using standard chemical manipulations and procedures similar to those used for the preparation of compound 5, except 5-(4-cyano-2-(3-methyloxetan-3-yl)-1H-imidazol-5-yl)-2,4-dimethylbenzoic acid (compound 203.2) was used in place of 3-(2,4-dimethyl-1H-imidazol-5-yl)-4-methylbenzoic acid (compound 5.7). m/z (ES+) 452 (M+H)$^+$. $^1$H NMR (400 MHz, DMSO-d$_6$): δ 13.01 (br, 1H), 7.84 (d, J=8.4 Hz, 2H), 7.60 (d, J=8.4 Hz, 2H), 7.38 (s, 1H), 7.24 (s, 1H), 4.94 (d, J=5.2 Hz, 2H), 4.53-4.32 (m, 4H), 4.09-3.96 (m, 3H), 2.36 (s, 3H), 2.35 (s, 3H), 1.68 (s, 3H).

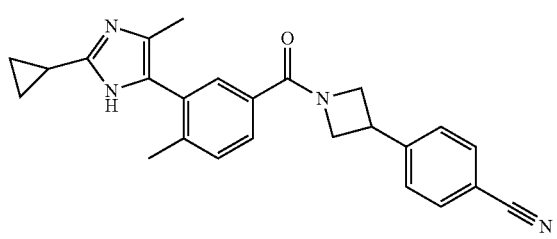 [SMILES: Cc1ccc(C(=O)N2CC(c3ccc(C#N)cc3)C2)cc1-c1[nH]c(C2CC2)nc1C]

Compound 204. 5-(5-(3-(4-Cyanophenyl)azetidine-1-carbonyl)-2-methylphenyl)-2-cyclopropyl-1H-imidazole-4-carbonitrile The title compound was prepared using standard chemical manipulations and procedures similar to those used for the preparation of compound 16, except cyclopropanecarbaldehyde was used in place of acetaldehyde and 4-(azetidin-3-yl)benzonitrile hydrochloride (compound 5.2) was used in place of 4-(piperidin-4-yl)benzonitrile hydrochloride (compound 1.2). m/z (ES+) 408 (M+H)$^+$.

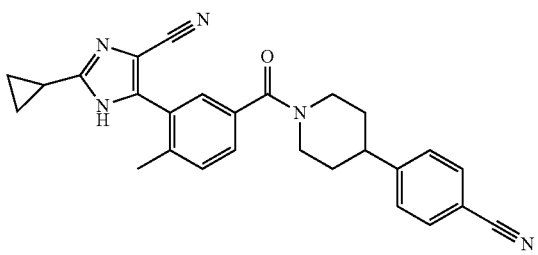 [SMILES: Cc1ccc(C(=O)N2CCC(c3ccc(C#N)cc3)CC2)cc1-c1[nH]c(C2CC2)nc1C#N]

Compound 205. 5-(5-(4-(4-Cyanophenyl)piperidine-1-carbonyl)-2-methylphenyl)-2-cyclopropyl-1H-imidazole-4-carbonitrile The title compound was prepared using standard chemical manipulations and procedures similar to those used for the preparation of compound 16, except cyclopropanecarbaldehyde was used in place of acetaldehyde. m/z (ES+) 436 (M+H)$^+$.

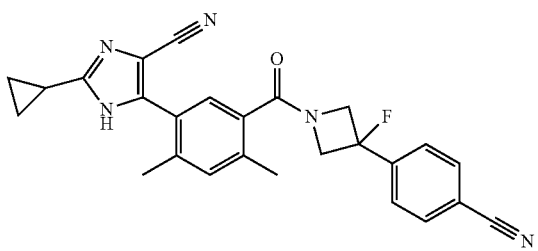 [SMILES: Cc1cc(C)c(-c2[nH]c(C3CC3)nc2C#N)cc1C(=O)N1CC(F)(c2ccc(C#N)cc2)C1]

Compound 206. 5-(5-(3-(4-Cyanophenyl)-3-fluoro-azetidine-1-carbonyl)-2,4-dimethylphenyl)-2-cyclopropyl-1H-imidazole-4-carbonitrile The title compound was prepared using standard chemical manipulations and procedures similar to those used for the preparation of compound 16, except cyclopropanecarbaldehyde was used in place of acetaldehyde and 4-(3-fluoroazetidin-3-yl)benzonitrile hydrochloride (compound 43.4) was used in place of 4-(piperidin-4-yl)benzonitrile hydrochloride (compound 1.2) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 440 (M+H)+.

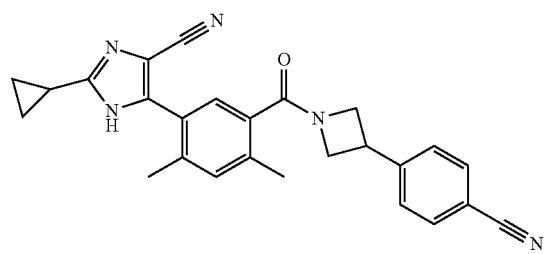 [SMILES: Cc1cc(C)c(-c2[nH]c(C3CC3)nc2C#N)cc1C(=O)N1CC(c2ccc(C#N)cc2)C1]

Compound 207. 5-(5-(3-(4-Cyanophenyl)azetidine-1-carbonyl)-2,4-dimethylphenyl)-2-cyclopropyl-1H-imidazole-4-carbonitrile The title compound was prepared using standard chemical manipulations and procedures similar to those used for the preparation of compound 16, except cyclopropanecarbaldehyde was used in place of acetaldehyde, 4-(azetidin-3-yl)benzonitrile hydrochloride (compound 5.2) was used in place of 4-(piperidin-4-yl)benzonitrile hydrochloride (compound 1.2) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 422 (M+H)+.

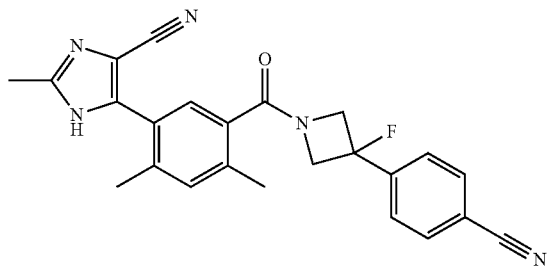 [SMILES: Cc1nc(C#N)c(-c2cc(C(=O)N3CC(F)(c4ccc(C#N)cc4)C3)c(C)cc2C)[nH]1]

Compound 208. 5-(5-(3-(4-Cyanophenyl)-3-fluoro-azetidine-1-carbonyl)-2,4-dimethylphenyl)-2-methyl-1H-imidazole-4-carbonitrile The title compound was prepared using standard chemical manipulations and procedures similar to those used for the preparation of compound 16, except 4-(3-fluoroazetidin-3-yl)benzonitrile hydrochloride (compound 43.4) was used in place of 4-(piperidin-4-yl)benzonitrile hydrochloride (compound 1.2) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 414 (M+H)+.

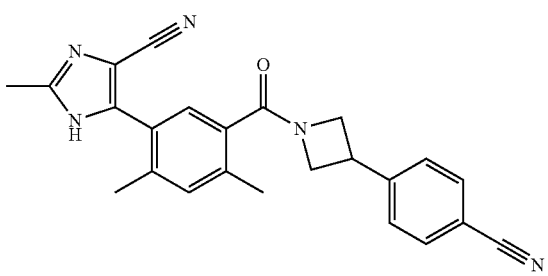 [SMILES: Cc1nc(C#N)c(-c2cc(C(=O)N3CC(c4ccc(C#N)cc4)C3)c(C)cc2C)[nH]1]

Compound 209. 5-(5-(3-(4-Cyanophenyl)azetidine-1-carbonyl)-2,4-dimethylphenyl)-2-methyl-1H-imidazole-4-carbonitrile The title compound was prepared using standard chemical manipulations and procedures similar to those used for the preparation of compound 16, except 4-(azetidin-3-yl)benzonitrile hydrochloride (compound 5.2) was used in place of 4-(piperidin-4-yl)benzonitrile hydrochloride (compound 1.2) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 396 (M+H)+.

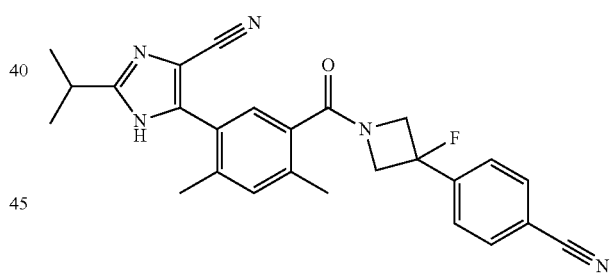

Compound 210. 5-(5-(3-(4-Cyanophenyl)-3-fluoro-azetidine-1-carbonyl)-2,4-dimethylphenyl)-2-isopropyl-1H-imidazole-4-carbonitrile The title compound was prepared using standard chemical manipulations and procedures similar to those used for the preparation of compound 16, except 4-(3-fluoroazetidin-3-yl)benzonitrile hydrochloride (compound 43.4) was used in place of 4-(piperidin-4-yl)benzonitrile hydrochloride (compound 1.2), methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate, and isobutyraldehyde was used in place of acetaldehyde. m/z (ES+) 442 (M+H)+.

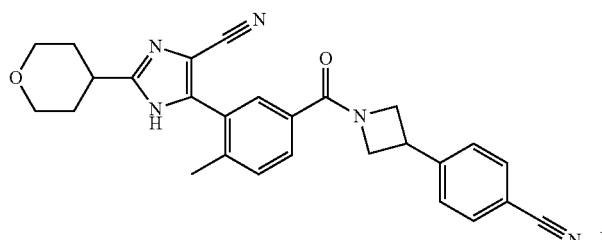

Compound 211. 5-(5-(3-(4-Cyanophenyl)azetidine-1-carbonyl)-2-methylphenyl)-2-(tetrahydro-2H-pyran-4-yl)-1H-imidazole-4-carbonitrile The title compound was prepared using standard chemical manipulations and procedures similar to those used for the preparation of compound 16, except 4-(azetidin-3-yl)benzonitrile hydrochloride (compound 5.2) was used in place of 4-(piperidin-4-yl)benzonitrile hydrochloride (compound 1.2) and tetrahydro-2H-pyran-4-carbaldehyde was used in place of acetaldehyde. m/z (ES+) 452 (M+H)$^+$.

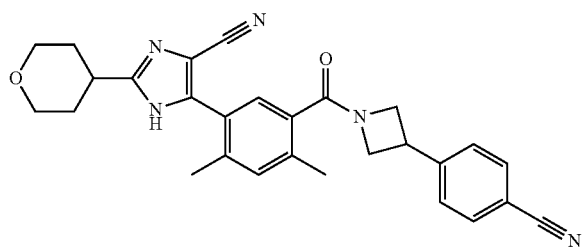 [SMILES: Cc1cc(C)c(-c2[nH]c(C3CCOCC3)nc2C#N)cc1C(=O)N1CC(c2ccc(C#N)cc2)C1]

Compound 212. 5-(5-(3-(4-Cyanophenyl)azetidine-1-carbonyl)-2,4-dimethylphenyl)-2-(tetrahydro-2H-pyran-4-yl)-1H-imidazole-4-carbonitrile The title compound was prepared using standard chemical manipulations and procedures similar to those used for the preparation of compound 16, except 4-(azetidin-3-yl)benzonitrile hydrochloride (compound 5.2) was used in place of 4-(piperidin-4-yl)benzonitrile hydrochloride (compound 1.2), tetrahydro-2H-pyran-4-carbaldehyde was used in place of acetaldehyde and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 466 (M+H)$^+$.

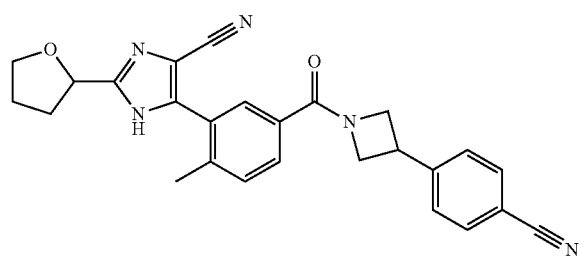 [SMILES: Cc1ccc(C(=O)N2CC(c3ccc(C#N)cc3)C2)cc1-c1[nH]c(C2CCCO2)nc1C#N]

Compound 213. 5-(5-(3-(4-Cyanophenyl)azetidine-1-carbonyl)-2-methylphenyl)-2-(tetrahydrofuran-2-yl)-1H-imidazole-4-carbonitrile The title compound was prepared using standard chemical manipulations and procedures similar to those used for the preparation of compound 16, 4-(azetidin-3-yl)benzonitrile hydrochloride (compound 5.2) was used in place of 4-(piperidin-4-yl)benzonitrile hydrochloride (compound 1.2) and tetrahydrofuran-2-carbaldehyde was used in place of acetaldehyde. m/z (ES+) 438 (M+H)$^+$.

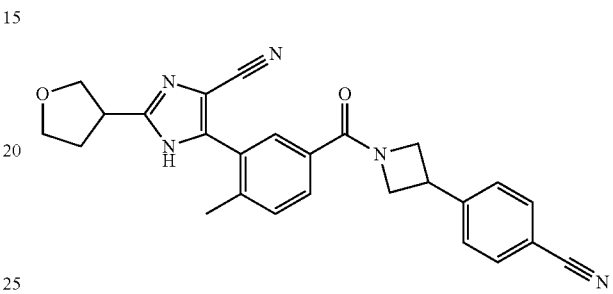

Compound 214. 5-(5-(3-(4-Cyanophenyl)azetidine-1-carbonyl)-2-methylphenyl)-2-(tetrahydrofuran-3-yl)-1H-imidazole-4-carbonitrile The title compound was prepared using standard chemical manipulations and procedures similar to those used for the preparation of compound 16, except 4-(azetidin-3-yl)benzonitrile hydrochloride (compound 5.2) was used in place of 4-(piperidin-4-yl)benzonitrile hydrochloride (compound 1.2) and tetrahydrofuran-3-carbaldehyde was used in place of acetaldehyde. m/z (ES+) 438 (M+H)$^+$.

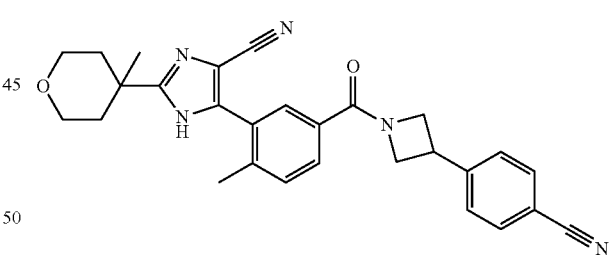

Compound 215. 5-(5-(3-(4-Cyanophenyl)azetidine-1-carbonyl)-2-methylphenyl)-2-(4-methyltetrahydro-2H-pyran-4-yl)-1H-imidazole-4-carbonitrile The title compound was prepared using standard chemical manipulations and procedures similar to those used for the preparation of compound 16, except 4-(azetidin-3-yl)benzonitrile hydrochloride (compound 5.2) was used in place of 4-(piperidin-4-yl)benzonitrile hydrochloride (compound 1.2) and 4-methyltetrahydro-2H-pyran-4-carbaldehyde (compound 188.3) was used in place of acetaldehyde. m/z (ES+) 466 (M+H)$^+$.

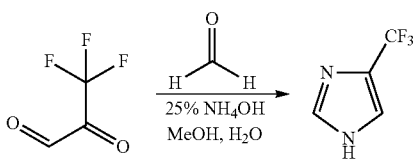

Compound 216.1. 4-(Trifluoromethyl)-1H-imidazole

Into a 1000-mL round-bottom flask, was placed a solution of 3,3,3-trifluoro-2-oxopropanal (143 mL, 111.1 mmol) in a solvent mixture of methanol and water (200/200 mL). An aqueous solution of formaldehyde (350 mL, 116.67 mmol, 35%) and ammonium hydroxide (30 mL, 25%) were added to the reaction. The resulting solution was stirred for 2 h at room temperature, then concentrated under reduced pressure. The solids were collected by filtration to give 2 g (13%) of the title compound as a white solid.

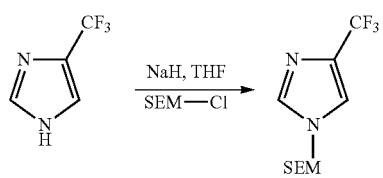 [SMILES: FC(F)(F)c1c[nH]cn1 ; C[Si](C)(C)CCOCCl ; C[Si](C)(C)CCOCn1cnc(C(F)(F)F)c1]

Compound 216.2. 4-(Trifluoromethyl)-1-((2-(trimethylsilyl)ethoxy)methyl)-1H-imidazole Into a 250-mL three neck round-bottom flask, which was purged and maintained with an inert atmosphere of nitrogen, was placed a solution of 4-(trifluoromethyl)-1H-imidazole (compound 216.1, 5 g, 36.74 mmol) in tetrahydrofuran (100 mL). This was followed by the addition of sodium hydride (1.6 g, 40.00 mmol, 60%) in portions at 0° C. and stirred for 1 h at 0° C. To this was added SEMCl (7.1 mL, 40.36 mmol) dropwise at 0° C. The resulting solution was stirred for 4 h at 0° C., then carefully quenched with 100 mL of brine. The pH of the solution was adjusted to 7-8 with hydrogen chloride (1 M). The aqueous phase was extracted with 2×100 mL of ethyl acetate and the combined organic layers were dried over anhydrous sodium sulfate and concentrated under reduced pressure. The residue was purified by silica gel chromatography with ethyl acetate/petroleum ether (1:5) as eluent to furnish 6 g (61%) of the title compound as a light yellow oil.

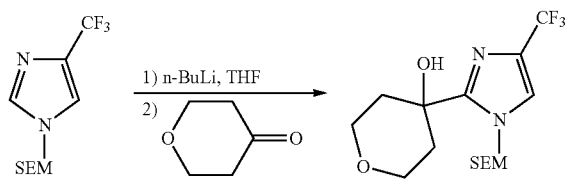

Compound 216.3. 4-(4-(Trifluoromethyl)-1-((2-(trimethylsilyl)ethoxy)methyl)-1H-imidazol-2-yl)tetrahydro-2H-pyran-4-ol Into a 100-mL three neck round-bottom flask, which was purged and maintained with an inert atmosphere of nitrogen, was placed a solution of 4-(trifluoromethyl)-1-((2-(trimethylsilyl)ethoxy)methyl)-1H-imidazole (compound 216.2, 5 g, 18.77 mmol) in tetrahydrofuran (50 mL). This was followed by the addition of n-butyllithium (9 mL, 22.5 mmol, 2.5N in hexane) dropwise at −78° C. and stirred for 1 h at −60° C. To this was added dihydro-2H-pyran-4(3H)-one (6 g, 59.93 mmol). The resulting solution was stirred for 4 h at 0° C. in an ice/salt bath, then quenched with 10 mL of water. The resulting solution was diluted with 100 mL of NH₄Cl (sat.). The aqueous phase was extracted with 2×100 mL of ethyl acetate. The combined organic layers were dried over anhydrous sodium sulfate and concentrated under reduced pressure. The residue was purified by silica gel chromatography with ethyl acetate/petroleum ether (1:4) as eluent to furnish 6 g (87%) of the title compound as a light yellow oil.

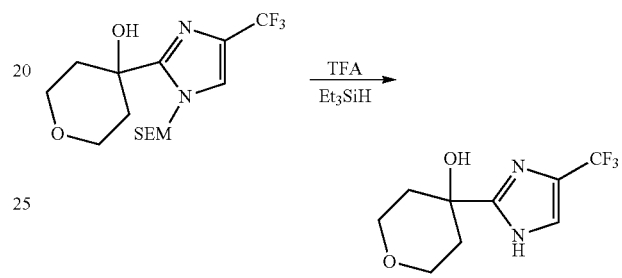

Compound 216.4. 4-(4-(Trifluoromethyl)-1H-imidazol-2-yl)tetrahydro-2H-pyran-4-ol Into a 25-mL round-bottom flask, was placed 4-(4-(trifluoromethyl)-1-((2-(trimethylsilyl)ethoxymethyl)-1H-imidazol-2-yl)tetrahydro-2H-pyran-4-ol (compound 216.3, 2 g, 5.46 mmol), Et₃SiH (2 mL) and trifluoroacetic acid (4 mL). The resulting solution was stirred for 2 h at room temperature. The pH of the solution was adjusted to 8 with sodium hydroxide (1 M). The resulting solution was diluted with 100 mL of brine. The aqueous phase was extracted with 2×100 mL of ethyl acetate. The combined organic layers were dried over anhydrous sodium sulfate and concentrated under reduced pressure. This resulted in 1.2 g (93%) of the title compound as a white solid.

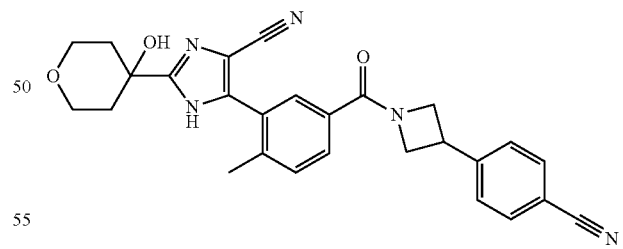

Compound 216. 5-(5-(3-(4-Cyanophenyl)azetidine-1-carbonyl)-2-methylphenyl)-2-(4-hydroxytetrahydro-2H-pyran-4-yl)-1H-imidazole-4-carbonitrile The title compound was prepared using standard chemical manipulations and procedures similar to those used for the preparation of compound 16, except 4-(4-(trifluoromethyl)-1H-imidazol-2-yl)tetrahydro-2H-pyran-4-ol (compound 216.4) was used in place of 2-methyl-4-(trifluoromethyl)-

1H-imidazole (compound 16.2) and 4-(azetidin-3-yl)benzonitrile hydrochloride (compound 5.2) was used in place of 4-(piperidin-4-yl)benzonitrile hydrochloride (compound 1.2). m/z (ES+) 468 (M+H)+.

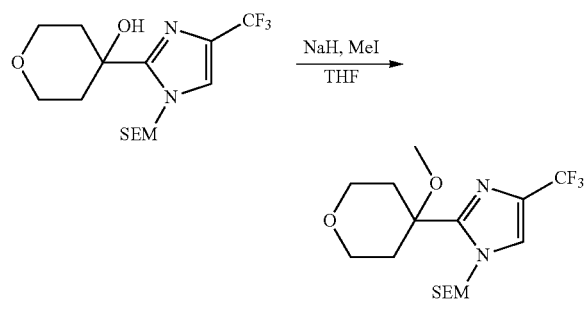

Compound 217.1. 2-(4-Methoxytetrahydro-2H-pyran-4-yl)-4-(trifluoromethyl)-1-((2-(trimethylsilyl)ethoxy)methyl)-1H-imidazole Into a 250-mL three neck round-bottom flask, which was purged and maintained with an inert atmosphere of nitrogen, was placed a solution of 4-(4-(trifluoromethyl)-1-((2-(trimethylsilyl)ethoxy)methyl)-1H-imidazol-2-yl)tetrahydro-2H-pyran-4-ol (compound 216.3, 2 g, 5.46 mmol) in tetrahydrofuran (100 mL). This was followed by the addition of sodium hydride (262 mg, 6.55 mmol, 60%) at −70° C. and stirred for 30 min. To this was added MeI (930 mg, 6.55 mmol). The resulting solution was stirred for 1 h at room temperature, then carefully quenched with 10 mL of water. The resulting mixture was diluted with 50 mL of brine. The aqueous phase was extracted with 2×50 mL of ethyl acetate. The combined organic layers were washed with 1×50 mL of brine, dried over anhydrous sodium sulfate and concentrated under reduced pressure. The residue was purified by silica gel chromatography with ethyl acetate/petroleum ether (1:3) as eluent to furnish 1.6 g (77%) of the title compound as light brown oil.

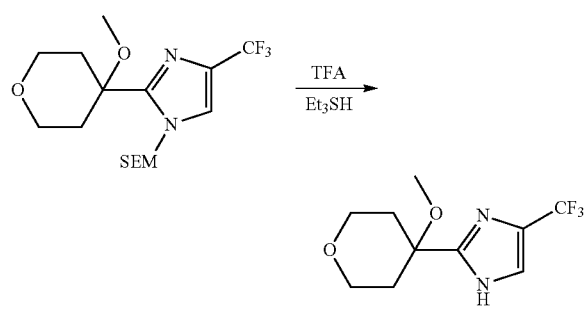

Compound 217.2. 2-(4-Methoxytetrahydro-2H-pyran-4-yl)-4-(trifluoromethyl)-1H-imidazole Into a 100-mL round-bottom flask, was placed 2-(4-methoxytetrahydro-2H-pyran-4-yl)-4-(trifluoromethyl)-1-((2-(trimethylsilyl)ethoxy)methyl)-1H-imidazole (compound 217.1, 1.3 g, 3.42 mmol), trifluoroacetic acid (4 mL), Et₃SiH (2 mL). The resulting solution was stirred overnight at 20° C., then quenched by the addition of 20 mL of water. The pH of the solution was adjusted to 8 with sodium hydroxide (1 M). The aqueous phase was extracted with 2×100 mL of ethyl acetate. The combined organic layers were washed with 2×50 mL of brine, dried over anhydrous sodium sulfate and concentrated under reduced pressure. This resulted in 1 g (crude) of the title compound as a light yellow oil.

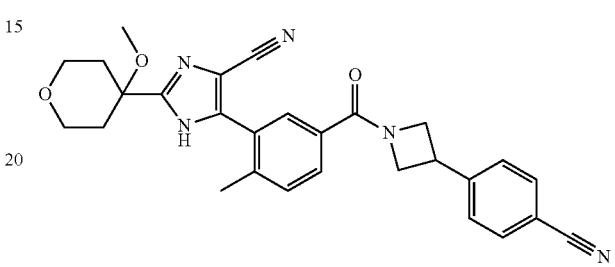

Compound 217. 5-(5-(3-(4-Cyanophenyl)azetidine-1-carbonyl)-2-methylphenyl)-2-(4-methoxytetrahydro-2H-pyran-4-yl)-1H-imidazole-4-carbonitrile The title compound was prepared using standard chemical manipulations and procedures similar to those used for the preparation of compound 16, except 2-(4-methoxytetrahydro-2H-pyran-4-yl)-4-(trifluoromethyl)-1H-imidazole (compound 217.2) was used in place of 2-methyl-4-(trifluoromethyl)-1H-imidazole (compound 16.2) and 4-(azetidin-3-yl)benzonitrile hydrochloride (compound 5.2) was used in place of 4-(piperidin-4-yl)benzonitrile hydrochloride (compound 1.2). m/z (ES+) 482 (M+H)+.

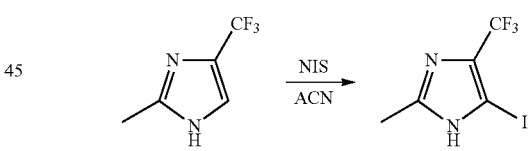

Compound 218.1. 5-Iodo-2-methyl-4-(trifluoromethyl)-1H-imidazole

Into a 50-mL round-bottom flask, was placed a solution of 2-methyl-4-(trifluoromethyl)-1H-imidazole (compound 16.2, 1.72 g, 11.46 mmol) in CH₃CN (25 mL). NIS (3.87 g, 17.20 mmol) was added to the reaction. The reaction mixture was stirred overnight at 85° C. The reaction mixture diluted with 50 mL of H₂O and extracted with 3×30 mL of ethyl acetate. The combined organic layers were washed with 2×20 mL of Na₂S₂O₃(sat.) and 2×20 mL of brine, dried over anhydrous sodium sulfate and concentrated under reduced pressure. This resulted in 4.32 g (crude) of the title compound as a brown oil.

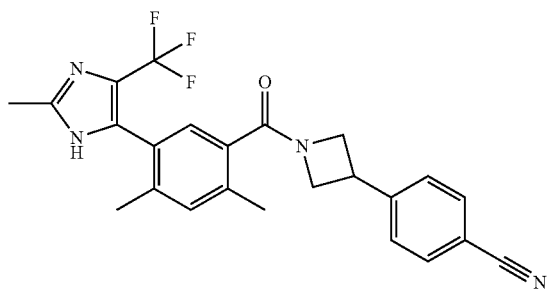 [SMILES: Cc1nc(C(F)(F)F)c(-c2cc(C(=O)N3CC(c4ccc(C#N)cc4)C3)c(C)cc2C)[nH]1]

Compound 218. 4-(1-(4-Methyl-3-(2-methyl-4-(trifluoromethyl)-1H-imidazol-5-yl)benzoyl)azetidin-3-yl)benzonitrile The title compound was prepared using standard chemical manipulations and procedures similar to those used for the preparation of compound 16, except 5-iodo-2-methyl-4-(trifluoromethyl)-1H-imidazole (compound 218.1) was used in place of 2-methyl-1H-imidazole-4-carbonitrile (Compound 16.3). m/z (ES+) 425 (M+H)$^+$.

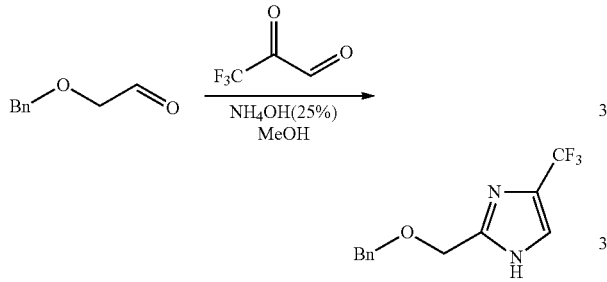

Compound 219.1. 2-((Benzyloxy)methyl)-4-(trifluoromethyl)-1H-imidazole

Into a 100-mL round-bottom flask, was placed a solution of 3,3,3-trifluoro-2-oxopropanal (2 g, 15.87 mmol) in methanol (30 mL). 2-(benzyloxy)acetaldehyde (2.8 g, 18.64 mmol) and ammonium hydroxide (25%) (36 mL, 63.48 mmol) were added to the reaction. The reaction mixture was stirred for 15 h at 20° C., then concentrated under reduced pressure. The residue was diluted with 20 mL of H$_2$O. The aqueous phase was extracted with 2×30 mL of ethyl acetate and the combined organic layers were washed with 2×20 mL of brine, dried over anhydrous sodium sulfate and concentrated under reduced pressure. This resulted in 4.2 g (crude) of the title compound as a yellow crude oil.

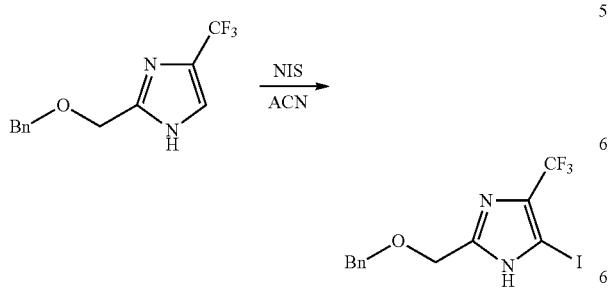

Compound 219.2. 2-((Benzyloxy)methyl)-5-iodo-4-(trifluoromethyl)-1H-imidazole

Into a 50-mL round-bottom flask, was placed a solution of 2-((benzyloxy)methyl)-4-(trifluoromethyl)-1H-imidazole (compound 219.1, 1.5 g, 5.85 mmol) in CH$_3$CN (18 mL). NIS (1.6 g, 7.02 mmol) was added to the reaction. The reaction mixture was stirred for 15 h at 85° C. The reaction mixture was diluted with 30 mL of H$_2$O. The aqueous phase was extracted with 2×30 mL of ethyl acetate. The combined organic layers were washed with 2×20 mL of Na$_2$S$_2$O$_3$(sat.) and 2×20 mL of brine, dried over anhydrous sodium sulfate and concentrated under reduced pressure. The residue was purified by silica gel chromatography with ethyl acetate/petroleum ether (1:100-1:2) as eluent to furnish 0.7 g (31%) of the title compound as a yellow oil.

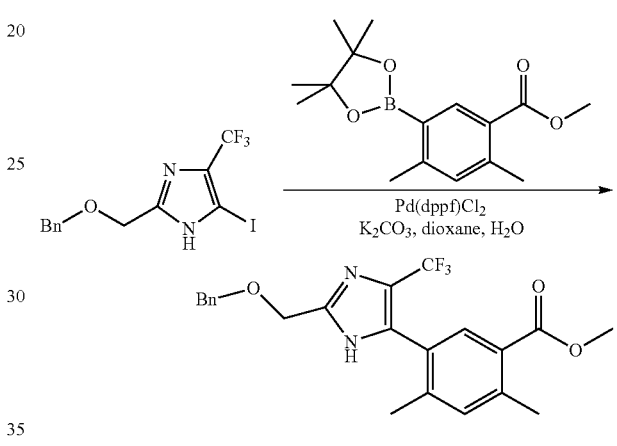

Compound 219.3. Methyl 5-(2-((benzyloxy)methyl)-4-(trifluoromethyl)-1H-imidazol-5-yl)-2,4-dimethylbenzoate Into a 50-mL three neck round-bottom flask, which was purged and maintained with an inert atmosphere of nitrogen, was placed a solution of 2-((benzyloxy)methyl)-5-iodo-4-(trifluoromethyl)-1H-imidazole (compound 219.2, 500 mg, 1.31 mmol) in dioxane (8 mL). Methyl 2,4-dimethyl-5-(tetramethyl-1,3,2-dioxaborolan-2-yl)benzoate (compound 160.1, 450 mg, 1.55 mmol), Pd(dppf)Cl$_2$ (0.1 g) and an aqueous solution of potassium carbonate (2 M) (3.25 mL) were added to the reaction. The reaction mixture was stirred for 1 h at 80° C., then diluted with 20 mL of H$_2$O. The aqueous phase was extracted with 2×30 mL of ethyl acetate. The combined organic layers were washed with 2×30 mL of brine and dried over anhydrous sodium sulfate. The residue was purified by silica gel chromatography with ethyl acetate/petroleum ether (1/20-1/4) as eluent to yield 0.2 g (37%) of the title compound as a light yellow solid.

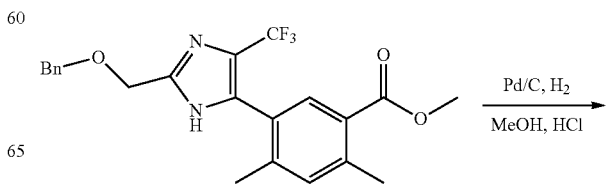

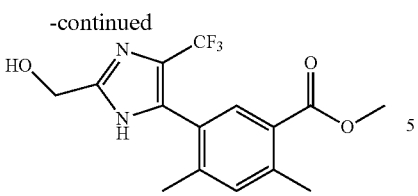

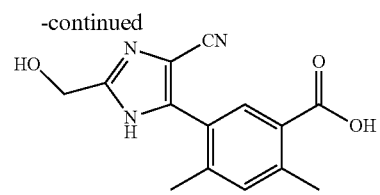

Compound 219.4. Methyl 5-(2-(hydroxymethyl)-4-(trifluoromethyl)-1H-imidazol-5-yl)-2,4-dimethylbenzoate Into a 50-mL round-bottom flask, under a nitrogen atmosphere, was placed a solution of methyl 5-(2-((benzyloxy)methyl)-4-(trifluoromethyl)-1H-imidazol-5-yl)-2,4-dimethylbenzoate (compound 219.3, 150 mg, 0.36 mmol) in methanol (8 mL). Palladium on carbon (150 mg, 1.00 equiv) and HCl (4 M, 2 mL) were added to the reaction under a nitrogen atmosphere. To the above hydrogen (1 atm) was introduced. The reaction mixture was stirred for 2 h at room temperature. The system was purged with nitrogen, then the solids were removed by filtration and the filtrate was concentrated under reduced pressure to give 100 mg (85%) of the title compound as a light yellow oil.

Compound 219.6. 5-(4-Cyano-2-(hydroxymethyl)-1H-imidazol-5-yl)-2,4-dimethylbenzoic acid Into a 25-mL round-bottom flask, was placed a solution of methyl 5-(4-cyano-2-(hydroxymethyl)-1H-imidazol-5-yl)-2,4-dimethylbenzoate (compound 219.6, 100 mg, 0.35 mmol) in methanol (10 mL) and a solution of NaOH (0.14 g, 3.5 mmol) in water (5 mL). The reaction mixture was stirred for 15 h at room temperature, then concentrated under reduced pressure. The pH of the solution was adjusted to 1-2 with hydrogen chloride (4 M). The resulting mixture was concentrated under reduced pressure. Methanol (5 mL) was added to the residue. The salt was filtered off, and the filtrate was concentrated under reduced pressure to give 200 mg (crude) of the title compound as a light yellow solid.

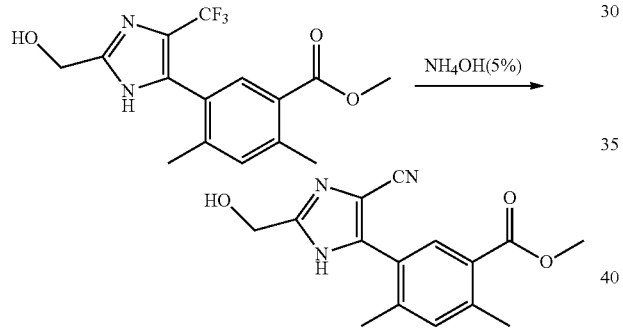

Compound 219. 5-(5-(3-(4-Cyanophenyl)-3-fluoroazetidine-1-carbonyl)-2,4-dimethylphenyl)-2-(hydroxymethyl)-1H-imidazole-4-carbonitrile Compound 219.5. Methyl 5-(4-cyano-2-(hydroxymethyl)-1H-imidazol-5-yl)-2,4-dimethylbenzoate Into a 50-mL round-bottom flask, was placed a solution of methyl 5-(2-((benzyloxy)methyl)-4-(trifluoromethyl)-1H-imidazol-5-yl)-2,4-dimethylbenzoate (compound 219.4, 100 mg, 0.30 mmol) in ammonium hydroxide (5%) (30 mL). The reaction mixture was stirred for 2 h at 60° C. The reaction mixture was extracted with 2×50 mL of dichloromethane, the organic layers combined, dried over anhydrous sodium sulfate and concentrated under reduced pressure. This resulted in 80 mg (92%) of the title compound as a light yellow oil.

The title compound was prepared using standard chemical manipulations and procedures similar to those used for the preparation of compound 5, except 5-(4-cyano-2-(hydroxymethyl)-1H-imidazol-5-yl)-2,4-dimethylbenzoic acid (compound 219.6) was used in place of 3-(2,4-dimethyl-1H-imidazol-5-yl)-4-methylbenzoic acid (compound 5.7) and 4-(3-fluoroazetidin-3-yl)benzonitrile hydrochloride (compound 43.4) was used in place of 4-(azetidin-3-yl)benzonitrile hydrochloride (compound 5.2). m/z (ES+) 430 (M+H)$^+$.

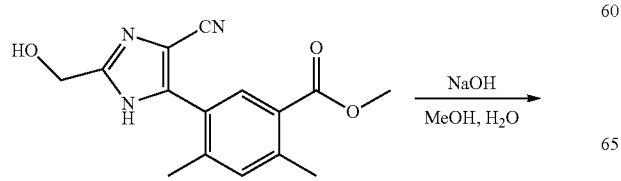

Compound 220. 5-(5-(3-(4-Cyanophenyl)azetidine-1-carbonyl)-2,4-dimethylphenyl)-2-(hydroxymethyl)-1H-imidazole-4-carbonitrile The title compound was prepared using standard chemical manipulations and procedures similar to those used for the preparation of compound 5, except 5-(4-cyano-2-(hydroxymethyl)-1H-imidazol-5-yl)-2,4-dimethylbenzoic acid (compound 219.6) was used in place of 3-(2,4-dimethyl-1H-imidazol-5-yl)-4-methylbenzoic acid (compound 5.7). m/z (ES+) 412 (M+H)$^+$.

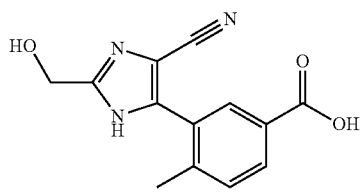 [SMILES: Cc1ccc(C(=O)O)cc1-c1[nH]c(CO)nc1C#N]

Compound 221.1. 3-(4-Cyano-2-(hydroxymethyl)-1H-imidazol-5-yl)-4-methylbenzoic acid The title compound was prepared using standard chemical manipulations and procedures similar to those used for the preparation of compound 219.6, except methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1).

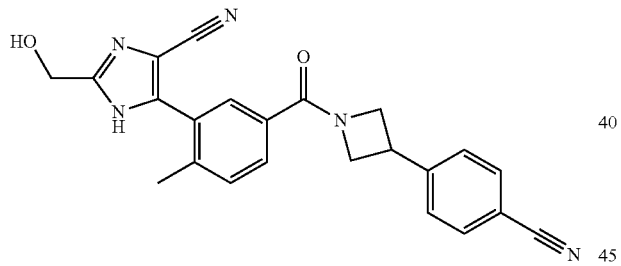

Compound 221. 4-(1-(4-Methyl-3-(4-methyl-2-(pyrrolidin-1-yl)-1H-imidazol-5-yl)benzoyl)azetidin-3-yl)benzonitrile The title compound was prepared using standard chemical manipulations and procedures similar to those used for the preparation of compound 5, except 3-(4-cyano-2-(hydroxymethyl)-1H-imidazol-5-yl)-4-methylbenzoic acid (compound 221.1) was used in place of 3-(2,4-dimethyl-1H-imidazol-5-yl)-4-methylbenzoic acid (compound 5.7). m/z (ES+) 398 (M+H)$^+$.

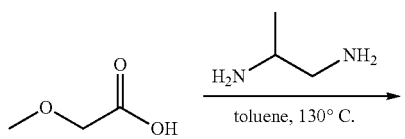

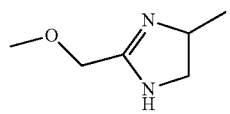

Compound 222.1. 2-(Methoxymethyl)-4-methyl-4,5-dihydro-1H-imidazole

Into a 500-mL round-bottom flask, was placed a solution of 2-methoxyacetic acid (20 g, 222.0 mmol) in toluene (200 mL). Propane-1,2-diamine (50 g, 674.5 mmol) was added to the reaction. The reaction mixture was stirred overnight at 130° C., then concentrated under reduced pressure. This resulted in 25 g (crude) of the title compound as a yellow oil.

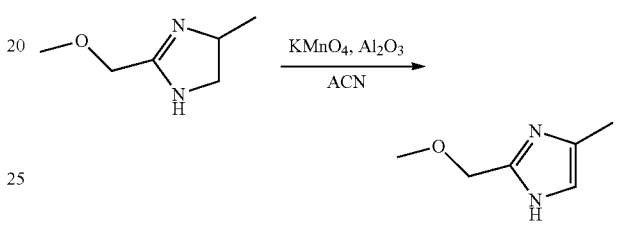

Compound 222.2. 2-(Methoxymethyl)-4-methyl-1H-imidazole

Into a 500-mL round-bottom flask, was placed a solution of 2-(methoxymethyl)-4-methyl-4,5-dihydro-1H-imidazole (compound 222.1, 19 g, 148.4 mmol) in acetonitrile (200 mL). Al$_2$O$_3$ (19 g, 182.7 mmol) was added to the reaction. This was followed by the addition of potassium permanganate (58 g, 367.1 mmol) in several batches at 0° C. The reaction mixture was stirred for 2 h at 0° C., then warmed to room temperature overnight. The reaction was quenched with 20 mL of sodium sulfite (sat.). The solids were removed by filtration and the filtrate was concentrated under reduced pressure. This resulted in 19 g (crude) of the title compound as yellow oil.

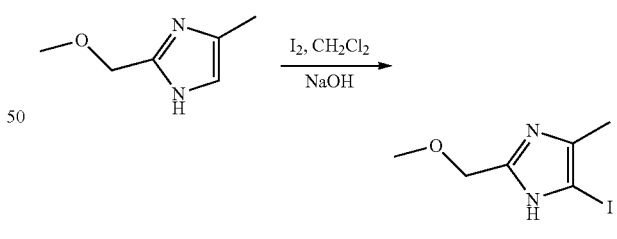

Compound 222.3. 5-Iodo-2-(methoxymethyl)-4-methyl-1H-imidazole

Into a 100-mL round-bottom flask, was placed a solution of 2-(methoxymethyl)-4-methyl-1H-imidazole (compound 222.2, 1.9 g, 15.06 mmol) in sodium hydroxide aqueous solution (30 mL, 2M). This was followed by the addition of a solution of iodine (7.7 g, 30.34 mmol) in dichloromethane (30 mL). The reaction mixture was stirred for 1 h at room temperature. The aqueous phase was collected and the pH was adjusted to 4 with hydrogen chloride (2M). The reaction mixture was extracted with 4×30 mL of dichloromethane and the organic layers combined. The resulting mixture was washed with 2×20 mL of sodium sulfite (sat.) and 3×30 mL of brine, dried over anhydrous sodium sulfate and concentrated under reduced pressure. This resulted in 1.2 g (32%) of the title compound as a yellow solid.

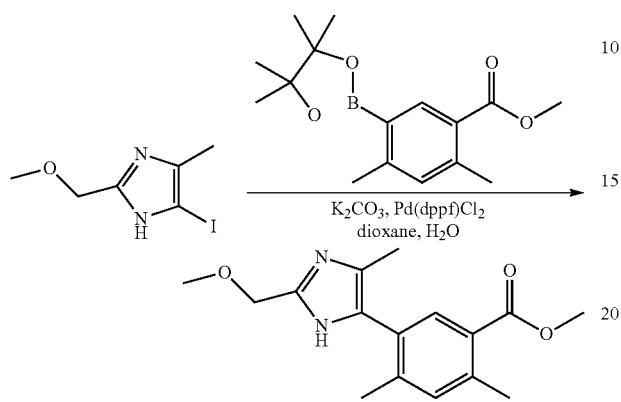

Compound 222.4. Methyl 5-(2-(methoxymethyl)-4-methyl-1H-imidazol-5-yl)-2,4-dimethylbenzoate Into a 50-mL three neck round-bottom flask, which was purged and maintained with an inert atmosphere of nitrogen, was placed a solution of 5-iodo-2-(methoxymethyl)-4-methyl-1H-imidazole (compound 222.3, 400 mg, 1.59 mmol) in 1,4-dioxane (15 mL). Methyl 2,4-dimethyl-5-(tetramethyl-1,3,2-dioxaborolan-2-yl)benzoate (compound 160.1, 510 mg, 1.76 mmol), a solution of potassium carbonate (662 mg, 4.79 mmol) in water (1 mL) and Pd(dppf)Cl₂ (234 mg, 0.32 mmol) were added to the reaction. The reaction mixture was stirred overnight at 90° C. The solids were removed by filtration and the filtrate was concentrated under reduced pressure. The residue was purified by silica gel chromatography with dichloromethane/ethyl acetate (1:1) as eluent to furnish 220 mg (48%) of the title compound as a yellow solid.

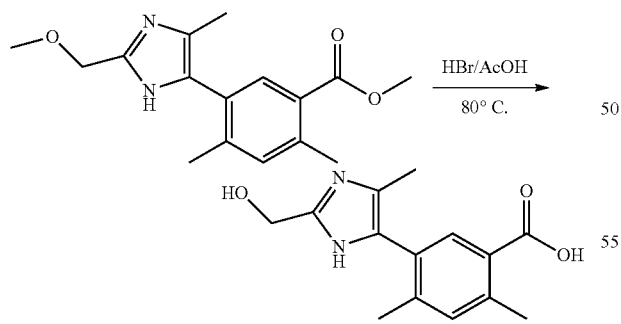

Compound 222.5. 5-(2-(Hydroxymethyl)-4-methyl-1H-imidazol-5-yl)-2,4-dimethylbenzoic acid Into a 100-mL round-bottom flask, was placed methyl 5-(2-(methoxymethyl)-4-methyl-1H-imidazol-5-yl)-2,4-dimethylbenzoate (compound 222.4, 220 mg, 0.76 mmol) and HBr (20 mL, 40% in HOAc). The reaction mixture was stirred overnight at 80° C. The resulting mixture was concentrated under reduced pressure. This resulted in 190 mg (crude) of the title compound as a brown solid.

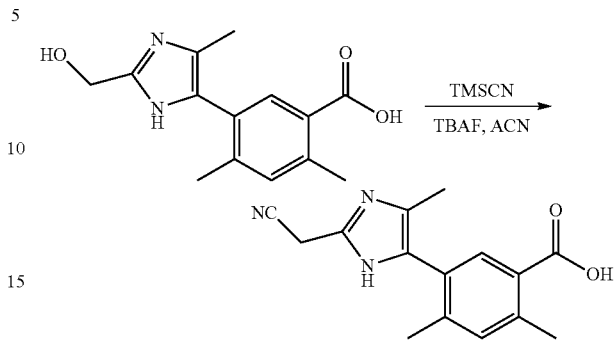

Compound 222.6. 5-(2-(Cyanomethyl)-4-methyl-1H-imidazol-5-yl)-2,4-dimethylbenzoic acid Into a 100-mL round-bottom flask, was placed a solution of trimethylsilanecarbonitrile (376 mg, 3.79 mmol) in acetonitrile (20 mL). Tetrabutylammonium fluoride (3.8 mL, 1 M in THF) was added to the reaction. This was followed by the addition of 5-(2-(hydroxymethyl)-4-methyl-1H-imidazol-5-yl)-2,4-dimethylbenzoic acid (compound 222.5, 190 mg, 0.73 mmol), in portions. The reaction mixture was stirred for 1 h at room temperature, then concentrated under reduced pressure. The residue was purified by silica gel chromatography with ethyl acetate/petroleum ether (1:1) as eluent to furnish 190 mg (97%) of the title compound as a yellow solid.

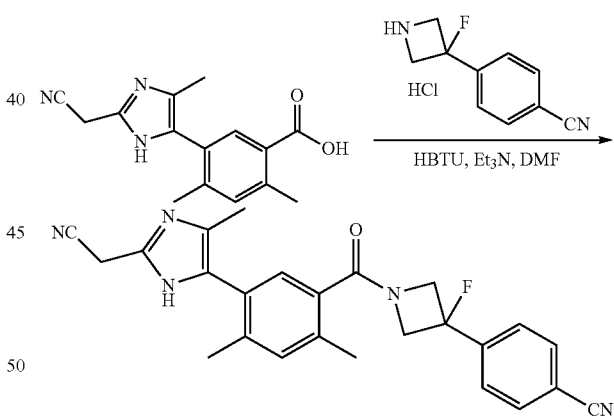

Compound 222. 4-(1-(5-(2-(Cyanomethyl)-4-methyl-1H-imidazol-5-yl)-2,4-dimethylbenzoyl)-3-fluoroazetidin-3-yl)benzonitrile Into a 100-mL round-bottom flask, was placed a solution of 5-(2-(cyanomethyl)-4-methyl-1H-imidazol-5-yl)-2,4-dimethylbenzoic acid (compound 222.6, 190 mg, 0.71 mmol) and HBTU (538 mg, 1.42 mmol) in N,N-dimethylformamide (3 mL). To the above were added a solution of 4-(3-fluoroazetidin-3-yl)benzonitrile hydrochloride (compound 43.4, 160 mg, 0.75 mmol) and triethylamine (197 µL, 1.42 mmol) in N,N-dimethylformamide (3 mL) dropwise. The reaction mixture was stirred for 1 h at room temperature. The crude product (150 mg) was purified by Prep-HPLC with the following conditions (1#-Pre-HPLC-001 (SHIMADZU)): Column, XBridge Prep C18 OBD Column, 5 m, 19*150 mm; mobile phase, Water with 50 mmol NH$_4$HCO$_3$ and acetonitrile (30% acetonitrile up to 44% in 7 min, hold 44% in 1 min, up to 100% in 1 min, down to 30% in 1 min); Detector, Waters 2489, 254 and 220 nm. This resulted in 45.9 mg (15%) of the title compound as a white solid. m/z (ES+) 428 (M+H)$^+$.

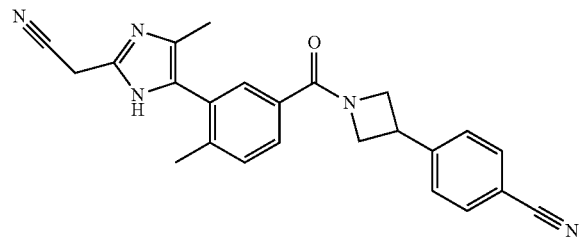 [SMILES: Cc1ccc(C(=O)N2CC(c3ccc(C#N)cc3)C2)cc1-c1[nH]c(CC#N)nc1C]

Compound 223. 4-(1-(3-(2-(Cyanomethyl)-4-methyl-1H-imidazol-5-yl)-4-methylbenzoyl)azetidin-3-yl)benzonitrile The title compound was prepared using standard chemical manipulations and procedures similar to those used for the preparation of compound 222, except methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1) and 4-(azetidin-3-yl)benzonitrile hydrochloride (compound 5.2) was used in place of 4-(3-fluoroazetidin-3-yl)benzonitrile hydrochloride (compound 43.4). m/z (ES+) 396 (M+H)$^+$.

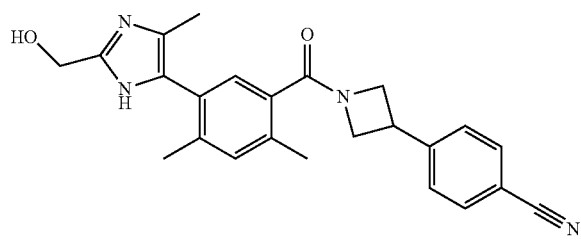 [SMILES: Cc1cc(C)c(-c2[nH]c(CO)nc2C)cc1C(=O)N1CC(c2ccc(C#N)cc2)C1]

Compound 224. 4-(1-(5-(2-(Hydroxymethyl)-4-methyl-1H-imidazol-5-yl)-2,4-dimethylbenzoyl)azetidin-3-yl)benzonitrile The title compound was prepared using standard chemical manipulations and procedures similar to those used for the preparation of compound 222, except 5-(2-(hydroxymethyl)-4-methyl-1H-imidazol-5-yl)-2,4-dimethylbenzoic acid (compound 222.5) was used in place of 5-(2-(cyanomethyl)-4-methyl-1H-imidazol-5-yl)-2,4-dimethylbenzoic acid (compound 222.6) and 4-(azetidin-3-yl)benzonitrile hydrochloride (compound 5.2) was used in place of 4-(3-fluoroazetidin-3-yl)benzonitrile hydrochloride (compound 43.4). m/z (ES+) 401 (M+H)$^+$.

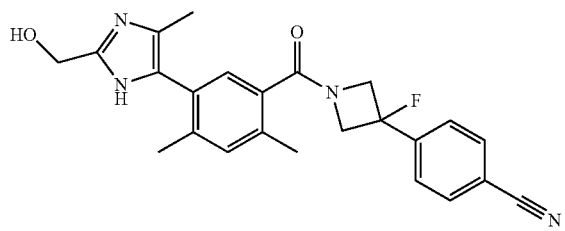 [SMILES: Cc1cc(C)c(-c2[nH]c(CO)nc2C)cc1C(=O)N1CC(F)(c2ccc(C#N)cc2)C1]

Compound 225. 4-(3-Fluoro-1-(5-(2-(hydroxymethyl)-4-methyl-1H-imidazol-5-yl)-2,4-dimethylbenzoyl)azetidin-3-yl)benzonitrile The title compound was prepared using standard chemical manipulations and procedures similar to those used for the preparation of compound 222, except 5-(2-(hydroxymethyl)-4-methyl-1H-imidazol-5-yl)-2,4-dimethylbenzoic acid (compound 222.5) was used in place of 5-(2-(cyanomethyl)-4-methyl-1H-imidazol-5-yl)-2,4-dimethylbenzoic acid (compound 222.6). m/z (ES+) 419 (M+H)$^+$.

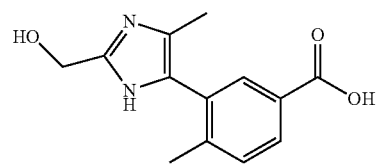 [SMILES: Cc1ccc(C(=O)O)cc1-c1[nH]c(CO)nc1C]

Compound 226.1. 3-(2-(Hydroxymethyl)-4-methyl-1H-imidazol-5-yl)-4-methylbenzoic acid The title compound was prepared using standard chemical manipulations and procedures similar to those used for the preparation of 5-(2-(hydroxymethyl)-4-methyl-1H-imidazol-5-yl)-2,4-dimethylbenzoic acid (compound 222.5), except methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1).

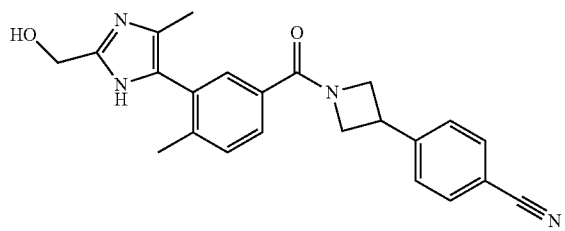 [SMILES: Cc1ccc(C(=O)N2CC(c3ccc(C#N)cc3)C2)cc1-c1[nH]c(CO)nc1C]

Compound 226. 4-(1-(3-(2-(Hydroxymethyl)-4-methyl-1H-imidazol-5-yl)-4-methylbenzoyl)azetidin-3-yl)benzonitrile The title compound was prepared using standard chemical manipulations and procedures similar to those used for the preparation of compound 222, except 3-(2-(hydroxymethyl)-4-methyl-1H-imidazol-5-yl)-4-methylbenzoic acid (compound 226.1) was used in place of 5-(2-(cyanomethyl)-

4-methyl-1H-imidazol-5-yl)-2,4-dimethylbenzoic acid (compound 222.6). m/z (ES+) 387 (M+H)+.

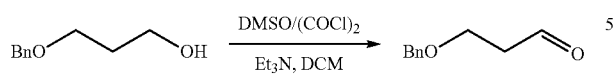

Compound 227.1. 3-(Benzyloxy)propanal

Into a 100-mL three neck round-bottom flask, which was purged and maintained with an inert atmosphere of nitrogen, was placed DMSO (5.1 mL, 71.79 mmol) in dichloromethane (40 mL). This was followed by the addition of oxalyl chloride (3.1 mL, 54.16 mmol) dropwise at −78° C. and stirred for 30 min at −78° C. To this was added a solution of 3-(benzyloxy)propan-1-ol (4.8 mL, 30.08 mmol) in dichloromethane (10 mL) dropwise at −78° C. The resulting solution was stirred for 1 h at −78° C., then triethylamine (16.5 mL, 118.59 mmol) was added to the reaction. The resulting solution was stirred for 1 h at −78 to −20° C., then quenched with 50 mL of NH4Cl (sat.). The aqueous phase was extracted with 2×50 mL of dichloromethane. The combined organic layers were dried over anhydrous sodium sulfate and concentrated under reduced pressure. The residue was purified by silica gel chromatography with EtOAc:PE (1:5) as eluent to furnish 2.0 g (40%) of the title compound as light yellow oil.

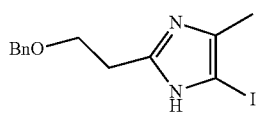 [SMILES: Cc1nc(CCOCc2ccccc2)[nH]c1I]

Compound 227.2. 2-(2-(Benzyloxy)ethyl)-5-iodo-4-methyl-1H-imidazole

The title compound was prepared using standard chemical manipulations and procedures similar to those used for the preparation of compound 160.2, except 3-(benzyloxy)propanal (compound 227.1) was used in place of cyclopropanecarbaldehyde.

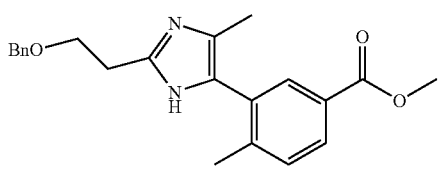 [SMILES: COC(=O)c1ccc(C)c(-c2[nH]c(CCOCc3ccccc3)nc2C)c1]

Compound 227.3. Methyl 3-(2-(2-(benzyloxy)ethyl)-4-methyl-1H-imidazol-5-yl)-4-methylbenzoate The title compound was prepared using standard chemical manipulations and procedures similar to those used for the preparation of compound 5.6, except 2-(2-(benzyloxy)ethyl)-5-iodo-4-methyl-1H-imidazole (compound 227.2) was used in place of 5-iodo-2,4-dimethyl-1H-imidazole (compound 5.5).

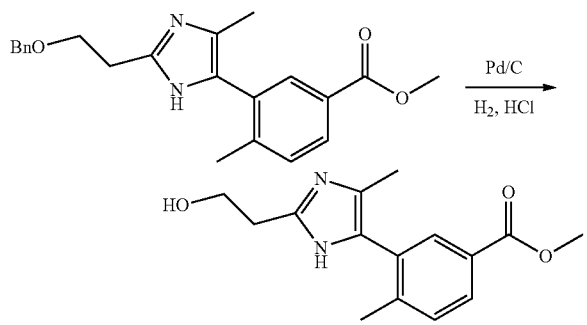

Compound 227.4. Methyl 3-(2-(2-hydroxyethyl)-4-methyl-1H-imidazol-5-yl)-4-methylbenzoate Into a 100-mL round-bottom flask, was placed a solution of methyl 3-(2-(2-(benzyloxy)ethyl)-4-methyl-1H-imidazol-5-yl)-4-methylbenzoate (compound 227.3, 100 mg, 0.27 mmol) in methanol (10 mL). Palladium on carbon (100 mg), hydrogen chloride (4M) (2.5 mL) were added to the reaction under N2. To the above hydrogen was introduced. The reaction mixture was stirred for 3 h at room temperature. The solids were filtered off and the filtrate was concentrated under reduced pressure. The pH of the solution was adjusted to 7 with sodium bicarbonate (sat.). The resulting solution was extracted with 4×20 mL of ethyl acetate. The organic layers were combined, dried over anhydrous sodium sulfate and concentrated under reduced pressure. This resulted in 60 mg (80%) of the title compound as a yellow oil.

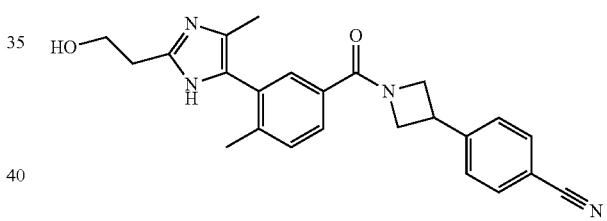

Compound 227. 4-(1-(3-(2-(2-Hydroxyethyl)-4-methyl-1H-imidazol-5-yl)-4-methylbenzoyl)azetidin-3-yl)benzonitrile The title compound was prepared using standard chemical manipulations and procedures similar to those used for the preparation of compound 5, except methyl 3-(2-(2-hydroxyethyl)-4-methyl-1H-imidazol-5-yl)-4-methylbenzoate (compound 227.4) was used in place of methyl 3-(2,4-dimethyl-1H-imidazol-5-yl)-4-methylbenzoate (compound 5.6). m/z (ES+) 401 (M+H)+.

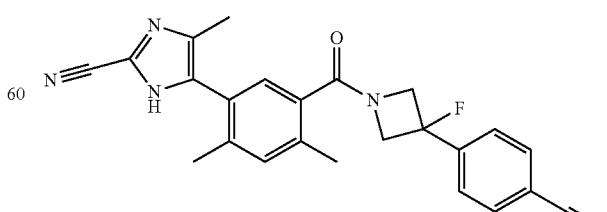

Compound 228. 5-(5-(3-(4-Cyanophenyl)-3-fluoroazetidine-1-carbonyl)-2,4-dimethylphenyl)-4-methyl-1H-imidazole-2-carbonitrile The title compound was prepared using standard chemical manipulations and procedures similar to those used for the preparation of compound 14, except 4-(3-fluoroazetidin-3-yl)benzonitrile hydrochloride (compound 43.4) was used in place of 4-(azetidin-3-yl)benzonitrile hydrochloride (compound 5.2) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 414 (M+H)+.

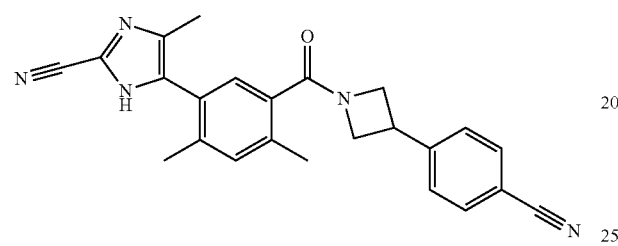

Compound 229. 5-(5-(3-(4-Cyanophenyl)azetidine-1-carbonyl)-2,4-dimethylphenyl)-4-methyl-1H-imidazole-2-carbonitrile The title compound was prepared using standard chemical manipulations and procedures similar to those used for the preparation of compound 14, except methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 396 (M+H)+.

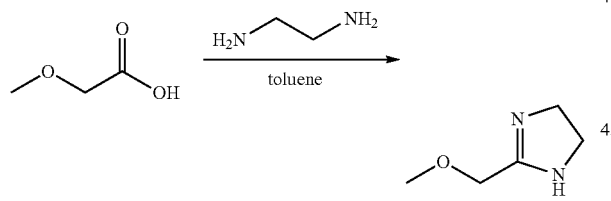

Compound 230.1. 2-(Methoxymethyl)-4,5-dihydro-1H-imidazole

Into a 250-mL round-bottom flask, was placed a solution of 2-methoxyacetic acid (20 g, 222.03 mmol) in toluene (60 mL). Ethane-1,2-diamine (133 g, 2.22 mol) was added to the reaction. The reaction mixture was stirred for 2 days at 130° C. The resulting mixture was concentrated under reduced pressure. This resulted in 20 g (79%) of the title compound as yellow crude oil.

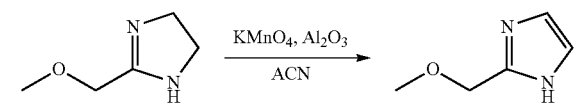

Compound 230.2. 2-(Methoxymethyl)-1H-imidazole

Into a 500-mL 3-neck round-bottom flask, was placed a solution of 2-(methoxymethyl)-4,5-dihydro-1H-imidazole (compound 230.1, 20 g, 175.21 mmol) in ACN (150 mL). $Al_2O_3$ (9 g, 87.6 mmol), KMnO4 (27.7 g, 175.21 mmol) were added to the reaction. The reaction mixture was stirred for 6 h at room temperature, then quenched with 30 mL of $Na_2SO_3$(sat). The solids were removed by filtration and the filtrate was concentrated under reduced pressure. This resulted in 15 g (crude) of the title compound as a yellow solid.

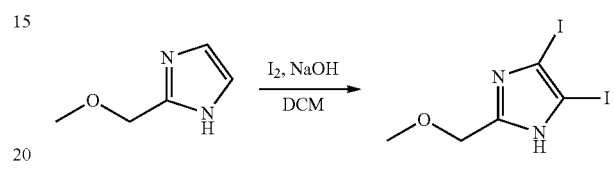

Compound 230.3. 4,5-Diiodo-2-(methoxymethyl)-1H-imidazole

Into a 500-mL round-bottom flask, was placed a solution of 2-(methoxymethyl)-1H-imidazole (compound 230.2, 15 g, 133.77 mmol) in sodium hydroxide aqueous solution (100 mL, 2M). A solution of $I_2$ (60 g, 236.22 mmol) in dichloromethane (100 mL) was added to the reaction. The reaction mixture was stirred for 3 h at 25° C. The aqueous phase was collected and diluted with 50 mL of $Na_2SO_3$(aq). The pH of the solution was adjusted to 6-7 with hydrogen chloride (2M). The reaction mixture was extracted with 3×50 mL of dichloromethane. The aqueous layers were combined and concentrated under reduced pressure. The residue was purified by silica gel chromatography with ethyl acetate/hexane (1:2) as eluent to furnish 4 g (8%) of the title compound as a white solid.

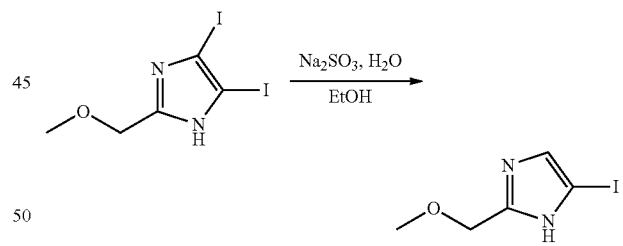

Compound 230.4. 5-Iodo-2-(methoxymethyl)-1H-imidazole

Into a 250-mL round-bottom flask, was placed a solution of 4,5-diiodo-2-(methoxymethyl)-1H-imidazole (compound 230.3, 2 g, 5.50 mmol) in ethanol (40 mL). A solution of $Na_2SO_3$ (5.9 g, 46.83 mmol) in water (80 mL) was added to the reaction. The reaction mixture was stirred overnight at 90° C. The resulting mixture was concentrated under reduced pressure. The residue was extracted with 3×20 mL of dichloromethane and the organic layers combined and concentrated under reduced pressure. This resulted in 1 g (76%) of the title compounds as yellow oil.

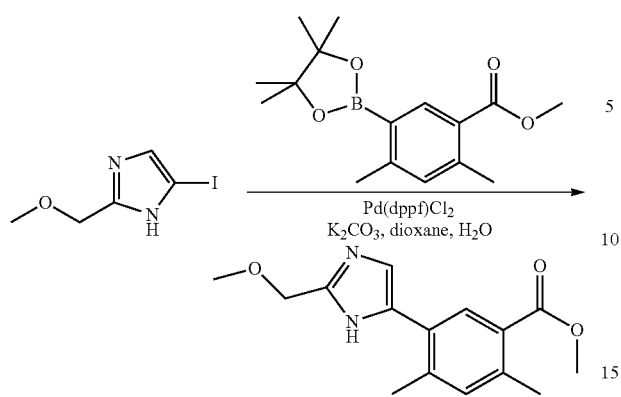

Compound 230.5. Methyl 5-(2-(methoxymethyl)-1H-imidazol-5-yl)-2,4-dimethylbenzoate Into a 100-mL three neck round-bottom flask, which was purged and maintained with an inert atmosphere of nitrogen, was placed a solution of 5-iodo-2-(methoxymethyl)-1H-imidazole (compound 230.4, 70 mg, 0.29 mmol) in dioxane (10 mL). Pd(dppf)Cl$_2$ (22 mg, 0.029 mmol), a solution of potassium carbonate (160 mg, 1.16 mmol) in water (2 mL), methyl 2,4-dimethyl-5-(tetramethyl-1,3,2-dioxaborolan-2-yl)benzoate (compound 160.1, 168 mg, 0.58 mmol) were added to the reaction. The reaction mixture was stirred overnight at 90° C., then quenched with 10 mL of H$_2$O. The aqueous phase was extracted with 3×10 mL of ethyl acetate and the combined organic layers were washed with 1×10 mL of brine, dried over anhydrous sodium sulfate and concentrated under reduced pressure. The residue was purified by silica gel chromatography with ethyl acetate/petroleum ether (1:1) as eluent to furnish 70 mg (87%) of the title compound as a white solid.

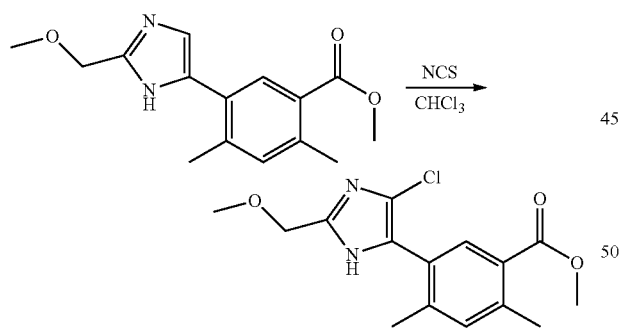

Compound 230.6. Methyl 5-(4-chloro-2-(methoxymethyl)-1H-imidazol-5-yl)-2,4-dimethylbenzoate Into a 100-mL round-bottom flask, was placed a solution of methyl 5-(2-(methoxymethyl)-1H-imidazol-5-yl)-2,4-dimethylbenzoate (compound 230.5, 70 mg, 0.26 mmol) in chloroform (6 mL). NCS (35 mg, 0.26 mmol) was added to the reaction. The reaction mixture was stirred overnight at room temperature, then quenched with 1 mL of water. The aqueous phase was extracted with 2×5 mL of dichloromethane and the combined organic layers were concentrated under reduced pressure. The residue was applied onto a silica gel chromatography with ethyl acetate/petroleum ether (1:10) as eluent to yield 30 mg (38%) of the title compound as a white crude solid.

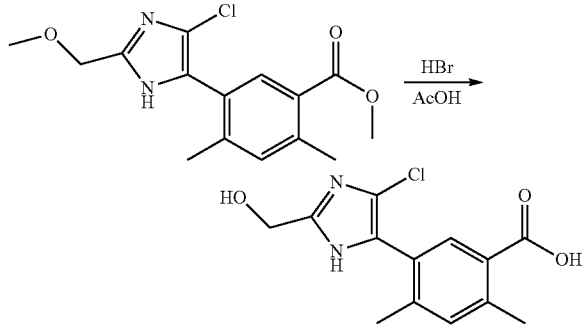

Compound 230.7. 5-(4-Chloro-2-(hydroxymethyl)-1H-imidazol-5-yl)-2,4-dimethylbenzoic acid Into a 50-mL round-bottom flask, was placed a solution of methyl 5-(4-chloro-2-(methoxymethyl)-1H-imidazol-5-yl)-2,4-dimethylbenzoate (compound 230.5, 20 mg, 0.06 mmol) in HBr (5 mL, 40% in AcOH). The reaction mixture was stirred overnight at 90° C. The resulting mixture was concentrated under reduced pressure. This resulted in 10 mg (55%) of the title compound as a yellow crude solid.

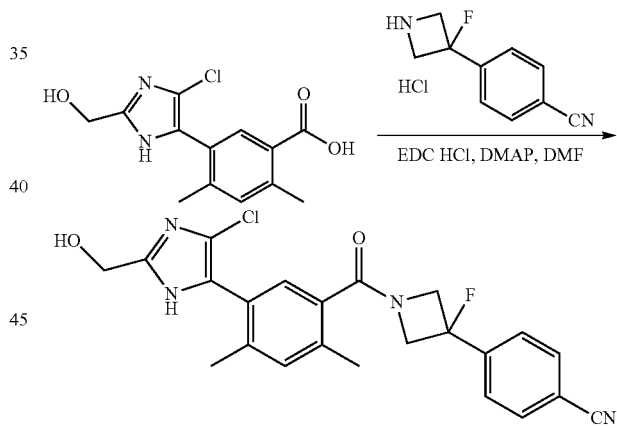

Compound 230. 4-(1-(5-(4-Chloro-2-(hydroxymethyl)-1H-imidazol-5-yl)-2,4-dimethylbenzoyl)-3-fluoroazetidin-3-yl)benzonitrile Into a 50-mL round-bottom flask, was placed a solution of 5-(4-chloro-2-(hydroxymethyl)-1H-imidazol-5-yl)-2,4-dimethylbenzoic acid (compound 230.6, 180 mg, 0.64 mmol) in N,N-dimethylformamide (15 mL). 4-(3-fluoroazetidin-3-yl)benzonitrile hydrochloride (compound 43.4, 165 mg, 0.78 mmol), EDC·HCl (245 mg, 1.28 mmol) and 4-dimethylaminopyridine (310 mg, 2.54 mmol) were added to the reaction. The reaction mixture was stirred overnight at 25° C. The reaction was then quenched with 5 mL of water. The reaction mixture was extracted with 3×10 mL of ethyl acetate and the organic layers combined. The resulting mixture was washed with 5×10 mL of brine. The resulting mixture was concentrated under reduced pressure. The crude product (200 mg) was purified by Prep-HPLC with the following conditions (1#-Pre-HPLC-001(SHIMADZU)): Column, SunFire Prep C18 OBD Column, 5 μm, 19*150 mm; mobile phase, WATER WITH 0.05% TFA and ACN (26.0% ACN up to 39.0% in 10 min, up to 100.0% in 2 min, down to 26.0% in 1 min); Detector, Waters 2489, 254 and 220 nm. This resulted in 84 mg (30%) of the title compound as a white solid. m/z (ES+) 439 (M+H)$^+$.

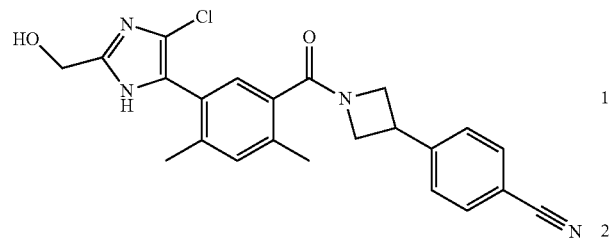

Compound 231. 4-(1-(5-(4-Chloro-2-(hydroxymethyl)-1H-imidazol-5-yl)-2,4-dimethylbenzoyl)azetidin-3-yl)benzonitrile The title compound was prepared using standard chemical manipulations and procedures similar to those used for the preparation of compound 230, except 4-(azetidin-3-yl)benzonitrile hydrochloride (compound 5.2) was used in place of 4-(3-fluoroazetidin-3-yl)benzonitrile hydrochloride (compound 43.4). m/z (ES+) 421 (M+H)$^+$.

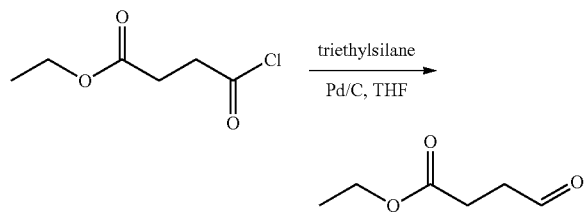

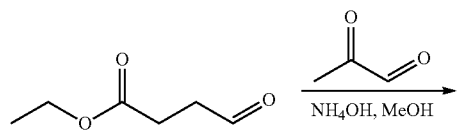

Compound 232.1. Ethyl 4-oxobutanoate

Into a 500-mL round-bottom flask, which was purged and maintained with an inert atmosphere of nitrogen, was placed a solution of ethyl 4-chloro-4-oxobutanoate (12 g, 72.91 mmol) in tetrahydrofuran (200 mL). The system was purged with nitrogen and palladium on carbon (2 g) was added to the reaction. This was followed by the addition of triethylsilane (16.5 mL, 103.20 mmol) dropwise with stirring at room temperature. The reaction mixture was stirred for 2 h at room temperature. The solids were filtered off and the filtrate was concentrated under reduced pressure to give 18 g (crude) of the title compound as a light yellow solid.

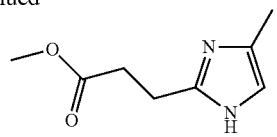

Compound 232.2. Methyl 3-(4-methyl-1H-imidazol-2-yl)propanoate

Into a 500-mL round-bottom flask, was placed a solution of ethyl 4-oxobutanoate (compound 232.1, 5.4 g, 41.49 mmol) in methanol (125 mL). An aqueous solution of 2-oxopropanal (35%) (28.5 mL, 49.96 mmol) and ammonium hydroxide (25%) (100 mL, 165.9 mmol) were added to the reaction. The reaction mixture was stirred for 2 h at 50° C. The resulting mixture was concentrated under reduced pressure. The residue was purified by silica gel chromatography with ethyl acetate as eluent to furnish 600 mg (8%) of the title compound as light yellow oil.

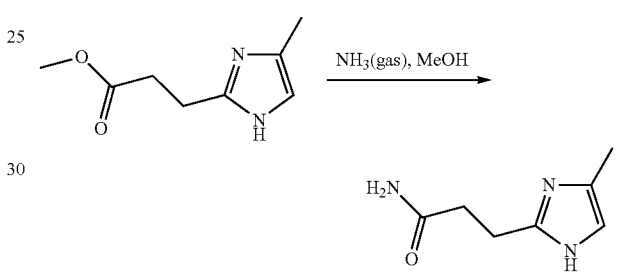

Compound 232.3. 3-(4-Methyl-1H-imidazol-2-yl)propanamide

Into a 100-mL round-bottom flask, was placed a solution of ethyl 3-(4-methyl-1H-imidazol-2-yl)propanoate (compound 232.2, 500 mg, 2.97 mmol) in methanol (10 mL). To the above NH$_3$(g) was bubbled through the solution. The reaction mixture was stirred for overnight at 50° C. The resulting mixture was concentrated under reduced pressure. This resulted in 346 mg (82%) of the title compound as a light yellow solid.

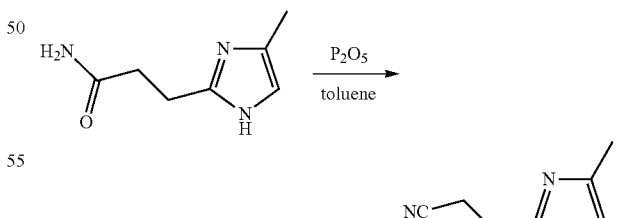

Compound 232.4. 3-(4-Methyl-1H-imidazol-2-yl)propanenitrile

Into a 250-mL three neck round-bottom flask, which was purged and maintained with an inert atmosphere of nitrogen, were placed a solution of 3-(4-methyl-1H-imidazol-2-yl)

propanamide (compound 232.3, 2 g, 13.06 mmol) in toluene (100 mL) and P₂O₅ (2 g, 14.08 mmol). The reaction mixture was stirred for 12 h at 120° C., then quenched with 100 mL of water. The aqueous phase was extracted with 2×200 mL of ethyl acetate and the combined organic layers were washed with 2×100 mL of sodium carbonate (sat.), dried over sodium sulfate and concentrated under reduced pressure. This resulted in 1 g (57%) of 3-(4-methyl-1H-imidazol-2-yl)propanenitrile as light yellow oil Compound 232. 4-(1-(5-(2-(2-Cyanoethyl)-4-methyl-1H-imidazol-5-yl)-2,4-dimethylbenzoyl)-3-fluoroazetidin-3-yl)benzonitrile The title compound was prepared using standard chemical manipulations and procedures similar to those used for the preparation of compound 5, except 3-(4-methyl-1H-imidazol-2-yl)propanenitrile (compound 232.4) was used in place of 2,4-dimethyl-1H-imidazole, methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4), and 4-(3-fluoroazetidin-3-yl)benzonitrile hydrochloride (compound 43.4) was used in place of 4-(azetidin-3-yl)benzonitrile hydrochloride (compound 5.2). m/z (ES+) 442 (M+H)⁺.

The compounds in TABLE 11 were prepared using standard chemical manipulations and procedures similar to those used for the preparation of compounds 222, 223, 231, and 232.

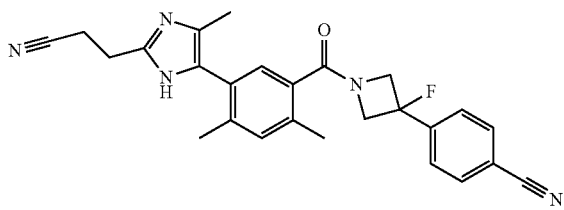 [SMILES: Cc1cc(C)c(-c2[nH]c(CCC#N)nc2C)cc1C(=O)N1CC(F)(c2ccc(C#N)cc2)C1]

TABLE 11

| Cpd | Name | Structure | m/z (ES+) (M + H)⁺ |
|---|---|---|---|
| 93 | 4-(1-(3-(4-chloro-2-(cyanomethyl)-1H-imidazol-5-yl)-4-methylbenzoyl)piperidin-4-yl)benzonitrile | 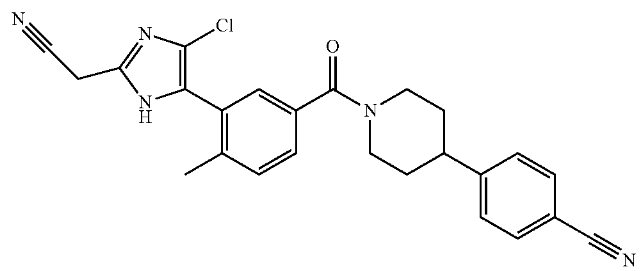 [SMILES: Cc1ccc(C(=O)N2CCC(c3ccc(C#N)cc3)CC2)cc1-c1[nH]c(CC#N)nc1Cl] | 444 |
| 143 | 4-(1-(3-(4-chloro-2-(2-cyanoethyl)-1H-imidazol-5-yl)-4-methylbenzoyl)azetidin-3-yl)benzonitrile | 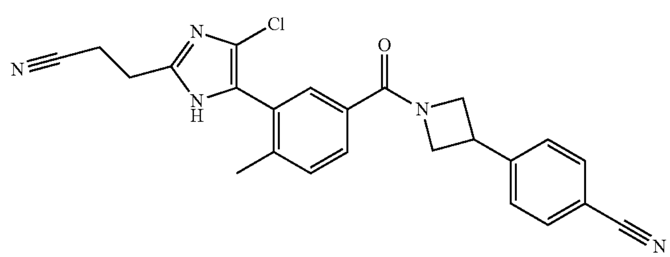 [SMILES: Cc1ccc(C(=O)N2CC(c3ccc(C#N)cc3)C2)cc1-c1[nH]c(CCC#N)nc1Cl] | 430 |
| 144 | 4-(1-(3-(4-chloro-2-(2-cyanoethyl)-1H-imidazol-5-yl)-4-methylbenzoyl)piperidin-4-yl)benzonitrile | 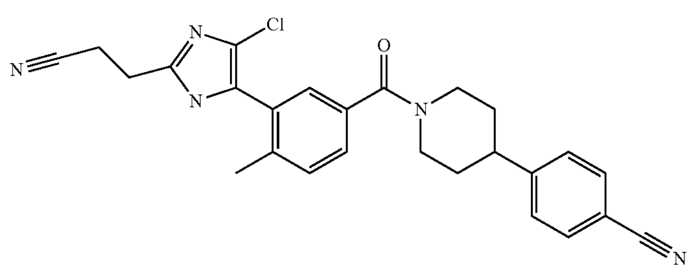 [SMILES: Cc1ccc(C(=O)N2CCC(c3ccc(C#N)cc3)CC2)cc1-c1[nH]c(CCC#N)nc1Cl] | 458 |

| Cpd | Name | Structure | m/z (ES+) (M + H)+ |
|---|---|---|---|
| 149 | 4-(1-(3-(4-chloro-2-(cyanomethyl)-1H-imidazol-5-yl)-4-methylbenzoyl)azetidin-3-yl)benzonitrile | 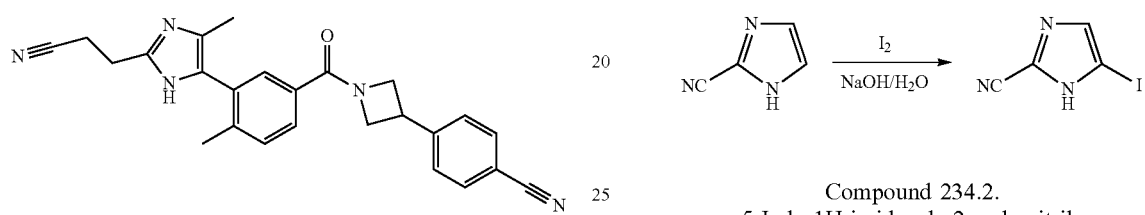 | 416 |

Compound 233. 4-(1-(3-(2-(2-Cyanoethyl)-4-methyl-1H-imidazol-5-yl)-4-methylbenzoyl)azetidin-3-yl)benzonitrile The title compound was prepared using standard chemical manipulations and procedures similar to those used for the preparation of compound 5, except 3-(4-methyl-1H-imidazol-2-yl)propanenitrile (compound 232.4) was used in place of 2,4-dimethyl-1H-imidazole. m/z (ES+) 410 (M+H)+.

Compound 234.1. 1H-Imidazole-2-carbonitrile

Into a 1-L round-bottom flask, was placed a solution of 1H-imidazole-2-carbaldehyde (5 g, 52.04 mmol) in N,N-dimethylformamide (200 mL). Triethylamine (10.8 mL, 77.97 mmol), hydroxylamine hydrochloride (3.95 g, 56.84 mmol, 1.10 equiv), 1-propanephosphonic anhydride solution and 2,4,6-tripropyl-1,3,5,2,4,6-trioxatriphosphorinane-2,4,6-trioxide solution (T₃P) (36.4 g, 114.40 mmol) were added to the reaction. The reaction mixture was stirred for 4 h at 100° C., cooled and then quenched with 500 mL of water/ice. The aqueous phase was extracted with 3×1 L of ethyl acetate, then the combined organic layers was washed with 2×1 L of brine, dried over anhydrous sodium sulfate and concentrated under reduced pressure. The residue was purified by silica gel chromatography with ethyl acetate/petroleum ether (1/2) as eluent to furnish 2 g (41%) of the title compound as an off-white solid.

Compound 234.2. 5-Iodo-1H-imidazole-2-carbonitrile

Into a 100-mL round-bottom flask, was placed a solution 1H-imidazole-2-carbonitrile (compound 234.1, 3.39 g, 36.42 mmol) in sodium hydroxide (54.7 mL, 2 M). Iodine (9.26 g, 36.46 mmol) was added to the reaction. The reaction mixture was stirred for 5 h at room temperature. The pH of the solution was adjusted to 5 with HCl (2 M). The aqueous phase was extracted with 3×80 mL of ethyl acetate. The combined organic layers were dried over anhydrous sodium sulfate and concentrated under reduced pressure. The residue was purified by silica gel chromatography with ethyl acetate/petroleum ether (1/1.5) as eluent to furnish 1.02 g (13%) of the title compound as a white solid.

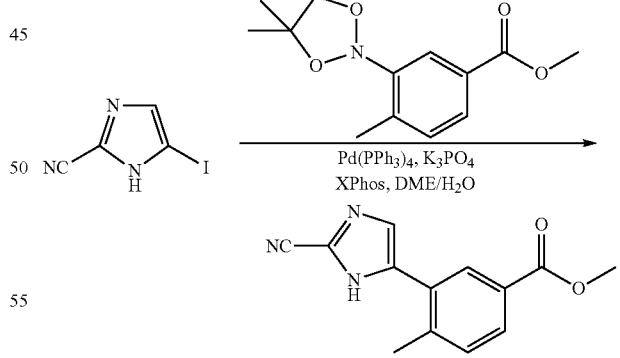

Compound 234.3. Methyl 3-(2-cyano-1H-imidazol-5-yl)-4-methylbenzoate

Into a 100-mL three neck round-bottom flask, which was purged and maintained with an inert atmosphere of nitrogen, was placed a solution of 5-iodo-1H-imidazole-2-carbonitrile (compound 234.2, 700 mg, 3.20 mmol) in a solvent mixture of DME and H₂O (30/3 mL). Methyl 4-methyl-3-(tetramethyl-1,3,2-dioxaborolan-2-yl)benzoate (compound 5.4, 1.06 g, 3.84 mmol), $K_3PO_4$ (2.71 g, 12.8 mmol), Xphos (152 mg, 0.32 mmol), Pd(PPh3)$_4$ (369 mg, 0.32 mmol) were added to the reaction. The reaction mixture was stirred overnight at 90° C., then concentrated under reduced pressure. The residue was diluted with 50 mL of ethyl acetate, then was washed with 3×20 mL of brine, dried over anhydrous sodium sulfate and concentrated under reduced pressure. The residue was purified by a silica gel chromatography with ethyl acetate/petroleum ether (1/2) as eluent to furnish 160 mg (21%) of the title compound as a white solid.

nol (4 mL). Then a solution of LiOH (45.4 mg, 1.90 mmol) in water (2 mL) was added to the reaction. The reaction mixture was stirred overnight at 30° C., then was concentrated under reduced pressure. The pH of the solution was adjusted to 3 with hydrogen chloride (1M) and was concentrated under reduced pressure. Methanol (5 mL) was added to the residue. The salt was filtered off, and the filtrate was concentrated under reduced pressure to give 150 mg (crude) of the title compound as a white solid.

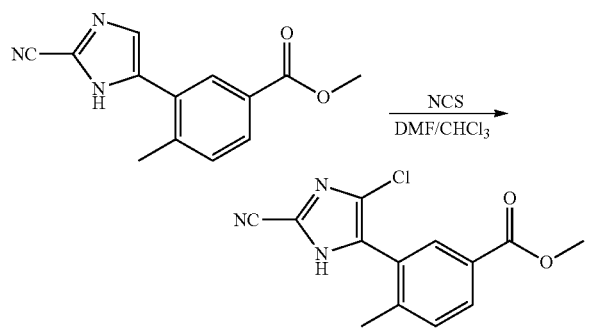

Compound 234.4. Methyl 3-(4-chloro-2-cyano-1H-imidazol-5-yl)-4-methylbenzoate

Into a 50-mL round-bottom flask, was placed a solution of methyl 3-(2-cyano-1H-imidazol-5-yl)-4-methylbenzoate (compound 234.3, 290 mg, 1.20 mmol) in a solvent mixture of DMF and CHCl$_3$ (4/20 mL). NCS (161 mg, 1.21 mmol, 1.00 equiv) was added to the above reaction mixture. The reaction mixture was stirred overnight at room temperature, then was concentrated under reduced pressure. The residue was diluted with 30 mL of EtOAc, then was washed with 3×15 mL of brine, dried over anhydrous sodium sulfate and concentrated under reduced pressure. The residue was purified by silica gel chromatography with ethyl acetate/petroleum ether (1/10-1/7) as eluent to furnish 160 mg (48%) of the title compound as light yellow oil.

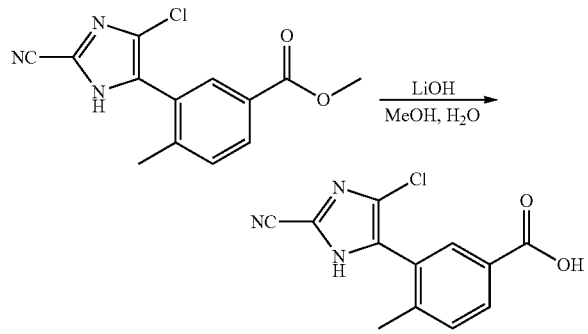

Compound 234.5. 3-(4-Chloro-2-cyano-1H-imidazol-5-yl)-4-methylbenzoic acid

Into a 25-mL round-bottom flask, was placed a solution of methyl 3-(4-chloro-2-cyano-1H-imidazol-5-yl)-4-methylbenzoate (compound 234.4, 130 mg, 0.47 mmol) in metha-

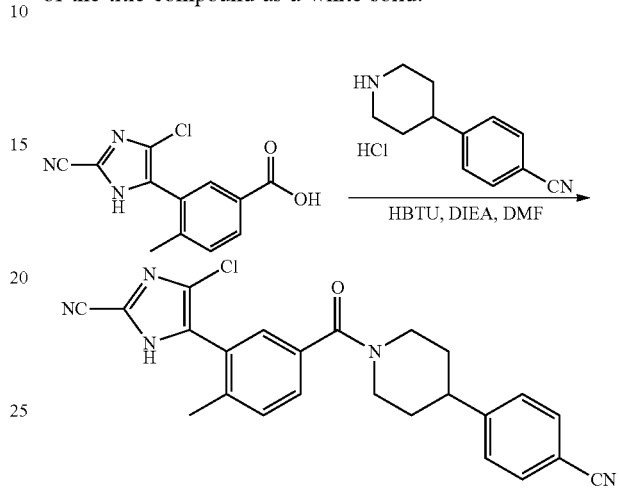

Compound 234. 4-Chloro-5-(5-(4-(4-cyanophenyl)piperidine-1-carbonyl)-2-methylphenyl)-1H-imidazole-2-carbonitrile Into a 25-mL round-bottom flask, was placed a solution of 3-(4-chloro-2-cyano-1H-imidazol-5-yl)-4-methylbenzoic acid (compound 234.5, 60 mg, 0.23 mmol) in N,N-dimethylformamide (2 mL). 4-(Piperidin-4-yl)benzonitrile hydrochloride (compound 1.2, 61 mg, 0.27 mmol), HBTU (131 mg, 0.35 mmol), DIEA (123 µL, 0.69 mmol) were added to the reaction. The reaction mixture was stirred for 30 min at 15° C. The reaction mixture was diluted with 40 mL of EtOAc, then was washed with 2×30 mL of brine and 2×30 mL of NH$_4$Cl (sat.), dried over anhydrous sodium sulfate and concentrated under reduced pressure. The crude product (160 mg) was purified by Prep-HPLC with the following conditions (2#-AnalyseHPLC-SHIMADZU(HPLC-10)): Column, SunFire Prep C18 OBD Column, 5 m, 19*150 mm; mobile phase, WATER WITH 0.05% TFA and MeCN (49.0% MeCN up to 62.0% in 7 min, up to 100.0% in 3 min, down to 49.0% in 1 min); Detector, Waters 2489, 254 and 220 nm. This resulted in 25.1 mg (25%) of the title compound as a white solid. m/z (ES+) 430 (M+H)$^+$.

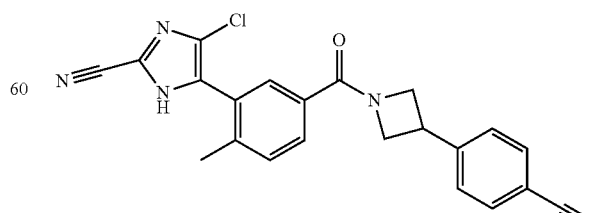

Compound 235. 4-Chloro-5-(5-(3-(4-cyanophenyl)azetidine-1-carbonyl)-2-methylphenyl)-1H-imidazole-2-carbonitrile The title compound was prepared using standard chemical manipulations and procedures similar to those used for the preparation of compound 234, except 4-(azetidin-3-yl)benzonitrile hydrochloride (compound 5.2) was used in place of 4-(piperidin-4-yl)benzonitrile hydrochloride (compound 1.2). m/z (ES+) 402 (M+H)+.

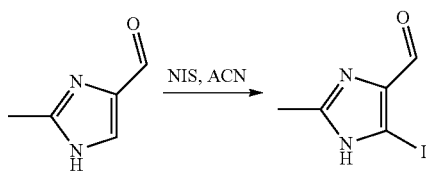

Compound 236.1. 5-Iodo-2-methyl-1H-imidazole-4-carbaldehyde

Into a 100-mL round-bottom flask, which was purged and maintained with an inert atmosphere of nitrogen, was placed a solution of 2-methyl-1H-imidazole-4-carbaldehyde (1.5 g, 13.6 mmol) in $CH_3CN$ (50 mL). NIS (3.7 g, 16.4 mmol) was added to the reaction. The reaction mixture was stirred for 4 h at 80° C., then was concentrated under reduced pressure. The residue was purified by silica gel chromatography with ethyl acetate/petroleum ether (3:1) as eluent to furnish 2.11 g (66%) of the title compound as a yellow solid.

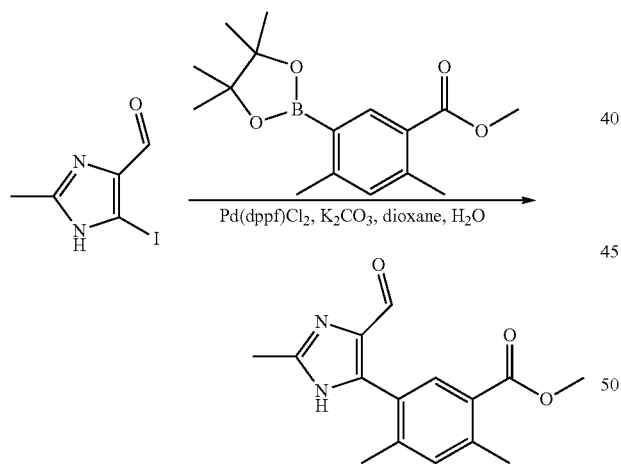

Compound 236.2. Methyl 5-(4-formyl-2-methyl-1H-imidazol-5-yl)-2,4-dimethylbenzoate Into a 100-mL three neck round-bottom flask, which was purged and maintained with an inert atmosphere of nitrogen, was placed a solution of 5-iodo-2-methyl-1H-imidazole-4-carbaldehyde (compound 236.1, 600 mg, 2.54 mmol) in dioxane (30 mL). Methyl 2,4-dimethyl-5-(tetramethyl-1,3,2-dioxaborolan-2-yl)benzoate (compound 160.1, 800 mg, 2.76 mmol), a solution of potassium carbonate (1.8 g, 13.0 mmol) in water (10 mL), and $Pd(dppf)Cl_2$ (400 mg, 0.55 mmol, 0.20 equiv) were added to the reaction. The reaction mixture was stirred for overnight at 80° C., then was quenched with 20 mL of water. The aqueous phase was extracted with 2×100 mL of ethyl acetate and the combined organic layers were washed with 2×50 mL of brine, dried over anhydrous sodium sulfate and concentrated under reduced pressure. The residue was purified by silica gel chromatography with ethyl acetate/petroleum ether (3:1) as eluent to furnish 400 mg (58%) of the title compound as a light yellow solid.

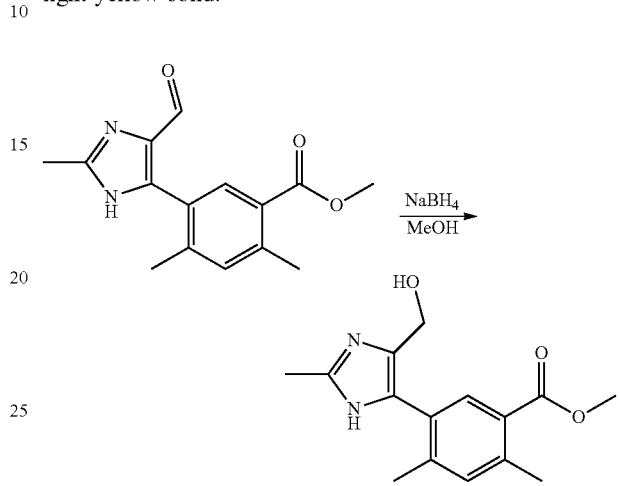

Compound 236.3. Methyl 5-(4-(hydroxymethyl)-2-methyl-1H-imidazol-5-yl)-2,4-dimethylbenzoate Into a 50-mL round-bottom flask, was placed a solution of methyl 5-(4-formyl-2-methyl-1H-imidazol-5-yl)-2,4-dimethylbenzoate (compound 236.2, 400 mg, 1.47 mmol) in methanol (20 mL). This was followed by the addition of $NaBH_4$ (100 mg, 2.64 mmol) in several batches at 0° C. The reaction mixture was stirred for 1 h at room temperature, then was used for next step directly.

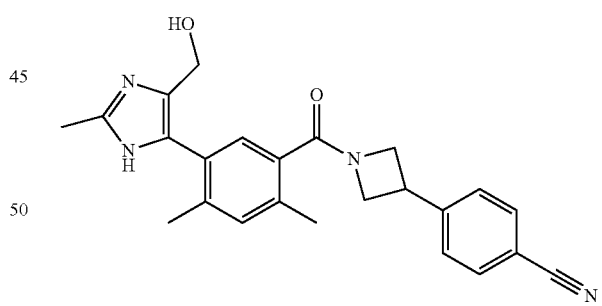

Compound 236. 4-(1-(5-(4-(Hydroxymethyl)-2-methyl-1H-imidazol-5-yl)-2,4-dimethylbenzoyl)azetidin-3-yl)benzonitrile The title compound was prepared using standard chemical manipulations and procedures similar to those used for the preparation of compound 5, except methyl 5-(4-(hydroxymethyl)-2-methyl-1H-imidazol-5-yl)-2,4-dimethylbenzoate (compound 236.3) was used in place of methyl 3-(2,4-dimethyl-1H-imidazol-5-yl)-4-methylbenzoate (compound 5.6). m/z (ES+) 401 (M+H)+.

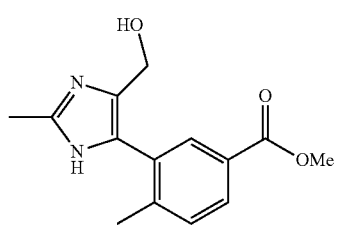 [SMILES: COC(=O)c1ccc(C)c(-c2[nH]c(C)nc2CO)c1]

Compound 237.1. Methyl 3-(4-(hydroxymethyl)-2-methyl-1H-imidazol-5-yl)-4-methylbenzoate The title compound was prepared using standard chemical manipulations and procedures similar to those used for the preparation of compound 236.3, except methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1).

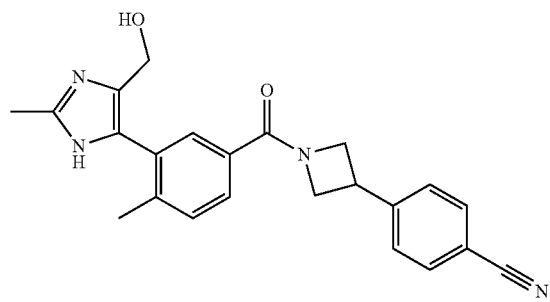 [SMILES: Cc1nc(CO)c(-c2cc(C(=O)N3CC(c4ccc(C#N)cc4)C3)ccc2C)[nH]1]

Compound 237. 4-(1-(3-(4-(Hydroxymethyl)-2-methyl-1H-imidazol-5-yl)-4-methylbenzoyl)azetidin-3-yl)benzonitrile The title compound was prepared using standard chemical manipulations and procedures similar to those used for the preparation of compound 5, except methyl 3-(4-(hydroxymethyl)-2-methyl-1H-imidazol-5-yl)-4-methylbenzoate (compound 237.1) was used in place of methyl 3-(2,4-dimethyl-1H-imidazol-5-yl)-4-methylbenzoate (compound 5.6). m/z (ES+) 387 (M+H)+.

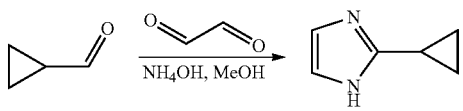

Compound 238.1. 2-Cyclopropyl-1H-imidazole

Into a 500-mL round-bottom flask, was placed a solution of cyclopropanecarbaldehyde (10.7 mL, 142.7 mmol) in methanol (60 mL). An aqueous solution of oxalaldehyde (18.0 mL, 157.1 mmol, 40%) was added to the reaction. This was followed by the addition of NH4OH (89 mL, 571.4 mmol) dropwise at 0° C. in 30 min. The reaction mixture was stirred overnight at room temperature, then concentrated under reduced pressure. The resulting solution was extracted with 3×100 mL of ethyl acetate. The combined organic layers were washed with 2×30 mL of brine, dried over anhydrous sodium sulfate and concentrated under reduced pressure. This resulted in 12 g (crude) of the title compound as a brown solid.

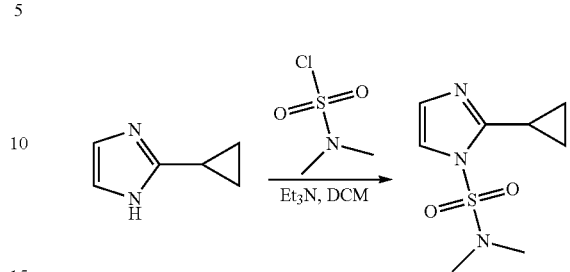

Compound 238.2. 2-Cyclopropyl-N,N-dimethyl-1H-imidazole-1-sulfonamide

Into a 500-mL round-bottom flask, was placed a solution of 2-cyclopropyl-1H-imidazole (compound 238.1, 12 g, 110.9 mmol) in dichloromethane (60 mL). Triethylamine (31.4 mL, 225.3 mmol), N,N-dimethylsulfamoyl chloride (13.2 mL, 121.87 mmol, 1.10 equiv) were added to the reaction. The reaction mixture was stirred for 4 h at room temperature, then quenched with 20 mL of water. The aqueous phase was extracted with 3×100 mL of dichloromethane. The combined organic layers were washed with 2×20 mL of brine, dried over anhydrous sodium sulfate and concentrated under vacuum. The residue was purified by silica gel chromatography with ethyl acetate/petroleum ether (1:4) as eluent to furnish 16 g (67%) of the title compound as a white solid.

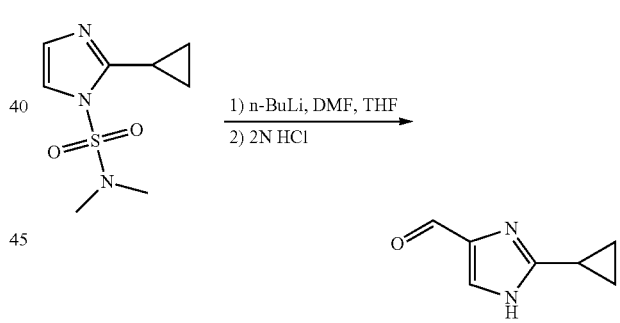

Compound 238.3. 2-Cyclopropyl-1H-imidazole-4-carbaldehyde

Into a 500-mL three neck round-bottom flask, which was purged and maintained with an inert atmosphere of nitrogen, was placed a solution of 2-cyclopropyl-N,N-dimethyl-1H-imidazole-1-sulfonamide (compound 238.2, 5 g, 23.23 mmol) in tetrahydrofuran (100 mL). This was followed by the addition of n-butyllithium (11.2 mL, 2.5M in THF) dropwise at −78° C. over a period of 30 min. To this was added DMF (11.8 mL, 152.55 mmol). The resulting solution was stirred for 30 min at −50° C., then hydrogen chloride (50 mL, 1M) was added. The reaction mixture was stirred for 2 h at room temperature. The pH of the solution was adjusted to 7-8 with sodium bicarbonate (sat). The resulting solution was extracted with 3×30 mL of ethyl acetate and the organic layers combined. The resulting mixture was washed with 2×10 mL of brine. The mixture was dried over anhydrous sodium sulfate and concentrated under reduced pressure. This resulted in 3 g (97%) of the title compound as a white solid.

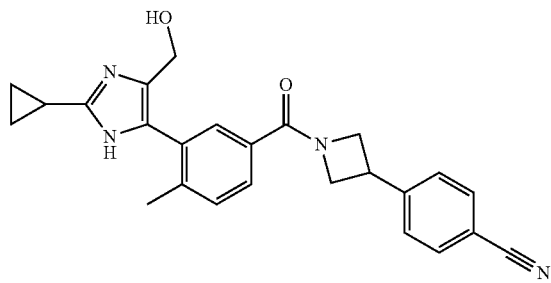 [SMILES: Cc1ccc(C(=O)N2CC(c3ccc(C#N)cc3)C2)cc1-c1[nH]c(C2CC2)nc1CO]

Compound 238. 4-(1-(3-(2-Cyclopropyl-4-(hydroxymethyl)-1H-imidazol-5-yl)-4-methylbenzoyl)azetidin-3-yl)benzonitrile The title compound was prepared using standard chemical manipulations and procedures similar to those used for the preparation of compound 236, except 2-cyclopropyl-1H-imidazole-4-carbaldehyde (compound 238.3) was used in place of 2-methyl-1H-imidazole-4-carbaldehyde and methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1). m/z (ES+) 413 (M+H)⁺.

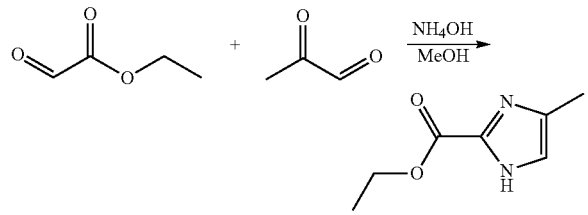

Compound 239.1. Ethyl 4-methyl-1H-imidazole-2-carboxylate

Into a 50-mL round-bottom flask, was placed a solution of ethyl 2-oxoacetate (400 mg, 3.92 mmol) in methanol (4 mL). A aqueous solution of 2-oxopropanal (565 mg, 3.92 mmol, 50%), ammonia (25%) (8.8 mL, 15.68 mmol) were added to the reaction. The reaction mixture was stirred for overnight at room temperature, then was concentrated under reduced pressure. The residue was purified by silica gel chromatography with ethyl acetate/petroleum ether (1/1) as eluent to furnish 200 mg (33%) of the title compound as a yellow solid.

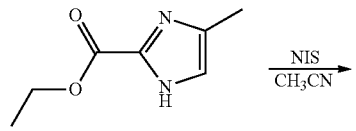

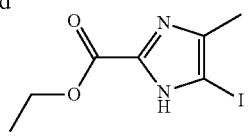

Compound 239.2. Ethyl 5-iodo-4-methyl-1H-imidazole-2-carboxylate

Into a 100-mL round-bottom flask, was placed a solution of ethyl 4-methyl-1H-imidazole-2-carboxylate (compound 239.1, 100 mg, 0.65 mmol) in CH₃CN (10 mL). NIS (218 mg, 0.97 mmol) was added to the reaction. The reaction mixture was stirred for overnight at room temperature, then concentrated under reduced pressure. The residue was dissolved with 30 mL of EtOAc, then was washed with 2×20 mL of brine, dried over anhydrous sodium sulfate and concentrated under reduced pressure. This resulted in 80 mg (44%) of the title compound as a yellow solid.

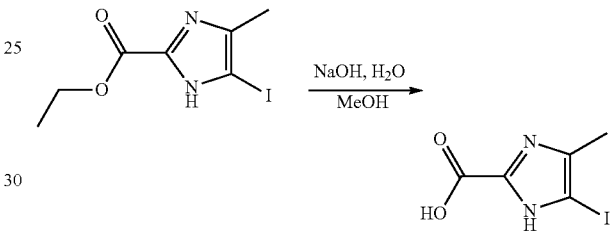

Compound 239.3. 5-Iodo-4-methyl-1H-imidazole-2-carboxylic acid

Into a 100-mL round-bottom flask, was placed a solution of ethyl 5-iodo-4-methyl-1H-imidazole-2-carboxylate (compound 239.2, 200 mg, 0.71 mmol) in methanol (4 mL). A solution of sodium hydroxide (114 mg, 2.85 mmol) in water (2 mL) was added to the reaction. The reaction mixture was stirred for 2 h at 60° C. The pH of the solution was adjusted to 1-2 with hydrogen chloride (1 M). The resulting mixture was concentrated under reduced pressure. Methanol (5 mL) was added to the residue. The salt was filtered off and the filtrate was concentrated under reduced pressure to give 290 mg (crude) of the title compound as a white solid.

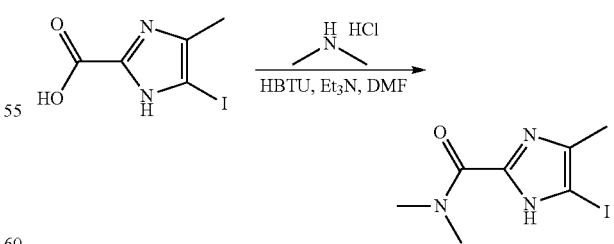

Compound 239.4. 5-Iodo-N,N,4-trimethyl-1H-imidazole-2-carboxamide

Into a 100-mL round-bottom flask, was placed a solution of 5-iodo-4-methyl-1H-imidazole-2-carboxylic acid (compound 239.3, 200 mg, 0.79 mmol) in N,N-dimethylformamide (4 mL). HBTU (602 mg, 1.59 mmol), dimethylamine hydrochloride (96 mg, 1.18 mmol) and triethylamine (552 µL, 3.96 mmol) were added to the reaction. The reaction mixture was stirred for 3 h at room temperature, then diluted with 50 mL of EtOAc. The organic layer was washed with 2×20 mL of brine, dried over anhydrous sodium sulfate and concentrated under reduced pressure. This resulted in 150 mg (68%) of the title compound as yellow oil.

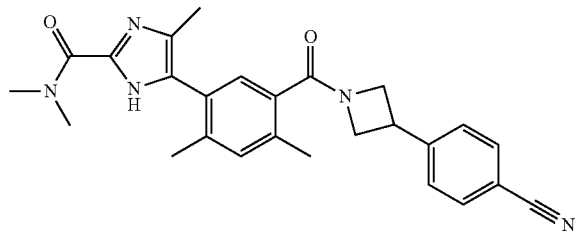 [SMILES: Cc1cc(C)c(-c2[nH]c(C(=O)N(C)C)nc2C)cc1C(=O)N1CC(c2ccc(C#N)cc2)C1]

Compound 239. 5-(5-(3-(4-Cyanophenyl)azetidine-1-carbonyl)-2,4-dimethylphenyl)-N,N,4-trimethyl-1H-imidazole-2-carboxamide The title compound was prepared using standard chemical manipulations and procedures similar to those used for the preparation of compound 5, except 5-iodo-N,N,4-trimethyl-1H-imidazole-2-carboxamide (compound 239.4) was used in place of 5-iodo-2,4-dimethyl-1H-imidazole (compound 5.5) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 442 (M+H)⁺.

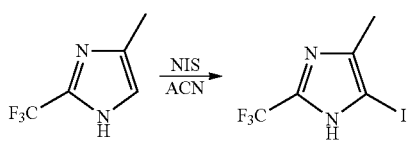

Compound 240.1.
5-Iodo-4-methyl-2-(trifluoromethyl)-1H-imidazole

Into a 250-mL round-bottom flask, was placed a solution of 4-methyl-2-(trifluoromethyl)-1H-imidazole (compound 14.1, 4.41 g, 29.38 mmol) in CH₃CN (100 mL). NIS (6.6 g, 29.34 mmol) was added to the reaction. The reaction mixture was stirred overnight at room temperature, then concentrated under reduced pressure. The reaction mixture was diluted with 300 mL of EtOAc. The organic layer was washed with 3×150 mL of brine, dried over anhydrous sodium sulfate and concentrated under reduced pressure. The residue was purified by silica gel chromatography with ethyl acetate/petroleum ether (1/30-1/20) as eluent to furnish 2.125 g (26%) of the title compound as a light yellow solid.

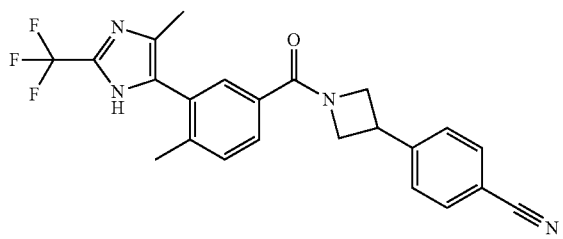 [SMILES: Cc1ccc(C(=O)N2CC(c3ccc(C#N)cc3)C2)cc1-c1[nH]c(C(F)(F)F)nc1C]

Compound 240. 4-(1-(4-Methyl-3-(4-methyl-2-(trifluoromethyl)-1H-imidazol-5-yl)benzoyl)azetidin-3-yl)benzonitrile The title compound was prepared using standard chemical manipulations and procedures similar to those used for the preparation of compound 16, except 5-iodo-4-methyl-2-(trifluoromethyl)-1H-imidazole (compound 240.1) was used in place of 5-iodo-2-methyl-1H-imidazole-4-carbonitrile (compound 16.4). m/z (ES+) 425 (M+H)⁺.

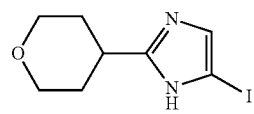 [SMILES: Ic1cnc(C2CCOCC2)[nH]1]

Compound 241.1. 5-Iodo-2-(tetrahydro-2H-pyran-4-yl)-1H-imidazole

The title compound was prepared using standard chemical manipulations and procedures similar to those used for the preparation of compound 44.3, except tetrahydro-2H-pyran-4-carbaldehyde was used in place of cyclopropanecarbaldehyde.

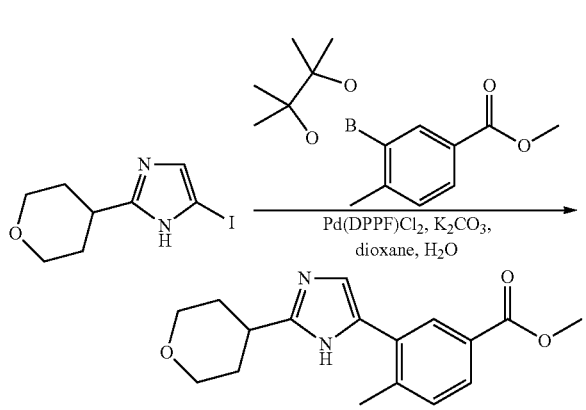

Compound 241.2. Methyl 4-methyl-3-(2-(tetrahydro-2H-pyran-4-yl)-1H-imidazol-5-yl)benzoate Into a 50-mL three neck round-bottom flask, which was purged and maintained with an inert atmosphere of nitrogen, was placed a solution of 5-iodo-2-(tetrahydro-2H-pyran-4-yl)-1H-imidazole (compound 241.1, 400 mg, 1.44 mmol) in dioxane (15 mL). Methyl 4-methyl-3-(4,4,5,5-tetramethyl-1,3,2-dioxaborolan-2-yl)benzoate (compound 5.4, 397 mg, 1.44 mmol), potassium carbonate (993 mg, 7.18 mmol), water (1.5 mL) and Pd(dppf)Cl2 (105 mg, 0.14 mmol, 0.10 equiv) were added to the reaction. The reaction mixture was stirred overnight at 90° C., then diluted with 120 mL of EtOAc. The organic layer was washed with 3×40 mL of brine, dried over anhydrous sodium sulfate and concentrated under reduced pressure. The residue was purified by silica gel chromatography with ethyl acetate as eluent to furnish 260 mg (60%) of the title compound as red oil.

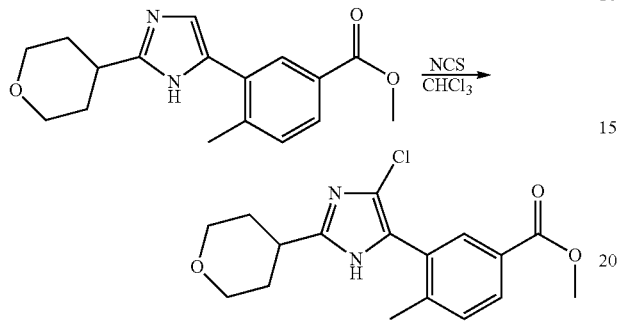

Compound 241.3. Methyl 3-(4-chloro-2-(tetrahydro-2H-pyran-4-yl)-1H-imidazol-5-yl)-4-methylbenzoate Into a 25-mL round-bottom flask, was placed a solution of methyl 4-methyl-3-(2-(tetrahydro-2H-pyran-4-yl)-1H-imidazol-5-yl)benzoate (compound 241.2, 260 mg, 0.87 mmol) in chloroform (3 mL). NCS (116 mg, 0.87 mmol) was added to the reaction. The reaction mixture was stirred for 4 h at 25° C., then concentrated under reduced pressure. The residue was dissolved in 50 mL of EtOAc, then was washed with 3×20 mL of brine, dried over anhydrous sodium sulfate and concentrated under reduced pressure. This resulted in 313 mg (crude) of the title compound as brown oil.

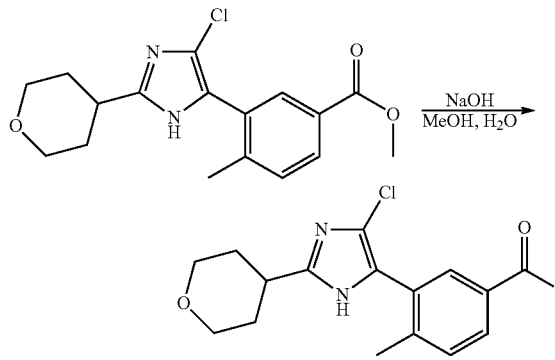

Compound 241.4. 3-(4-Chloro-2-(tetrahydro-2H-pyran-4-yl)-1H-imidazol-5-yl)-4-methylbenzoic acid Into a 50-mL round-bottom flask, was placed a solution of methyl 3-(4-chloro-2-(tetrahydro-2H-pyran-4-yl)-1H-imidazol-5-yl)-4-methylbenzoate (compound 241.3, 290 mg, 0.87 mmol) in methanol (6 mL). Then a solution of sodium hydroxide (139 mg, 3.48 mmol) in water (3 mL) was added to the reaction. The reaction mixture was stirred for 1 h at 60° C., then concentrated under reduced pressure. The pH of the solution was adjusted to 1 with hydrogen chloride (2 M). The resulting mixture was concentrated under reduced pressure. Methanol (10 mL) was added to the residue. The salt was filtered off, and the filtrate was concentrated under reduced pressure to give 300 mg of the title compound as a brown solid.

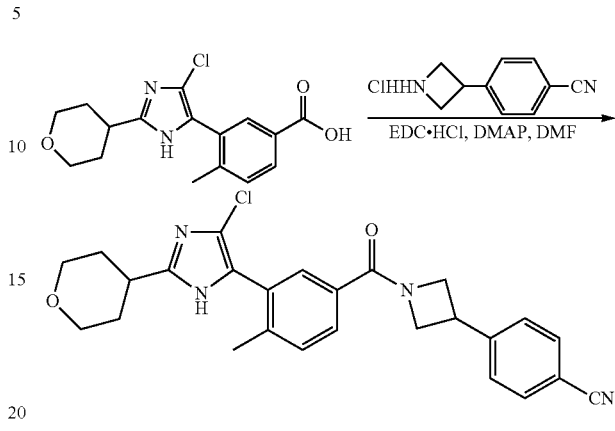

Compound 241. 4-(1-(3-(4-Chloro-2-(tetrahydro-2H-pyran-4-yl)-1H-imidazol-5-yl)-4-methylbenzoyl)azetidin-3-yl)benzonitrile Into a 25-mL round-bottom flask, was placed a solution of 3-(4-chloro-2-(tetrahydro-2H-pyran-4-yl)-1H-imidazol-5-yl)-4-methylbenzoic acid (compound 241.4, 150 mg, 0.47 mmol) in N,N-dimethylformamide (3 mL). 4-(Azetidin-3-yl)benzonitrile hydrochloride (compound 5.2, 91 mg, 0.47 mmol), EDC·HCl (180 mg, 0.94 mmol), 4-dimethylaminopyridine (114 mg, 0.93 mmol) were added to the reaction. The reaction mixture was stirred for 3 h at 25° C., then diluted with 80 mL of EtOAc. The organic layer was washed with 3×50 mL of brine, dried over anhydrous sodium sulfate and concentrated under reduced pressure. The crude product (300 mg) was purified by Prep-HPLC with the following conditions (1#-Pre-HPLC-001(SHIMADZU)): Column, SunFire Prep C18 OBD Column, 5 μm, 19*150 mm; mobile phase, WATER WITH 0.05% TFA and ACN (25.0% ACN up to 39.0% in 8 min, hold 39.0% in 1 min, up to 100.0% in 3 min, down to 25.0% in 1 min); Detector, Waters 2489, 254 and 220 nm. This resulted in 133.3 mg (62%) of the title compound as a light yellow solid. m/z (ES+) 461 (M+H)$^+$.

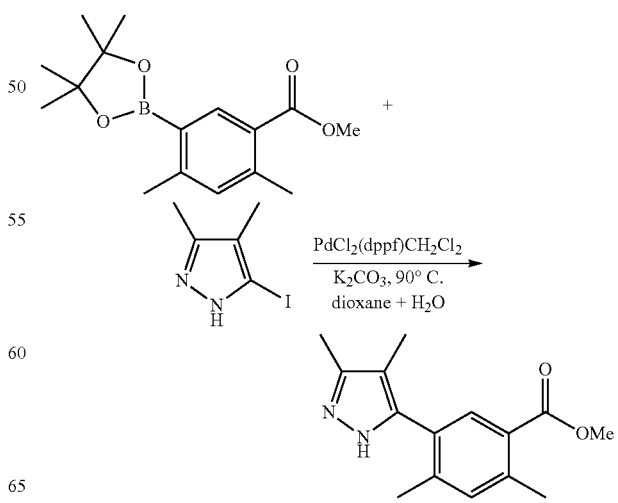

Compound 242.1. Methyl 5-(3,4-dimethyl-1H-pyrazol-5-yl)-2,4-dimethylbenzoate The title compound was prepared using standard chemical manipulations and procedures similar to those used for the preparation of compound 59.2, except methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 259 (M+H)+.

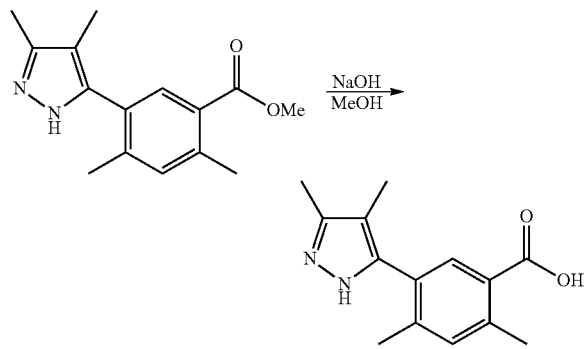

Compound 242.2. 5-(3,4-Dimethyl-1H-pyrazol-5-yl)-2,4-dimethylbenzoic acid

The title compound was prepared using standard chemical manipulations and procedures similar to those used for the preparation of compound 59.3, except methyl 5-(3,4-dimethyl-1H-pyrazol-5-yl)-2,4-dimethylbenzoate (compound 242.1) was used in place of methyl 3-(3,4-dimethyl-1H-pyrazol-5-yl)-4-methylbenzoate (compound 59.2). m/z (ES+) 245 (M+H)+.

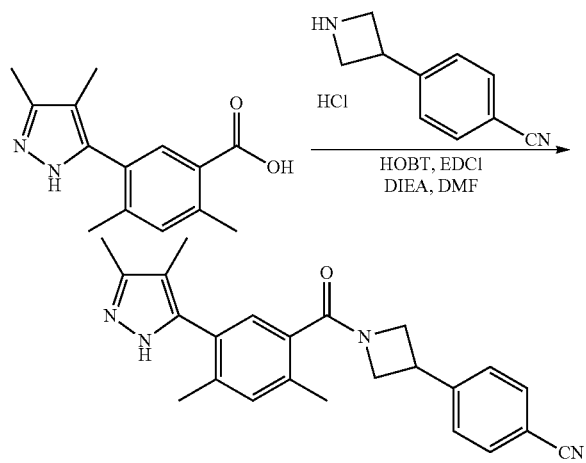

Compound 242. 4-(1-(5-(3,4-Dimethyl-1H-pyrazol-5-yl)-2,4-dimethylbenzoyl)azetidin-3-yl)benzonitrile The title compound was prepared using standard chemical manipulations and procedures similar to those used for the preparation of compound 59, except 5-(3,4-dimethyl-1H-pyrazol-5-yl)-2,4-dimethylbenzoic acid (compound 242.2) was used in place of 3-(3,4-dimethyl-1H-pyrazol-5-yl)-4-methylbenzoic acid (compound 59.3). m/z (ES+) 385 (M+H)+.

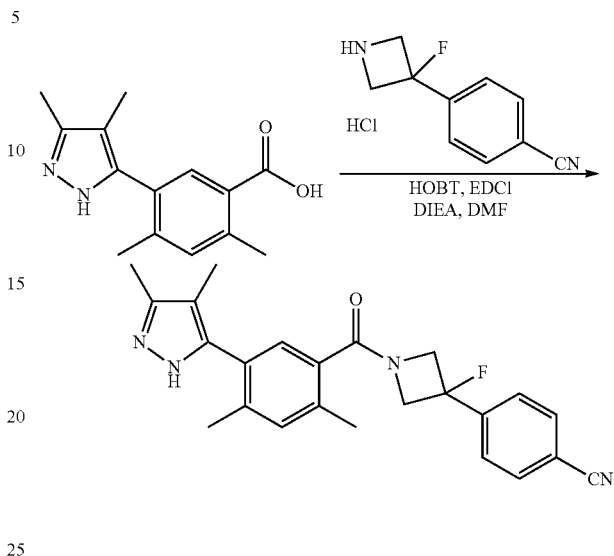

Compound 243. 4-(1-(5-(3,4-Dimethyl-1H-pyrazol-5-yl)-2,4-dimethylbenzoyl)-3-fluoroazetidin-3-yl)benzonitrile The title compound was prepared using standard chemical manipulations and procedures similar to those used for the preparation of compound 60, except 5-(3,4-dimethyl-1H-pyrazol-5-yl)-2,4-dimethylbenzoic acid (compound 242.2) was used in place of 3-(3,4-dimethyl-1H-pyrazol-5-yl)-4-methylbenzoic acid (compound 59.3). m/z (ES+) 403 (M+H)+.

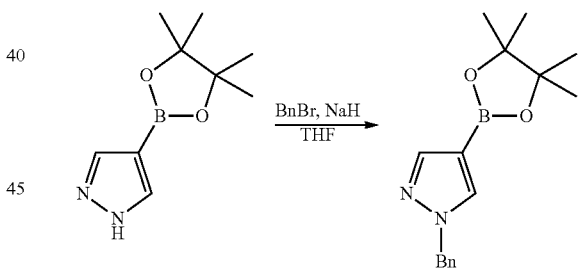

Compound 244.1. 1-Benzyl-4-(4,4,5,5-tetramethyl-1,3,2-dioxaborolan-2-yl)-1H-pyrazole Into a 100-mL three neck round-bottom flask, was placed a solution of 4-(4,4,5,5-tetramethyl-1,3,2-dioxaborolan-2-yl)-1H-pyrazole (3.60 g, 18.6 mmol) in THF (50 mL). Sodium hydride (742 mg, 18.6 mmol, 60% dispersion in mineral oil) was carefully added in portions at 0° C. The resulting mixture was stirred for 30 min at 0° C., then benzyl bromide (2.21 mL, 18.6 mmol) was added. The resulting mixture was stirred overnight at room temperature, then carefully quenched with water (10 mL). The pH of the mixture was adjusted to 9-10 with aqueous HCl (2 M) and the aqueous phase was extracted with EtOAc (300 mL). The combined organic layers were washed with brine (2×150 mL), dried (Na2SO4), filtered and concentrated under vacuum. The residue was purified by silica gel chromatography with ethyl acetate/petroleum ether (1/2) as eluent to yield the title compound as a yellow oil (3.47 g, 66%).

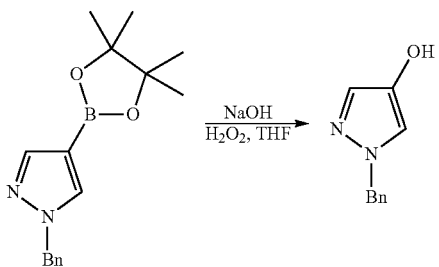

Compound 244.2. 1-Benzyl-1H-pyrazol-4-ol

Into a 100-mL three neck round-bottom flask, was placed a solution of 1-benzyl-4-(4,4,5,5-tetramethyl-1,3,2-dioxaborolan-2-yl)-1H-pyrazole (compound 244.1, 3.47 g, 12.2 mmol) in tetrahydrofuran (35 mL). Sodium hydroxide (980 mg, 24.5 mmol) was added and then the mixture was cooled to 0° C. Hydrogen peroxide (2.51 mL, 24.4 mmol) was carefully added drop-wise and the resulting mixture was stirred for 2 h at room temperature. The reaction was carefully quenched with aqueous $Na_2S_2O_3$(sat.) (20 mL). The aqueous phase was extracted with EtOAc (300 mL) and the combined organic layers were washed with brine (2×150 mL), dried ($Na_2SO_4$), filtered, and concentrated under reduced pressure. The residue was purified by silica gel chromatography with ethyl acetate/petroleum ether (1/1) as eluent to furnish the title compound as a white solid (1.64 g, 77%).

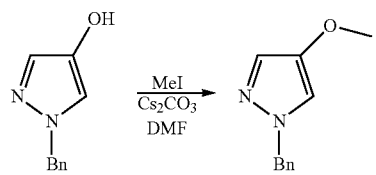

Compound 244.3. 1-Benzyl-4-methoxy-1H-pyrazole

Into a 100-mL round-bottom flask, was placed a solution of 1-benzyl-1H-pyrazol-4-ol (compound 244.2, 1.40 g, 8.04 mmol) in N,N-dimethylformamide (20 mL). Iodomethane (703 μL, 11.3 mmol) and $Cs_2CO_3$ (3.68 g, 11.3 mmol,) were added and the resulting mixture was stirred for 3 h at room temperature. The mixture was concentrated under reduced pressure, then diluted with EtOAc (200 mL). The mixture was washed with brine (3×80 mL), and the organic layer was dried ($Na_2SO_4$), filtered and concentrated under reduced pressure to obtain the title compound as a yellow oil (1.30 g, 86%).

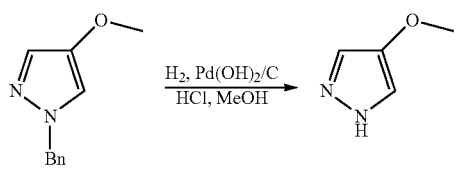

Compound 244.4. 4-Methoxy-1H-pyrazole

Into a 100-mL round-bottom flask, was placed a solution of 1-benzyl-4-methoxy-1H-pyrazole (compound 244.3, 666 mg, 3.54 mmol) in methanol (10 mL). Hydrogen chloride (1 M, 1 mL) and $Pd(OH)_2$/C (20 wt %, 670 mg) were added and the mixture was purged with nitrogen then charged with hydrogen. The mixture was stirred under hydrogen overnight at room temperature, then purged with nitrogen. The solids were removed by filtration and the filtrate was concentrated under reduced pressure to obtain the title compound as a brown oil (0.36 g, crude).

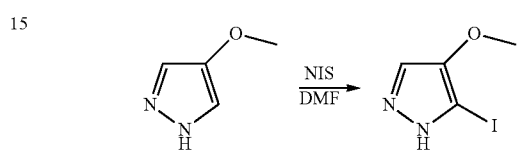

Compound 244.5. 3-Iodo-4-methoxy-1H-pyrazole

Into a 50-mL round-bottom flask, was placed 4-methoxy-1H-pyrazole (compound 244.4, 360 mg, 3.67 mmol) in N,N-dimethylformamide (4 mL). NIS (830 mg, 3.69 mmol) was added portion-wise and the resulting mixture was stirred overnight at room temperature. The mixture was diluted with ethyl acetate (40 mL), then washed with brine (3×10 mL), dried ($Na_2SO_4$), filtered and concentrated under reduced pressure. The residue was purified by silica gel chromatography with ethyl acetate/petroleum ether (1:10) as the eluent to obtain the title compound as a white solid (0.54 g, 66%).

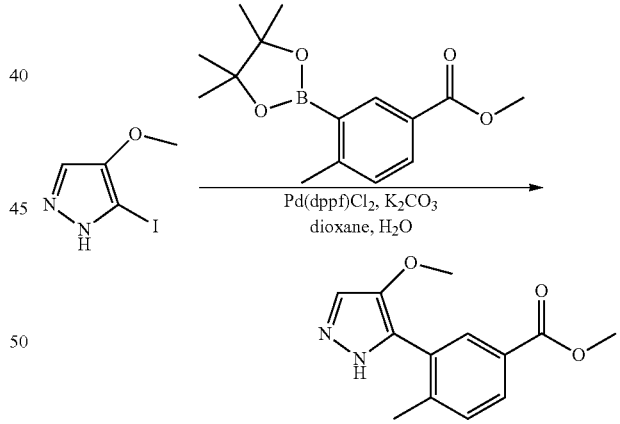

Compound 244.6. Methyl 3-(4-methoxy-1H-pyrazol-5-yl)-4-methylbenzoate

Into a 50-mL three neck round-bottom flask, purged and maintained with nitrogen, was placed a solution of methyl 4-methyl-3-(4,4,5,5-tetramethyl-1,3,2-dioxaborolan-2-yl) benzoate (414 mg, 1.50 mmol) in dioxane (6 mL). Potassium carbonate (2 M, 2.5 mL, 5.00 mmol), 3-iodo-4-methoxy-1H-pyrazole (compound 244.5, 224 mg, 1.00 mmol), Pd(dppf)Cl$_2$ (73 mg, 0.10 mmol) were added to the reaction and the resulting mixture was stirred overnight at 90° C. The resulting mixture was cooled, then diluted with EtOAc (80 mL) and washed with brine (2×30 mL), dried (Na₂SO₄), filtered and concentrated under reduced pressure. The residue was purified by a silica gel column chromatography with ethyl acetate/petroleum ether (1/1) as eluent to obtain the title compound as a yellow oil (180 mg, 73%).

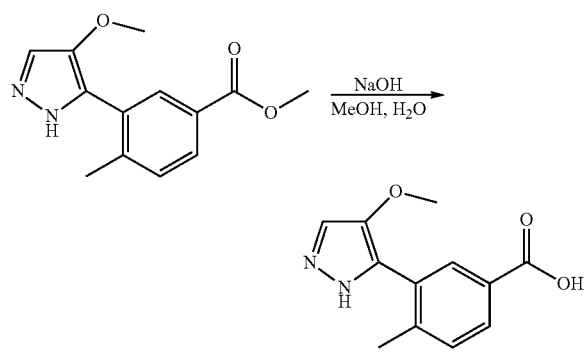

Compound 244.7.
3-(4-Methoxy-1H-pyrazol-5-yl)-4-methylbenzoic acid

Into a 50-mL round-bottom flask, was placed a solution of methyl 3-(4-methoxy-1H-pyrazol-5-yl)-4-methylbenzoate (compound 244.6, 180 mg, 0.73 mmol) in methanol (4 mL). Sodium hydroxide (117 mg, 2.92 mmol) in water (2 mL) was added and the resulting solution was stirred for 3 h at 60° C., then concentrated under reduced pressure. The pH of the residue was adjusted to 1 with aqueous hydrogen chloride (1 M), then concentrated under reduced pressure. Methanol (5 mL) was added to the residue and the solids were filtered from the solution. The filtrate was concentrated under reduced pressure to obtain the title compound as a light yellow solid (353 mg, crude).

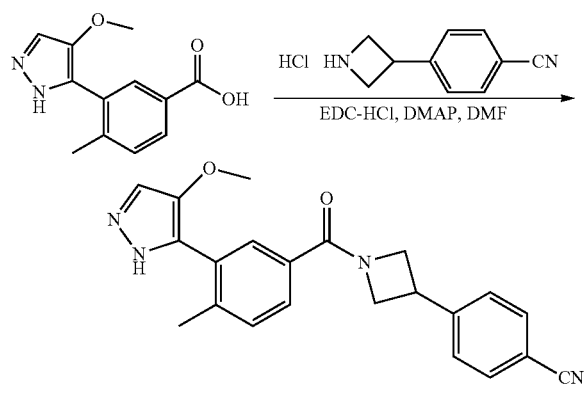

Compound 244. 4-(1-(3-(4-Methoxy-1H-pyrazol-5-yl)-4-methylbenzoyl)azetidin-3-yl)benzonitrile Into a 25-mL round-bottom flask, was placed a solution of 3-(4-methoxy-1H-pyrazol-5-yl)-4-methylbenzoic acid (compound 244.7, 60 mg, 0.26 mmol) in N,N-dimethylformamide (2 mL). 4-(Azetidin-3-yl)benzonitrile hydrochloride (75 mg, 0.39 mmol), EDC-HCl (99 mg, 0.52 mmol), and 4-dimethylaminopyridine (63 mg, 0.52 mmol) were added and the solution was stirred for 2 h at room temperature. The reaction was diluted with EtOAc (30 mL) and washed with brine (3×15 mL), dried (Na₂SO₄), filtered and concentrated under reduced pressure. The crude product (150 mg) was purified by Prep-HPLC with the following conditions (1#-Pre-HPLC-010(Waters)): Column, SunFire Prep C18 OBD Column, 5 μm, 19*150 mm; mobile phase, water with 0.05% TFA and CH₃CN (35.0% CH₃CN up to 50.0% in 10 min, up to 100% in 1 min, down to 35.0% in 2 min); Detector, UV 254 & 220 nm. The fractions contained pure product were combined and lyophilized to obtain the title compound as an off-white solid (44.3 mg, 46%). m/z (ES+) 373 (M+H⁺).

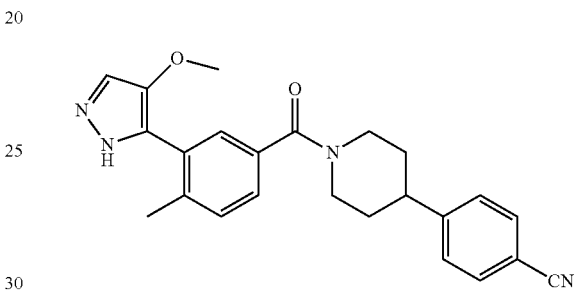

Compound 245. 4-(1-(3-(4-Methoxy-1H-pyrazol-5-yl)-4-methylbenzoyl)piperidin-4-yl)benzonitrile The title compound was prepared using standard chemical manipulations and procedures similar to those used for the preparation of compound 244, except 4-(piperidin-4-yl)benzonitrile hydrochloride (compound 1.2) was used in place of 4-(azetidin-3-yl)benzonitrile hydrochloride (compound 5.2). m/z (ES+) 401 (M+H⁺).

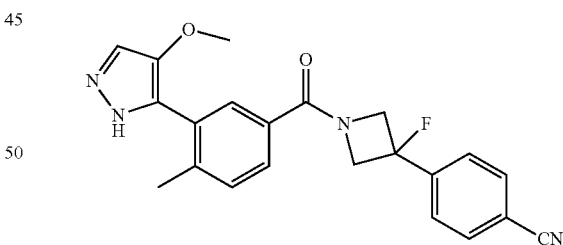

Compound 246. 4-(3-Fluoro-1-(3-(4-methoxy-1H-pyrazol-5-yl)-4-methylbenzoyl)azetidin-3-yl)benzonitrile The title compound was prepared using standard chemical manipulations and procedures similar to those used for the preparation of compound 244, except 4-(3-fluoroazetidin-3-yl)benzonitrile hydrochloride (compound 43.4) was used in place of 4-(azetidin-3-yl)benzonitrile hydrochloride (compound 5.2). m/z (ES+) 391 (M+H⁺).

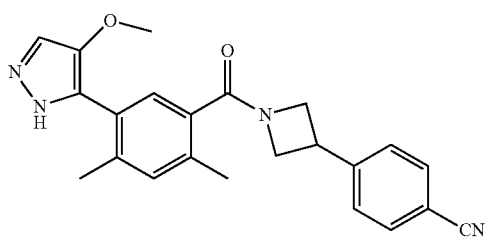 [SMILES: COc1cn[nH]c1-c1cc(C(=O)N2CC(c3ccc(C#N)cc3)C2)c(C)cc1C]

Compound 247. 4-(1-(5-(4-Methoxy-1H-pyrazol-5-yl)-2,4-dimethylbenzoyl)azetidin-3-yl)benzonitrile The title compound was prepared using standard chemical manipulations and procedures similar to those used for the preparation of compound 244, except methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 387 (M+H$^+$).

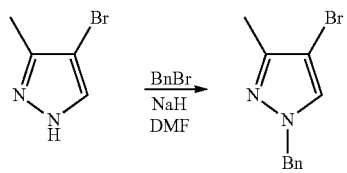

Compound 248.1. 1-Benzyl-4-bromo-3-methyl-1H-pyrazole

Into a 500-mL 3-neck round-bottom flask, was placed a solution of 4-bromo-3-methyl-1H-pyrazole (20.0 g, 124 mmol) in N,N-dimethylformamide (100 mL). The system was purged with nitrogen, then the solution was cooled to 0° C. Sodium hydride (60% dispersion in mineral oil, 10.0 g, 250 mmol) was carefully added portion-wise and then the resulting mixture was stirred for 30 min at room temperature. The mixture was cooled to 0° C., then benzyl bromide (22.1 mL, 186 mmol) was added drop-wise and the resulting mixture was stirred overnight at room temperature. The mixture was carefully quenched by drop-wise addition of water (40 mL), then the mixture was extracted with ethyl acetate (3×200 mL). The combined organic extracts were washed with brine (4×100 mL), dried (Na$_2$SO$_4$), filleted and concentrated under reduced pressure to obtain the title compound as a yellow oil (24.9 g, 80%).

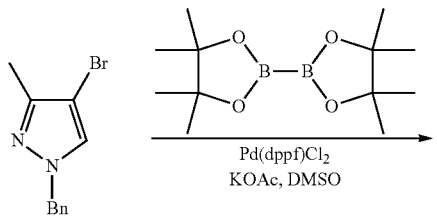

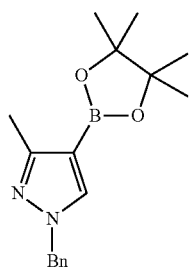

Compound 248.2. 1-Benzyl-3-methyl-4-(4,4,5,5-tetramethyl-1,3,2-dioxaborolan-2-yl)-1H-pyrazole Into a 250-mL three neck round-bottom flask, which was purged and maintained with an inert atmosphere of nitrogen, was placed a solution of 1-benzyl-4-bromo-3-methyl-1H-pyrazole (compound 248.1, 24.5 g, 97.6 mmol) in DMSO (160 mL). 4,4,4',4',5,5,5',5'-Octamethyl-2,2'-bi(1,3,2-dioxaborolane) (29.9 g, 118 mmol), Pd(dppf)Cl$_2$ (7.16 g, 9.79 mmol) and KOAc (28.8 g, 293 mmol) were added. The resulting mixture was stirred overnight at 90° C., then cooled and quenched with water (100 mL). The mixture was extracted with ethyl acetate (3×100 mL) and the combined organic extracts were washed brine (4×100 mL), dried (Na$_2$SO$_4$), filtered and concentrated under reduced pressure. The residue was purified by a silica gel column with ethyl acetate/petroleum ether (1:20) as eluent to obtain the title compound as a yellow oil (10.64 g, 37%).

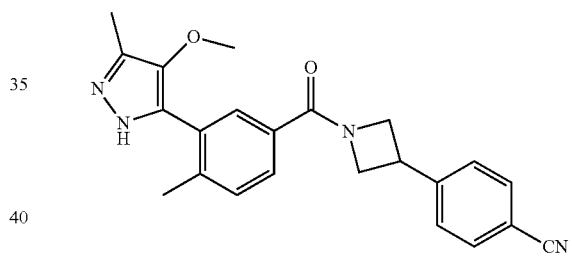

Compound 248. 4-(1-(3-(4-Methoxy-3-methyl-1H-pyrazol-5-yl)-4-methylbenzoyl)azetidin-3-yl)benzonitrile The title compound was prepared using standard chemical manipulations and procedures similar to those used for the preparation of compound 244, except 1-benzyl-3-methyl-4-(4,4,5,5-tetramethyl-1,3,2-dioxaborolan-2-yl)-1H-pyrazole (compound 248.2) was used in place of 1-benzyl-4-(4,4,5,5-tetramethyl-1,3,2-dioxaborolan-2-yl)-1H-pyrazole (compound 244.1). m/z (ES+) 387 (M+H$^+$).

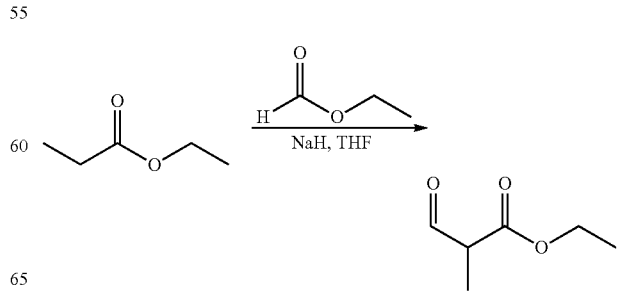

Compound 249.1. Ethyl 2-methyl-3-oxopropanoate

Into a 500-mL 3-neck round-bottom flask, which was purged and maintained with an inert atmosphere of nitrogen, was placed a solution of ethyl propionate (11.3 mL, 97.9 mmol) in tetrahydrofuran (160 mL). The solution was cooled to 0° C., then sodium hydride (4.1 g, 103 mmol, 60% dispersion in mineral oil) was added in portions. The mixture was stirred at 0° C. for 10 min, then ethyl formate (7.92 mL, 98.5 mmol) was added and the resulting mixture was stirred overnight at room temperature. The reaction was carefully quenched water (100 mL) by drop-wise addition and the mixture was extracted with ethyl acetate (2×100 mL). The combined organic extracts were dried (Na$_2$SO$_4$), filtered and concentrated under reduced pressure. The crude product was purified by distillation under reduced pressure (50 mm Hg) and the fraction between 70-80° C. was collected to obtain the title compound as a colorless liquid (3.0 g, 24%).

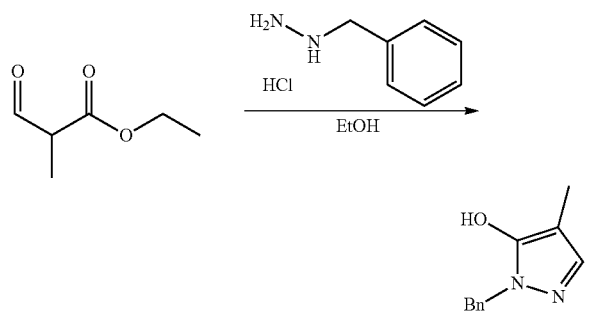

Compound 249.2. 1-Benzyl-4-methyl-1H-pyrazol-5-ol

Into a 100-mL round-bottom flask, was placed a solution of ethyl 2-methyl-3-oxopropanoate (compound 249.1, 500 mg, 3.84 mmol) in ethanol (15 mL). Benzylhydrazine hydrochloride (730 mg, 4.66 mmol) was added and the reaction was stirred for 5 h at 80° C., then concentrated under reduced pressure. The residue was purified by a silica gel chromatography with dichloromethane/methanol (30:1) as eluent to obtain the title compound as a yellow oil (430 mg, 59%).

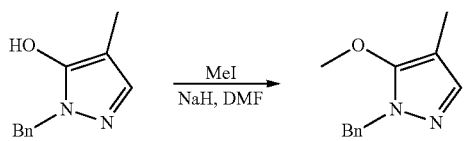

Compound 249.3. 1-Benzyl-5-methoxy-4-methyl-1H-pyrazole

Into a 100-mL round-bottom flask, was placed a solution of 1-benzyl-4-methyl-1H-pyrazol-5-ol (compound 249.2, 2.0 g, 10.6 mmol) in N,N-dimethylformamide (15 mL). The solution was cooled to 0° C., then sodium hydride (600 mg, 15.00 mmol, 60% dispersion in mineral oil) was added in portions and the resulting mixture was stirred for 10 min at 0° C. Iodomethane (878 μL, 14.1 mmol) was added and the resulting mixture was stirred for 3 h at room temperature, then carefully quenched by drop-wise addition of water (10 mL). The mixture was extracted ethyl acetate (3×40 mL) and the combined organic extracts were washed with brine (3×20 mL), dried (Na$_2$SO$_4$), filtered and concentrated under reduced pressure. The residue was purified by a silica gel chromatography with ethyl acetate/petroleum ether (1:8) as eluent to obtain the title compound as a yellow oil (500 mg, 23%).

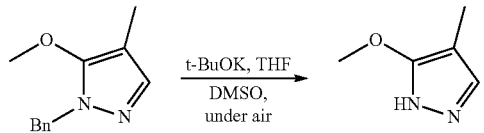

Compound 249.4. 5-Methoxy-4-methyl-1H-pyrazole

Into a 100-mL round-bottom flask, was placed a solution of 1-benzyl-5-methoxy-4-methyl-1H-pyrazole (compound 249.3, 300 mg, 1.48 mmol) in DMSO (10 mL). Potassium tert-butoxide (11 mL, 11 mmol, 1 M in THF) was added slowly and the resulting mixture was stirred overnight at room temperature under dry air conditions. The pH of the solution was adjusted to 7-8 with aqueous HCl (2M), diluted with additional water and the mixture was extracted with ethyl acetate (3×30 mL). The combined organic extracts were washed with brine (3×20 mL), dried (Na$_2$SO$_4$), filtered and concentrated under reduced pressure. The residue was purified by silica gel chromatography with ethyl acetate/petroleum ether (1:8) as eluent to obtain the title compound as a yellow oil (150 mg, 90%).

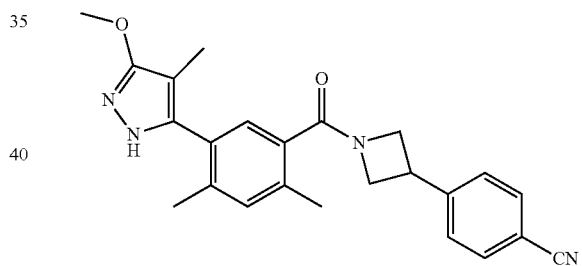

Compound 249. 4-(1-(5-(3-Methoxy-4-methyl-1H-pyrazol-5-yl)-2,4-dimethylbenzoyl)azetidin-3-yl)benzonitrile The title compound was prepared using standard chemical manipulations and procedures similar to those used for the preparation of compound 244, except 5-methoxy-4-methyl-1H-pyrazole (compound 249.4) was used in place 4-methoxy-1H-pyrazole (compound 244.4) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4) m/z (ES+) 401 (M+H$^+$).

Compound 250.1. 5-Iodo-4-methyl-1H-pyrazole

NIS (5.62 g, 24.98 mmol) was added portion-wise to a solution of 4-methyl-1H-pyrazole (Aldrich, 2.05 g, 24.97 mmol) in acetonitrile (50 mL). The mixture was heated at 60° C. for 30 minutes, then cooled to room temperature. The mixture was partitioned between EtOAc (300 mL) and water (80 mL). The organic layer was washed with saturated sodium thiosulfate (50 mL), brine (50 mL), dried (MgSO$_4$) and concentrated under reduced pressure. The residue was purified by silica gel column chromatography (hexanes:EtOAc, 5:1) to yield the title compound as a white solid (2.3 g, 45%). m/z (ES+) 209 (M+H)$^+$.

Compound 250.2. 5-Iodo-4-methyl-1-((2-(trimethylsilyl)ethoxy)methyl)-1H-pyrazole NaH (0.48 g, 12.2 mmol, 60%) was added to a solution of 5-iodo-4-methyl-1H-pyrazole (compound 250.1, 2.3 g, 11.1 mmol) in THF (20 mL) at 0° C. The mixture was stirred at 0° C. for 30 minutes, then 2-(trimethylsilyl)ethoxymethyl chloride (2.15 mL, 12.2 mmol) was added. The resulting mixture was stirred at room temperature for 3 hours, and then carefully quenched with a small amount of water and partitioned between EtOAc (200 mL) and water (50 mL). The organic layer was washed with brine (50 mL), dried (MgSO$_4$) and concentrated under reduced pressure. The residue was purified with by silica gel column chromatography (hexanes:EtOAc, 10:1) to yield the title compound as a light yellow oil (3.15 g, 84%). m/z (ES+) 339 (M+H)$^+$.

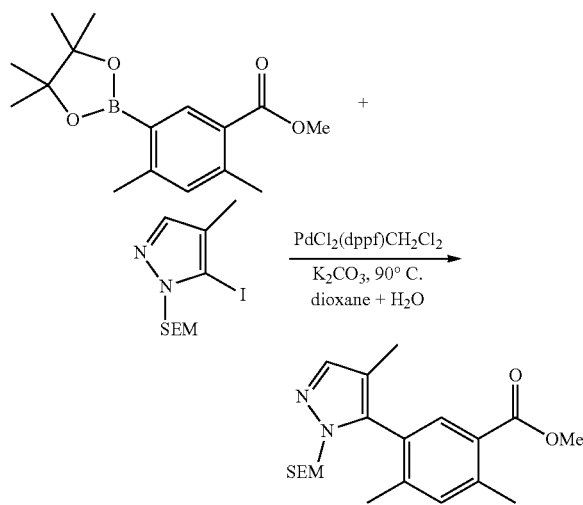

Compound 250.3. Methyl 2,4-dimethyl-5-(4-methyl-1-((2-(trimethylsilyl)ethoxy) methyl)-1H-pyrazol-5-yl)benzoate Methyl 2,4-dimethyl-5-(4,4,5,5-tetramethyl-1,3,2-dioxaborolan-2-yl)benzoate (compound 160.1, 2.7 g, 9.32 mmol), 5-iodo-4-methyl-1-((2-(trimethylsilyl)ethoxy)methyl)-1H-pyrazole (compound 250.2, 3.15 g, 9.32 mmol), K$_2$CO$_3$ (6.42 g, 46.6 mmol) and PdCl$_2$(dppf) CH$_2$Cl$_2$ (0.76 g, 0.93 mmol) were added to a round bottom flask. The flask was purged with argon, then dioxane (50 mL) and water (20 mL) were added and the mixture was heated at 90° C. for 16 hours. The mixture was cooled to room temperature and then partitioned between EtOAc (300 mL) and water (50 mL). The organic layer was washed with brine (50 mL), dried (MgSO$_4$) and concentrated under reduced pressure. The residue was purified by silica gel column chromatography (hexanes:EtOAc, 10:1) to yield the title compound as a light brown oil (3.0 g, 86%). m/z (ES+) 375 (M+H)$^+$.

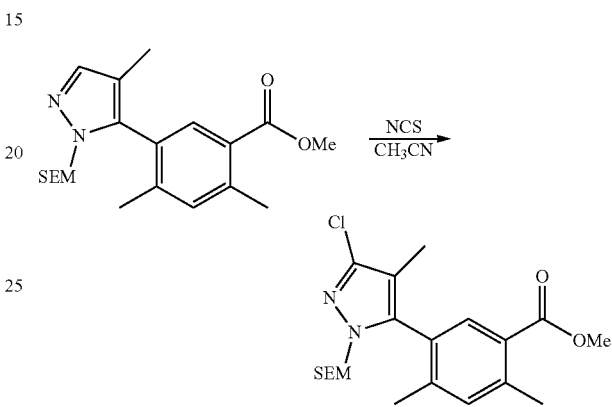

Compound 250.4. Methyl 5-(3-chloro-4-methyl-1-((2-(trimethylsilyl)ethoxy) methyl)-1H-pyrazol-5-yl)-2,4-dimethylbenzoate To a solution of methyl 2,4-dimethyl-5-(4-methyl-1-((2-(trimethylsilyl)ethoxy) methyl)-1H-pyrazol-5-yl)benzoate (compound 250.3, 3.0 g, 8.02 mmol) in acetonitrile (20 mL) was added NCS (1.07 g, 8.02 mmol). The mixture was stirred at room temperature overnight, then partitioned between EtOAc (200 mL) and water (50 mL). The organic layer was washed with saturated sodium thiosulfate (50 mL), brine (50 mL), dried (MgSO$_4$) and concentrated under reduced pressure. The residue was purified with by silica gel column chromatography (hexanes:EtOAc, 20:1) to yield the title compound as a colorless oil (2.0 g, 61%). m/z (ES+) 409 (M+H)$^+$.

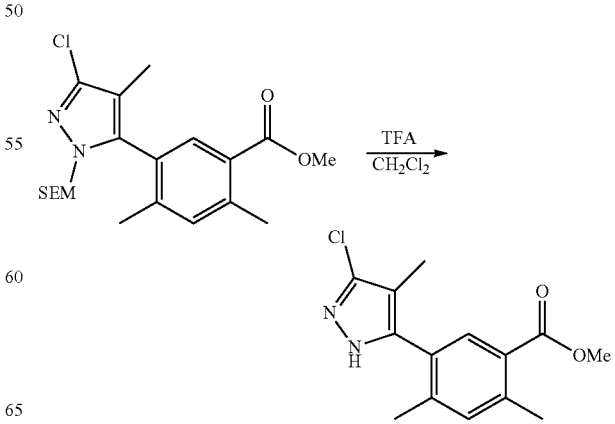

Compound 250.5. Methyl 5-(3-chloro-4-methyl-1H-pyrazol-5-yl)-2,4-dimethylbenzoate TFA (10 mL) was carefully added to a solution of 5-(3-chloro-4-methyl-1-((2-(trimethylsilyl)ethoxy) methyl)-1H-pyrazol-5-yl)-2,4-dimethylbenzoate (compound 250.4, 2.0 g, 4.90 mmol) in CH$_2$Cl$_2$ (10 mL). The mixture was stirred at room temperature for 2 hours, then the solvents were removed under reduced pressure. The residue was dissolved in EtOAc (200 mL) and washed with sat. NaHCO$_3$ (50 mL), brine (50 mL), dried (MgSO$_4$) and concentrated under reduced pressure. The residue was purified by silica gel column chromatography (hexanes:EtOAc, 4:1) to yield the title compound as white foam (1.13 g, 83%). m/z (ES+) 279 (M+H)$^+$.

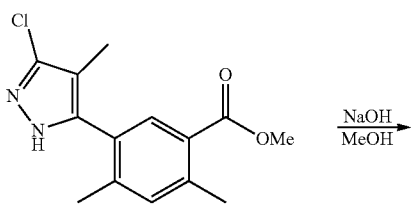

Compound 250.6. 5-(3-Chloro-4-methyl-1H-pyrazol-5-yl)-2,4-dimethylbenzoic acid NaOH (2 M in water, 8 mL, 16 mmol) was added to a solution of methyl 5-(3-chloro-4-methyl-1H-pyrazol-5-yl)-2,4-dimethylbenzoate (compound 250.5, 1.10 g, 3.96 mmol) in MeOH (10 mL). The mixture was stirred at room temperature overnight and the solvents were removed under the reduced pressure. The residue was cooled to 0° C. and acidified to pH ~3-4 with 1M HCl in water. The resulting white solids were filtered, washed with water and dried to give the title compound as a white solid (1.07 g, 90%). m/z (ES+) 265 (M+H)$^+$.

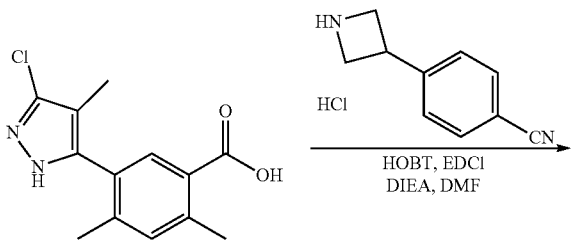

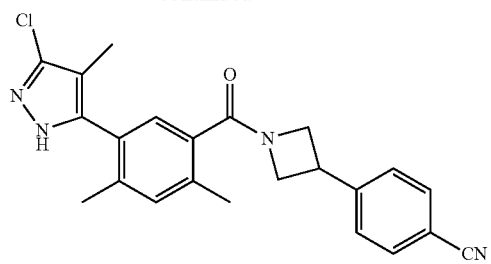

Compound 250. 4-(1-(5-(3-Chloro-4-methyl-1H-pyrazol-5-yl)-2,4-dimethylbenzoyl)azetidin-3-yl)benzonitrile The title compound was prepared using standard chemical manipulations and procedures similar to those used for the preparation of compound 5, except 5-(3-chloro-4-methyl-1H-pyrazol-5-yl)-2,4-dimethylbenzoic acid (compound 250.6) was used in place of 3-(2,4-dimethyl-1H-imidazol-5-yl)-4-methylbenzoic acid (compound 5.7). m/z (ES+) 405 (M+H)$^+$.

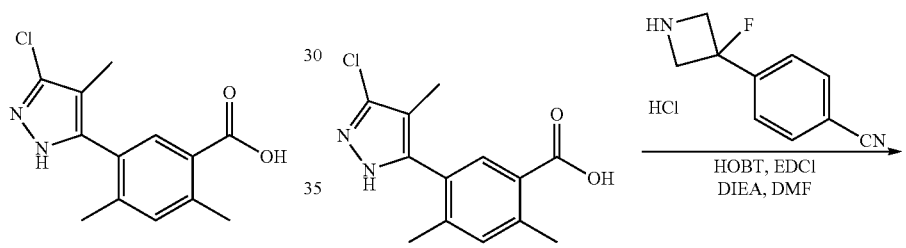

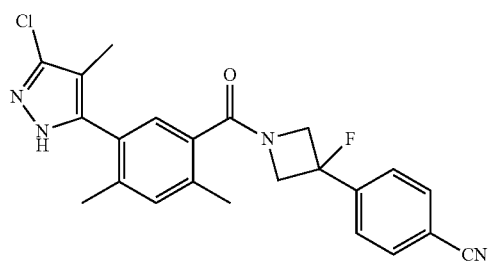 [SMILES: Cc1ccc(C(=O)N2CC(F)(c3ccc(C#N)cc3)C2)cc1-c1[nH]nc(Cl)c1C]

Compound 251. 4-(1-(5-(3-Chloro-4-methyl-1H-pyrazol-5-yl)-2,4-dimethylbenzoyl)-3-fluoroazetidin-3-yl)benzonitrile The title compound was prepared using standard chemical manipulations and procedures similar to those used for the preparation of compound 5, except 5-(3-chloro-4-methyl-1H-pyrazol-5-yl)-2,4-dimethylbenzoic acid (compound 250.6) was used in place of 3-(2,4-dimethyl-1H-imidazol-5-yl)-4-methylbenzoic acid (compound 5.7) and 4-(3-fluoroazetidin-3-yl)benzonitrile hydrochloride (compound 43.4) was used in place of 4-(azetidin-3-yl)benzonitrile hydrochloride (compound 5.2). m/z (ES+) 423 (M+H)$^+$.

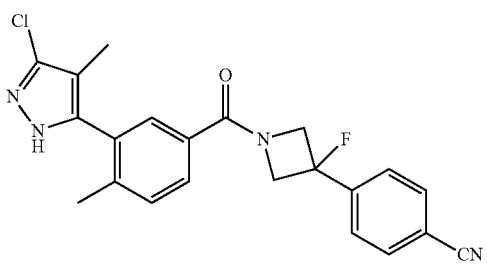

Compound 252. 4-(1-(3-(3-Chloro-4-methyl-1H-pyrazol-5-yl)-4-methylbenzoyl)-3-fluoroazetidin-3-yl)benzonitrile The title compound was prepared using standard chemical manipulations and procedures similar to those used for the preparation of compound 250, except methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1) and 4-(3-fluoroazetidin-3-yl)benzonitrile hydrochloride (compound 43.4) was used in place of 4-(azetidin-3-yl)benzonitrile hydrochloride (compound 5.2). m/z (ES+) 409 (M+H+).

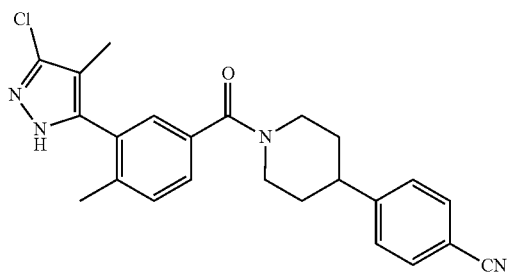 [SMILES: Cc1ccc(C(=O)N2CCC(c3ccc(C#N)cc3)CC2)cc1-c1[nH]nc(Cl)c1C]

Compound 253. 4-(1-(3-(3-Chloro-4-methyl-1H-pyrazol-5-yl)-4-methylbenzoyl)piperidin-4-yl)benzonitrile The title compound was prepared using standard chemical manipulations and procedures similar to those used for the preparation of compound 250, except methyl 4-methyl-3-(4,4,5,5-tetramethyl-1,3,2-dioxaborolan-2-yl)benzoate (compound 5.4) was used in place of methyl 2,4-dimethyl-5-(4,4,5,5-tetramethyl-1,3,2-dioxaborolan-2-yl)benzoate (compound 160.1) and 4-(piperidin-4-yl)benzonitrile hydrochloride (compound 1.2) was used in place of 4-(azetidin-3-yl)benzonitrile hydrochloride (compound 5.2). m/z (ES+) 419 (M+H+).

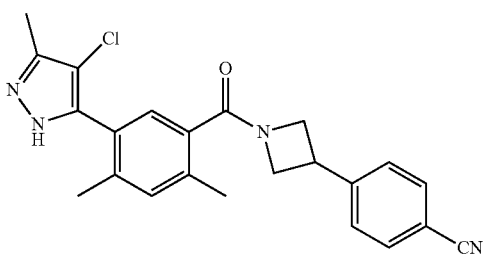 [SMILES: Cc1cc(C)c(-c2[nH]nc(C)c2Cl)cc1C(=O)N1CC(c2ccc(C#N)cc2)C1]

Compound 136. 4-(1-(5-(4-Chloro-3-methyl-1H-pyrazol-5-yl)-2,4-dimethylbenzoyl)azetidin-3-yl)benzonitrile The title compound was prepared using standard chemical manipulations and procedures similar to those used for the preparation of compound 51, except 5-bromo-3-methyl-1H-pyrazole was used in place of 5-iodo-1H-pyrazole. m/z (ES+) 405 (M+H+).

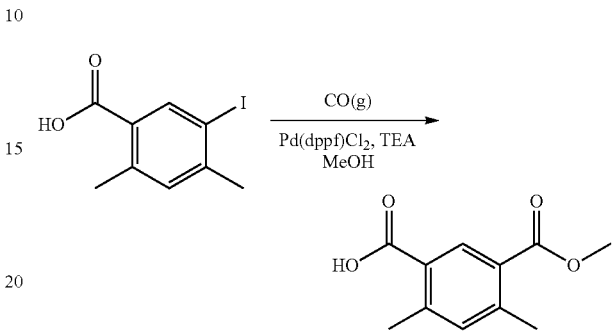

Compound 255.1. 5-(Methoxycarbonyl)-2,4-dimethylbenzoic acid

A solution of 5-iodo-2,4-dimethylbenzoic acid (5.0 g, 18.1 mmol) in methanol (45 mL) was added to a 100-mL pressure tank reactor (40 atm). Triethylamine (7.57 mL, 54.3 mmol) and Pd(dppf)Cl2 (1.3 g, 1.8 mmol) were added and the system was purged with nitrogen. CO (g) was very carefully introduced. Caution: carbon monoxide is a very toxic gas. The reaction was heated at 90° C. overnight, then cooled to room temperature and very carefully evacuated. The solvent was removed under reduced pressure. The pH of the residue was adjusted to 1-2 with aq HCl (6 M), diluted with additional water, then extracted with EtOAc (2×100 mL). The combined organic extracts were washed brine (3×10 mL), dried (Na2SO4), filtered and concentrated under reduced pressure. The residue was purified by a silica gel column with ethyl acetate/hexane (1:1) as eluent to obtain the title compound as a red solid (2.3 g, 61%).

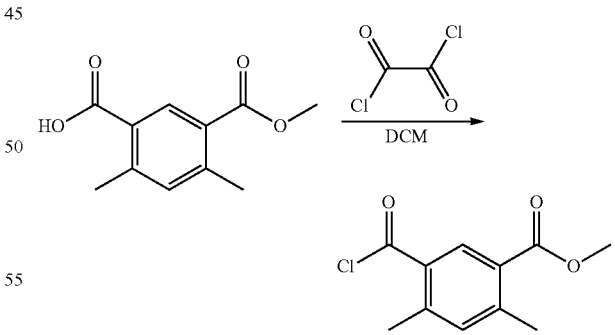

Compound 255.2. Methyl 5-(chlorocarbonyl)-2,4-dimethylbenzoate

Into a 100-mL round-bottom flask, was placed a solution of 5-(methoxycarbonyl)-2,4-dimethylbenzoic acid (compound 255.1, 100 mg, 0.48 mmol) in dichloromethane (10 mL). Oxalyl chloride (80 µL, 0.95 mmol) was added and the resulting solution was stirred for 1 h at 40° C., then concentrated under reduced pressure to obtain the title compound as a white solid (80 mg, 74%).

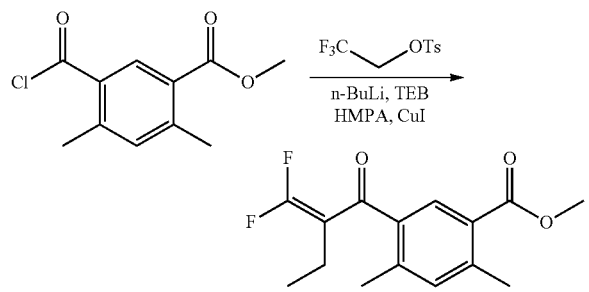

Compound 255.3. Methyl 5-(2-(difluoromethylene)butanoyl)-2,4-dimethylbenzoate Into a 100-mL three neck round-bottom flask, which was purged and maintained with an inert atmosphere of argon, was placed a solution of 2,2,2-trifluoroethyl 4-methylbenzenesulfonate (1.00 g, 3.93 mmol) in THF (30 mL). The solution was cooled to −78° C., then n-BuLi (5.0 mL, 1.6 M in hexane, 8.0 mmol) was added drop-wise and the mixture was stirred at −78° C. for 40 min. Triethylborane (TEB) (5.0 mL, 1 M in THF, 5.0 mmol) was slowly added and the mixture was stirred at −78° C. for 1 h, then at room temperature for 3 h. The solution was cooled to 0° C., then hexamethylphosphoramide (HMPA) (6 mL) and CuI (1.5 g, 7.9 mmol) were added and the mixture was stirred at room temperature for 30 min. A solution of methyl 5-(chlorocarbonyl)-2,4-dimethylbenzoate (compound 255.2, 530 mg, 2.34 mmol) in THF (30 mL) was carefully added and stirred at room temperature for 30 min. The pH of the mixture was carefully adjusted to 7 with aqueous $H_3PO_4$ and the mixture was partitioned. The aqueous phase was extracted with ethyl acetate (3×20 mL) and the combined organic layers were concentrated under reduced pressure. The residue was purified by silica gel column chromatography with ethyl acetate/petroleum ether (1:40) as eluent to obtain the title compound as a yellow oil (250 mg, 38%).

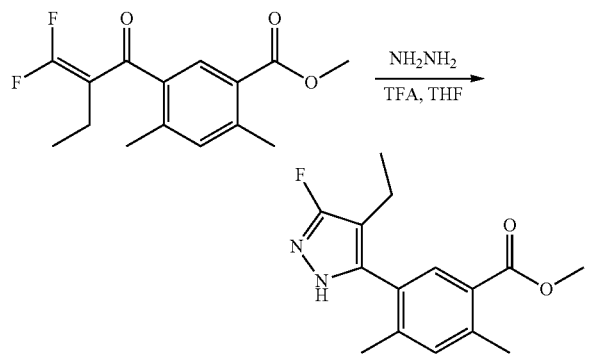

Compound 255.4. Methyl 5-(4-ethyl-3-fluoro-1H-pyrazol-5-yl)-2,4-dimethylbenzoate Into a 250-mL round-bottom flask, was placed a solution of methyl 5-(2-(difluoromethylene)butanoyl)-2,4-dimethylbenzoate (compound 255.3, 175 mg, 0.62 mmol) in THF (100 mL). At room temperature, hydrazine hydrate (120 μL, 2.48 mmol) was added followed by trifluoroacetic acid (144 μL, 1.88 mmol), then the solution was stirred at 50° C. for 1.5 h. The reaction was cooled to room temperature, carefully diluted with water and the mixture was extracted with ethyl acetate (3×50 mL). The combined organic extracts were dried ($Na_2SO_4$), filtered and concentrated under reduced pressure. The residue was purified by a silica gel column with ethyl acetate/hexane (1:10) as eluent to obtain the title compound as a yellow oil (90 mg, 53%).

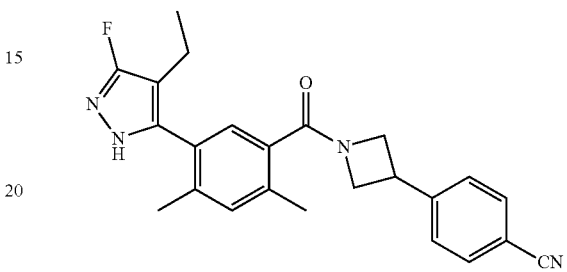

Compound 255. 4-(1-(5-(4-Ethyl-3-fluoro-1H-pyrazol-5-yl)-2,4-dimethylbenzoyl)azetidin-3-yl)benzonitrile The title compound was prepared using standard chemical manipulations and procedures similar to those used for the preparation of compound 244, except methyl 5-(4-ethyl-3-fluoro-1H-pyrazol-5-yl)-2,4-dimethylbenzoate (compound 255.4) was used in place methyl 3-(4-methoxy-1H-pyrazol-5-yl)-4-methylbenzoate (compound 244.6). m/z (ES+) 403 (M+H⁺).

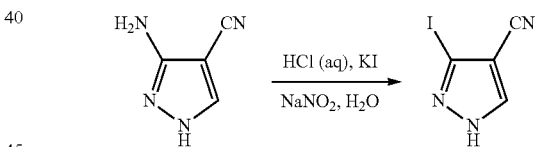

Compound 256.1. 3-Iodo-1H-pyrazole-4-carbonitrile

Into a 100-mL three neck round-bottom flask, was placed a solution of 3-amino-1H-pyrazole-4-carbonitrile (1.00 g, 9.25 mmol) in hydrogen chloride (12 M, 8 mL). The reaction solution was cooled to 0° C., then a solution of sodium nitrite (800 mg, 11.6 mmol) in water (5.8 mL) was carefully added dropwise and the mixture was stirred for 1 h at 0° C. KI (1.91 g, 11.6 mmol) was added and the resulting mixture was stirred for 3 h at room temperature. The pH of the solution was carefully adjusted to 10 with aqueous sodium hydroxide (3 M) and then extracted with ethyl acetate (3×100 mL). The combined organic layers were dried ($Na_2SO_4$), filtered and concentrated under reduced pressure to obtain the title compound as a white solid (700 mg, 35%).

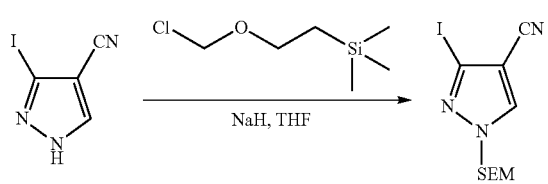

Compound 256.2. 3-Iodo-1-((2-(trimethylsilyl)ethoxy)methyl)-1H-pyrazole-4-carbonitrile Into a 100-mL round-bottom flask, was placed a solution of 3-iodo-1H-pyrazole-4-carbonitrile (compound 256.1, 5.00 g, 22.8 mmol) in tetrahydrofuran (10 mL). The solution was cooled to 0° C. under nitrogen, then sodium hydride (1.1 g, 27.4 mmol, 60% dispersion in mineral oil) was added in portions. The resulting mixture was stirred at 0° C. for 30 min, then (2-(chloromethoxy)ethyl)trimethylsilane (6.05 mL, 34.2 mmol) was added to the reaction. The resulting mixture was stirred for overnight at room temperature, then carefully quenched with water/ice (30 mL). The aqueous phase was extracted with ethyl acetate (2×100 mL) and the combined organic layers were dried (Na$_2$SO$_4$), filtered and concentrated under reduced pressure. The residue was purified by a silica gel chromatography with ethyl acetate/petroleum ether (20:1) as eluent to obtain the title compound as a colorless oil (7.2 g, 90%).

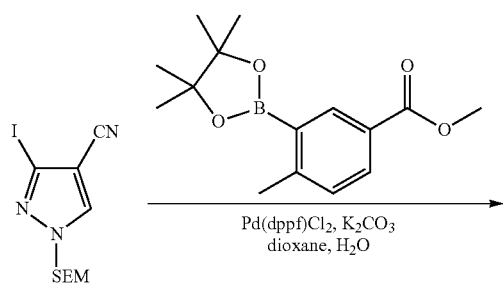

Compound 256.3. Methyl 3-(4-cyano-1-((2-(trimethylsilyl)ethoxy)methyl)-1H-pyrazol-5-yl)-4-methylbenzoate Into a 250-mL three neck round-bottom flask, which was purged and maintained with an inert atmosphere of nitrogen, was placed a solution of 3-iodo-1-((2-(trimethylsilyl)ethoxy)methyl)-1H-pyrazole-4-carbonitrile (compound 256.2, 2.73 g, 7.82 mmol, 1.00 equiv) in dioxane (30 mL). Methyl 4-methyl-3-(4,4,5,5-tetramethyl-1,3,2-dioxaborolan-2-yl)benzoate (2.59 g, 9.38 mmol), Pd(dppf)Cl$_2$ (570 mg, 0.78 mmol), and a solution of potassium carbonate (3.24 g, 23.4 mmol) in water (3 mL) were added to the reaction. The resulting mixture was stirred overnight at 90° C., then cooled and diluted with EtOAc (500 mL). The resulting mixture was washed with brine (2×100 mL), dried (Na$_2$SO$_4$), filtered and concentrated under reduced pressure.

The residue was purified by a silica gel chromatography with ethyl acetate/petroleum ether (40:1) as eluent to obtained the title compound as a yellow oil (1.9 g, 65%).

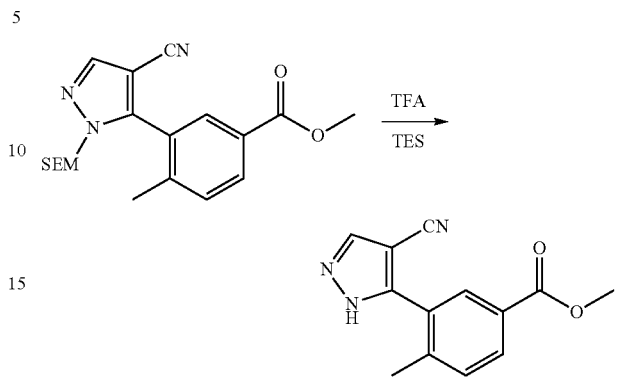

Compound 256.4. Methyl 3-(4-cyano-1H-pyrazol-5-yl)-4-methylbenzoate

Into a 50-mL round-bottom flask, was placed a solution of methyl 3-(4-cyano-1-((2-(trimethylsilyl)ethoxy)methyl)-1H-pyrazol-5-yl)-4-methylbenzoate (compound 256.3, 1.9 g, 5.11 mmol) in triethylsilane (4 mL) and trifluoroacetic acid (8 mL). The resulting solution was stirred for 4 h at room temperature, then concentrated under reduced pressure. The pH of the residue was carefully adjusted to 7-8 with aqueous sodium bicarbonate (sat.), then the aqueous phase was extracted with ethyl acetate (2×100 mL). The combined organic layers were dried (Na$_2$SO$_4$), filtered and concentrated under reduced pressure. The residue was purified by silica gel chromatography with ethyl acetate/petroleum ether (20/1) as eluent to obtain the title compound as a white solid (600 mg, 49%).

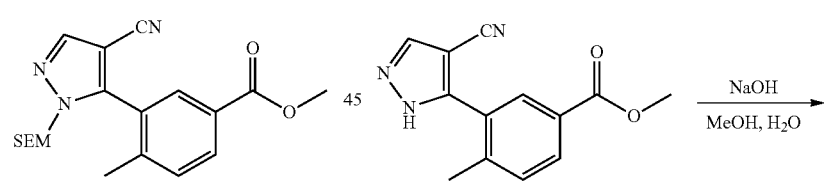

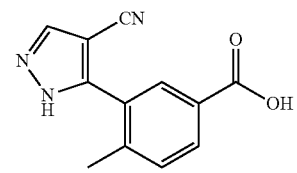

Compound 256.5. 3-(4-Cyano-1H-pyrazol-5-yl)-4-methylbenzoic acid

The title compound was prepared using standard chemical manipulations and procedures similar to those used for the preparation of compound 244.7, except methyl 3-(4-cyano-1H-pyrazol-5-yl)-4-methylbenzoate (compound 256.4) was used in place of methyl 3-(4-methoxy-1H-pyrazol-5-yl)-4-methylbenzoate (compound 244.6).

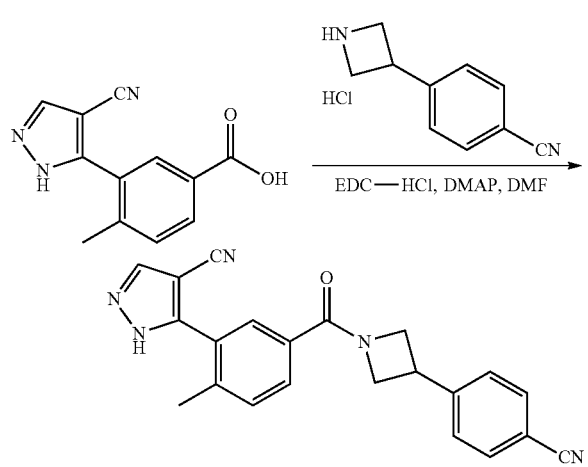

Compound 256. 5-(5-(3-(4-Cyanophenyl)azetidine-1-carbonyl)-2-methylphenyl)-1H-pyrazole-4-carbonitrile The title compound was prepared using standard chemical manipulations and procedures similar to those used for the preparation of compound 244, except 3-(4-cyano-1H-pyrazol-5-yl)-4-methylbenzoic acid (compound 256.5) was used in place of 3-(4-methoxy-1H-pyrazol-5-yl)-4-methylbenzoic acid (compound 244.7). m/z (ES+) 368 (M+H$^+$).

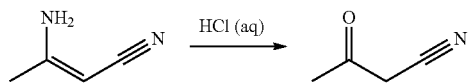

Compound 257.1. 3-Oxobutanenitrile

Into a 250-mL round-bottom flask, which was purged and maintained with an inert atmosphere of nitrogen, was carefully placed (Z)-3-aminobut-2-enenitrile (20.0 g, 244 mmol) and aqueous hydrogen chloride (6 M) (80 mL). The mixture was stirred for 3 h at 80° C., then the solids were removed by filtration. The filtrate was extracted with ethyl acetate (3×100 mL) and the combined organic extracts were dried (Na$_2$SO$_4$), filtered and concentrated under reduced pressure to obtain the title compound as a yellow solid (10 g, 49%).

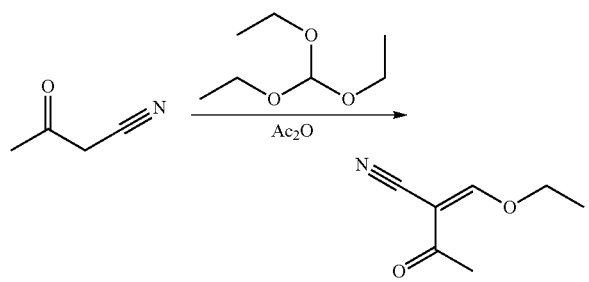

Compound 257.2. (Z)-2-(Ethoxymethylene)-3-oxobutanenitrile

Into a round-bottom flask, which was purged and maintained with an inert atmosphere of nitrogen, was placed a solution of 3-oxobutanenitrile (compound 257.1, 16.0 g, 193 mmol) in acetic anhydride (48 mL). Triethyl orthoformate (96 mL, 577 mmol) was added and the reaction was stirred for 2 h at 130° C., then concentrated under reduced pressure to obtain the title compound as a red solid (10 g, 37%).

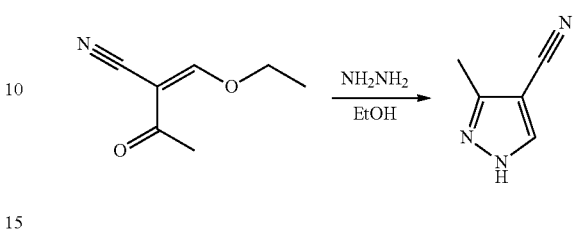

Compound 257.3. 3-Methyl-1H-pyrazole-4-carbonitrile

Into a 50-mL round-bottom flask, was placed a solution of (Z)-2-(ethoxymethylene)-3-oxobutanenitrile (compound 257.2, 5.00 g, 35.9 mmol) in ethanol (10 mL). The solution was cooled to 0° C., then hydrazine monohydrate (2.09 mL, 43.1 mmol) was added and the reaction was stirred for 1 h at 10° C. The reaction was diluted with water (10 mL) and then extracted with ethyl acetate (3×50 mL). The combined organic extracts were dried (Na$_2$SO$_4$), filtered and concentrated under reduced pressure. The residue was purified by a silica gel column with ethyl acetate/petroleum ether (1:10) as eluent to obtain the title compound as a yellow solid (2.0 g, 52%).

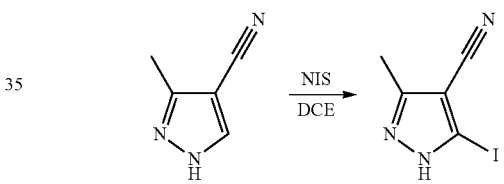

Compound 257.4. 5-Iodo-3-methyl-1H-pyrazole-4-carbonitrile

Into a 10-mL sealed tube, was placed a solution of 3-methyl-1H-pyrazole-4-carbonitrile (compound 257.3, 2.0 g, 18.7 mmol) in DCE (6 mL). NIS (4.20 g, 18.7 mmol) was added to the reaction and the mixture was irradiated with microwave radiation for 1 h at 150° C. The reaction was cooled, then carefully quenched with aqueous Na$_2$S$_2$O$_3$ (sat., 20 mL). The mixture was partitioned and the aqueous layer was extracted with ethyl acetate (100 mL). The combined organic layers were washed with brine (5×30 mL), dried (Na$_2$SO$_4$), filtered and concentrated under reduced pressure. The residue was purified by silica gel chromatography with ethyl acetate/petroleum ether (1:10) as eluent to obtain the title compound as a yellow solid (900 mg, 21%).

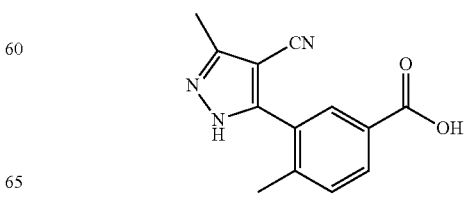

Compound 257.5. 3-(4-Cyano-3-methyl-1H-pyrazol-5-yl)-4-methylbenzoic acid

The title compound was prepared using standard chemical manipulations and procedures similar to those used for the preparation of compound 256.5, except 5-iodo-3-methyl-1H-pyrazole-4-carbonitrile (compound 257.4) was used in place 3-iodo-1H-pyrazole-4-carbonitrile (compound 256.1).

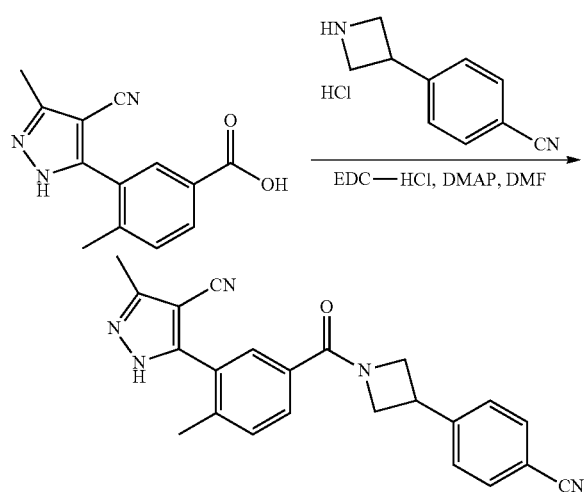

Compound 257. 5-(5-(3-(4-Cyanophenyl)azetidine-1-carbonyl)-2-methylphenyl)-3-methyl-1H-pyrazole-4-carbonitrile The title compound was prepared using standard chemical manipulations and procedures similar to those used for the preparation of compound 244, except 3-(4-cyano-3-methyl-1H-pyrazol-5-yl)-4-methylbenzoic acid (compound 257.5) was used in place of 3-(4-methoxy-1H-pyrazol-5-yl)-4-methylbenzoic acid (compound 244.7). m/z (ES+) 382 (M+H+).

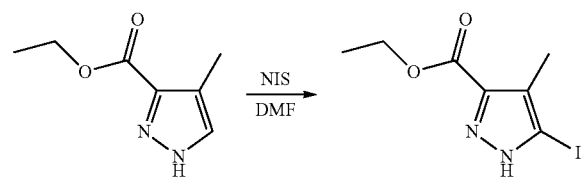

Compound 258.1. Ethyl 5-iodo-4-methyl-1H-pyrazole-3-carboxylate

Into a 250-mL round-bottom flask, was placed a solution of ethyl 4-methyl-1H-pyrazole-3-carboxylate (600 mg, 3.89 mmol) in N,N-dimethylformamide (20 mL). NIS (2.2 g, 9.78 mmol) was added and the resulting mixture was stirred for 6 h at 50° C., then quenched with water (10 mL). The mixture was extracted with ethyl acetate (3×40 mL) and the combined organic extracts were washed with aqueous $Na_2S_2O_3$ (sat., 2×30 mL) and brine (2×20 mL), dried ($Na_2SO_4$), filtered and concentrated under reduced pressure. The residue was purified by a silica gel chromatography with ethyl acetate/petroleum ether (1:10) as eluent to obtain the title compound as a white solid (800 mg, 73%).

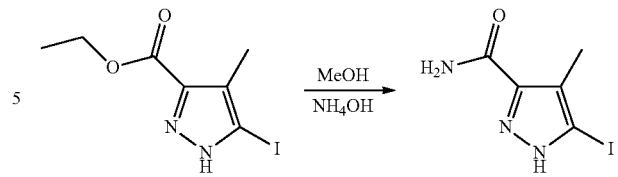

Compound 258.2. 5-Iodo-4-methyl-1H-pyrazole-3-carboxamide

Into a 100-mL round-bottom flask, was placed a solution of ethyl 5-iodo-4-methyl-1H-pyrazole-3-carboxylate (compound 258.1, 500 mg, 1.79 mmol) in methanol (5 mL). Then ammonium hydroxide (15 mL, 25% aq.) was added and the resulting solution was stirred overnight at 60° C. The mixture was concentrated under reduced pressure to obtain the title compound as a white solid (400 mg, 89%).

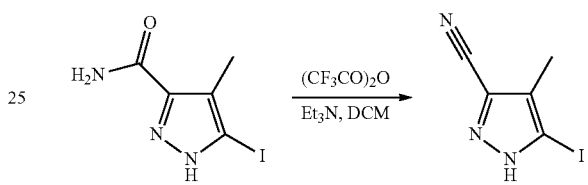

Compound 258.3. 5-Iodo-4-methyl-1H-pyrazole-3-carbonitrile

Into a 100-mL round-bottom flask, was placed a solution of 5-iodo-4-methyl-1H-pyrazole-3-carboxamide (compound 258.2, 800 mg, 3.19 mmol) in dichloromethane (10 mL). The solution was cooled to 0° C., then trifluoroacetic anhydride (1.32 mL, 9.5 mmol) and triethylamine (3.16 mL, 22.7 mmol) were each added carefully drop-wise. The mixture was stirred for 2 h at 0° C., then the pH was carefully adjusted to 7-8 with aqueous sodium bicarbonate (10%). The aqueous phase was extracted with ethyl acetate (2×40 mL) and the combined organic layers were washed with 2×10 mL of brine (2×10 mL), dried ($Na_2SO_4$), filtered and concentrated under reduced pressure. The residue was purified by a silica gel chromatography with ethyl acetate/petroleum ether (1:10) as eluent to obtain the title compound as a white solid (280 mg, 38%).

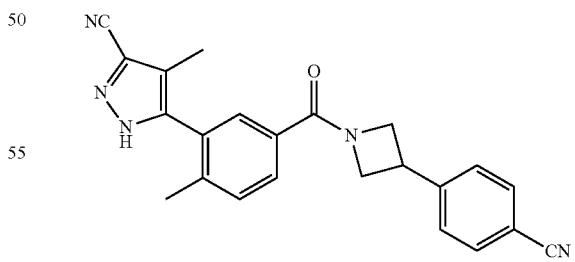

Compound 258. 5-(5-(3-(4-Cyanophenyl)azetidine-1-carbonyl)-2-methylphenyl)-4-methyl-1H-pyrazole-3-carbonitrile The title compound was prepared using standard chemical manipulations and procedures similar to those used for the preparation of compound 244, except 5-iodo-4-methyl-1H-pyrazole-3-carbonitrile (compound 258.3) was used in place of 3-iodo-4-methoxy-1H-pyrazole (compound 244.5). m/z (ES+) 382 (M+H$^+$).

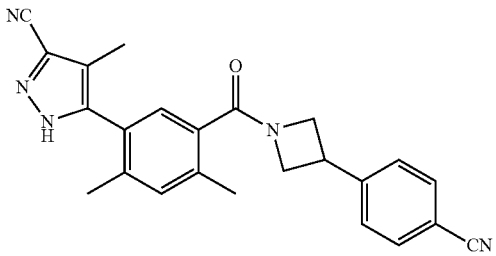 [SMILES: Cc1cc(C)c(-c2[nH]nc(C#N)c2C)cc1C(=O)N1CC(c2ccc(C#N)cc2)C1]

Compound 259. 5-(5-(3-(4-Cyanophenyl)azetidine-1-carbonyl)-2,4-dimethylphenyl)-4-methyl-1H-pyrazole-3-carbonitrile The title compound was prepared using standard chemical manipulations and procedures similar to those used for the preparation of compound 258, except methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 396 (M+H$^+$).

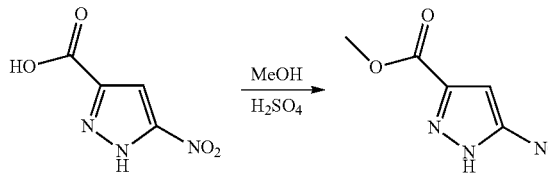

Compound 260.1. Methyl 5-nitro-1H-pyrazole-3-carboxylate

Into a 100-mL round-bottom flask, was placed a solution of 5-nitro-1H-pyrazole-3-carboxylic acid (3.0 g, 19.1 mmol) in methanol (50 mL). Sulfuric acid (3 mL) was carefully added and the resulting solution was stirred overnight at 80° C., then concentrated under reduced pressure. The pH of the solution was carefully adjusted to 7 with aqueous sodium bicarbonate (sat.), then extracted with ethyl acetate (3×50 mL). The combined organic extracts were washed with brine (3×50 mL), dried (Na$_2$SO$_4$), filtered and concentrated under reduced pressure to obtain the title compound as a yellow solid (2.3 g, 70%).

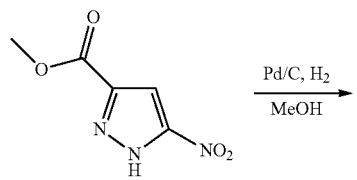

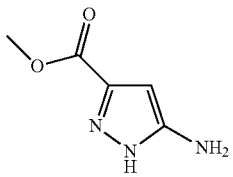

Compound 260.2. Methyl 5-amino-1H-pyrazole-3-carboxylate

Into a 100-mL round-bottom flask, was placed a solution of methyl 5-nitro-1H-pyrazole-3-carboxylate (compound 260.1, 2.5 g, 14.6 mmol) in methanol (10 mL). The system was purged with nitrogen, then palladium/carbon (10 wt % Pd, 0.8 g) was added. The system was charged with hydrogen (1 atm) and the mixture was stirred overnight at room temperature. The system was purged with nitrogen, then the solids were removed by filtration. The filtrate was concentrated under reduced pressure to obtain the title compound as an off-white solid (1.5 g, 73%).

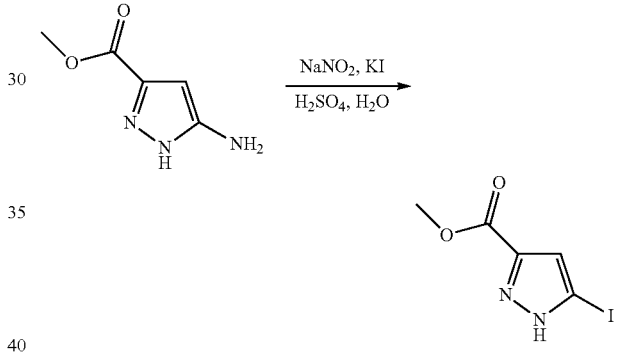

Compound 260.3. Methyl 5-iodo-1H-pyrazole-3-carboxylate

Into a 100-mL three neck round-bottom flask, which was purged and maintained with an inert atmosphere of nitrogen, was placed a solution of methyl-5-amino-1H-pyrazole-3-carboxylate (compound 260.2, 1.0 g, 7.1 mmol) in a carefully prepared solution of sulfuric acid (15 mL) into water (30 mL)(Caution: addition of sulfuric acid to water is exothermic). The solution was cooled to 0° C., then a solution of NaNO2 (0.53 g, 7.7 mmol) in water (5 mL) was added drop-wise. The resulting mixture was stirred for 2 h at 0° C., then a solution of KI (1.4 g, 8.4 mmol) in water (5 mL) was added drop-wise at 0° C. The resulting mixture was stirred overnight at room temperature, then the pH of the mixture was carefully adjusted to 7 with aqueous sodium bicarbonate (sat.). The mixture was extracted with ethyl acetate (3×50 mL) and the combined organic extracts were washed with brine (3×50 mL), dried (Na$_2$SO$_4$), filtered and concentrated under reduced pressure. The residue was purified by a silica gel chromatography with ethyl acetate/petroleum ether (1:5) as eluent to obtain the title compound as a yellow solid (0.6 g, 30%).

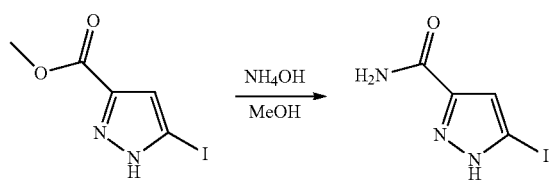

Compound 260.4.
5-Iodo-1H-pyrazole-3-carboxamide

Into a 100-mL round-bottom flask, was placed a solution of methyl 5-iodo-1H-pyrazole-3-carboxylate (compound 260.3, 900 mg, 3.57 mmol) in methanol (5 mL). Ammonia (25% aq.) (15 mL) was added and the resulting solution was stirred overnight at 60° C., then cooled and concentrated under reduced pressure to obtain the title compound as a white solid (0.8 g, 95%).

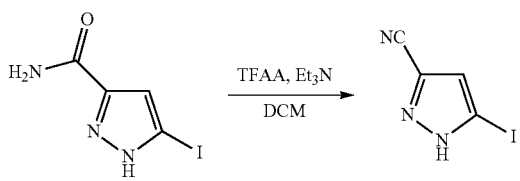

Compound 260.5.
5-Iodo-1H-pyrazole-3-carbonitrile

Into a 100-mL round-bottom flask, was placed a solution of 5-iodo-1H-pyrazole-3-carboxamide (compound 260.4, 1.00 g, 4.22 mmol) in dichloromethane (10 mL). The solution was cooled to 0° C., then trifluoroacetic anhydride (1.8 mL, 12.9 mmol) and triethylamine (4.11 mL, 29.5 mmol) were added carefully drop-wise. The mixture was stirred for 2 h at 0° C., then the pH was carefully adjusted to 7-8 with aqueous sodium bicarbonate (10%). The aqueous phase was extracted with ethyl acetate (3×30 mL) and the combined organic layers were washed with brine (2×20 mL), dried ($Na_2SO_4$), filtered and concentrated under reduced pressure. The residue was purified by silica gel chromatography with ethyl acetate/petroleum ether (1:10) as eluent to obtain the title compound as a light yellow solid (180 mg, 19%).

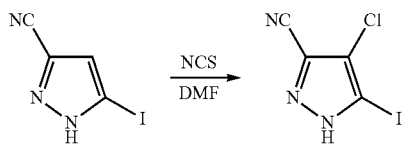

Compound 260.6.
4-Chloro-5-iodo-1H-pyrazole-3-carbonitrile

Into a 50-mL round-bottom flask, was placed a solution of 5-iodo-1H-pyrazole-3-carbonitrile (compound 260.5, 100 mg, 0.46 mmol) in N,N-dimethylformamide (10 mL). NCS (61.6 mg, 0.46 mmol) was added and the resulting mixture was stirred for 2 h at 50° C., then quenched with water (10 mL). The mixture was extracted with ethyl acetate (3×10 mL) and the combined organic extracts were washed with brine (3×10 mL), dried ($Na_2SO_4$), filtered and concentrated under reduced pressure. The residue was purified by silica gel column with ethyl acetate/petroleum ether (1:2) as eluent to obtain the title compound as a yellow oil (100 mg, 86%).

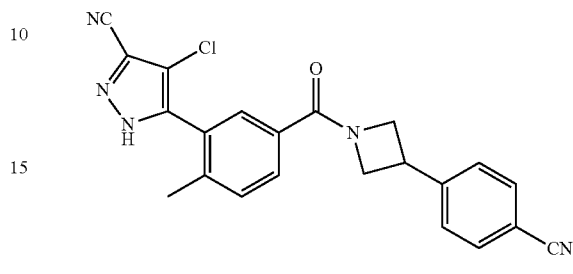

Compound 260. 4-Chloro-5-(5-(3-(4-cyanophenyl)azetidine-1-carbonyl)-2-methylphenyl)-1H-pyrazole-3-carbonitrile The title compound was prepared using standard chemical manipulations and procedures similar to those used for the preparation of compound 244, except 4-chloro-5-iodo-1H-pyrazole-3-carbonitrile (compound 260.6) was used in place of 3-iodo-4-methoxy-1H-pyrazole (compound 244.5). m/z (ES+) 402 (M+H$^+$).

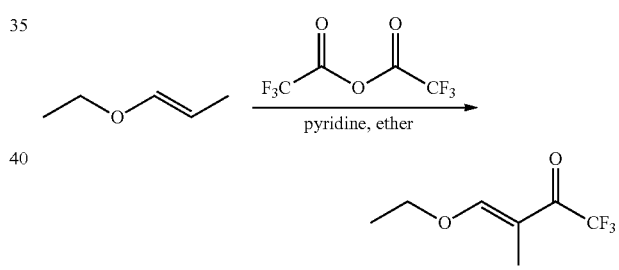

Compound 261.1. (E)-4-Ethoxy-1,1,1-trifluoro-3-methylbut-3-en-2-one

Into a 50-mL 3-neck round-bottom flask, which was purged and maintained with an inert atmosphere of nitrogen, was placed a solution trifluoroacetic anhydride (3.31 mL, 23.8 mmol) and diethyl ether (20 mL). The solution was cooled to −10° C., then a solution mix of (E)-1-ethoxyprop-1-ene (2.82 mL, 25.5 mmol) and pyridine (1.94 mL, 24.0 mmol) was added drop-wise at −10° C. The resulting solution was stirred overnight at room temperature, then diluted with diethyl ether (50 mL). The solids were removed by filtration and the filtrate was concentrated under reduced pressure. The residue was diluted with water (100 mL) and extracted with DCM (3×50 mL). The combined organic extracts were washed with aq HCl (0.1 M, 3×100 mL) and water (100 mL), dried ($Na_2SO_4$), filtered and concentrated under reduced pressure to obtain the title compound as a colorless oil (2.6 g, 60%).

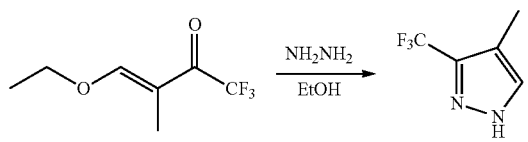

Compound 261.2.
4-Methyl-3-(trifluoromethyl)-1H-pyrazole

Into a 100-mL round-bottom flask, was placed (E)-4-ethoxy-1,1,1-trifluoro-3-methylbut-3-en-2-one (compound 261.1, 2.6 g, 14.3 mmol) in EtOH (20 mL). Hydrazine hydrate (1.8 mL, 38 mmol) was added and the resulting solution was stirred for 2 h at 80° C. The reaction was concentrated under reduced pressure to obtain the title compound as a yellow oil (2 g, crude).

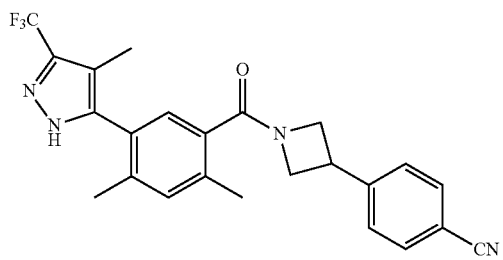 [SMILES: Cc1cc(C)c(-c2[nH]nc(C(F)(F)F)c2C)cc1C(=O)N1CC(c2ccc(C#N)cc2)C1]

Compound 261. 4-(1-(2,4-Dimethyl-5-(4-methyl-3-(trifluoromethyl)-1H-pyrazol-5-yl)benzoyl)azetidin-3-yl)benzonitrile The title compound was prepared using standard chemical manipulations and procedures similar to those used for the preparation of compound 244, except 4-methyl-3-(trifluoromethyl)-1H-pyrazole (compound 261.2) was used in place 4-methoxy-1H-pyrazole (compound 244.4) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 439 (M+H$^+$).

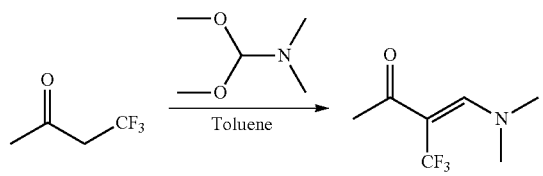

Compound 262.1. (Z)-4-(Dimethylamino)-3-(trifluoromethyl)but-3-en-2-one

Into a 100-mL round-bottom flask, was placed 4,4,4-trifluorobutan-2-one (1.7 mL, 15.86 mmol, 1.00 equiv) in toluene (45 mL). 1,1-Dimethoxy-N,N-dimethylmethanamine (4.21 mL, 31.7 mmol) was added and the resulting solution was stirred for 4 h at 100° C., then concentrated under reduced pressure to obtain the title compound as yellow oil (2.0 g, crude).

Compound 262.2.
3-Methyl-4-(trifluoromethyl)-1H-pyrazole

Into a 50-mL round-bottom flask, was placed a solution of (Z)-4-(dimethylamino)-3-(trifluoromethyl)but-3-en-2-one (compound 262.1, 2.0 g, 11.0 mmol) in ethanol (30 mL). Hydrazine hydrate (3.7 mL, 77 mmol) was added and the resulting solution was stirred overnight at 75° C., then cooled and concentrated under reduced pressure. The residue was purified by a silica gel chromatography with ethyl acetate/petroleum ether (1:2) as eluent to obtain the title compound as a white solid (1.0 g, 61%).

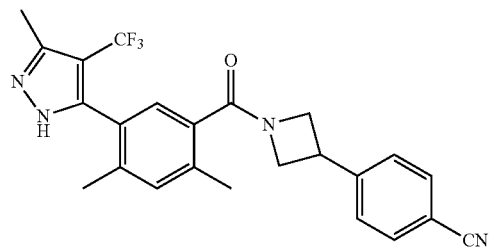 [SMILES: Cc1cc(C)c(-c2[nH]nc(C)c2C(F)(F)F)cc1C(=O)N1CC(c2ccc(C#N)cc2)C1]

Compound 262. 4-(1-(2,4-Dimethyl-5-(3-methyl-4-(trifluoromethyl)-1H-pyrazol-5-yl)benzoyl)azetidin-3-yl)benzonitrile The title compound was prepared using standard chemical manipulations and procedures similar to those used for the preparation of compound 244, except 3-methyl-4-(trifluoromethyl)-1H-pyrazole (compound 262.2) was used in place 4-methoxy-1H-pyrazole (compound 244.4) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 439 (M+H$^+$).

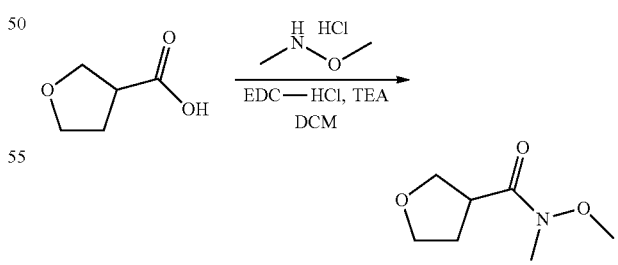

Compound 263.1.
N-Methoxy-N-methyltetrahydrofuran-3-carboxamide

Into a 250-mL round-bottom flask, was placed a solution of tetrahydrofuran-3-carboxylic acid (10 g, 86.1 mmol) in dichloromethane (200 mL). EDC-HCl (18.2 g, 94.9 mmol), N,O-dimethylhydroxylamine hydrochloride (10 g, 103 mmol) and triethylamine (24.0 mL, 172 mmol) were added and the resulting mixture was stirred overnight at room temperature. The mixture was diluted with DCM (50 mL) and washed with aqueous HCl (1 M, 3×10 mL), sodium bicarbonate (sat., 2×30 mL) and brine (3×20 mL). The organic layer was dried (Na$_2$SO$_4$), filtered and concentrated under reduced pressure to obtain the title compound as light yellow oil (6.71 g, 49%).

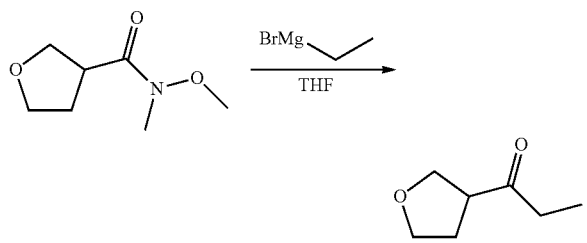

Compound 263.2. 1-(Tetrahydrofuran-3-yl)propan-1-one

Into a 250-mL 3-neck round-bottom flask, was placed a solution of N-methoxy-N-methyltetrahydrofuran-3-carboxamide (compound 263.1, 6.71 g, 42.2 mmol) in tetrahydrofuran (100 mL). The system was purged with nitrogen, then cooled to 0° C. Ethylmagnesium bromide (3M in diethyl ether, 17 mL, 51 mmol) was added drop-wise at 0° C. over 30 min. The resulting solution was stirred overnight at 40° C., then cooled and carefully quenched with aqueous HCl (1M, 10 mL). The resulting mixture was concentrated under reduced pressure and the residue was diluted with water (10 mL). The mixture was extracted with ethyl acetate (3×30 mL) and the combined organic extracts were washed with brine (2×10 mL), dried (Na$_2$SO$_4$), filtered and concentrated under reduced pressure. Obtained the title compound as a light yellow oil (4.5 g, 83%).

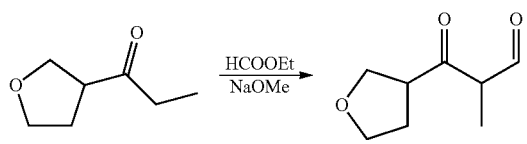

Compound 263.3. 2-Methyl-3-oxo-3-(tetrahydrofuran-3-yl)propanal

Into a 100-mL round-bottom flask, was placed 1-(tetrahydrofuran-3-yl)propan-1-one (compound 263.2, 2.5 g, 19.5 mmol), sodium methoxide (1.4 g, 25.9 mmol) and ethyl formate (20 mL). The mixture was stirred overnight at room temperature, then concentrated under reduced pressure. The residue was purified by a silica gel column chromatography with ethyl acetate/petroleum ether (1:20 to 1:5) as eluent to obtain the title compound as a yellow solid (2.0 g, 66%).

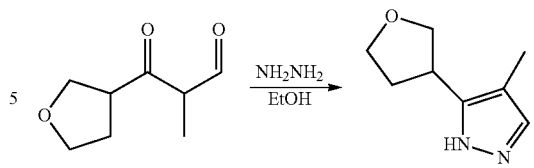

Compound 263.4. 4-Methyl-5-(tetrahydrofuran-3-yl)-1H-pyrazole

Into a 100-mL round-bottom flask, was placed a solution of 2-methyl-3-oxo-3-(tetrahydrofuran-3-yl)propanal (compound 263.3, 3.00 g, 19.2 mmol) in ethanol (25 mL). Hydrazine hydrate (1.16 mL, 24 mmol) was added and the resulting solution was stirred for 3 h at 80° C. The resulting mixture was concentrated under reduced pressure to obtain the title compound as a colorless oil (3.5 g, crude).

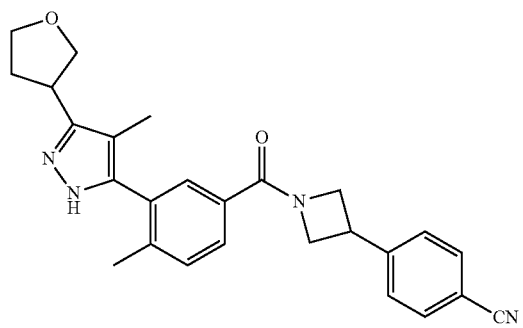 [SMILES: Cc1ccc(C(=O)N2CC(c3ccc(C#N)cc3)C2)cc1-c1[nH]nc(C2CCOC2)c1C]

Compound 263. 4-(1-(4-Methyl-3-(4-methyl-3-(tetrahydrofuran-3-yl)-1H-pyrazol-5-yl)benzoyl)azetidin-3-yl)benzonitrile The title compound was prepared using standard chemical manipulations and procedures similar to those used for the preparation of compound 244, except 4-methyl-5-(tetrahydrofuran-3-yl)-1H-pyrazole (compound 263.4) was used in place of 4-methoxy-1H-pyrazole (compound 244.4). m/z (ES+) 427 (M+H$^+$).

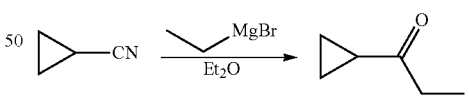

Compound 264.1. 1-Cyclopropylpropan-1-one

Into a 250-mL 3-neck round-bottom flask purged and maintained with an inert atmosphere of nitrogen, was placed cyclopropanecarbonitrile (20.0 g, 22.0 mL, 298 mmol) in diethyl ether (100 mL). The solution was cooled to 10° C., then ethylmagnesium bromide (3 M in diethyl ether, 109 mL, 327 mmol) was added drop-wise over 10 min. The resulting solution was stirred overnight at 40° C., then cooled and carefully quenched with aqueous NH$_4$Cl (sat., 100 mL). The layers were partitioned and the aqueous phase was extracted ethyl acetate (3×200 mL). The combined organic layers were washed with brine (3×200 mL), dried

345

(Na₂SO₄), filtered and concentrated under reduced pressure. The crude product was purified by distillation under reduced pressure (50 mm Hg) and the fraction collected at 50° C. was the title compound (11 g, 38%).

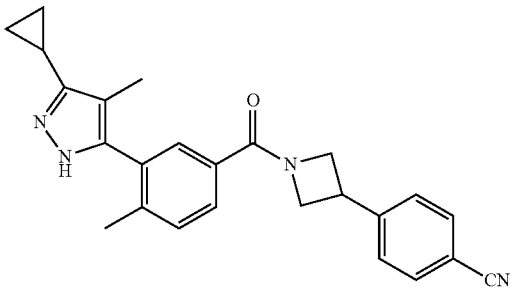 [SMILES: Cc1ccc(C(=O)N2CC(c3ccc(C#N)cc3)C2)cc1-c1[nH]nc(C2CC2)c1C]

Compound 264. 4-(1-(3-(3-Cyclopropyl-4-methyl-1H-pyrazol-5-yl)-4-methylbenzoyl)azetidin-3-yl)benzonitrile The title compound was prepared using standard chemical manipulations and procedures similar to those used for the preparation of compound 263, except 1-cyclopropylpropan-1-one (compound 264.1) was used in place of 1-(tetrahydrofuran-3-yl)propan-1-one (compound 263.2). m/z (ES+) 397 (M+H)⁺.

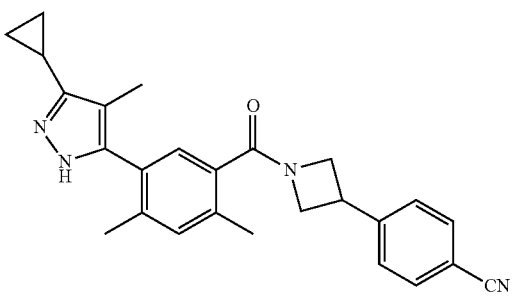 [SMILES: Cc1cc(C)c(-c2[nH]nc(C3CC3)c2C)cc1C(=O)N1CC(c2ccc(C#N)cc2)C1]

Compound 265. 4-(1-(5-(3-Cyclopropyl-4-methyl-1H-pyrazol-5-yl)-2,4-dimethylbenzoyl)azetidin-3-yl)benzonitrile The title compound was prepared using standard chemical manipulations and procedures similar to those used for the preparation of compound 263, except 1-cyclopropylpropan-1-one (compound 264.1) was used in place of 1-(tetrahydrofuran-3-yl)propan-1-one (compound 263.2) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 411 (M+H⁺).

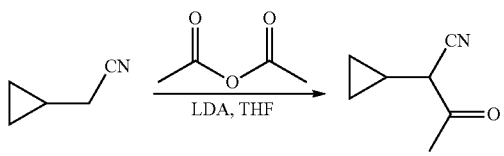

346

Compound 266.1. 2-Cyclopropyl-3-oxobutanenitrile

Into a 100-mL three neck round-bottom flask, which was purged and maintained with an inert atmosphere of argon, was placed a solution of 2-cyclopropylacetonitrile (3.70 mL, 40.1 mmol) in THF (20 mL). The solution was cooled to −78° C., then LDA (2 M in THF, 30 mL, 60 mmol) was added drop-wise and the mixture was stirred for 1 h at −78° C. A solution of acetic anhydride (4.54 mL, 48.0 mmol) in tetrahydrofuran (10 mL) was added drop-wise at −78° C. The mixture was stirred for 1 h at 15° C., then carefully quenched with citric acid (10% aq, 200 mL). The mixture was extracted with diethyl ether (2×70 mL) and the combined organic extracts were washed with brine (50 mL), dried (Na₂SO₄), filtered and concentrated under reduced pressure to obtain the title compound, which was used in the next step without purification.

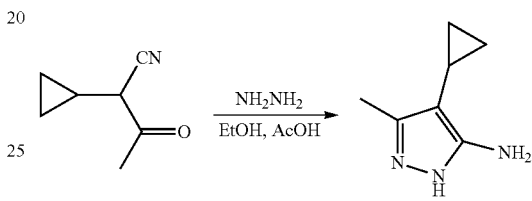

Compound 266.2. 4-Cyclopropyl-3-methyl-1H-pyrazol-5-amine

Into a 250-mL round-bottom flask, was placed a solution of 2-cyclopropyl-3-oxobutanenitrile (compound 266.1, 4.0 g, 32.5 mmol) in ethanol (18 mL). AcOH (3 mL) and hydrazine hydrate (3.15 mL, 65 mmol) were added and the reaction was stirred overnight at 80° C. The reaction was cooled, then the pH was carefully adjusted to 9 with NaHCO₃ (aq. sat.). The mixture was diluted with water, then extracted with ethyl acetate (6×60 mL) and the combined organic extracts were washed with brine (80 mL), dried (Na₂SO₄), filtered and concentrated under reduced pressure to obtain the title compound as a brown oil (4.17 g, crude), which was used in the next step without purification.

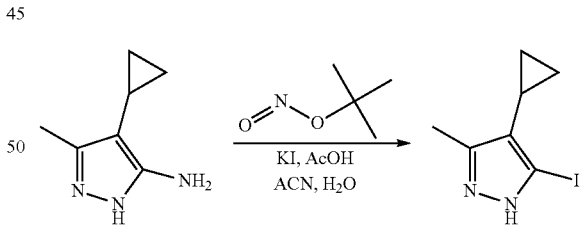

Compound 266.3. 4-Cyclopropyl-5-iodo-3-methyl-1H-pyrazole

Into a 250-mL 3-neck round-bottom flask, was placed a solution of 4-cyclopropyl-3-methyl-1H-pyrazol-5-amine (compound 266.2, 3.8 g, 27.7 mmol) in ACN (40 mL). The solution was cooled to 0° C., then AcOH (4.8 mL, 83 mmol) was carefully added followed by a drop-wise addition of a solution of KI (11.5 g, 69.3 mmol) in water (40 mL). The mixture was stirred for 10 min at 0° C., then tert-butyl nitrite (8.24 mL, 69.3 mmol) in ACN (40 mL) was added drop-wise. The resulting mixture was stirred at 0° C. for 10 min, then at room temperature for 2 h. The pH of the reaction was carefully adjusted to 8 with sodium bicarbonate (aq. sat.) and extracted with ethyl acetate (4×50 mL). The combined organic extracts were washed with Na₂S₂O₃ (aq. sat., 80 mL) and brine (2×80 mL), dried (Na₂SO₄), filtered and concentrated under reduced pressure. The residue was purified by a silica gel chromatography with ethyl acetate/petroleum ether (1:2) as eluent to obtain the title compound as a yellow solid (1.71 g, 25%).

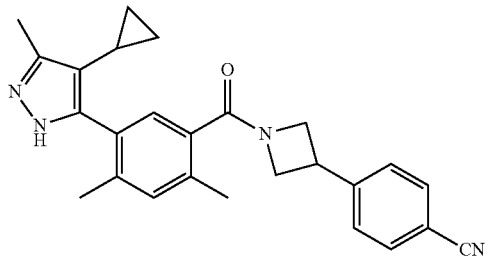 [SMILES: Cc1cc(C)c(-c2[nH]nc(C)c2C2CC2)cc1C(=O)N1CC(c2ccc(C#N)cc2)C1]

Compound 266. 4-(1-(5-(4-Cyclopropyl-3-methyl-1H-pyrazol-5-yl)-2,4-dimethylbenzoyl)azetidin-3-yl)benzonitrile The title compound was prepared using standard chemical manipulations and procedures similar to those used for the preparation of compound 244, except 4-cyclopropyl-5-iodo-3-methyl-1H-pyrazole (compound 266.3.) was used in place of 3-iodo-4-methoxy-1H-pyrazole (compound 244.5) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 411 (M+H)⁺.

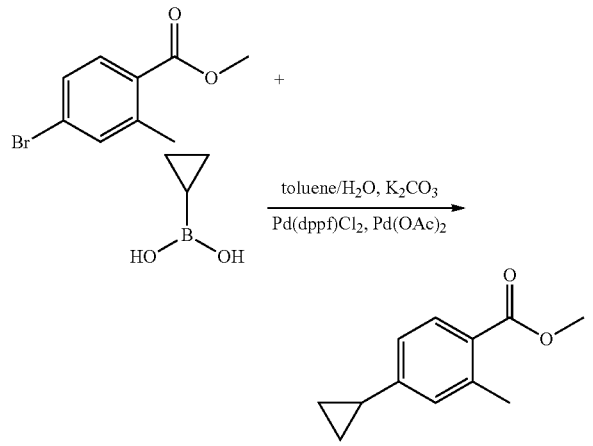

Compound 267.1. Methyl 4-cyclopropyl-2-methylbenzoate

To a solution of methyl 4-bromo-2-methylbenzoate (5.00 g, 20.7 mmol, 1.00 equiv, 95%) in a mixture of toluene and H₂O (20 mL/1 mL) were added potassium carbonate (6.10 g, 44.1 mmol, 2.00 equiv), cyclopropylboronic acid (2.30 g, 26.8 mmol, 1.20 equiv), Pd(dppf)Cl₂ (900 mg, 1.23 mmol, 0.05 equiv), and Pd(OAc)₂ (250 mg, 1.12 mmol, 0.05 equiv). The reaction mixture was purged with nitrogen and stirred at 80° C. overnight. After cooling to room temperature, the mixture was then concentrated under reduced pressure. The resulting residue was purified via silica gel column chromatography with ethyl acetate/petroleum ether (1:50) as eluent to yield 2.68 g (61%) of methyl 4-cyclopropyl-2-methylbenzoate as a colorless oil.

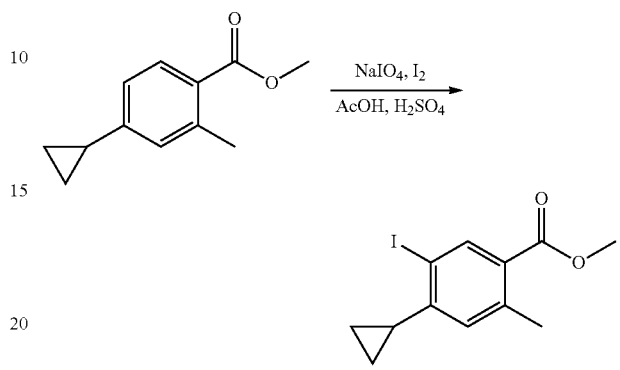

Compound 267.2. Methyl 4-cyclopropyl-5-iodo-2-methylbenzoate

To a solution of methyl 4-cyclopropyl-2-methylbenzoate (compound 267.1, 2.68 g, 13.4 mmol, 1.00 equiv, 95%) in AcOH (50 mL) were added NaIO₄ (1.51 g, 7.08 mmol, 0.50 equiv), I₂ (3.58 g, 14.1 mmol, 1.00 equiv), and sulfuric acid (201 mg, 2.01 mmol, 0.15 equiv, 98%). The reaction mixture was stirred at 110° C. overnight. After cooling to ambient temperature, 100 mL of water was added. The resulting mixture was diluted with 100 mL of ethyl acetate, then washed with 3×30 mL of Na₂S₂O₃ (aq., sat.) and 1×30 mL of brine. The organic phase was dried over anhydrous sodium sulfate and concentrated under reduced pressure. The residue was purified via silica gel column chromatography with ethyl acetate/petroleum ether (1/50) as eluent to yield 2.00 g (45%) of methyl 4-cyclopropyl-5-iodo-2-methylbenzoate as a colorless oil.

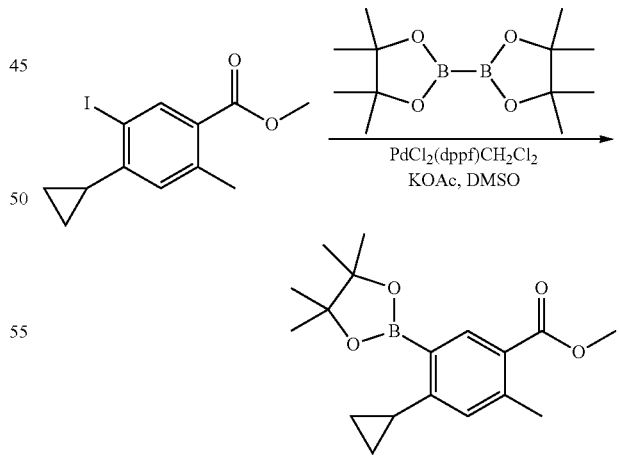

Compound 267.3. Methyl 4-cyclopropyl-2-methyl-5-(4,4,5,5-tetramethyl-1,3,2-dioxaborolan-2-yl)benzoate The title compound was prepared using standard chemical manipulations and procedures similar to those used for the preparation of compound 5.4, except methyl 4-cyclopropyl-5-iodo-2-methylbenzoate (compound 267.2) was used in place of methyl 3-iodo-4-methylbenzoate (compound 5.3).

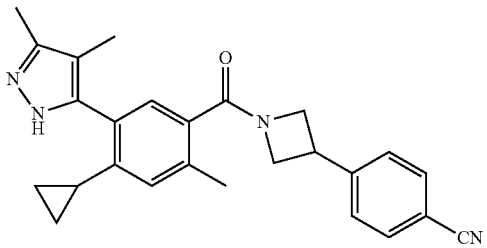 [SMILES: Cc1cc(C2CC2)c(-c2[nH]nc(C)c2C)cc1C(=O)N1CC(c2ccc(C#N)cc2)C1]

Compound 267. 4-(1-(4-Cyclopropyl-5-(3,4-dimethyl-1H-pyrazol-5-yl)-2-methylbenzoyl)azetidin-3-yl)benzonitrile The title compound was prepared using standard chemical manipulations and procedures similar to those used for the preparation of compound 59, except methyl 4-cyclopropyl-2-methyl-5-(4,4,5,5-tetramethyl-1,3,2-dioxaborolan-2-yl)benzoate (compound 267.3) was used in place of methyl 4-methyl-3-(4,4,5,5-tetramethyl-1,3,2-dioxaborolan-2-yl)benzoate (compound 5.4). m/z (ES+) 411 (M+H)+.

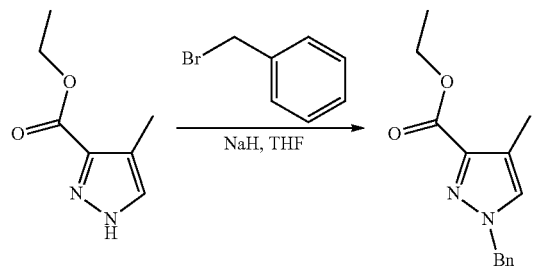

Compound 268.1. Ethyl 1-benzyl-4-methyl-1H-pyrazole-3-carboxylate

Into a 100-mL 3-neck round-bottom flask, was placed a solution of ethyl 4-methyl-1H-pyrazole-3-carboxylate (1.0 g, 6.5 mmol) in tetrahydrofuran (20 mL). The solution was cooled to 0° C., then sodium hydride (360 mg, 9.00 mmol, 60% dispersion in mineral oil) was added in portions and the mixture was stirred for 20 min. Benzyl bromide (904 μL, 7.60 mmol) was added at 0° C., then the resulting mixture was stirred for 1.5 h at room temperature. The reaction was carefully quenched with by drop-wise addition of water (35 mL) and the mixture was extracted with ethyl acetate (3×100 mL). The combined organic extracts were washed with of brine (3×100 mL), dried (Na$_2$SO$_4$), filtered and concentrated under reduced pressure. The residue was purified by a silica gel chromatography with ethyl acetate/petroleum ether (1:20-1:2) as eluent to obtain the title compound as a yellow solid (1.0 g, 63%).

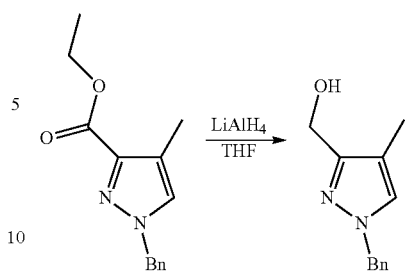

Compound 268.2. (1-Benzyl-4-methyl-1H-pyrazol-3-yl)methanol

Into a 100-mL 3-neck round-bottom flask, which was purged and maintained with an inert atmosphere of nitrogen, was placed a solution of ethyl 1-benzyl-4-methyl-1H-pyrazole-3-carboxylate (compound 268.1, 2.3 g, 9.42 mmol) in THF (30 mL). The solution was cooled to 0° C., then LiAlH$_4$ (360 mg, 9.49 mmol, 1.00 equiv) was carefully added in portions. The resulting mixture was stirred for 1 h at room temperature, then carefully quenched by drop-wise addition of water (400 μL), then aqueous NaOH (10%, 400 μL), followed by additional water (1.2 mL). The solids were removed by filtration and the filtrate was dried (Na$_2$SO$_4$), filtered and concentrated under reduced pressure to obtain the title compound as a yellow oil (1.7 g, 89%).

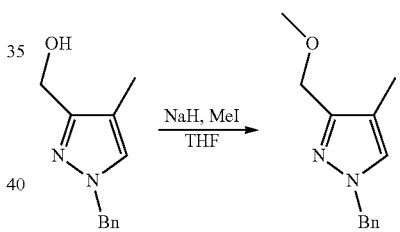

Compound 268.3. 1-Benzyl-3-(methoxymethyl)-4-methyl-1H-pyrazole

Into a 250-mL 3-neck round-bottom flask, was placed a solution of (1-benzyl-4-methyl-1H-pyrazol-3-yl)methanol (compound 268.2, 1.7 g, 8.4 mmol) in THF (50 mL). The solution was cooled to 0° C., then sodium hydride (470 mg, 11.8 mmol, 60% dispersion in mineral oil) was added in portions at 0° C., and then the mixture was stirred for 20 min. Iodomethane (750 μL, 12 mmol) was added at 0° C., then the resulting mixture was stirred for 2 h at room temperature. The reaction was carefully quenched by drop-wise addition of water (30 mL) and the mixture was extracted with ethyl acetate (3×100 mL). The combined organic extracts were washed with brine (3×100 mL), dried (Na$_2$SO$_4$), filtered and concentrated under reduced pressure. The residue was purified by a silica gel chromatography with ethyl acetate/petroleum ether (1:10) as eluent to obtain the title compound as a yellow oil (1.5 g, 83%).

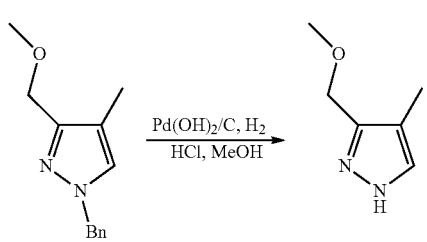

Compound 268.4. 3-(Methoxymethyl)-4-methyl-1H-pyrazole

Into a 100-mL round-bottom flask, was placed a solution of 1-benzyl-3-(methoxymethyl)-4-methyl-1H-pyrazole (compound 268.3, 700 mg, 3.24 mmol) in methanol (10 mL). The system was purged with nitrogen, then Pd(OH)$_2$/C (70 mg, 20 wt %) and aqueous HCl (2 M, 0.3 mL) were carefully added. The system was then charged with hydrogen (1 atm) and the resulting mixture was stirred for 2 days at room temperature. The system was purged with nitrogen, then the solids were removed by filtration and the filtrate was concentrated under reduced pressure. The pH of the residue was adjusted to 7 with aqueous sodium bicarbonate (sat.) and extracted with ethyl acetate (3×50 mL). The combined organic extracts were washed with brine (2×30 mL), dried (Na$_2$SO$_4$), filtered and concentrated under reduced pressure to obtain the title compound as a yellow oil (500 mg, crude).

Compound 268. 4-(1-(5-(3-(Methoxymethyl)-4-methyl-1H-pyrazol-5-yl)-2,4-dimethylbenzoyl)azetidin-3-yl)benzonitrile The title compound was prepared using standard chemical manipulations and procedures similar to those used for the preparation of compound 244, except 3-(methoxymethyl)-4-methyl-1H-pyrazole (compound 268.4) was used in place of 4-methoxy-1H-pyrazole (compound 244.4) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4) m/z (ES+) 415 (M+H)$^+$.

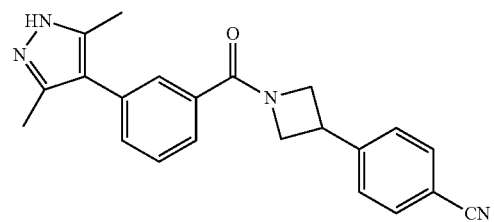 [SMILES: Cc1n[nH]c(C)c1-c1cccc(C(=O)N2CC(c3ccc(C#N)cc3)C2)c1]

Compound 269. 4-(1-(3-(3,5-Dimethyl-1H-pyrazol-4-yl)benzoyl)azetidin-3-yl)benzonitrile The title compound was prepared using standard chemical manipulations and procedures similar to those used for the preparation of compound 5, except 3-iodobenzoic acid was used in place of 3-iodo-4-methylbenzoic acid and 4-bromo-3,5-dimethyl-1H-pyrazole was used in place of 5-iodo-2,4-dimethyl-1H-imidazole (compound 5.5). m/z (ES+) 357 (M+H)$^+$.

The compounds in TABLE 12 were prepared using standard chemical manipulations and procedures similar to those used for the preparation of compound 263.

TABLE 12

| Cpd | Name | Structure | m/z (ES+) (M + H)$^+$ |
|---|---|---|---|
| 330 | 4-(1-(2,4-dimethyl-5-(4-methyl-3-(tetrahydrofuran-3-yl)-1H-pyrazol-5-yl)benzoyl)azetidin-3-yl)benzonitrile | 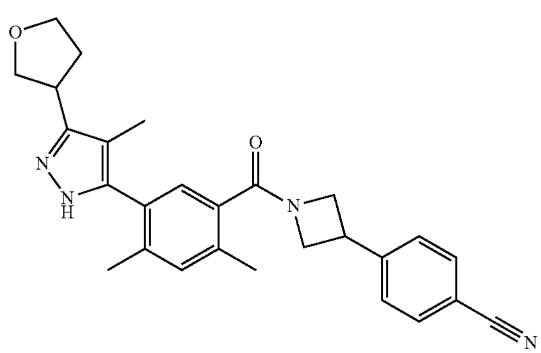 [SMILES: Cc1cc(C)c(-c2[nH]nc(C3CCOC3)c2C)cc1C(=O)N1CC(c2ccc(C#N)cc2)C1] | 441 |

TABLE 12-continued

| Cpd | Name | Structure | m/z (ES+) (M + H)+ |
|---|---|---|---|
| 331 | 4-(1-(2,4-dimethyl-5-(4-methyl-3-(tetrahydro-2H-pyran-4-yl)-1H-pyrazol-5-yl)benzoyl)azetidin-3-yl)benzonitrile | 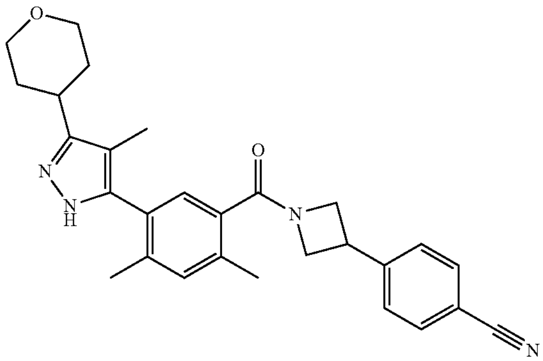 | 455 |
| 274 | 4-(1-(2,4-dimethyl-5-(4-methyl-3-(tetrahydrofuran-2-yl)-1H-pyrazol-5-yl)benzoyl)azetidin-3-yl)benzonitrile | 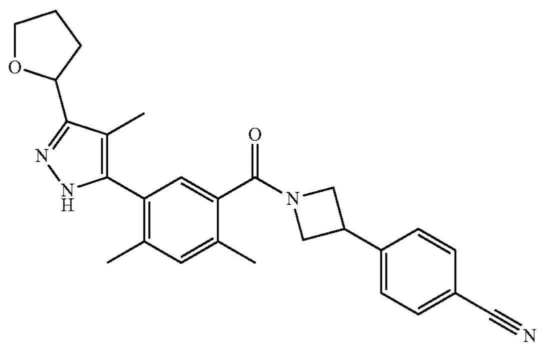 [SMILES: Cc1cc(C)c(-c2[nH]nc(C3CCCO3)c2C)cc1C(=O)N1CC(c2ccc(C#N)cc2)C1] | 441 |

The compounds in TABLE 13 were prepared using standard chemical manipulations and procedures similar to those used for the preparation of compound 268.

TABLE 13

| Cpd | Name | Structure | m/z (ES+) (M + H)+ |
|---|---|---|---|
| 275 | 4-(1-(5-(3-((cyclopropylmethoxy)methyl)-4-methyl-1H-pyrazol-5-yl)-2,4-dimethylbenzoyl)azetidin-3-yl)benzonitrile | 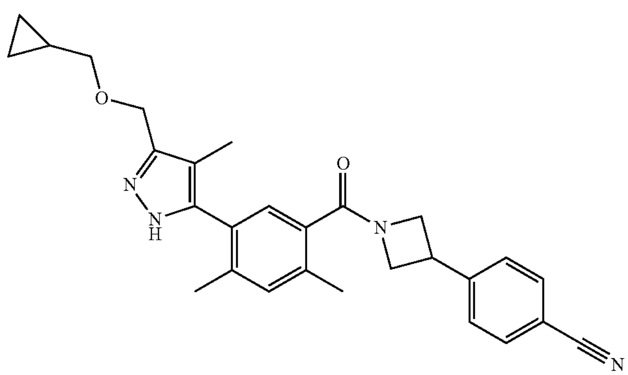 [SMILES: Cc1cc(C)c(-c2[nH]nc(COCC3CC3)c2C)cc1C(=O)N1CC(c2ccc(C#N)cc2)C1] | 455 |

TABLE 13-continued

| Cpd | Name | Structure | m/z (ES+) (M + H)+ |
|---|---|---|---|
| 286 | 4-(1-(5-(3-(hydroxymethyl)-4-methyl-1H-pyrazol-5-yl)-2,4-dimethylbenzoyl)azetidin-3-yl)benzonitrile | 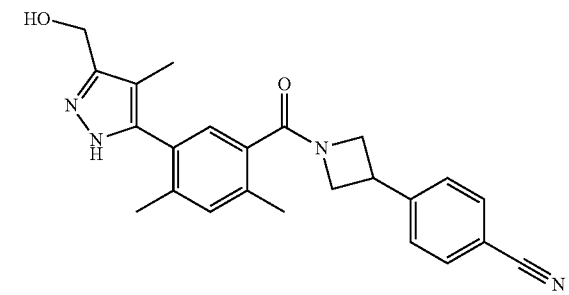 [SMILES: Cc1cc(C)c(-c2[nH]nc(CO)c2C)cc1C(=O)N1CC(c2ccc(C#N)cc2)C1] | 401 |
| 309 | 4-(1-(2,4-dimethyl-5-(4-methyl-3-((oxetan-3-yloxy(methyl)-1H-pyrazol-5-yl)benzoyl)azetidin-3-yl)benzonitrile | 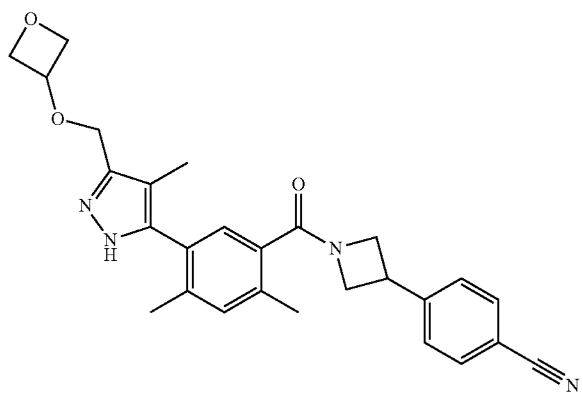 [SMILES: Cc1cc(C)c(-c2[nH]nc(COC3COC3)c2C)cc1C(=O)N1CC(c2ccc(C#N)cc2)C1] | 457 |
| 356 | (5-(5-(3-(4-cyanophenyl)azetidine-1-carbonyl)-2,4-dimethylphenyl)-4-methyl-1H-pyrazol-3-yl)methyl acetate | 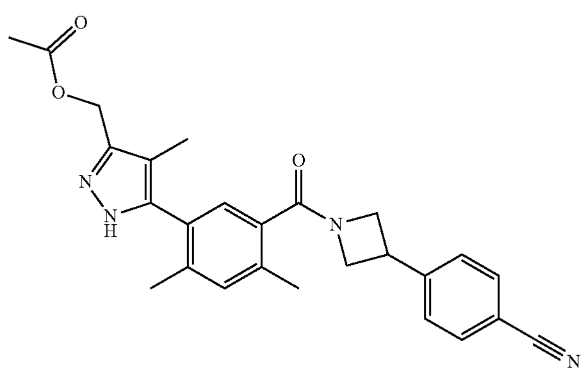 [SMILES: CC(=O)OCc1n[nH]c(-c2cc(C(=O)N3CC(c4ccc(C#N)cc4)C3)c(C)cc2C)c1C] | 443 |
| 350 | 4-(1-(5-(3-(isopropoxymethyl)-4-methyl-1H-pyrazol-5-yl)-2,4-dimethylbenzoyl)azetidin-3-yl)benzonitrile | 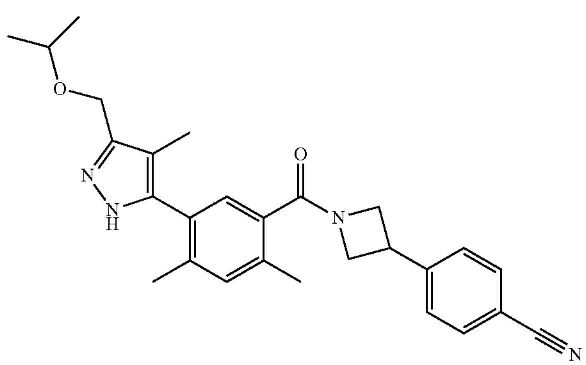 [SMILES: Cc1cc(C)c(-c2[nH]nc(COC(C)C)c2C)cc1C(=O)N1CC(c2ccc(C#N)cc2)C1] | 443 |

TABLE 13-continued

| Cpd | Name | Structure | m/z (ES+) (M + H)+ |
|---|---|---|---|
| 312 | 4-(1-(2,4-dimethyl-5-(4-methyl-3-((2,2,2-trifluoroethoxy)methyl)-1H-pyrazol-5-yl)benzoyl)azetidin-3-yl)benzonitrile | 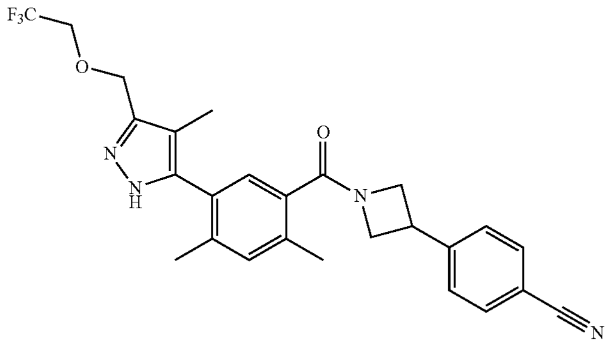 [SMILES: Cc1cc(C)c(-c2[nH]nc(COCC(F)(F)F)c2C)cc1C(=O)N1CC(c2ccc(C#N)cc2)C1] | 483 |

The compounds in TABLE 14 were prepared using standard chemical manipulations and procedures similar to those used for the preparation of compound 249.

TABLE 14

| Cpd | Name | Structure | m/z (ES+) (M + H)+ |
|---|---|---|---|
| 277 | 4-(1-(5-(3-(cyclopropylmethoxy)-4-methyl-1H-pyrazol-5-yl)-2,4-dimethylbenzoyl)azetidin-3-yl)benzonitrile | 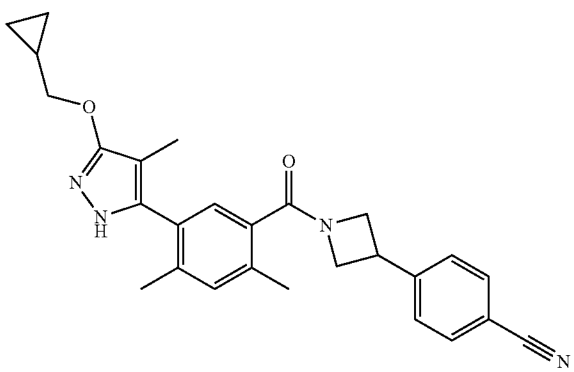 [SMILES: Cc1cc(C)c(-c2[nH]nc(OCC3CC3)c2C)cc1C(=O)N1CC(c2ccc(C#N)cc2)C1] | 441 |
| 276 | 4-(1-(5-(3-(2-methoxyethoxy)-4-methyl-1H-pyrazol-5-yl)-2,4-dimethylbenzoyl)azetidin-3-yl)benzonitrile | 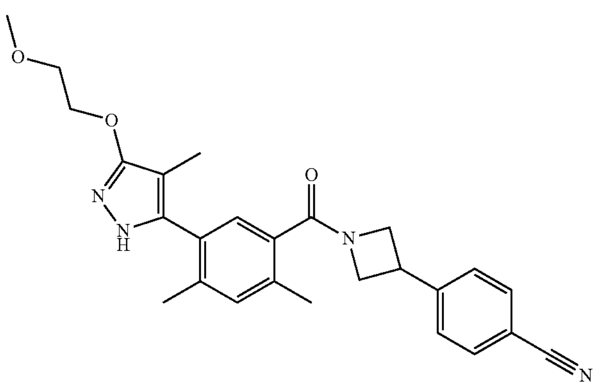 [SMILES: COCCOc1n[nH]c(-c2cc(C(=O)N3CC(c4ccc(C#N)cc4)C3)c(C)cc2C)c1C] | 445 |

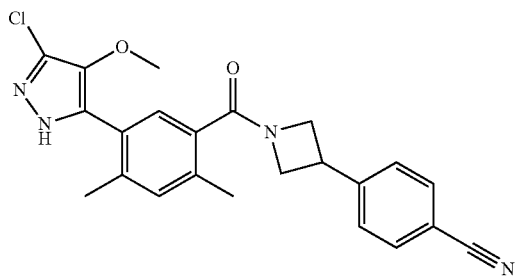 [SMILES: COc1c(Cl)n[nH]c1-c1cc(C(=O)N2CC(c3ccc(C#N)cc3)C2)c(C)cc1C]

Compound 279. 4-(1-(5-(3-Chloro-4-methoxy-1H-pyrazol-5-yl)-2,4-dimethylbenzoyl)azetidin-3-yl)benzonitrile The title compound was prepared using standard chemical manipulations and procedures similar to those used for the preparation of compounds 244 and 250. m/z (ES+) 421 (M+H)$^+$.

Compound 281.1. 3-(Methoxymethyl)-1H-pyrazole

The title compound was prepared using standard chemical manipulations and procedures similar to those used for the preparation of compound 268.4, except methyl 1H-pyrazole-3-carboxylate was used instead of methyl 4-methyl-1H-pyrazole-3-carboxylate.

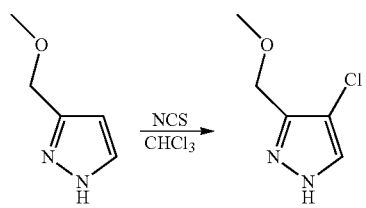

Compound 281.2. 4-Chloro-3-(methoxymethyl)-1H-pyrazole

To a solution of 3-(methoxymethyl)-1H-pyrazole (compound 281.1, 200 mg, 1.78 mmol) in chloroform (20 mL) was added NCS (237 mg, 1.77 mmol). The reaction mixture was stirred overnight at room temperature, then quenched with 20 mL of H$_2$O. The aqueous phase was extracted with 3×50 mL of ethyl acetate. The combined organic layers were washed with 3×20 mL of brine, dried over anhydrous sodium sulfate and concentrated under reduced pressure. The residue was purified by silica gel chromatography with EtOAc:PE (1:2) as the eluent to furnish 50 mg (19%) of the title compound as a white solid.

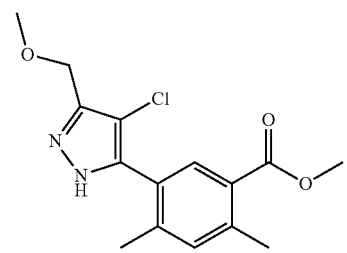

Compound 281.3. Methyl 5-(4-chloro-3-(methoxymethyl)-1H-pyrazol-5-yl)-2,4-dimethylbenzoate The title compound was prepared using standard chemical manipulations and procedures similar to those used for the preparation of compound 244.6, except 4-chloro-3-(methoxymethyl)-1H-pyrazole (compound 281.2) was used instead of 4-methoxy-1H-pyrazole (compound 244.4).

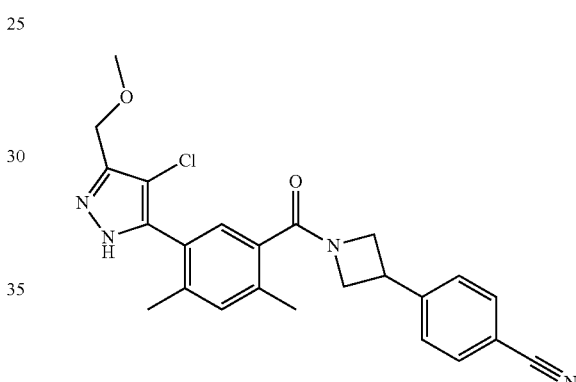

Compound 281. 4-(1-(5-(4-Chloro-3-(methoxymethyl)-1H-pyrazol-5-yl)-2,4-dimethylbenzoyl)azetidin-3-yl)benzonitrile The title compound was prepared using standard chemical manipulations and procedures similar to those used for the preparation of compound 244, except methyl 5-(4-chloro-3-(methoxymethyl)-1H-pyrazol-5-yl)-2,4-dimethylbenzoate (compound 281.3) was used instead of methyl 3-(4-methoxy-1H-pyrazol-5-yl)-4-methylbenzoate (compound 244.6). m/z (ES+) 435 (M+H)$^+$.

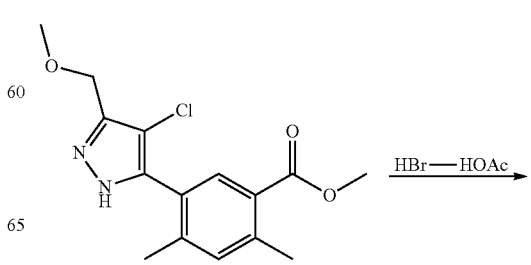

-continued

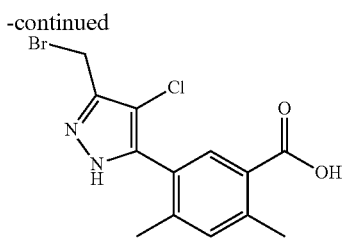

Compound 304.1. 5-(3-(Bromomethyl)-4-chloro-1H-pyrazol-5-yl)-2,4-dimethylbenzoic acid A mixture of methyl 5-(4-chloro-3-(methoxymethyl)-1H-pyrazol-5-yl)-2,4-dimethylbenzoate (compound 281.3, 20 mg, 0.06 mmol) and HBr—HOAc (5 mL) was stirred overnight at 80° C., then concentrated under reduced pressure to yield 20 mg (90%) of the title compound as a yellow oil.

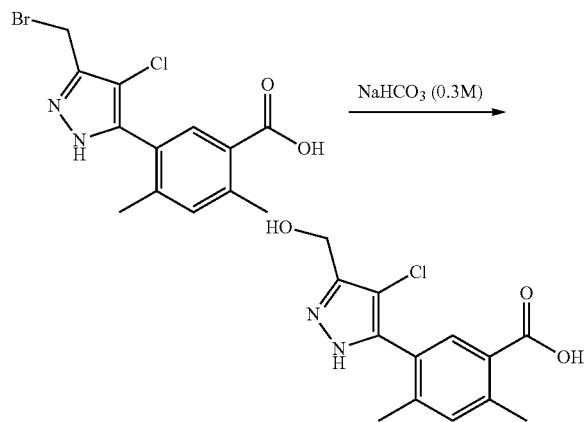

Compound 304.2. 5-(4-Chloro-3-(hydroxymethyl)-1H-pyrazol-5-yl)-2,4-dimethylbenzoic acid A mixture of 5-(3-(bromomethyl)-4-chloro-1H-pyrazol-5-yl)-2,4-dimethylbenzoic acid (compound 304.1, 200 mg, 0.58 mmol) and NaHCO$_3$ (0.3 M, 10 mL) was stirred for 30 min at room temperature, then concentrated under reduced pressure. This resulted in 200 mg (crude) of the title compound as a white solid.

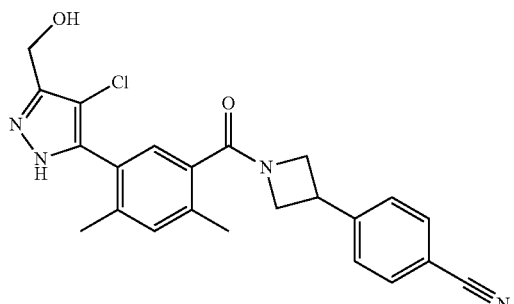

Compound 304. 4-(1-(5-(4-Chloro-3-(hydroxymethyl)-1H-pyrazol-5-yl)-2,4-dimethylbenzoyl)azetidin-3-yl)benzonitrile The title compound was prepared using standard chemical manipulations and procedures similar to those used for the preparation of compound 244, except 5-(4-chloro-3-(hydroxymethyl)-1H-pyrazol-5-yl)-2,4-dimethylbenzoic acid (compound 304.2) was used instead of 3-(4-methoxy-1H-pyrazol-5-yl)-4-methylbenzoic acid (compound 244.7). m/z (ES+) 421 (M+H)$^+$.

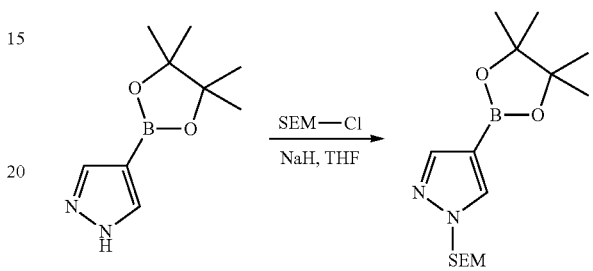

Compound 280.1. 4-(4,4,5,5-Tetramethyl-1,3,2-dioxaborolan-2-yl)-1-((2-(trimethylsilyl)ethoxy)methyl)-1H-pyrazole Into a 250-mL three neck round-bottom flask, which was purged and maintained with an inert atmosphere of nitrogen, was placed a solution of 4-(tetramethyl-1,3,2-dioxaborolan-2-yl)-1H-pyrazole (5.82 g, 30.0 mmol) in tetrahydrofuran (80 mL). This was followed by the addition of NaH (70%) (2.05 g, 85.4 mmol) in portions at 0° C. To this was added SEMCl (6.4 mL, 36.1 mmol) dropwise. The reaction mixture was stirred overnight at room temperature, then quenched with 50 mL of NH$_4$Cl (sat). The aqueous phase was extracted with 2×100 mL of ethyl acetate and the combined organic layers were dried over anhydrous sodium sulfate and concentrated under reduced pressure. This resulted in 7 g (72%) of the title compound as colorless oil.

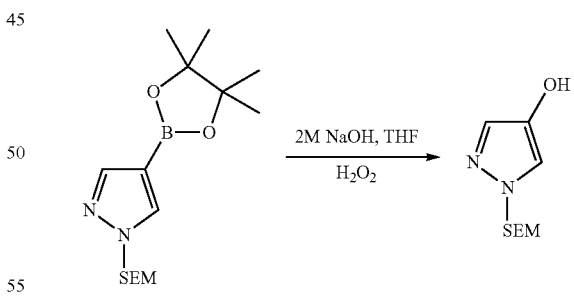

Compound 280.2. 1-((2-(Trimethylsilyl)ethoxy)methyl)-1H-pyrazol-4-ol

To a solution of 4-(4,4,5,5-tetramethyl-1,3,2-dioxaborolan-2-yl)-1-((2-(trimethylsilyl)ethoxy)methyl)-1H-pyrazole (compound 280.1, 9.7 g, 30.0 mmol) in THF (100 mL) was added 2M sodium hydroxide (aq.) (30 mL) dropwise. To this was added H$_2$O$_2$ (30%) (22.7 mL) dropwise at 0° C. The reaction mixture was stirred for 2 h at room temperature, then quenched with 50 mL of water. The aqueous phase was extracted with 2×150 mL of ethyl acetate and the combined organic layers were dried over anhydrous sodium sulfate and concentrated under reduced pressure. This resulted in 4.3 g (67%) of the title compound as a white solid.

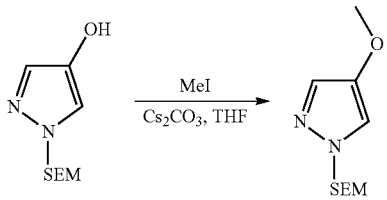

Compound 280.3. 4-Methoxy-1-((2-(trimethylsilyl)ethoxy)methyl)-1H-pyrazole

To a solution of 1-((2-(trimethylsilyl)ethoxy)methyl)-1H-pyrazol-4-ol (compound 280.2, 2.14 g, 10.0 mmol) in tetrahydrofuran (50 mL) was added $Cs_2CO_3$ (6.5 g, 20.0 mmol) in portions. To this was added $CH_3I$ (1.25 mL, 20.0 mmol) dropwise. The reaction mixture was stirred for 3 h at room temperature, then concentrated under reduced pressure. The resulting residue was dissolved in 100 mL of EtOAc. The solids were filtered off and the filtrate was concentrated under reduced pressure. This resulted in 2.1 g (92%) of the title compound as a colorless oil.

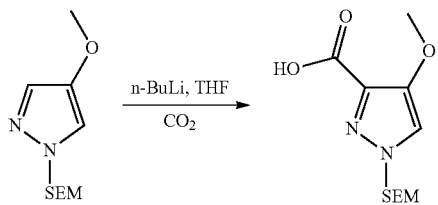

Compound 280.4. 4-Methoxy-1-((2-(trimethylsilyl)ethoxy)methyl)-1H-pyrazole-3-carboxylic acid Into a 250-mL three neck round-bottom flask, which was purged and maintained with an inert atmosphere of nitrogen, was placed a solution of 4-methoxy-1-((2-(trimethylsilyl)ethoxy)methyl)-1H-pyrazole (compound 280.3, 4.6 g, 20.0 mmol) in tetrahydrofuran (50 mL). This was followed by the addition of n-BuLi (2.5 M in hexane) (10 mL) dropwise at −78° C. The reaction mixture was stirred for 1 h at −60° C. To this was added $CO_2$(solid) (5 g) with stirring at −78° C. The reaction mixture was warmed slowly to room temperature and was stirred for 1 h, then quenched with 10 mL of $NH_4Cl$ (sat.). The pH value of the solution was adjusted to 5-6 with HCl (1 M). The aqueous phase was extracted with 2×100 mL of ethyl acetate and the combined organic layers were dried over sodium sulfate and concentrated under reduced pressure. This resulted in 5 g (92%) of the title compound as a white solid.

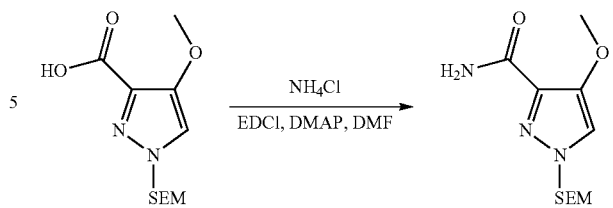

Compound 280.5. 4-Methoxy-1-((2-(trimethylsilyl)ethoxy)methyl)-1H-pyrazole-3-carboxamide To a solution of 4-methoxy-1-((2-(trimethylsilyl)ethoxy)methyl)-1H-pyrazole-3-carboxylic acid (compound 280.4, 5 g, 18.4 mmol) in N,N-dimethylformamide (50 mL) were added EDC-HCl (7 g, 36.5 mmol), $NH_4Cl$ (1.97 g, 36.8 mmol) and 4-dimethylaminopyridine (8.95 g, 73.3 mmol). The mixture was stirred for 2 h at room temperature, then warmed to 50° C. for 3 h. The reaction mixture was quenched with 30 mL of $NH_4Cl$ (sat). The aqueous phase was extracted with 2×100 mL of ethyl acetate. The combined organic layers were washed with 3×100 mL of $NH_4Cl$ (sat), dried over anhydrous sodium sulfate and concentrated under reduced pressure. The residue was purified by silica gel chromatography with ethyl acetate/petroleum ether (1:5) as the eluent to furnish 1.3 g (26%) of the title compound.

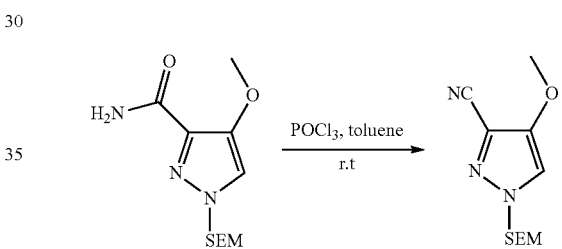

Compound 280.6. 4-Methoxy-1-((2-(trimethylsilyl)ethoxy)methyl)-1H-pyrazole-3-carbonitrile To a solution of 4-methoxy-1-((2-(trimethylsilyl)ethoxy)methyl)-1H-pyrazole-3-carboxamide (compound 280.5, 1.08 g, 4.0 mmol) in toluene (25 mL) was added $POCl_3$ (1.86 mL, 20.0 mmol) dropwise at 0° C. The mixture was stirred for 2 h at 50° C., then quenched with 30 mL of sodium bicarbonate (sat.). The aqueous phase was extracted with 2×100 mL of ethyl acetate and the combined organic layers were dried over anhydrous sodium sulfate and concentrated under reduced pressure. The residue was purified by silica gel chromatography with ethyl acetate/petroleum ether (1:6) as the eluent to yield 500 mg (49%) of the title compound as a white solid.

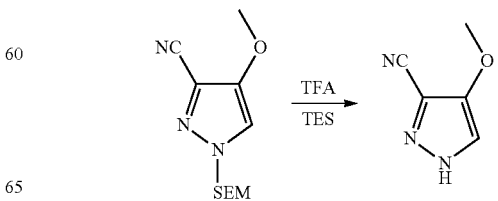

Compound 280.7.
4-Methoxy-1H-pyrazole-3-carbonitrile

A mixture of 4-methoxy-1-((2-(trimethylsilyl)ethoxy)methyl)-1H-pyrazole-3-carbonitrile (compound 280.6, 500 mg, 1.97 mmol) and trifluoroacetic acid (10 mL) in TES (5 mL) was stirred for 2 h at room temperature, then concentrated under reduced pressure. The residue was purified by silica gel chromatography with ethyl acetate/petroleum ether (1:2) as the eluent to furnish 210 mg (86%) of the title compound as a white solid.

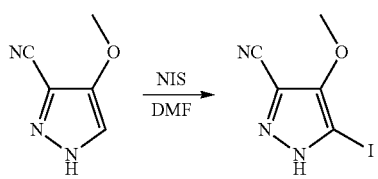

Compound 280.8.
5-Iodo-4-methoxy-1H-pyrazole-3-carbonitrile

To a solution of 4-methoxy-1H-pyrazole-3-carbonitrile (compound 280.7, 200 mg, 1.62 mmol) in N,N-dimethylformamide (15 mL) was added NIS (549 mg, 2.44 mmol). The reaction mixture was stirred for 2 h at 70° C., then quenched with 20 mL of $Na_2S_2O_3$ (sat.). The aqueous phase was extracted with 2×50 mL of ethyl acetate. The combined organic layers were dried over anhydrous sodium sulfate and concentrated under reduced pressure. The residue was purified by silica gel chromatography with ethyl acetate/petroleum ether (1:6) as the eluent to furnish 330 mg (82%) of the title compound as a white solid.

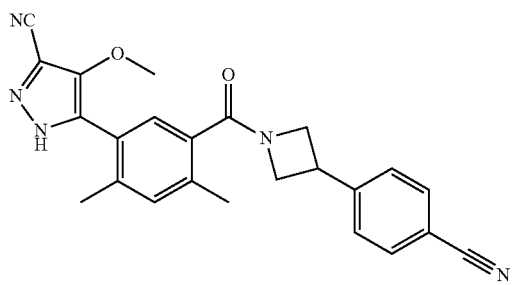 [SMILES: COc1c(C#N)n[nH]c1-c1cc(C(=O)N2CC(c3ccc(C#N)cc3)C2)c(C)cc1C]

Compound 280. 5-(5-(3-(4-Cyanophenyl)azetidine-1-carbonyl)-2,4-dimethylphenyl)-4-methoxy-1H-pyrazole-3-carbonitrile The title compound was prepared using standard chemical manipulations and procedures similar to those used for the preparation of compound 244, except 5-iodo-4-methoxy-1H-pyrazole-3-carbonitrile (compound 280.8) was used instead of 4-chloro-5-iodo-1H-pyrazole-3-carbonitrile (compound 260.6) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 412 (M+H+).

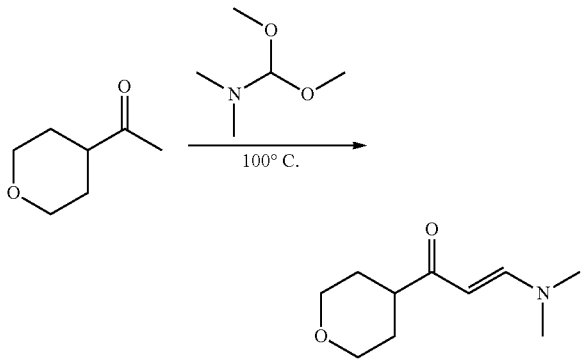

Compound 294.1. (E)-3-(Dimethylamino)-1-(tetrahydro-2H-pyran-4-yl)prop-2-en-1-one To a sealed tube were added 1-(tetrahydro-2H-pyran-4-yl)ethanone (3.00 g, 23.4 mmol) and DMF-DMA (6.2 mL, 46.8 mmol). The reaction mixture was heated at 100° C. overnight. The resulting mixture was concentrated under reduced pressure to afford 4.00 g (crude) of the title compound as light yellow oil.

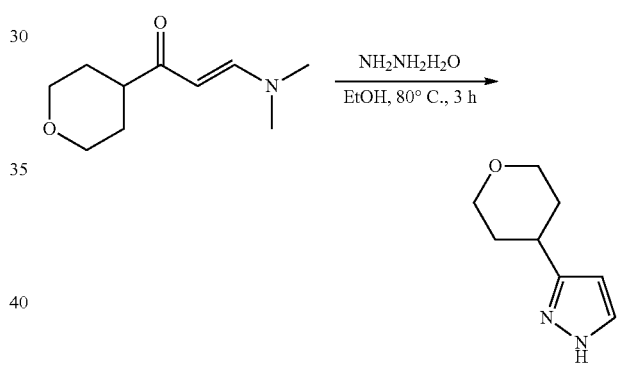

Compound 294.2.
3-(Tetrahydro-2H-pyran-4-yl)-1H-pyrazole

To a solution of (E)-3-(dimethylamino)-1-(tetrahydro-2H-pyran-4-yl)prop-2-en-1-one (compound 294.1, 4.3 g, 23.4 mmol) in ethanol (20 mL) was added $NH_2NH_2 \cdot H_2O$ (1.41 g, 28.2 mmol). The reaction mixture was stirred for 3 h at 80° C. The resulting mixture was concentrated under reduced pressure to yield 4.45 g (crude) of the title compound as a light yellow solid.

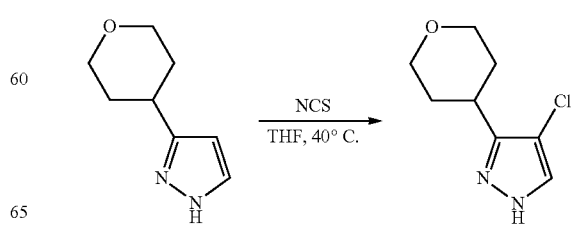

Compound 294.3. 4-Chloro-3-(tetrahydro-2H-pyran-4-yl)-1H-pyrazole

To a solution of 3-(tetrahydro-2H-pyran-4-yl)-1H-pyrazole (compound 294.2, 3.5 g, 23.0 mmol) in tetrahydrofuran (20 mL) was added NCS (3.4 g, 25.4 mmol). The reaction mixture was stirred overnight at 40° C. The resulting mixture was concentrated under reduced pressure. This resulted in 4.75 g (crude) of the title compound as a light yellow solid.

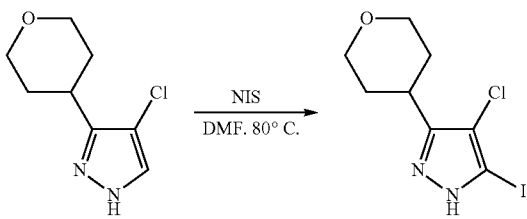

Compound 294.4. 4-Chloro-5-iodo-3-(tetrahydro-2H-pyran-4-yl)-1H-pyrazole

To a solution of 4-chloro-3-(tetrahydro-2H-pyran-4-yl)-1H-pyrazole (compound 294.3, 3.00 g, 16.1 mmol) in N,N-dimethylformamide (20 mL) was added NIS (7.26 g, 32.3 mmol). The reaction mixture was stirred overnight at 80° C. The reaction mixture was diluted with 50 mL $Na_2S_2O_3$ (sat.). The aqueous phase was extracted with 3×100 mL of ethyl acetate. The combined organic layers were dried over anhydrous sodium sulfate and concentrated under reduced pressure. The residue was purified by silica gel chromatography with ethyl acetate/petroleum ether (1/8-1/5) as the eluent to furnish 4.05 g (81%) of the title compound as a white solid.

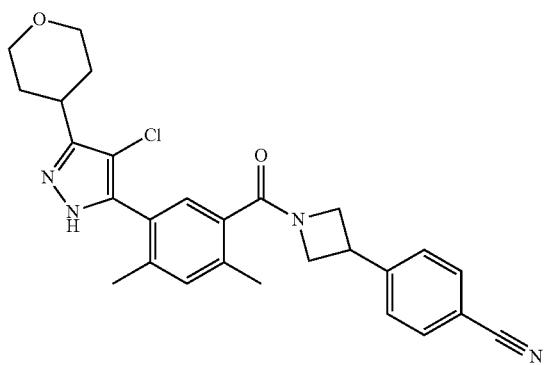

Compound 294. 4-(1-(5-(4-Chloro-3-(tetrahydro-2H-pyran-4-yl)-1H-pyrazol-5-yl)-2,4-dimethylbenzoyl)azetidin-3-yl)benzonitrile The title compound was prepared using standard chemical manipulations and procedures similar to those used for the preparation of compound 244, except 4-chloro-5-iodo-3-(tetrahydro-2H-pyran-4-yl)-1H-pyrazole (compound 294.4) was used instead of was used in place 4-methoxy-1H-pyrazole (compound 244.4) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 475 (M+H)⁺.

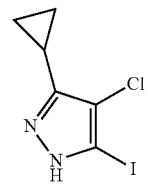

Compound 293.1. 4-Chloro-3-cyclopropyl-5-iodo-1H-pyrazole

The title compound was prepared using standard chemical manipulations and procedures similar to those used for the preparation of compound 294.4, except 1-cyclopropylethanone was used instead of 1-(tetrahydro-2H-pyran-4-yl)ethanone.

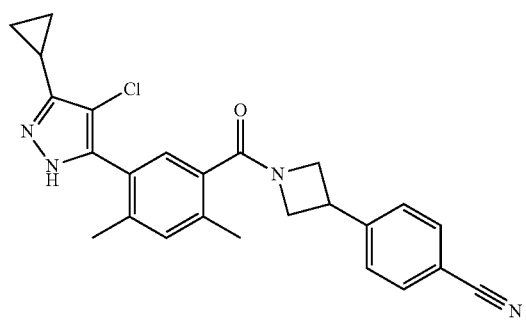 [SMILES: Cc1cc(C)c(-c2[nH]nc(C3CC3)c2Cl)cc1C(=O)N1CC(c2ccc(C#N)cc2)C1]

Compound 293. 4-(1-(5-(4-Chloro-3-cyclopropyl-1H-pyrazol-5-yl)-2,4-dimethylbenzoyl)azetidin-3-yl)benzonitrile The title compound was prepared using standard chemical manipulations and procedures similar to those used for the preparation of compound 294, except 4-chloro-3-cyclopropyl-5-iodo-1H-pyrazole (compound 293.1) was used instead of 4-chloro-5-iodo-3-(tetrahydro-2H-pyran-4-yl)-1H-pyrazole (compound 294.4). m/z (ES+) 431 (M+H)⁺.

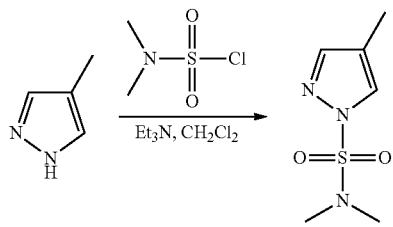

Compound 305.1. N,N,4-Trimethyl-1H-pyrazole-1-sulfonamide

Into a 500-mL round-bottom flask purged and maintained with an inert atmosphere of nitrogen, was placed a solution of 4-methyl-1H-pyrazole (10.4 g, 127.2 mmol) in $CH_2Cl_2$ (200 mL). N,N-dimethylsulfamoyl chloride (17.14 mL, 167.1 mmol) and triethylamine (35 mL, 251.1 mmol) were added to the reaction. The reaction mixture was stirred for 30 min at 0° C. in a water/ice bath and then stirred overnight at room temperature. The reaction was quenched with NaHCO$_3$ (sat.) (40 mL) and the aqueous phase was extracted with 3×200 mL of EtOAc. The combined organic phase was dried over anhydrous sodium sulfate and concentrated under reduced pressure. The residue was purified by silica gel chromatography with ethyl acetate/hexanes (1:6) as the eluent to afford the title compound (22.2 g, 92%) as a light yellow oil.

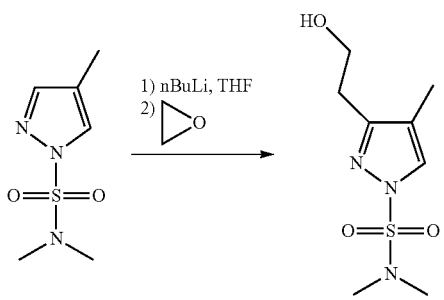

Compound 305.2. 3-(2-Hydroxyethyl)-N,N,4-trimethyl-1H-pyrazole-1-sulfonamide

Into a 50-mL three-neck round-bottom flask purged and maintained with an inert atmosphere of nitrogen, was placed a solution of N,N,4-trimethyl-1H-pyrazole-1-sulfonamide (compound 305.1, 1.19 g, 6.26 mmol) in THF (24 mL). n-BuLi (3 mL, 7.5 mmol, 2.5 M in hexanes) was added to the reaction dropwise at −78° C. The resulting mixture was stirred for 30 min at −78° C. This was followed by the addition of a solution of oxirane (5.6 mL, 113.51 mmol) in THF (4 mL) at −78° C. The reaction mixture was then brought to room temperature and stirred for 3 h. The reaction was quenched with 10 mL of NH$_4$Cl (sat.) and the aqueous phase was extracted with 3×50 mL of EtOAc. The combined organic layers were dried over Na$_2$SO$_4$. The solvent was removed to give the crude product which was purified by silica gel chromatography with hexanes/EtOAc (3:1) as the eluent to furnish 636 mg (44%) of the title compound as light yellow oil.

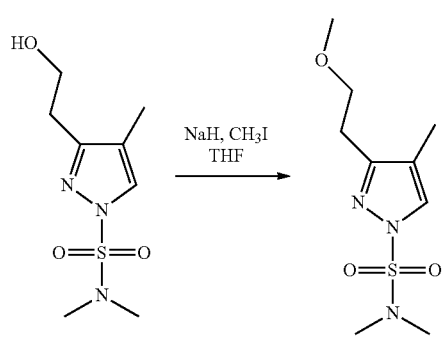 [SMILES: Cc1cn(S(=O)(=O)N(C)C)nc1CCO ; COCCc1nn(S(=O)(=O)N(C)C)cc1C]

Compound 305.3. 3-(2-Methoxyethyl)-N,N,4-trimethyl-1H-pyrazole-1-sulfonamide

Into a 50-mL round-bottom flask purged and maintained with an inert atmosphere of nitrogen, was placed a solution of 3-(2-hydroxyethyl)-N,N,4-trimethyl-1H-pyrazole-1-sulfonamide (compound 305.2, 636 mg, 2.73 mmol) in THF (10 mL). Sodium hydride (131 mg, 60% in mineral oil, 3.27 mmol) was added at 0° C. and stirred for 30 min at 0° C. This was followed by the addition of CH$_3$I (204 µL, 3.28 mmol). The reaction mixture was stirred for 3 h at room temperature. The reaction was quenched with 10 mL of NH$_4$Cl (sat.) and the aqueous phase was extracted with 3×50 mL of EtOAc. The combined organic phases were dried over Na$_2$SO$_4$. After filtration, the filtrate was concentrated under reduced pressure to give the crude product which was purified by silica gel chromatography with hexanes/EtOAc (15:1-8:1) as the eluent to give 452 mg (67%) of the title compound as a yellow oil.

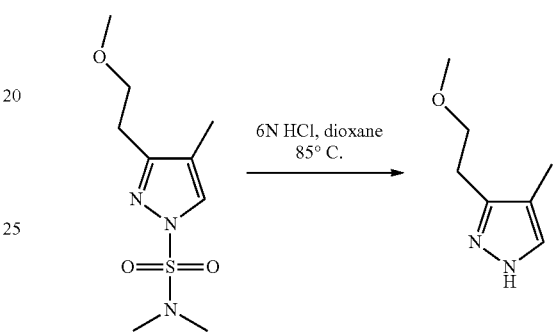

Compound 305.4.
3-(2-Methoxyethyl)-4-methyl-1H-pyrazole

Into a 50-mL round-bottom flask purged and maintained with an inert atmosphere of nitrogen, was placed a solution of 3-(2-methoxyethyl)-N,N,4-trimethyl-1H-pyrazole-1-sulfonamide (compound 305.3, 440 mg, 1.78 mmol) in dioxane (10 mL). HCl (10 mL, 6 M, 30 mmol) was added to the reaction mixture. The reaction mixture was stirred for 1 h at 85° C., then cooled to room temperature and carefully neutralized with NaHCO$_3$ aq (sat.) to pH-8. The aqueous phase was extracted with 3×50 mL of EtOAc and the combined organic layers were dried over Na$_2$SO$_4$. After filtration, the filtrate was concentrated under reduced pressure to give the crude product which was used in the next step without further purification.

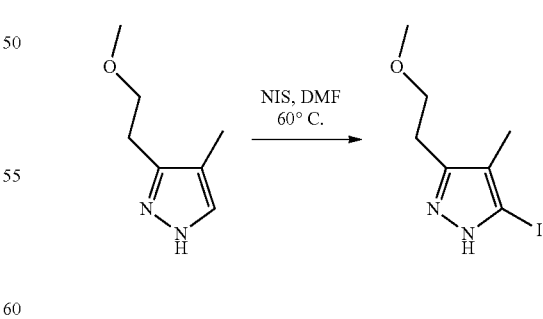

Compound 305.5.
5-Iodo-3-(2-methoxyethyl)-4-methyl-1H-pyrazole

Into a 50-mL round-bottom flask (1 atm) purged and maintained with an inert atmosphere of nitrogen, was placed a solution of 3-(2-methoxyethyl)-4-methyl-1H-pyrazole (compound 305.4, 249 mg, 1.78 mmol) in N,N-dimethylformamide (10 mL). NIS (482 mg, 2.14 mmol, 1.20 equiv) was added to the reaction. The reaction mixture was stirred for 2 h at 60° C., then cooled and quenched with 5 mL of NH₄Cl (sat.). The aqueous phase was extracted with 3×30 mL of EtOAc and the combined organic layers were dried over Na₂SO₄. After filtration, the filtrate was concentrated under reduced pressure to give the crude product which was purified by silica gel chromatography with hexanes/EtOAc (5:1) as the eluent to yield 328 mg (69% over two steps) of the title compound as a brown oil.

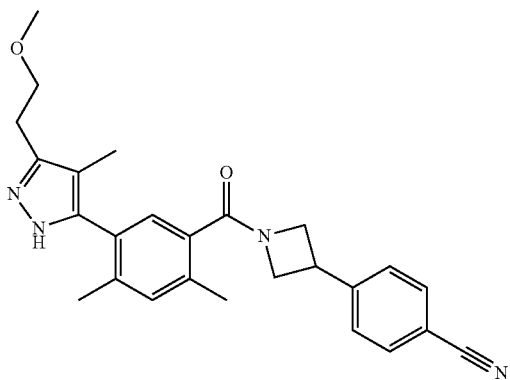 [SMILES: COCCc1n[nH]c(-c2cc(C(=O)N3CC(c4ccc(C#N)cc4)C3)c(C)cc2C)c1C]

Compound 305. 4-(1-(5-(3-(2-Methoxyethyl)-4-methyl-1H-pyrazol-5-yl)-2,4-dimethylbenzoyl)azetidin-3-yl)benzonitrile The title compound was prepared using standard chemical manipulations and procedures similar to those used for the preparation of compound 244, except 5-iodo-3-(2-methoxyethyl)-4-methyl-1H-pyrazole (compound 305.5) was used instead of 3-iodo-4-methoxy-1H-pyrazole (compound 244.5) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 429 (M+H)⁺.

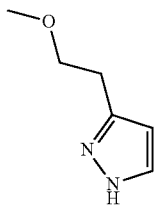

Compound 307.1. 3-(2-Methoxyethyl)-1H-pyrazole

The title compound was prepared using standard chemical manipulations and procedures similar to those used for the preparation of compound 305.4, except 1H-pyrazole was used instead of 4-methyl-1H-pyrazole.

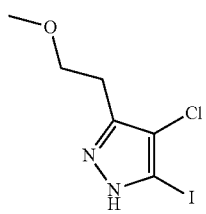

Compound 307.2. 4-Chloro-5-iodo-3-(2-methoxyethyl)-1H-pyrazole

The title compound was prepared using standard chemical manipulations and procedures similar to those used for the preparation of compound 294.4, except 3-(2-methoxyethyl)-1H-pyrazole (compound 307.1) was used instead of 3-(tetrahydro-2H-pyran-4-yl)-1H-pyrazole (compound 294.2).

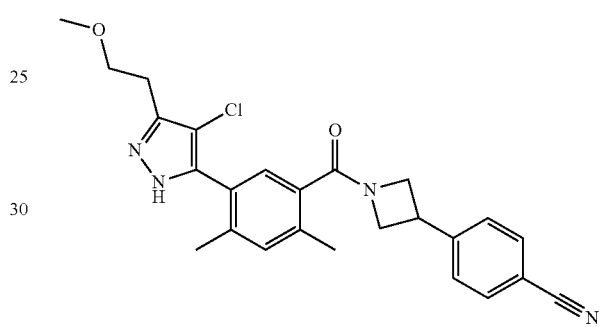

Compound 307. 4-(1-(5-(4-Chloro-3-(2-methoxyethyl)-1H-pyrazol-5-yl)-2,4-dimethylbenzoyl)azetidin-3-yl)benzonitrile The title compound was prepared using standard chemical manipulations and procedures similar to those used for the preparation of compound 244, except 4-chloro-5-iodo-3-(2-methoxyethyl)-1H-pyrazole (compound 307.2) was used instead of 3-iodo-4-methoxy-1H-pyrazole (compound 244.5) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 449 (M+H)⁺.

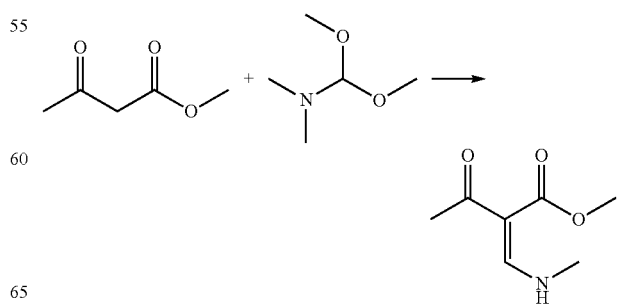

Compound 357.1. (Z)-Methyl 2-((dimethylamino)methylene)-3-oxobutanoate

Into a 250-mL round-bottom flask, was placed methyl 3-oxobutanoate (10.8 g, 92.6 mmol) and (dimethoxymethyl) dimethylamine (12.7 mL, 95.3 mmol). The resulting solution was stirred for 2.5 h at 80° C., then concentrated under reduced pressure to yield 14.5 g (crude) of the title compound as a red solid.

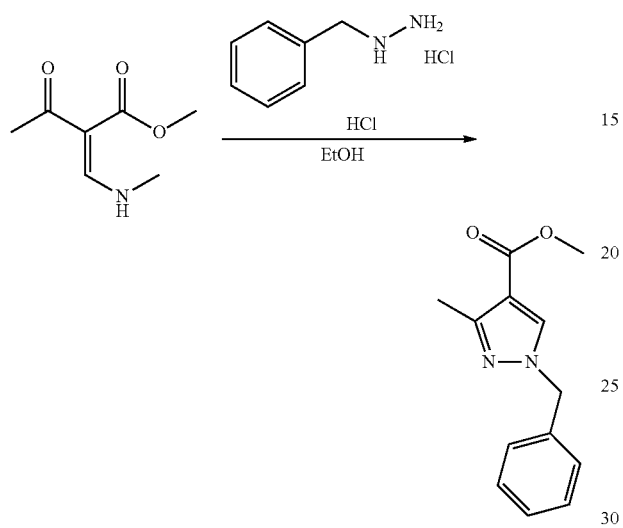

Compound 357.2. Methyl 1-benzyl-3-methyl-1H-pyrazole-4-carboxylate

To a solution of (Z)-methyl 2-((dimethylamino)methylene)-3-oxobutanoate (15.8 g, 92.5 mmol) in ethanol (50 mL) was added 1-benzylhydrazine dihydrochloride (18 g, 92.3 mmol). The resulting solution was stirred for 3.5 h at 80° C., then concentrated under reduced pressure. The residue was dissolved in 200 mL of ethyl acetate. The organic layer was washed with 1×40 mL of water and 2×40 mL of brine, dried over anhydrous sodium sulfate and concentrated under reduced pressure. The residue was purified by silica gel chromatography with ethyl acetate/petroleum ether (1:4) as the eluent to furnish 12.4 g (58%) of the title compound as a yellow solid.

Compound 357. 4-(1-(5-(4-(Methoxymethyl)-3-methyl-1H-pyrazol-5-yl)-2,4-dimethylbenzoyl)azetidin-3-yl)benzonitrile

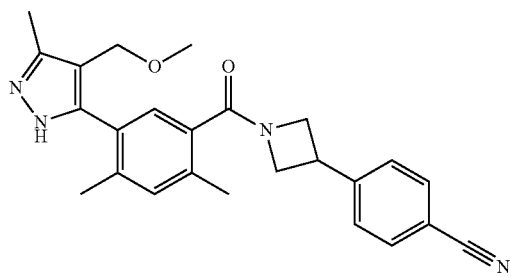 [SMILES: COCc1c(C)n[nH]c1-c1cc(C(=O)N2CC(c3ccc(C#N)cc3)C2)c(C)cc1C]

The title compound was prepared using standard chemical manipulations and procedures similar to those used for the preparation of compound 268, except methyl 1-benzyl-3-methyl-1H-pyrazole-4-carboxylate (compound 357.2) was used instead of ethyl 1-benzyl-4-methyl-1H-pyrazole-3-carboxylate (compound 268.1). m/z (ES+) 415 (M+H)$^+$.

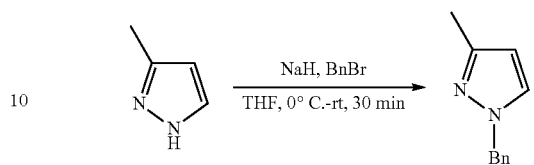

Compound 314.1. 1-Benzyl-3-methyl-1H-pyrazole

To a solution of 3-methyl-1H-pyrazole (5.00 g, 60.9 mmol) in tetrahydrofuran (30 mL) was added sodium hydride (60%) (4.88 g, 203 mmol) in portions at 0° C. and stirred for 30 min under nitrogen. To the above mixture was added benzyl bromide (8.7 mL, 73.1 mmol). The reaction mixture was stirred for 1 h at room temperature, then carefully quenched with 150 mL of water. The aqueous phase was extracted with 3×30 mL of EtOAc. The combined organic layers were dried over anhydrous sodium sulfate and concentrated under reduced pressure to afford 5.66 g (54%) of the title compound as light yellow oil.

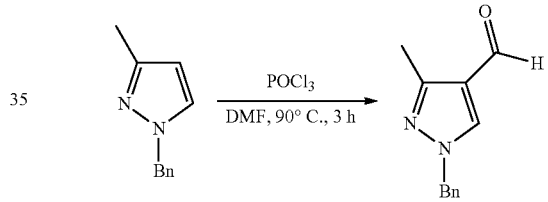

Compound 314.2. 1-Benzyl-3-methyl-1H-pyrazole-4-carbaldehyde

To a solution of 1-benzyl-3-methyl-1H-pyrazole (compound 314.1, 1.00 g, 5.81 mmol) in N,N-dimethylformamide (3 mL) was added POCl$_3$ (493 µL, 5.28 mmol) dropwise. The reaction mixture was stirred for 3 h at 90° C. under nitrogen. The reaction mixture was diluted with 50 mL of H$_2$O. The pH of the solution was adjusted to 7 with sodium hydroxide (2 M). The aqueous phase was extracted with 3×20 mL of ethyl acetate and the combined organic layers were dried over anhydrous sodium sulfate and concentrated under reduced pressure to yield 1.42 g (crude) of the title compound as a brown oil.

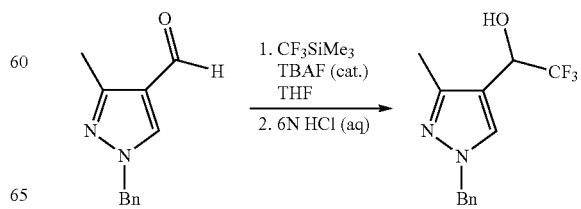

Compound 314.3. 1-(1-Benzyl-3-methyl-1H-pyrazol-4-yl)-2,2,2-trifluoroethanol To a solution of 1-benzyl-3-methyl-1H-pyrazole-4-carbaldehyde (compound 314.2, 1.20 g, 5.99 mmol) in tetrahydrofuran (15 mL) was added CF₃SiMe₃ (1.33 mL, 9.01 mmol) and TBAF (0.11 mL, 0.11 mmol, 1M solution in THF). The mixture was stirred for 10 min at room temperature under nitrogen. This was followed by the addition of aqueous HCl (6 M) (1 mL). The reaction mixture was stirred for another 10 min at room temperature, then diluted with 50 mL of H₂O. The aqueous phase was extracted with 3×20 mL of ethyl acetate and the combined organic layers were dried over anhydrous sodium sulfate and concentrated under reduced pressure. The residue was purified by silica gel chromatography with ethyl acetate/petroleum ether (1/5-1/2) as the eluent to furnish 1.15 g (71%) of the title compound as a light yellow solid.

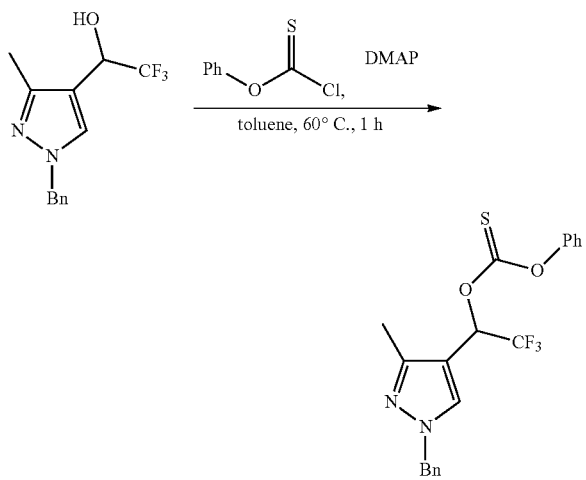

Compound 314.4. O-(1-(1-Benzyl-1H-pyrazol-4-yl)-2,2,2-trifluoroethyl)O-phenyl carbonothioate To a solution of 1-(1-benzyl-3-methyl-1H-pyrazol-4-yl)-2,2,2-trifluoroethanol (compound 314.3, 1.15 g, 4.26 mmol) in toluene (15 mL) were added 4-dimethylaminopyridine (1.47 g, 12.0 mmol) and phenyl chloromethanethioate (1.04 g, 6.02 mmol). The reaction mixture was stirred for 1 h at 60° C. under nitrogen, then concentrated under reduced pressure. The residue was purified by silica gel chromatography with ethyl acetate/petroleum ether (1/15) as the eluent to yield 1.34 g (77%) of the title compound as a light yellow oil.

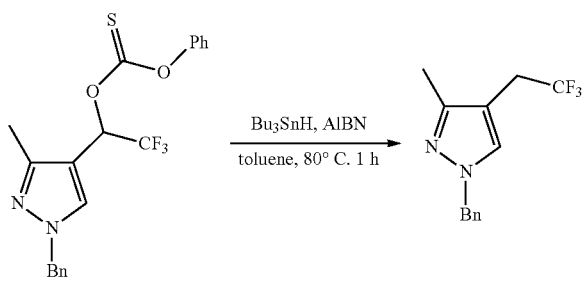

Compound 314.5. 1-Benzyl-3-methyl-4-(2,2,2-trifluoroethyl)-1H-pyrazole

To a solution of O-(1-(1-benzyl-1H-pyrazol-4-yl)-2,2,2-trifluoroethyl)O-phenyl carbonothioate (compound 314.4, 1.34 g, 3.30 mmol) in toluene (20 mL) was added Bn₃SnH (3.84 mL, 13.2 mmol), AIBN (320 mg, 1.95 mmol). The reaction mixture was stirred for 1 h at 80° C. under nitrogen, then concentrated under reduced pressure. The residue was purified by silica gel chromatography with ethyl acetate/petroleum ether (1:20) as the eluent to furnish 650 mg (78%) of the title compound as a colorless oil.

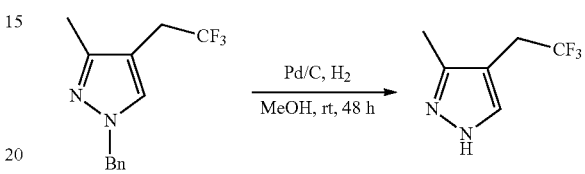

Compound 314.6. 3-Methyl-4-(2,2,2-trifluoroethyl)-1H-pyrazole

To a solution of 1-benzyl-3-methyl-4-(2,2,2-trifluoroethyl)-1H-pyrazole (compound 314.5, 700 mg, 2.75 mmol) in methanol (10 mL) was added palladium on carbon (700 mg, 10 wt. %) and HCl (4 M) (3 mL). The reaction mixture was hydrogenated for 48 h at room temperature under 1 atmosphere of hydrogen. The solids were removed via filtration. The filtrate was evaporated under reduced pressure and diluted with 50 mL of water. The pH of the solution was adjusted to 7 with NaOH (2 M). The aqueous phase was extracted with 5×20 mL of ethyl acetate and the combined organic layers were dried over anhydrous sodium sulfate and concentrated under reduced pressure to afford 230 mg (51%) of the title compound as a light yellow oil.

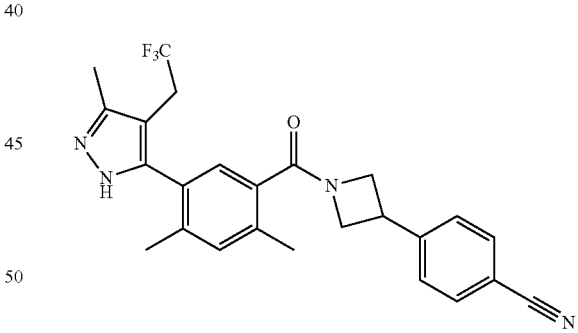

Compound 314. 4-(1-(2,4-Dimethyl-5-(3-methyl-4-(2,2,2-trifluoroethyl)-1H-pyrazol-5-yl)benzoyl)azetidin-3-yl)benzonitrile The title compound was prepared using standard chemical manipulations and procedures similar to those used for the preparation of compound 244, except 3-methyl-4-(2,2,2-trifluoroethyl)-1H-pyrazole (compound 314.6) was used instead of 4-methoxy-1H-pyrazole (compound 244.4) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 453 (M+H)⁺.

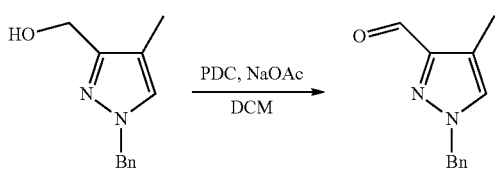

Compound 313.1.
1-Benzyl-4-methyl-1H-pyrazole-3-carbaldehyde

To a solution of (1-benzyl-4-methyl-1H-pyrazol-3-yl)methanol (compound 268.2, 3 g, 14.8 mmol) in dichloromethane (100 mL) was added PDC (11.3 g, 30.1 mmol), molecular sieves (3 g) and NaOAc (300 mg) were added to the reaction mixture. The reaction mixture was stirred for 4 h at room temperature. The solids were removed by filtration and the filtrate was concentrated under reduced pressure. The residue was purified by a silica gel chromatography with ethyl acetate/petroleum ether (1/10) as the eluent to yield 1 g (34%) of the title compound as a colorless oil.

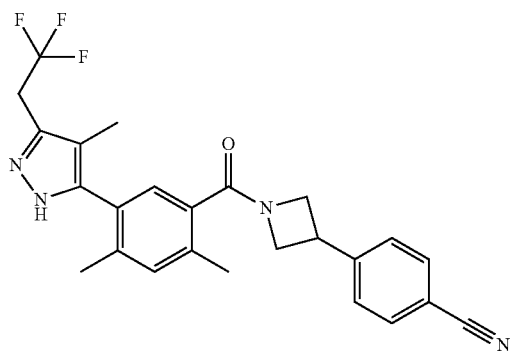 [SMILES: Cc1cc(C)c(-c2[nH]nc(CC(F)(F)F)c2C)cc1C(=O)N1CC(c2ccc(C#N)cc2)C1]

Compound 313. 4-(1-(2,4-Dimethyl-5-(4-methyl-3-(2,2,2-trifluoroethyl)-1H-pyrazol-5-yl)benzoyl)azetidin-3-yl)benzonitrile The title compound was prepared using standard chemical manipulations and procedures similar to those used for the preparation of compound 314, except 1-benzyl-4-methyl-1H-pyrazole-3-carbaldehyde (compound 313.1) was used instead of 1-benzyl-3-methyl-1H-pyrazole-4-carbaldehyde (compound 314.2). m/z (ES+) 453 (M+H)⁺.

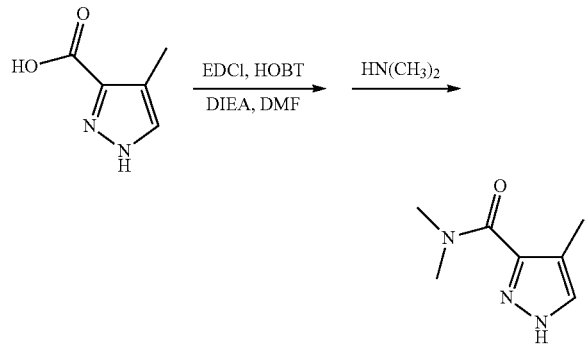

Compound 374.1.
N,N,4-Trimethyl-1H-pyrazole-3-carboxamide

To a mixture of 4-methyl-1H-pyrazole-3-carboxylic acid (1.00 g, 7.93 mmol), HOBT (1.07 g, 7.93 mmol) and EDCI (2.27 g, 11.89 mmol) in DMF (10 mL) was added DIEA (2.74 mL, 15.86 mmol). After the mixture was stirred at room temperature for 16 hours, dimethylamine (2M in THF, 11.89 mL, 23.79 mmol) was added. The mixture was stirred at room temperature for 3 hours, then partitioned between EtOAc (300 mL) and water (30 mL). The organics was washed with brine (3×30 mL) and the combined aqueous material was back extracted with EtOAc (2×50 mL). All organic extracts were combined, dried (MgSO₄), filtered and concentrated under reduced pressure. The residue was purified by silica gel column chromatography (5% MeOH in CH₂Cl₂) to obtain the title compound as a brown oil (1.1 g, 92%). m/z (ES+) 154 (M+H)⁺.

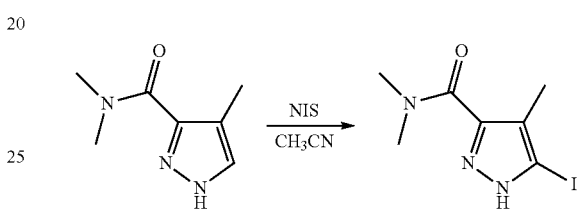

Compound 374.2.
5-Iodo-N,N,4-trimethyl-1H-pyrazole-3-carboxamide

To a solution of N,N,4-trimethyl-1H-pyrazole-3-carboxamide (compound 374.1, 0.98 g, 6.40 mmol) in CH₃CN (10 mL) was added NIS (1.59 g, 7.04 mmol). The mixture was stirred at room temperature for 16 hours then quenched with sat. Na₂SO₃ solution (5 mL). The mixture was partitioned between EtOAc (200 mL) and water (30 mL). The EtOAc layer was washed with brine (30 mL), dried (MgSO₄) and concentrated. The residue was purified with column chromatography (50% EtOAc in hexanes to 100% EtOAc) to give the product as a brown solid (1.79 g, 100%). m/z (ES+) 280 (M+H)⁺.

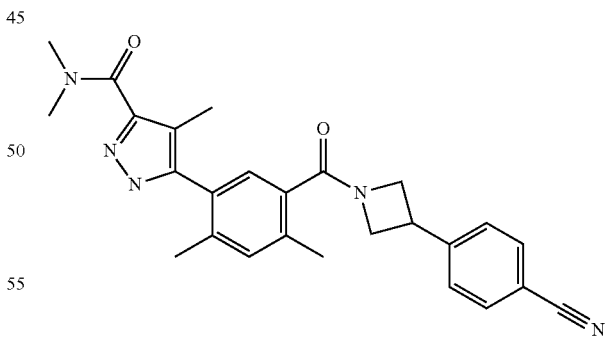

Compound 374. 5-(5-(3-(4-Cyanophenyl)azetidine-1-carbonyl)-2,4-dimethylphenyl)-N,N,4-trimethyl-1H-pyrazole-3-carboxamide The title compound was prepared using the standard chemical manipulations and procedures similar to those used for the preparation of compound 5, except 5-iodo-N,N,4-trimethyl-1H-pyrazole-3-carboxamide (compound 374.2)

was used instead of 5-iodo-2,4-dimethyl-1H-imidazole (compound 5.5) and methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4). m/z (ES+) 442 (M+H)+.

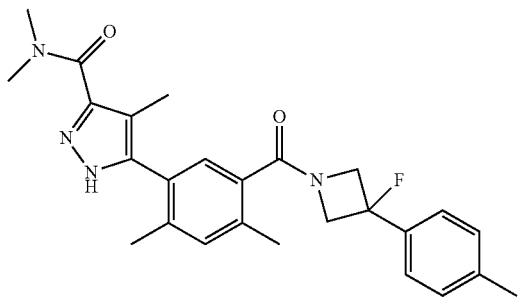

Compound 375. 5-(5-(3-Fluoro-3-(p-tolyl)azetidine-1-carbonyl)-2,4-dimethylphenyl)-N,N,4-trimethyl-1H-pyrazole-3-carboxamide The title compound was prepared using the standard chemical manipulations and procedures similar to those used for the preparation of compound 5, except 5-iodo-N,N,4-trimethyl-1H-pyrazole-3-carboxamide (compound 374.2) was used instead of 5-iodo-2,4-dimethyl-1H-imidazole (compound 5.5), methyl 2,4-dimethyl-5-(4,4,5,5-tetramethyl-1,3,2-dioxaborolan-2-yl)benzoate (compound 160.1) was used in place of methyl 4-methyl-3-(4,4,5,5-tetramethyl-1,3,2-dioxaborolan-2-yl)benzoate (compound 5.4) and 4-(3-fluoroazetidin-3-yl)benzonitrile hydrochloride (compound 43.4) was used in place of 4-(azetidin-3-yl)benzonitrile hydrochloride (compound 5.2). m/z (ES+) 460 (M+H)+.

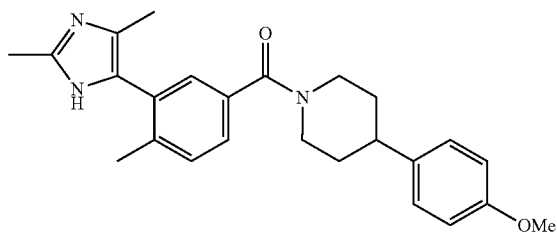 [SMILES: COc1ccc(C2CCN(C(=O)c3ccc(C)c(-c4[nH]c(C)nc4C)c3)CC2)cc1]

Compound 329. (3-(2,4-Dimethyl-1H-imidazol-5-yl)-4-methylphenyl)(4-(4-methoxyphenyl)piperidin-1-yl)methanone The title compound was prepared using the standard chemical manipulations and procedures similar to those used for the preparation of compound 5, except 4-(4-methoxyphenyl)piperidine hydrochloric acid salt was used instead of 4-(azetidin-3-yl)benzonitrile hydrochloride (compound 5.2). m/z (ES+) 404 (M+H)+.

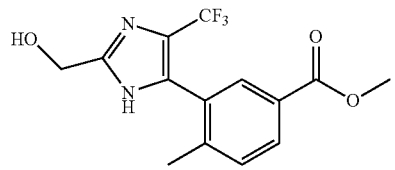 [SMILES: COC(=O)c1ccc(C)c(-c2[nH]c(CO)nc2C(F)(F)F)c1]

Compound 284.1. Methyl 3-(2-(hydroxymethyl)-4-(trifluoromethyl)-1H-imidazol-5-yl)-4-methylbenzoate The title compound was prepared using standard chemical manipulations and procedures similar to those used for the preparation of compound 219.4, except methyl 4-methyl-3-(4,4,5,5-tetramethyl-1,3,2-dioxaborolan-2-yl)benzoate (compound 5.4) was used instead of methyl 2,4-dimethyl-5-(4,4,5,5-tetramethyl-1,3,2-dioxaborolan-2-yl)benzoate (compound 160.1).

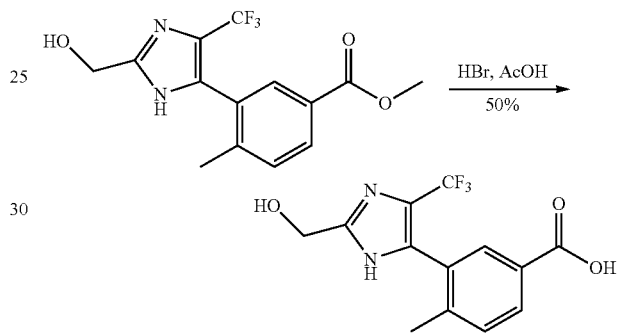

Compound 284.2. 3-(2-(Hydroxymethyl)-4-(trifluoromethyl)-1H-imidazol-5-yl)-4-methylbenzoic acid Into a 100-mL round-bottom flask, was placed methyl 3-(2-(hydroxymethyl)-4-(trifluoromethyl)-1H-imidazol-5-yl)-4-methylbenzoate (compound 284.1, 2 g, 6.36 mmol), HBr (40% in AcOH) (50 mL). The reaction mixture was stirred for 12 h at 80° C. The crude product (100 mL) was purified by Flash-Prep-HPLC with the following conditions (IntelFlash-1): mobile phase, CH3CN:H2O=1:1; Detector, UV 254 nm to yield 1 g (52%) of the title compound as a light yellow solid.

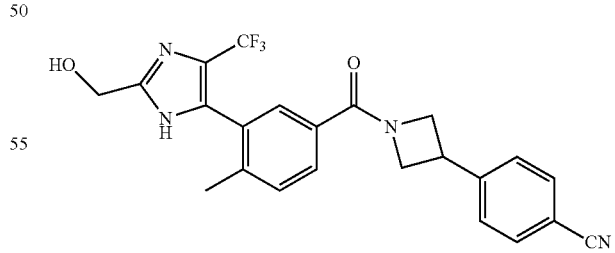

Compound 284. 4-(1-(3-(2-(Hydroxymethyl)-4-(trifluoromethyl)-1H-imidazol-5-yl)-4-methylbenzoyl)azetidin-3-yl)benzonitrile The title compound was prepared using standard chemical manipulations and procedures similar to those used for the preparation of compound 5, except 3-(2-(hydroxymethyl)-4-(trifluoromethyl)-1H-imidazol-5-yl)-4-methylbenzoic acid (compound 284.2) was used in place of 3-(2,4-dimethyl-1H-imidazol-5-yl)-4-methylbenzoic acid (compound 5.7). m z (ES+) 441 (M+H)⁺.

The compounds in TABLE 15 were prepared using standard chemical manipulations and procedures similar to those used for the preparation of compound 284.

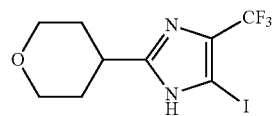

TABLE 15

| Cpd | Name | Structure | m/z (ES+) (M + H)⁺ |
|---|---|---|---|
| 285 | 4-(3-fluoro-1-(3-(2-(hydroxymethyl)-4-(trifluoromethyl)-1H-imidazol-5-yl)-4-methylbenzoyl)azetidin-3-yl)benzonitrile | 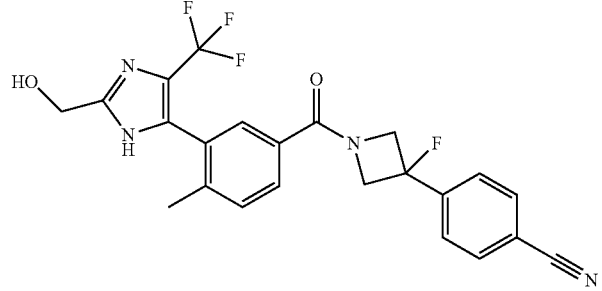 [SMILES: Cc1ccc(C(=O)N2CC(F)(c3ccc(C#N)cc3)C2)cc1-c1[nH]c(CO)nc1C(F)(F)F] | 459 |
| 352 | 4-(1-(3-(2-(2-hydroxyethyl)-4-(trifluoromethyl)-1H-imidazol-5-yl)-4-methylbenzoyl)azetidin-3-yl)benzonitrile | 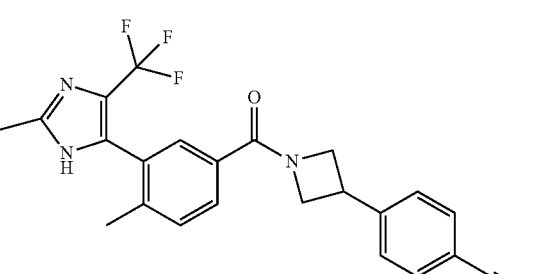 | 455 |
| 362 | 4-(1-(3-(2-(2-methoxyethyl)-4-(trifluoromethyl)-1H-imidazol-5-yl)-4-methylbenzoyl)azetidin-3-yl)benzonitrile | 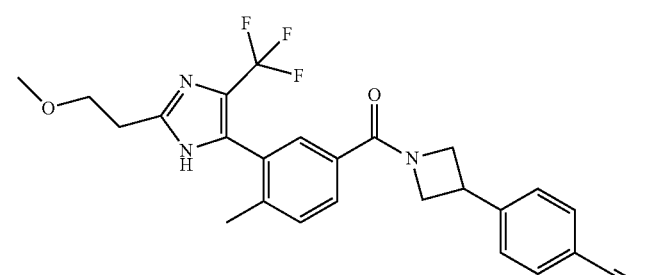 | 468 |
| 360 | 4-(1-(3-(2-(methoxymethyl)-4-(trifluoromethyl)-1H-imidazol-5-yl)-4-methylbenzoyl)azetidin-3-yl)benzonitrile | 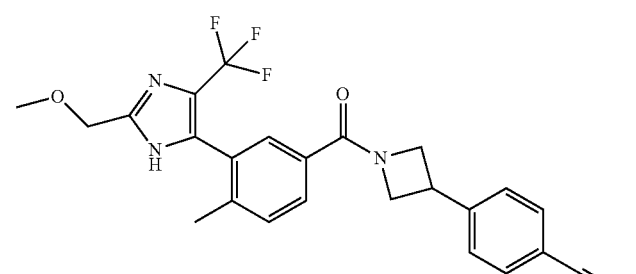 | 455 |

Compound 287.1. 5-Iodo-2-(tetrahydro-2H-pyran-4-yl)-4-(trifluoromethyl)-1H-imidazole The title compound was prepared using standard chemical manipulations and procedures similar to those used for the preparation of compound 202.2, except tetrahydro-2H-pyran-4-carbaldehyde was used instead of 3-methlyoxetane-3-carbaldehyde.

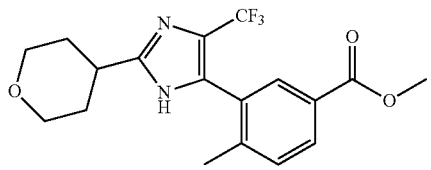 [SMILES: COC(=O)c1ccc(C)c(-c2[nH]c(C3CCOCC3)nc2C(F)(F)F)c1]

Compound 287.2. Methyl 4-methyl-3-(2-(tetrahydro-2H-pyran-4-yl)-4-(trifluoromethyl)-1H-imidazol-5-yl)benzoate The title compound was prepared using standard chemical manipulations and procedures similar to those used for the preparation of compound 202.4, except 5-iodo-2-(tetrahydro-2H-pyran-4-yl)-4-(trifluoromethyl)-1H-imidazole (compound 287.1) was used instead of 5-iodo-2-(3-methyl-oxetan-3-yl)-1H-imidazole-4-carbonitrile (compound 202.3).

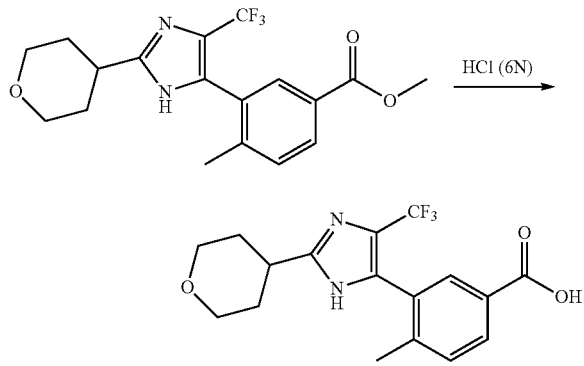

Compound 287.3. 4-Methyl-3-(2-(tetrahydro-2H-pyran-4-yl)-4-(trifluoromethyl)-1H-imidazol-5-yl)benzoic acid A solution of methyl 4-methyl-3-(2-(tetrahydro-2H-pyran-4-yl)-4-(trifluoromethyl)-1H-imidazol-5-yl)benzoate (compound 287.2, 50 mg, 0.14 mmol) in HCl (6 M) (2 mL) was stirred for 5 h at 80° C., then concentrated under reduced pressure. This resulted 200 mg (crude) of the title compound as a brown solid which was used in the next step without further purification.

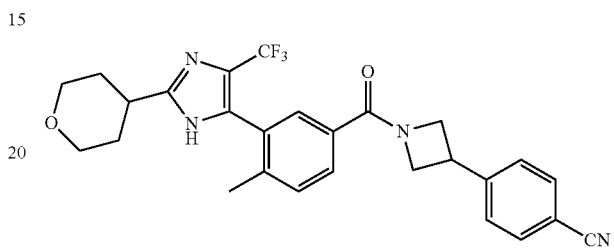

Compound 287. 4-(1-(4-Methyl-3-(2-(tetrahydro-2H-pyran-4-yl)-4-(trifluoromethyl)-1H-imidazol-5-yl)benzoyl)azetidin-3-yl)benzonitrile The title compound was prepared using standard chemical manipulations and procedures similar to those used for the preparation of compound 202, except 4-methyl-3-(2-(tetrahydro-2H-pyran-4-yl)-4-(trifluoromethyl)-1H-imidazol-5-yl)benzoic acid (compound 287.3) was used instead of 3-(4-cyano-2-(3-methyloxetan-3-yl)-1H-imidazol-5-yl)-4-methylbenzoic acid (compound 202.5). m/z (ES+) 495 (M+H)$^+$.

The compounds in TABLE 16 were prepared using standard chemical manipulations and procedures similar to those used for the preparation of compounds 287 and 202.

TABLE 16

| Cpd | Name | Structure | m/z (ES+) (M + H)$^+$ |
|---|---|---|---|
| 288 | 4-(1-(4-methyl-3-(2-(4-methyltetrahydro-2H-pyran-4-yl)-4-(trifluoromethyl)-1H-imidazol-5-yl)benzoyl)azetidin-3-yl)benzonitrile | 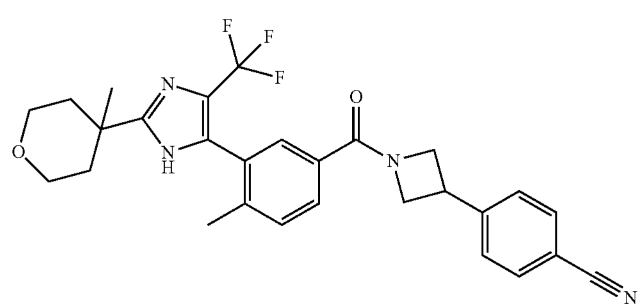 [SMILES: Cc1ccc(C(=O)N2CC(c3ccc(C#N)cc3)C2)cc1-c1[nH]c(C2(C)CCOCC2)nc1C(F)(F)F] | 509 |

TABLE 16-continued

| Cpd | Name | Structure | m/z (ES+) (M + H)+ |
|---|---|---|---|
| 290 | 4-(1-(4-methyl-3-(2-(1-methylpiperidin-4-yl)-4-(trifluoromethyl)-1H-imidazol-5-yl)benzoyl)azetidin-3-yl)benzonitrile | 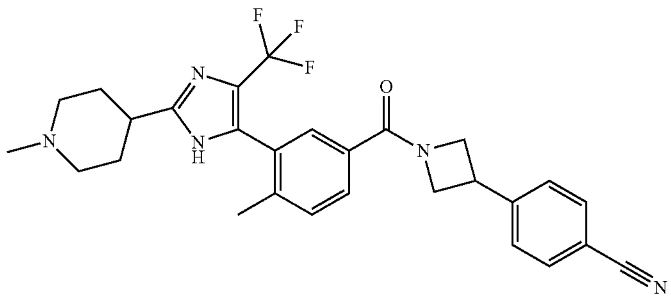 [SMILES: Cc1ccc(C(=O)N2CC(c3ccc(C#N)cc3)C2)cc1-c1[nH]c(C2CCN(C)CC2)nc1C(F)(F)F] | 508 |
| 291 | methyl 4-(5-(5-(3-(4-cyanophenyl)azetidine-1-carbonyl)-2-methylphenyl)-4-(trifluoromethyl)-1H-imidazol-2-yl)piperidine-1-carboxylate | 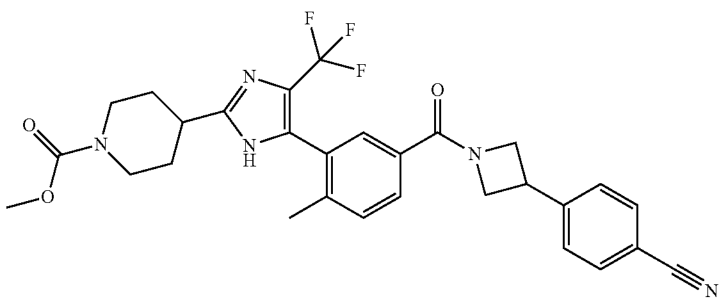 [SMILES: COC(=O)N1CCC(c2nc(C(F)(F)F)c(-c3cc(C(=O)N4CC(c5ccc(C#N)cc5)C4)ccc3C)[nH]2)CC1] | 552 |
| 292 | 4-(1-(4-methyl-3-(2-(1-methylpyrrolidin-3-yl)-4-(trifluoromethyl)-1H-imidazol-5-yl)benzoyl)azetidin-3-yl)benzonitrile | 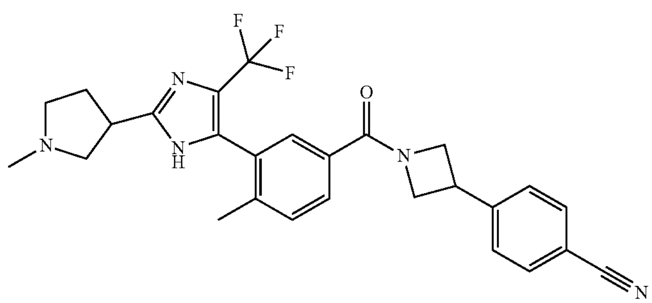 [SMILES: Cc1ccc(C(=O)N2CC(c3ccc(C#N)cc3)C2)cc1-c1[nH]c(C2CCN(C)C2)nc1C(F)(F)F] | 494 |
| 289 | 4-(1-(4-methyl-3-(2-(3-methyloxetan-3-yl)-4-(trifluoromethyl)-1H-imidazol-5-yl)benzoyl)azetidin-3-yl)benzonitrile | 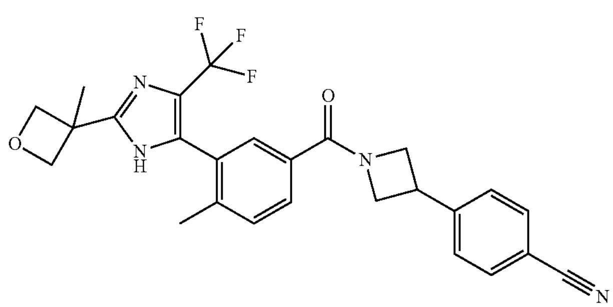 [SMILES: Cc1ccc(C(=O)N2CC(c3ccc(C#N)cc3)C2)cc1-c1[nH]c(C2(C)COC2)nc1C(F)(F)F] | 481 |

The compounds in TABLE 17 were prepared using standard chemical manipulations and procedures similar to those used for the preparation of compounds 230 and 231.

TABLE 17

| Cpd | Name | Structure | m/z (ES+) (M + H)+ |
|---|---|---|---|
| 353 | 4-(1-(3-(4-chloro-2-(2-hydroxyethyl)-1H-imidazol-5-yl)-4-methylbenzoyl)azetidin-3-yl)benzonitrile | 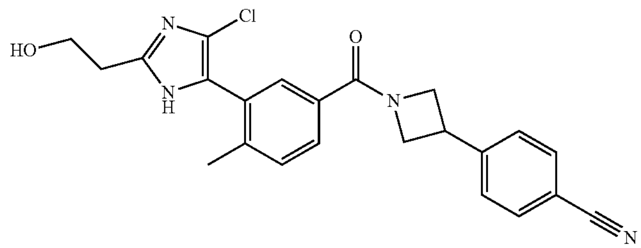 [SMILES: Cc1ccc(C(=O)N2CC(c3ccc(C#N)cc3)C2)cc1-c1[nH]c(CCO)nc1Cl] | 421 |
| 354 | 4-(1-(3-(4-chloro-2-(2-hydroxyethyl)-1H-imidazol-5-yl)-4-methylbenzoyl)-3-fluoroazetidin-3-yl)benzonitrile | 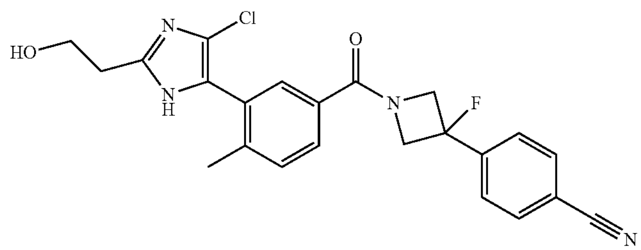 [SMILES: Cc1ccc(C(=O)N2CC(F)(c3ccc(C#N)cc3)C2)cc1-c1[nH]c(CCO)nc1Cl] | 439 |
| 359 | 4-(1-(3-(4-chloro-2-(methoxymethyl)-1H-imidazol-5-yl)-4-methylbenzoyl)azetidin-3-yl)benzonitrile | 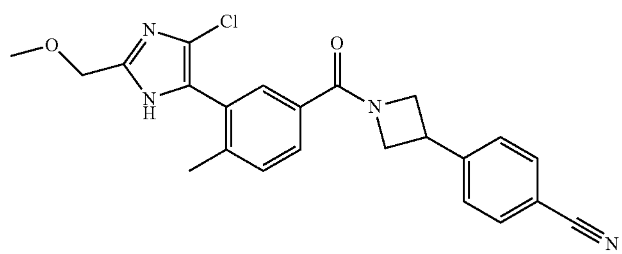 [SMILES: COCc1nc(Cl)c(-c2cc(C(=O)N3CC(c4ccc(C#N)cc4)C3)ccc2C)[nH]1] | 421 |
| 361 | 4-(1-(3-(4-chloro-2-(2-methoxyethyl)-1H-imidazol-5-yl)-4-methylbenzoyl)azetidin-3-yl)benzonitrile | 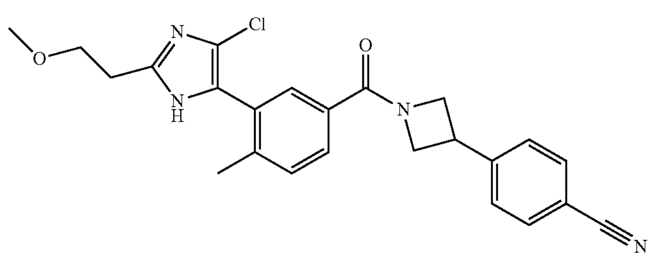 [SMILES: COCCc1nc(Cl)c(-c2cc(C(=O)N3CC(c4ccc(C#N)cc4)C3)ccc2C)[nH]1] | 435 |

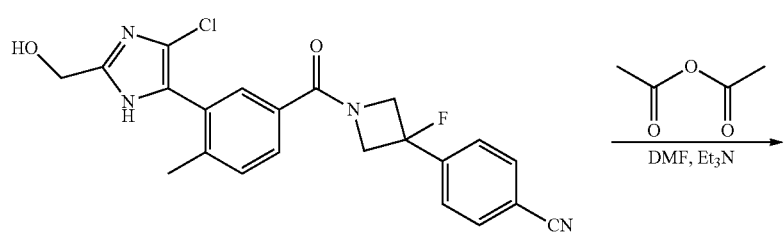

-continued

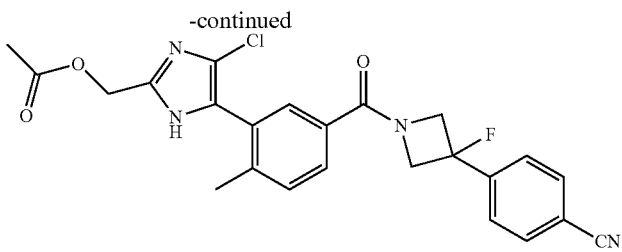

Compound 283. (4-Chloro-5-(5-(3-(4-cyanophenyl)-3-fluoroazetidine-1-carbonyl)-2-methylphenyl)-1H-imidazol-2-yl)methyl acetate Into a 50-mL round-bottom flask, was placed a solution of 4-(1-(3-(4-chloro-2-(hydroxymethyl)-1H-imidazol-5-yl)-4-methylbenzoyl)piperidin-4-yl)benzonitrile (compound 29, 40 mg, 0.09 mmol) in N,N-dimethylformamide (3 mL). Triethylamine (14 μL, 0.10 mmol) was added to the reaction at 0° C., followed by acetic anhydride (10 μL, 0.10 mmol). The reaction mixture was stirred for 2 h at room temperature, then diluted with 10 mL of ethyl acetate. The organic layer was washed with 3×5 mL of brine, dried over anhydrous sodium sulfate and concentrated under reduced pressure. The crude product (35 mg) was purified by Prep-HPLC with the following conditions (Prep-HPLC-020): Column, SunFire Prep C18 OBD Column, 5 um, 19*100 mm; mobile phase, WATER WITH 0.05% TFA and MeCN (10% MeCN up to 70% in 6 min, up to 95% in 1 min, down to 10% in 1 min); Detector, Waters 2489 254 & 220 nm. This resulted in 15 mg (34%) of the title compound as a white solid. m/z (ES+) 467 (M+H)+.

The compounds in TABLE 18 were prepared using standard chemical manipulations and procedures similar to those used for the preparation of compounds 185, 192 and 194.

TABLE 18

| Cpd | Name | Structure | m/z (ES+) (M + H)+ |
|---|---|---|---|
| 344 | methyl 4-(5-(5-(3-(4-cyanophenyl)azetidine-1-carbonyl)-2-methylphenyl)-4-methyl-1H-imidazol-2-yl)-4-hydroxypiperidine-1-carboxylate | 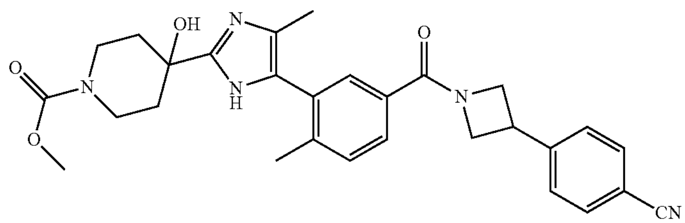 [SMILES: COC(=O)N1CCC(O)(c2nc(C)c(-c3cc(C(=O)N4CC(c5ccc(C#N)cc5)C4)ccc3C)[nH]2)CC1] | 514 |
| 345 | methyl 4-(5-(5-(3-(4-cyanophenyl)azetidine-1-carbonyl)-2-methylphenyl)-4-methyl-1H-imidazol-2-yl)-4-methoxypiperidine-1-carboxylate | 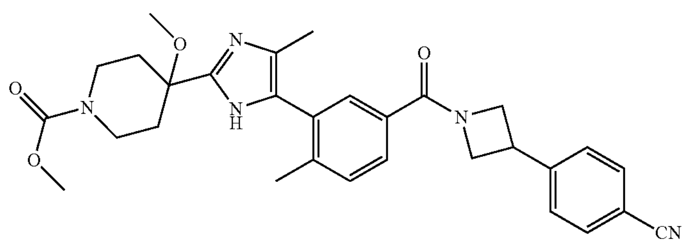 [SMILES: COC(=O)N1CCC(OC)(c2nc(C)c(-c3cc(C(=O)N4CC(c5ccc(C#N)cc5)C4)ccc3C)[nH]2)CC1] | 528 |

The compounds in TABLE 19 were prepared using standard chemical manipulations and procedures similar to those used for the preparation of compounds 185 and 241.

TABLE 19

| Cpd | Name | Structure | m/z (ES+) (M + H)+ |
|---|---|---|---|
| 346 | 4-(1-(3-(4-chloro-2-(4-methyltetrahydro-2H-pyran-4-yl)-1H-imidazol-5-yl)-4-methylbenzoyl)azetidin-3-yl)benzonitrile | 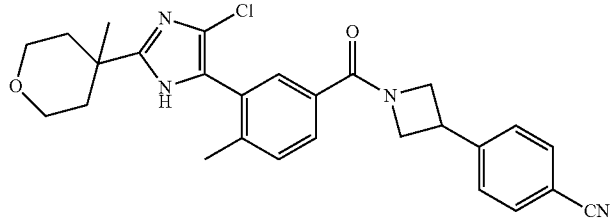 | 475 |

TABLE 19-continued

| Cpd | Name | Structure | m/z (ES+) (M + H)+ |
|---|---|---|---|
| 347 | 4-(1-(3-(4-chloro-2-(4-methyltetrahydro-2H-pyran-4-yl)-1H-imidazol-5-yl)-4-methylbenzoyl)-3-fluoroazetidin-3-yl)benzonitrile | 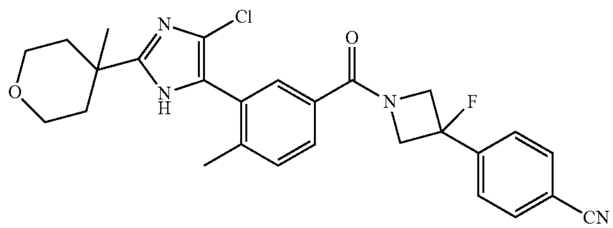 | 494 |
| 348 | methyl 4-(4-chloro-5-(5-(3-(4-cyanophenyl)azetidine-1-carbonyl)-2-methylphenyl)-1H-imidazol-2-yl)-4-methylpiperidine-1-carboxylate | 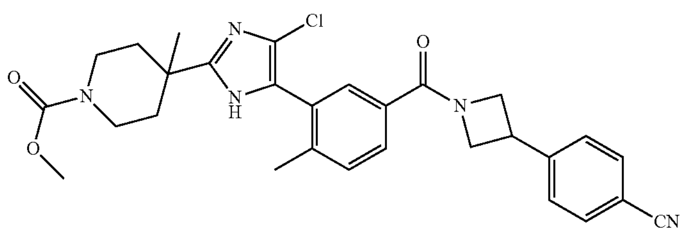 [SMILES: COC(=O)N1CCC(C)(c2nc(Cl)c(-c3cc(C(=O)N4CC(c5ccc(C#N)cc5)C4)ccc3C)[nH]2)CC1] | 532 |

The compounds in TABLE 20 were prepared using standard chemical manipulations and procedures similar to those used for the preparation of compound 14.

TABLE 20

| Cpd | Name | Structure | m/z (ES+) (M + H)+ |
|---|---|---|---|
| 358 | 4-(3-fluoro-1-(4-methyl-3-(4-methyl-2-(trifluoromethyl)-1H-imidazol-5-yl)benzoyl)azetidin-3-yl)benzonitrile | 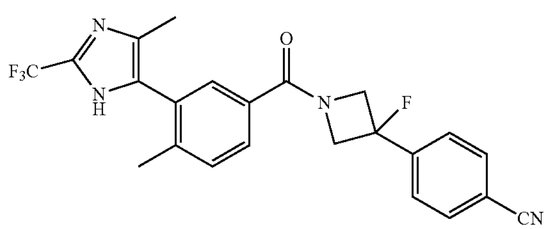 [SMILES: Cc1ccc(C(=O)N2CC(F)(c3ccc(C#N)cc3)C2)cc1-c1[nH]c(C(F)(F)F)nc1C] | 443 |
| 366 | 4-(1-(2,4-dimethyl-5-(4-methyl-2-(trifluoromethyl)-1H-imidazol-5-yl)benzoyl)azetidin-3-yl)benzonitrile | 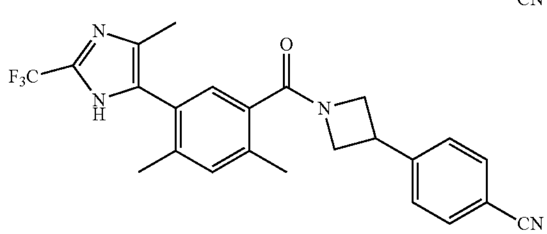 | 439 |
| 367 | 4-(1-(2,4-dimethyl-5-(4-methyl-2-(trifluoromethyl)-1H-imidazol-5-yl)benzoyl)-3-fluoroazetidin-3-yl)benzonitrile | 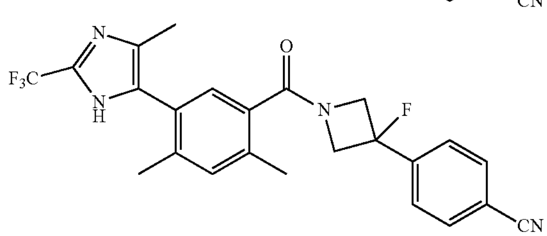 | 457 |

TABLE 20-continued

| Cpd | Name | Structure | m/z (ES+) (M + H)+ |
|---|---|---|---|
| 363 | 4-(1-(3-(4-ethyl-2-(trifluoromethyl)-1H-imidazol-5-yl)-4-methylbenzoyl)azetidin-3-yl)benzonitrile | 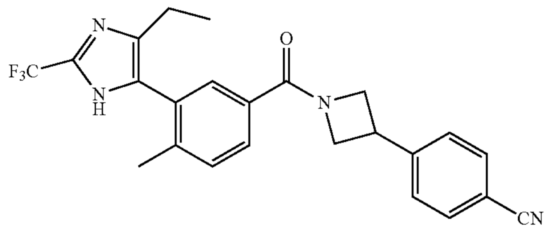 [SMILES: CCc1nc(C(F)(F)F)[nH]c1-c1cc(C(=O)N2CC(c3ccc(C#N)cc3)C2)ccc1C] | 439 |
| 364 | 4-(1-(3-(4-(methoxymethyl)-2-(trifluoromethyl)-1H-imidazol-5-yl)-4-methylbenzoyl)azetidin-3-yl)benzonitrile | 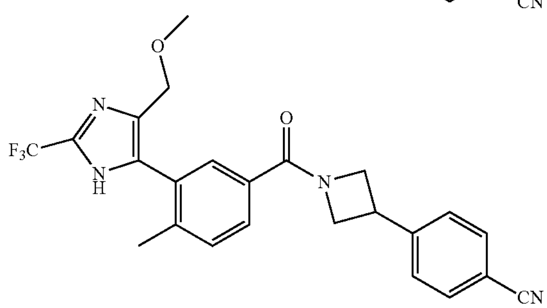 | 455 |
| 365 | 4-(1-(3-(4-cyclopropyl-2-(trifluoromethyl)-1H-imidazol-5-yl)-4-methylbenzoyl)azetidin-3-yl)benzonitrile | 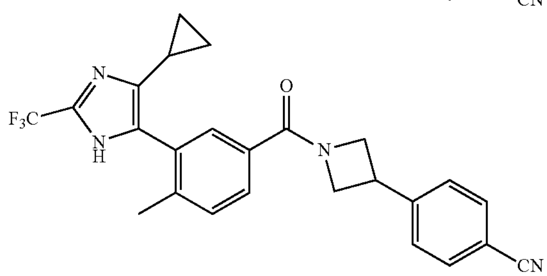 | 451 |

The compounds in TABLE 21 were prepared using standard chemical manipulations and procedures similar to those used for the preparation of compound 218.

TABLE 21

| Cpd | Name | Structure | m/z (ES+) (M + H)+ |
|---|---|---|---|
| 368 | 4-(3-fluoro-1-(4-methyl-3-(2-methyl-4-(trifluoromethyl)-1H-imidazol-5-yl)benzoyl)azetidin-3-yl)benzonitrile | 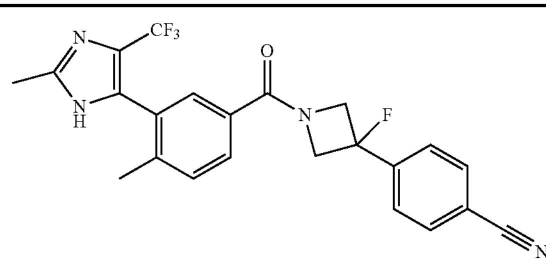 | 443 |
| 369 | 4-(1-(2,4-dimethyl-5-(2-methyl-4-(trifluoromethyl)-1H-imidazol-5-yl)benzoyl)azetidin-3-yl)benzonitrile | 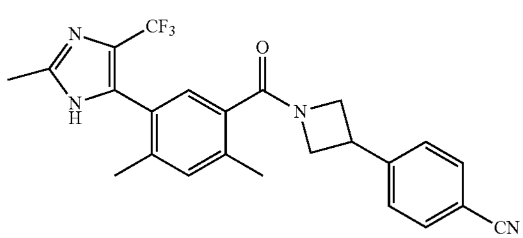 [SMILES: Cc1nc(C(F)(F)F)c(-c2cc(C(=O)N3CC(c4ccc(C#N)cc4)C3)c(C)cc2C)[nH]1] | 439 |

TABLE 21-continued

| Cpd | Name | Structure | m/z (ES+) (M + H)+ |
|---|---|---|---|
| 370 | 4-(1-(2,4-dimethyl-5-(2-methyl-4-(trifluoromethyl)-1H-imidazol-5-yl)benzoyl)-3-fluoroazetidin-3-yl)benzonitrile | 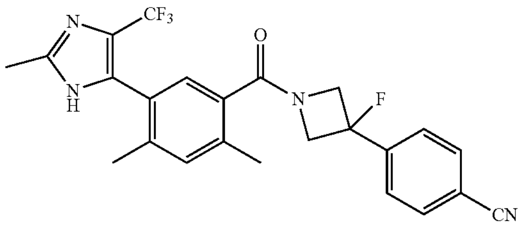 [SMILES: Cc1nc(C(F)(F)F)c(-c2cc(C(=O)N3CC(F)(c4ccc(C#N)cc4)C3)c(C)cc2C)[nH]1] | 457 |

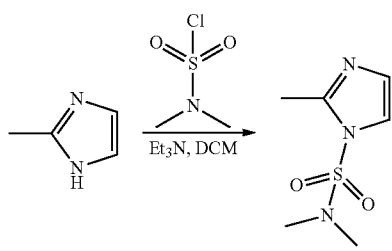

Compound 282.1.
N,N,2-Trimethyl-1H-imidazole-1-sulfonamide

To a solution of 2-methyl-1H-imidazole (10 g, 121.8 mmol) in dichloromethane (100 mL) was added N,N-dimethylsulfamoyl chloride (14.4 mL, 133.7 mmol) and triethylamine (34 mL, 244.1 mmol). The reaction mixture was stirred overnight at room temperature, then quenched with 10 mL of water and extracted with 1×50 mL of DCM. The organic layer was washed with 2×20 mL of brine, dried over anhydrous sodium sulfate and concentrated under reduced pressure. The residue was purified by silica gel chromatography with ethyl acetate/petroleum ether (1:2) as the eluent to furnish 20 g (87%) of the title compound as a yellow oil.

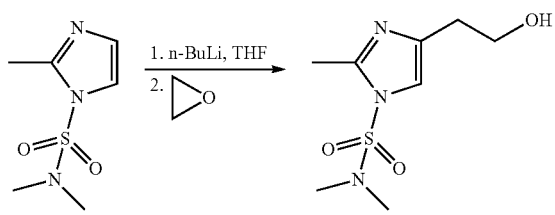

Compound 282.2. 4-(2-Hydroxyethyl)-N,N,2-trimethyl-1H-imidazole-1-sulfonamide

Into a 250-mL three neck round-bottom flask, which was purged and maintained with an inert atmosphere of nitrogen, was placed a solution of N,N,2-trimethyl-1H-imidazole-1-sulfonamide (compound 282.1, 6.4 g, 33.8 mmol) in tetrahydrofuran (50 mL). This was followed by the addition of n-BuLi (2.5M in hexane) (16.3 mL, 40.6 mmol) dropwise with stirring at −78° C. The reaction mixture was stirred for 1 h at −78° C. Oxirane (12.1 mL, 242.89 mmol) was added dropwise at −30° C. The reaction mixture was stirred for 2 h at room temperature, then quenched with 10 mL of water.

The aqueous phase was extracted with 3×30 mL of ethyl acetate. The combined organic layers were washed with 3×20 mL of brine, dried over anhydrous sodium sulfate and concentrated under reduced pressure. The residue was purified by silica gel chromatography with EtOAc:MeOH (40:1) as the eluent to yield 3.4 g (43%) of the title compound as a white solid.

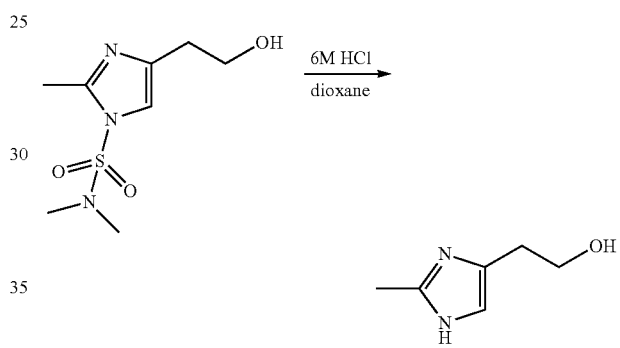

Compound 282.3.
2-(2-Methyl-1H-imidazol-4-yl)ethanol

To a solution of 4-(2-hydroxyethyl)-N,N,2-trimethyl-1H-imidazole-1-sulfonamide (compound 282.2, 1 g, 4.29 mmol) in 1,4-dioxane (30 mL) was added HCl (6 M, 30 mL). The reaction mixture was stirred for 4 h at 85° C., then concentrated under reduced pressure. The pH of the solution was adjusted to 7-8 with NaHCO₃ (sat.). The resulting mixture was concentrated under reduced pressure to afford 3 g (crude) of the title compound as a white solid.

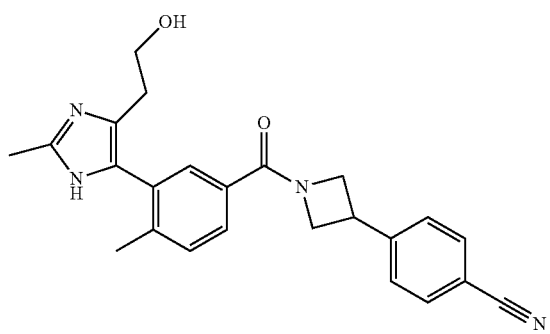 [SMILES: Cc1nc(CCO)c(-c2cc(C(=O)N3CC(c4ccc(C#N)cc4)C3)ccc2C)[nH]1]

Compound 282. 4-(1-(3-(4-(2-Hydroxyethyl)-2-methyl-1H-imidazol-5-yl)-4-methylbenzoyl)azetidin-3-yl)benzonitrile The title compound was prepared using standard chemical manipulations and procedures similar to those used for the preparation of compound 5, except 2-(2-methyl-1H-imidazol-4-yl)ethanol (compound 282.3) was used instead of 2,4-dimethyl-1H-imidazole. m/z (ES+) 401 (M+H)+.

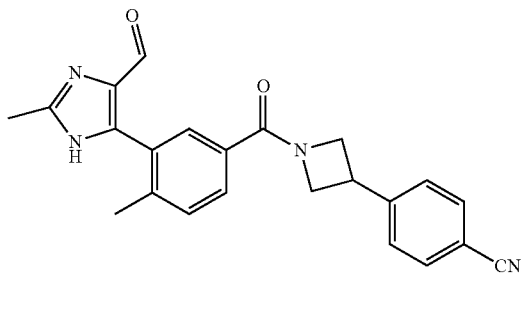 [SMILES: Cc1nc(C=O)c(-c2cc(C(=O)N3CC(c4ccc(C#N)cc4)C3)ccc2C)[nH]1]

Compound 295.1. 4-(1-(3-(4-Formyl-2-methyl-1H-imidazol-5-yl)-4-methylbenzoyl)azetidin-3-yl)benzonitrile The title compound was prepared using standard chemical manipulations and procedures similar to those used for the preparation of compound 5, except 5-iodo-2-methyl-1H-imidazole-4-carbaldehyde (compound 236.1) was used instead of 5-iodo-2,4-dimethyl-1H-imidazole (compound 5.5).

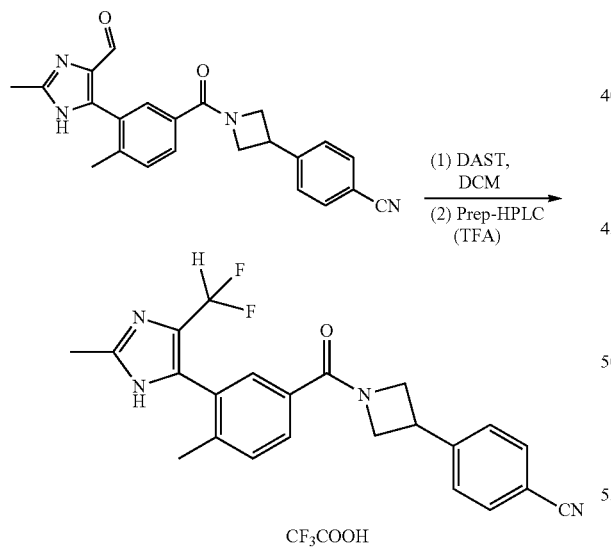

Compound 295. 4-(1-(3-(4-(Difluoromethyl)-2-methyl-1H-imidazol-5-yl)-4-methylbenzoyl)azetidin-3-yl)benzonitrile To a solution of 4-(1-(3-(4-formyl-2-methyl-1H-imidazol-5-yl)-4-methylbenzoyl)azetidin-3-yl)benzonitrile (compound 295.1, 100 mg, 0.26 mmol) in dichloromethane (10 mL) was added DAST (103 μL, 0.78 mmol) at −70° C. The reaction mixture was stirred for 5 h at room temperature. The pH of the solution was adjusted to 7 with sodium bicarbonate (sat.). The aqueous phase was extracted with 20 mL of dichloromethane and the combined organic layers were washed with 3×10 mL of brine, dried over anhydrous sodium sulfate and concentrated under reduced pressure. The residue was purified by silica gel chromatography with ethyl acetate/petroleum ether (1:20-1:2) as the eluent. The crude product (100 mg) was purified by Prep-HPLC with the following conditions (Prep-HPLC-020): Column, SunFire Prep C18 OBD Column, 5 um, 19*100 mm; mobile phase, WATER WITH 0.05% TFA and ACN (16.0% up to 30.0% in 7 min, up to 95.0% in 1 min, down to 16.0% in 1 min); Detector, Waters 2489 254 & 220 nm. This resulted in 48.7 mg (36%) of the title compound as a white solid. m/z (ES+) 407 (M+H)+.

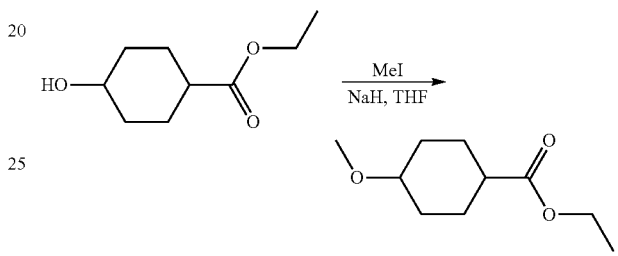

Compound 300.1. Ethyl 4-methoxycyclohexanecarboxylate

Into a 100-mL round-bottom flask, was placed a solution of ethyl 4-hydroxycyclohexane-1-carboxylate (1 g, 5.81 mmol) in tetrahydrofuran (20 mL). Sodium hydride (349 mg, 8.72 mmol, 60%) was added to the reaction at 0° C. in portions, then stirred for 20 min. This was followed by the addition of CH$_3$I (865 μL, 11.6 mmol) at 0° C. The reaction mixture was stirred overnight at room temperature, quenched with 6 mL of brine and extracted with 3×40 mL of ether. The combined organic layers were washed with 2×20 mL of brine, dried over anhydrous sodium sulfate and concentrated under reduced pressure to afford 800 mg (74%) of the title compound as a colorless oil.

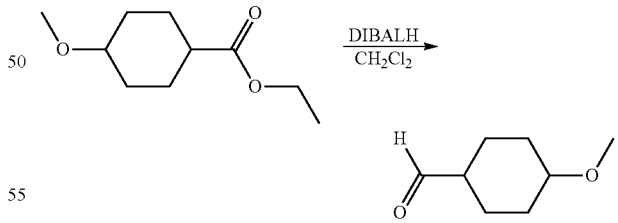

Compound 300.2. 4-Methoxycyclohexanecarbaldehyde

Into a 100-mL 3-neck round-bottom flask purged and maintained with an inert atmosphere of nitrogen, was placed a solution of ethyl 4-methoxycyclohexane-1-carboxylate (1.3 g, 6.98 mmol) in dichloromethane (30 mL). This was followed by the addition of DIBAL-H (1 M in hexanes) (9 mL, 9 mmol) dropwise at −78° C. The reaction mixture was stirred for 3 h at −78° C., then quenched with 10 mL of NH₄Cl (sat.). The aqueous phase was extracted with 3×50 mL of ethyl acetate. The combined organic layers were washed with 3×50 mL of brine, dried over anhydrous sodium sulfate and concentrated under reduced pressure. This resulted in 1 g (crude) of the title compound as a colorless oil.

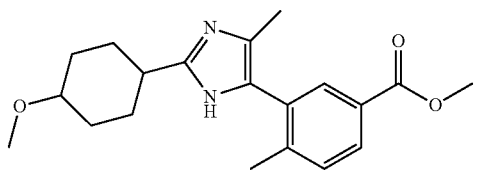

Compound 300.2. methyl 3-(2-(4-methoxycyclohexyl)-4-methyl-1H-imidazol-5-yl)-4-methylbenzoate The title compound was prepared using standard chemical manipulations and procedures similar to those used for the preparation of compound 160.3, except 4-methoxycyclohexanecarbaldehyde (compound 300.2) was used instead of cyclopropanecarbaldehyde and methyl 4-methyl-3-(4,4,5,5-tetramethyl-1,3,2-dioxaborolan-2-yl)benzoate (compound 5.4) was used instead of except methyl 2,4-dimethyl-5-(4,4,5,5-tetramethyl-1,3,2-dioxaborolan-2-yl)benzoate (compound 160.1).

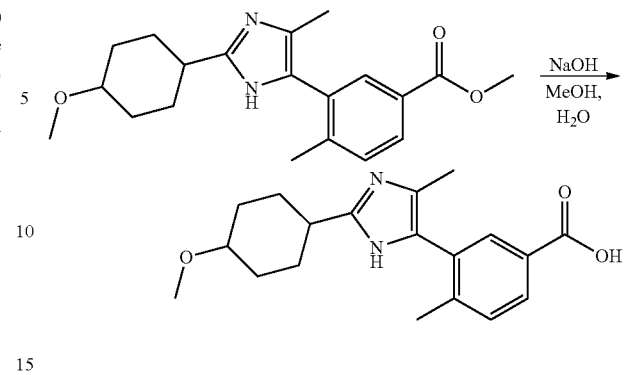

Compound 300.3. 3-(2-(4-Methoxycyclohexyl)-4-methyl-1H-imidazol-5-yl)-4-methylbenzoic acid Into a 50-mL round-bottom flask, was placed a solution of methyl 3-(2-(4-methoxycyclohexyl)-4-methyl-1H-imidazol-5-yl)-4-methylbenzoate (compound 300.2, 150 mg, 0.44 mmol) in methanol (4 mL). A solution of NaOH (70 mg, 1.75 mmol) in water (2 mL) was added to the reaction. The reaction mixture was stirred for 3 h at 50° C., then concentrated under reduced pressure. The reaction mixture was diluted with 2 mL of water. The pH of the solution was adjusted to 1 with HCl (2 M) and concentrated under reduced pressure. This resulted in 240 mg (crude) of the title compound as a light yellow solid.

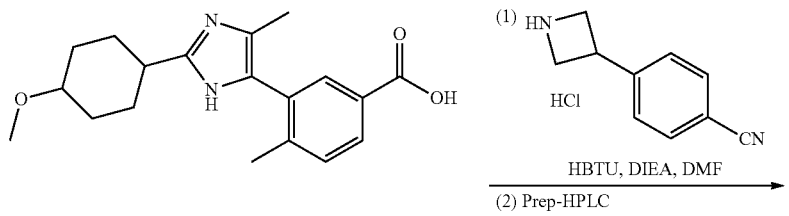

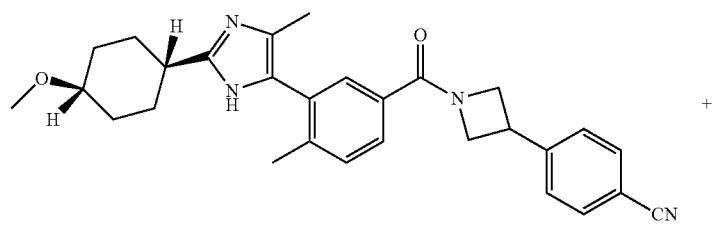

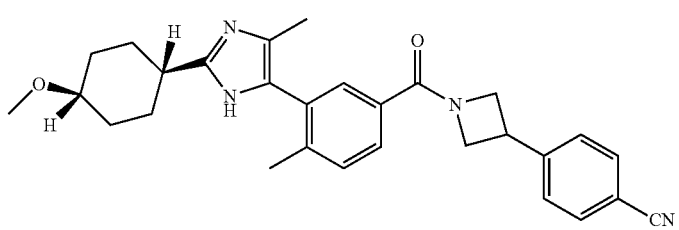

Compounds 300.A and 300.B. 4-(1-(3-(2-(4-Methoxycyclohexyl)-4-methyl-1H-imidazol-5-yl)-4-methylbenzoyl)azetidin-3-yl)benzonitrile Into a 50-mL round-bottom flask, was placed a solution of 3-(2-(4-methoxycyclohexyl)-4-methyl-1H-imidazol-5-yl)-4-methylbenzoic acid (compound 300.3, 140 mg, 0.43 mmol) in N,N-dimethylformamide (3 mL). 4-(Azetidin-3-yl)benzonitrile hydrochloride (compound 5.2, 82.8 mg, 0.43 mmol), HBTU (242.6 mg, 0.64 mmol) and DIEA (228 µL, 1.28 mmol) were added to the reaction. The reaction mixture was stirred for 1 overnight at room temperature, then diluted with 60 mL of EtOAc. The organic layer was washed with 3×20 mL of brine, dried over anhydrous sodium sulfate and concentrated under reduced pressure. The crude product (150 mg) was purified by Prep-HPLC with the following conditions (Prep-HPLC-020): Column, SunFire Prep C18 OBD Column, 5 µm, 19*100 mm; mobile phase, and (20.0% up to 27.0% in 10 min, up to 95.0% in 3 min, down to 20.0% in 1 min); Detector, Waters 2489 254 & 220 nm. This resulted in 18.4 mg (9%) of compound 300.A as a white solid and 59.2 mg (30%) of compound 300.B as an off-white solid. m/z (ES+) 469 (M+H)+.

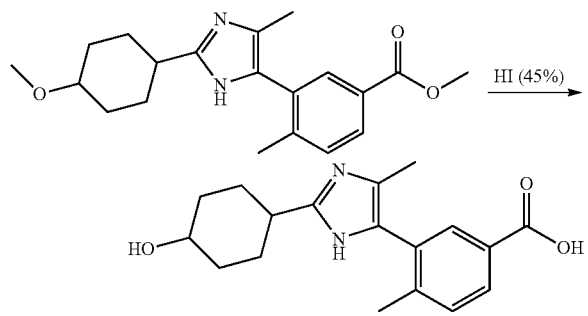

Compound 332.1. 3-(2-(4-Hydroxycyclohexyl)-4-methyl-1H-imidazol-5-yl)-4-methylbenzoic acid A solution of methyl 3-(2-(4-methoxycyclohexyl)-4-methyl-1H-imidazol-5-yl)-4-methylbenzoate (compound 300.2, 300 mg, 0.88 mmol) in HI (45% in water) (3 mL) was stirred for 2 h at 60° C., then concentrated under reduced pressure. This resulted in 500 mg (crude) of the title compound as brown oil which was used into the next step without further purification.

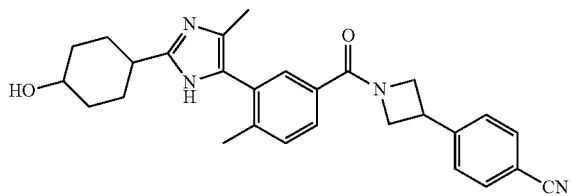 [SMILES: Cc1ccc(C(=O)N2CC(c3ccc(C#N)cc3)C2)cc1-c1[nH]c(C2CCC(O)CC2)nc1C]

Compound 332. 4-(3-(3-(2-(4-Hydroxycyclohexyl)-4-methyl-1H-imidazol-5-yl)-4-methylbenzoyl)cyclobutyl)benzonitrile The title compound was prepared using standard chemical manipulations and procedures similar to those used for the preparation of compound 5, except 3-(2-(4-hydroxycyclohexyl)-4-methyl-1H-imidazol-5-yl)-4-methylbenzoic acid (compound 332.1) was used instead of 3-(2,4-dimethyl-1H-imidazol-5-yl)-4-methylbenzoic acid hydrochloride (compound 5.7). m/z (ES+) 455 (M+H)+.

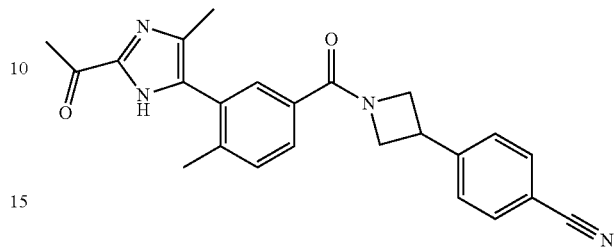

Compound 355.1. 4-(1-(3-(2-Acetyl-4-methyl-1H-imidazol-5-yl)-4-methylbenzoyl)azetidin-3-yl)benzonitrile The title compound was prepared using standard chemical manipulations and procedures similar to those used for the preparation of compound 5, except 1-(4-methyl-H-imidazol-2-yl)ethanone was used in place of 2,4-dimethyl-1H-imidazole.

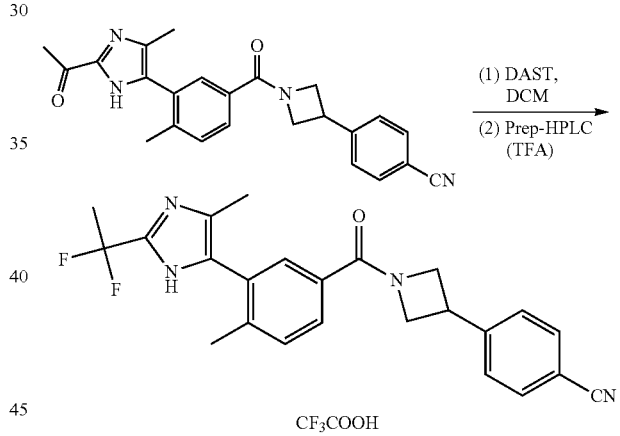

Compound 355. 4-(1-(3-(2-(1,1-Difluoroethyl)-4-methyl-1H-imidazol-5-yl)-4-methylbenzoyl)azetidin-3-yl)benzonitrile Into a 50-mL round-bottom flask purged and maintained with an inert atmosphere of nitrogen, was placed a solution of 4-(1-(3-(2-acetyl-4-methyl-1H-imidazol-5-yl)-4-methylbenzoyl)azetidin-3-yl)benzonitrile (compound 355.1, 85 mg, 0.21 mmol) in dichloromethane (15 mL). This was followed by the addition of DAST (82 µL, 0.62 mmol). The reaction mixture was stirred for 4 days at room temperature, while adding fifteen additional equivalent of DAST over 4 days. The reaction was then quenched by the addition of 10 mL of water. The aqueous phase was extracted with 3×50 mL of dichloromethane and the combined organic layers were dried over anhydrous sodium sulfate and concentrated under reduced pressure. The residue was purified by silica gel chromatography with ethyl acetate/hexanes (6:1) as the eluent. The crude product (54 mg) was purified by Prep- HPLC with the following conditions (Prep-HPLC-020): Column, SunFire Prep C18 OBD Column, 5 um, 19*100 mm; mobile phase, WATER WITH 0.05% TFA and MeCN (24.0% MeCN up to 38.0% in 5 min, up to 95.0% in 1 min, down to 34.0% in 1 min); Detector, Waters 2489 254 & 220 nm. This resulted in 42.8 mg (38%) of the title compound (trifluoroacetic acid salt) as a white solid. m/z (ES+) 421 (M+H)+.

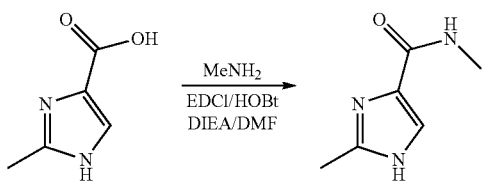

Compound 371.1.
N,2-Dimethyl-1H-imidazole-4-carboxamide

2-Methyl-1H-imidazole-4-carboxylic acid (378 mg, 3 mmol), EDCI (745 mg, 3.9 mmol), HOBt (253 mg, 1.5 mmol), DIEA (1.6 mL, 9 mmol) and methyl amine (2M in THF) (3.6 mL, 7.2 mmol) were dissolved in DMF (10 mL) and stirred at room temperature for 16 hours. After removal of DMF, the residue was dry loaded and purified by flash chromatography (SiO$_2$; 0-10% methanol in DCM and 1% NH$_4$OH) to give 280 mg (67%) of the title compound. m/z (ES+) 140 (M+H)+.

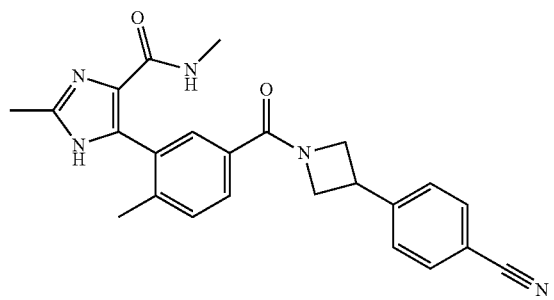 [SMILES: CNC(=O)c1nc(C)[nH]c1-c1cc(C(=O)N2CC(c3ccc(C#N)cc3)C2)ccc1C]

Compound 371. 5-(5-(3-(4-Cyanophenyl)azetidine-1-carbonyl)-2-methylphenyl)-N,2-dimethyl-1H-imidazole-4-carboxamide The title compound was prepared using standard chemical manipulations and procedures similar to those used for the preparation of compound 5, except N,2-dimethyl-1H-imidazole-4-carboxamide (compound 371.1) was used instead of 2,4-dimethyl-1H-imidazole. m/z (ES+) 414 (M+H)+.

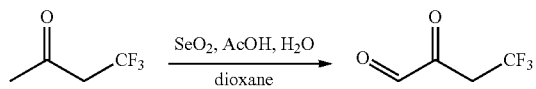

Compound 349.1. 4,4,4-Trifluoro-2-oxobutanal

To a solution of SeO$_2$ (4.23 g, 38.1 mmol) in dioxane (25 mL) was added AcOH/H$_2$O (1 mL/1 mL). 4,4,4-Trifluorobutan-2-one (3.81 mL, 31.7 mmol) was added dropwise to the above reaction mixture. The resulting solution was stirred overnight at 100° C. The solution was used in the next step without any further work-up or purification.

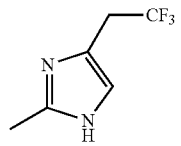

Compound 349.2.
2-Methyl-4-(2,2,2-trifluoroethyl)-1H-imidazole

The title compound was prepared using standard chemical manipulations and procedures similar to those used for the preparation of compound 159.1, except 4,4,4-trifluoro-2-oxobutanal (compound 349.1) was used instead of methylglyoxal.

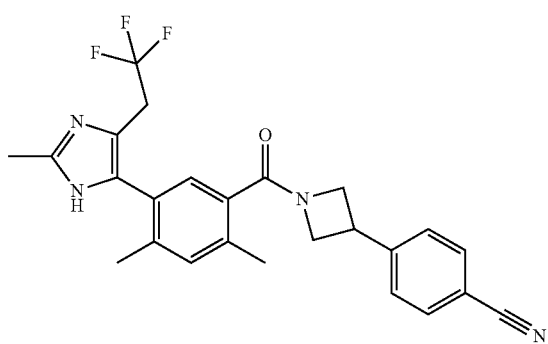 [SMILES: Cc1nc(CC(F)(F)F)c(-c2cc(C(=O)N3CC(c4ccc(C#N)cc4)C3)c(C)cc2C)[nH]1]

Compound 349. 4-(1-(2,4-Dimethyl-5-(2-methyl-4-(2,2,2-trifluoroethyl)-1H-imidazol-5-yl)benzoyl)azetidin-3-yl)benzonitrile The title compound was prepared using standard chemical manipulations and procedures similar to those used for the preparation of compound 159, except 2-methyl-4-(2,2,2-trifluoroethyl)-1H-imidazole (compound 349.2) was used instead of 2-isopropyl-4-methyl-1H-imidazole (compound 159.1). m/z (ES+) 453 (M+H)+.

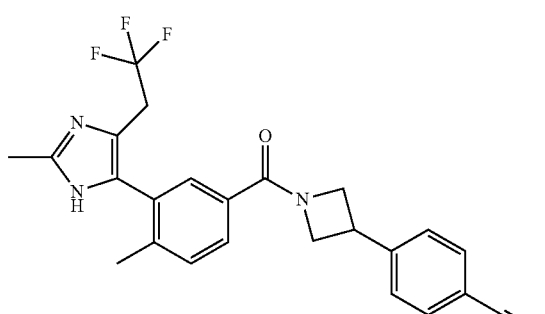

Compound 296. 4-(1-(4-Methyl-3-(2-methyl-4-(2,2,2-trifluoroethyl)-1H-imidazol-5-yl)benzoyl)azetidin-3-yl)benzonitrile The title compound was prepared using standard chemical manipulations and procedures similar to those used for the preparation of compound 159, except 2-methyl-4-(2,2,2-trifluoroethyl)-1H-imidazole (compound 349.2) was used instead of 2-isopropyl-4-methyl-1H-imidazole (compound 159.1) and methyl 4-methyl-3-(4,4,5,5-tetramethyl-1,3,2-dioxaborolan-2-yl)benzoate (compound 5.4) was used instead of methyl 2,4-dimethyl-5-(4,4,5,5-tetramethyl-1,3,2-dioxaborolan-2-yl)benzoate (compound 160.1). m/z (ES+) 439 (M+H)⁺.

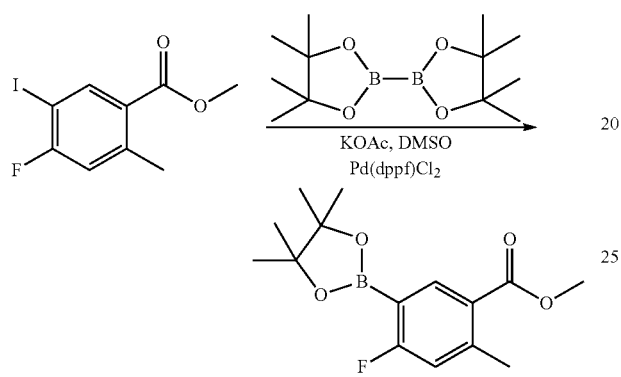

Compound 377.1. Methyl 4-fluoro-2-methyl-5-(4,4,5,5-tetramethyl-1,3,2-dioxaborolan-2-yl)benzoate Into a 250-mL round-bottom flask purged and maintained with an inert atmosphere of nitrogen, was placed a solution of methyl 4-fluoro-5-iodo-2-methylbenzoate (compound 101.2, 5.04 g, 17.1 mmol) in DMSO (50 mL). 4,4,5,5-Tetramethyl-2-(tetramethyl-1,3,2-dioxaborolan-2-yl)-1,3,2-dioxaborolane (5.23 g, 20.6 mmol), KOAc (5.04 g, 51.4 mmol), Pd(dppf)Cl₂ (2.51 g, 3.43 mmol) were added to the reaction. The reaction mixture was stirred for 2 h at 90° C., then cooled and diluted with 300 mL of EtOAc. The solids were filtered off and the filtrate was washed with 3×30 mL of brine (sat.). The organic layer was dried over anhydrous sodium sulfate and concentrated under reduced pressure. The residue was purified by silica gel chromatography with ethyl acetate/petroleum ether (1/30) as the eluent to furnish 3.97 g (79%) of the title compound as an off-white solid.

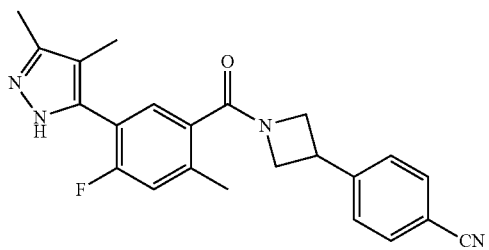 [SMILES: Cc1cc(F)c(-c2[nH]nc(C)c2C)cc1C(=O)N1CC(c2ccc(C#N)cc2)C1]

Compound 377.2. 4-(1-(5-(3,4-Dimethyl-1H-pyrazol-5-yl)-4-fluoro-2-methylbenzoyl)azetidin-3-yl)benzonitrile The title compound was prepared using standard chemical manipulations and procedures similar to those used for the preparation of compound 59, except methyl 4-fluoro-2-methyl-5-(4,4,5,5-tetramethyl-1,3,2-dioxaborolan-2-yl)benzoate (compound 377.1) was used in place of methyl 4-methyl-3-(4,4,5,5-tetramethyl-1,3,2-dioxaborolan-2-yl)benzoate (compound 5.4). m/z (ES+) 389 (M+H)⁺.

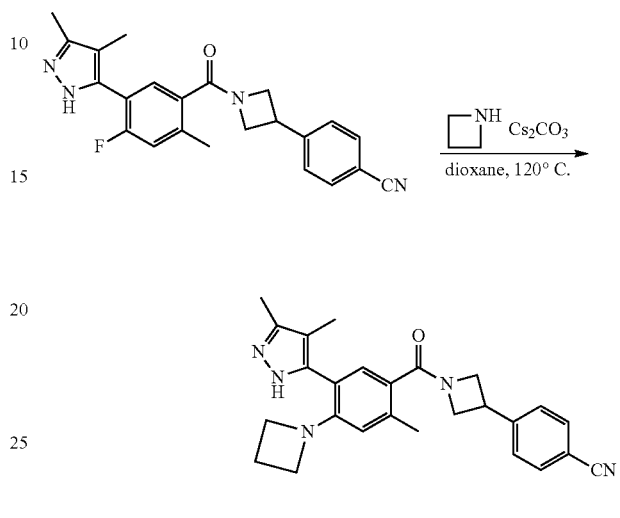

Compound 377. 4-(1-(4-(Azetidin-1-yl)-5-(3,4-dimethyl-1H-pyrazol-5-yl)-2-methylbenzoyl)azetidin-3-yl)benzonitrile Into a 5-mL sealed tube, was placed a solution of 4-(1-(5-(3,4-dimethyl-1H-pyrazol-5-yl)-4-fluoro-2-methylbenzoyl)azetidin-3-yl)benzonitrile (compound 377.2, 120 mg, 0.31 mmol) in dioxane (3 mL). Azetidine (833 μL, 12.4 mmol) and Cs₂CO₃ (1.01 g, 3.09 mmol) were added to the reaction. The reaction mixture was stirred for 20 h at 120° C., then cooled with a water/ice bath. The resulting solution was diluted with 30 mL of EtOAc. The organic layer was washed with 3×20 mL of brine, dried over anhydrous sodium sulfate and concentrated under reduced pressure. The crude product (200 mg) was purified by Prep-HPLC with the following conditions (Prep-HPLC-020): Column, SunFire Prep C18 OBD Column, 5 um, 19*100 mm; mobile phase, Water with 10 mmol NH₄HCO₃ and MeCN (36.0% MeCN up to 50.0% in 6 min, up to 95.0% in 2 min, down to 36.0% in 1 min); Detector, waters 2489 254 & 220 nm. This resulted in 56 mg (43%) of the title compound as a white solid. m/z (ES+) 426 (M+H)⁺.

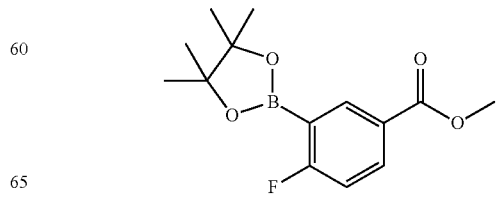

Compound 376.1. Methyl 4-fluoro-3-(4,4,5,5-tetramethyl-1,3,2-dioxaborolan-2-yl)benzoate The title compound was prepared using standard chemical manipulations and procedures similar to those used for the preparation of compound 377.1, except methyl 4-fluoro-3-iodobenzoate (compound 132.1) was used instead of methyl 4-fluoro-5-iodo-2-methylbenzoate (compound 101.2).

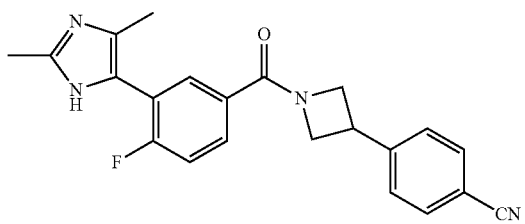 [SMILES: Cc1nc(C)c(-c2cc(C(=O)N3CC(c4ccc(C#N)cc4)C3)ccc2F)[nH]1]

Compound 376.2. 4-(1-(3-(2,4-Dimethyl-1H-imidazol-5-yl)-4-fluorobenzoyl)azetidin-3-yl)benzonitrile The title compound was prepared using standard chemical manipulations and procedures similar to those used for the preparation of compound 5, except methyl 4-fluoro-3-(4,4,5,5-tetramethyl-1,3,2-dioxaborolan-2-yl)benzoate (compound 376.1) was used instead of methyl 4-methyl-3-(4,4,5,5-tetramethyl-1,3,2-dioxaborolan-2-yl)benzoate (compound 5.4).

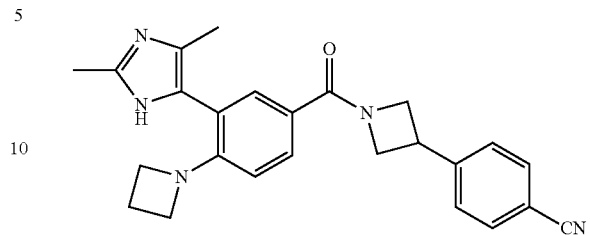

Compound 376. 4-(1-(4-(Azetidin-1-yl)-3-(2,4-dimethyl-1H-imidazol-5-yl)benzoyl)azetidin-3-yl)benzonitrile The title compound was prepared using standard chemical manipulations and procedures similar to those used for the preparation of compound 377, except 4-(1-(3-(2,4-dimethyl-1H-imidazol-5-yl)-4-fluorobenzoyl)azetidin-3-yl)benzonitrile (compound 376.2) was used instead of 4-(1-(5-(3,4-dimethyl-1H-pyrazol-5-yl)-4-fluoro-2-methylbenzoyl)azetidin-3-yl)benzonitrile (compound 377.2). m/z (ES+) 412 (M+H)$^+$.

The compounds in TABLE 22 were prepared using standard chemical manipulations and procedures similar to those used for the preparation of compounds 14, 101, 375 and 376.

TABLE 22

| Cpd | Name | Structure | m/z (ES+) (M + H)$^+$ |
|---|---|---|---|
| 382 | 4-(1-(4-(azetidin-1-yl)-3-(4-methyl-2-(trifluoromethyl)-1H-imidazol-5-yl)benzoyl)azetidin-3-yl)benzonitrile | 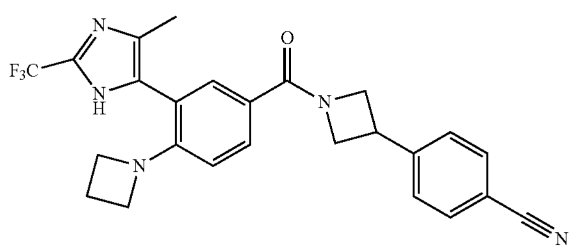 [SMILES: Cc1nc(C(F)(F)F)[nH]c1-c1cc(C(=O)N2CC(c3ccc(C#N)cc3)C2)ccc1N1CCC1] | 466 |
| 383 | 4-(1-(3-(2,4-dimethyl-1H-imidazol-5-yl)-4-(3-methylazetidin-1-yl)benzoyl)azetidin-3-yl)benzonitrile | 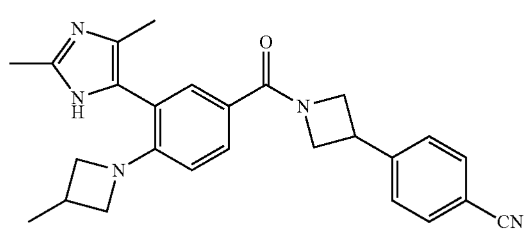 [SMILES: Cc1nc(C)c(-c2cc(C(=O)N3CC(c4ccc(C#N)cc4)C3)ccc2N2CC(C)C2)[nH]1] | 426 |
| 384 | 4-(1-(3-(2,4-dimethyl-1H-imidazol-5-yl)-4-(pyrrolidin-1-yl)benzoyl)azetidin-3-yl)benzonitrile | 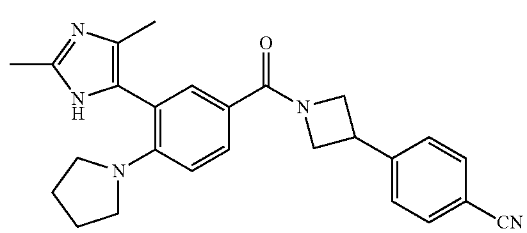 [SMILES: Cc1nc(C)c(-c2cc(C(=O)N3CC(c4ccc(C#N)cc4)C3)ccc2N2CCCC2)[nH]1] | 426 |

TABLE 22-continued

| Cpd | Name | Structure | m/z (ES+) (M + H)+ |
|---|---|---|---|
| 385 | 4-(1-(3-(2,4-dimethyl-1H-imidazol-5-yl)-4-(3-methoxypyrrolidin-1-yl)benzoyl)azetidin-3-yl)benzonitrile | 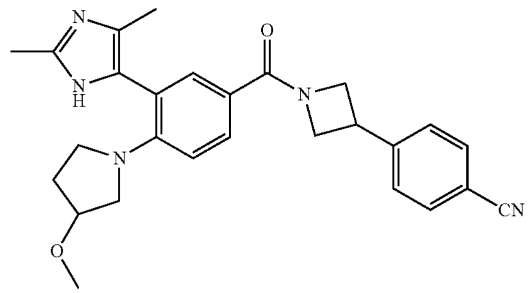 [SMILES: COC1CCN(c2ccc(C(=O)N3CC(c4ccc(C#N)cc4)C3)cc2-c2[nH]c(C)nc2C)C1] | 456 |

Compound 378. 4-(1-(4-Chloro-3-(2,4-dimethyl-1H-imidazol-5-yl)benzoyl)azetidin-3-yl)benzonitrile The title compound was prepared using standard chemical manipulations and procedures similar to those used for the preparation of compound 50, except 4-(azetidin-3-yl)benzonitrile hydrochloride (compound 5.2) was used in place of 4-(piperidin-4-yl)benzonitrile hydrochloride (compound 1.2). m/z (ES+) 391 (M+H)+.

Compound 379. 4-(1-(3-(2,4-dimethyl-1H-imidazol-5-yl)-4-(trifluoromethyl)benzoyl)azetidin-3-yl)benzonitrile The title compound was prepared using standard chemical manipulations and procedures similar to those used for the preparation of compound 50 and 378. m/z (ES+) 425 (M+H)+.

Compound 380. 4-(1-(3-(2-((cis)-4-methoxycyclohexyl)-4-(trifluoromethyl)-1H-imidazol-5-yl)-4-methylbenzoyl)azetidin-3-yl)benzonitrile The title compound was prepared using standard chemical manipulations and procedures similar to those used for the preparation of compounds 202, 287, 300A and 300B. m/z (ES+) 523 (M+H)+.

Compound 381. 4-(1-(3-(2-((trans)-4-methoxycyclohexyl)-4-(trifluoromethyl)-1H-imidazol-5-yl)-4-methylbenzoyl)azetidin-3-yl)benzonitrile The title compound was prepared using standard chemical manipulations and procedures similar to those used for the preparation of compounds 202, 287, 300A and 300B. m/z (ES+) 523 (M+H)+.

The compounds of the present disclosure in TABLE 26 below were, or may be, prepared using the foregoing procedures, as well as standard chemical manipulations and procedures similar to the foregoing procedures.

Example 2

Activity of Compound of the Present Disclosure

Antiviral Activity

The antiviral activities of the compounds were assessed using the HCV1b replicon system. The replicon was constructed using the ET (luc-ubi-neo/ET) cell line, a Huh7 human hepatoma cell line harboring an HCV replicon with a stable luciferase (Luc) reporter and three cell culture-adaptive mutations (Pietschmann, et al (2002) *J. Virol.* 76:4008-4021). The HCV replicon antiviral evaluation assay examined the effects of compounds at ten three-fold dilutions. Sub-confluent cultures of the ET line were plated out into 96-well plates that were dedicated for the analysis of cell viability (cytotoxicity) or antiviral activity and the next day drugs were added to the appropriate wells. Cells were processed 72 hr later when the cells are still sub-confluent. $EC_{50}$ (concentrations inhibiting the HCV RNA replicon by 50%), $CC_{50}$ (concentration decreasing cell viability by 50%) and SI (selective index: $CC_{50}/EC_{50}$) values were determined. HCV RNA replicon levels were assessed using the Bright-Glo™ Luciferase Assay System (Promega) to measure replicon-derived Luc activity. The CellTiter-Glo™ Luminescent Cell Viability Assay (Promega) was used to estimate cell viability. Inhibition of HCV for selected compounds is disclosed in TABLE 26. None of the compounds in TABLE 26 caused material cytotoxicity at the highest concentrations tested.

FASN Inhibition by Compounds of the Present Disclosure

Determination of FASN Biochemical Activity:

The FASN enzyme was isolated from SKBr3 cells. SKBr3 is a human breast cancer cell-line with high levels of FASN expression. It is estimated that FASN comprises about 25% of the cytosolic proteins in this cell line. SKBr3 cells were homogenized in a dounce homogenizer then centrifuged for 15 minutes at 4° C. to remove particulate matter. The supernatant was then analyzed for protein content, diluted to the appropriate concentration, and used to measure FASN activity. The presence of FASN was confirmed by western blot analysis. A similar method for isolation of FASN from SKBr3 cells is described in Teresa, P. et al. (*Clin. Cancer Res.* 2009; 15(24), 7608-7615).

FASN activity of the SKBr3 cell extract was determined by measuring either NADPH oxidation or the amount of thiol-containing coenzyme A (CoA) released during the fatty acid synthase reaction. The dye CPM (7-diethylamino-3-(4'-maleimidyl-phenyl)-4-methylcoumarin) contains a thiol reactive group that increases its fluorescence emission on reaction with the sulfhydryl group of CoA. The biochemical activities shown in TABLE 26 were determined using the fluorescence measurement of CoA release via a procedure described in Chung C. C. et al. (*Assay and Drug Development Technologies*, 2008, 6(3), 361-374).

FASN Inhibitors have Oncology Efficacy

Experimental Procedures

Cell Viability Assay:

For drug treatment, PANC-1 cells were plated in 96-well plates at a concentration of $1.0 \times 10^3$ per well in medium (Advanced MEM containing 1% or 10% FBS). Serial 3-fold dilutions of compounds 160, 161, 242, or 164 were prepared in DMSO and further diluted 1:10 in Advanced MEM for addition to the assay solution. 24-hours after cell plating, advanced MEM-diluted compound was added to make a final reaction volume of 100 ul per well. Final drug concentrations in assay wells were 10,000, 3,300, 1,100, 370, 123, 41, 14, 5, and 0 nmol/L. Assays were done in triplicate at each drug concentration 10 days after compound addition. The number of viable cells was measured using the Cell Titer-Glo assay (Promega) according to the manufactures instructions. Luminosity per well was determined and the signal intensity was analyzed versus drug concentration. For each FASN inhibitor, the concentration of drug resulting in 50% inhibition of the maximum signal was determined, and this value was reported as the $IC_{50}$.

Xenograft Tumor Growth Inhibition Efficacy Study:

For xenograft tumor development and drug treatment, female BALB/c-nude mice, 8-9 weeks of age, were inoculated subcutaneously at the right flank with PANC-1 tumor cells ($5 \times 10^6$) in 0.1 ml of PBS. The day of tumor cell inoculation is denoted as day 0. Drug treatment was initiated when the mean tumor size reached 149 mm³ (day 15). Drug administration to tumor-bearing mice (n=10 per group) was according to the following regimen: compound 161: 30 or 60 mg/kg once daily (Qd); compound 242: 30 or 60 mg/kg once daily (Qd); C75 (trans-4-methylene-2-octyl-5-oxotetrahydrofuran-3-carboxylic acid): 30 mg/kg once every 5 days (Q5d); gemcitabine 40 mg/kg once every 3 days (Q3d). The administered dose of C75 was lowered to 20 mg/kg once every 5 days following the first dose, due to drug-induced weight loss and toxicity. Mice were assigned into treatment groups using a randomized block design based upon their tumor volumes. This ensured that all the groups were comparable at the start of treatment. Tumor sizes were measured twice weekly in two dimensions using a caliper, and the volumes were expressed in mm³ using the formula: V=0.5 a×b2 where a and b were the long and short diameters of the tumor, respectively. The study was terminated 6 hours post the $18^{th}$ Qd dose on day 32 after tumor inoculation. Tumor growth inhibition (TGI) was calculated as the percentage of tumor growth, relative to tumor size at the start of treatment, in drug-treated groups compared to vehicle-treated groups. The Mann-Whitney U test was used to assess statistical significance of the mean tumor size between drug and vehicle-treated groups.

Results

FASN Inhibition Inhibits Tumor Cell Growth and Induces Cell Death:

To test for effects of FASN inhibition on tumor cell survival, a pancreatic tumor cell line (PANC-1) was treated with multiple FASN inhibitors, and $IC_{50}$ values were determined from a 9-point dose response cell viability assay. Cell survival $IC_{50}$ values were determined 10 days following addition of FASN inhibitor compounds to the tumor cells (TABLE 23). FASN cell survival $IC_{50}$ values were in agreement with previously determined FASN biochemical and-cell-based $IC_{50}$ values in palmitate synthesis and HCV replicon assays. Alignment of IC50 values in phenotypic (cell survival) and mechanistic (palmitate synthesis) assays demonstrates that tumor cell death induced by FASN inhibitor treatment is a direct result of FASN inhibition.

TABLE 23

FASN inhibitor in vitro cell assay $IC_{50}$ values

| Treatment | Survival PANC-1 (nM) | HCV HeLa (nM) | Palmitate HeLa (nM) | FASN Biochem. (nM) |
|---|---|---|---|---|
| Compound 160 | $16^a$ | 7 | 24 | 17 |
| Compound 161 | $112^a$ | 34 | 51 | 32 |
| Compound 242 | $42^b$ | 77 | 74 | 42 |
| Compound 164 | $1.2^b$ | 2 | 27 | 19 |

[a]Advanced MEM cell medium with 10% FBS
[b]Advanced MEM cell medium with 1% FBS FASN Inhibition Inhibits In Vivo Xenograft Tumor Growth:

To test for the effects of FASN inhibition on in vivo tumor growth, PANC-1 xenograft tumors were inoculated subcutaneously in female BALB/c-nude mice. When the xenograft tumors grew to an average of 149 mm³ (day 15 following tumor cell inoculation), drug treatment was initiated with 3-V Biosciences reversible FASN inhibitors (compound 161 or 242) or control compounds (C75 or gemcitabine) to determine tumor growth inhibition activity of the different compounds in the PANC-1 xenograft tumor model. Drug treatment groups consisted of 10-tumor-bearing mice per group. The FASN inhibitors, compounds 161 and 242 both demonstrated tumor growth inhibition activity in a dose-responsive manner. Compound 161 dosed at 60 mg/kg once daily for 18 days resulted in 52% tumor growth inhibition compared to vehicle treated mice, and compound 242 dosed at 100 mg/kg once daily for 18 days resulted in 57% tumor growth inhibition compared to vehicle treated mice (TABLES 24 and 25). Once daily 30 mg/kg doses of compounds 161 and 242 resulted in 31% and 19% tumor growth inhibition, respectively. C75, the irreversible FASN inhibitor control compound was dosed initially at 30 mg/kg once every 5 days; however, toxicity of this compound required a dose adjustment to 20 mg/kg once every 5 days. The C75 treatment group after 18 days (3 doses) showed 65% tumor growth inhibition. Six of the ten mice in the C75 treatment group died from C75-related toxicity during the 18-day study. Gemcitabine treated PANC-1 tumor-bearing mice (40 mg/kg once every 3 days) showed 96 percent tumor growth inhibition. Tumor growth inhibition induced by compounds 161 and 242, C75, and gemcitabine was statistically significant compared to vehicle treated mice. The results from this study demonstrate that reversible FASN inhibitors discovered at 3-V Biosciences are well tolerated in PANC-1 xenograft tumor-bearing mice, and that once-daily dosing of the inhibitors as a single agent cancer therapeutic is associated with statistically significant tumor growth inhibition compared to vehicle treated mice. Additional studies to investigate dosing levels, schedules, and in combination with existing standard of care chemotherapies are being pursued.

Tumor Volumes

The tumor sizes of each treatment group at different time points are shown in TABLE 24.

TABLE 24

Mean tumor sizes in the different treatment groups

| | Tumor volume (mm³)[a] | | | | | |
|---|---|---|---|---|---|---|
| Treatment | 15 | 19 | 22 | 26 | 29 | 32 |
| Compound 161 (30 mg/kg) | 150 ± 13 | 159 ± 10 | 211 ± 17 | 297 ± 31 | 379 ± 53 | 479 ± 69 |
| Compound 161 (60 mg/kg) | 150 ± 13 | 178 ± 23 | 213 ± 32 | 207 ± 33 | 261 ± 51 | 413 ± 83 |
| Compound 242 (30 mg/kg) | 149 ± 12 | 219 ± 24 | 240 ± 18 | 304 ± 21 | 394 ± 24 | 543 ± 38 |
| Compound 242 (100 mg/kg) | 149 ± 13 | 157 ± 15 | 187 ± 22 | 247 ± 29 | 300 ± 39 | 378 ± 59 |
| C75 (30/20 mg/kg) | 150 ± 15 | 164 ± 22 | 156 ± 26 | 213 ± 43 | 367 ± 77 | 403 ± 83 |
| Gemcitabine (40 mg/kg) | 149 ± 12 | 144 ± 16 | 152 ± 14 | 177 ± 20 | 172 ± 21 | 165 ± 27 |
| Vehicle 1 (0.5% CMC) | 148 ± 11 | 200 ± 23 | 242 ± 32 | 423 ± 57 | 491 ± 57 | 638 ± 108 |
| Vehicle 2 (20% DMSO, 80% PBS) | 146 ± 11 | 212 ± 11 | 277 ± 18 | 409 ± 18 | 474 ± 24 | 614 ± 29 |

Note:
[a]Mean ± SEM.

Tumor Growth Inhibition

The tumor growth inhibition (TGI) and statistical analysis of each treatment group at the study conclusion (day 32) is summarized in TABLE 25.

TABLE 25

Antitumor activity of compounds 161 and 242 as a single agent in the treatment of subcutaneous PANC-1 human pancreatic cancer xenograft model

| Treatment | TGI vs. Vehicle 1 (%) | P-value vs. Vehicle 1 | TGI vs. Vehicle 2 (%) | P-value vs. Vehicle 2 |
|---|---|---|---|---|
| Compound 161 (30 mg/kg) | 31 | 0.310 | 29 | 0.052 |
| Compound 161 (60 mg/kg) | 52 | 0.188 | 51 | 0.014 |
| Compound 242 (30 mg/kg) | 19 | 0.950 | 16 | 0.244 |
| Compound 242 (100 mg/kg) | 57 | 0.043 | 56 | 0.002 |
| C75 (30/20 mg/kg) | 65 | 0.024 | 64 | 0.002 |
| Gemcitabine (40 mg/kg) | 96 | <0.001 | 96 | <0.001 |
| Vehicle 1 (0.5% CMC) | — | — | — | 1.000 |
| Vehicle 2 (20% DMSO, 80% PBS) | — | 1.000 | — | — |

TABLE 26

Compounds of the present disclosure.

| Structure | Cpd | Hu FASN IC50 (μM) | HCV GT1b EC50 (μM) |
|---|---|---|---|
| 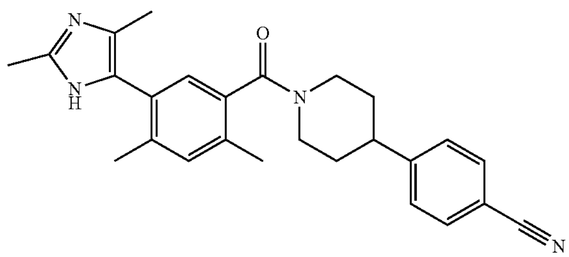 [SMILES: Cc1nc(C)c(-c2cc(C(=O)N3CCC(c4ccc(C#N)cc4)CC3)c(C)cc2C)[nH]1] | 1 | 0.024 | 0.027 |
| 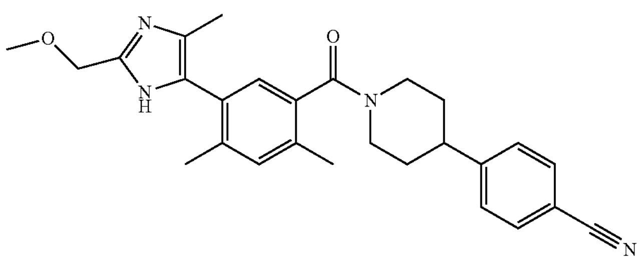 [SMILES: COCc1nc(C)c(-c2cc(C(=O)N3CCC(c4ccc(C#N)cc4)CC3)c(C)cc2C)[nH]1] | 2 | 0.041 | 0.037 |
| 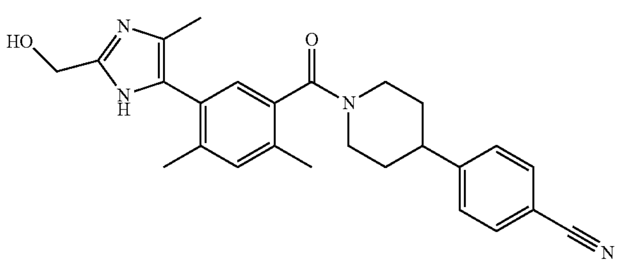 [SMILES: Cc1cc(C)c(-c2[nH]c(CO)nc2C)cc1C(=O)N1CCC(c2ccc(C#N)cc2)CC1] | 3 | 0.032 | 0.068 |
| 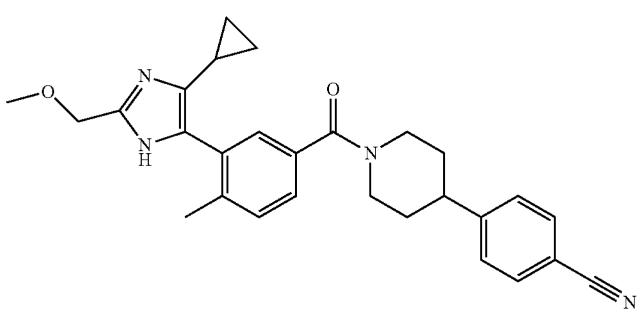 [SMILES: COCc1nc(C2CC2)c(-c2cc(C(=O)N3CCC(c4ccc(C#N)cc4)CC3)ccc2C)[nH]1] | 4 | 0.053 | 0.081 |
| 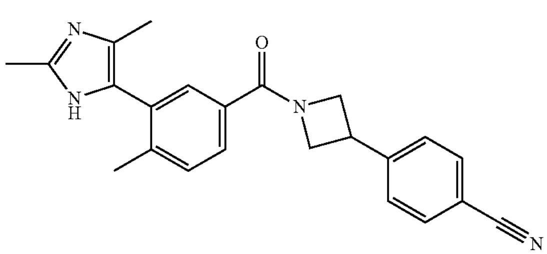 [SMILES: Cc1nc(C)c(-c2cc(C(=O)N3CC(c4ccc(C#N)cc4)C3)ccc2C)[nH]1] | 5 | 0.010 | 0.009 |

TABLE 26-continued

Compounds of the present disclosure.

| Structure | Cpd | Hu FASN IC50 (μM) | HCV GT1b EC50 (μM) |
|---|---|---|---|
| (structure) | 6 | 0.105 | 0.086 |
| (structure) | 7 | 0.006 | 0.003 |
| (structure) | 8 | 0.040 | 0.050 |
| (structure) | 9 | 0.025 | 0.030 |
| (structure) | 10 | 0.027 | 0.030 |
| (structure) | 11 | 0.036 | 0.044 |

TABLE 26-continued
Compounds of the present disclosure.
| Structure | Cpd | Hu FASN IC50 (μM) | HCV GT1b EC50 (μM) |
|---|---|---|---|
| 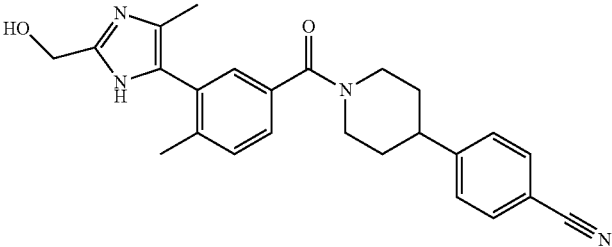 [SMILES: Cc1ccc(C(=O)N2CCC(c3ccc(C#N)cc3)CC2)cc1-c1[nH]c(CO)nc1C] | 12 | 0.036 | 0.160 |
| 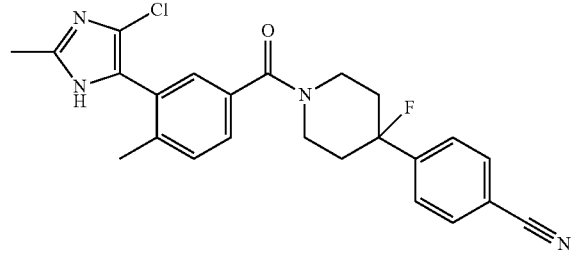 [SMILES: Cc1nc(Cl)c(-c2cc(C(=O)N3CCC(F)(c4ccc(C#N)cc4)CC3)ccc2C)[nH]1] | 13 | 0.006 | 0.005 |
| 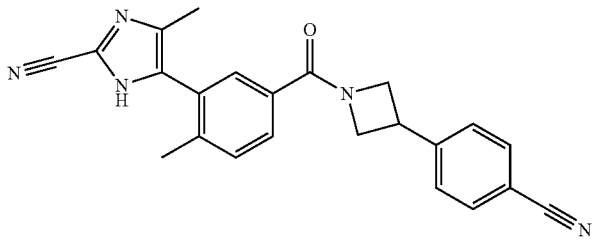 | 14 | 0.027 | 0.031 |
| 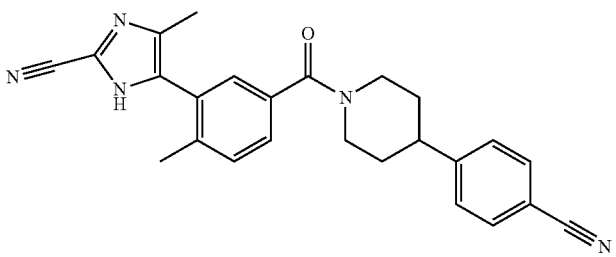 [SMILES: Cc1ccc(C(=O)N2CCC(c3ccc(C#N)cc3)CC2)cc1-c1[nH]c(C#N)nc1C] | 15 | 0.026 | 0.022 |
| 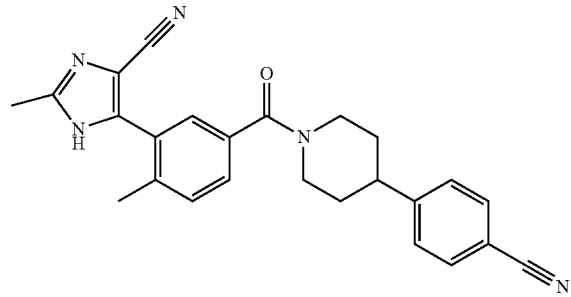 [SMILES: Cc1nc(C#N)c(-c2cc(C(=O)N3CCC(c4ccc(C#N)cc4)CC3)ccc2C)[nH]1] | 16 | 0.018 | 0.013 |

TABLE 26-continued

Compounds of the present disclosure.

| Structure | Cpd | Hu FASN IC50 (μM) | HCV GT1b EC50 (μM) |
|---|---|---|---|
| 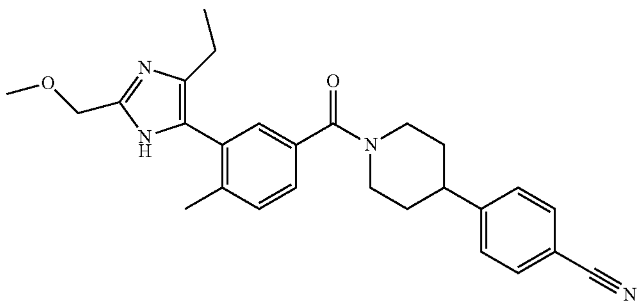 [SMILES: CCc1nc(COC)[nH]c1-c1cc(C(=O)N2CCC(c3ccc(C#N)cc3)CC2)ccc1C] | 17 | 0.045 | 0.081 |
| 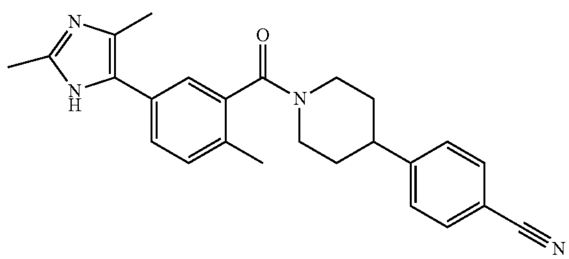 [SMILES: Cc1nc(C)c(-c2ccc(C)c(C(=O)N3CCC(c4ccc(C#N)cc4)CC3)c2)[nH]1] | 18 | 0.540 | |
| 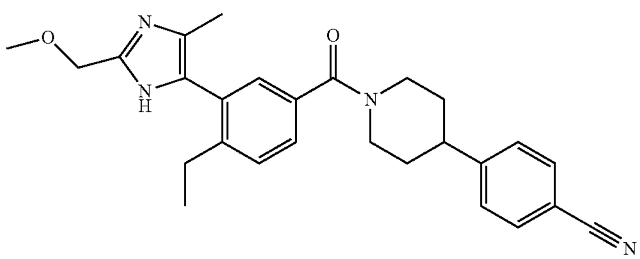 [SMILES: CCc1ccc(C(=O)N2CCC(c3ccc(C#N)cc3)CC2)cc1-c1[nH]c(COC)nc1C] | 19 | 0.030 | 0.042 |
| 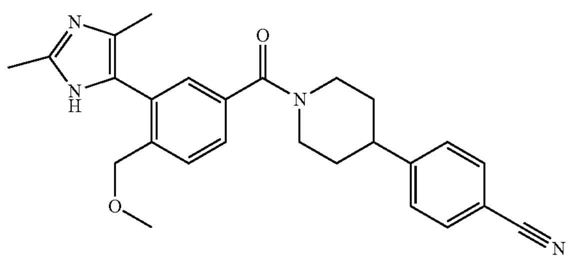 [SMILES: COCc1ccc(C(=O)N2CCC(c3ccc(C#N)cc3)CC2)cc1-c1[nH]c(C)nc1C] | 20 | 0.165 | 0.130 |
| 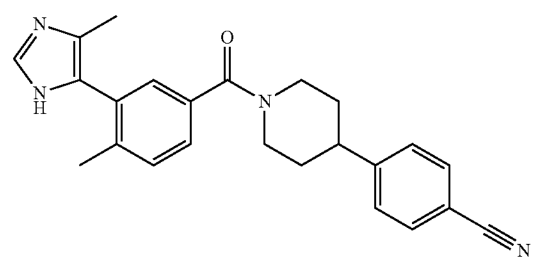 [SMILES: Cc1ccc(C(=O)N2CCC(c3ccc(C#N)cc3)CC2)cc1-c1[nH]cnc1C] | 21 | 0.207 | 0.390 |

TABLE 26-continued

Compounds of the present disclosure.

| Structure | Cpd | Hu FASN IC50 (μM) | HCV GT1b EC50 (μM) |
|---|---|---|---|
| 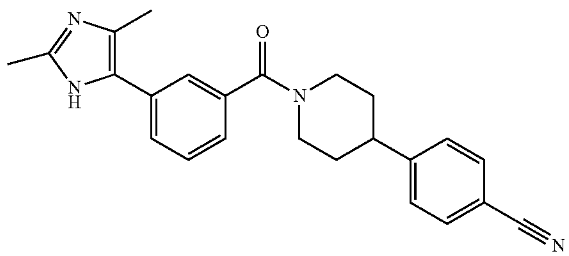 [SMILES: Cc1nc(C)c(-c2cccc(C(=O)N3CCC(c4ccc(C#N)cc4)CC3)c2)[nH]1] | 22 | 1.690 | 2.220 |
| 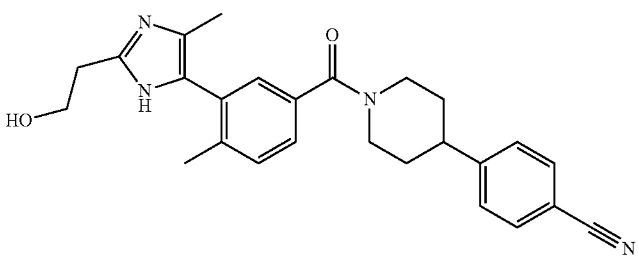 [SMILES: Cc1ccc(C(=O)N2CCC(c3ccc(C#N)cc3)CC2)cc1-c1[nH]c(CCO)nc1C] | 23 | 0.029 | 0.093 |
| 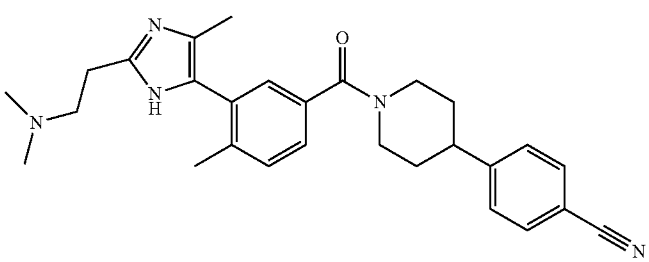 [SMILES: Cc1ccc(C(=O)N2CCC(c3ccc(C#N)cc3)CC2)cc1-c1[nH]c(CCN(C)C)nc1C] | 24 | 0.041 | 0.097 |
| 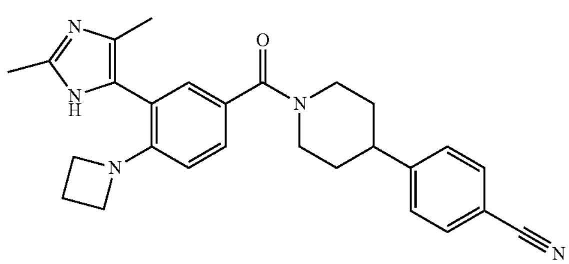 [SMILES: Cc1nc(C)c(-c2cc(C(=O)N3CCC(c4ccc(C#N)cc4)CC3)ccc2N2CCC2)[nH]1] | 25 | | 0.019 |
| 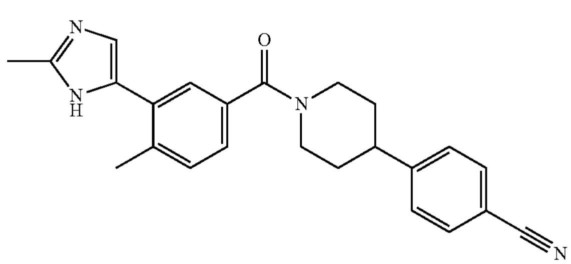 [SMILES: Cc1ncc(-c2cc(C(=O)N3CCC(c4ccc(C#N)cc4)CC3)ccc2C)[nH]1] | 26 | 0.245 | |

TABLE 26-continued

Compounds of the present disclosure.

| Structure | Cpd | Hu FASN IC50 (μM) | HCV GT1b EC50 (μM) |
|---|---|---|---|
| (structure) | 27 | 0.009 | 0.005 |
| (structure) | 28 | 0.048 | 0.011 |
| (structure) | 29 | 0.024 | 0.009 |
| (structure) | 30 | 0.016 | 0.013 |
| (structure) | 31 | 0.011 | 0.003 |

TABLE 26-continued

Compounds of the present disclosure.

| Structure | Cpd | Hu FASN IC50 (μM) | HCV GT1b EC50 (μM) |
|---|---|---|---|
| (structure) | 32 | 0.012 | 0.003 |
| (structure) | 33 | 0.080 | |
| (structure) | 34 | 0.048 | |
| (structure) | 35 | 2.870 | 2.780 |
| (structure) | 36 | 9.190 | |
| (structure) | 37 | 0.032 | 0.032 |

TABLE 26-continued
Compounds of the present disclosure.
| Structure | Cpd | Hu FASN IC50 (µM) | HCV GT1b EC50 (µM) |
|---|---|---|---|
| 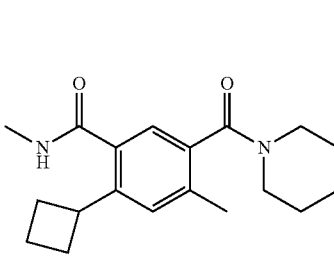 | 38 | 0.104 | 0.640 |
| 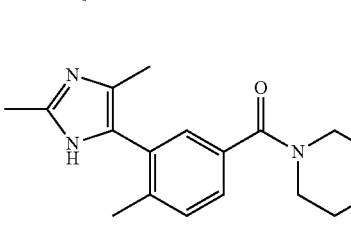 | 39 | 0.420 | 0.980 |
| 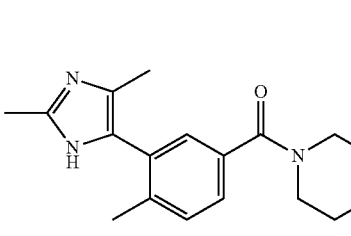 | 40 | 0.620 | 1.700 |
| 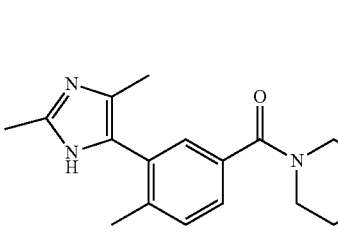 | 41 | 50.000 | |
| 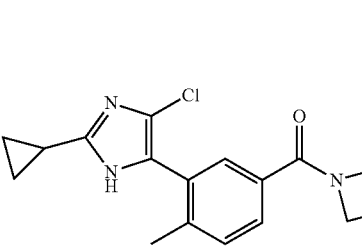 | 42 | 0.032 | 0.115 |
| 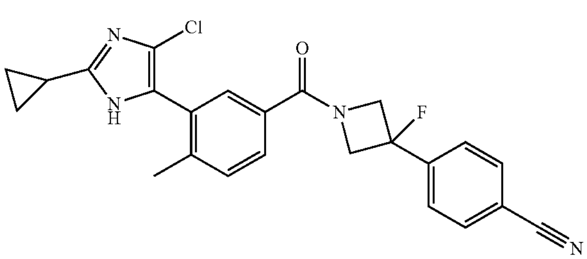 [SMILES: Cc1ccc(C(=O)N2CC(F)(c3ccc(C#N)cc3)C2)cc1-c1[nH]c(C2CC2)nc1Cl] | 43 | 0.012 | 0.004 |

TABLE 26-continued
Compounds of the present disclosure.
| Structure | Cpd | Hu FASN IC50 (μM) | HCV GT1b EC50 (μM) |
|---|---|---|---|
| 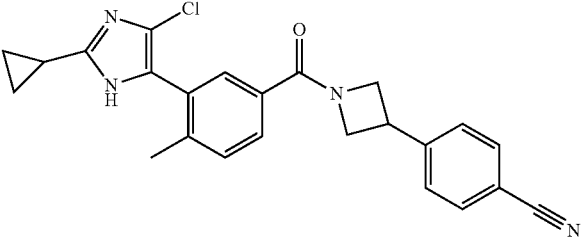 [SMILES: Cc1ccc(C(=O)N2CC(c3ccc(C#N)cc3)C2)cc1-c1[nH]c(C2CC2)nc1Cl] | 44 | 0.007 | 0.003 |
| 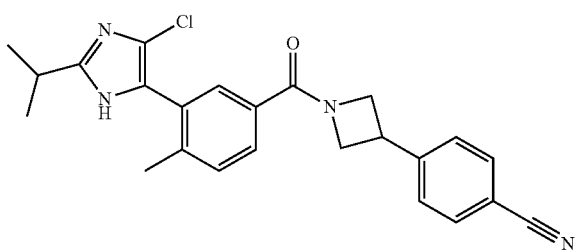 [SMILES: Cc1ccc(C(=O)N2CC(c3ccc(C#N)cc3)C2)cc1-c1[nH]c(C(C)C)nc1Cl] | 45 | 0.009 | 0.002 |
| 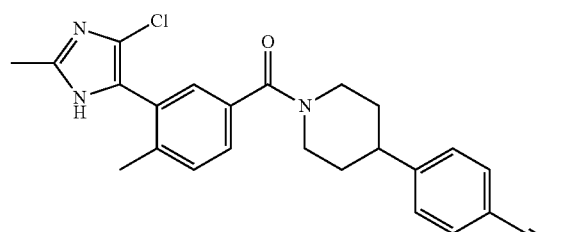 | 46 | 0.005 | 0.004 |
| 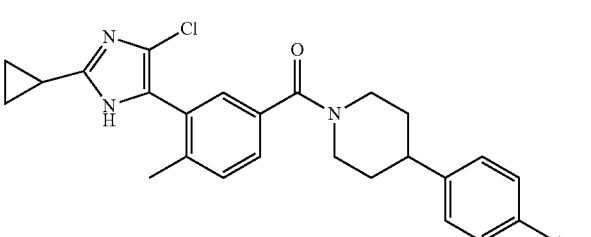 | 47 | 0.007 | 0.003 |
| 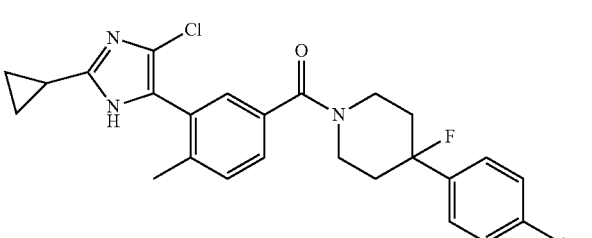 | 48 | 0.009 | 0.004 |

TABLE 26-continued

Compounds of the present disclosure.

| Structure | Cpd | Hu FASN IC50 (μM) | HCV GT1b EC50 (μM) |
|---|---|---|---|
| 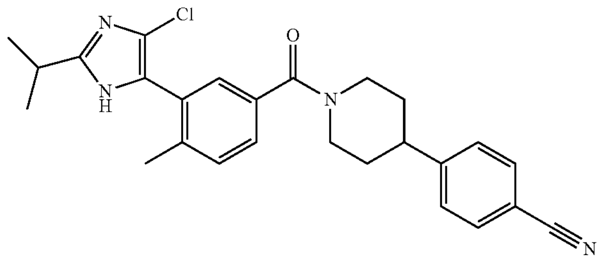 [SMILES: Cc1ccc(C(=O)N2CCC(c3ccc(C#N)cc3)CC2)cc1-c1[nH]c(C(C)C)nc1Cl] | 49 | 0.009 | 0.003 |
| 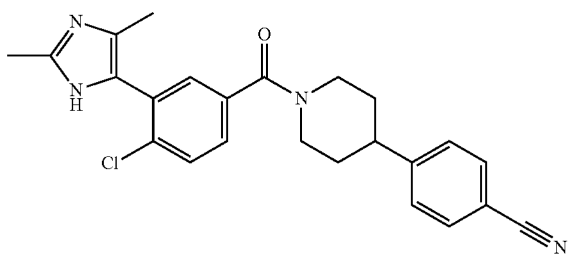 [SMILES: Cc1nc(C)c(-c2cc(C(=O)N3CCC(c4ccc(C#N)cc4)CC3)ccc2Cl)[nH]1] | 50 | 0.145 | 0.250 |
| 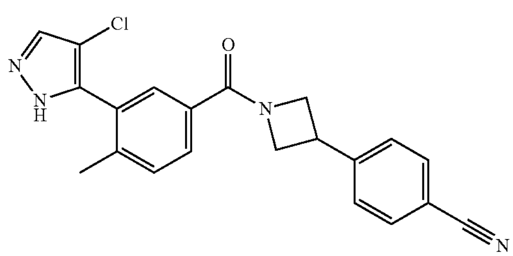 [SMILES: Cc1ccc(C(=O)N2CC(c3ccc(C#N)cc3)C2)cc1-c1[nH]ncc1Cl] | 51 | 0.019 | 0.051 |
| 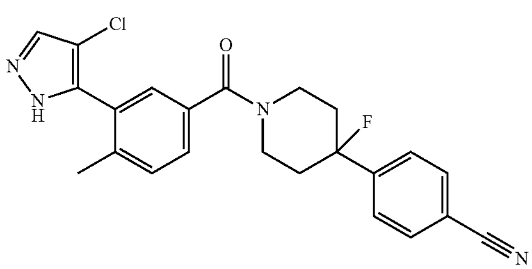 [SMILES: Cc1ccc(C(=O)N2CCC(F)(c3ccc(C#N)cc3)CC2)cc1-c1[nH]ncc1Cl] | 52 | 0.046 | 0.280 |
| 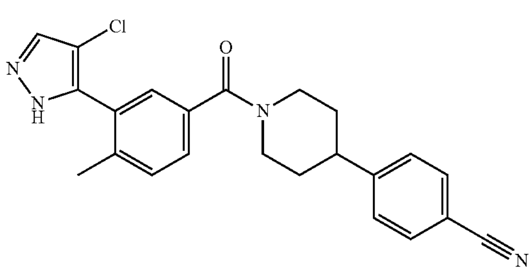 [SMILES: Cc1ccc(C(=O)N2CCC(c3ccc(C#N)cc3)CC2)cc1-c1[nH]ncc1Cl] | 53 | 0.033 | 0.100 |

TABLE 26-continued
Compounds of the present disclosure.
| Structure | Cpd | Hu FASN IC50 (μM) | HCV GT1b EC50 (μM) |
|---|---|---|---|
| 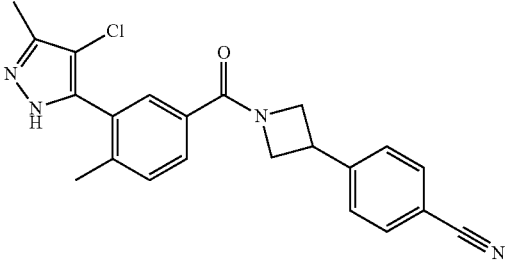 [SMILES: Cc1ccc(C(=O)N2CC(c3ccc(C#N)cc3)C2)cc1-c1[nH]nc(C)c1Cl] | 54 | 0.020 | 0.033 |
| 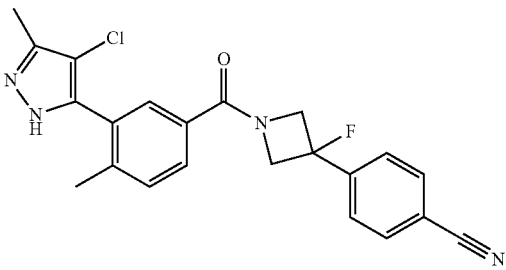 [SMILES: Cc1ccc(C(=O)N2CC(F)(c3ccc(C#N)cc3)C2)cc1-c1[nH]nc(C)c1Cl] | 55 | 0.086 | 0.320 |
| 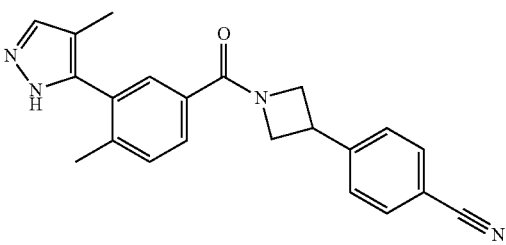 [SMILES: Cc1ccc(C(=O)N2CC(c3ccc(C#N)cc3)C2)cc1-c1[nH]ncc1C] | 56 | 0.021 | 0.032 |
| 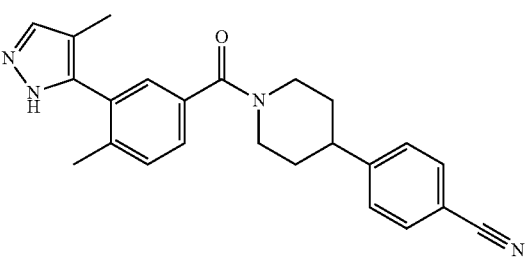 [SMILES: Cc1ccc(C(=O)N2CCC(c3ccc(C#N)cc3)CC2)cc1-c1[nH]ncc1C] | 57 | 0.097 | |
| 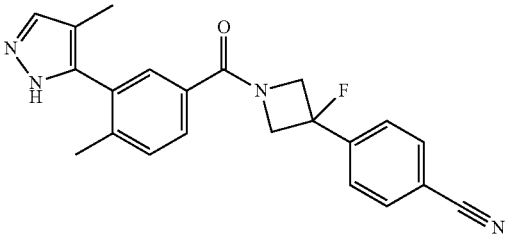 [SMILES: Cc1ccc(C(=O)N2CC(F)(c3ccc(C#N)cc3)C2)cc1-c1[nH]ncc1C] | 58 | 0.102 | 0.310 |

US 10,053,450 B2
TABLE 26-continued
Compounds of the present disclosure.
| Structure | Cpd | Hu FASN IC50 (μM) | HCV GT1b EC50 (μM) |
|---|---|---|---|
| 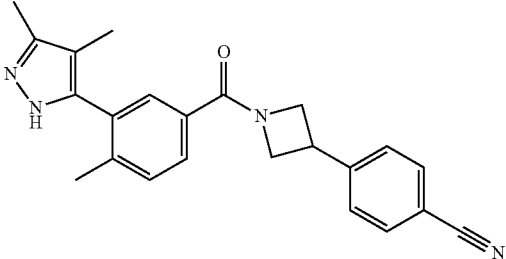 [SMILES: Cc1ccc(C(=O)N2CC(c3ccc(C#N)cc3)C2)cc1-c1[nH]nc(C)c1C] | 59 | 0.033 | 0.063 |
| 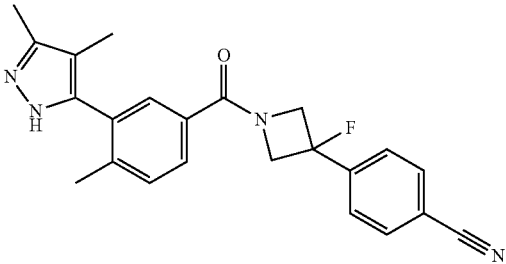 [SMILES: Cc1ccc(C(=O)N2CC(F)(c3ccc(C#N)cc3)C2)cc1-c1[nH]nc(C)c1C] | 60 | 0.110 | 0.360 |
| 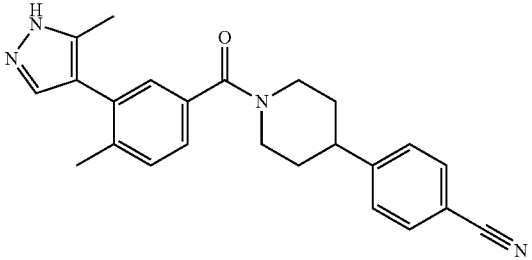 [SMILES: Cc1ccc(C(=O)N2CCC(c3ccc(C#N)cc3)CC2)cc1-c1cn[nH]c1C] | 61 | 0.310 | |
| 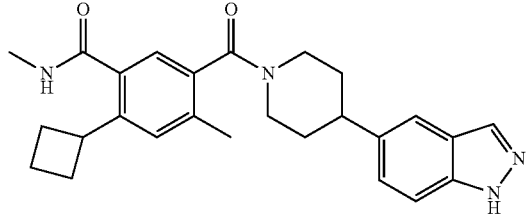 [SMILES: CNC(=O)c1cc(C(=O)N2CCC(c3ccc4[nH]ncc4c3)CC2)c(C)cc1C1CCC1] | 62 | 0.650 | 0.760 |
| 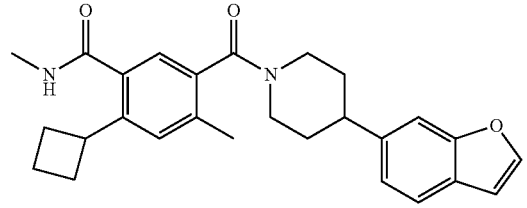 [SMILES: CNC(=O)c1cc(C(=O)N2CCC(c3ccc4ccoc4c3)CC2)c(C)cc1C1CCC1] | 63 | 1.180 | 6.170 |
| 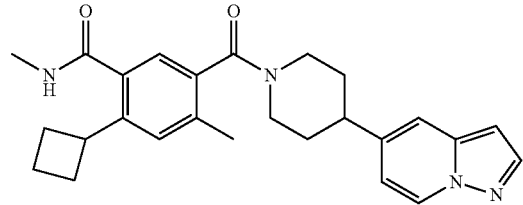 [SMILES: CNC(=O)c1cc(C(=O)N2CCC(c3ccn4nccc4c3)CC2)c(C)cc1C1CCC1] | 64 | 1.550 | 1.940 |

TABLE 26-continued

Compounds of the present disclosure.

| Structure | Cpd | Hu FASN IC50 (μM) | HCV GT1b EC50 (μM) |
|---|---|---|---|
| 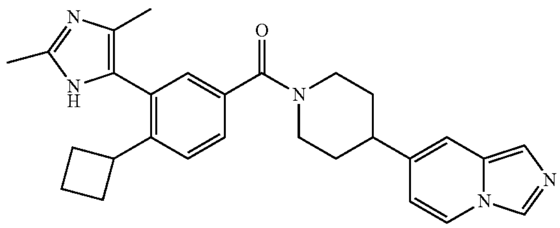 [SMILES: Cc1nc(C)c(-c2cc(C(=O)N3CCC(c4ccn5cncc5c4)CC3)ccc2C2CCC2)[nH]1] | 65 | 0.050 | 0.096 |
| 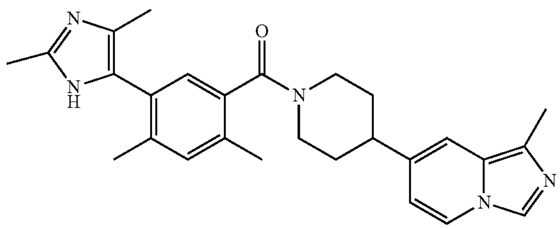 [SMILES: Cc1nc(C)c(-c2cc(C(=O)N3CCC(c4ccn5cnc(C)c5c4)CC3)c(C)cc2C)[nH]1] | 66 | 2.370 | 15.000 |
| 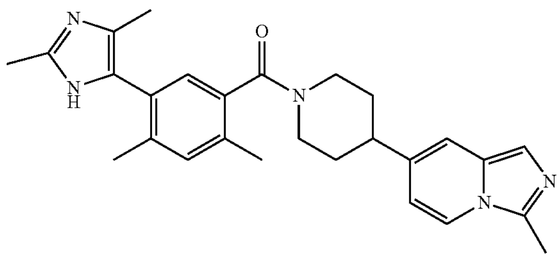 [SMILES: Cc1nc(C)c(-c2cc(C(=O)N3CCC(c4ccn5c(C)ncc5c4)CC3)c(C)cc2C)[nH]1] | 67 | 2.490 | |
| 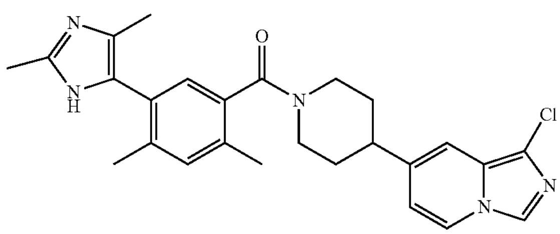 | 68 | 0.150 | 0.240 |
| 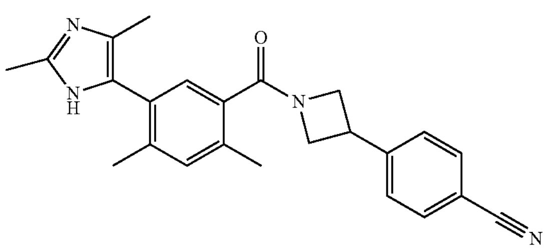 [SMILES: Cc1nc(C)c(-c2cc(C(=O)N3CC(c4ccc(C#N)cc4)C3)c(C)cc2C)[nH]1] | 69 | 0.018 | 0.016 |
| 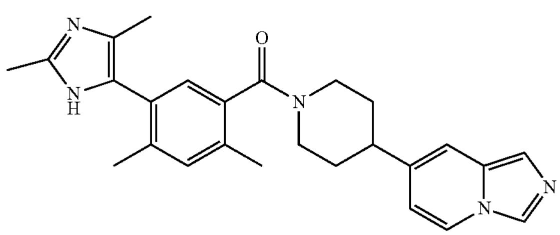 [SMILES: Cc1nc(C)c(-c2cc(C(=O)N3CCC(c4ccn5cncc5c4)CC3)c(C)cc2C)[nH]1] | 70 | 0.205 | 0.680 |

TABLE 26-continued
Compounds of the present disclosure.
| Structure | Cpd | Hu FASN IC50 (μM) | HCV GT1b EC50 (μM) |
|---|---|---|---|
| 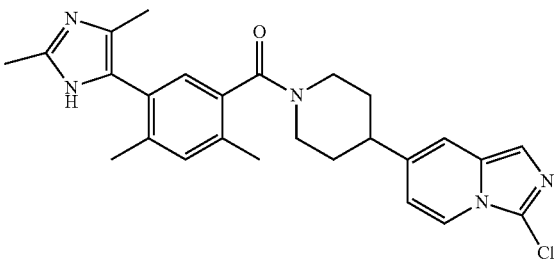 [SMILES: Cc1nc(C)c(-c2cc(C(=O)N3CCC(c4ccn5c(Cl)ncc5c4)CC3)c(C)cc2C)[nH]1] | 71 | 0.300 | 0.710 |
| 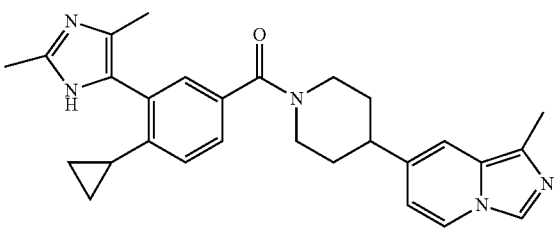 [SMILES: Cc1nc(C)c(-c2cc(C(=O)N3CCC(c4ccn5cnc(C)c5c4)CC3)ccc2C2CC2)[nH]1] | 72 | 0.420 | 2.220 |
| 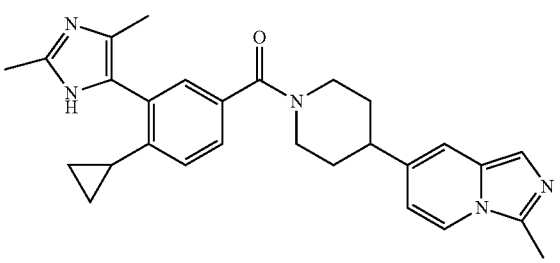 [SMILES: Cc1nc(C)c(-c2cc(C(=O)N3CCC(c4ccn5c(C)ncc5c4)CC3)ccc2C2CC2)[nH]1] | 73 | 1.000 | 2.570 |
| 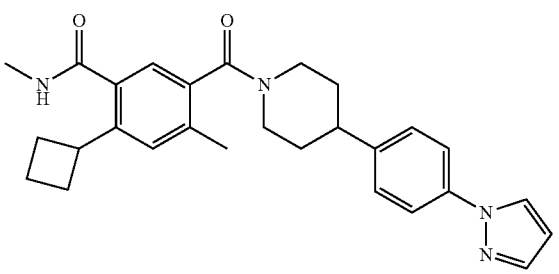 [SMILES: CNC(=O)c1cc(C(=O)N2CCC(c3ccc(-n4cccn4)cc3)CC2)c(C)cc1C1CCC1] | 74 | 0.460 | 0.730 |
| 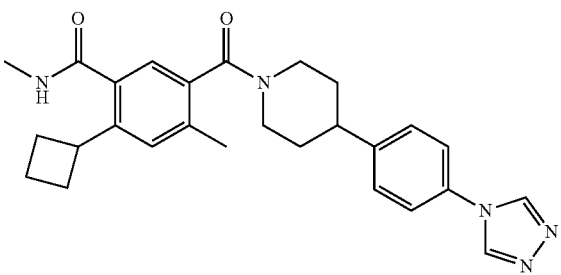 [SMILES: CNC(=O)c1cc(C(=O)N2CCC(c3ccc(-n4cnnc4)cc3)CC2)c(C)cc1C1CCC1] | 75 | 0.073 | 0.111 |
| 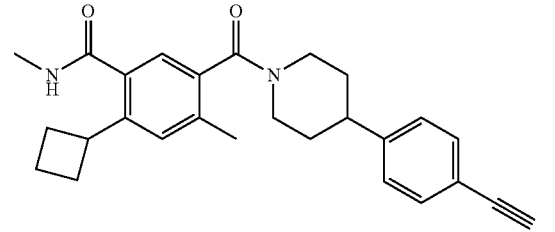 [SMILES: C#Cc1ccc(C2CCN(C(=O)c3cc(C(=O)NC)c(C4CCC4)cc3C)CC2)cc1] | 76 | 0.069 | 0.245 |

TABLE 26-continued
Compounds of the present disclosure.
| Structure | Cpd | Hu FASN IC50 (μM) | HCV GT1b EC50 (μM) |
|---|---|---|---|
| 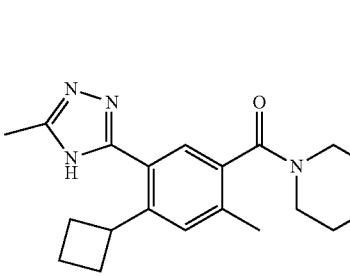 | 77 | 0.125 | 0.170 |
| 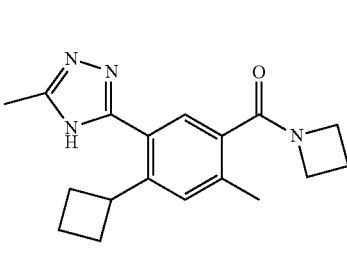 | 78 | 3.670 | 5.420 |
| 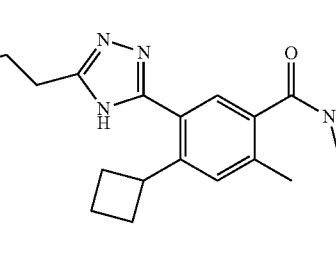 | 79 | 0.059 | 0.150 |
| 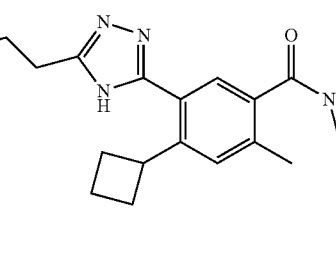 | 80 | 0.057 | 0.295 |
| 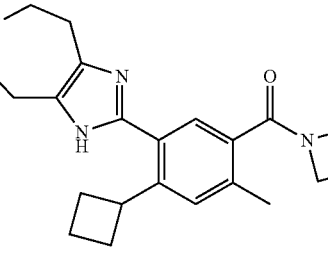 | 81 | 0.054 | 0.200 |
| 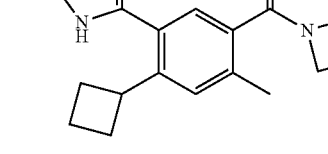 | 82 | 0.020 | 0.036 |

TABLE 26-continued

Compounds of the present disclosure.

| Structure | Cpd | Hu FASN IC50 (µM) | HCV GT1b EC50 (µM) |
|---|---|---|---|
| 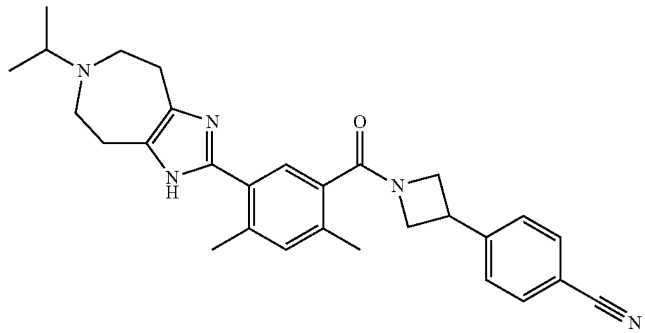 [SMILES: Cc1cc(C)c(-c2nc3c([nH]2)CCN(C(C)C)CC3)cc1C(=O)N1CC(c2ccc(C#N)cc2)C1] | 83 | 0.062 | 0.089 |
| 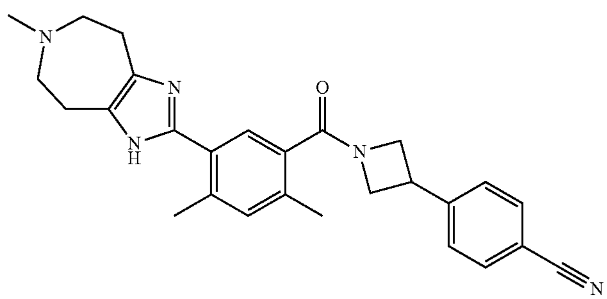 [SMILES: Cc1cc(C)c(-c2nc3c([nH]2)CCN(C)CC3)cc1C(=O)N1CC(c2ccc(C#N)cc2)C1] | 84 | 0.112 | 0.540 |
| 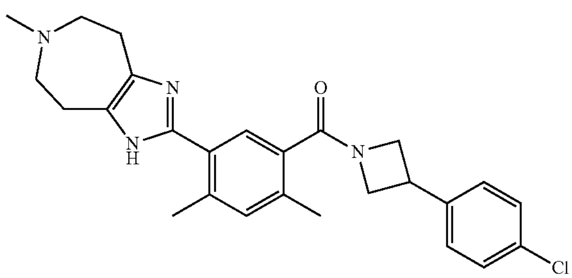 [SMILES: Cc1cc(C)c(-c2nc3c([nH]2)CCN(C)CC3)cc1C(=O)N1CC(c2ccc(Cl)cc2)C1] | 85 | 0.057 | |
| 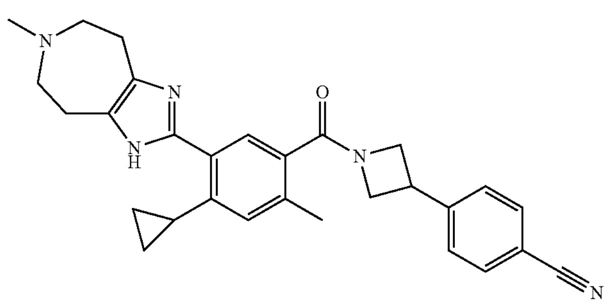 [SMILES: Cc1cc(C2CC2)c(-c2nc3c([nH]2)CCN(C)CC3)cc1C(=O)N1CC(c2ccc(C#N)cc2)C1] | 86 | 0.086 | 0.850 |
| 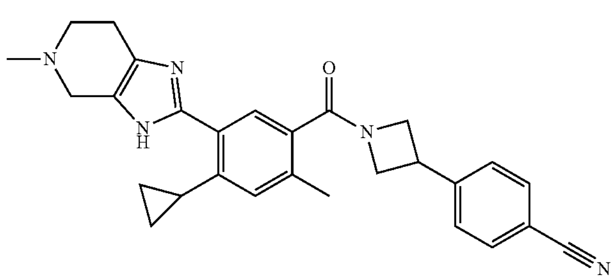 [SMILES: Cc1cc(C2CC2)c(-c2nc3c([nH]2)CN(C)CC3)cc1C(=O)N1CC(c2ccc(C#N)cc2)C1] | 87 | 0.040 | 0.029 |

US 10,053,450 B2
TABLE 26-continued
Compounds of the present disclosure.
| Structure | Cpd | Hu FASN IC50 (µM) | HCV GT1b EC50 (µM) |
|---|---|---|---|
| 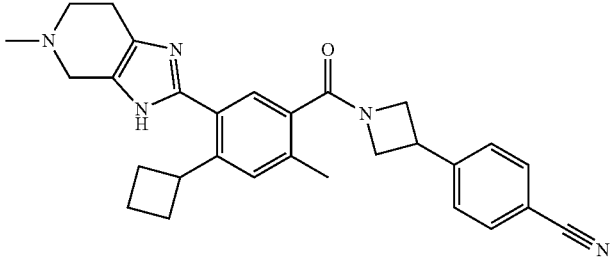 [SMILES: Cc1cc(C2CCC2)c(-c2nc3c([nH]2)CN(C)CC3)cc1C(=O)N1CC(c2ccc(C#N)cc2)C1] | 88 | 0.021 | 0.009 |
| 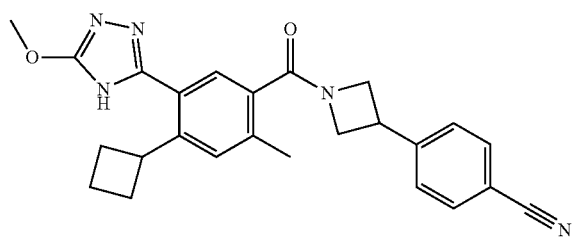 [SMILES: COc1nnc(-c2cc(C(=O)N3CC(c4ccc(C#N)cc4)C3)c(C)cc2C2CCC2)[nH]1] | 89 | 0.049 | 0.087 |
| 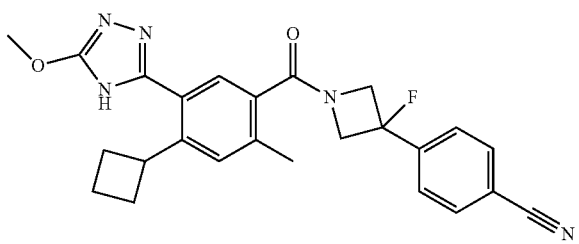 [SMILES: COc1nnc(-c2cc(C(=O)N3CC(F)(c4ccc(C#N)cc4)C3)c(C)cc2C2CCC2)[nH]1] | 90 | 0.071 | 0.165 |
| 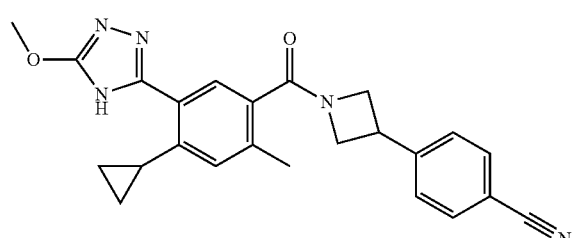 | 91 | 0.140 | 0.140 |
| 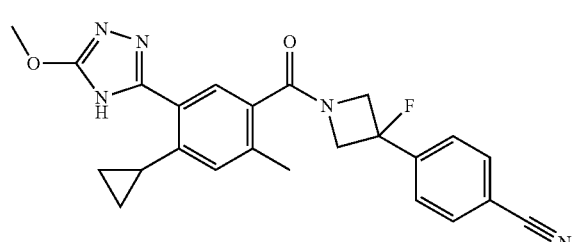 | 92 | 0.140 | 0.230 |
| 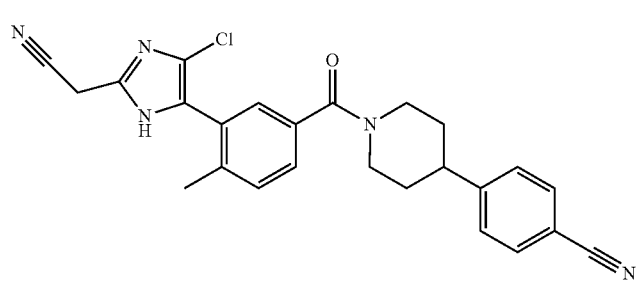 [SMILES: Cc1ccc(C(=O)N2CCC(c3ccc(C#N)cc3)CC2)cc1-c1[nH]c(CC#N)nc1Cl] | 93 | 0.034 | |

TABLE 26-continued

Compounds of the present disclosure.

| Structure | Cpd | Hu FASN IC50 (μM) | HCV GT1b EC50 (μM) |
|---|---|---|---|
| 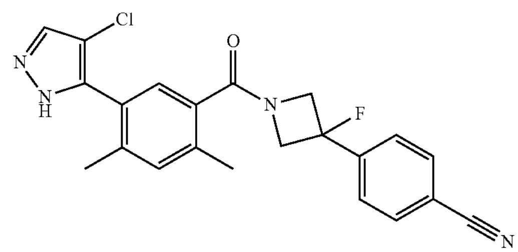 [SMILES: Cc1cc(C)c(-c2[nH]ncc2Cl)cc1C(=O)N1CC(F)(c2ccc(C#N)cc2)C1] | 94 | 0.029 | 0.630 |
| 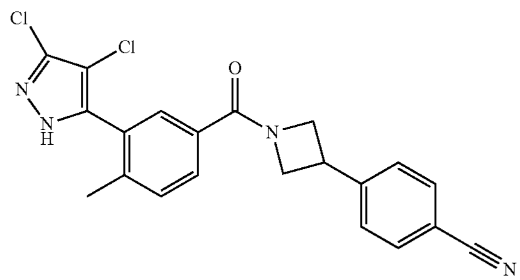 [SMILES: Cc1ccc(C(=O)N2CC(c3ccc(C#N)cc3)C2)cc1-c1[nH]nc(Cl)c1Cl] | 95 | 0.030 | 0.008 |
| 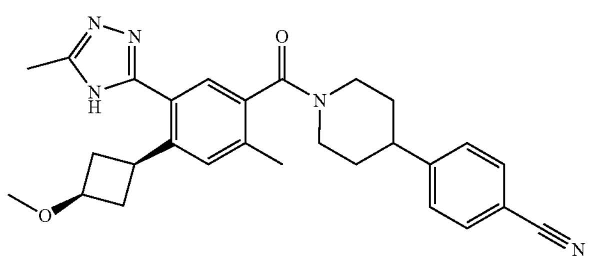 [SMILES: CO[C@H]1C[C@@H](c2cc(C)c(C(=O)N3CCC(c4ccc(C#N)cc4)CC3)cc2-c2nnc(C)[nH]2)C1] | 96 | 0.270 | |
| 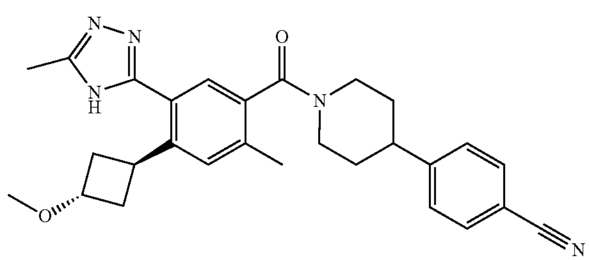 [SMILES: CO[C@H]1C[C@H](c2cc(C)c(C(=O)N3CCC(c4ccc(C#N)cc4)CC3)cc2-c2nnc(C)[nH]2)C1] | 97 | 0.190 | |
| 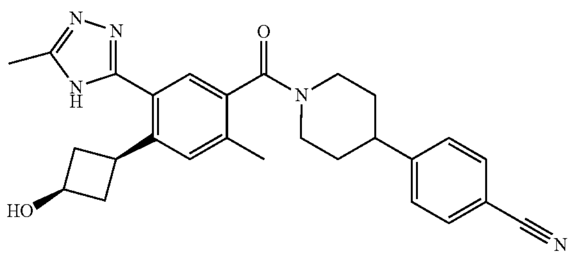 [SMILES: Cc1nnc(-c2cc(C(=O)N3CCC(c4ccc(C#N)cc4)CC3)c(C)cc2[C@H]2C[C@@H](O)C2)[nH]1] | 98 | 0.240 | 0.960 |

TABLE 26-continued

Compounds of the present disclosure.

| Structure | Cpd | Hu FASN IC50 (μM) | HCV GT1b EC50 (μM) |
|---|---|---|---|
| 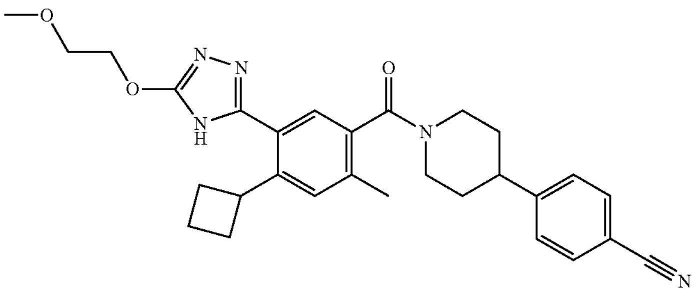 [SMILES: COCCOc1nnc(-c2cc(C(=O)N3CCC(c4ccc(C#N)cc4)CC3)c(C)cc2C2CCC2)[nH]1] | 99 | 0.045 |  |
| 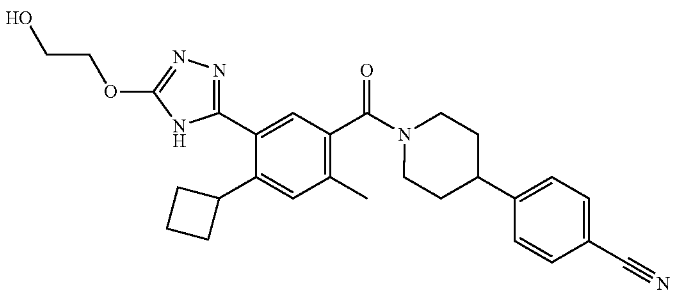 [SMILES: Cc1cc(C2CCC2)c(-c2nnc(OCCO)[nH]2)cc1C(=O)N1CCC(c2ccc(C#N)cc2)CC1] | 100 | 0.055 | 0.070 |
| 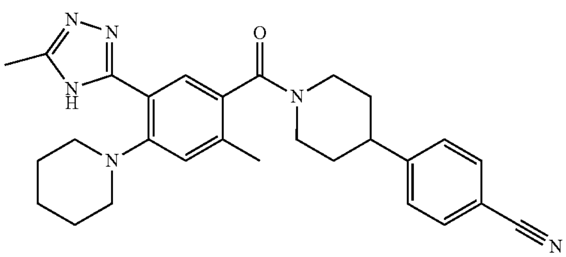 | 101 | 0.530 |  |
| 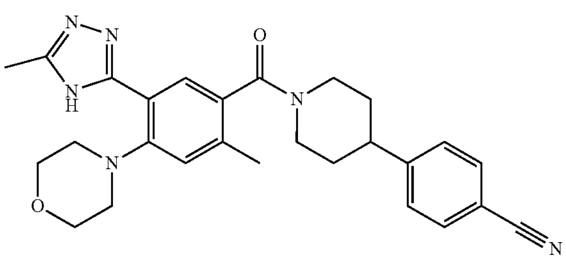 [SMILES: Cc1nnc(-c2cc(C(=O)N3CCC(c4ccc(C#N)cc4)CC3)c(C)cc2N2CCOCC2)[nH]1] | 102 | 0.890 |  |
| 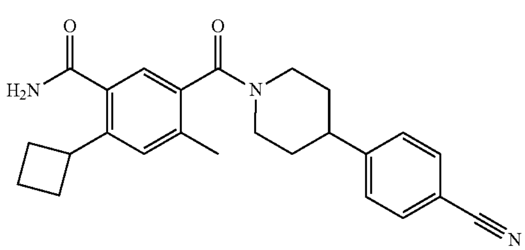 [SMILES: Cc1cc(C2CCC2)c(C(N)=O)cc1C(=O)N1CCC(c2ccc(C#N)cc2)CC1] | 103 | 0.135 |  |

TABLE 26-continued

Compounds of the present disclosure.

| Structure | Cpd | Hu FASN IC50 (μM) | HCV GT1b EC50 (μM) |
|---|---|---|---|
| 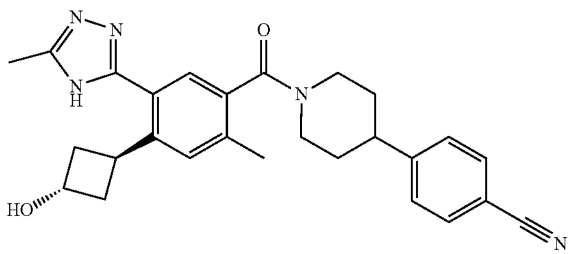 [SMILES: Cc1nnc(-c2cc(C(=O)N3CCC(c4ccc(C#N)cc4)CC3)c(C)cc2[C@H]2C[C@H](O)C2)[nH]1] | 104 | 0.070 | 0.270 |
| 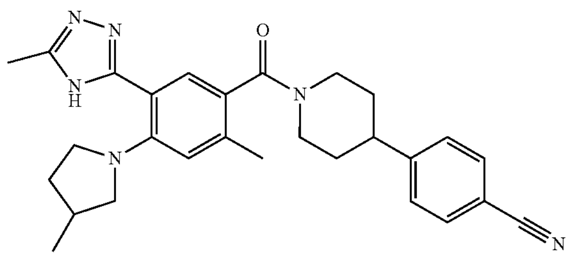 [SMILES: Cc1nnc(-c2cc(C(=O)N3CCC(c4ccc(C#N)cc4)CC3)c(C)cc2N2CCC(C)C2)[nH]1] | 105 | 0.070 | 0.030 |
| 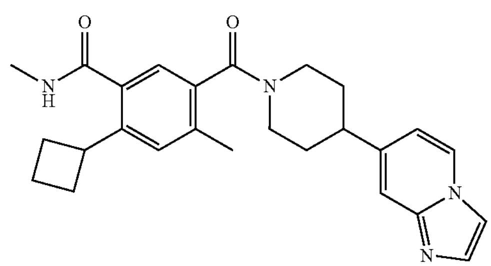 [SMILES: CNC(=O)c1cc(C(=O)N2CCC(c3ccn4ccnc4c3)CC2)c(C)cc1C1CCC1] | 106 | 50.000 | 20.000 |
| 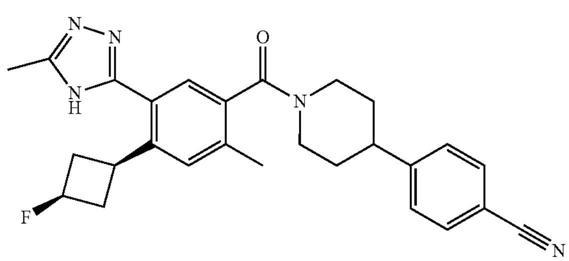 [SMILES: Cc1nnc(-c2cc(C(=O)N3CCC(c4ccc(C#N)cc4)CC3)c(C)cc2[C@H]2C[C@@H](F)C2)[nH]1] | 107 | 5.580 | 20.000 |
| 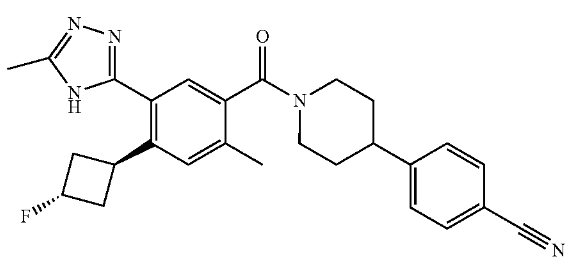 [SMILES: Cc1nnc(-c2cc(C(=O)N3CCC(c4ccc(C#N)cc4)CC3)c(C)cc2[C@H]2C[C@H](F)C2)[nH]1] | 108 | 2.250 | 15.000 |
| 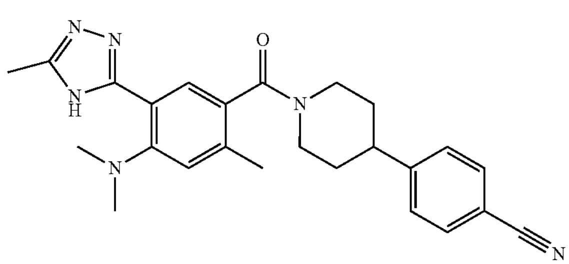 [SMILES: Cc1nnc(-c2cc(C(=O)N3CCC(c4ccc(C#N)cc4)CC3)c(C)cc2N(C)C)[nH]1] | 109 | 0.280 | 0.350 |

TABLE 26-continued

Compounds of the present disclosure.

| Structure | Cpd | Hu FASN IC50 (µM) | HCV GT1b EC50 (µM) |
|---|---|---|---|
| 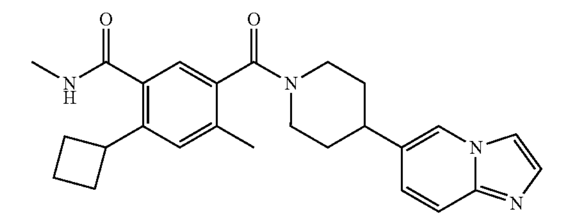 [SMILES: CNC(=O)c1cc(C(=O)N2CCC(c3ccc4nccn4c3)CC2)c(C)cc1C1CCC1] | 110 | 11.020 | 20.000 |
| 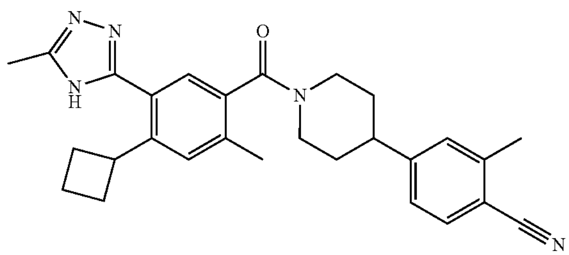 [SMILES: Cc1nnc(-c2cc(C(=O)N3CCC(c4ccc(C#N)c(C)c4)CC3)c(C)cc2C2CCC2)[nH]1] | 111 | 0.230 | 1.980 |
| 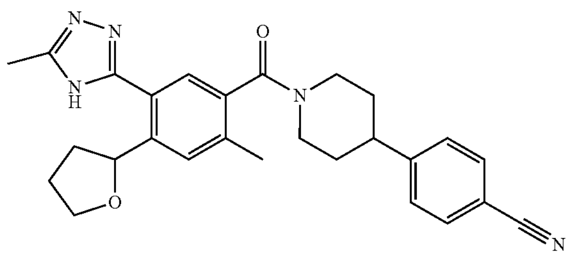 [SMILES: Cc1nnc(-c2cc(C(=O)N3CCC(c4ccc(C#N)cc4)CC3)c(C)cc2C2CCCO2)[nH]1] | 112 | 0.840 | 1.490 |
| 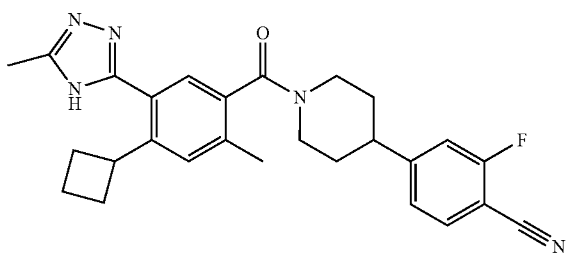 [SMILES: Cc1nnc(-c2cc(C(=O)N3CCC(c4ccc(C#N)c(F)c4)CC3)c(C)cc2C2CCC2)[nH]1] | 113 | 0.145 | 0.270 |
| 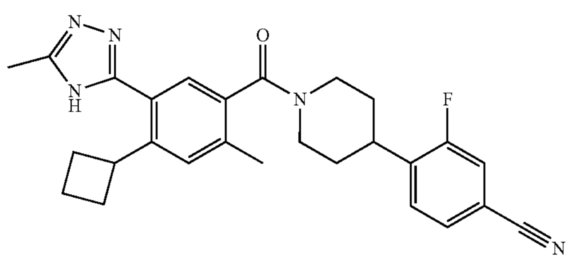 [SMILES: Cc1nnc(-c2cc(C(=O)N3CCC(c4ccc(C#N)cc4F)CC3)c(C)cc2C2CCC2)[nH]1] | 114 | 0.200 | 0.450 |
| 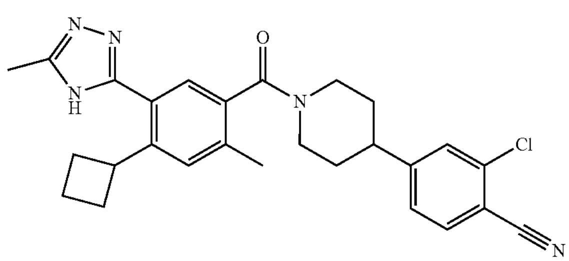 [SMILES: Cc1nnc(-c2cc(C(=O)N3CCC(c4ccc(C#N)c(Cl)c4)CC3)c(C)cc2C2CCC2)[nH]1] | 115 | 0.320 | 1.210 |

TABLE 26-continued

Compounds of the present disclosure.

| Structure | Cpd | Hu FASN IC50 (μM) | HCV GT1b EC50 (μM) |
|---|---|---|---|
| 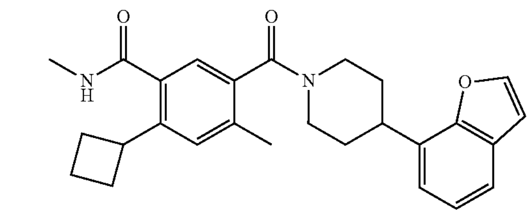 [SMILES: CNC(=O)c1cc(C(=O)N2CCC(c3cccc4ccoc34)CC2)c(C)cc1C1CCC1] | 116 | 50.000 | 20.000 |
| 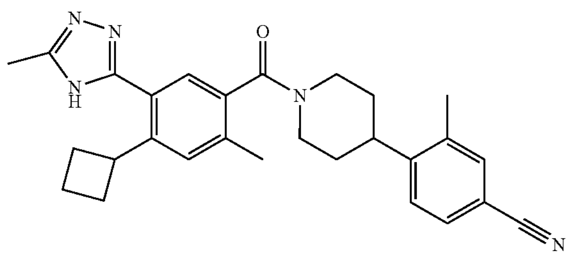 | 117 | 0.980 | 3.330 |
| 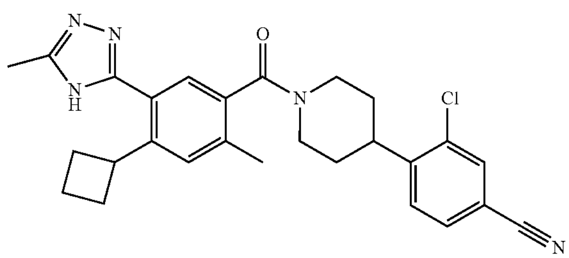 [SMILES: Cc1nnc(-c2cc(C(=O)N3CCC(c4ccc(C#N)cc4Cl)CC3)c(C)cc2C2CCC2)[nH]1] | 118 | 0.680 | 3.180 |
| 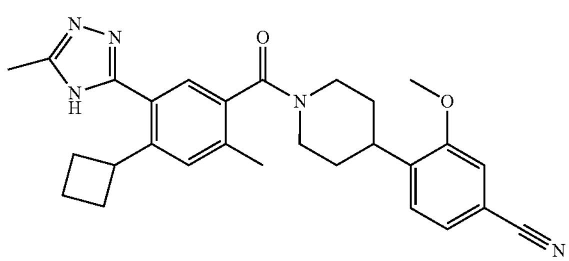 [SMILES: COc1cc(C#N)ccc1C1CCN(C(=O)c2cc(-c3nnc(C)[nH]3)c(C3CCC3)cc2C)CC1] | 119 | 4.480 | 10.000 |
| 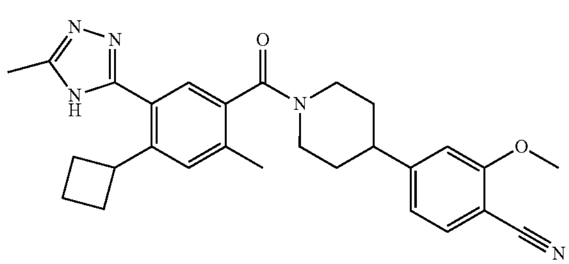 | 120 | 1.300 | 10.000 |
| 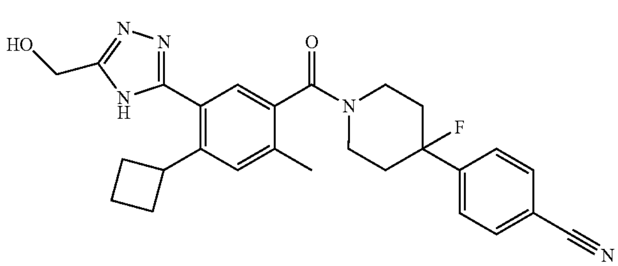 [SMILES: Cc1cc(C2CCC2)c(-c2nnc(CO)[nH]2)cc1C(=O)N1CCC(F)(c2ccc(C#N)cc2)CC1] | 121 | 0.030 | 0.240 |

TABLE 26-continued
Compounds of the present disclosure.
| Structure | Cpd | Hu FASN IC50 (μM) | HCV GT1b EC50 (μM) |
|---|---|---|---|
| 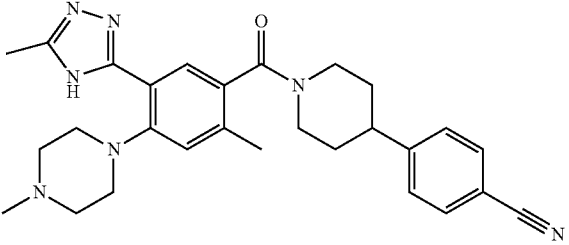 [SMILES: Cc1nnc(-c2cc(C(=O)N3CCC(c4ccc(C#N)cc4)CC3)c(C)cc2N2CCN(C)CC2)[nH]1] | 122 | 3.440 | |
| 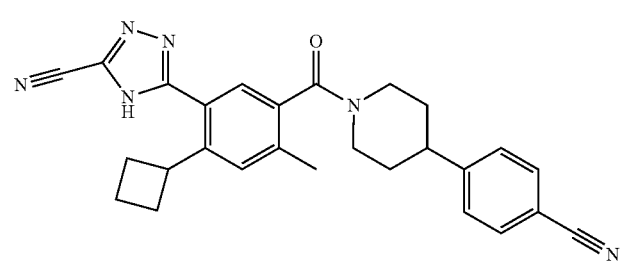 [SMILES: Cc1cc(C2CCC2)c(-c2nnc(C#N)[nH]2)cc1C(=O)N1CCC(c2ccc(C#N)cc2)CC1] | 123 | 3.710 | |
| 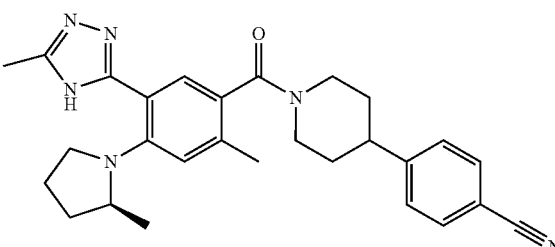 | 124 | 0.140 | 0.230 |
| 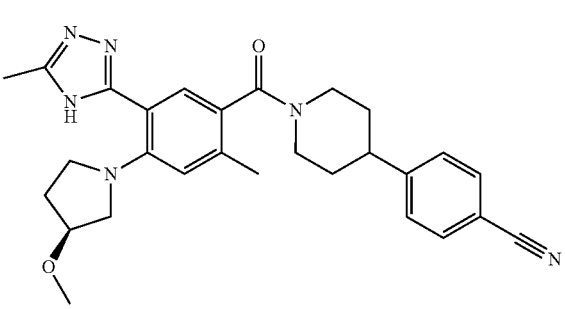 [SMILES: CO[C@H]1CCN(c2cc(C)c(C(=O)N3CCC(c4ccc(C#N)cc4)CC3)cc2-c2nnc(C)[nH]2)C1] | 125 | 0.110 | 0.110 |
| 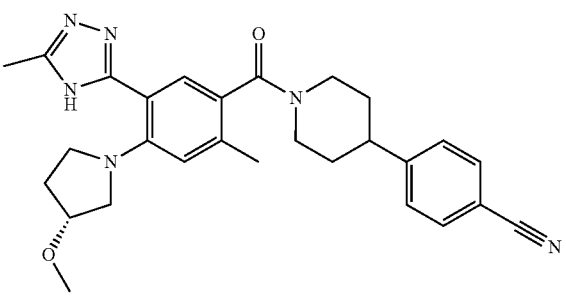 [SMILES: CO[C@@H]1CCN(c2cc(C)c(C(=O)N3CCC(c4ccc(C#N)cc4)CC3)cc2-c2nnc(C)[nH]2)C1] | 126 | 1.130 | |

TABLE 26-continued
Compounds of the present disclosure.
| Structure | Cpd | Hu FASN IC50 (μM) | HCV GT1b EC50 (μM) |
|---|---|---|---|
| 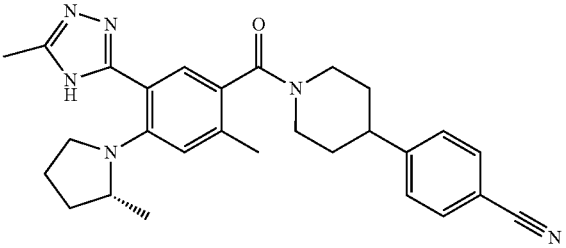 [SMILES: Cc1nnc(-c2cc(C(=O)N3CCC(c4ccc(C#N)cc4)CC3)c(C)cc2N2CCC[C@H]2C)[nH]1] | 127 | 3.270 | |
| 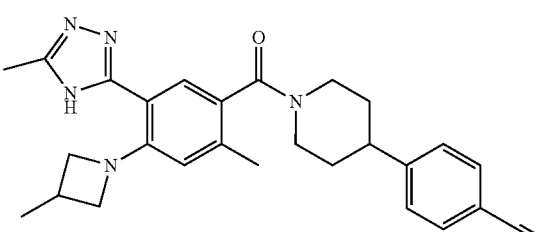 | 128 | 0.098 | 0.120 |
| 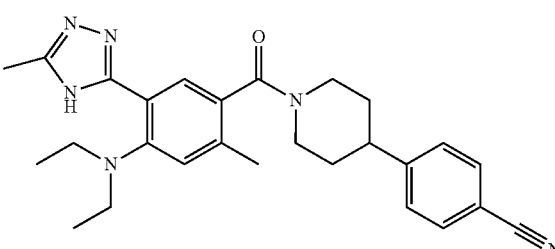 | 129 | 1.210 | 2.150 |
| 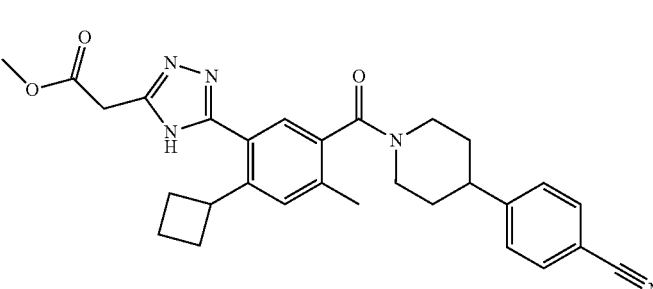 | 130 | 0.082 | 3.200 |
| 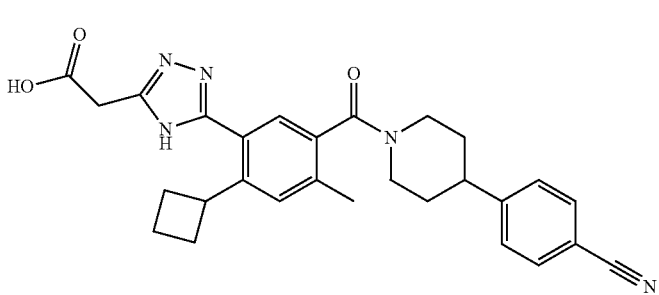 [SMILES: Cc1cc(C2CCC2)c(-c2nnc(CC(=O)O)[nH]2)cc1C(=O)N1CCC(c2ccc(C#N)cc2)CC1] | 131 | 0.185 | 2.200 |

TABLE 26-continued
Compounds of the present disclosure.
| Structure | Cpd | Hu FASN IC50 (µM) | HCV GT1b EC50 (µM) |
|---|---|---|---|
| 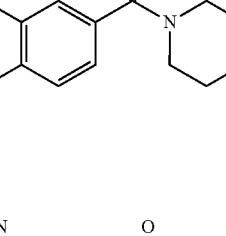 | 132 | 0.210 | 0.340 |
| 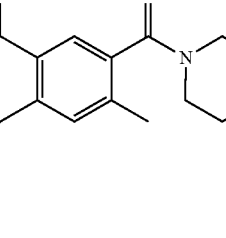 | 133 | 0.065 | 0.080 |
| 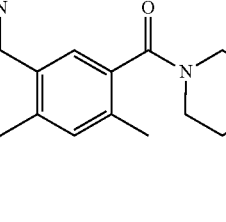 | 134 | 0.099 | 0.230 |
| 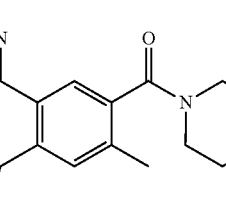 | 135 | | |
| 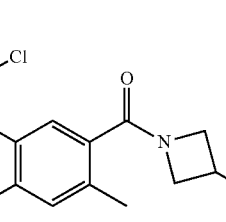 | 136 | 0.026 | 0.052 |
| 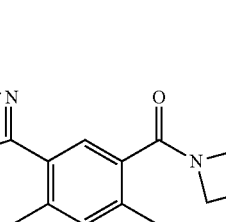 | 137 | 0.105 | 0.230 |

TABLE 26-continued

Compounds of the present disclosure.

| Structure | Cpd | Hu FASN IC50 (μM) | HCV GT1b EC50 (μM) |
|---|---|---|---|
| 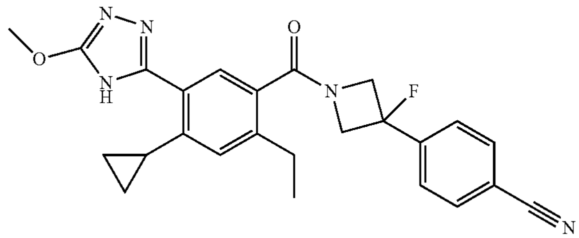 [SMILES: CCc1cc(C2CC2)c(-c2nnc(OC)[nH]2)cc1C(=O)N1CC(F)(c2ccc(C#N)cc2)C1] | 138 | 0.120 | 0.250 |
| 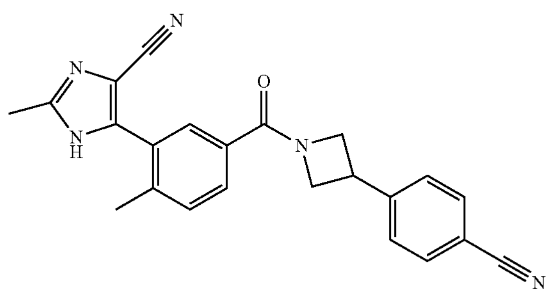 [SMILES: Cc1nc(C#N)c(-c2cc(C(=O)N3CC(c4ccc(C#N)cc4)C3)ccc2C)[nH]1] | 139 | 0.017 | 0.014 |
| 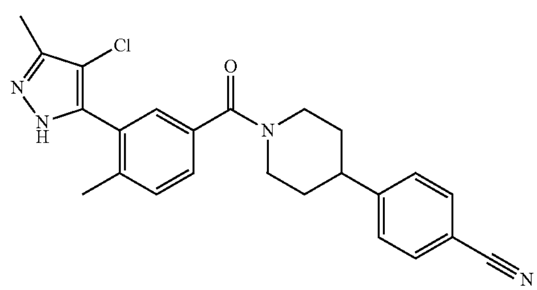 [SMILES: Cc1ccc(C(=O)N2CCC(c3ccc(C#N)cc3)CC2)cc1-c1[nH]nc(C)c1Cl] | 140 | 0.080 | 0.240 |
| 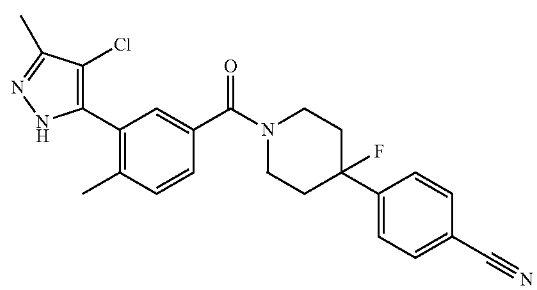 [SMILES: Cc1ccc(C(=O)N2CCC(F)(c3ccc(C#N)cc3)CC2)cc1-c1[nH]nc(C)c1Cl] | 141 | 0.099 | 0.280 |
| 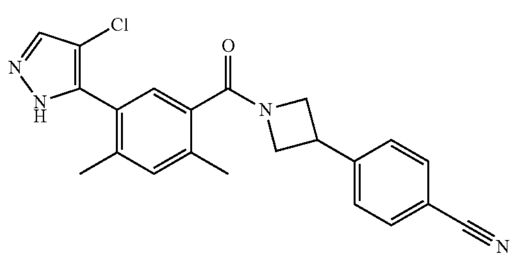 [SMILES: Cc1cc(C)c(-c2[nH]ncc2Cl)cc1C(=O)N1CC(c2ccc(C#N)cc2)C1] | 142 | 0.024 | 0.018 |

TABLE 26-continued

Compounds of the present disclosure.

| Structure | Cpd | Hu FASN IC50 (μM) | HCV GT1b EC50 (μM) |
|---|---|---|---|
| 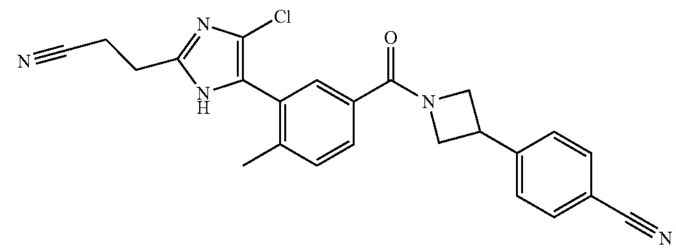 [SMILES: Cc1ccc(C(=O)N2CC(c3ccc(C#N)cc3)C2)cc1-c1[nH]c(CCC#N)nc1Cl] | 143 | 0.018 | 0.002 |
| 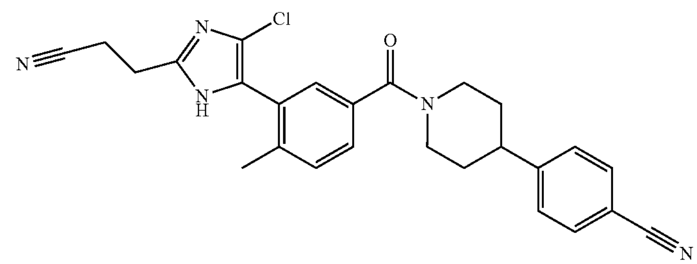 [SMILES: Cc1ccc(C(=O)N2CCC(c3ccc(C#N)cc3)CC2)cc1-c1[nH]c(CCC#N)nc1Cl] | 144 | 0.020 | 0.003 |
| 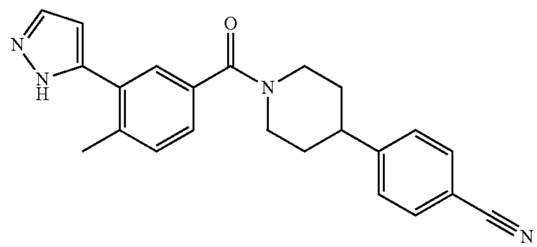 [SMILES: Cc1ccc(C(=O)N2CCC(c3ccc(C#N)cc3)CC2)cc1-c1ccn[nH]1] | 145 | 2.170 | 20.000 |
| 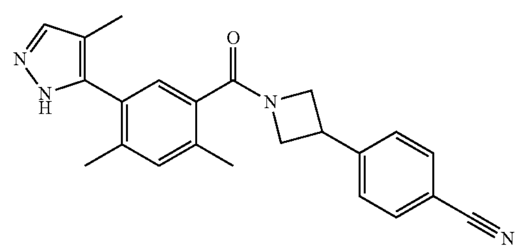 [SMILES: Cc1cc(C)c(-c2[nH]ncc2C)cc1C(=O)N1CC(c2ccc(C#N)cc2)C1] | 146 | 0.062 | 0.017 |
| 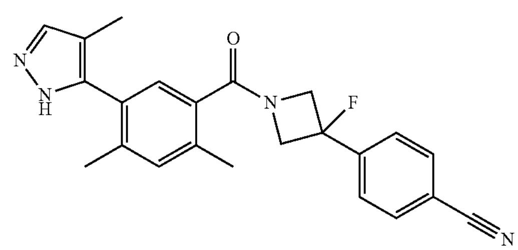 [SMILES: Cc1cc(C)c(-c2[nH]ncc2C)cc1C(=O)N1CC(F)(c2ccc(C#N)cc2)C1] | 147 | 0.120 | |
| 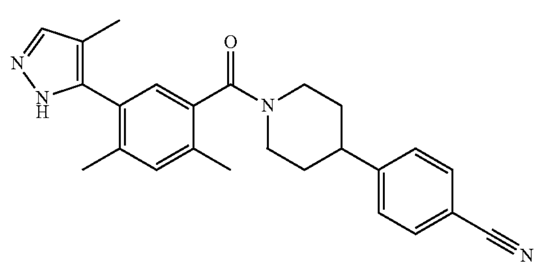 [SMILES: Cc1cc(C)c(-c2[nH]ncc2C)cc1C(=O)N1CCC(c2ccc(C#N)cc2)CC1] | 148 | 0.084 | |

TABLE 26-continued
Compounds of the present disclosure.
| Structure | Cpd | Hu FASN IC50 (μM) | HCV GT1b EC50 (μM) |
|---|---|---|---|
| 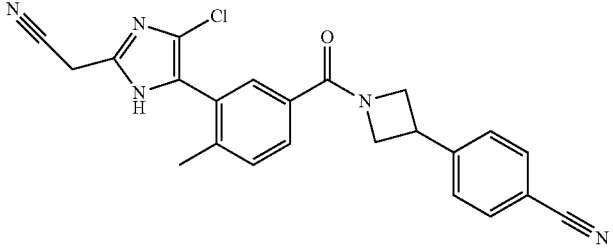 | 149 | 0.021 | |
| 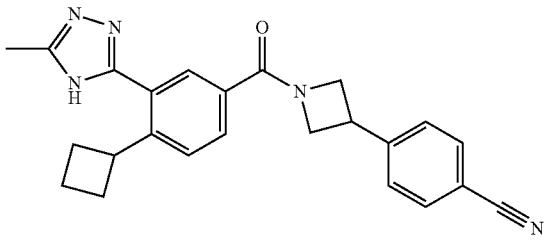 [SMILES: Cc1nnc(-c2cc(C(=O)N3CC(c4ccc(C#N)cc4)C3)ccc2C2CCC2)[nH]1] | 150 | 0.097 | |
| 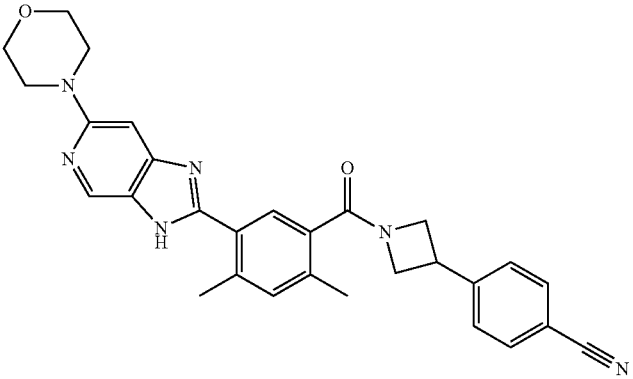 [SMILES: Cc1cc(C)c(-c2nc3cc(N4CCOCC4)ncc3[nH]2)cc1C(=O)N1CC(c2ccc(C#N)cc2)C1] | 151 | 0.057 | 0.026 |
| 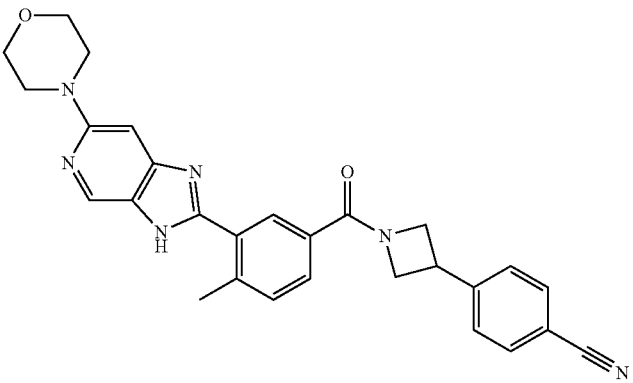 [SMILES: Cc1ccc(C(=O)N2CC(c3ccc(C#N)cc3)C2)cc1-c1nc2cc(N3CCOCC3)ncc2[nH]1] | 152 | 0.290 | 0.380 |

TABLE 26-continued

Compounds of the present disclosure.

| Structure | Cpd | Hu FASN IC50 (µM) | HCV GT1b EC50 (µM) |
|---|---|---|---|
| 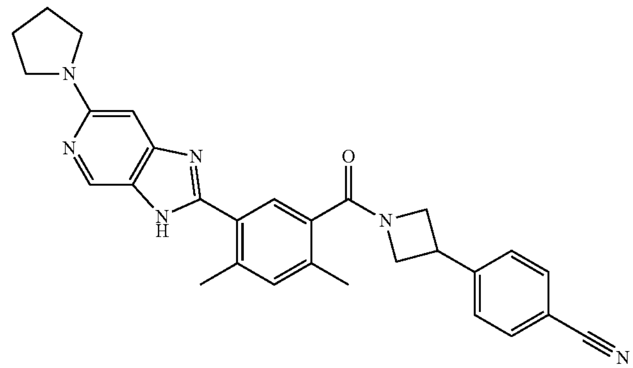 [SMILES: Cc1cc(C)c(-c2nc3cc(N4CCCC4)ncc3[nH]2)cc1C(=O)N1CC(c2ccc(C#N)cc2)C1] | 153 | 0.036 | 0.032 |
| 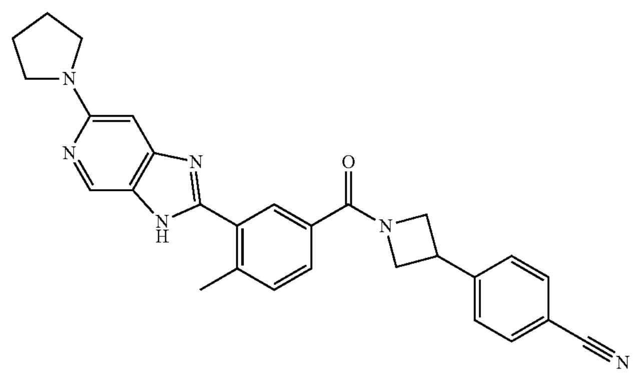 [SMILES: Cc1ccc(C(=O)N2CC(c3ccc(C#N)cc3)C2)cc1-c1nc2cc(N3CCCC3)ncc2[nH]1] | 154 | 0.094 | 0.380 |
| 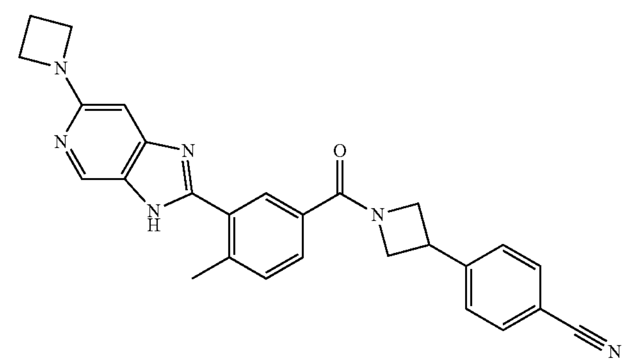 [SMILES: Cc1ccc(C(=O)N2CC(c3ccc(C#N)cc3)C2)cc1-c1nc2cc(N3CCC3)ncc2[nH]1] | 155 | 0.590 | |
| 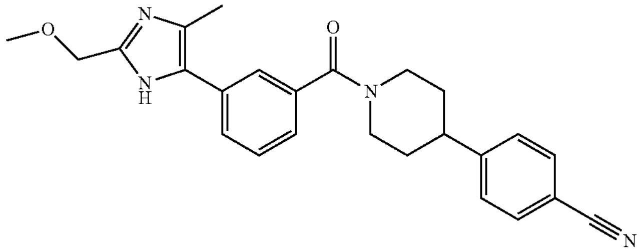 [SMILES: COCc1nc(C)c(-c2cccc(C(=O)N3CCC(c4ccc(C#N)cc4)CC3)c2)[nH]1] | 156 | 1.495 | |

TABLE 26-continued

Compounds of the present disclosure.

| Structure | Cpd | Hu FASN IC50 (μM) | HCV GT1b EC50 (μM) |
|---|---|---|---|
| 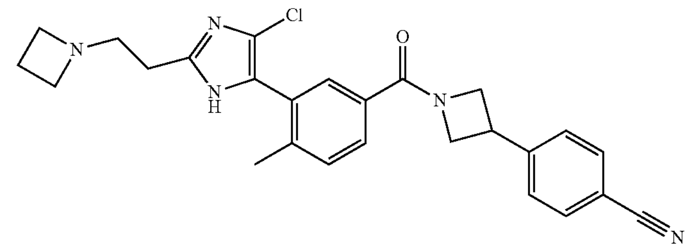 [SMILES: Cc1ccc(C(=O)N2CC(c3ccc(C#N)cc3)C2)cc1-c1[nH]c(CCN2CCC2)nc1Cl] | 157 | 0.210 | 0.056 |
| 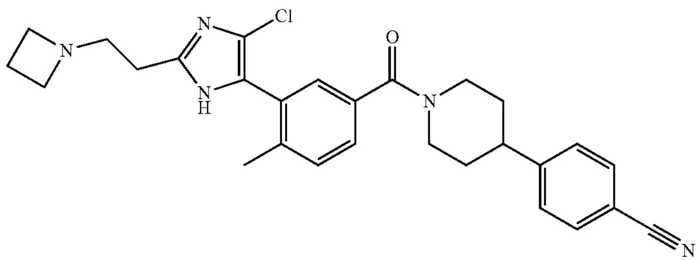 [SMILES: Cc1ccc(C(=O)N2CCC(c3ccc(C#N)cc3)CC2)cc1-c1[nH]c(CCN2CCC2)nc1Cl] | 158 | | 0.028 |
| 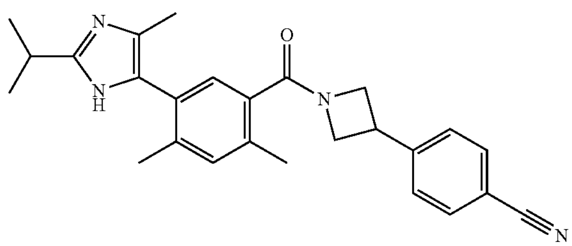 [SMILES: Cc1cc(C)c(-c2[nH]c(C(C)C)nc2C)cc1C(=O)N1CC(c2ccc(C#N)cc2)C1] | 159 | 0.021 | 0.016 |
| 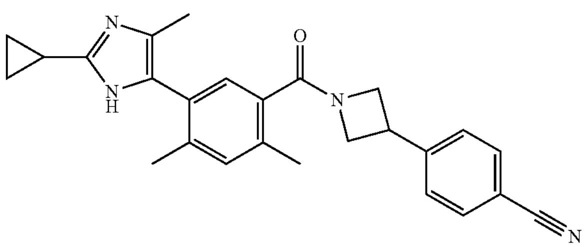 [SMILES: Cc1cc(C)c(-c2[nH]c(C3CC3)nc2C)cc1C(=O)N1CC(c2ccc(C#N)cc2)C1] | 160 | 0.017 | 0.007 |
| 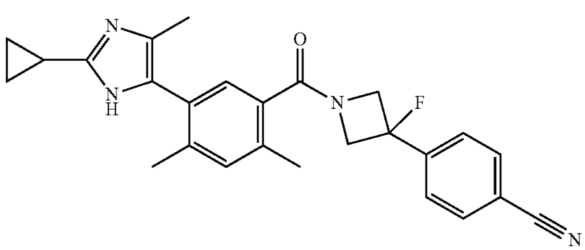 [SMILES: Cc1cc(C)c(-c2[nH]c(C3CC3)nc2C)cc1C(=O)N1CC(F)(c2ccc(C#N)cc2)C1] | 161 | 0.026 | 0.034 |
| 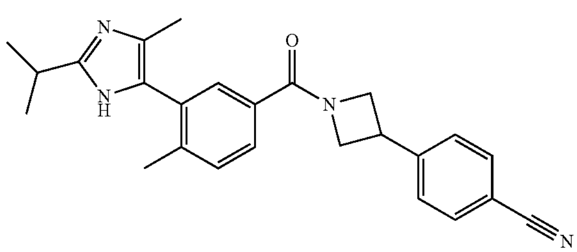 [SMILES: Cc1ccc(C(=O)N2CC(c3ccc(C#N)cc3)C2)cc1-c1[nH]c(C(C)C)nc1C] | 162 | 0.019 | 0.006 |

TABLE 26-continued

Compounds of the present disclosure.

| Structure | Cpd | Hu FASN IC50 (μM) | HCV GT1b EC50 (μM) |
|---|---|---|---|
| 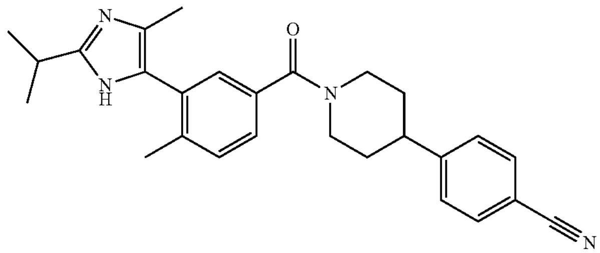 [SMILES: Cc1ccc(C(=O)N2CCC(c3ccc(C#N)cc3)CC2)cc1-c1[nH]c(C(C)C)nc1C] | 163 | 0.037 | 0.027 |
| 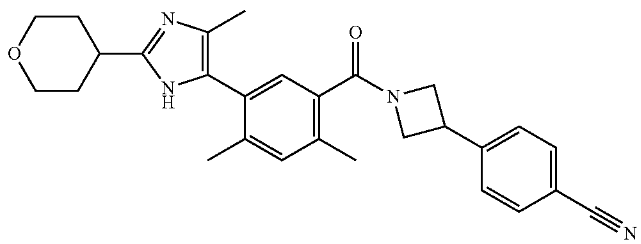 [SMILES: Cc1cc(C)c(-c2[nH]c(C3CCOCC3)nc2C)cc1C(=O)N1CC(c2ccc(C#N)cc2)C1] | 164 | 0.019 | 0.002 |
| 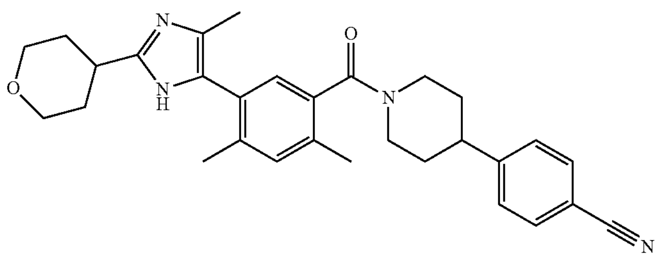 [SMILES: Cc1cc(C)c(-c2[nH]c(C3CCOCC3)nc2C)cc1C(=O)N1CCC(c2ccc(C#N)cc2)CC1] | 165 | 0.038 | 0.018 |
| 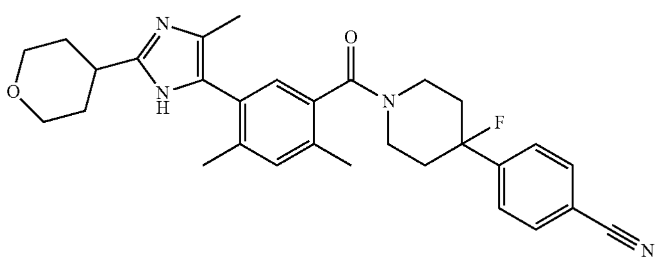 [SMILES: Cc1cc(C)c(-c2[nH]c(C3CCOCC3)nc2C)cc1C(=O)N1CCC(F)(c2ccc(C#N)cc2)CC1] | 166 | 0.040 | 0.016 |
| 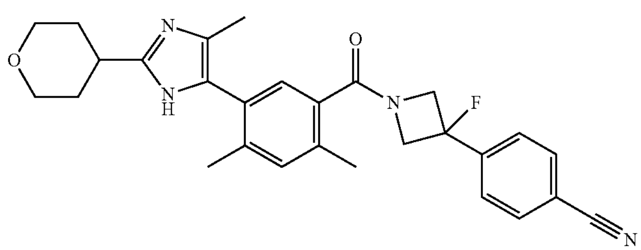 [SMILES: Cc1cc(C)c(-c2[nH]c(C3CCOCC3)nc2C)cc1C(=O)N1CC(F)(c2ccc(C#N)cc2)C1] | 167 | 0.061 | 0.025 |
| 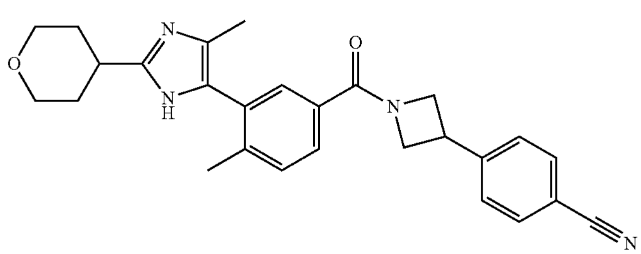 [SMILES: Cc1ccc(C(=O)N2CC(c3ccc(C#N)cc3)C2)cc1-c1[nH]c(C2CCOCC2)nc1C] | 168 | 0.011 | 0.002 |

TABLE 26-continued
Compounds of the present disclosure.
| Structure | Cpd | Hu FASN IC50 (μM) | HCV GT1b EC50 (μM) |
|---|---|---|---|
| 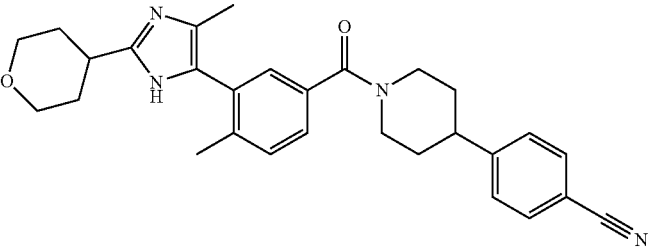 [SMILES: Cc1ccc(C(=O)N2CCC(c3ccc(C#N)cc3)CC2)cc1-c1[nH]c(C2CCOCC2)nc1C] | 169 | 0.035 | 0.010 |
| 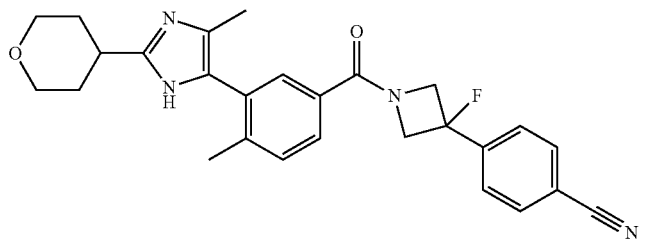 [SMILES: Cc1ccc(C(=O)N2CC(F)(c3ccc(C#N)cc3)C2)cc1-c1[nH]c(C2CCOCC2)nc1C] | 170 | 0.040 | |
| 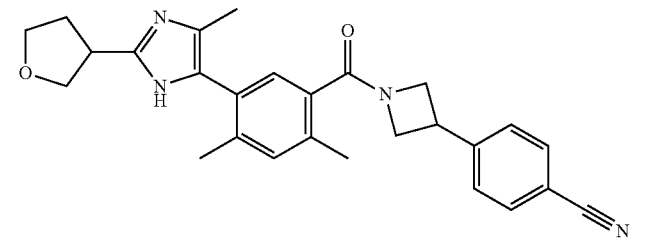 [SMILES: Cc1cc(C)c(-c2[nH]c(C3CCOC3)nc2C)cc1C(=O)N1CC(c2ccc(C#N)cc2)C1] | 171 | 0.021 | 0.005 |
| 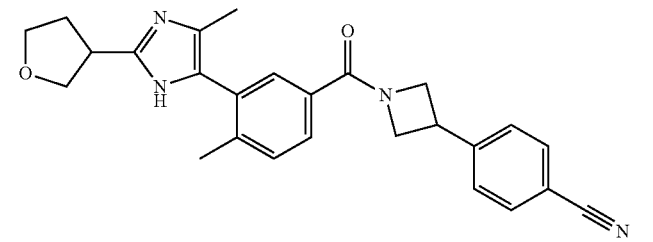 [SMILES: Cc1ccc(C(=O)N2CC(c3ccc(C#N)cc3)C2)cc1-c1[nH]c(C2CCOC2)nc1C] | 172 | 0.011 | 0.001 |
| 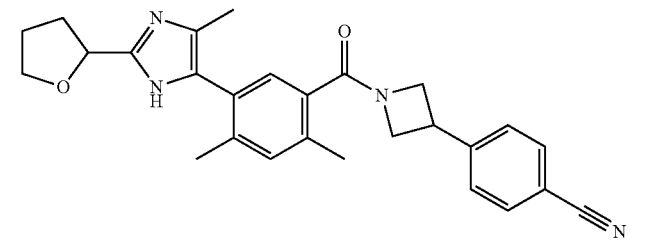 [SMILES: Cc1cc(C)c(-c2[nH]c(C3CCCO3)nc2C)cc1C(=O)N1CC(c2ccc(C#N)cc2)C1] | 173 | 0.035 | 0.018 |
| 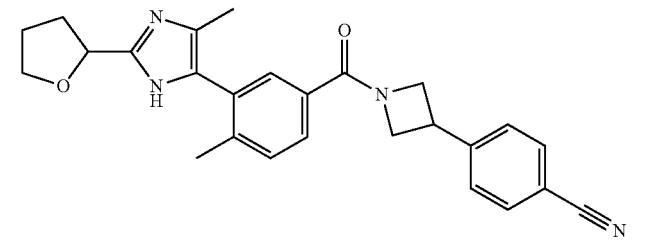 [SMILES: Cc1ccc(C(=O)N2CC(c3ccc(C#N)cc3)C2)cc1-c1[nH]c(C2CCCO2)nc1C] | 174 | 0.037 | 0.011 |

TABLE 26-continued

Compounds of the present disclosure.

| Structure | Cpd | Hu FASN IC50 (μM) | HCV GT1b EC50 (μM) |
|---|---|---|---|
| 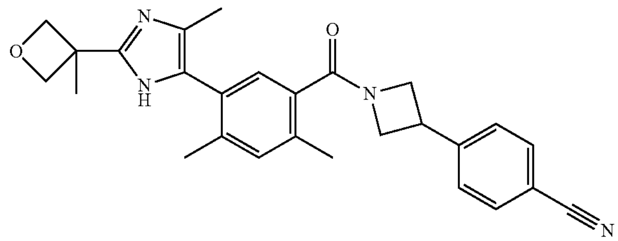 [SMILES: Cc1cc(C)c(-c2[nH]c(C3(C)COC3)nc2C)cc1C(=O)N1CC(c2ccc(C#N)cc2)C1] | 175 | 0.020 | 0.006 |
| 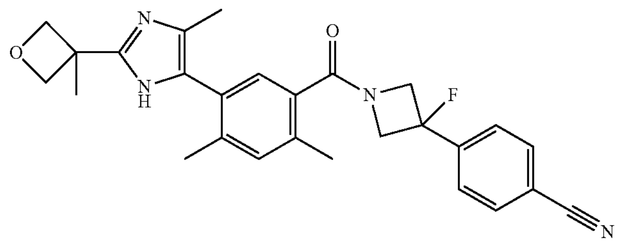 [SMILES: Cc1cc(C)c(-c2[nH]c(C3(C)COC3)nc2C)cc1C(=O)N1CC(F)(c2ccc(C#N)cc2)C1] | 176 | 0.024 | 0.016 |
| 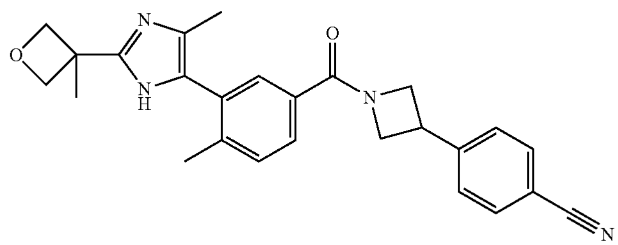 [SMILES: Cc1ccc(C(=O)N2CC(c3ccc(C#N)cc3)C2)cc1-c1[nH]c(C2(C)COC2)nc1C] | 177 | 0.011 | 0.001 |
| 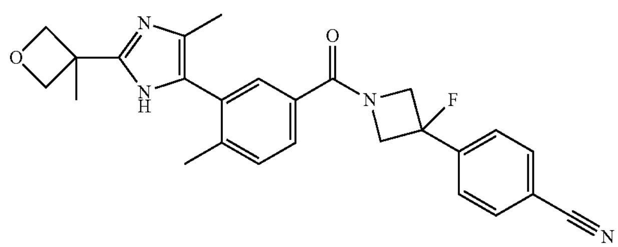 [SMILES: Cc1ccc(C(=O)N2CC(F)(c3ccc(C#N)cc3)C2)cc1-c1[nH]c(C2(C)COC2)nc1C] | 178 | 0.027 | 0.006 |
| 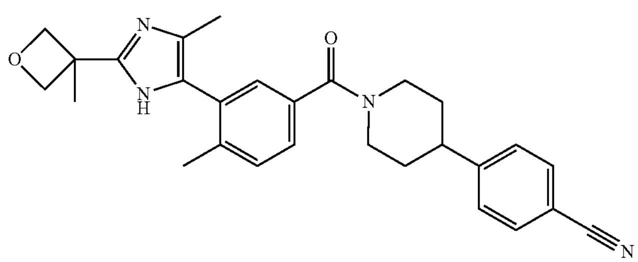 [SMILES: Cc1ccc(C(=O)N2CCC(c3ccc(C#N)cc3)CC2)cc1-c1[nH]c(C2(C)COC2)nc1C] | 179 | 0.025 | 0.013 |
| 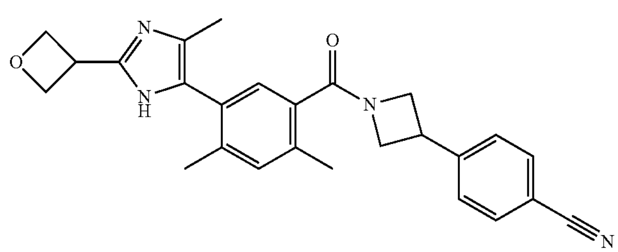 [SMILES: Cc1cc(C)c(-c2[nH]c(C3COC3)nc2C)cc1C(=O)N1CC(c2ccc(C#N)cc2)C1] | 180 | 0.034 | 0.007 |

TABLE 26-continued

Compounds of the present disclosure.

| Structure | Cpd | Hu FASN IC50 (μM) | HCV GT1b EC50 (μM) |
|---|---|---|---|
| 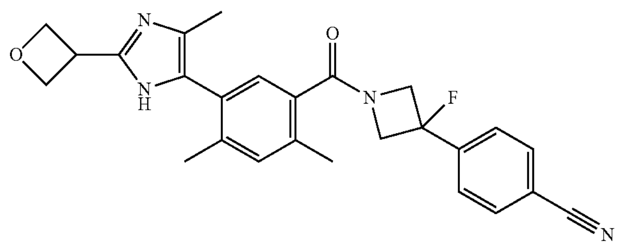 [SMILES: Cc1cc(C)c(-c2[nH]c(C3COC3)nc2C)cc1C(=O)N1CC(F)(c2ccc(C#N)cc2)C1] | 181 | 0.068 | 0.021 |
| 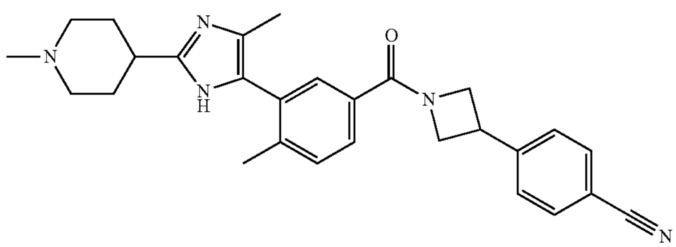 [SMILES: Cc1ccc(C(=O)N2CC(c3ccc(C#N)cc3)C2)cc1-c1[nH]c(C2CCN(C)CC2)nc1C] | 182 | 0.038 | 0.079 |
| 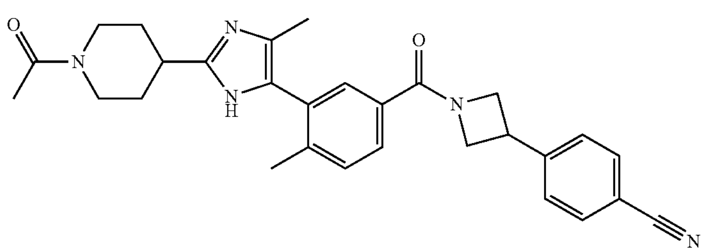 | 183 | 0.029 | |
| 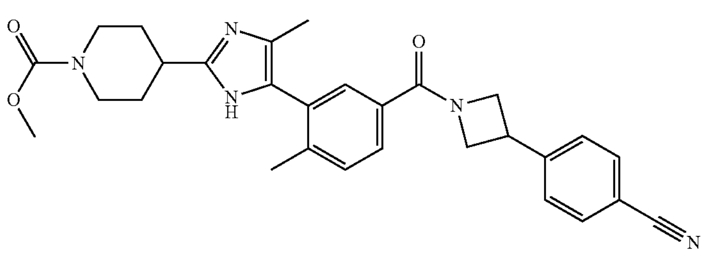 [SMILES: COC(=O)N1CCC(c2nc(C)c(-c3cc(C(=O)N4CC(c5ccc(C#N)cc5)C4)ccc3C)[nH]2)CC1] | 184 | 0.009 | 0.002 |
| 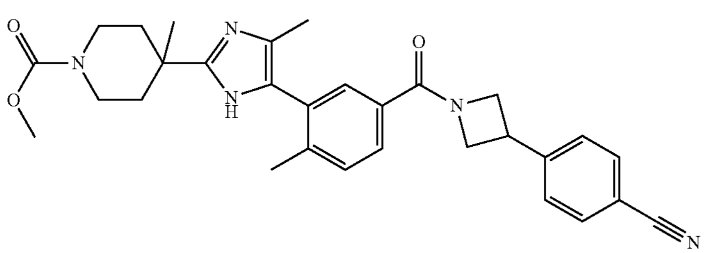 [SMILES: COC(=O)N1CCC(C)(c2nc(C)c(-c3cc(C(=O)N4CC(c5ccc(C#N)cc5)C4)ccc3C)[nH]2)CC1] | 185 | 0.033 | |
| 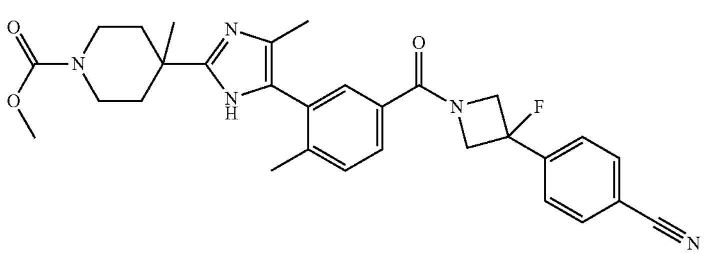 | 186 | 0.066 | 0.025 |

TABLE 26-continued

Compounds of the present disclosure.

| Structure | Cpd | Hu FASN IC50 (μM) | HCV GT1b EC50 (μM) |
|---|---|---|---|
| 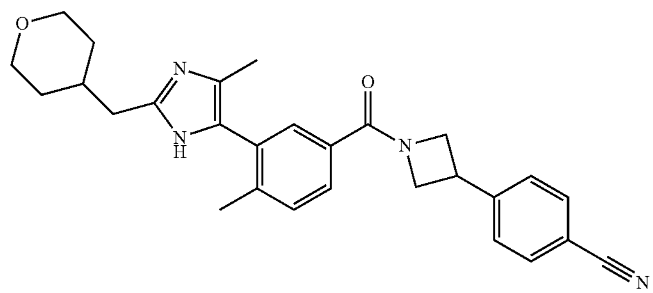 [SMILES: Cc1ccc(C(=O)N2CC(c3ccc(C#N)cc3)C2)cc1-c1[nH]c(CC2CCOCC2)nc1C] | 187 | 0.063 | |
| 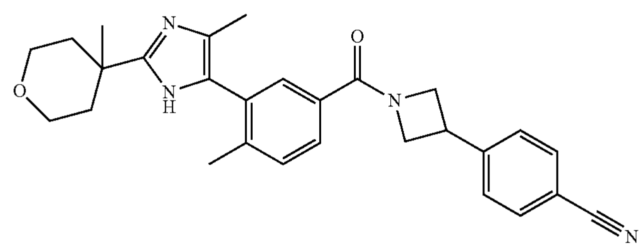 [SMILES: Cc1ccc(C(=O)N2CC(c3ccc(C#N)cc3)C2)cc1-c1[nH]c(C2(C)CCOCC2)nc1C] | 188 | 0.052 | 0.007 |
| 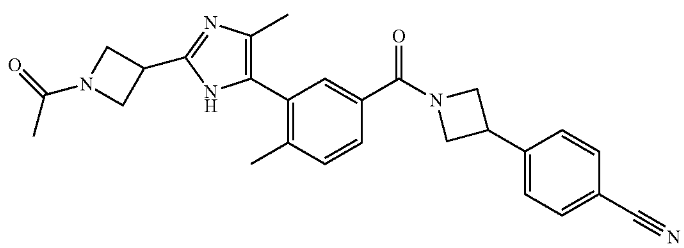 [SMILES: CC(=O)N1CC(c2nc(C)c(-c3cc(C(=O)N4CC(c5ccc(C#N)cc5)C4)ccc3C)[nH]2)C1] | 189 | 0.020 | 0.045 |
| 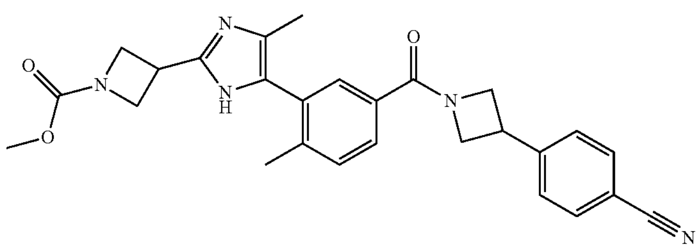 [SMILES: COC(=O)N1CC(c2nc(C)c(-c3cc(C(=O)N4CC(c5ccc(C#N)cc5)C4)ccc3C)[nH]2)C1] | 190 | 0.008 | |
| 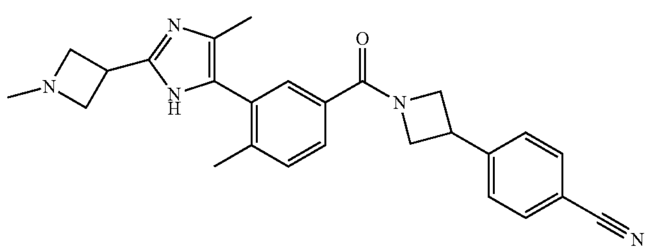 [SMILES: Cc1ccc(C(=O)N2CC(c3ccc(C#N)cc3)C2)cc1-c1[nH]c(C2CN(C)C2)nc1C] | 191 | 0.065 | 0.150 |
| 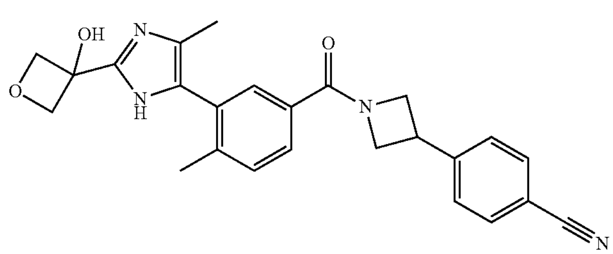 [SMILES: Cc1ccc(C(=O)N2CC(c3ccc(C#N)cc3)C2)cc1-c1[nH]c(C2(F)COC2)nc1C] | 192 | 0.024 | 0.010 |

TABLE 26-continued
Compounds of the present disclosure.
| Structure | Cpd | Hu FASN IC50 (μM) | HCV GT1b EC50 (μM) |
|---|---|---|---|
| 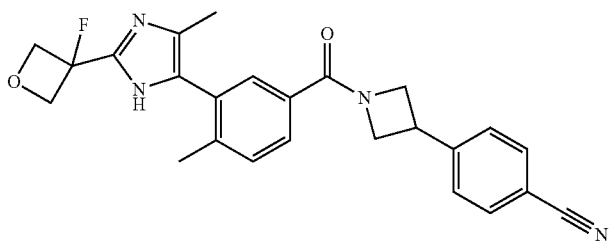 | 193 | 0.065 | 0.370 |
| 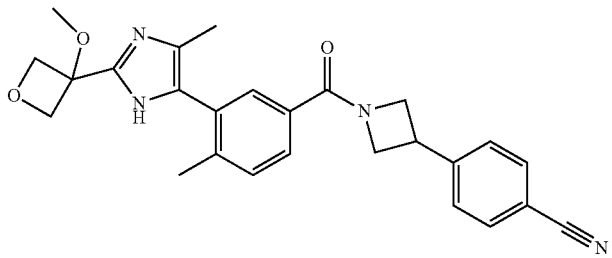 [SMILES: COC1(c2nc(C)c(-c3cc(C(=O)N4CC(c5ccc(C#N)cc5)C4)ccc3C)[nH]2)COC1] | 194 | 0.025 | 0.004 |
| 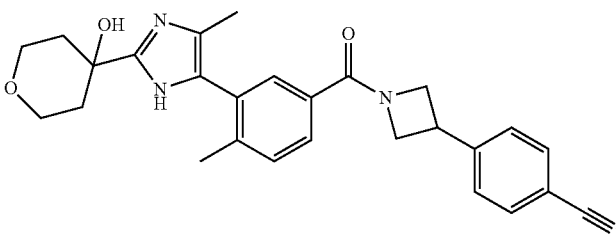 | 195 | 0.013 | 0.004 |
| 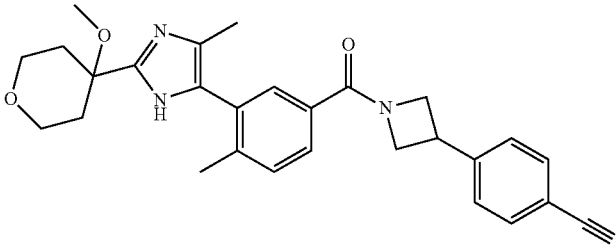 | 196 | 0.015 | |
| 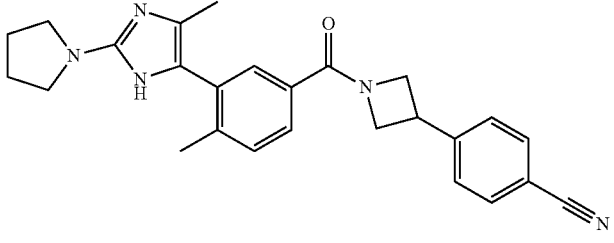 [SMILES: Cc1ccc(C(=O)N2CC(c3ccc(C#N)cc3)C2)cc1-c1[nH]c(N2CCCC2)nc1C] | 197 | 0.870 | 0.730 |
| 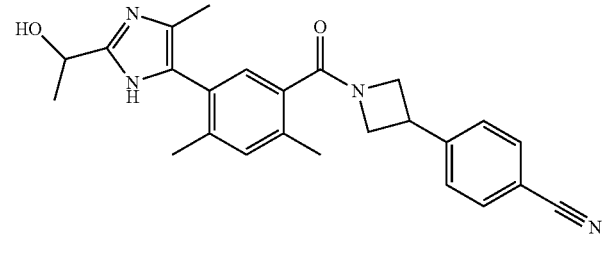 [SMILES: Cc1cc(C)c(-c2[nH]c(C(C)O)nc2C)cc1C(=O)N1CC(c2ccc(C#N)cc2)C1] | 198 | 0.054 | 0.018 |

TABLE 26-continued

Compounds of the present disclosure.

| Structure | Cpd | Hu FASN IC50 (μM) | HCV GT1b EC50 (μM) |
|---|---|---|---|
| 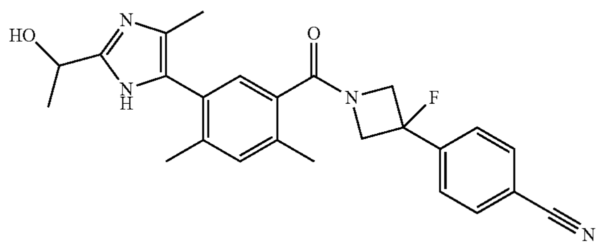 [SMILES: Cc1cc(C)c(-c2[nH]c(C(C)O)nc2C)cc1C(=O)N1CC(F)(c2ccc(C#N)cc2)C1] | 199 | 0.110 | 0.024 |
| 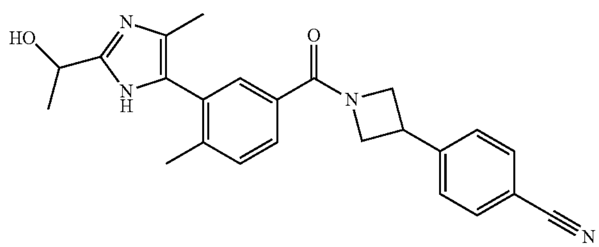 [SMILES: Cc1ccc(C(=O)N2CC(c3ccc(C#N)cc3)C2)cc1-c1[nH]c(C(C)O)nc1C] | 200 | 0.027 | 0.019 |
| 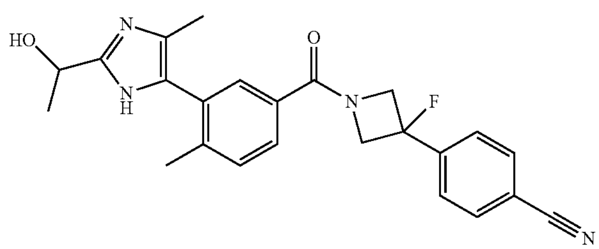 [SMILES: Cc1ccc(C(=O)N2CC(F)(c3ccc(C#N)cc3)C2)cc1-c1[nH]c(C(C)O)nc1C] | 201 | 0.130 | 0.054 |
| 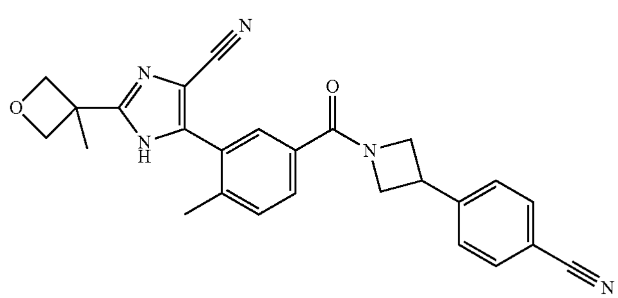 [SMILES: Cc1ccc(C(=O)N2CC(c3ccc(C#N)cc3)C2)cc1-c1[nH]c(C2(C)COC2)nc1C#N] | 202 | 0.020 | 0.012 |
| 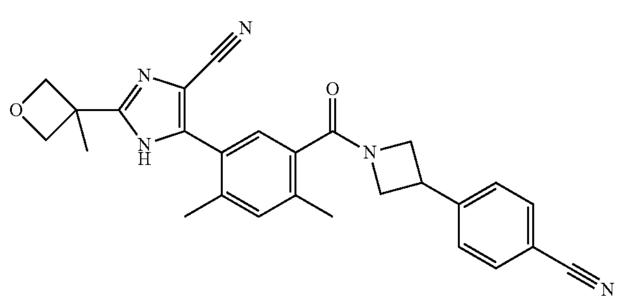 [SMILES: Cc1cc(C)c(-c2[nH]c(C3(C)COC3)nc2C#N)cc1C(=O)N1CC(c2ccc(C#N)cc2)C1] | 203 | 0.035 | 0.021 |

TABLE 26-continued

Compounds of the present disclosure.

| Structure | Cpd | Hu FASN IC50 (μM) | HCV GT1b EC50 (μM) |
|---|---|---|---|
| 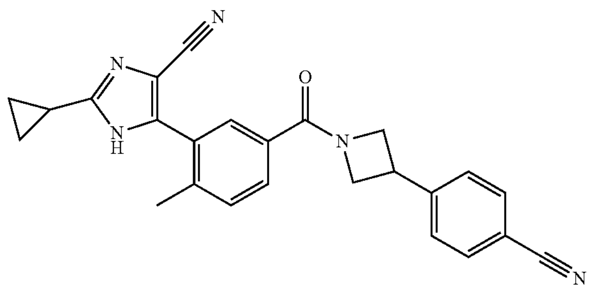 [SMILES: Cc1ccc(C(=O)N2CC(c3ccc(C#N)cc3)C2)cc1-c1[nH]c(C2CC2)nc1C#N] | 204 | 0.010 | 0.005 |
| 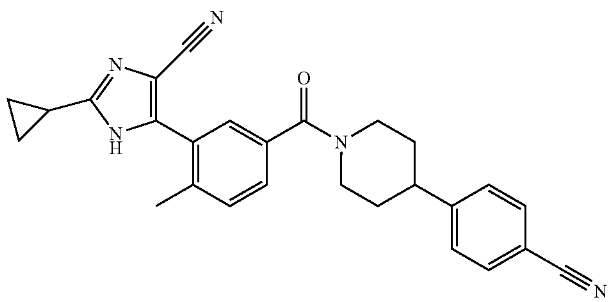 [SMILES: Cc1ccc(C(=O)N2CCC(c3ccc(C#N)cc3)CC2)cc1-c1[nH]c(C2CC2)nc1C#N] | 205 | 0.016 | 0.009 |
| 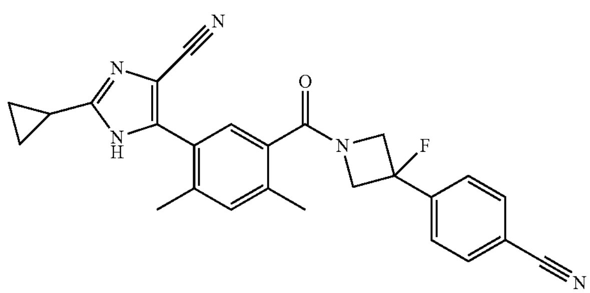 [SMILES: Cc1cc(C)c(-c2[nH]c(C3CC3)nc2C#N)cc1C(=O)N1CC(F)(c2ccc(C#N)cc2)C1] | 206 | 0.024 | 0.026 |
| 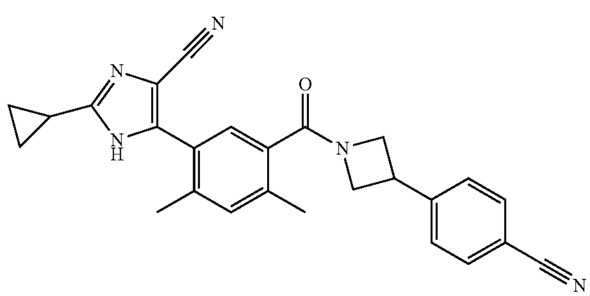 [SMILES: Cc1cc(C)c(-c2[nH]c(C3CC3)nc2C#N)cc1C(=O)N1CC(c2ccc(C#N)cc2)C1] | 207 | 0.035 | 0.012 |
| 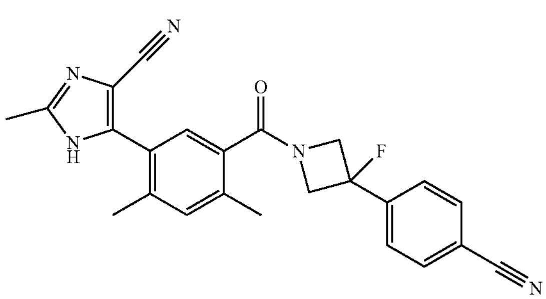 [SMILES: Cc1nc(C#N)c(-c2cc(C(=O)N3CC(F)(c4ccc(C#N)cc4)C3)c(C)cc2C)[nH]1] | 208 | 0.036 | 0.025 |

TABLE 26-continued

Compounds of the present disclosure.

| Structure | Cpd | Hu FASN IC50 (μM) | HCV GT1b EC50 (μM) |
|---|---|---|---|
| 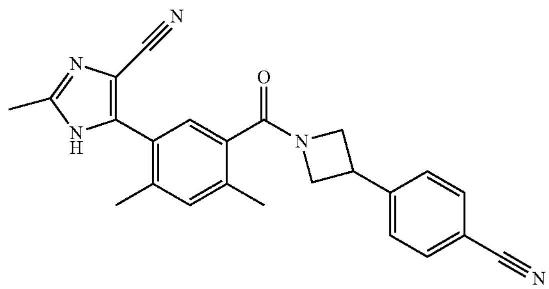 [SMILES: Cc1nc(C#N)c(-c2cc(C(=O)N3CC(c4ccc(C#N)cc4)C3)c(C)cc2C)[nH]1] | 209 | 0.024 | 0.005 |
| 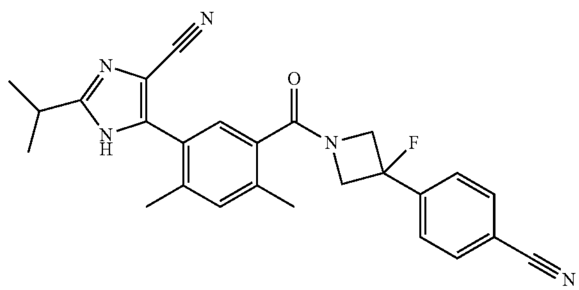 [SMILES: Cc1cc(C)c(-c2[nH]c(C(C)C)nc2C#N)cc1C(=O)N1CC(F)(c2ccc(C#N)cc2)C1] | 210 | 0.020 | 0.017 |
| 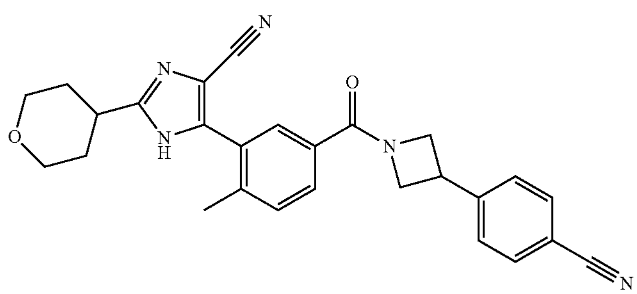 [SMILES: Cc1ccc(C(=O)N2CC(c3ccc(C#N)cc3)C2)cc1-c1[nH]c(C2CCOCC2)nc1C#N] | 211 | 0.011 | 0.006 |
| 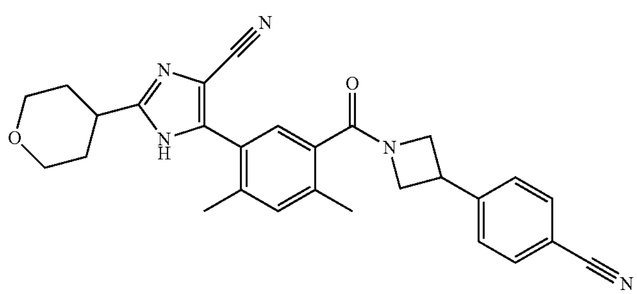 [SMILES: Cc1cc(C)c(-c2[nH]c(C3CCOCC3)nc2C#N)cc1C(=O)N1CC(c2ccc(C#N)cc2)C1] | 212 | 0.018 | 0.013 |
| 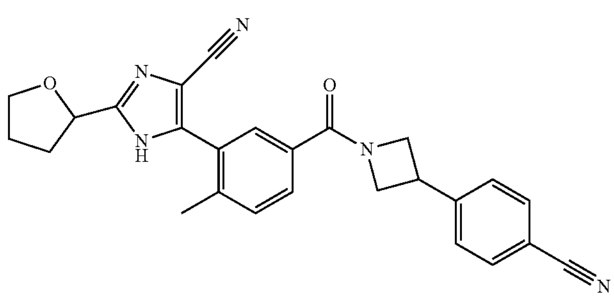 [SMILES: Cc1ccc(C(=O)N2CC(c3ccc(C#N)cc3)C2)cc1-c1[nH]c(C2CCCO2)nc1C#N] | 213 | 0.065 | 0.051 |

TABLE 26-continued

Compounds of the present disclosure.

| Structure | Cpd | Hu FASN IC50 (μM) | HCV GT1b EC50 (μM) |
|---|---|---|---|
| 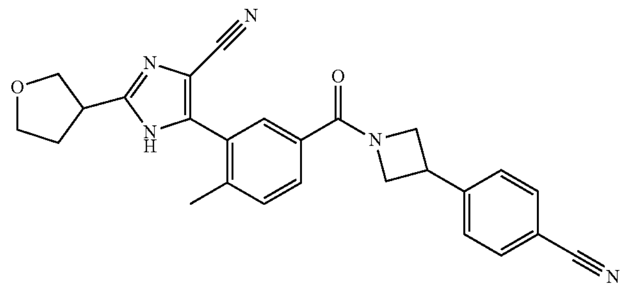 [SMILES: Cc1ccc(C(=O)N2CC(c3ccc(C#N)cc3)C2)cc1-c1[nH]c(C2CCOC2)nc1C#N] | 214 | 0.014 | 0.006 |
| 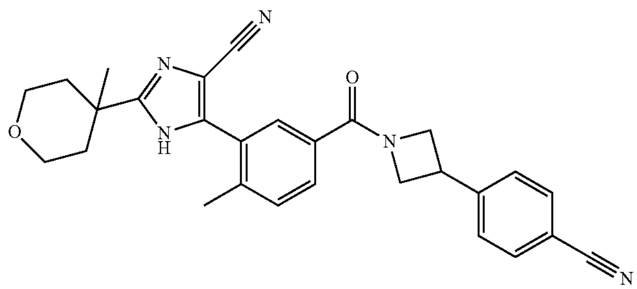 [SMILES: Cc1ccc(C(=O)N2CC(c3ccc(C#N)cc3)C2)cc1-c1[nH]c(C2(C)CCOCC2)nc1C#N] | 215 | 0.048 | |
| 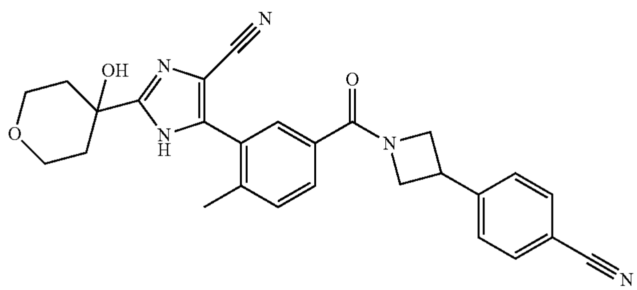 [SMILES: Cc1ccc(C(=O)N2CC(c3ccc(C#N)cc3)C2)cc1-c1[nH]c(C2(O)CCOCC2)nc1C#N] | 216 | 0.079 | 0.026 |
| 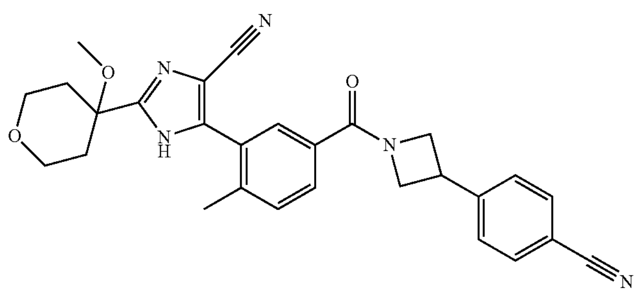 [SMILES: COC1(c2nc(C#N)c(-c3cc(C(=O)N4CC(c5ccc(C#N)cc5)C4)ccc3C)[nH]2)CCOCC1] | 217 | 0.052 | |
| 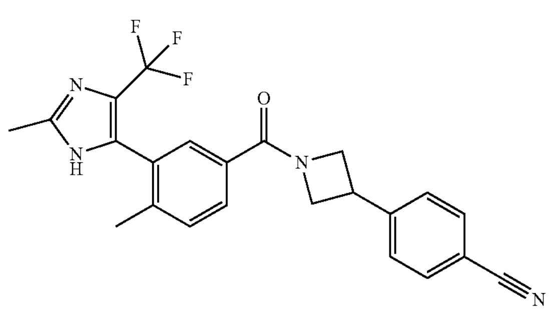 [SMILES: Cc1nc(C(F)(F)F)c(-c2cc(C(=O)N3CC(c4ccc(C#N)cc4)C3)ccc2C)[nH]1] | 218 | 0.015 | 0.003 |

TABLE 26-continued
Compounds of the present disclosure.
| Structure | Cpd | Hu FASN IC50 (μM) | HCV GT1b EC50 (μM) |
|---|---|---|---|
| 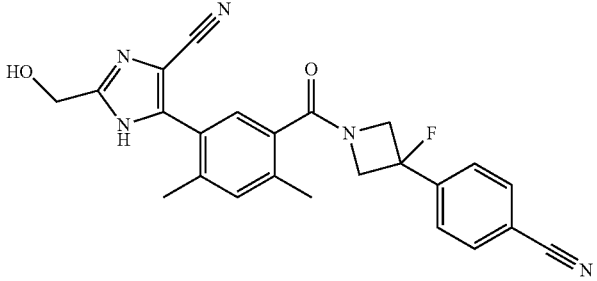 [SMILES: Cc1cc(C)c(-c2[nH]c(CO)nc2C#N)cc1C(=O)N1CC(F)(c2ccc(C#N)cc2)C1] | 219 | 0.059 | 0.040 |
| 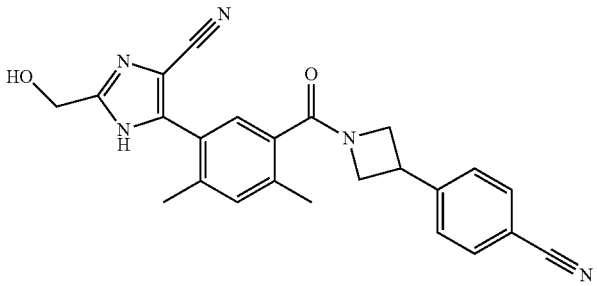 [SMILES: Cc1cc(C)c(-c2[nH]c(CO)nc2C#N)cc1C(=O)N1CC(c2ccc(C#N)cc2)C1] | 220 | 0.050 | 0.079 |
| 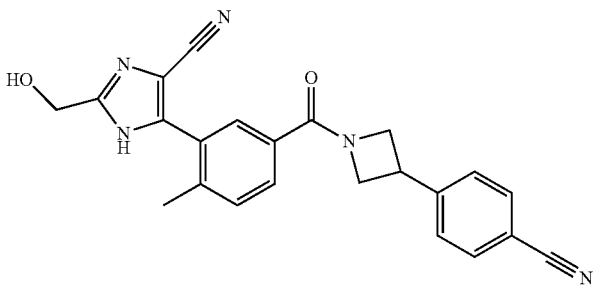 [SMILES: Cc1ccc(C(=O)N2CC(c3ccc(C#N)cc3)C2)cc1-c1[nH]c(CO)nc1C#N] | 221 | 0.043 | 0.120 |
| 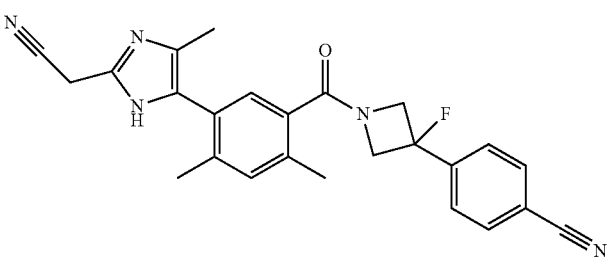 [SMILES: Cc1cc(C)c(-c2[nH]c(CC#N)nc2C)cc1C(=O)N1CC(F)(c2ccc(C#N)cc2)C1] | 222 | 0.053 | 0.033 |
| 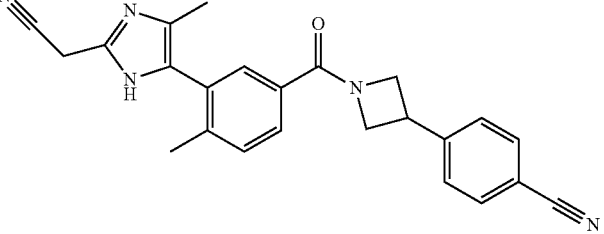 | 223 | 0.023 | 0.015 |

TABLE 26-continued

Compounds of the present disclosure.

| Structure | Cpd | Hu FASN IC50 (μM) | HCV GT1b EC50 (μM) |
|---|---|---|---|
| (structure) | 224 | 0.031 | 0.038 |
| (structure) | 225 | 0.059 | 0.066 |
| (structure) | 226 | 0.088 | 0.070 |
| (structure) | 227 | 0.012 | 0.013 |
| (structure) | 228 | 0.027 | 0.022 |
| (structure) | 229 | 0.042 | 0.012 |

TABLE 26-continued
Compounds of the present disclosure.
| Structure | Cpd | Hu FASN IC50 (μM) | HCV GT1b EC50 (μM) |
|---|---|---|---|
| 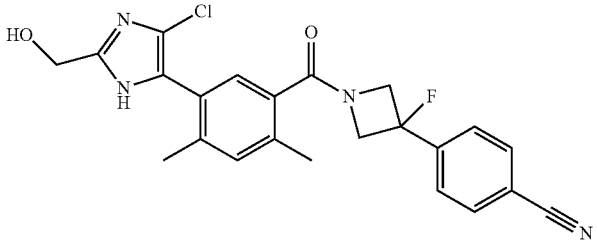 [SMILES: Cc1cc(C)c(-c2[nH]c(CO)nc2Cl)cc1C(=O)N1CC(F)(c2ccc(C#N)cc2)C1] | 230 | 0.017 | 0.007 |
| 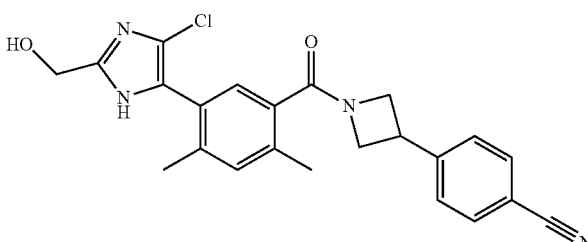 | 231 | 0.019 | 0.002 |
| 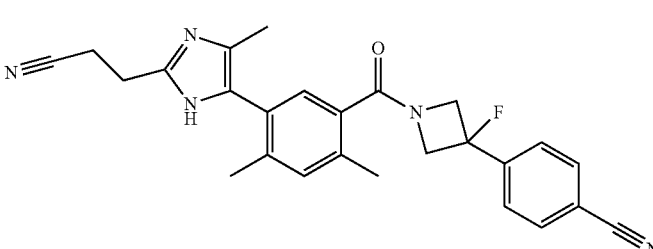 | 232 | 0.020 | 0.013 |
| 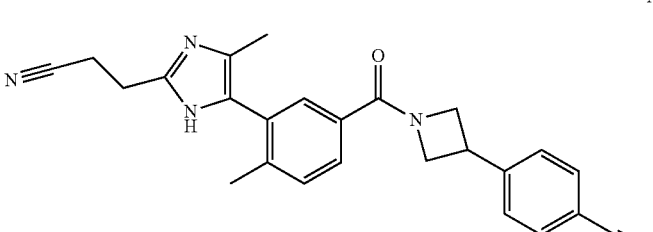 | 233 | 0.011 | 0.002 |
| 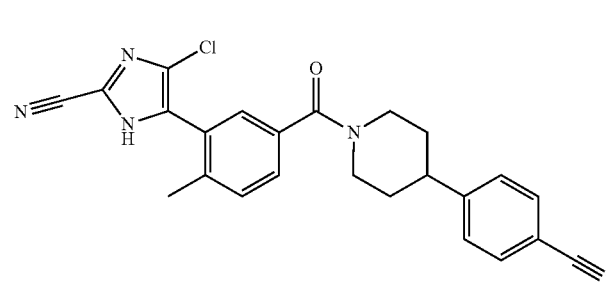 | 234 | 0.053 | 1.600 |
| 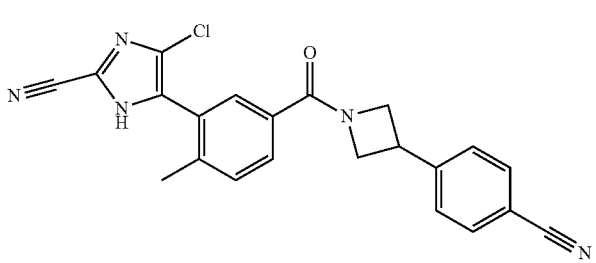 [SMILES: Cc1ccc(C(=O)N2CC(c3ccc(C#N)cc3)C2)cc1-c1[nH]c(C#N)nc1Cl] | 235 | 0.039 | 1.100 |

TABLE 26-continued

Compounds of the present disclosure.

| Structure | Cpd | Hu FASN IC50 (μM) | HCV GT1b EC50 (μM) |
|---|---|---|---|
| (structure) | 236 | 0.019 | 0.019 |
| (structure) | 237 | 0.016 | 0.014 |
| (structure) | 238 | 0.010 | 0.001 |
| (structure) | 239 | 0.440 | 0.430 |
| (structure) | 240 | 0.053 | 0.032 |

TABLE 26-continued

Compounds of the present disclosure.

| Structure | Cpd | Hu FASN IC50 (μM) | HCV GT1b EC50 (μM) |
|---|---|---|---|
| 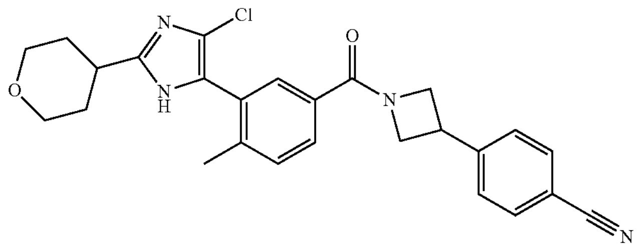 [SMILES: Cc1ccc(C(=O)N2CC(c3ccc(C#N)cc3)C2)cc1-c1[nH]c(C2CCOCC2)nc1Cl] | 241 | 0.009 | 0.000 |
| 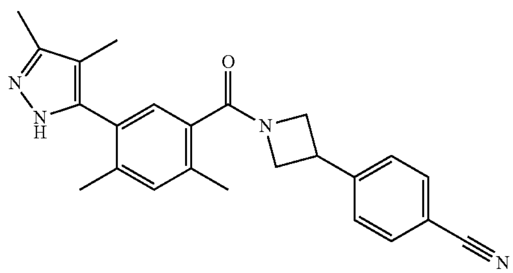 [SMILES: Cc1cc(C)c(-c2[nH]nc(C)c2C)cc1C(=O)N1CC(c2ccc(C#N)cc2)C1] | 242 | 0.060 | 0.069 |
| 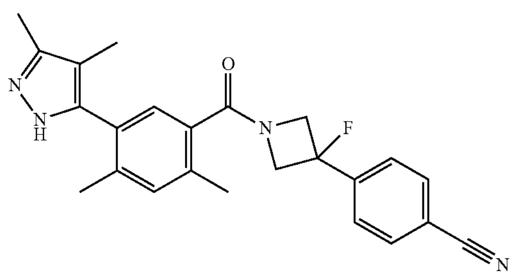 [SMILES: Cc1cc(C)c(-c2[nH]nc(C)c2C)cc1C(=O)N1CC(F)(c2ccc(C#N)cc2)C1] | 243 | 0.170 | 0.450 |
| 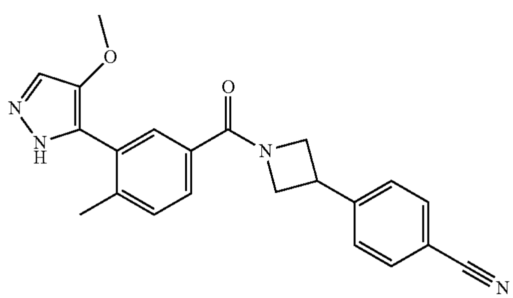 [SMILES: COc1cn[nH]c1-c1cc(C(=O)N2CC(c3ccc(C#N)cc3)C2)ccc1C] | 244 | 0.150 | 0.120 |
| 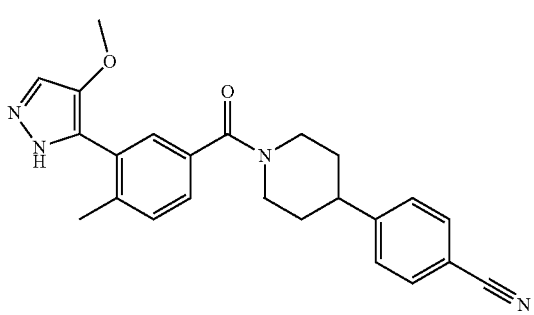 [SMILES: COc1cn[nH]c1-c1cc(C(=O)N2CCC(c3ccc(C#N)cc3)CC2)ccc1C] | 245 | 0.109 | |

TABLE 26-continued
Compounds of the present disclosure.
| Structure | Cpd | Hu FASN IC50 (μM) | HCV GT1b EC50 (μM) |
|---|---|---|---|
| 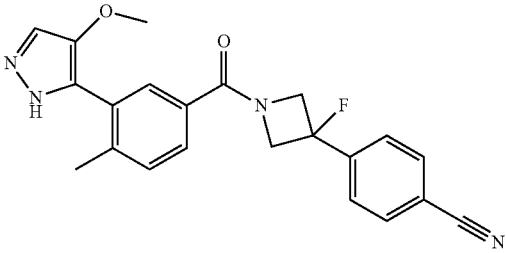 [SMILES: COc1cn[nH]c1-c1cc(C(=O)N2CC(F)(c3ccc(C#N)cc3)C2)ccc1C] | 246 | 0.340 | 0.740 |
| 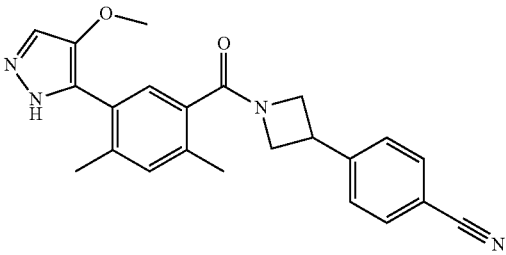 [SMILES: COc1cn[nH]c1-c1cc(C(=O)N2CC(c3ccc(C#N)cc3)C2)c(C)cc1C] | 247 | 0.110 | |
| 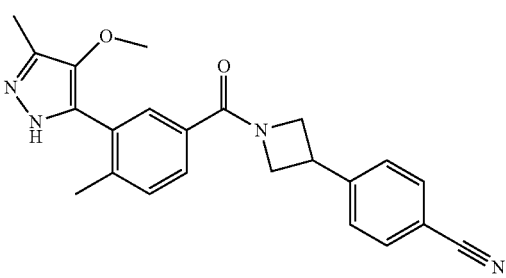 [SMILES: COc1c(C)n[nH]c1-c1cc(C(=O)N2CC(c3ccc(C#N)cc3)C2)ccc1C] | 248 | 0.075 | 0.077 |
| 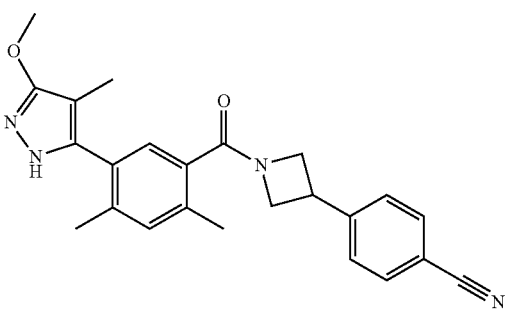 [SMILES: COc1n[nH]c(-c2cc(C(=O)N3CC(c4ccc(C#N)cc4)C3)c(C)cc2C)c1C] | 249 | 0.043 | 0.026 |
| 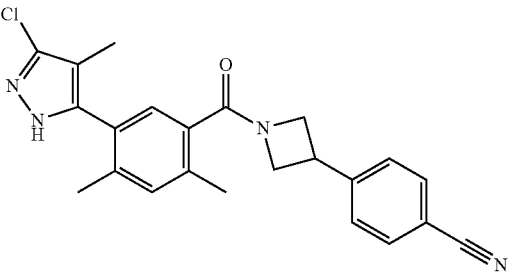 [SMILES: Cc1cc(C)c(-c2[nH]nc(Cl)c2C)cc1C(=O)N1CC(c2ccc(C#N)cc2)C1] | 250 | 0.051 | 0.075 |

TABLE 26-continued

Compounds of the present disclosure.

| Structure | Cpd | Hu FASN IC50 (μM) | HCV GT1b EC50 (μM) |
|---|---|---|---|
| 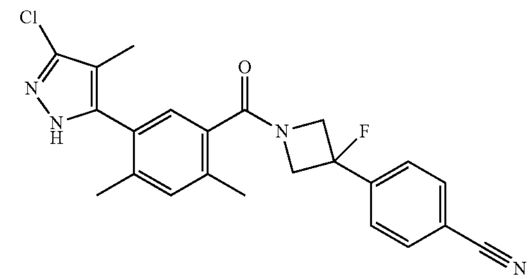 [SMILES: Cc1cc(C)c(-c2[nH]nc(Cl)c2C)cc1C(=O)N1CC(F)(c2ccc(C#N)cc2)C1] | 251 | 0.178 | 0.340 |
| 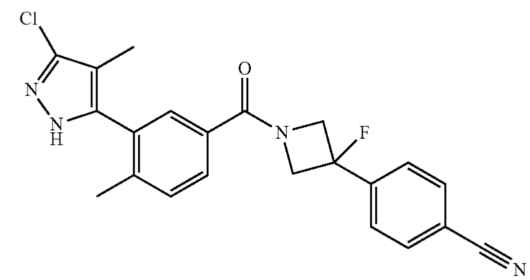 [SMILES: Cc1ccc(C(=O)N2CC(F)(c3ccc(C#N)cc3)C2)cc1-c1[nH]nc(Cl)c1C] | 252 | 0.095 | 0.230 |
| 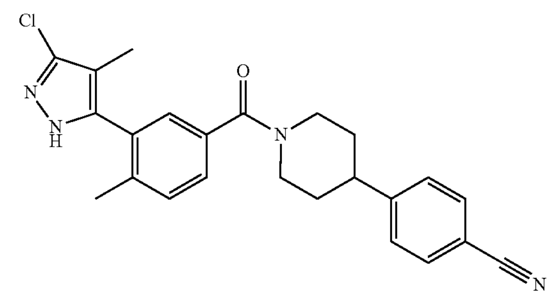 [SMILES: Cc1ccc(C(=O)N2CCC(c3ccc(C#N)cc3)CC2)cc1-c1[nH]nc(Cl)c1C] | 253 | 0.080 | 0.220 |
| 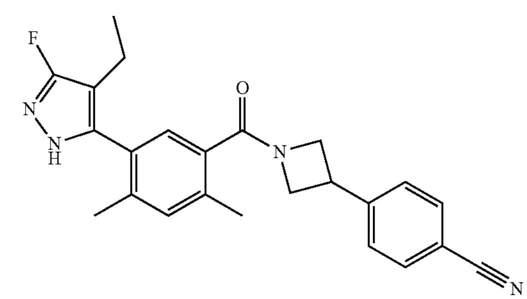 [SMILES: CCc1c(F)n[nH]c1-c1cc(C(=O)N2CC(c3ccc(C#N)cc3)C2)c(C)cc1C] | 255 | 0.063 | 0.083 |
| 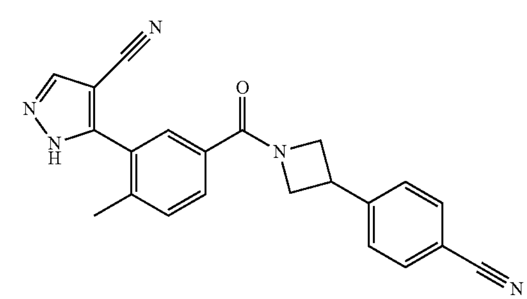 [SMILES: Cc1ccc(C(=O)N2CC(c3ccc(C#N)cc3)C2)cc1-c1[nH]ncc1C#N] | 256 | 0.210 | |

TABLE 26-continued
Compounds of the present disclosure.
| Structure | Cpd | Hu FASN IC50 (μM) | HCV GT1b EC50 (μM) |
|---|---|---|---|
| 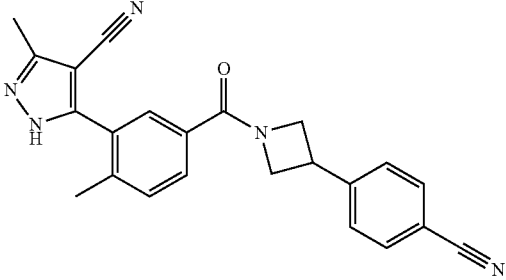 [SMILES: Cc1ccc(C(=O)N2CC(c3ccc(C#N)cc3)C2)cc1-c1[nH]nc(C)c1C#N] | 257 | 0.440 | 0.660 |
| 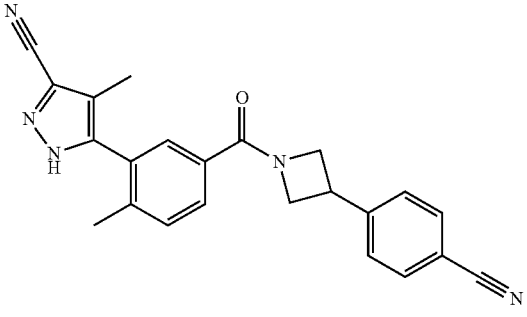 [SMILES: Cc1ccc(C(=O)N2CC(c3ccc(C#N)cc3)C2)cc1-c1[nH]nc(C#N)c1C] | 258 | 0.058 | |
| 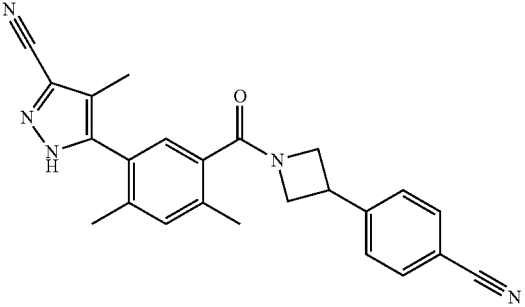 [SMILES: Cc1cc(C)c(-c2[nH]nc(C#N)c2C)cc1C(=O)N1CC(c2ccc(C#N)cc2)C1] | 259 | 0.140 | 0.082 |
| 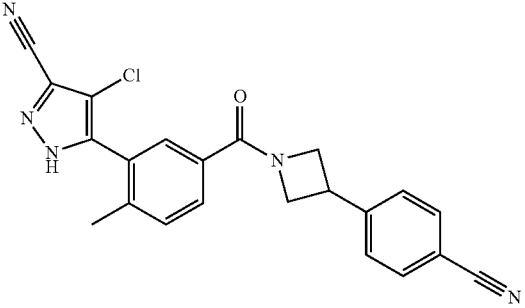 [SMILES: Cc1ccc(C(=O)N2CC(c3ccc(C#N)cc3)C2)cc1-c1[nH]nc(C#N)c1Cl] | 260 | 0.067 | 0.250 |

TABLE 26-continued

Compounds of the present disclosure.

| Structure | Cpd | Hu FASN IC50 (μM) | HCV GT1b EC50 (μM) |
|---|---|---|---|
| 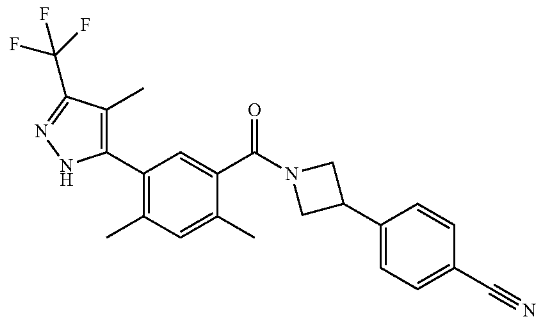 [SMILES: Cc1cc(C)c(-c2[nH]nc(C(F)(F)F)c2C)cc1C(=O)N1CC(c2ccc(C#N)cc2)C1] | 261 | 0.190 | 0.170 |
| 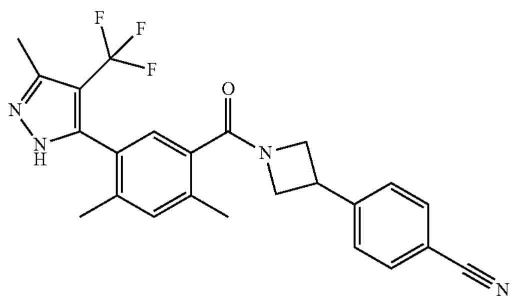 [SMILES: Cc1cc(C)c(-c2[nH]nc(C)c2C(F)(F)F)cc1C(=O)N1CC(c2ccc(C#N)cc2)C1] | 262 | 0.140 | 0.190 |
| 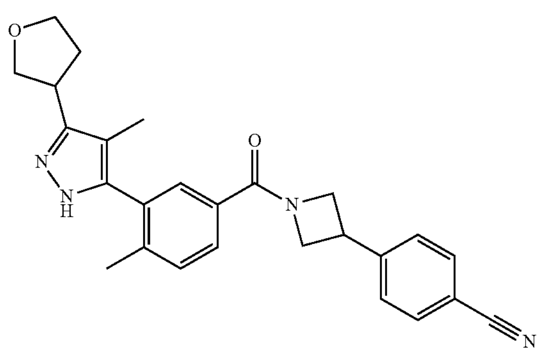 [SMILES: Cc1ccc(C(=O)N2CC(c3ccc(C#N)cc3)C2)cc1-c1[nH]nc(C2CCOC2)c1C] | 263 | 0.094 | 0.067 |
| 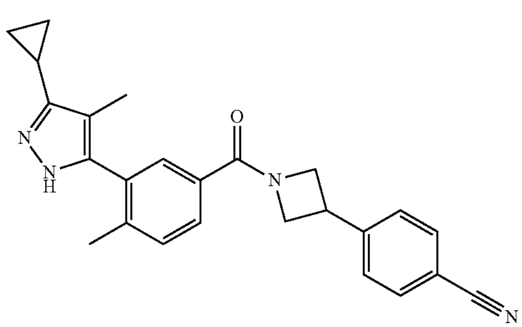 [SMILES: Cc1ccc(C(=O)N2CC(c3ccc(C#N)cc3)C2)cc1-c1[nH]nc(C2CC2)c1C] | 264 | 0.056 | 0.088 |

TABLE 26-continued

Compounds of the present disclosure.

| Structure | Cpd | Hu FASN IC50 (μM) | HCV GT1b EC50 (μM) |
| --- | --- | --- | --- |
| 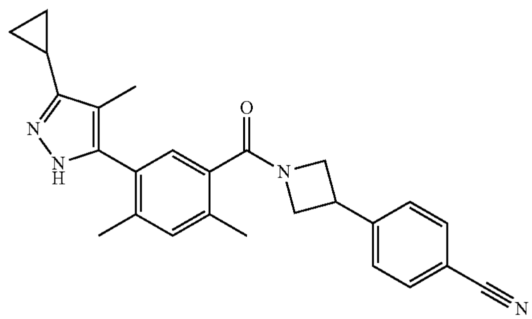 [SMILES: Cc1cc(C)c(-c2[nH]nc(C3CC3)c2C)cc1C(=O)N1CC(c2ccc(C#N)cc2)C1] | 265 | 0.110 | |
| 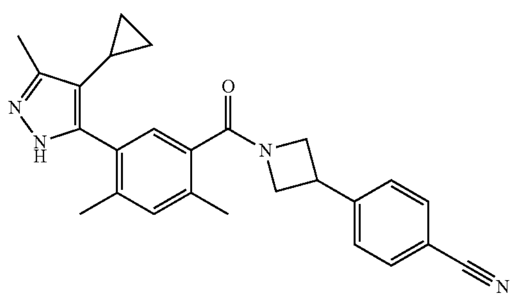 [SMILES: Cc1cc(C)c(-c2[nH]nc(C)c2C2CC2)cc1C(=O)N1CC(c2ccc(C#N)cc2)C1] | 266 | 0.200 | 0.260 |
| 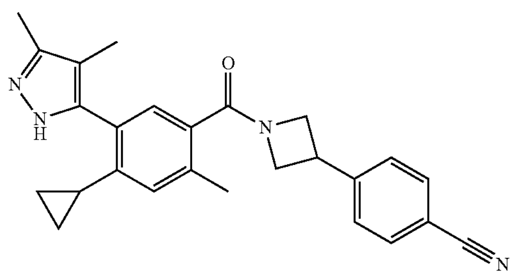 [SMILES: Cc1cc(C2CC2)c(-c2[nH]nc(C)c2C)cc1C(=O)N1CC(c2ccc(C#N)cc2)C1] | 267 | 0.100 | 0.150 |
| 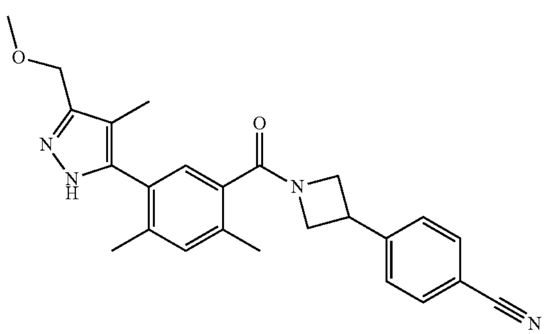 [SMILES: COCc1n[nH]c(-c2cc(C(=O)N3CC(c4ccc(C#N)cc4)C3)c(C)cc2C)c1C] | 268 | 0.059 | 0.029 |
| 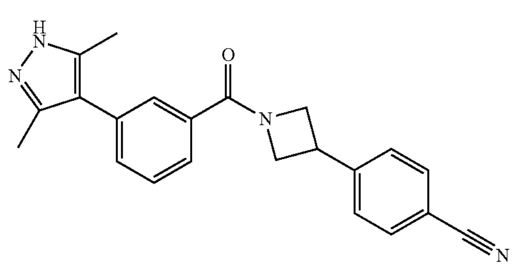 [SMILES: Cc1n[nH]c(C)c1-c1cccc(C(=O)N2CC(c3ccc(C#N)cc3)C2)c1] | 269 | 50.000 | |

TABLE 26-continued

Compounds of the present disclosure.

| Structure | Cpd | Hu FASN IC50 (μM) | HCV GT1b EC50 (μM) |
|---|---|---|---|
| 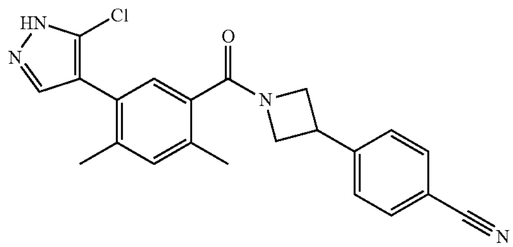 [SMILES: Cc1cc(C)c(-c2cn[nH]c2Cl)cc1C(=O)N1CC(c2ccc(C#N)cc2)C1] | 270 | | |
| 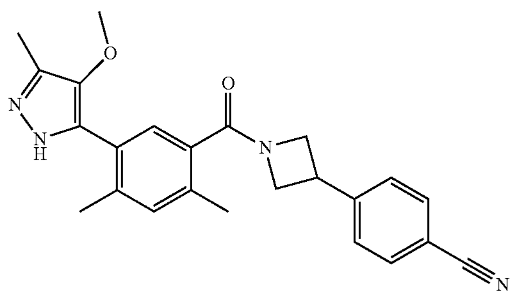 [SMILES: COc1c(C)n[nH]c1-c1cc(C(=O)N2CC(c3ccc(C#N)cc3)C2)c(C)cc1C] | 271 | | |
| 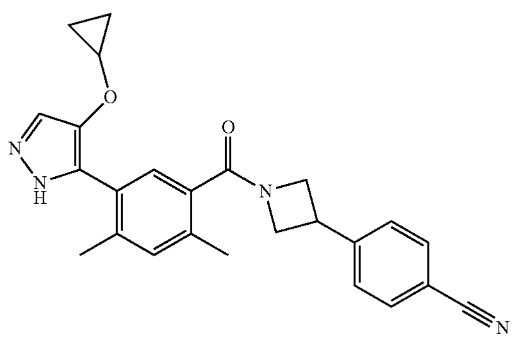 [SMILES: Cc1cc(C)c(-c2[nH]ncc2OC2CC2)cc1C(=O)N1CC(c2ccc(C#N)cc2)C1] | 272 | | |
| 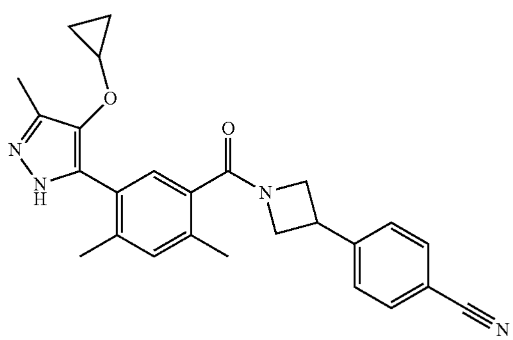 [SMILES: Cc1cc(C)c(-c2[nH]nc(C)c2OC2CC2)cc1C(=O)N1CC(c2ccc(C#N)cc2)C1] | 273 | | |
| 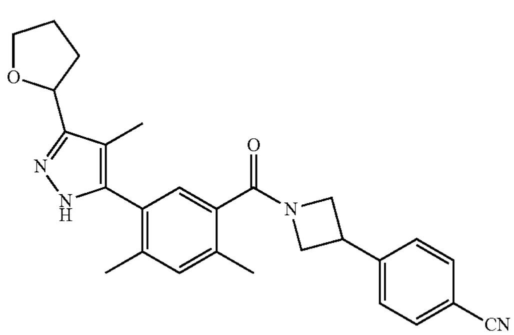 [SMILES: Cc1cc(C)c(-c2[nH]nc(C3CCCO3)c2C)cc1C(=O)N1CC(c2ccc(C#N)cc2)C1] | 274 | 0.051 | 0.016 |

TABLE 26-continued

Compounds of the present disclosure.

| Structure | Cpd | Hu FASN IC50 (μM) | HCV GT1b EC50 (μM) |
|---|---|---|---|
| 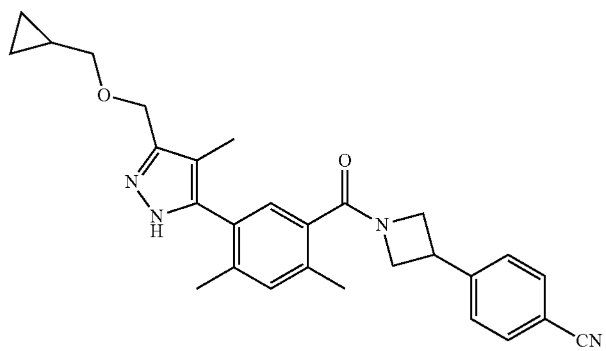 [SMILES: Cc1cc(C)c(-c2[nH]nc(COCC3CC3)c2C)cc1C(=O)N1CC(c2ccc(C#N)cc2)C1] | 275 | 0.057 | 0.038 |
| 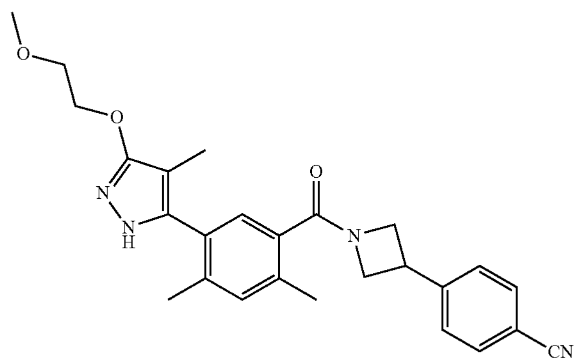 [SMILES: COCCOc1n[nH]c(-c2cc(C(=O)N3CC(c4ccc(C#N)cc4)C3)c(C)cc2C)c1C] | 276 | 50 | 20 |
| 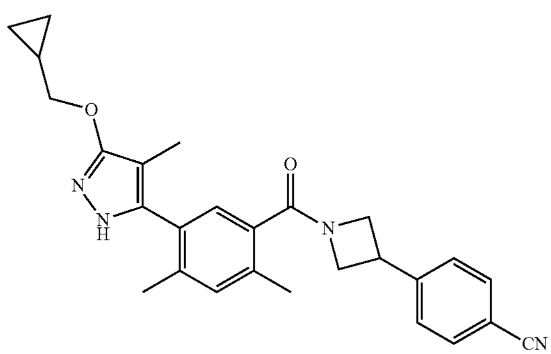 [SMILES: Cc1cc(C)c(-c2[nH]nc(OCC3CC3)c2C)cc1C(=O)N1CC(c2ccc(C#N)cc2)C1] | 277 | 50 | 20 |
| 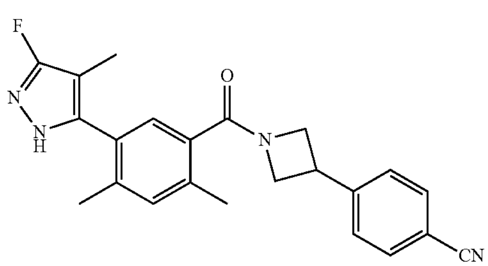 [SMILES: Cc1cc(C)c(-c2[nH]nc(F)c2C)cc1C(=O)N1CC(c2ccc(C#N)cc2)C1] | 278 | | |

TABLE 26-continued

Compounds of the present disclosure.

| Structure | Cpd | Hu FASN IC50 (μM) | HCV GT1b EC50 (μM) |
|---|---|---|---|
| 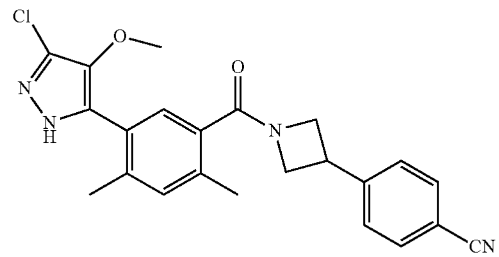 [SMILES: COc1c(Cl)n[nH]c1-c1cc(C(=O)N2CC(c3ccc(C#N)cc3)C2)c(C)cc1C] | 279 | 0.11 | 0.039 |
| 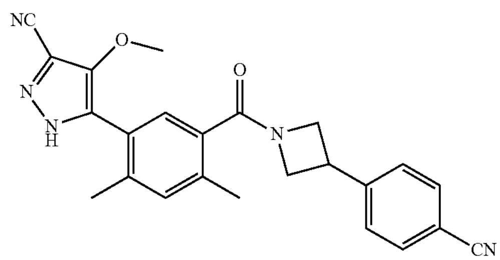 [SMILES: COc1c(C#N)n[nH]c1-c1cc(C(=O)N2CC(c3ccc(C#N)cc3)C2)c(C)cc1C] | 280 | 0.089 | 0.15 |
| 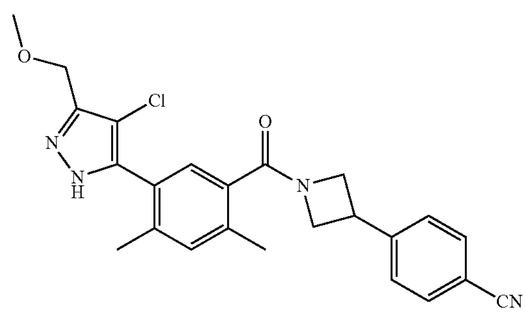 | 281 | 0.072 | 0.021 |
| 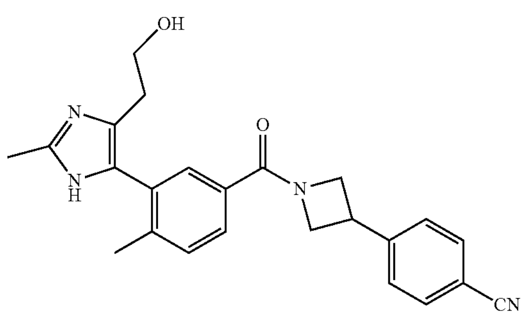 [SMILES: Cc1nc(CCO)c(-c2cc(C(=O)N3CC(c4ccc(C#N)cc4)C3)ccc2C)[nH]1] | 282 | 0.091 | 0.15 |
| 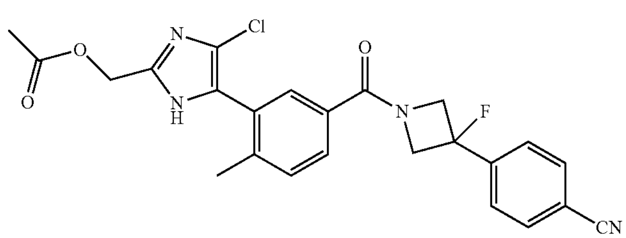 [SMILES: CC(=O)OCc1nc(Cl)c(-c2cc(C(=O)N3CC(F)(c4ccc(C#N)cc4)C3)ccc2C)[nH]1] | 283 | 0.064 | 0.082 |

TABLE 26-continued
Compounds of the present disclosure.
| Structure | Cpd | Hu FASN IC50 (μM) | HCV GT1b EC50 (μM) |
|---|---|---|---|
| 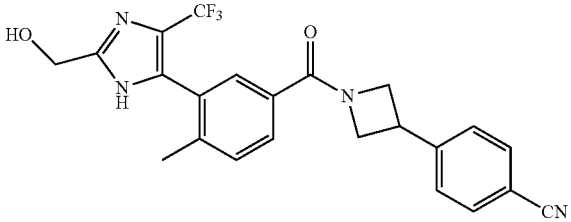 | 284 | 0.044 | 0.01 |
| 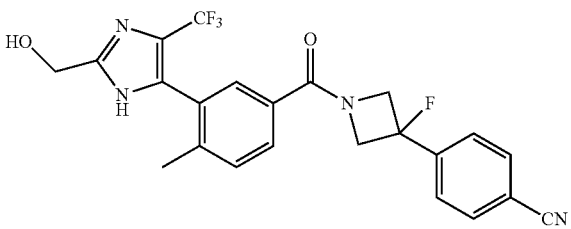 [SMILES: Cc1ccc(C(=O)N2CC(F)(c3ccc(C#N)cc3)C2)cc1-c1[nH]c(CO)nc1C(F)(F)F] | 285 | 0.048 | 0.027 |
| 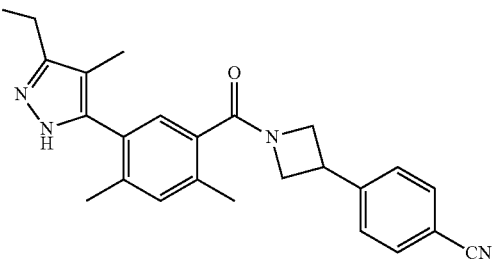 | 286 | 0.061 | 0.027 |
| 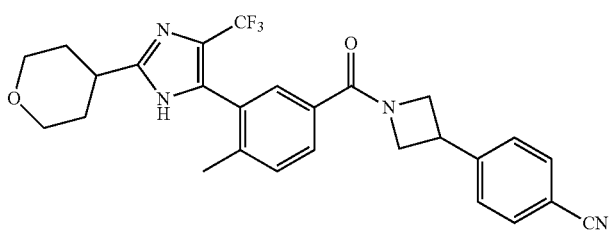 | 287 | 0.029 | 0.003 |
| 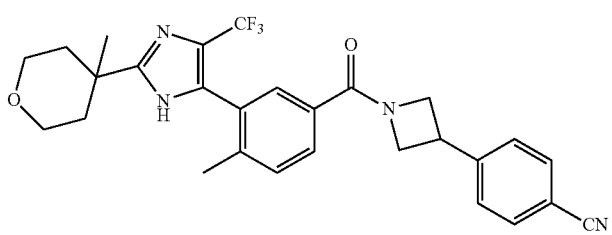 [SMILES: Cc1ccc(C(=O)N2CC(c3ccc(C#N)cc3)C2)cc1-c1[nH]c(C2(C)CCOCC2)nc1C(F)(F)F] | 288 | 0.026 | 0.01 |
| 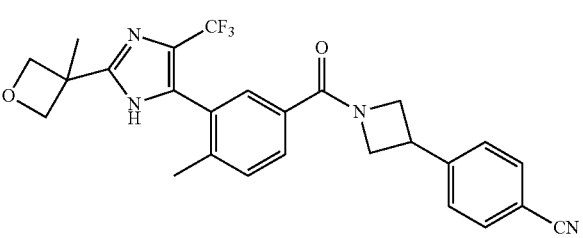 [SMILES: Cc1ccc(C(=O)N2CC(c3ccc(C#N)cc3)C2)cc1-c1[nH]c(C2(C)COC2)nc1C(F)(F)F] | 289 | 0.018 | 0.01 |

TABLE 26-continued
Compounds of the present disclosure.
| Structure | Cpd | Hu FASN IC50 (μM) | HCV GT1b EC50 (μM) |
|---|---|---|---|
| 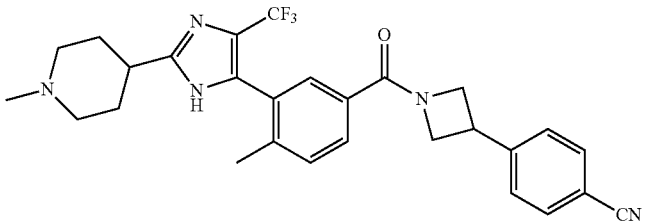 [SMILES: Cc1ccc(C(=O)N2CC(c3ccc(C#N)cc3)C2)cc1-c1[nH]c(C2CCN(C)CC2)nc1C(F)(F)F] | 290 | 0.021 | 0.029 |
| 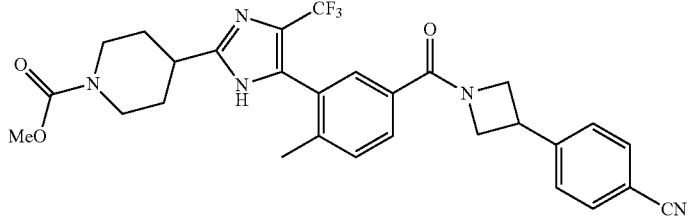 [SMILES: COC(=O)N1CCC(c2nc(C(F)(F)F)c(-c3cc(C(=O)N4CC(c5ccc(C#N)cc5)C4)ccc3C)[nH]2)CC1] | 291 | 0.02 | 0.003 |
| 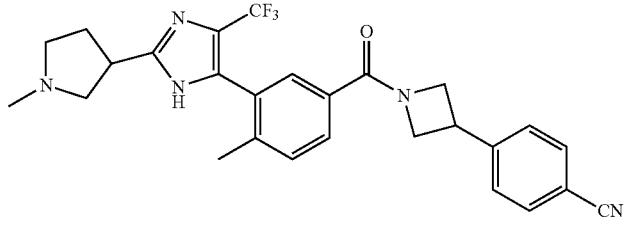 [SMILES: Cc1ccc(C(=O)N2CC(c3ccc(C#N)cc3)C2)cc1-c1[nH]c(C2CCN(C)C2)nc1C(F)(F)F] | 292 | 0.044 | 0.033 |
| 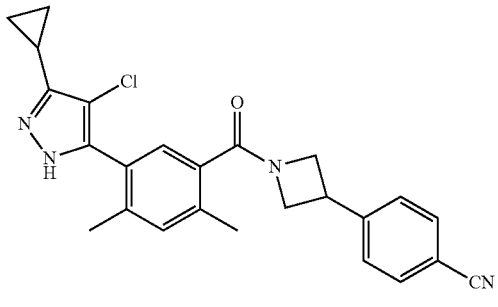 [SMILES: Cc1cc(C)c(-c2[nH]nc(C3CC3)c2Cl)cc1C(=O)N1CC(c2ccc(C#N)cc2)C1] | 293 | 0.064 | 0.12 |
| 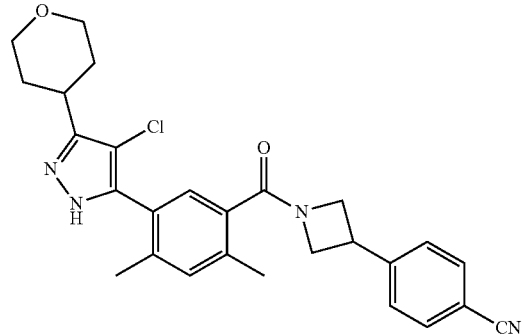 [SMILES: Cc1cc(C)c(-c2[nH]nc(C3CCOCC3)c2Cl)cc1C(=O)N1CC(c2ccc(C#N)cc2)C1] | 294 | 0.049 | 0.041 |

TABLE 26-continued
Compounds of the present disclosure.
| Structure | Cpd | Hu FASN IC50 (μM) | HCV GT1b EC50 (μM) |
|---|---|---|---|
| 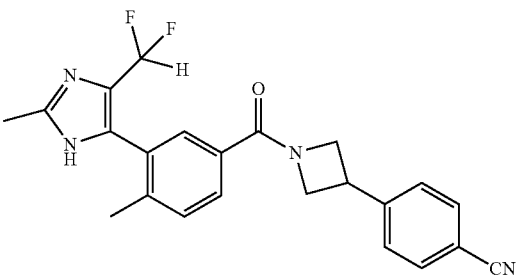 [SMILES: Cc1nc(C(F)F)c(-c2cc(C(=O)N3CC(c4ccc(C#N)cc4)C3)ccc2C)[nH]1] | 295 | 0.031 | 0.037 |
| 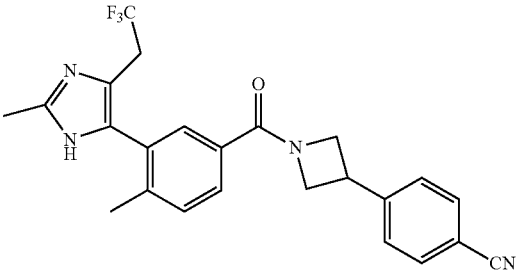 [SMILES: Cc1nc(CC(F)(F)F)c(-c2cc(C(=O)N3CC(c4ccc(C#N)cc4)C3)ccc2C)[nH]1] | 296 | 0.024 | |
| 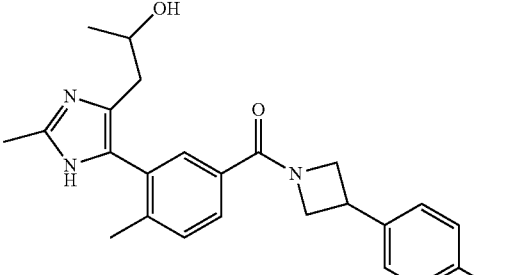 | 297 | | |
| 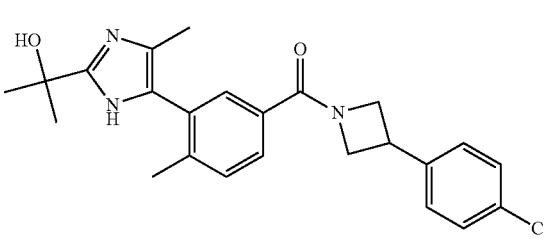 | 298 | | |
| 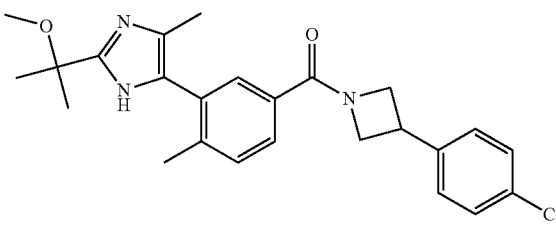 | 299 | | |
| 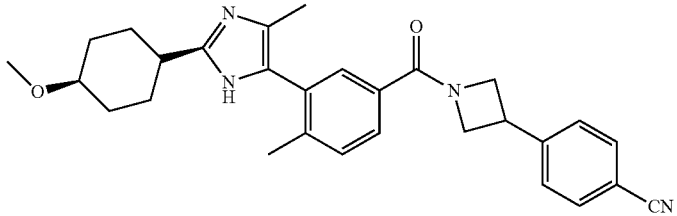 | 300A | 0.026 | 0.007 |

TABLE 26-continued

Compounds of the present disclosure.

| Structure | Cpd | Hu FASN IC50 (μM) | HCV GT1b EC50 (μM) |
|---|---|---|---|
| 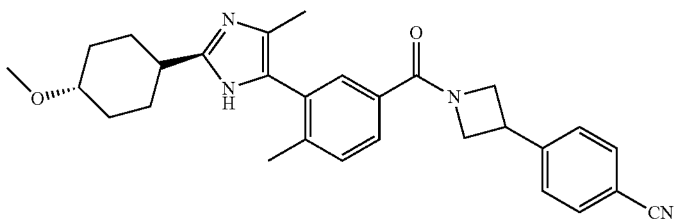 | 300B | 0.024 | 0.003 |
| 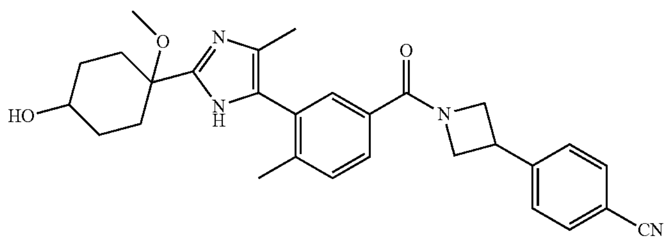 [SMILES: COC1(c2nc(C)c(-c3cc(C(=O)N4CC(c5ccc(C#N)cc5)C4)ccc3C)[nH]2)CCC(O)CC1] | 301 | | |
| 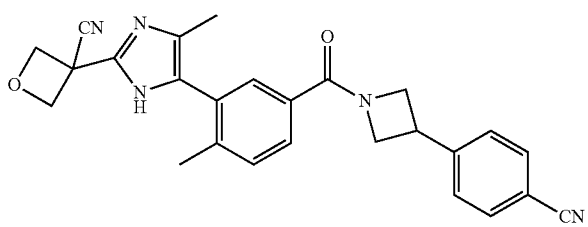 [SMILES: Cc1ccc(C(=O)N2CC(c3ccc(C#N)cc3)C2)cc1-c1[nH]c(C2(C#N)COC2)nc1C] | 302 | | |
| 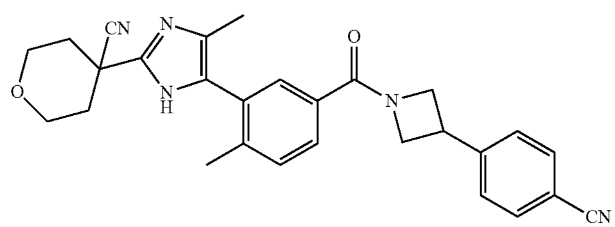 [SMILES: Cc1ccc(C(=O)N2CC(c3ccc(C#N)cc3)C2)cc1-c1[nH]c(C2(C#N)CCOCC2)nc1C] | 303 | | |
| 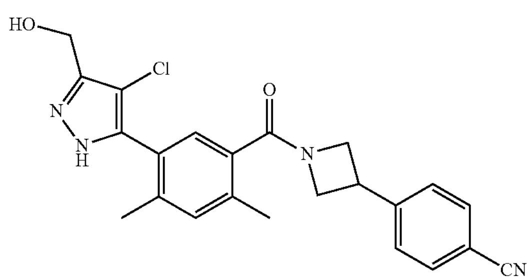 [SMILES: Cc1cc(C)c(-c2[nH]nc(CO)c2Cl)cc1C(=O)N1CC(c2ccc(C#N)cc2)C1] | 304 | 0.021 | |
| 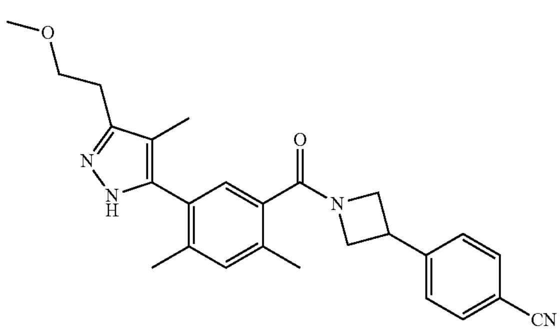 [SMILES: COCCc1n[nH]c(-c2cc(C(=O)N3CC(c4ccc(C#N)cc4)C3)c(C)cc2C)c1C] | 305 | 0.078 | 0.077 |

TABLE 26-continued

Compounds of the present disclosure.

| Structure | Cpd | Hu FASN IC50 (µM) | HCV GT1b EC50 (µM) |
|---|---|---|---|
| 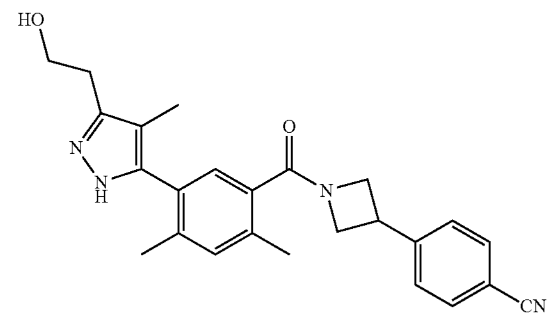 [SMILES: Cc1cc(C)c(-c2[nH]nc(CCO)c2C)cc1C(=O)N1CC(c2ccc(C#N)cc2)C1] | 306 | | |
| 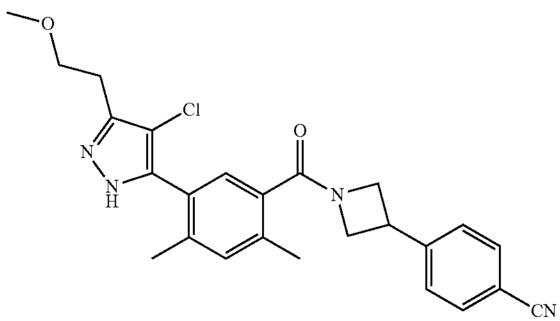 [SMILES: COCCc1n[nH]c(-c2cc(C(=O)N3CC(c4ccc(C#N)cc4)C3)c(C)cc2C)c1Cl] | 307 | | 0.056 |
| 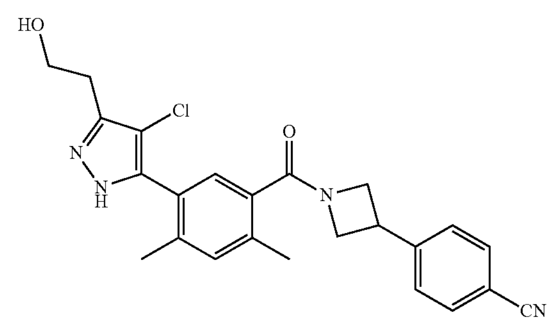 [SMILES: Cc1cc(C)c(-c2[nH]nc(CCO)c2Cl)cc1C(=O)N1CC(c2ccc(C#N)cc2)C1] | 308 | | |
| 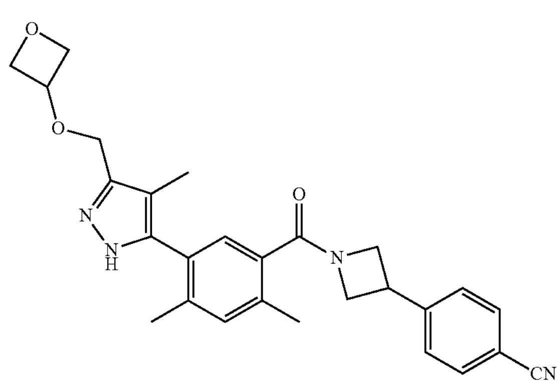 [SMILES: Cc1cc(C)c(-c2[nH]nc(COC3COC3)c2C)cc1C(=O)N1CC(c2ccc(C#N)cc2)C1] | 309 | | 0.037 |

TABLE 26-continued

Compounds of the present disclosure.

| Structure | Cpd | Hu FASN IC50 (μM) | HCV GT1b EC50 (μM) |
|---|---|---|---|
| 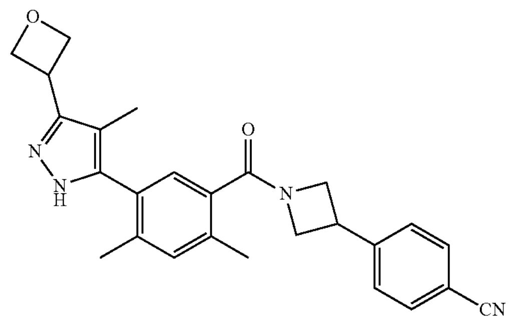 [SMILES: Cc1cc(C)c(-c2[nH]nc(C3COC3)c2C)cc1C(=O)N1CC(c2ccc(C#N)cc2)C1] | 310 | | |
| 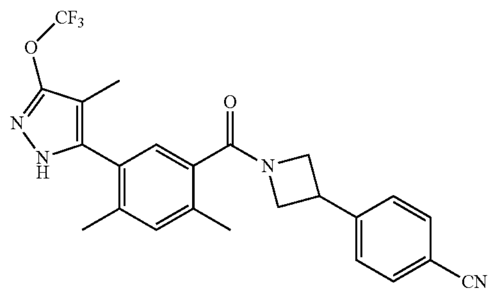 | 311 | | |
| 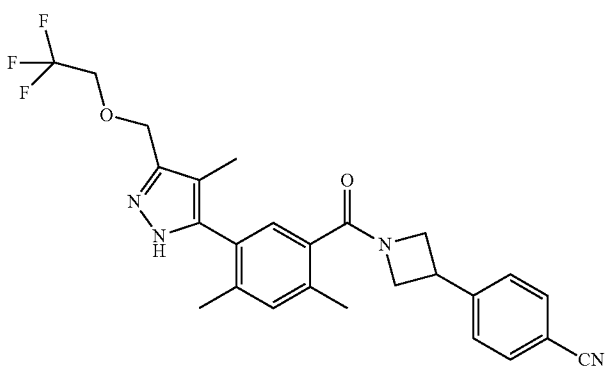 [SMILES: Cc1cc(C)c(-c2[nH]nc(COCC(F)(F)F)c2C)cc1C(=O)N1CC(c2ccc(C#N)cc2)C1] | 312 | 0.037 | |
| 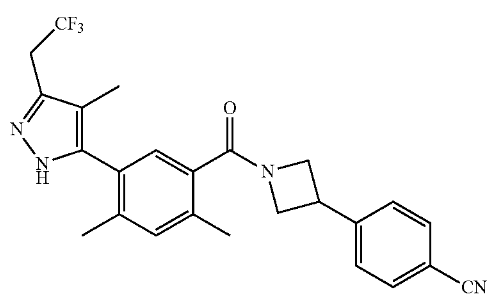 [SMILES: Cc1cc(C)c(-c2[nH]nc(CC(F)(F)F)c2C)cc1C(=O)N1CC(c2ccc(C#N)cc2)C1] | 313 | 0.1 | |
| 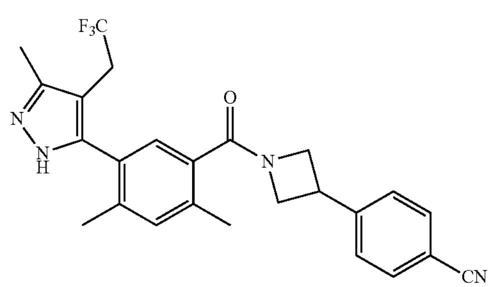 [SMILES: Cc1cc(C)c(-c2[nH]nc(C)c2CC(F)(F)F)cc1C(=O)N1CC(c2ccc(C#N)cc2)C1] | 314 | 0.46 | |

TABLE 26-continued
Compounds of the present disclosure.
| Structure | Cpd | Hu FASN IC50 (μM) | HCV GT1b EC50 (μM) |
|---|---|---|---|
| 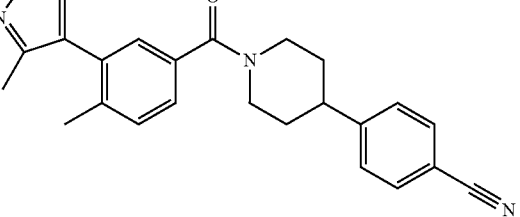 | 315 | | |
| 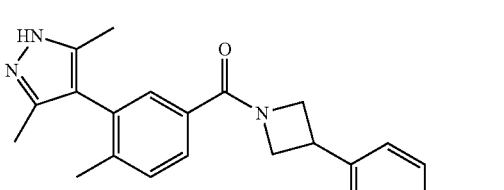 | 316 | | |
| 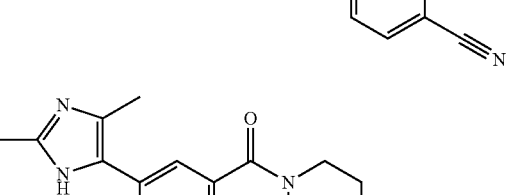 | 317 | | |
| 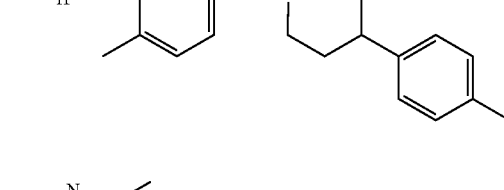 | 318 | | |
| 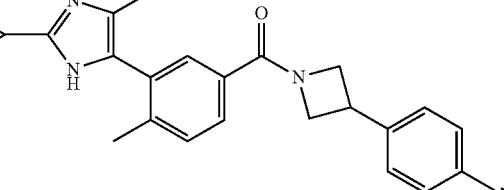 | 320 | | |
| 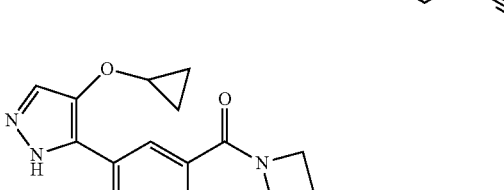 | 321 | | |

TABLE 26-continued
Compounds of the present disclosure.
| Structure | Cpd | Hu FASN IC50 (μM) | HCV GT1b EC50 (μM) |
|---|---|---|---|
| 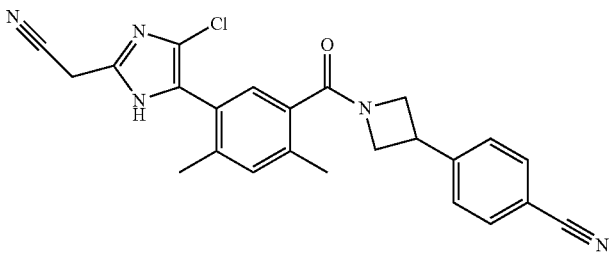 [SMILES: Cc1cc(C)c(-c2[nH]c(CC#N)nc2Cl)cc1C(=O)N1CC(c2ccc(C#N)cc2)C1] | 322 | | |
| 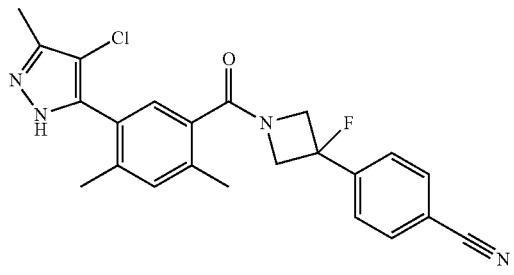 [SMILES: Cc1cc(C)c(-c2[nH]nc(C)c2Cl)cc1C(=O)N1CC(F)(c2ccc(C#N)cc2)C1] | 323 | | |
| 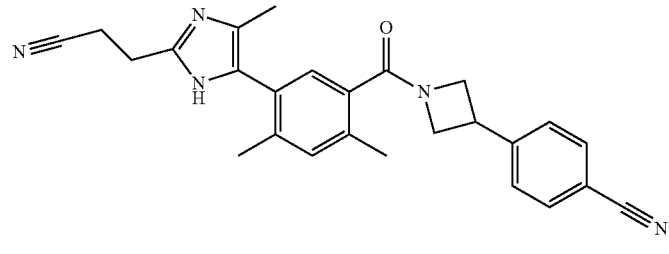 [SMILES: Cc1cc(C)c(-c2[nH]c(CCC#N)nc2C)cc1C(=O)N1CC(c2ccc(C#N)cc2)C1] | 324 | | |
| 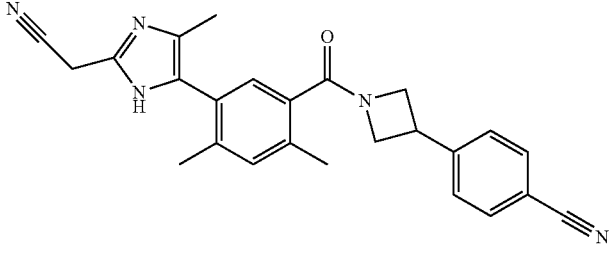 [SMILES: Cc1cc(C)c(-c2[nH]c(CC#N)nc2C)cc1C(=O)N1CC(c2ccc(C#N)cc2)C1] | 325 | | |
| 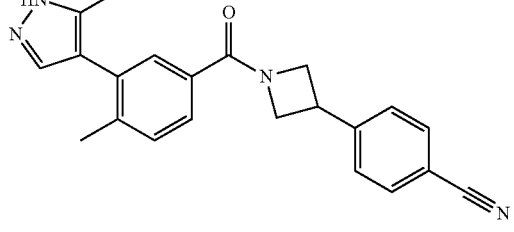 | 326 | | |

TABLE 26-continued
Compounds of the present disclosure.
| Structure | Cpd | Hu FASN IC50 (μM) | HCV GT1b EC50 (μM) |
|---|---|---|---|
| 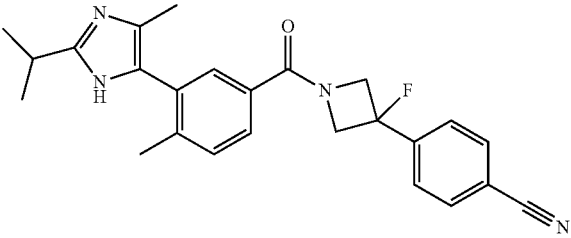 [SMILES: Cc1ccc(C(=O)N2CC(F)(c3ccc(C#N)cc3)C2)cc1-c1[nH]c(C(C)C)nc1C] | 327 | | |
| 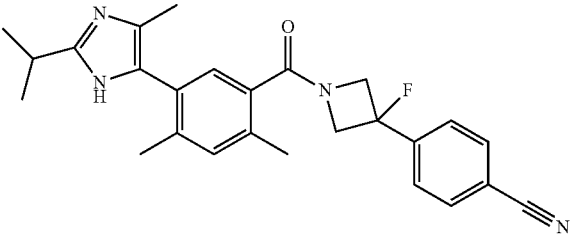 [SMILES: Cc1cc(C)c(-c2[nH]c(C(C)C)nc2C)cc1C(=O)N1CC(F)(c2ccc(C#N)cc2)C1] | 328 | | |
| 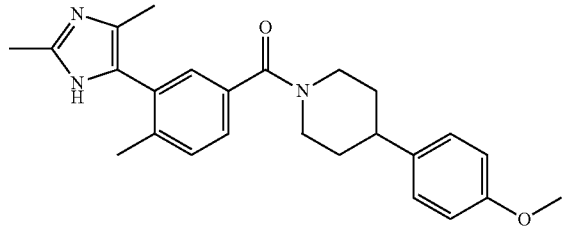 | 329 | 0.089 | |
| 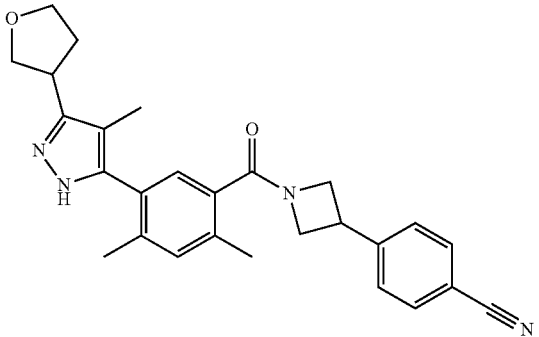 [SMILES: Cc1cc(C)c(-c2[nH]nc(C3CCOC3)c2C)cc1C(=O)N1CC(c2ccc(C#N)cc2)C1] | 330 | 0.1 | 0.028 |
| 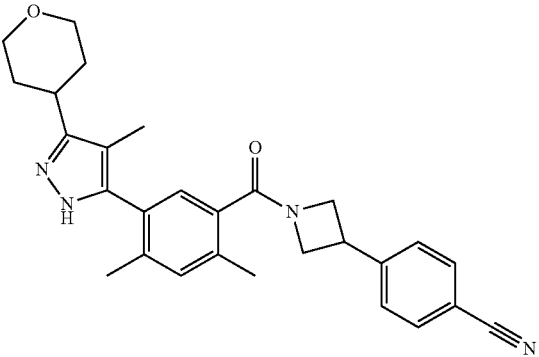 [SMILES: Cc1cc(C)c(-c2[nH]nc(C3CCOCC3)c2C)cc1C(=O)N1CC(c2ccc(C#N)cc2)C1] | 331 | 0.11 | 0.021 |

TABLE 26-continued
Compounds of the present disclosure.
| Structure | Cpd | Hu FASN IC50 (µM) | HCV GT1b EC50 (µM) |
|---|---|---|---|
| 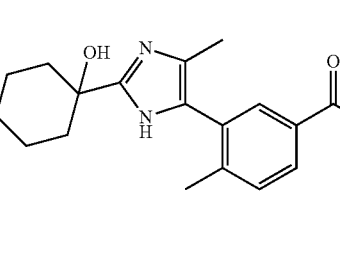 | 332 | 0.01 | |
| 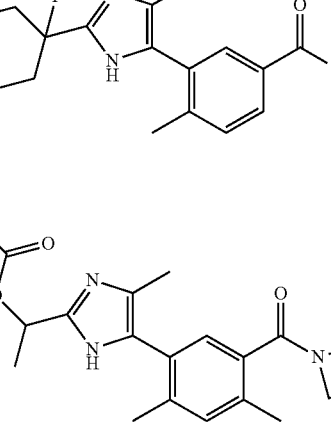 | 333 | | |
| 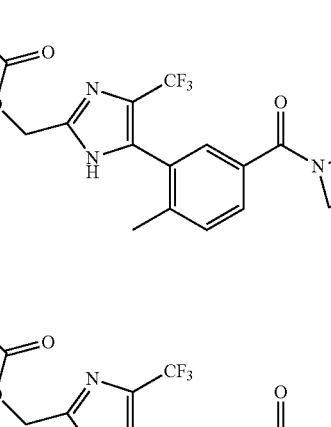 | 334 | | |
| 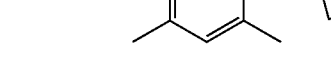 | 335 | | |
| 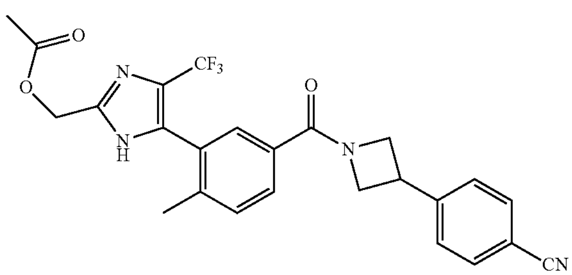 | 336 | | |
| 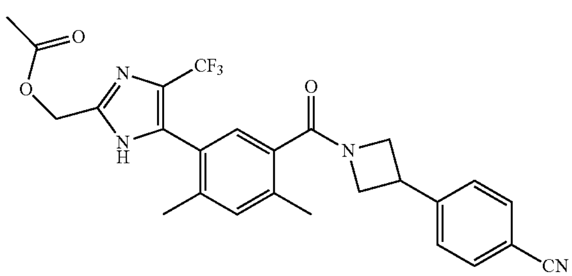 [SMILES: CC(=O)OCc1nc(C(F)(F)F)c(-c2cc(C(=O)N3CC(c4ccc(C#N)cc4)C3)c(C)cc2C)[nH]1] | 337 | | |

TABLE 26-continued
Compounds of the present disclosure.
| Structure | Cpd | Hu FASN IC50 (μM) | HCV GT1b EC50 (μM) |
|---|---|---|---|
| 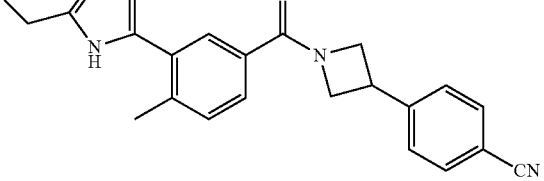 | 338 | | |
| 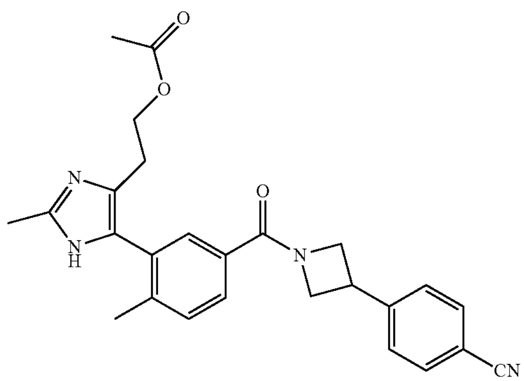 [SMILES: CC(=O)OCCc1nc(C)[nH]c1-c1cc(C(=O)N2CC(c3ccc(C#N)cc3)C2)ccc1C] | 339 | | |
| 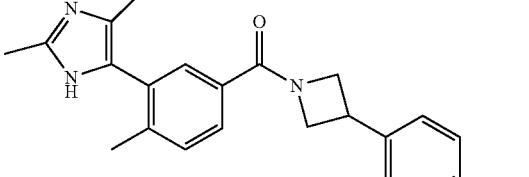 | 340 | | |
| 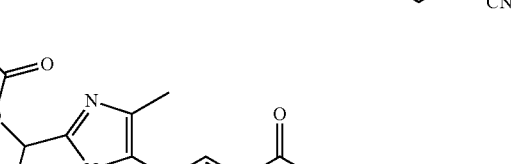 | 341 | | |
| 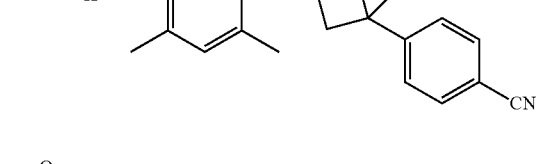 | 342 | | |

TABLE 26-continued

Compounds of the present disclosure.

| Structure | Cpd | Hu FASN IC50 (μM) | HCV GT1b EC50 (μM) |
|---|---|---|---|
| 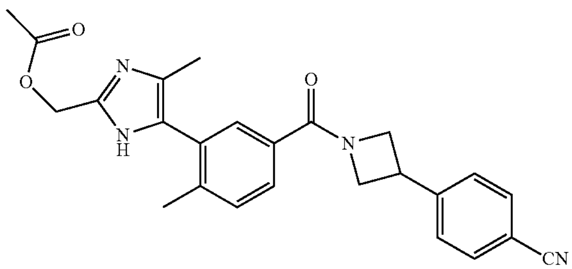 [SMILES: CC(=O)OCc1nc(C)c(-c2cc(C(=O)N3CC(c4ccc(C#N)cc4)C3)ccc2C)[nH]1] | 343 | | |
| 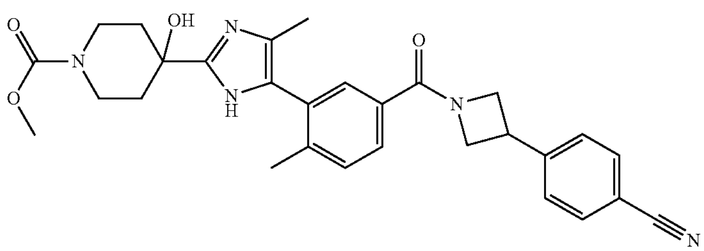 [SMILES: COC(=O)N1CCC(O)(c2nc(C)c(-c3cc(C(=O)N4CC(c5ccc(C#N)cc5)C4)ccc3C)[nH]2)CC1] | 344 | 0.024 | 0.013 |
| 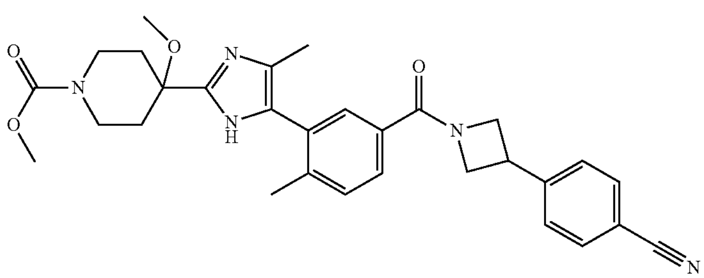 [SMILES: COC(=O)N1CCC(OC)(c2nc(C)c(-c3cc(C(=O)N4CC(c5ccc(C#N)cc5)C4)ccc3C)[nH]2)CC1] | 345 | 0.035 | 0.006 |
| 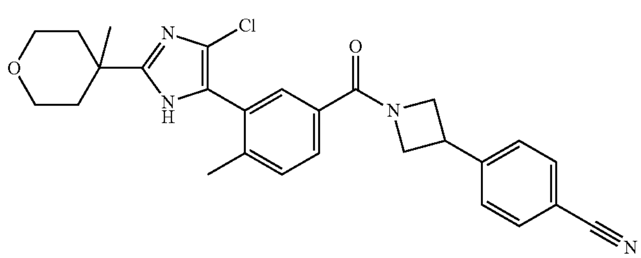 [SMILES: Cc1ccc(C(=O)N2CC(c3ccc(C#N)cc3)C2)cc1-c1[nH]c(C2(C)CCOCC2)nc1Cl] | 346 | 0.018 | 0.0001 |
| 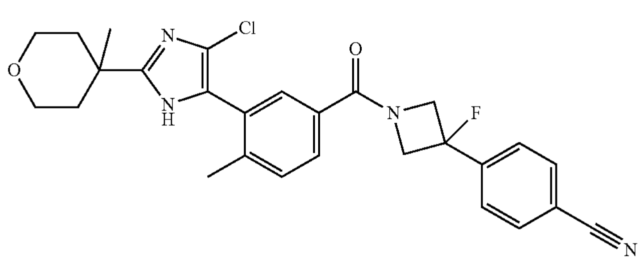 [SMILES: Cc1ccc(C(=O)N2CC(F)(c3ccc(C#N)cc3)C2)cc1-c1[nH]c(C2(C)CCOCC2)nc1Cl] | 347 | 0.016 | 0.005 |

TABLE 26-continued
Compounds of the present disclosure.
| Structure | Cpd | Hu FASN IC50 (μM) | HCV GT1b EC50 (μM) |
|---|---|---|---|
| 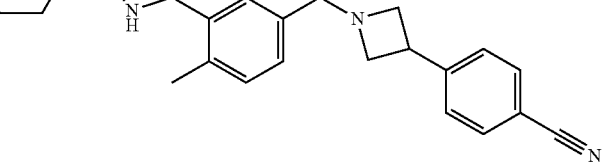 | 348 | 0.014 | 0.002 |
| 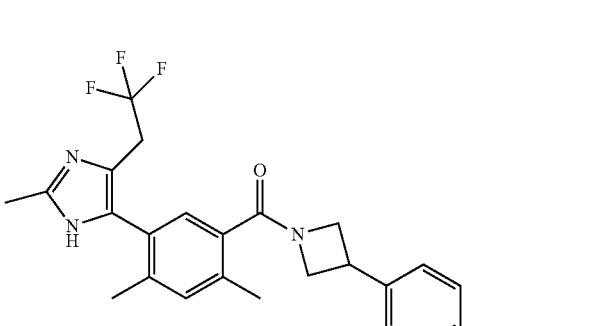 | 349 | 0.019 | |
| 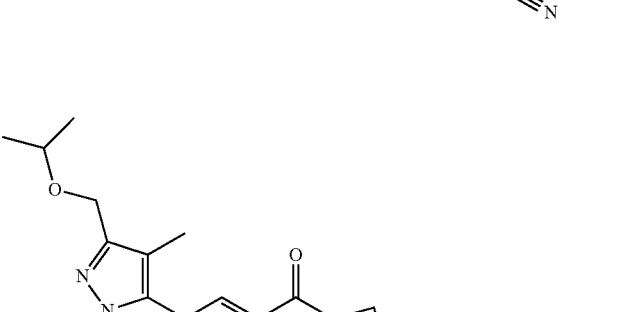 | 350 | 0.055 | |
| 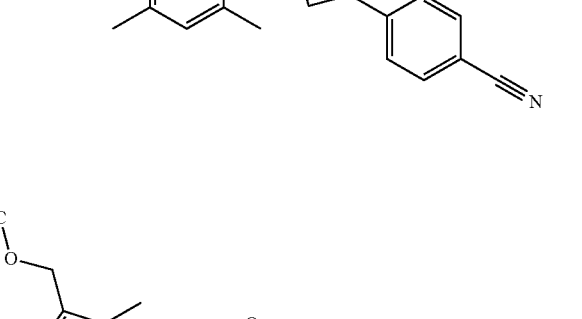 | 351 | | |

TABLE 26-continued

Compounds of the present disclosure.

| Structure | Cpd | Hu FASN IC50 (μM) | HCV GT1b EC50 (μM) |
|---|---|---|---|
| 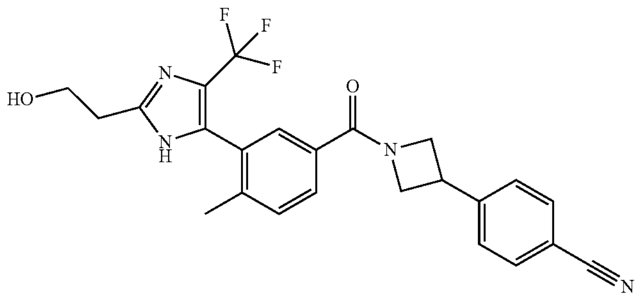 [SMILES: Cc1ccc(C(=O)N2CC(c3ccc(C#N)cc3)C2)cc1-c1[nH]c(CCO)nc1C(F)(F)F] | 352 | 0.011 | |
| 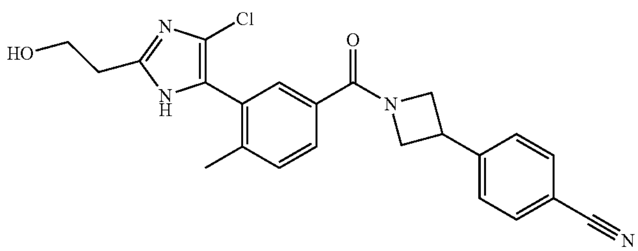 [SMILES: Cc1ccc(C(=O)N2CC(c3ccc(C#N)cc3)C2)cc1-c1[nH]c(CCO)nc1Cl] | 353 | 0.009 | |
| 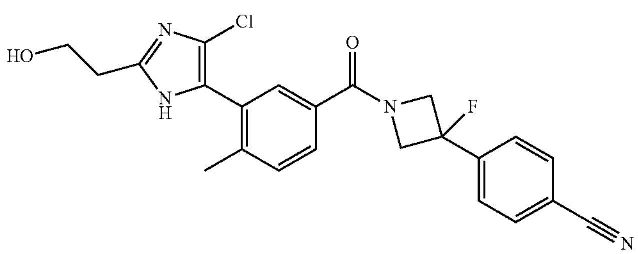 [SMILES: Cc1ccc(C(=O)N2CC(F)(c3ccc(C#N)cc3)C2)cc1-c1[nH]c(CCO)nc1Cl] | 354 | 0.018 | |
| 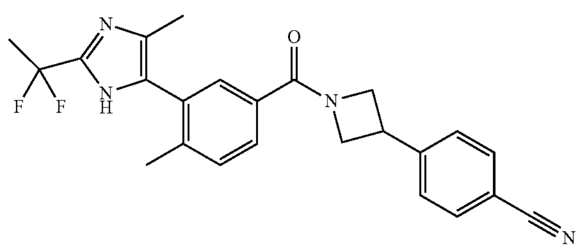 [SMILES: Cc1ccc(C(=O)N2CC(c3ccc(C#N)cc3)C2)cc1-c1[nH]c(C(C)(F)F)nc1C] | 355 | 0.082 | |
| 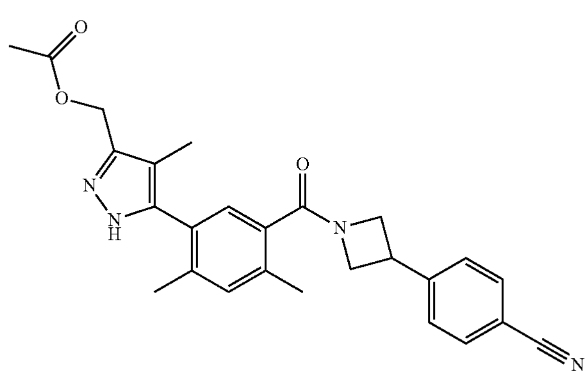 [SMILES: CC(=O)OCc1n[nH]c(-c2cc(C(=O)N3CC(c4ccc(C#N)cc4)C3)c(C)cc2C)c1C] | 356 | 0.851 | |

TABLE 26-continued

Compounds of the present disclosure.

| Structure | Cpd | Hu FASN IC50 (μM) | HCV GT1b EC50 (μM) |
|---|---|---|---|
| 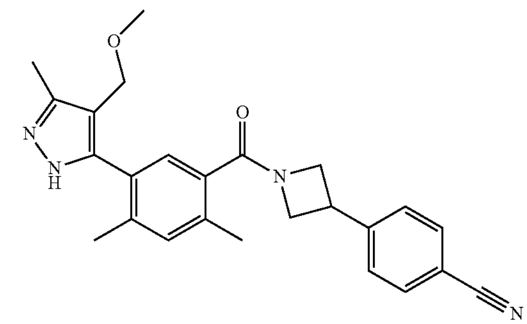 [SMILES: COCc1c(C)n[nH]c1-c1cc(C(=O)N2CC(c3ccc(C#N)cc3)C2)c(C)cc1C] | 357 | 0.087 | |
| 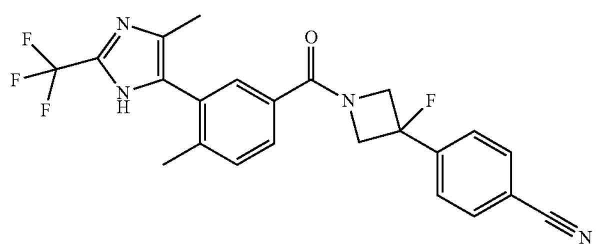 [SMILES: Cc1ccc(C(=O)N2CC(F)(c3ccc(C#N)cc3)C2)cc1-c1[nH]c(C(F)(F)F)nc1C] | 358 | 0.110 | |
| 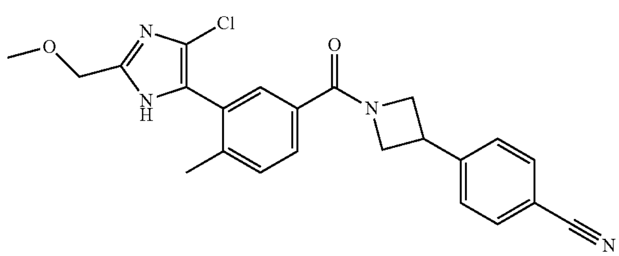 [SMILES: COCc1nc(Cl)c(-c2cc(C(=O)N3CC(c4ccc(C#N)cc4)C3)ccc2C)[nH]1] | 359 | 0.014 | |
| 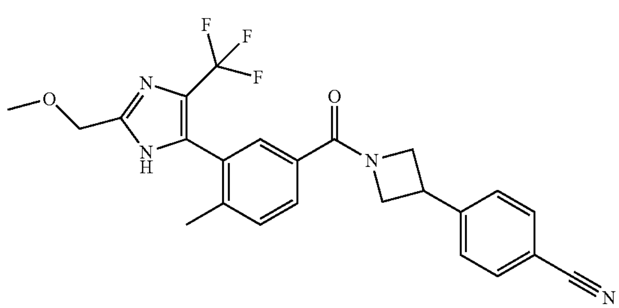 [SMILES: COCc1nc(C(F)(F)F)c(-c2cc(C(=O)N3CC(c4ccc(C#N)cc4)C3)ccc2C)[nH]1] | 360 | 0.012 | |
| 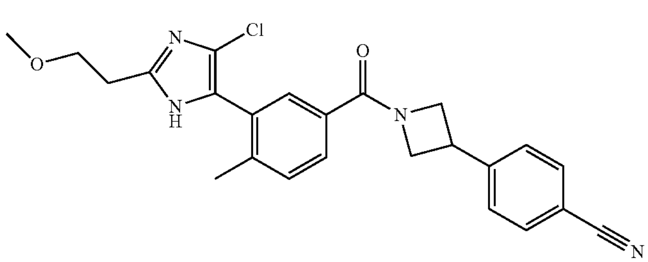 [SMILES: COCCc1nc(Cl)c(-c2cc(C(=O)N3CC(c4ccc(C#N)cc4)C3)ccc2C)[nH]1] | 361 | 0.013 | |

TABLE 26-continued

Compounds of the present disclosure.

| Structure | Cpd | Hu FASN IC50 (μM) | HCV GT1b EC50 (μM) |
|---|---|---|---|
| 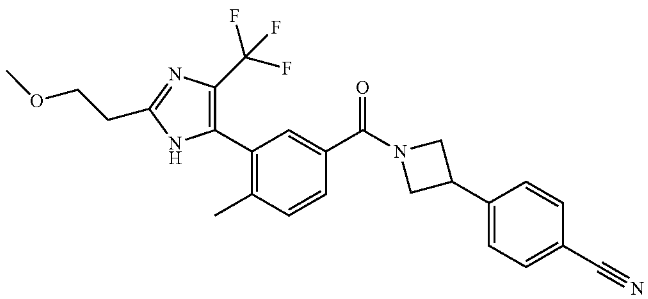 [SMILES: COCCc1nc(C(F)(F)F)c(-c2cc(C(=O)N3CC(c4ccc(C#N)cc4)C3)ccc2C)[nH]1] | 362 | 0.011 | |
| 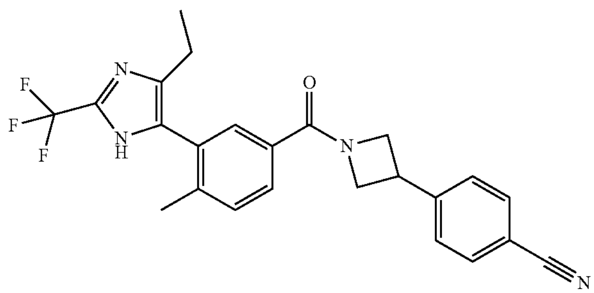 [SMILES: CCc1nc(C(F)(F)F)[nH]c1-c1cc(C(=O)N2CC(c3ccc(C#N)cc3)C2)ccc1C] | 363 | 0.021 | |
| 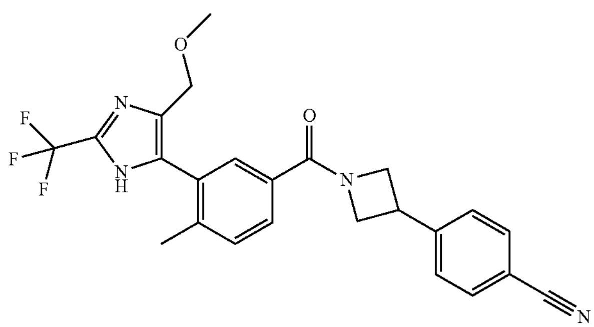 [SMILES: COCc1nc(C(F)(F)F)[nH]c1-c1cc(C(=O)N2CC(c3ccc(C#N)cc3)C2)ccc1C] | 364 | 0.040 | |
| 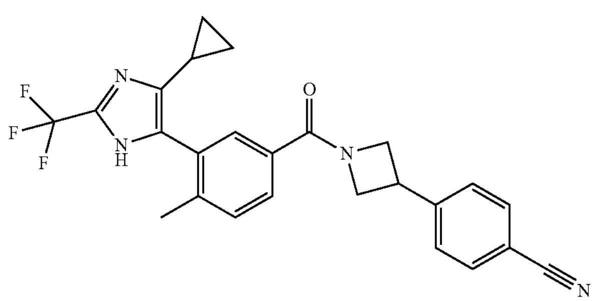 [SMILES: Cc1ccc(C(=O)N2CC(c3ccc(C#N)cc3)C2)cc1-c1[nH]c(C(F)(F)F)nc1C1CC1] | 365 | 0.023 | |
| 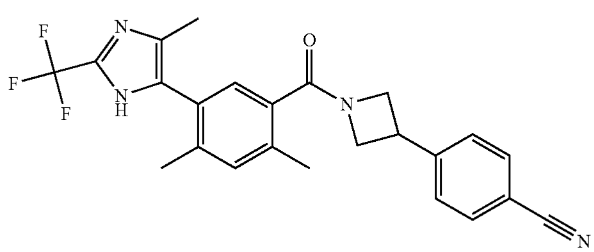 [SMILES: Cc1cc(C)c(-c2[nH]c(C(F)(F)F)nc2C)cc1C(=O)N1CC(c2ccc(C#N)cc2)C1] | 366 | 0.022 | |

TABLE 26-continued

Compounds of the present disclosure.

| Structure | Cpd | Hu FASN IC50 (μM) | HCV GT1b EC50 (μM) |
|---|---|---|---|
| 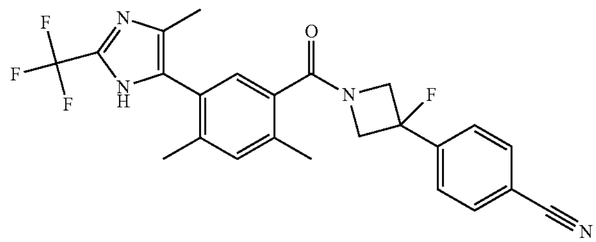 [SMILES: Cc1cc(C)c(-c2[nH]c(C(F)(F)F)nc2C)cc1C(=O)N1CC(F)(c2ccc(C#N)cc2)C1] | 367 | 0.040 | |
| 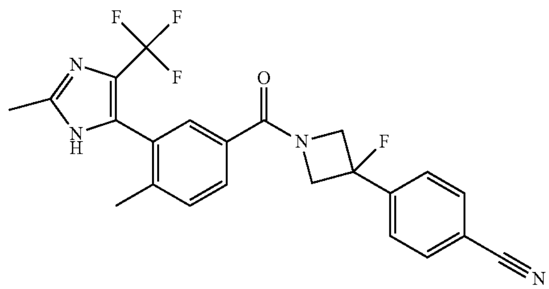 [SMILES: Cc1nc(C(F)(F)F)c(-c2cc(C(=O)N3CC(F)(c4ccc(C#N)cc4)C3)ccc2C)[nH]1] | 368 | 0.012 | |
| 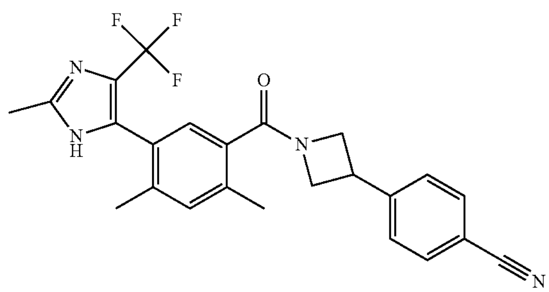 [SMILES: Cc1nc(C(F)(F)F)c(-c2cc(C(=O)N3CC(c4ccc(C#N)cc4)C3)c(C)cc2C)[nH]1] | 369 | 0.014 | |
| 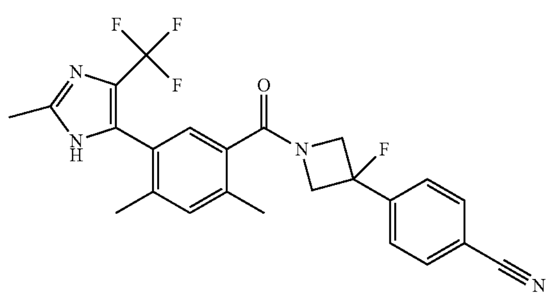 [SMILES: Cc1nc(C(F)(F)F)c(-c2cc(C(=O)N3CC(F)(c4ccc(C#N)cc4)C3)c(C)cc2C)[nH]1] | 370 | 0.012 | |
| 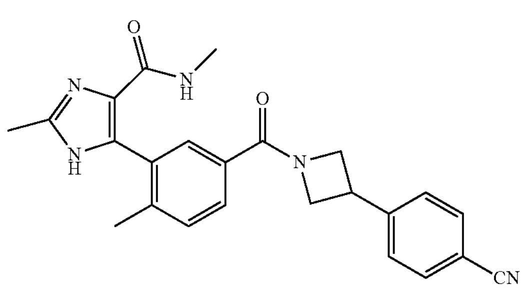 [SMILES: CNC(=O)c1nc(C)[nH]c1-c1cc(C(=O)N2CC(c3ccc(C#N)cc3)C2)ccc1C] | 371 | 0.82 | |

TABLE 26-continued

Compounds of the present disclosure.

| Structure | Cpd | Hu FASN IC50 (μM) | HCV GT1b EC50 (μM) |
|---|---|---|---|
| (structure) | 374 | 0.024 | |
| (structure) | 375 | | |
| (structure) | 376 | 0.029 | |
| (structure) | 377 | 0.029 | |
| (structure) | 378 | 0.072 | |

TABLE 26-continued

Compounds of the present disclosure.

| Structure | Cpd | Hu FASN IC50 (μM) | HCV GT1b EC50 (μM) |
|---|---|---|---|
| 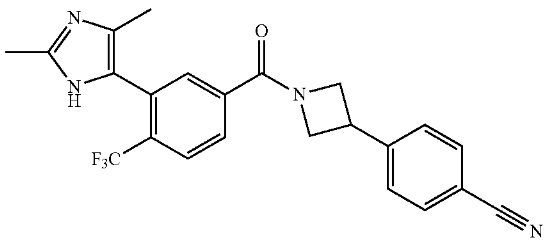 [SMILES: Cc1nc(C)c(-c2cc(C(=O)N3CC(c4ccc(C#N)cc4)C3)ccc2C(F)(F)F)[nH]1] | 379 | 0.059 | |
| 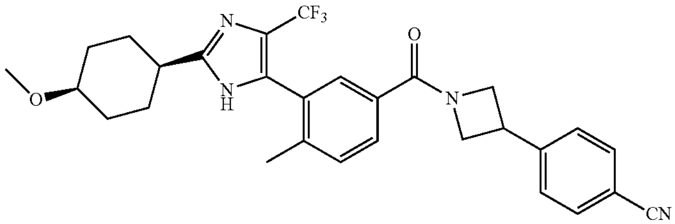 [SMILES: CO[C@H]1CC[C@@H](c2nc(C(F)(F)F)c(-c3cc(C(=O)N4CC(c5ccc(C#N)cc5)C4)ccc3C)[nH]2)CC1] | 380 | 0.013 | |
| 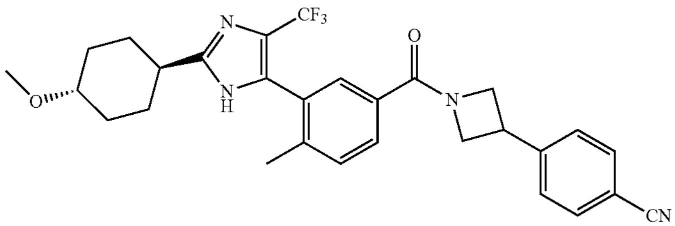 [SMILES: CO[C@H]1CC[C@H](c2nc(C(F)(F)F)c(-c3cc(C(=O)N4CC(c5ccc(C#N)cc5)C4)ccc3C)[nH]2)CC1] | 381 | 0.009 | |
| 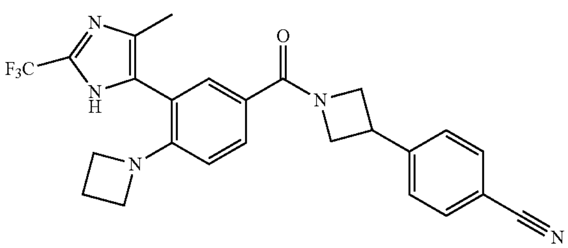 [SMILES: Cc1nc(C(F)(F)F)[nH]c1-c1cc(C(=O)N2CC(c3ccc(C#N)cc3)C2)ccc1N1CCC1] | 382 | 0.018 | |
| 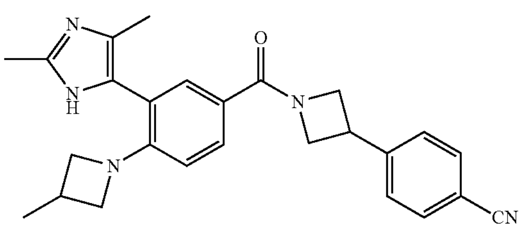 | 383 | 0.024 | |
| 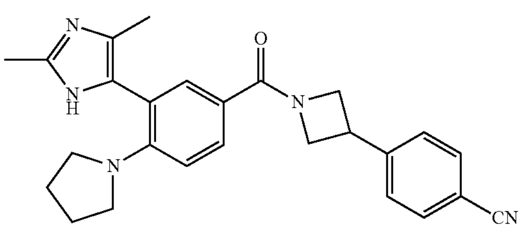 [SMILES: Cc1nc(C)c(-c2cc(C(=O)N3CC(c4ccc(C#N)cc4)C3)ccc2N2CCCC2)[nH]1] | 384 | 0.012 | |

TABLE 26-continued

Compounds of the present disclosure.

| Structure | Cpd | Hu FASN IC50 (μM) | HCV GT1b EC50 (μM) |
|---|---|---|---|
| 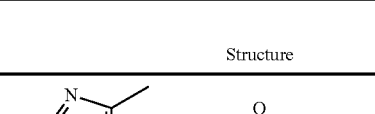 | 385 | 0.04 | |

While preferred aspects of the present invention have been shown and described herein, it will be obvious to those skilled in the art that such aspects are provided by way of example only. Numerous variations, changes, and substitutions will now occur to those skilled in the art without departing from the invention. It should be understood that various alternatives to the aspects of the invention described herein can be employed in practicing the invention. It is intended that the following claims define the scope of the invention and that methods and structures within the scope of these claims and their equivalents be covered thereby.

All publications and patent applications cited in this specification are herein incorporated by reference as if each individual publication or patent application were specifically and individually indicated to be incorporated by reference.

What is claimed is:

1. A compound of Formula III:

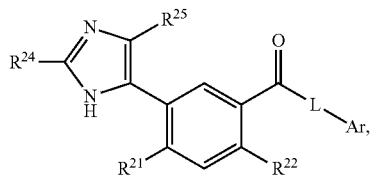

III or a pharmaceutically acceptable salt thereof, wherein:

L-Ar is

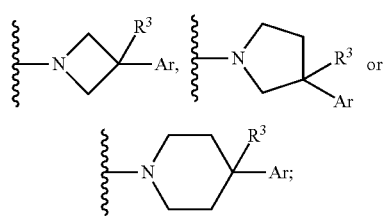

Ar is

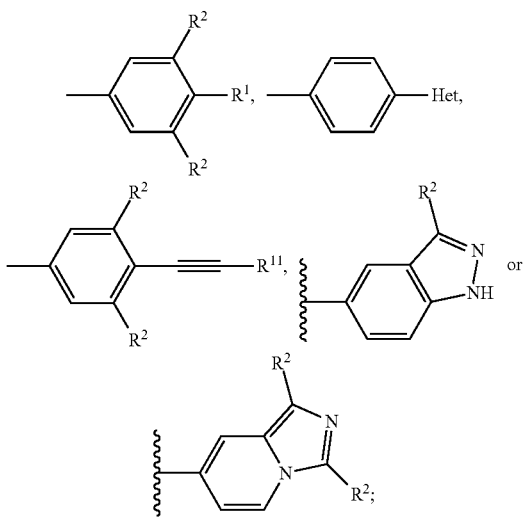

Het is a 5- to 6-membered heteroaryl;

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogens;

each $R^2$ is independently hydrogen, halogen or $C_1$-$C_4$ alkyl;

$R^3$ is H or F;

$R^{11}$ is H or —$CH_3$;

$R^{21}$ is H, halogen, $C_1$-$C_4$ alkyl, $C_3$-$C_5$ cycloalkyl or 4- to 6-membered heterocycle;

$R^{22}$ is H, halogen, or $C_1$-$C_2$ alkyl;

$R^{24}$ is H, —CN, —($C_1$-$C_4$ alkyl)-CN, $C_1$-$C_4$ alkyl, $C_1$-$C_4$ haloalkyl, —($C_1$-$C_4$ alkyl)-OH, —($C_1$-$C_4$ alkyl)-N($R^{241}$)$_2$, —($C_1$-$C_4$ alkyl)$_t$-O$_u$—($C_3$-$C_6$ cycloalkyl), —($C_1$-$C_4$ alkyl)$_t$-O$_u$—(4- to 6-membered heterocycle) or —($C_1$-$C_4$ alkyl)-O—($C_1$-$C_4$ alkyl), wherein each of the —$C_1$-$C_4$ alkyl, $C_3$-$C_6$ cycloalkyl and 4- to 6-membered heterocycle moieties is optionally substituted, and wherein:

t is 0 or 1;

u is 0 or 1;

with the proviso that when u is 1, t is 1; and each $R^{241}$ is independently H or $C_1$-$C_2$ alkyl; and $R^{25}$ is halogen, —CN, —($C_1$-$C_4$ alkyl)-CN, $C_1$-$C_2$ alkyl, $C_1$-$C_2$ haloalkyl, or cyclopropyl, wherein each of the —$C_1$-$C_2$ alkyl and cyclopropyl moieties is optionally substituted.

2. The compound of claim 1, wherein when L-Ar is

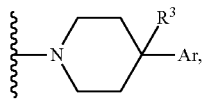

Ar is not

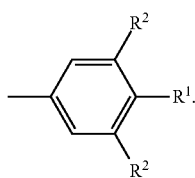

3. The compound of claim 1, wherein L-Ar is

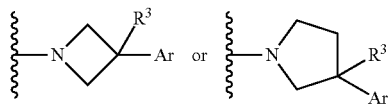

and Ar is

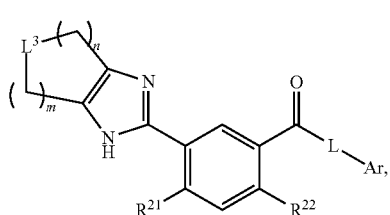

4. The compound of claim 1, wherein $R^1$ is halogen, —CN or $C_1$-$C_2$ haloalkyl.

5. The compound of claim 1, wherein $R^2$ is H.

6. The compound of claim 1, wherein $R^{21}$ is halogen, $C_1$-$C_4$ alkyl or $C_3$-$C_5$ cycloalkyl.

7. The compound of claim 1, wherein $R^{22}$ is H or —$CH_3$.

8. The compound of claim 1, wherein $R^{24}$ is H, —CN, —($C_1$-$C_4$ alkyl)-CN, $C_1$-$C_4$ alkyl, $C_1$-$C_4$ haloalkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_6$ cycloalkyl), —($C_1$-$C_4$ alkyl)$_t$-$O_u$—(4- to 6-membered heterocycle) or —($C_1$-$C_4$ alkyl)-O—($C_1$-$C_4$ alkyl).

9. The compound of claim 1, wherein when $R^{24}$ is —($C_1$-$C_4$ alkyl)-CN, $C_1$-$C_4$ alkyl, $C_1$-$C_4$ haloalkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_6$ cycloalkyl), —($C_1$-$C_4$ alkyl)$_t$-$O_u$—(4- to 6-membered heterocycle) or —($C_1$-$C_4$ alkyl)-O—($C_1$-$C_4$ alkyl), $R^{24}$ is substituted with one or more substituents selected from $C_1$-$C_2$ alkyl, oxo, —CN, halogen, alkanoyl, alkoxycarbonyl, —OH and $C_1$-$C_2$ alkoxy.

10. The compound of claim 1, wherein $R^{25}$ is halogen, —CN, $C_1$-$C_2$ alkyl or cyclopropyl.

11. The compound of claim 1, wherein when $R^{25}$ is —($C_1$-$C_4$ alkyl)-CN, $C_1$-$C_2$ alkyl, $C_1$-$C_2$ haloalkyl, or cyclopropyl, $R^{25}$ is substituted with one or more substituents selected from —OH, halogen, $C_1$-$C_2$ alkyl, alkoxy, and alkylcarbonyloxy.

12. A compound of Formula I or Formula IV:

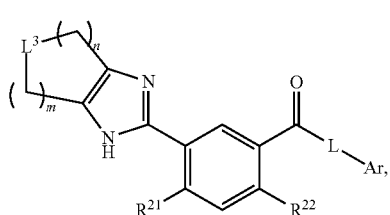

or

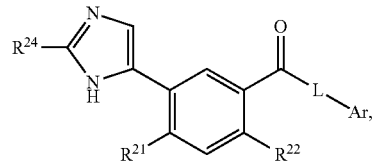

or a pharmaceutically acceptable salt thereof, wherein:

$L^3$ is —$CH_2$—, —$CH(R^{50})$—, —O—, —$N(R^{50})$—, —$N[C(O)R^{50}]$— or —$N[C(O)OR^{50}]$—, wherein $R^{50}$ is $C_1$-$C_6$ alkyl, $C_3$-$C_5$ cycloalkyl, or 4- to 6-membered heterocycle;

n is 1, 2, or 3;

m is 1 or 2 with the proviso that n+m≥3;

L-Ar is

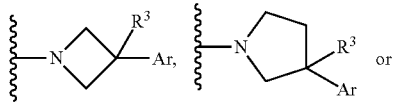

Ar is

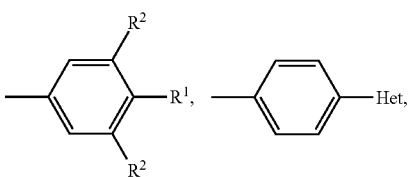

-continued

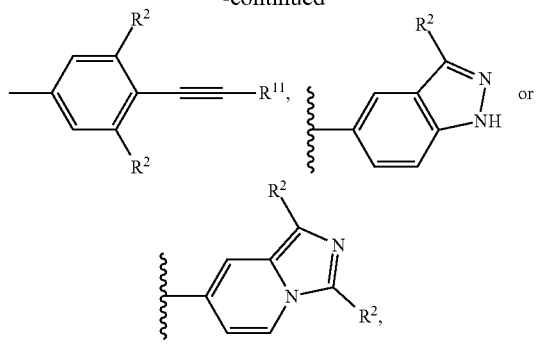 or

Het is a 5- to 6-membered heteroaryl;
$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, le is optionally substituted with one or more halogens;
each $R^2$ is independently hydrogen, halogen or $C_1$-$C_4$ alkyl;
$R^3$ is H or F;
$R^{11}$ is H or —$CH_3$;
$R^{21}$ is H, halogen, $C_1$-$C_4$ alkyl, $C_3$-$C_5$ cycloalkyl or a 4- to 6-membered heterocycle;
$R^{22}$ is H, halogen, or $C_1$-$C_2$ alkyl; and
$R^{24}$ is H, $C_1$-$C_4$ alkyl, $C_1$-$C_4$ haloalkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_5$ cycloalkyl), —($C_1$-$C_4$ alkyl)$_t$-$O_u$-(4- to 6-membered heterocycle) or —($C_1$-$C_4$ alkyl)-O—($C_1$-$C_4$ alkyl), wherein:
t is 0 or 1;
u is 0 or 1;
with the proviso that when u is 1, t is 1; and
$R^{241}$ is H or $C_1$-$C_2$ alkyl.

13. A pharmaceutical composition comprising a compound of claim 1, or a pharmaceutically acceptable salt thereof and a pharmaceutically acceptable carrier, excipient, or diluent.

14. A method of treating a hepatitis C infection in a subject comprising administering to the subject a therapeutically effective amount of a compound of claim 1, or a pharmaceutically acceptable salt thereof.

15. A method of inhibiting fatty acid synthase activity in a subject by administering to the subject a therapeutically effective amount of a compound of claim 1, or a pharmaceutically acceptable salt thereof.

16. A method of treating cancer in a subject comprising administering to the subject a therapeutically effective amount of a compound of claim 1, or a pharmaceutically acceptable salt thereof, wherein the cancer is selected from the group consisting of breast, lung, thyroid, lymph node, kidney, ureter, bladder, ovary, teste, prostate, bone, skeletal muscle, bone marrow, stomach, esophagus, small bowel, colon, rectum, pancreas, liver, smooth muscle, brain, spinal cord, nerves, ear, eye, nasopharynx, oropharynx, salivary gland, or heart tissue.

17. The method of claim 16, wherein the cancer is breast cancer, pancreatic cancer, or colon cancer.

18. The method of claim 16, wherein the cancer is pancreatic cancer.

19. The compound of claim 3, wherein Ar is

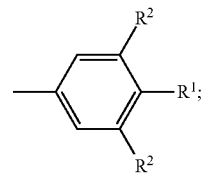

20. The compound of claim 4, wherein $R^1$ is —CN.
21. The compound of claim 6, wherein $R^{21}$ is —$CH_3$.
22. The compound of claim 7, wherein $R^{22}$ is —$CH_3$.
23. The compound of claim 8, wherein $R^{24}$ is methyl, isopropyl, cyclopropyl, —CN, haloalkyl, or —($C_1$-$C_2$ alkyl)-CN.
24. The compound of claim 9, wherein when $R^{24}$ is —($C_1$-$C_4$ alkyl)-CN, $C_1$-$C_4$ alkyl, $C_1$-$C_4$ haloalkyl, —($C_1$-$C_4$ alkyl)-OH, —($C_1$-$C_4$ alkyl)-N($R^{241}$)$_2$, —($C_1$-$C_4$ alkyl)$_t$-$O_u$—($C_3$-$C_6$ cycloalkyl), —($C_1$-$C_4$ alkyl)$_t$-$O_u$—(4- to 6-membered heterocycle) or —($C_1$-$C_4$ alkyl)-O—($C_1$-$C_4$ alkyl), $R^{24}$ is substituted with one or more substituents selected from methyl, —F, methoxy, —C(=O)$CH_3$ and —C(=O)—$OCH_3$.
25. The compound of claim 11, wherein $R^{25}$ is —$CH_2OCH_3$.
26. The compound of claim 11, wherein when $R^{25}$ is —($C_1$-$C_4$ alkyl)-CN, $C_1$-$C_2$ alkyl, $C_1$-$C_2$ haloalkyl, or cyclopropyl, $R^{25}$ is substituted with one or more substituents selected from —F, methyl, methoxy and —O—C(=O)—$CH_3$.
27. A pharmaceutical composition comprising a compound of claim 12, or a pharmaceutically acceptable salt thereof and a pharmaceutically acceptable carrier, excipient, or diluent.
28. A method of treating a hepatitis C infection in a subject comprising administering to the subject a therapeutically effective amount of a compound of claim 12, or a pharmaceutically acceptable salt thereof.
29. A method of inhibiting fatty acid synthase activity in a subject by administering to the subject a therapeutically effective amount of a compound of claim 12, or a pharmaceutically acceptable salt thereof.
30. A method of treating cancer in a subject comprising administering to the subject a therapeutically effective amount of a compound of claim 12, or a pharmaceutically acceptable salt thereof, wherein the cancer is selected from the group consisting of breast, lung, thyroid, lymph node, kidney, ureter, bladder, ovary, teste, prostate, bone, skeletal muscle, bone marrow, stomach, esophagus, small bowel, colon, rectum, pancreas, liver, smooth muscle, brain, spinal cord, nerves, ear, eye, nasopharynx, oropharynx, salivary gland, or heart tissue.
31. The method of claim 30, wherein the cancer is breast cancer, pancreatic cancer, or colon cancer.
32. The method of claim 30, wherein the cancer is pancreatic cancer.
33. The compound of claim 1, wherein $R^{25}$ is —$C_1$-$C_2$ alkyl optionally substituted with an alkoxy group.

* * * * *

UNITED STATES PATENT AND TRADEMARK OFFICE
CERTIFICATE OF CORRECTION

PATENT NO. : 10,053,450 B2
APPLICATION NO. : 15/201824
DATED : August 21, 2018
INVENTOR(S) : Johan D. Oslob et al.

It is certified that error appears in the above-identified patent and that said Letters Patent is hereby corrected as shown below:

At Column 563, Claim number 12, Line number 20, replace:
"Ie"
With:
--$R^1$--

Signed and Sealed this
Thirteenth Day of November, 2018

Andrei Iancu
*Director of the United States Patent and Trademark Office*